United States Patent
Jung et al.

(10) Patent No.: US 11,053,228 B2
(45) Date of Patent: Jul. 6, 2021

(54) CONDENSED CYCLIC COMPOUND, COMPOSITION INCLUDING THE CONDENSED CYCLIC COMPOUND, AND ORGANIC LIGHT-EMITTING DEVICE INCLUDING THE CONDENSED CYCLIC COMPOUND

(71) Applicants: Samsung Electronics Co., Ltd., Suwon-si (KR); Samsung SDI Co., Ltd., Yongin-si (KR)

(72) Inventors: Yongsik Jung, Yongin-si (KR); Soonok Jeon, Suwon-si (KR); Eunsuk Kwon, Suwon-si (KR); Sangmo Kim, Hwaseong-si (KR); Juhyun Kim, Suwon-si (KR); Jhunmo Son, Yongin-si (KR); Yeonsook Chung, Seoul (KR); Joonghyuk Kim, Seoul (KR)

(73) Assignees: SAMSUNG ELECTRONICS CO., LTD., Gyeonggi-Do (KR); SAMSUNG SDI CO., LTD., Gyeonggi-Do (KR)

( * ) Notice: Subject to any disclaimer, the term of this patent is extended or adjusted under 35 U.S.C. 154(b) by 0 days.

(21) Appl. No.: 16/510,187

(22) Filed: Jul. 12, 2019

(65) Prior Publication Data
US 2020/0031812 A1    Jan. 30, 2020

(30) Foreign Application Priority Data

Jul. 20, 2018 (KR) .................. 10-2018-0084762

(51) Int. Cl.
| | |
|---|---|
| *C07D 407/10* | (2006.01) |
| *H01L 51/00* | (2006.01) |
| *C07D 403/10* | (2006.01) |
| *C07D 405/10* | (2006.01) |
| *C07D 405/14* | (2006.01) |
| *C07D 403/04* | (2006.01) |
| *C07D 403/14* | (2006.01) |
| *C07D 401/10* | (2006.01) |
| *C07F 7/08* | (2006.01) |
| *C07F 15/00* | (2006.01) |
| *H01L 51/50* | (2006.01) |
| *C07D 409/10* | (2006.01) |

(52) U.S. Cl.
CPC ......... *C07D 407/10* (2013.01); *C07D 401/10* (2013.01); *C07D 403/04* (2013.01); *C07D 403/10* (2013.01); *C07D 403/14* (2013.01); *C07D 405/10* (2013.01); *C07D 405/14* (2013.01); *C07D 409/10* (2013.01); *C07F 7/0816* (2013.01); *C07F 15/002* (2013.01); *C07F 15/004* (2013.01); *C07F 15/0093* (2013.01); *H01L 51/0072* (2013.01); *H01L 51/0073* (2013.01); *H01L 51/0074* (2013.01); *H01L 51/5056* (2013.01); *H01L 51/5072* (2013.01)

(58) Field of Classification Search
CPC .. C07D 407/10; C07D 403/10; C07D 405/10; C07D 403/04; C07D 403/14; C07D 405/14; C07D 401/10; C07D 409/10; H01L 51/0072
See application file for complete search history.

(56) References Cited

U.S. PATENT DOCUMENTS

| | | | |
|---|---|---|---|
| 8,273,467 B2 | 9/2012 | Sano et al. | |
| 9,209,410 B2 | 12/2015 | Iwakuma et al. | |
| 9,425,407 B2 * | 8/2016 | Hwang | H01L 51/0058 |
| 10,236,452 B2 * | 3/2019 | Jeong | C07D 307/77 |
| 10,243,149 B2 * | 3/2019 | Kang | H01L 51/009 |
| 2014/0231772 A1 | 8/2014 | Shiomi et al. | |
| 2016/0118601 A1 | 4/2016 | Huh et al. | |
| 2016/0190477 A1 * | 6/2016 | Kawakami | C07D 405/12 257/40 |
| 2019/0013481 A1 | 1/2019 | Chihaya et al. | |

FOREIGN PATENT DOCUMENTS

| | | | |
|---|---|---|---|
| EP | 3072943 A1 | | 9/2016 |
| JP | 2007-126403 A | | 5/2007 |
| JP | 2014-096572 A | | 5/2014 |
| JP | 2014096572 | * | 5/2014 |
| JP | 2017119663 A | | 7/2017 |
| KR | 10-2010-0032888 A | | 3/2010 |
| KR | 10-2013-0043671 A | | 4/2013 |
| KR | 10-2014-0090133 A | | 7/2014 |
| KR | 10-2015-0087045 A | | 7/2015 |
| KR | 2017035376 | * | 3/2017 |
| KR | 10-2017-0037135 A | | 4/2017 |
| WO | 2011132575 A1 | | 10/2011 |
| WO | 2012-015017 A1 | | 2/2012 |
| WO | 2015-111864 A1 | | 7/2015 |
| WO | 2018139662 | * | 8/2018 |
| WO | 2018237389 | * | 12/2018 |
| WO | 2019004254 A1 | | 1/2019 |
| WO | 2019191665 A1 | | 10/2019 |

OTHER PUBLICATIONS

Extended European search report issued by the European Patent Office dated Dec. 13, 2019 in the examination of he European Patent Application No. 19184904.1, which corresponds to the U.S. Application above.

* cited by examiner

*Primary Examiner* — D Margaret M Seaman
(74) *Attorney, Agent, or Firm* — Cantor Colburn LLP

(57) ABSTRACT

A condensed cyclic compound represented by Formula 1:

Ar$_1$-L$_1$-Ar$_2$        Formula 1 wherein, in Formula 1, Ar$_1$, Ar$_2$, and L are the same as described in the specification.

20 Claims, 1 Drawing Sheet

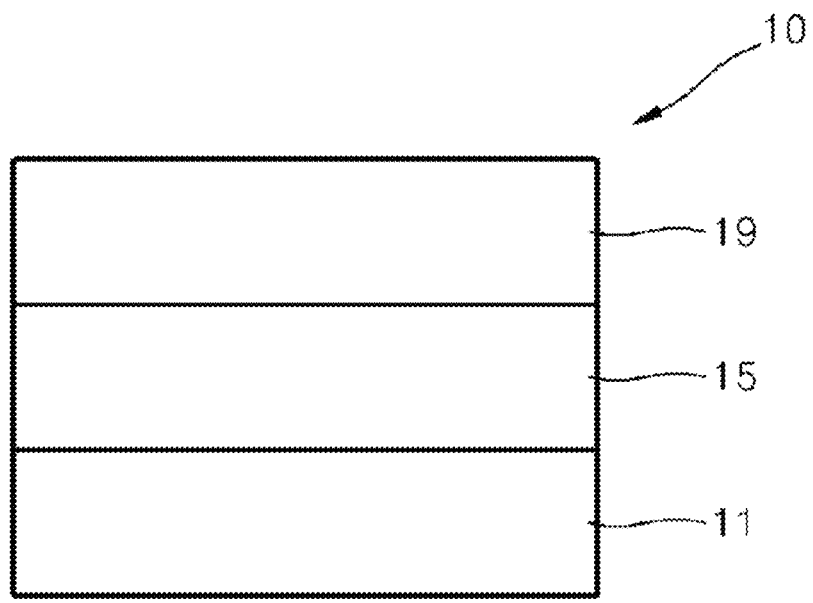

CONDENSED CYCLIC COMPOUND, COMPOSITION INCLUDING THE CONDENSED CYCLIC COMPOUND, AND ORGANIC LIGHT-EMITTING DEVICE INCLUDING THE CONDENSED CYCLIC COMPOUND

CROSS-REFERENCE TO RELATED APPLICATION

This application claims priority to Korean Patent Application No. 10-2018-0084762, filed on Jul. 20, 2018, in the Korean Intellectual Property Office, and all the benefits accruing therefrom under 35 U.S.C. § 119, the content of which is incorporated herein in its entirety by reference.

BACKGROUND

1. Field

One or more embodiments relate to a condensed cyclic compound, a composition including the same, and an organic light-emitting device including the condensed cyclic compound.

2. Description of the Related Art

Organic light-emitting devices (OLEDs) are self-emission devices that produce full-color images, and that also have wide viewing angles, high contrast ratios, short response times, and excellent characteristics in terms of brightness, driving voltage, and response speed.

In an example, an organic light-emitting device includes an anode, a cathode, and an organic layer disposed between the anode and the cathode, wherein the organic layer includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. Carriers, such as holes and electrons, recombine in the emission layer to produce excitons. These excitons transit from an excited state to a ground state, thereby generating light.

Various types of organic light emitting devices are known. However, there still remains a need in OLEDs having low driving voltage, high efficiency, high brightness, and long lifespan.

SUMMARY

Aspects of the present disclosure provide a novel condensed cyclic compound, a composition including the condensed cyclic compound, and an organic light-emitting device including the condensed cyclic compound.

Additional aspects will be set forth in part in the description which follows and, in part, will be apparent from the description, or may be learned by practice of the presented embodiments.

An aspect provides a condensed cyclic compound represented by Formula 1:

$$Ar_1-L_1-Ar_2. \qquad \text{Formula 1}$$

In Formula 1, $L_1$ may be a group represented by Formula 2, $Ar_1$ may be a group represented by Formula 3A, and $Ar_2$ may be a group represented by Formula 3B, and in Formula 1, $L_1$ may include at least one cyano group:

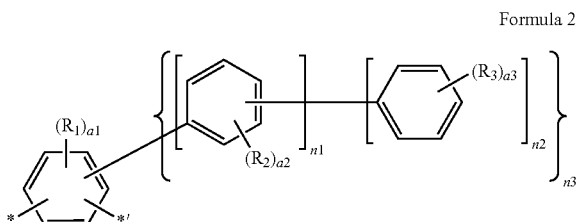

Formula 2

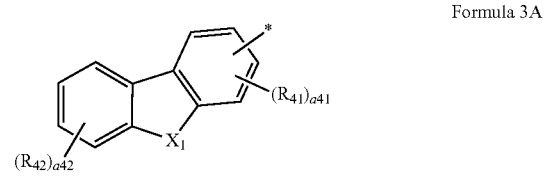

Formula 3A

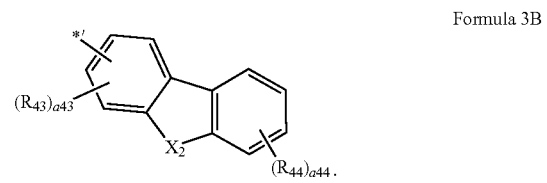

Formula 3B

In Formulae 2, 3A, and 3B, $X_1$ and $X_2$ may each independently be O or S, $R_1$ to $R_3$ and $R_{41}$ to $R_{44}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), and —B($Q_6$)($Q_7$), a1, a41, and a43 may each independently be an integer from 0 to 3, a2, a42, and a44 may each independently be an integer from 0 to 4, a3 may be an integer from 0 to 5, n1 may be an integer from 0 to 5, n2 and n3 may each independently be an integer from 1 to 4,

* in Formula 2 indicates a binding site to $Ar_1$ in Formula 1,

*' in Formula 2 indicates a binding site to $Ar_2$ in Formula 1,

* in Formula 3A and *' in Formula 3B each indicate a binding site to $L_1$ in Formula 1, at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_{60}$ alkoxy group, each substituted with at least one selected from deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{24}$)($Q_{25}$), and —B($Q_{26}$)($Q_{27}$); and —Si($Q_{31}$)($Q_{32}$)($Q_{33}$), —N($Q_{34}$)($Q_{35}$), and —B($Q_{36}$)($Q_{37}$), and $Q_1$ to $Q_7$, $Q_{11}$ to $Q_{17}$, $Q_{21}$ to $Q_{27}$, and $Q_{31}$ to $Q_{37}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

Another aspect provides a composition including a first compound and a second compound, wherein the first compound may be the condensed cyclic compound, the second compound may be a compound including at least one selected from a carbazole group, a dibenzofuran group, a dibenzothiophene group, an indenocarbazole group, an indolocarbazole group, a benzofurocarbazole group, a benzothienocarbazole group, an acridine group, a dihydroacridine group, and a triindolobenzene group and not including an electron withdrawing group, the electron withdrawing group may be selected from:
—F, —$CFH_2$, —$CF_2H$, —$CF_3$, —CN, and —$NO_2$;

a $C_1$-$C_{60}$ alkyl group substituted with at least one selected from —F, —$CFH_2$, —$CF_2H$, —$CF_3$, —CN, and —$NO_2$;

a $C_1$-$C_{60}$ heteroaryl group and a monovalent non-aromatic condensed heteropolycyclic group, each including *=N—*' as a ring-forming moiety; and a $C_1$-$C_{60}$ heteroaryl group and a monovalent non-aromatic condensed heteropolycyclic group, each substituted with at least one selected from deuterium, —F, —$CFH_2$, —$CF_2H$, —$CF_3$, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and each including *=N—*' as a ring-forming moiety.

Another aspect provides an organic light-emitting device including:

a first electrode;

a second electrode; and an organic layer disposed between the first electrode and the second electrode, wherein the organic layer may include an emission layer, and wherein the organic layer may include at least one condensed cyclic compound represented by Formula 1 or a composition including at least one condensed cyclic compound represented by Formula 1.

BRIEF DESCRIPTION OF THE DRAWING

These and/or other aspects will become apparent and more readily appreciated from the following description of the embodiments, taken in conjunction with the FIGURE which is a schematic view of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

A condensed cyclic compound according to an embodiment may be represented by Formula 1:

$Ar_1$-$L_1$-$Ar_2$.     Formula 1

In Formula 1, $L_1$ may be a group represented by Formula 2, $Ar_1$ may be a group represented by Formula 3A, and $Ar_2$ may be a group represented by Formula 3B:

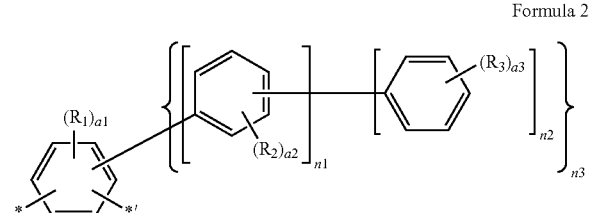

Formula 2

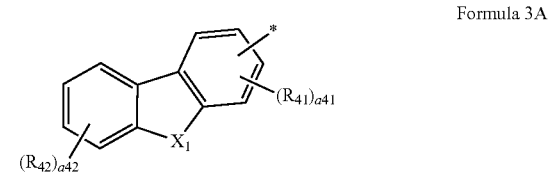

Formula 3A

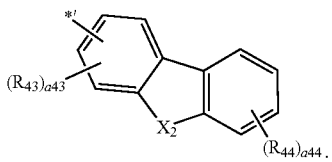

Formulae 2, 3A, and 3B may each independently be the same as described herein.

In Formula 1, $L_1$ (that is, a group represented by Formula 2) may include at least one cyano group (for example, one, two, three, four, five, six, seven, or eight cyano groups).

In an embodiment, the group represented by Formula 2 may include two or more benzene rings (for example, two, three, four, or five benzene rings) linked via a single bond.

In one or more embodiments, $Ar_1$ and $Ar_2$ in Formula 1 may be identical to each other.

In one or more embodiments, $Ar_1$ and $Ar_2$ in Formula 1 may be different from each other.

$X_1$ and $X_2$ in Formulae 3A and 3B may each independently be O or S.

In an embodiment, $X_1$ and $X_2$ may be identical to each other.

In one or more embodiments, $X_1$ and $X_2$ may be different from each other.

In one or more embodiments,
i) $X_1$ and $X_2$ may be identical to each other, and the number of carbon to which $L_1$ in Formula 1 is linked in Formula 3A and the number of carbon to which $L_1$ in Formula 1 is linked in Formula 3B may be identical to each other (for example, Compound 1 or the like);
ii) $X_1$ and $X_2$ may be different from each other, and the number of carbon to which $L_1$ in Formula 1 is linked in Formula 3A and the number of carbon to which $L_1$ in Formula 1 is linked in Formula 3B may be identical to each other (for example, Compound 1745 or the like);
iii) $X_1$ and $X_2$ may be identical to each other, and the number of carbon to which $L_1$ in Formula 1 is linked in Formula 3A and the number of carbon to which $L_1$ in Formula 1 is linked in Formula 3B may be different from each other (for example, Compound 1269 or the like); or
iv) $X_1$ and $X_2$ may be different from each other, and the number of carbon to which $L_1$ in Formula 1 is linked in Formula 3A and the number of carbon to which $L_1$ in Formula 1 is linked in Formula 3B may be different from each other (for example, Compound 1646 or the like).

In Formulae 2, 3A, and 3B, $R_1$ to $R_3$ and $R_{41}$ to $R_{44}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), and —B($Q_6$)($Q_7$), wherein $Q_1$ to $Q_7$ are the same as defined above.

For example, $R_1$ to $R_3$ and $R_{41}$ to $R_{44}$ may each independently be selected from:
hydrogen, deuterium, —F, a hydroxyl group, a cyano group, and a nitro group;
a $C_1$-$C_{20}$ alkyl group and a $C_1$-$C_{20}$ alkoxy group, each unsubstituted or substituted with at least one selected from deuterium, —F, a hydroxyl group, a cyano group, and a nitro group;
a cyclopentyl group, a cyclohexyl group, a cyclopentenyl group, a cyclohexenyl group, a cycloheptenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyridinyl group, a pyridoindolyl group, a benzofuropyridinyl group, a benzothienopyridinyl group, a pyrimidoindolyl group, a benzofuropyrimidinyl group, a benzothienopyrimidinyl group, a phenoxazinyl group, a pyridobenzooxazinyl group, and a pyridobenzothiazinyl group, each unsubstituted or substituted with at least one selected from deuterium, —F, a hydroxyl group, a cyano group, a nitro group, a $C_1$-$C_{20}$ alkyl group, a $C_1$-$C_{20}$ alkoxy group, a phenyl group, a biphenyl group, and a terphenyl group; and
—Si($Q_1$)($Q_2$)($Q_3$), —N($Q_4$)($Q_5$) and —B($Q_6$)($Q_7$), and $Q_1$ to $Q_7$ may each independently be a $C_1$-$C_{20}$ alkyl group or a $C_6$-$C_{60}$ aryl group.

In one or more embodiments, $R_1$ to $R_3$ and $R_{41}$ to $R_{44}$ may each independently be selected from:
hydrogen, deuterium, —F, a hydroxyl group, a cyano group, and a nitro group;
a $C_1$-$C_{20}$ alkyl group and a $C_1$-$C_{20}$ alkoxy group, each unsubstituted or substituted with at least one selected from deuterium, —F, a hydroxyl group, a cyano group, and a nitro group;

a phenyl group, a biphenyl group, a terphenyl group, a fluorenyl group, and a carbazolyl group, each unsubstituted or substituted with at least one selected from deuterium, —F, a hydroxyl group, a cyano group, a nitro group, a $C_1$-$C_{20}$ alkyl group, a $C_1$-$C_{20}$ alkoxy group, a phenyl group, a biphenyl group, and a terphenyl group; and —Si($Q_1$)($Q_2$)($Q_3$) and —N($Q_4$)($Q_5$), and $Q_1$ to $Q_7$ may each independently be a $C_1$-$C_{20}$ alkyl group or a $C_6$-$C_{60}$ aryl group, but embodiments of the present disclosure are not limited thereto.

In Formulae 2, 3A, and 3B, a1 to a3 and a41 to a44 respectively indicate the number of groups $R_1$ to $R_3$ and groups $R_{41}$ to $R_{44}$, a1, a41, and a43 may each independently be an integer from 0 to 3, a2, a42, and a44 may each independently be an integer from 0 to 4, and a3 may be an integer from 0 to 5. When each of a1 to a3 and a41 to a44 is two or more, groups $R_1$ to $R_3$ and groups $R_{41}$ to $R_{44}$ may be identical to or different from each other, respectively.

For example, a1 to a3 and a41 to a44 may each independently be 0 or 1, but embodiments of the present disclosure are not limited thereto.

In an embodiment, in Formula 2, at least one selected from groups $R_1$ in the number of a1, groups $R_2$ in the number of a2, and groups $R_3$ in the number of a3 (for example, one, two, three, four, or five selected from groups $R_1$ in the number of a1, groups $R_2$ in the number of a2, and groups $R_3$ in the number of a3) may be a cyano group.

In one or more embodiments, in Formula 2, $R_1$ may not be a cyano group.

In one or more embodiments, in Formula 2, $R_1$ may not be a cyano group, one, two, three, four, or five, selected from groups $R_2$ in the number of a2 and groups $R_3$ in the number of a3 may be a cyano group.

In Formula 2, n1 to n3 respectively indicate the number of moieties, n1 may be an integer from 0 to 5, and n2 and n3 may each independently be an integer from 1 to 4. When n1 is 0, a moiety represented by

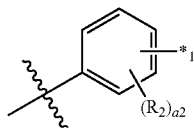

in Formula 2 may be a single bond, when n1 is two or more, two or more moieties represented by

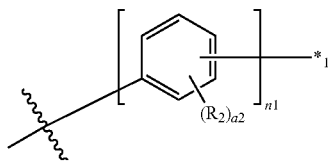

in Formula 2 may be identical to or different from each other, when n2 is two or more, two or more moieties represented by

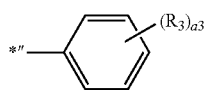

in Formula 2 may be identical to or different from each other, and when n3 is two or more, two or more moieties represented by

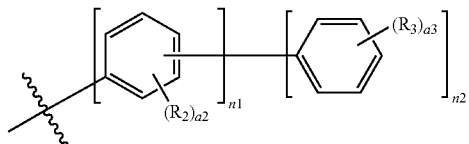

in Formula 2 may be identical to or different from each other.

For example, n1 in Formula 2 may be 0, 1, or 2.

In an embodiment, n2 and n3 in Formula 2 may each independently be 1 or 2.

In an embodiment in Formula 2,
i) n1 may be 0, and n2 may be 1; ii) n1 and n2 may each be 1; iii) n1 may be 2, and n2 may be 1; or iv) n1 may be 1, and n2 may be 2, and n3 may be 1 or 2, but embodiments of the present disclosure are not limited thereto.

* in Formula 2 indicates a binding site to $Ar_1$ in Formula 1, *' in Formula 2 indicates a binding site to $Ar_2$ in Formula 1, and * in Formula 3A and *' in Formula 3B each indicate a binding site to $L_1$ in Formula 1.

In an embodiment,
in Formula 2, n3 may be 1, and a moiety represented by

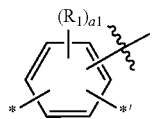

may be selected from groups represented by Formulae 4-1 to 4-12, or in Formula 2, n3 may be 2, and a moiety represented by

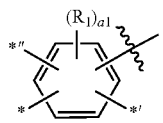

may be selected from groups represented by Formulae 4-13 to 4-48:

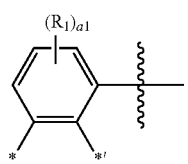

4-1

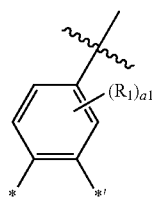

4-2

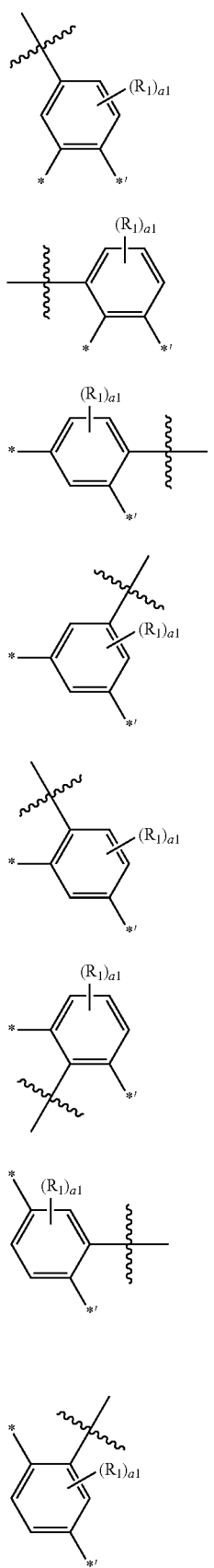

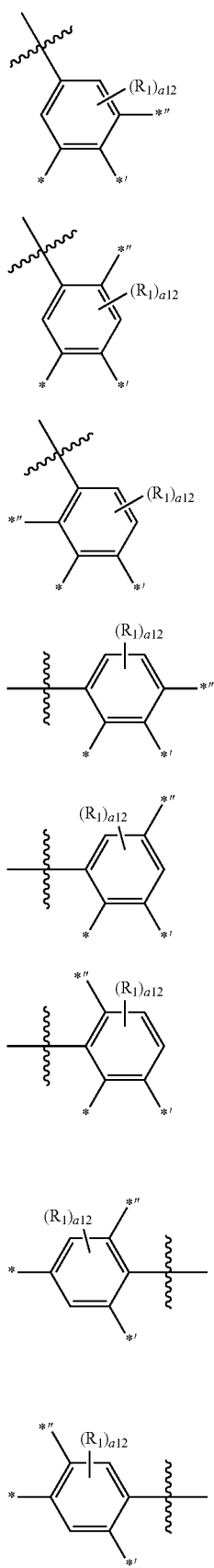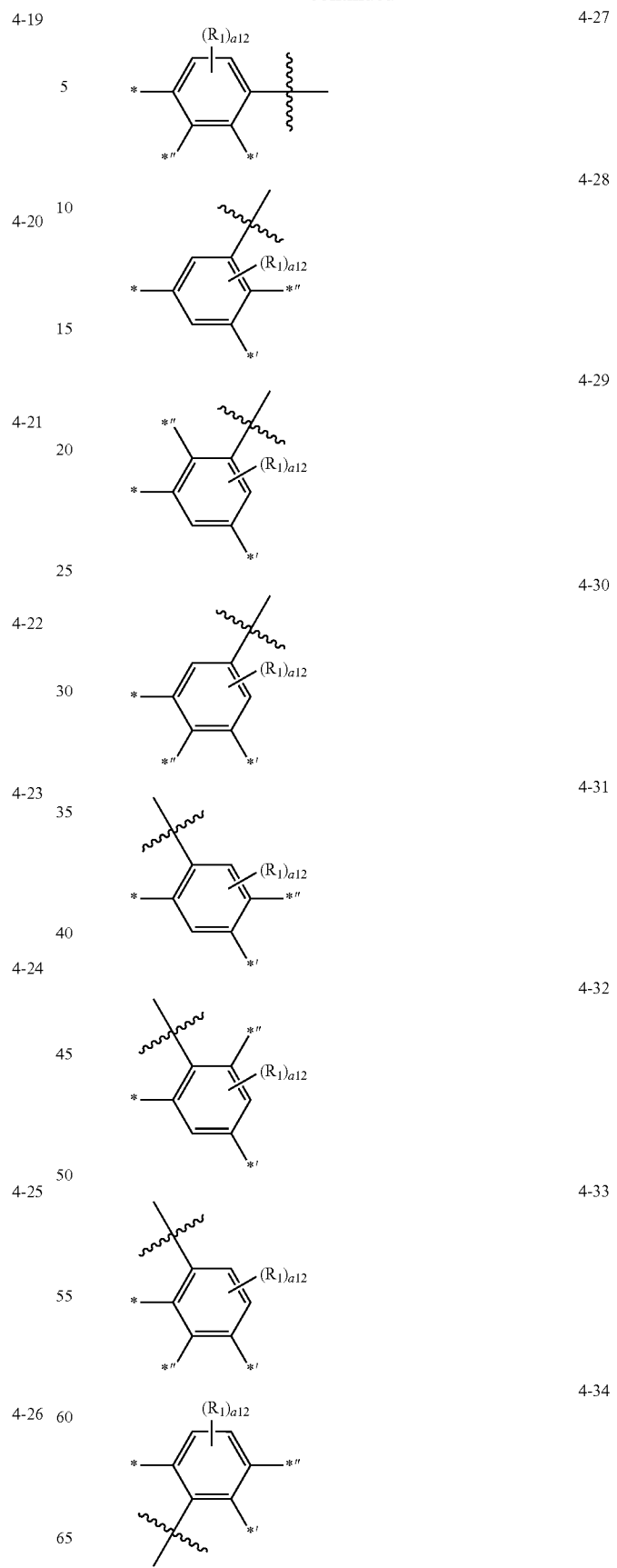

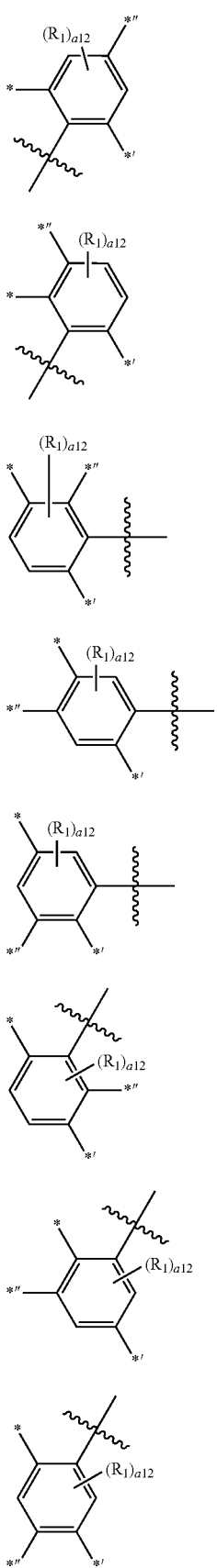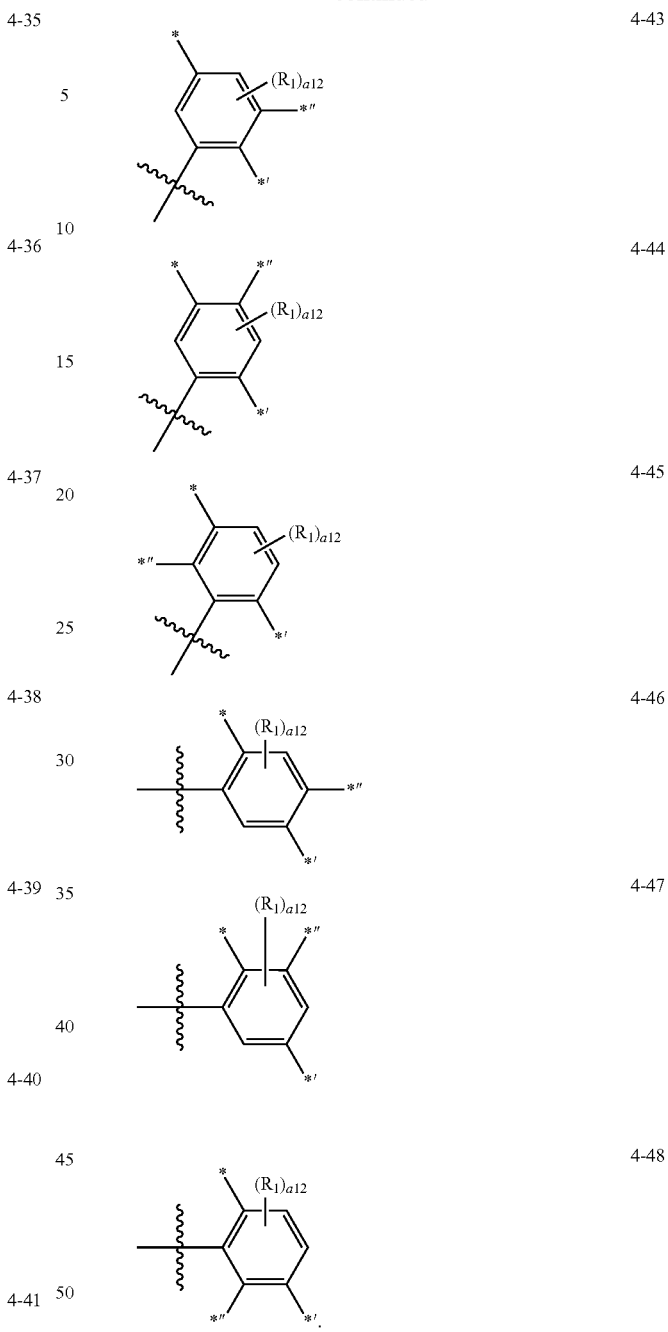
In Formulae 4-1 to 4-48,
$R_1$ and a1 may each independently be the same as described herein,
a12 may be an integer from 0 to 2,
\* indicates a binding site to $Ar_1$ in Formula 1,
\*' indicates a binding site to $Ar_2$ in Formula 1, and
⌇ and \*'' each indicate a binding site to a neighboring benzene ring in Formula 2.
For example, $R_1$ in Formulae 4-1 to 4-48 may not be a cyano group.

In one or more embodiments,
in Formula 2, n2 may be 1, and a moiety represented by
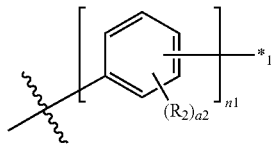
may be selected from groups represented by Formulae 5-1 to 5-12, and
in Formula 2, n2 may be 2, and a moiety represented by
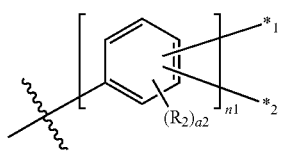
may be selected from groups represented by Formulae 5-13 to 5-24:
5-1
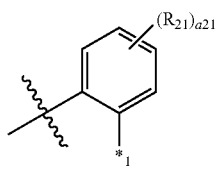
5-2
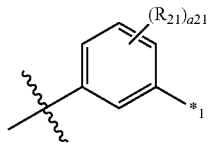
5-3
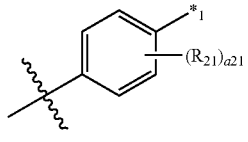
5-4
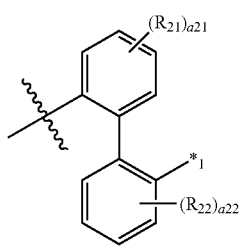
5-5
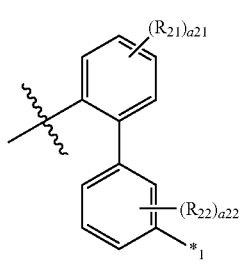
5-6
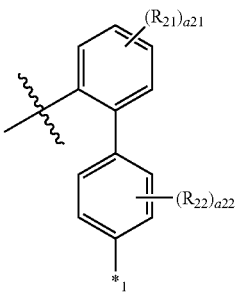
5-7
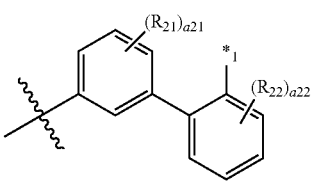
5-8
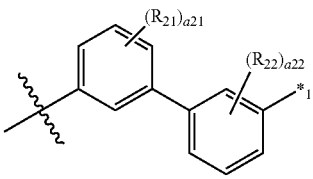
5-9
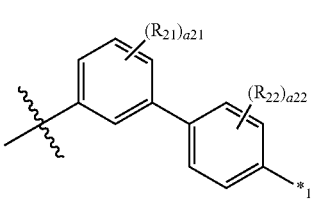
5-10
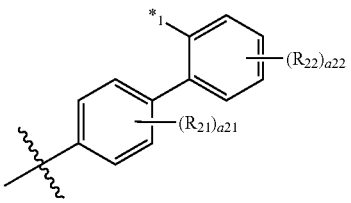
5-11
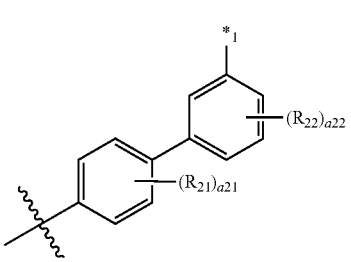
5-12
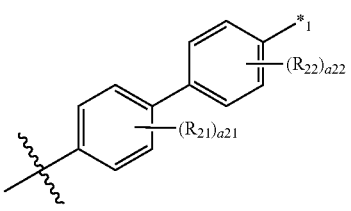

5-13 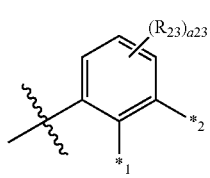

5-14 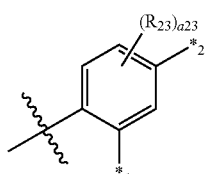

5-15 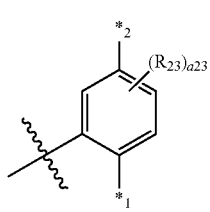

5-16 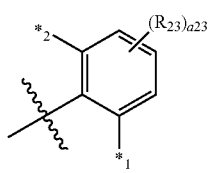

5-17 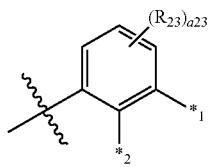

5-18 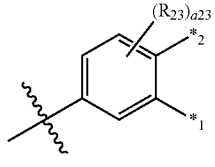

5-19 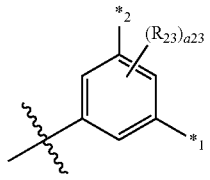

5-20 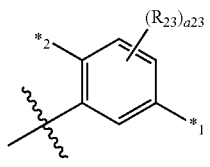

5-21 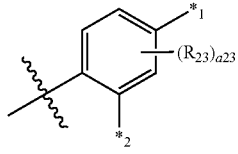

5-22 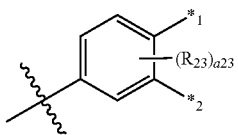

5-23 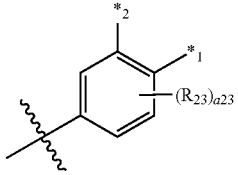

5-24 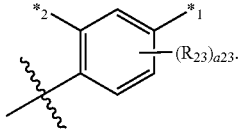

In Formulae 5-1 to 5-24, $R_{21}$ to $R_{23}$ may each independently be the same as described in connection with $R_2$, a21 and a22 may each independently be an integer from 0 to 4, a23 may be an integer from 0 to 3, ∽ indicates a binding site to a left benzene ring in Formula 2, and *1 and *2 each indicate a binding site to a right benzene ring in Formula 2.

In one or more embodiments, a moiety represented by

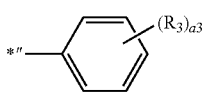

in Formula 2 may be selected from groups represented by Formulae 6-1 to 6-21:

6-1 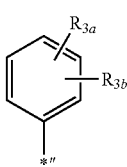

6-2 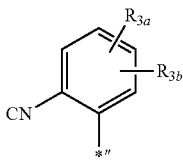

6-3 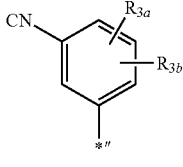

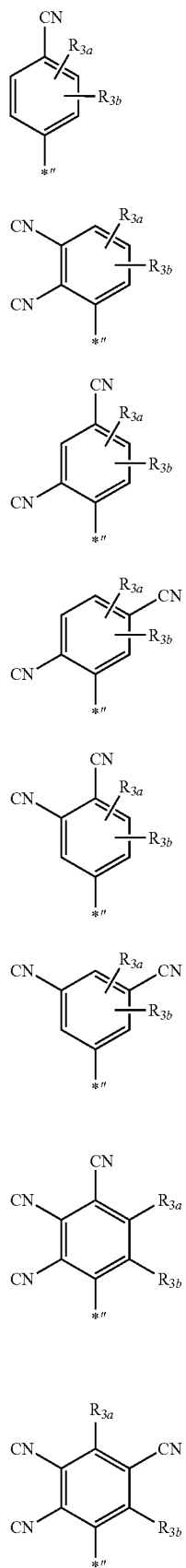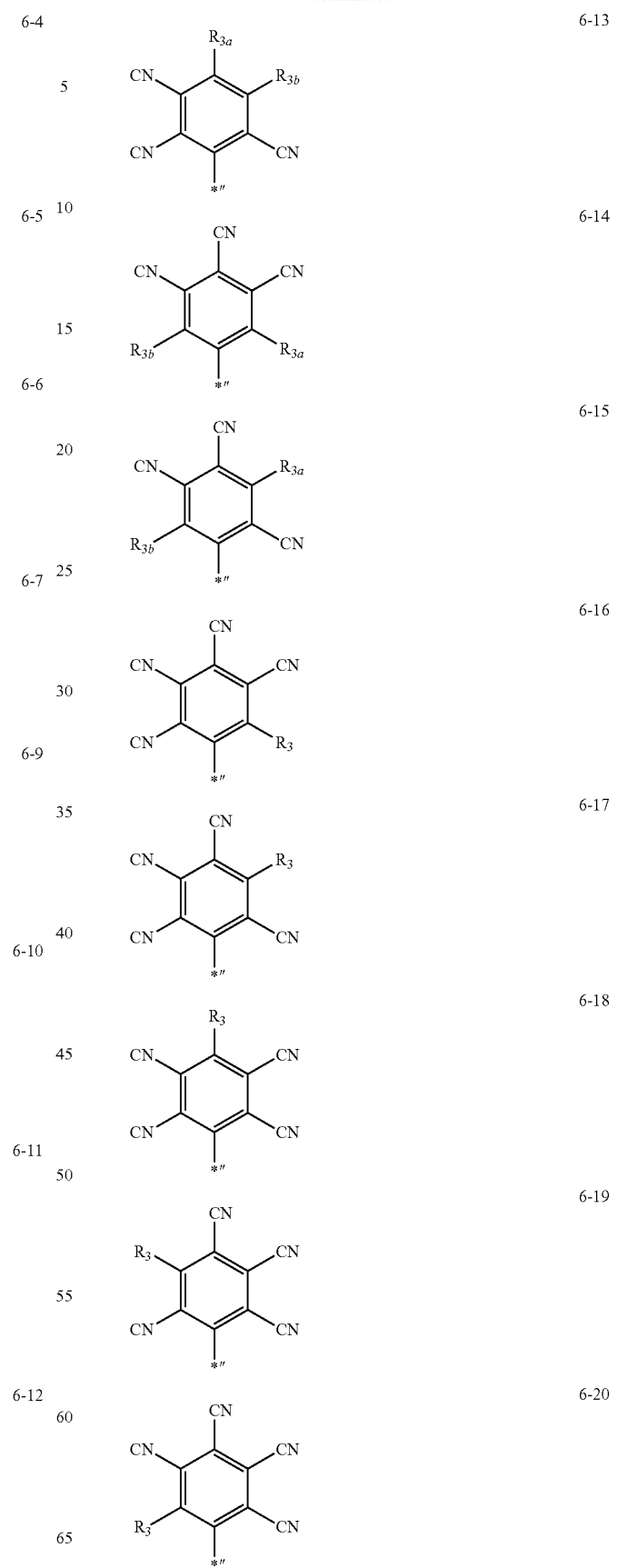

-continued 6-21

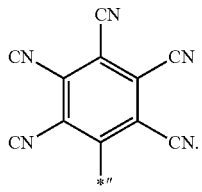

In Formulae 6-1 to 6-21, $R_3$ may be the same as described herein, $R_{3a}$ and $R_{3b}$ may each independently be the same as described in connection with $R_3$, and *''' indicates a binding site to a neighboring benzene ring in Formula 2.

For example, in Formulae 6-1 to 6-21, $R_3$, $R_{3a}$, and $R_{3b}$ may not be a cyano group.

In one or more embodiments, $Ar_1$ in Formula 1 may be selected from groups represented by Formulae 3A-1 to 3A-4, and $Ar_2$ in Formula 1 may be selected from groups represented by Formulae 3B-1 to 3B-4:

3A-1

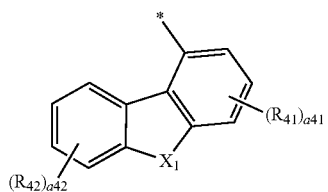

3A-2

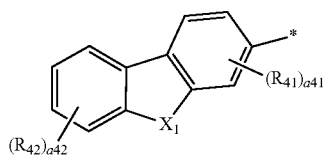

3A-3

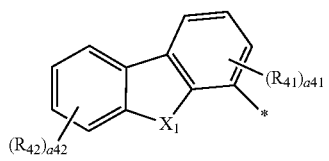

3A-4

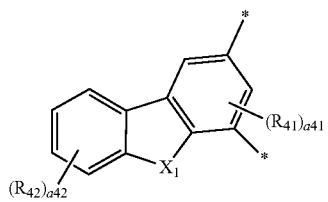

3B-1

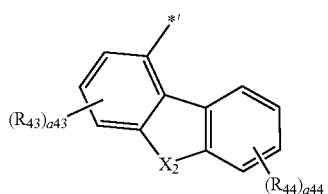

3B-2

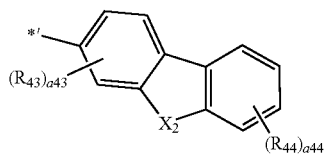

3B-3

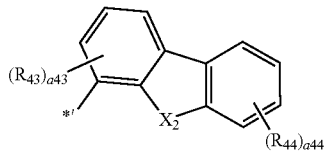

3B-4

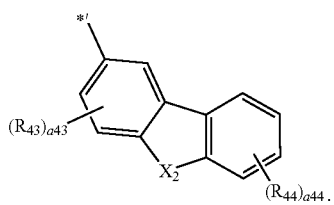

In Formulae 3A-1 to 3A-4 and 3B-1 to 3B-4, $R_{41}$ to $R_{44}$ and a41 to a44 may each independently be the same as described herein, and * and *' each indicate a binding site to $L_1$ in Formula 1.

In one or more embodiments, $Ar_1$ in Formula 1 may be selected from groups represented by Formulae 3A(1) to 3A(30), and $Ar_2$ in Formula 1 may be selected from groups represented by Formulae 3B(1) to 36(30), but embodiments of the present disclosure are not limited thereto:

3A(1)

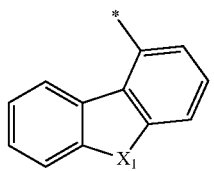

3A(2)

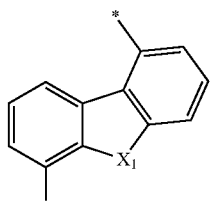

3A(3)

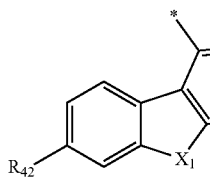

3A(4)

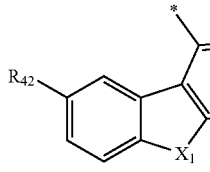

3A(5)

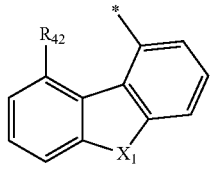

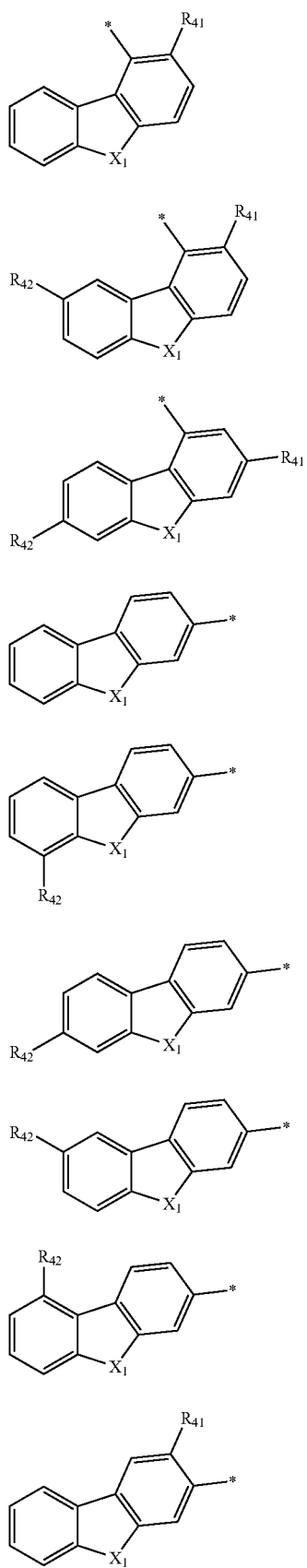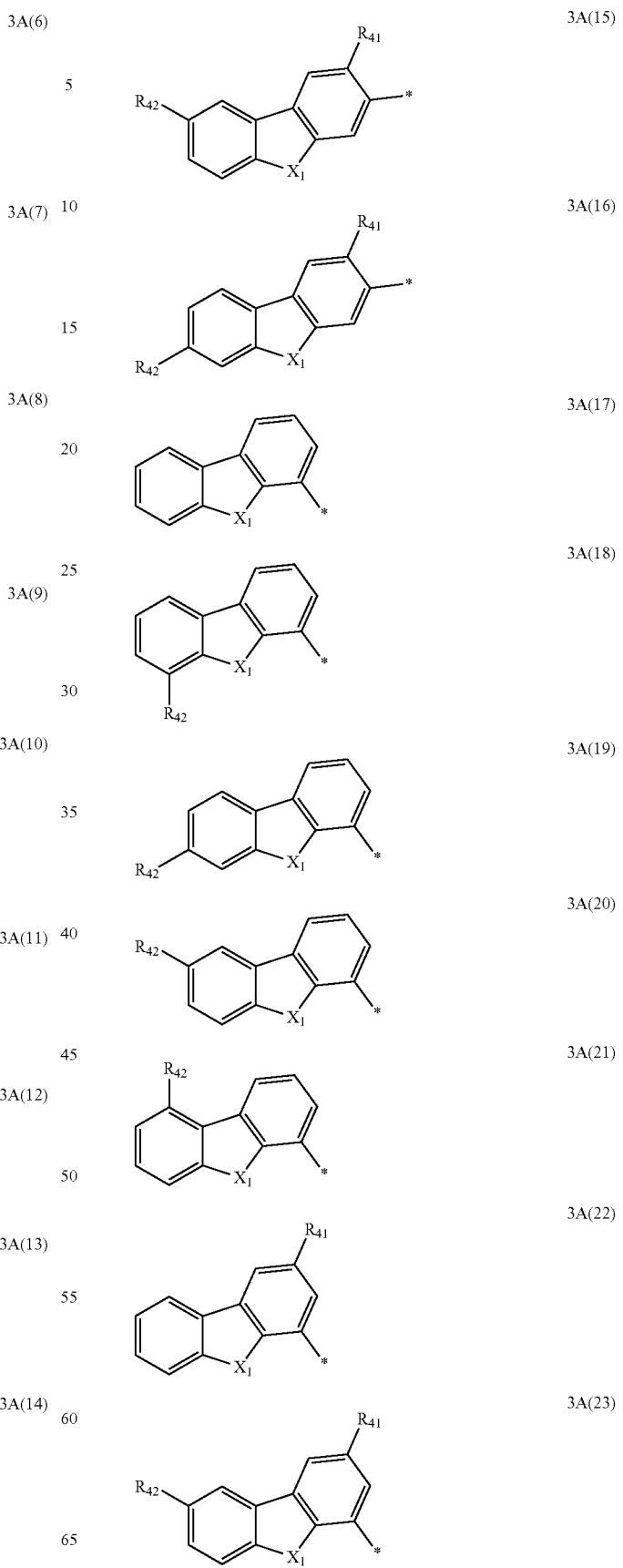

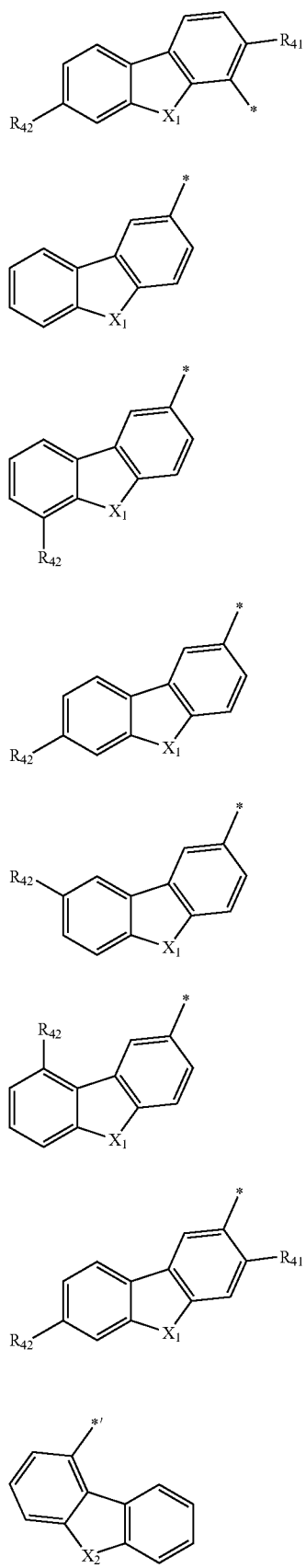
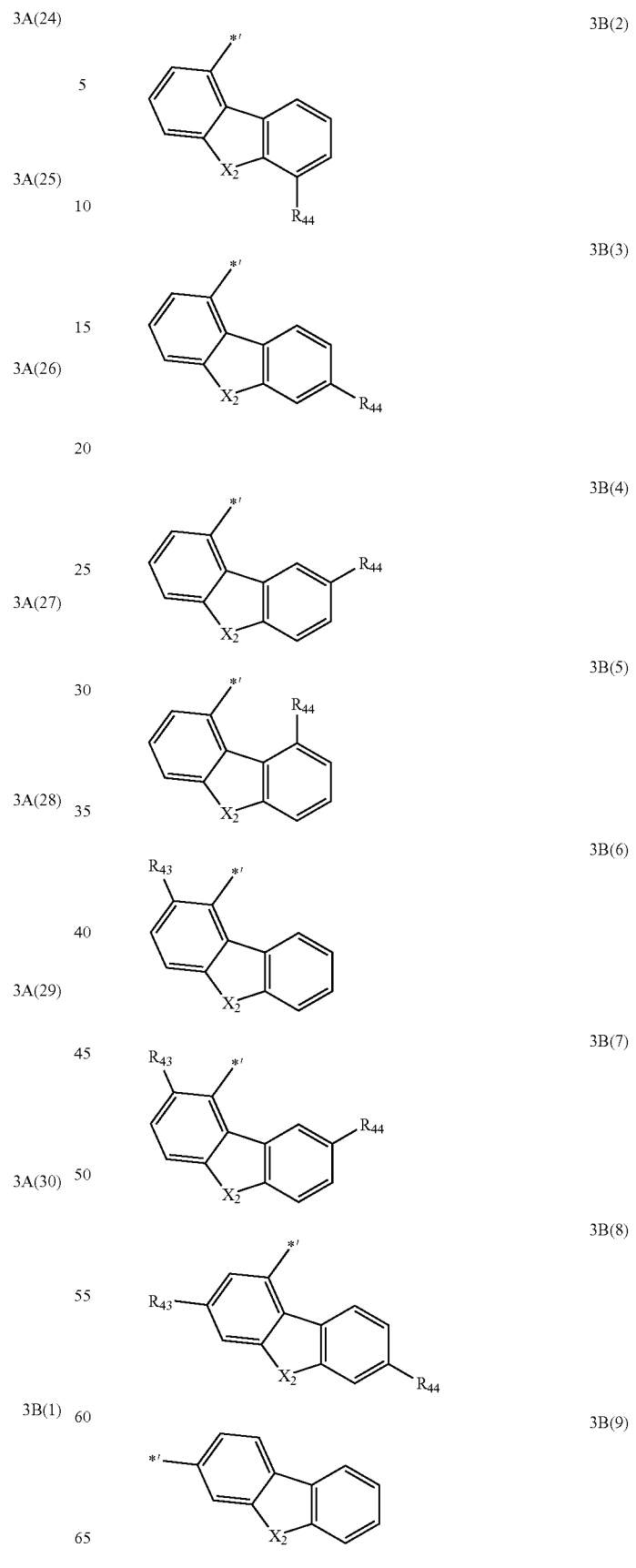

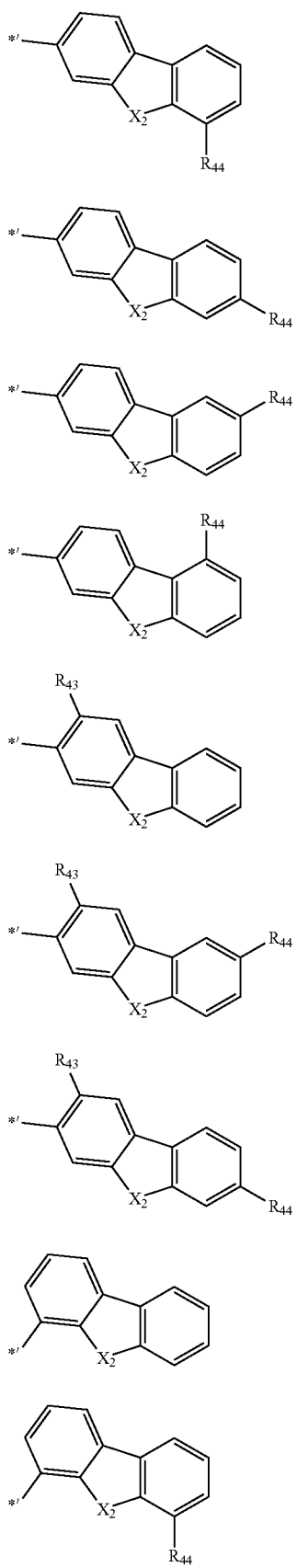
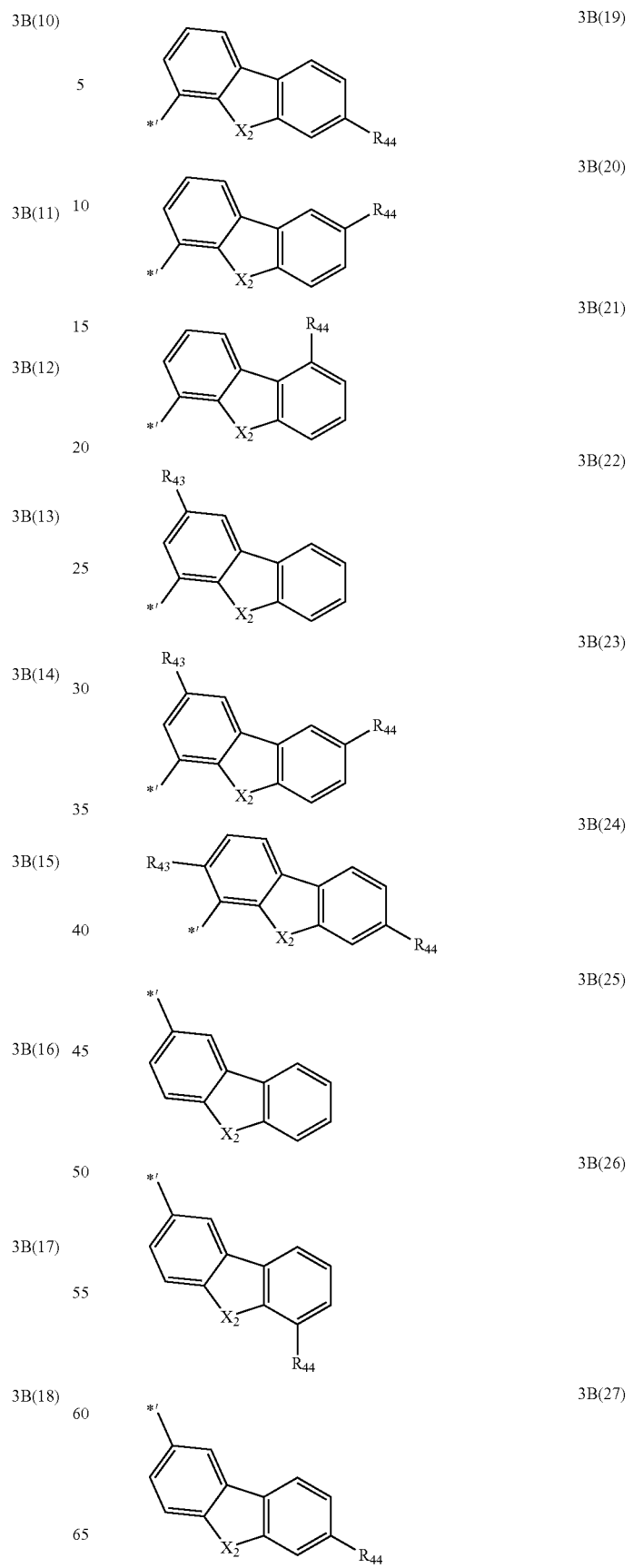

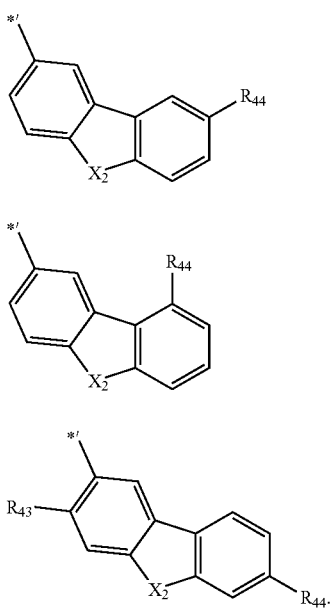
3B(28)
3B(29)
3B(30)
In Formulae 3A(1) to 3A(30) and 3B(1) to 36(30), $R_{41}$ to $R_{44}$ may each independently be the same as described herein, $R_{41}$ to $R_{44}$ may not be hydrogen, and * and *' each indicate a binding site to $L_1$ in Formula 1.
In one or more embodiments, the condensed cyclic compound may be represented by one selected from Formulae 1(1) to 1(20):
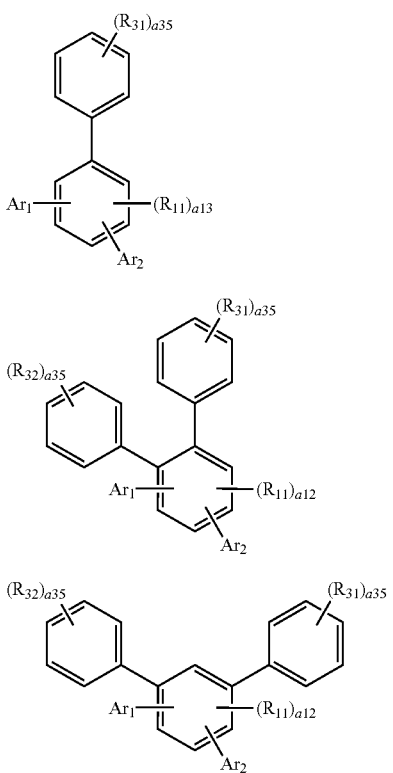
1(1)
1(2)
1(3)
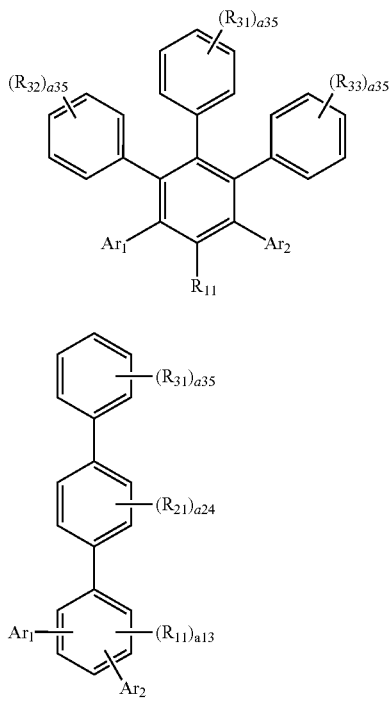
1(4)
1(5)
1(6)
1(7)
1(8)

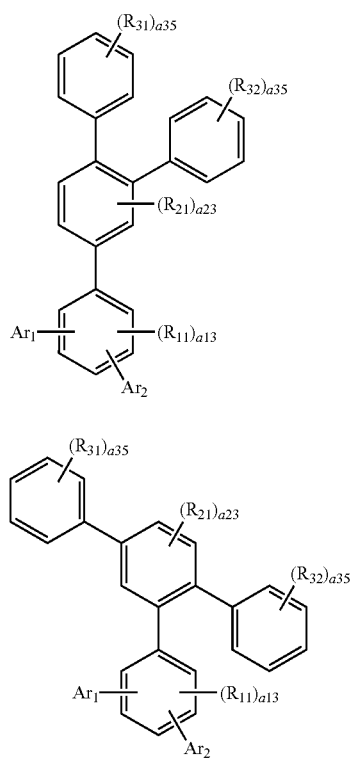
1(9)
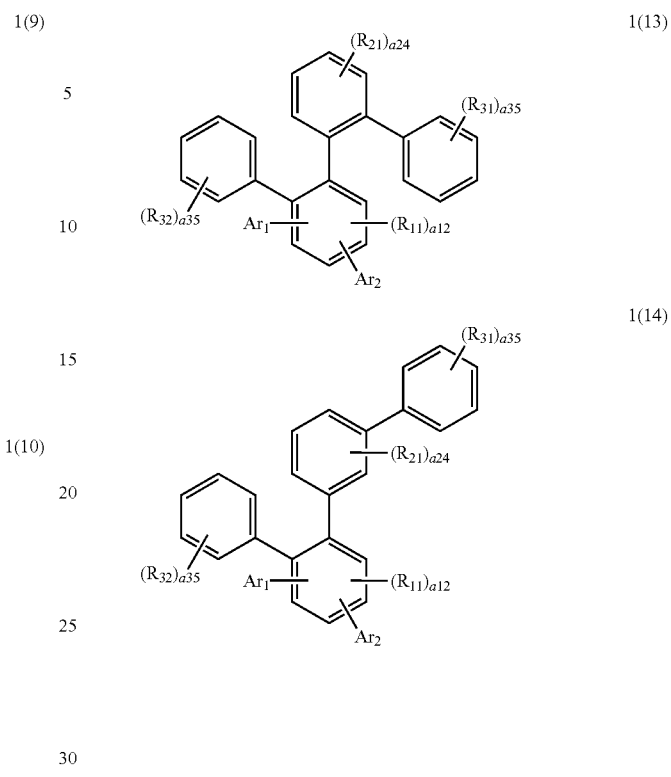
1(10)
1(11)
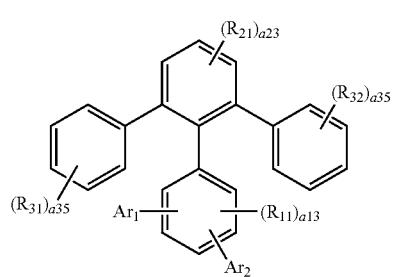
1(12)
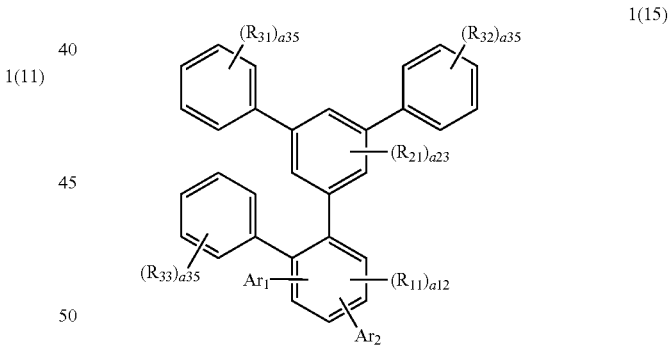
1(13)
1(14)
1(15)
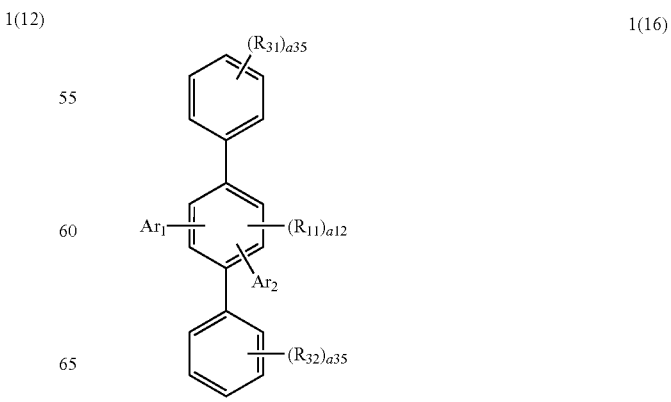
1(16)

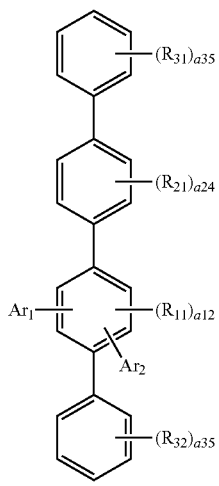

1(17)

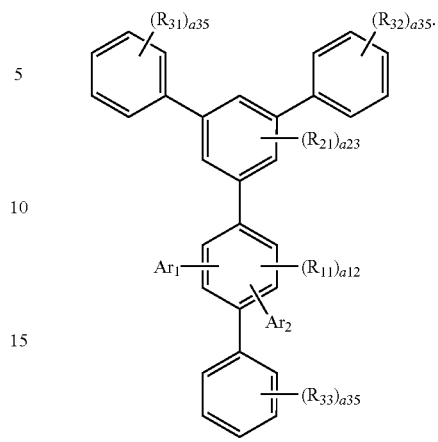

1(18)

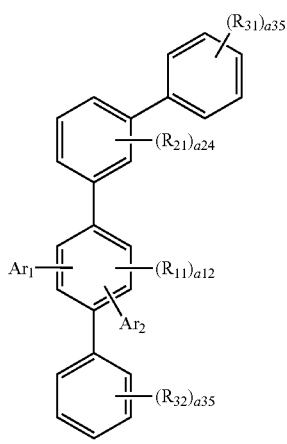

1(19)

1(20)

In Formulae 1(1) to 1(20),

Ar₁ and Ar₂ may each independently be the same as described herein, $R_{11}$ may be the same as described in connection with $R_1$, a12 may be an integer from 0 to 2, and a13 may be an integer from 0 to 3, $R_{21}$ may be the same as described in connection with $R_2$, a23 may be an integer from 0 to 3, and a24 may be an integer from 0 to 4, and $R_{31}$ to $R_{33}$ may each independently be the same as described in connection with $R_3$, and a35 may be an integer from 0 to 5.

For example, i) at least one selected from $R_{11}$ and $R_{31}$ in Formula 1(1), ii) at least one selected from $R_{11}$, $R_{31}$, and $R_{32}$ in Formulae 1(2), 1(3), and 1(16), iii) at least one selected from $R_{11}$ and $R_{31}$ to $R_{33}$ in Formula 1(4), iv) at least one selected from $R_{11}$, $R_{21}$, and $R_{31}$ in Formulae 1(5) and 1(6), v) at least one selected from $R_{11}$, $R_{21}$, $R_{31}$, and $R_{32}$ in Formulae 1(8) to 1(11), 1(13), 1(14), and 1(17) to 1(19), and vi) at least one selected from $R_{11}$, $R_{21}$, and $R_{31}$ to $R_{33}$ in Formulae 1(12), 1(15), and 1(20) may be a cyano group.

In one or more embodiments, the condensed cyclic compound represented by Formula 1 may include one to ten cyano groups, for example, one, two, three, four, five, six, seven, or eight cyano groups, but embodiments of the present disclosure are not limited thereto.

In one or more embodiments, the condensed cyclic compound may be one selected from Compounds 1 to 1920:

1

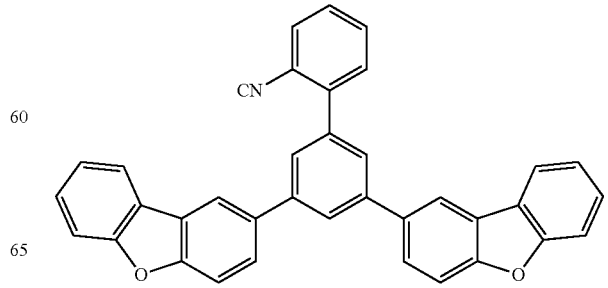

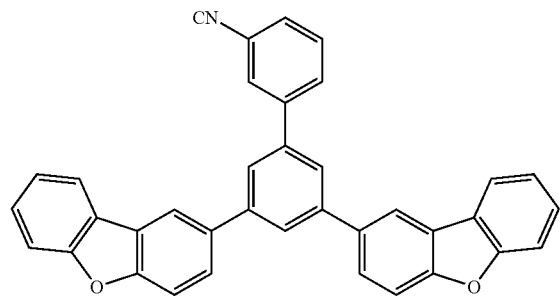
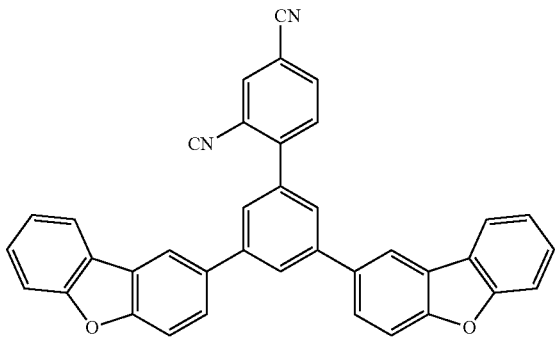
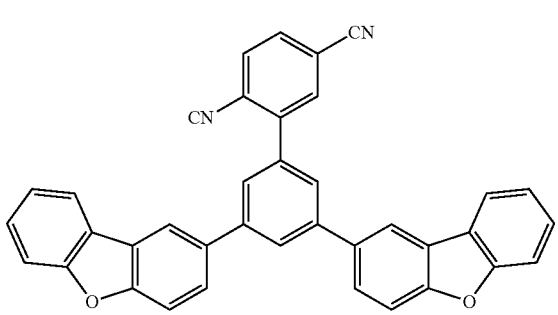
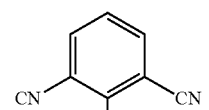
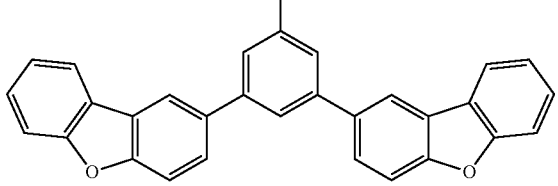
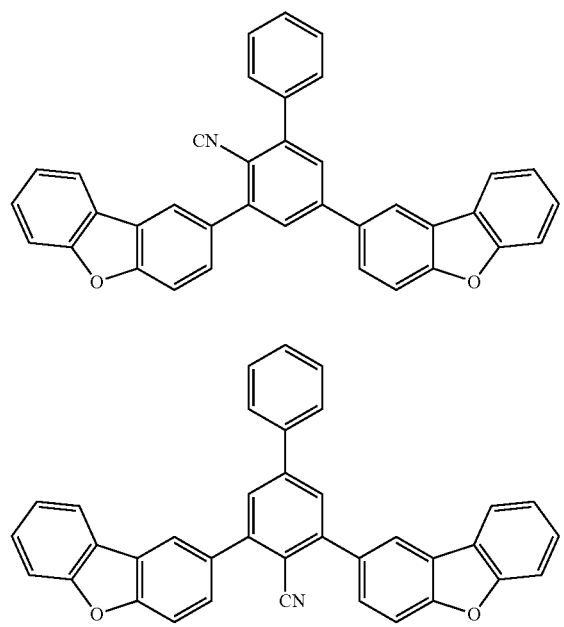
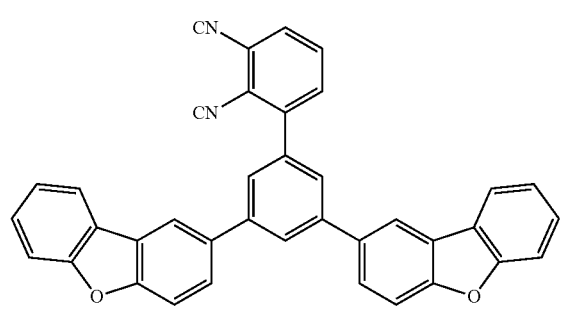
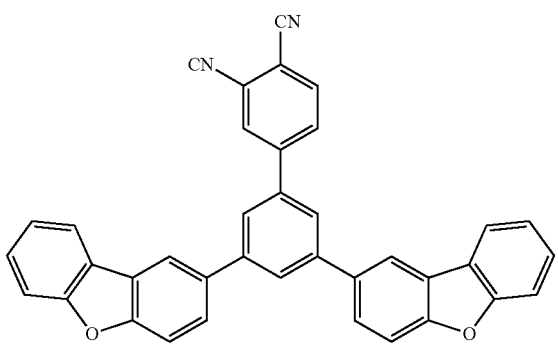

11
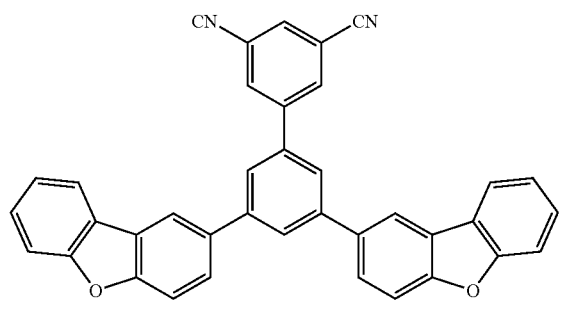
12
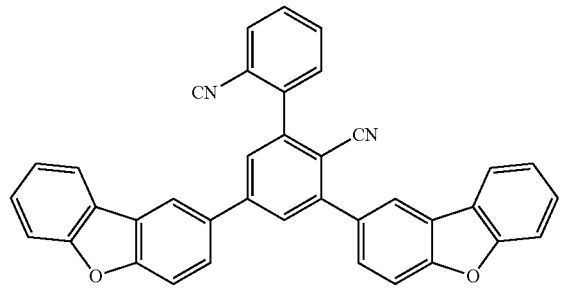
13
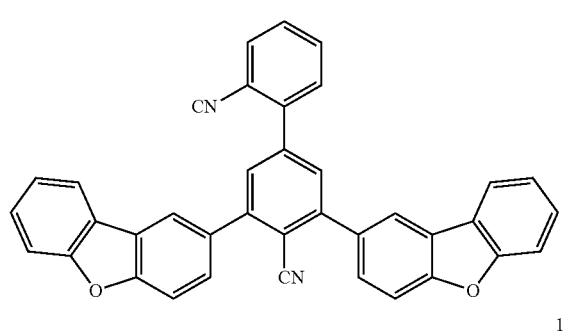
14
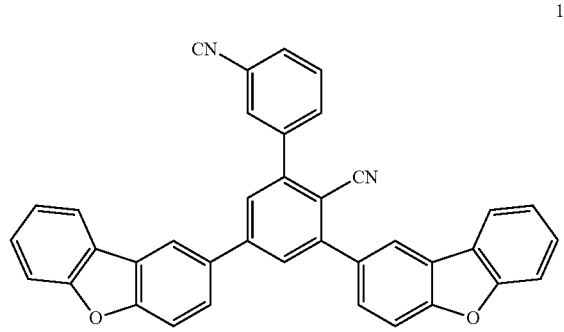
15
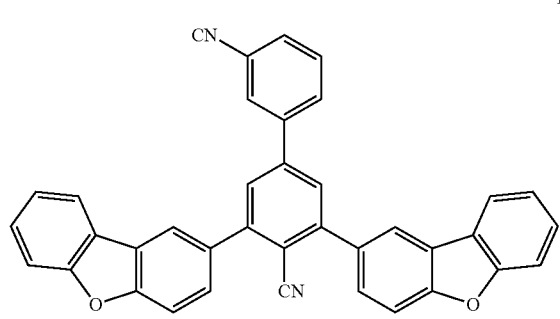
16
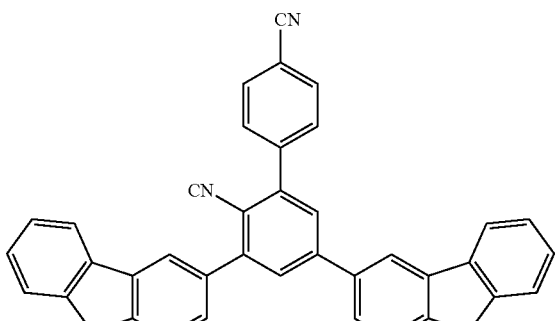
17
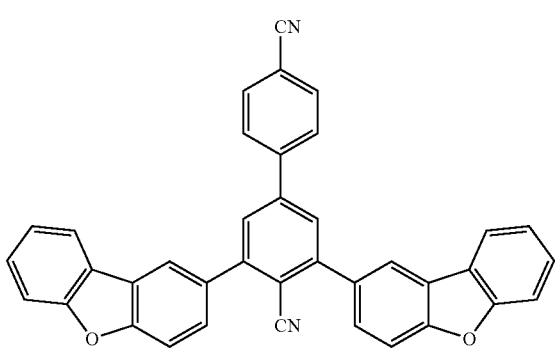
18
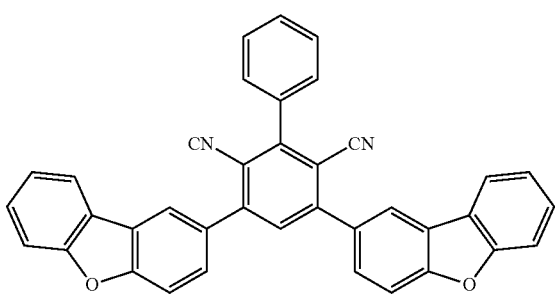
19
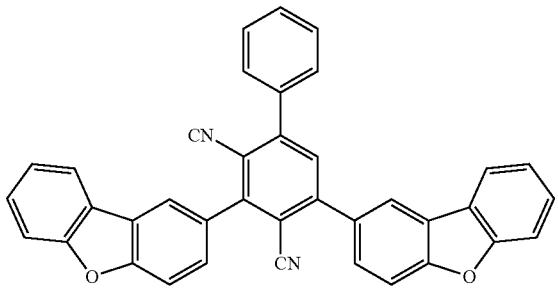

41
-continued
20
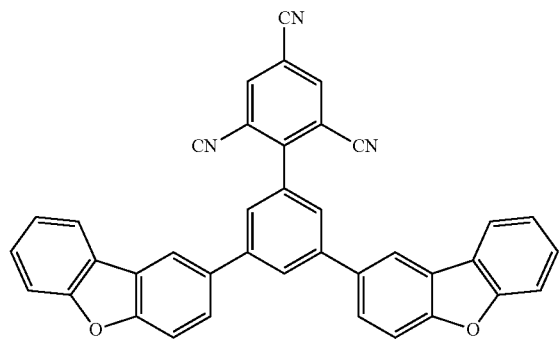
21
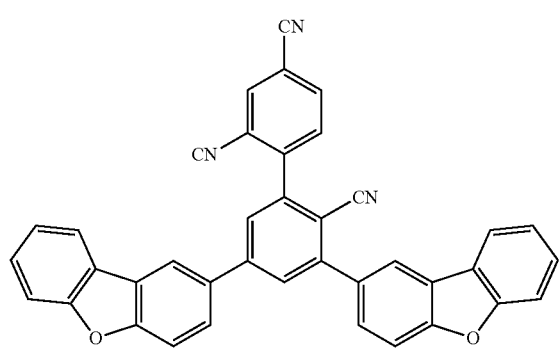
22
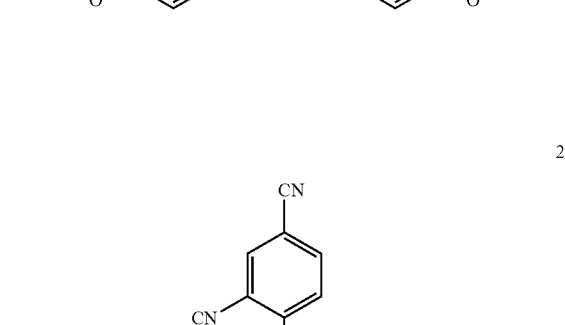
23
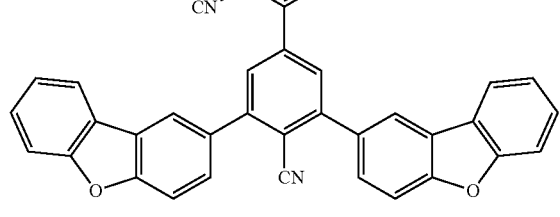
42
-continued
24
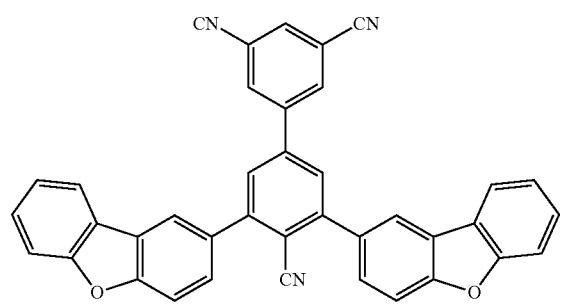
25
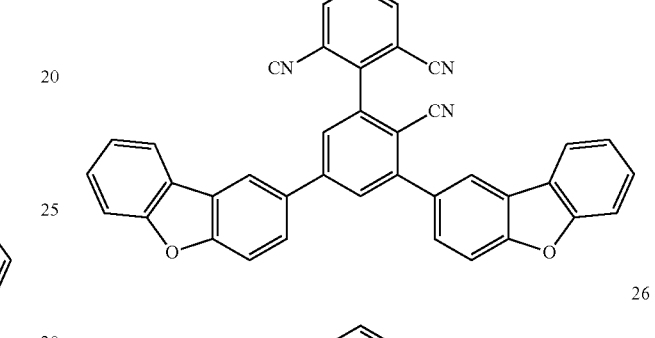
26
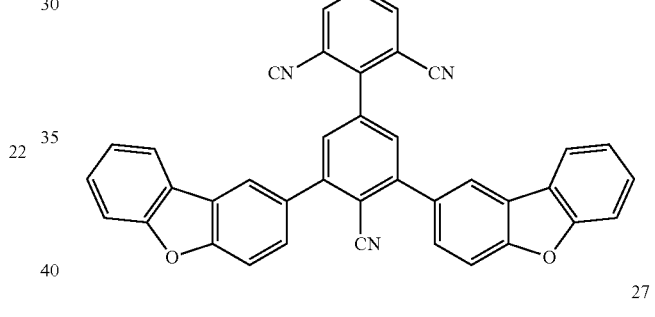
27
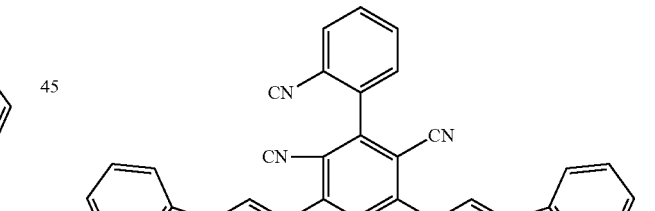
28

29
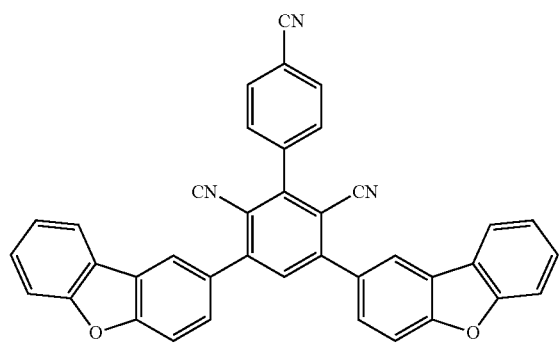
30
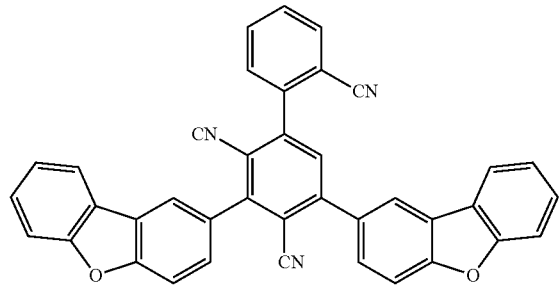
31
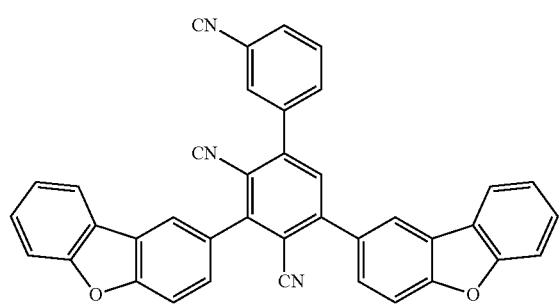
32
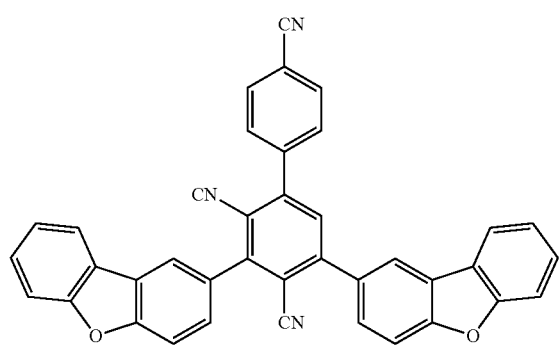
33
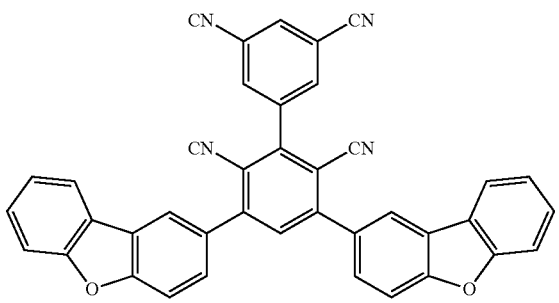
34
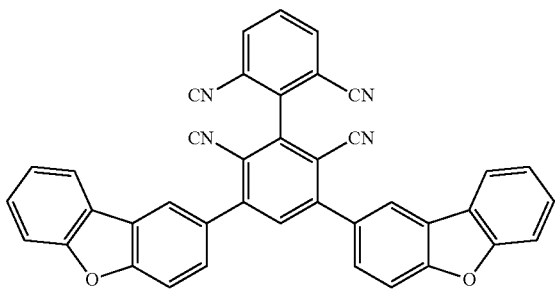
35
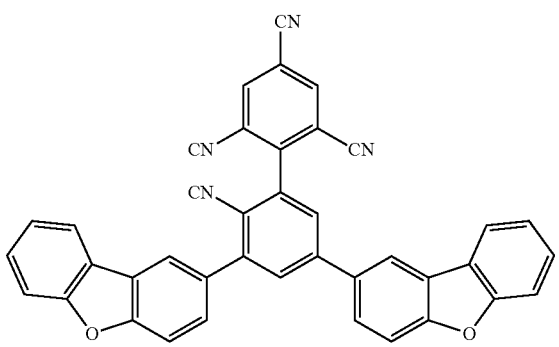
36
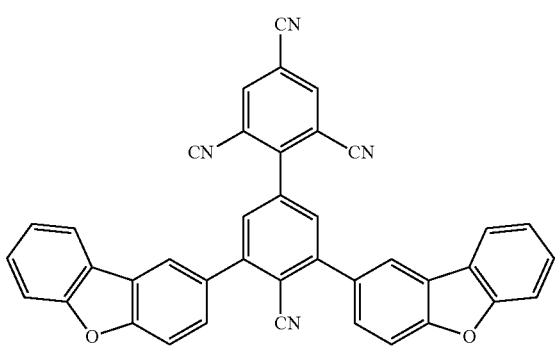

37
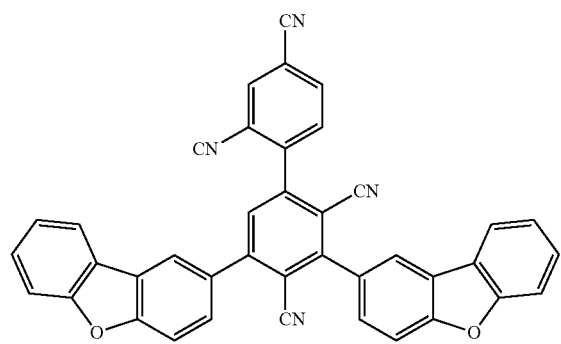
38
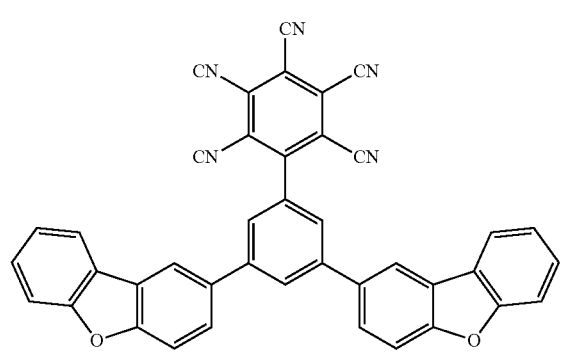
39
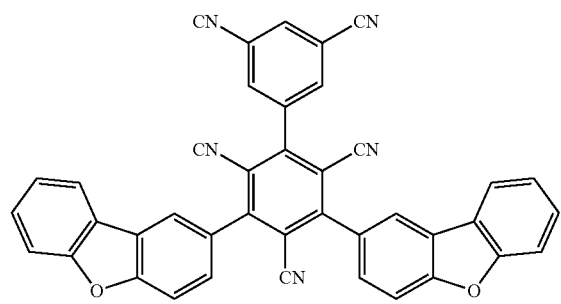
40
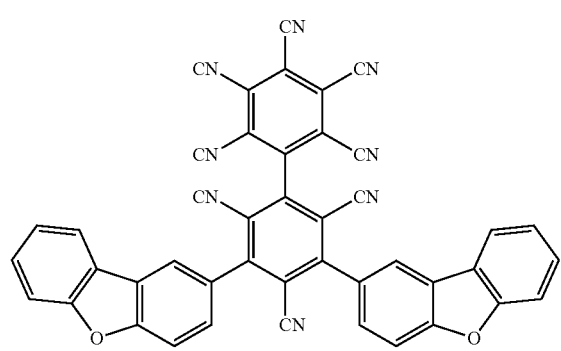
41
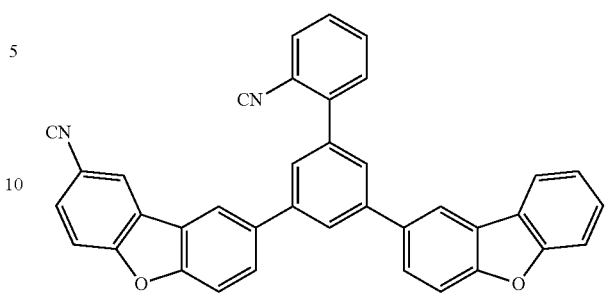
42
43
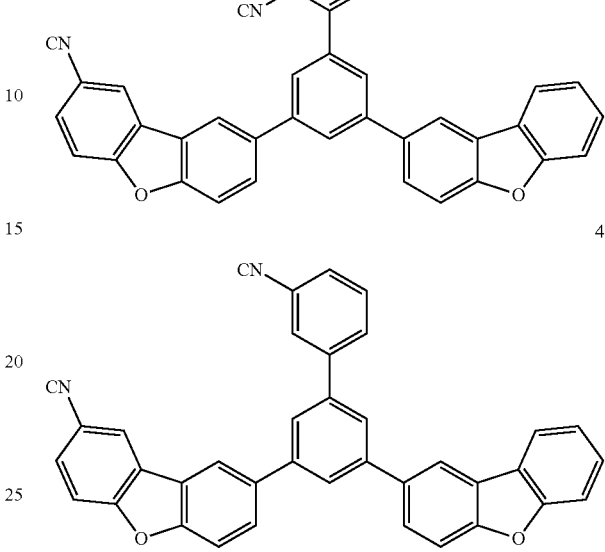
44
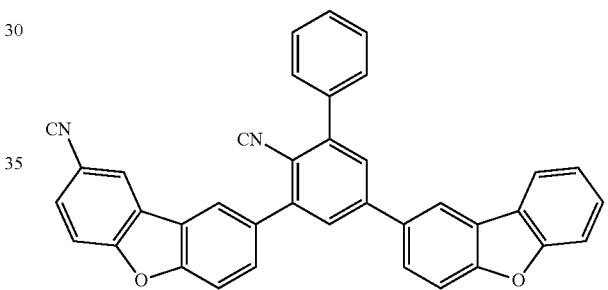
45
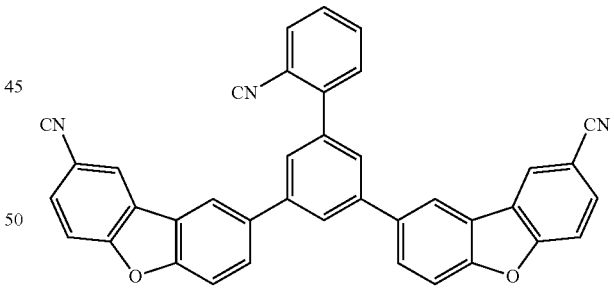
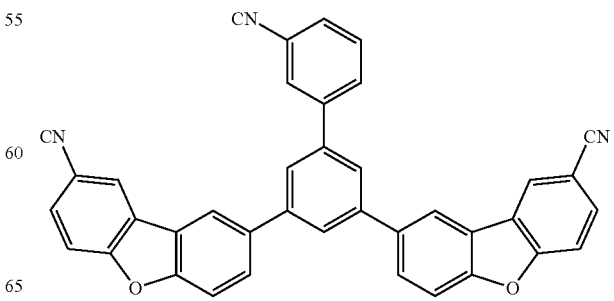

-continued
46
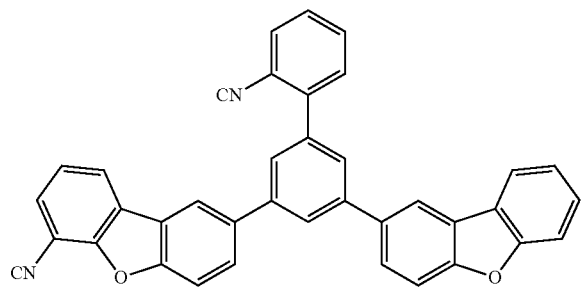
47
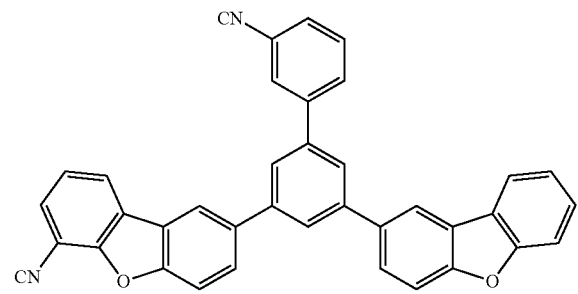
48
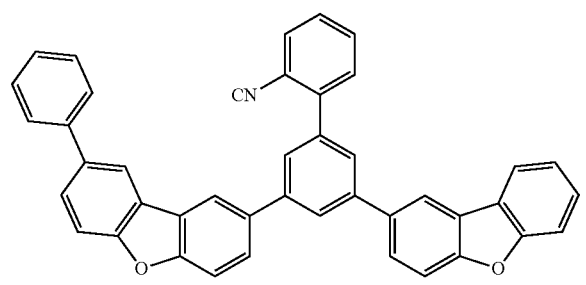
49
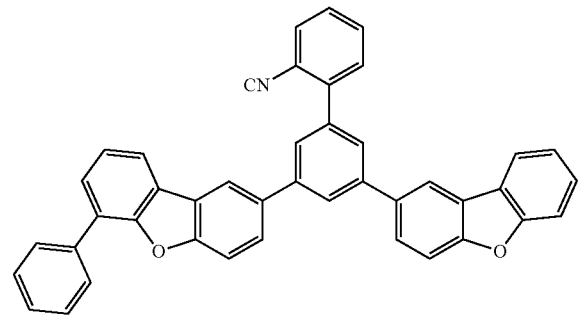
50
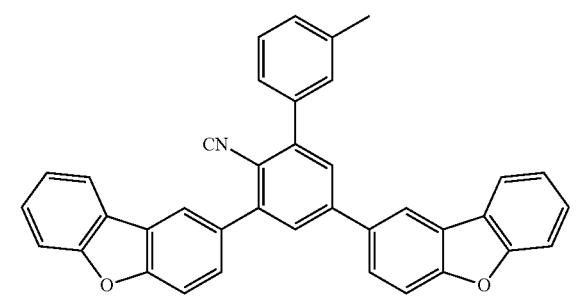
-continued
51
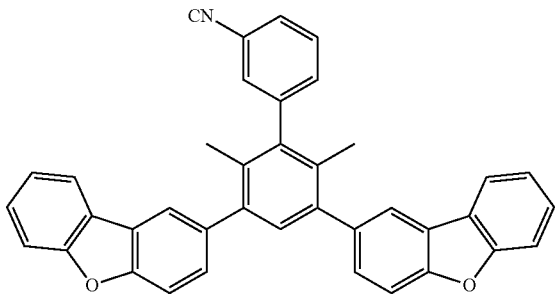
52
53
54
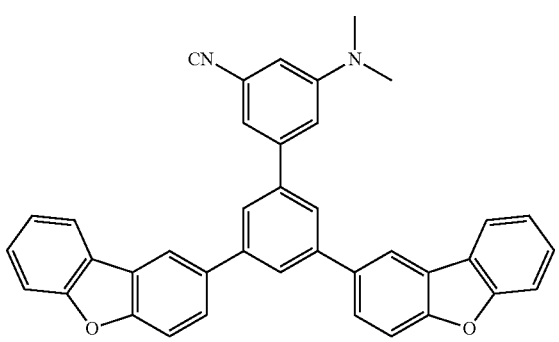

-continued
55
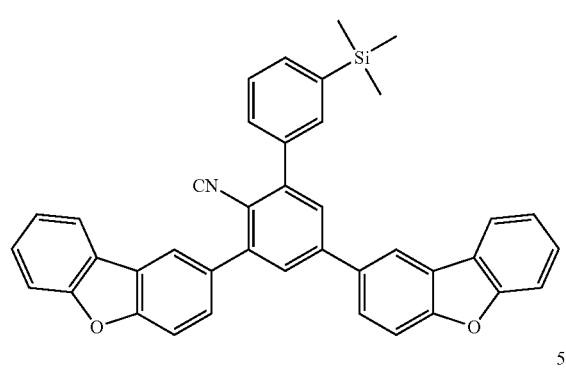
56
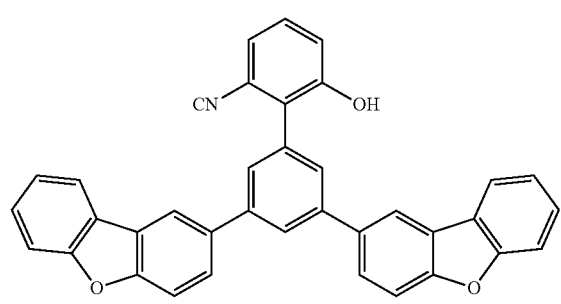
57
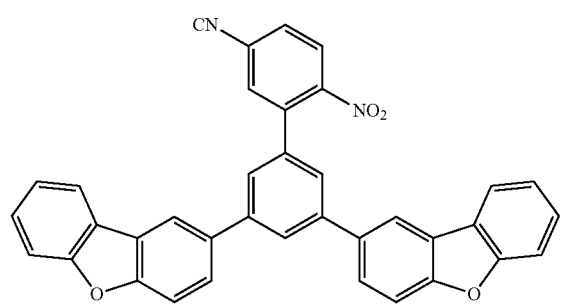
58
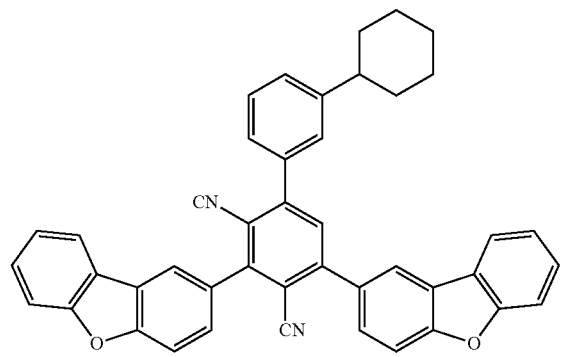
-continued
59
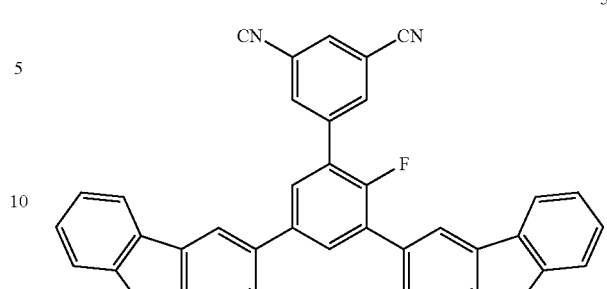
60
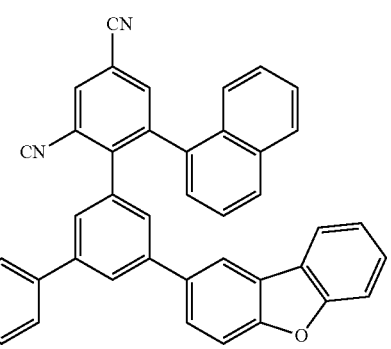
61
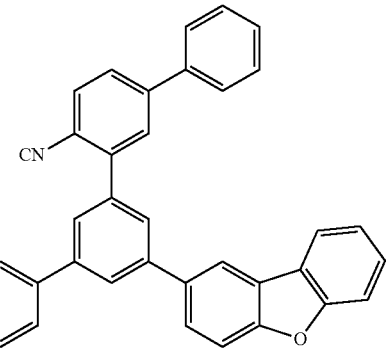
62
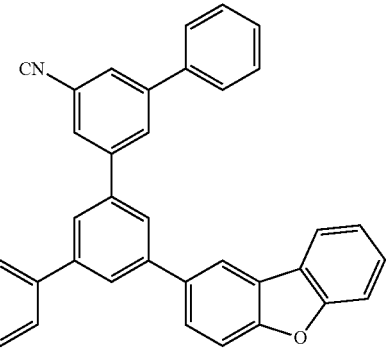

63
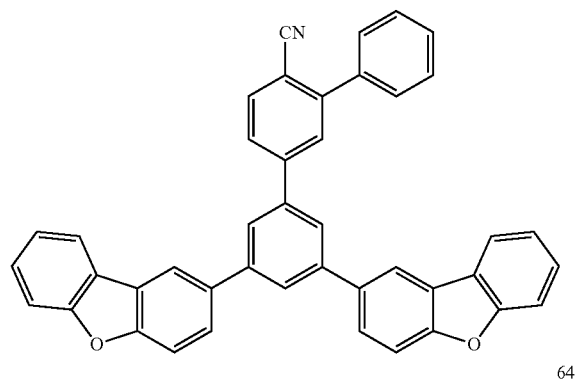
64
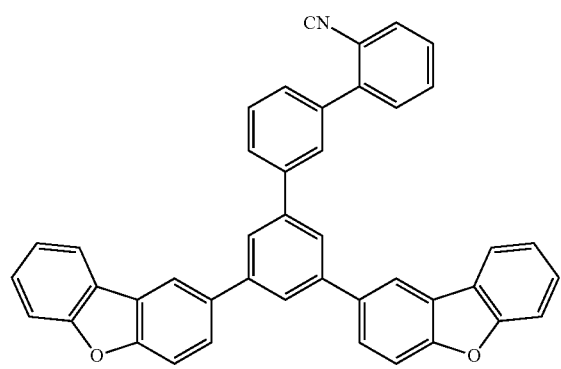
65
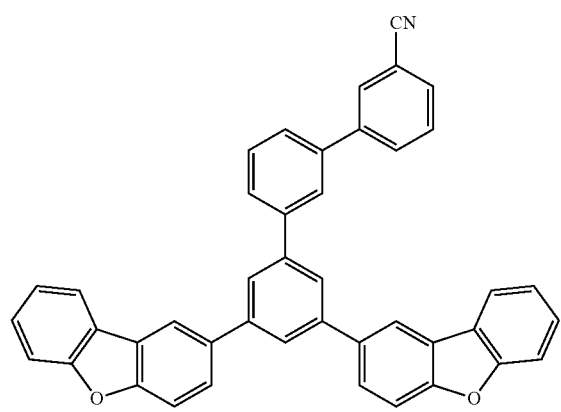
66
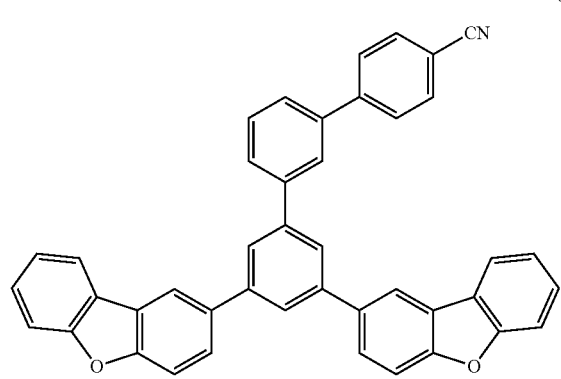
67
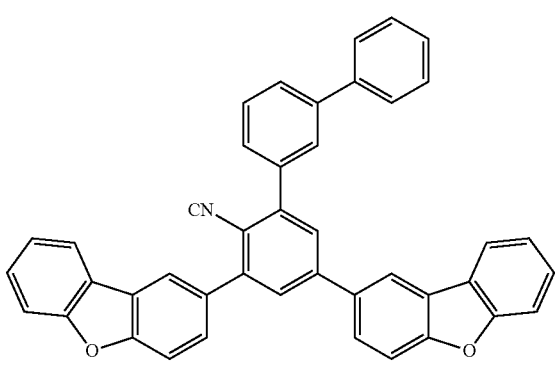
68
69
70
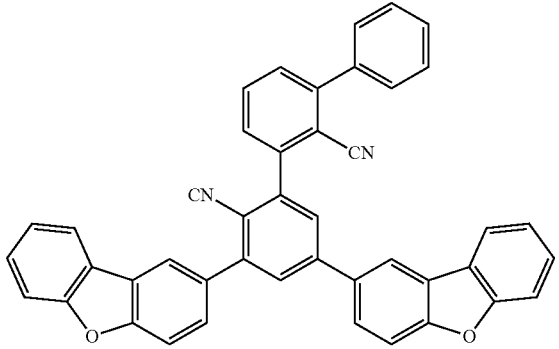

71
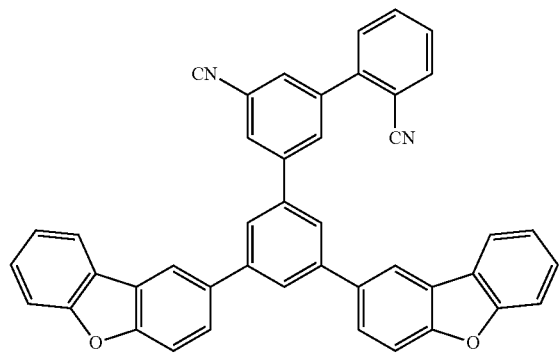
72
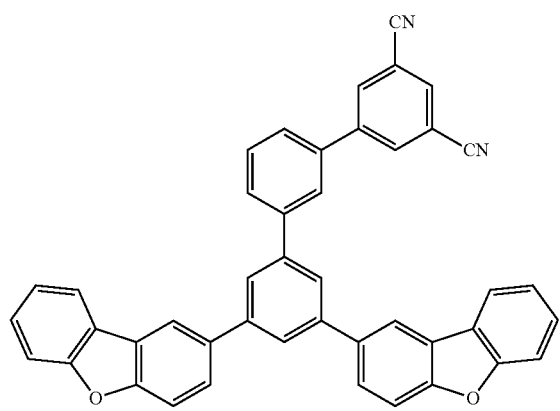
73
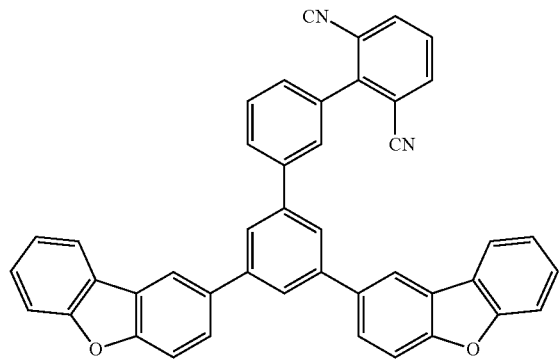
74
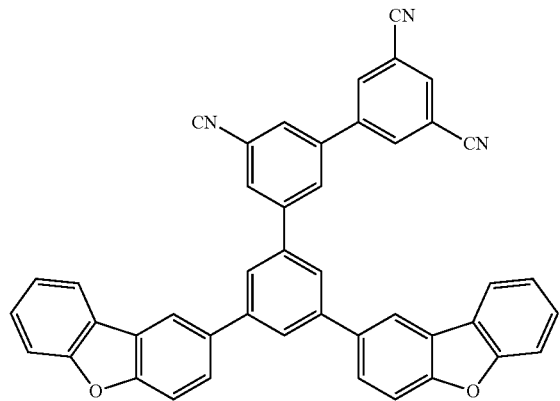
75
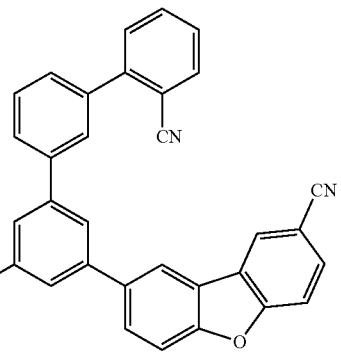
76
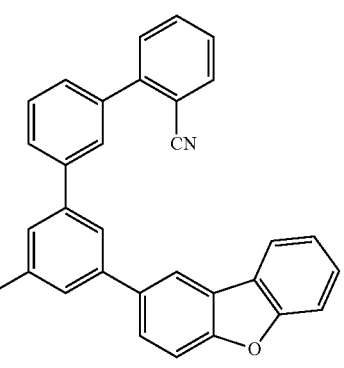
77
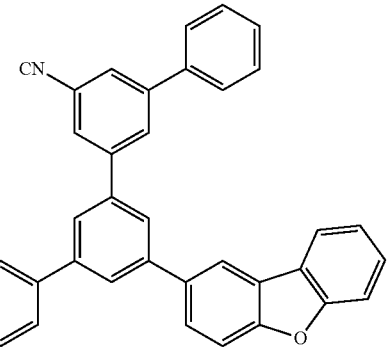
78
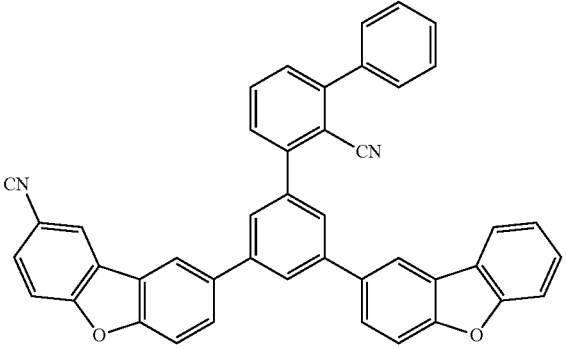

79
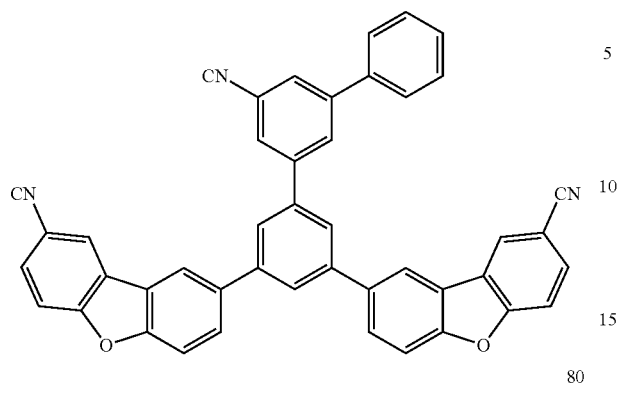
80
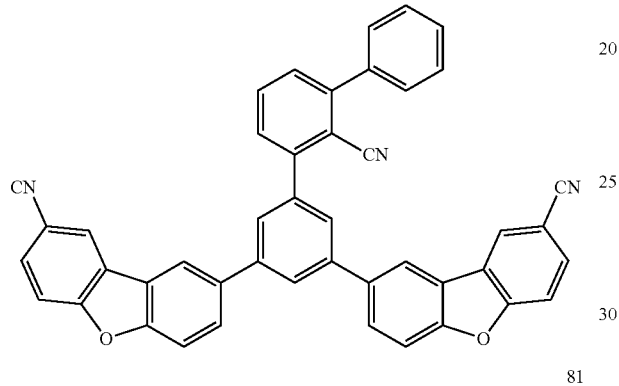
81
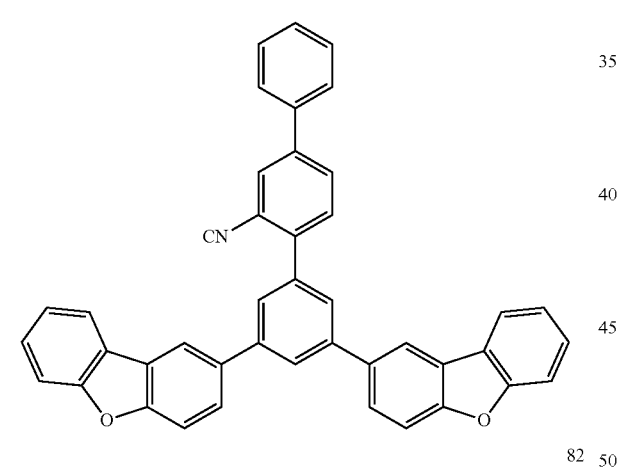
82
83
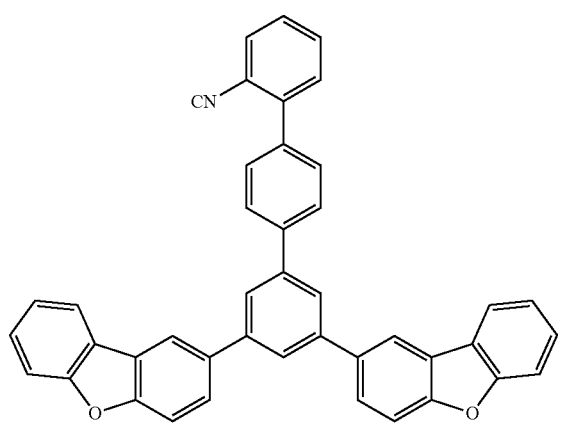
84
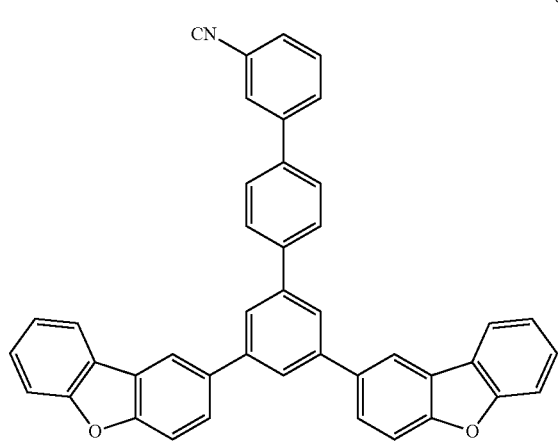
85
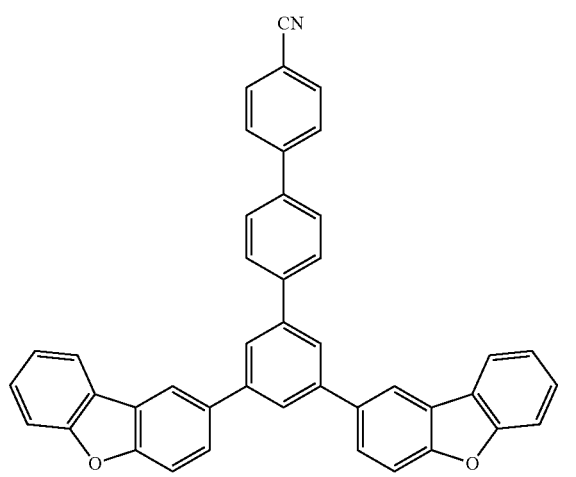

86
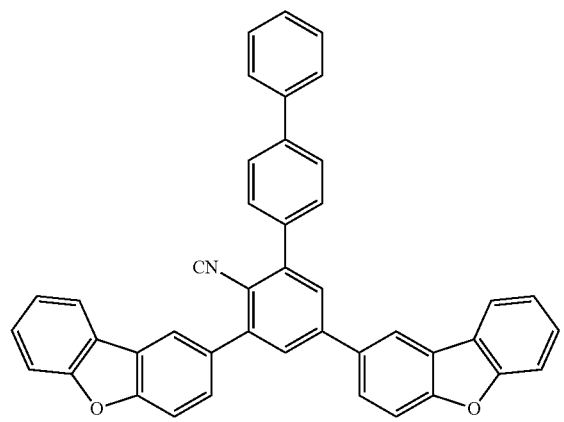
87
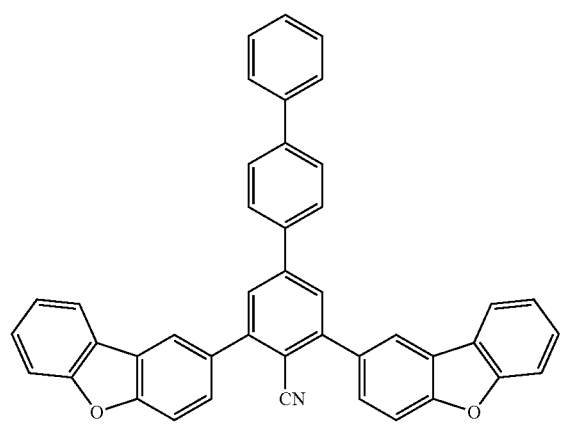
88
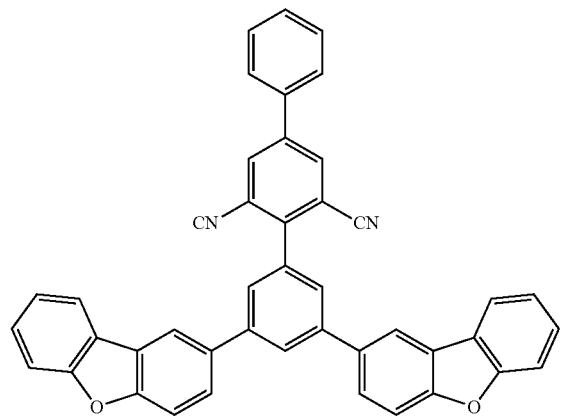
89
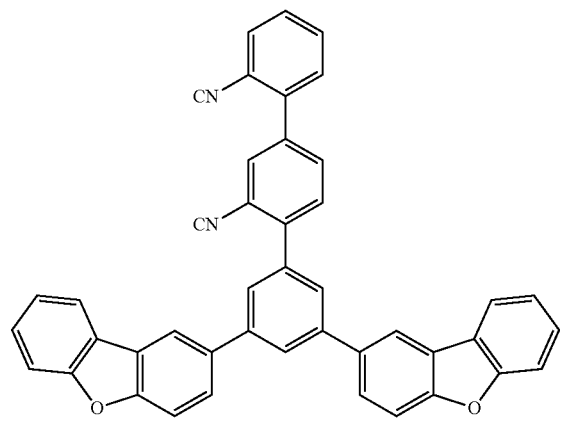
90
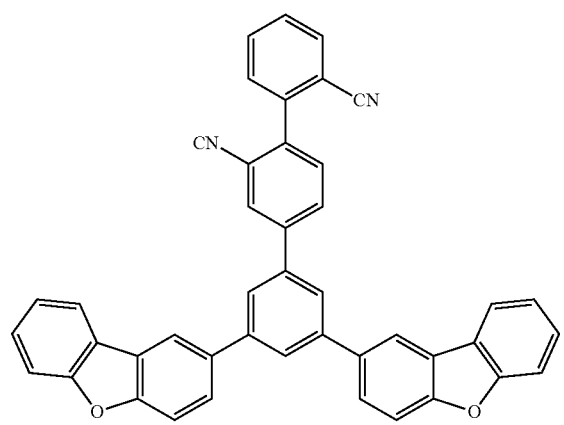
91
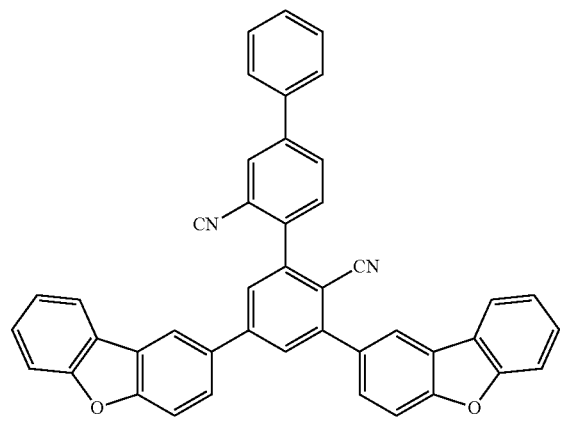

92
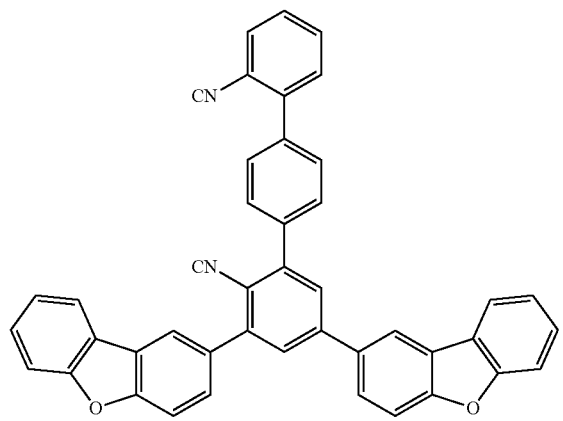
95
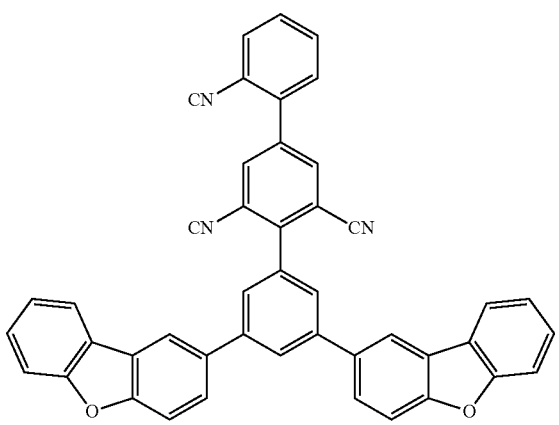
93
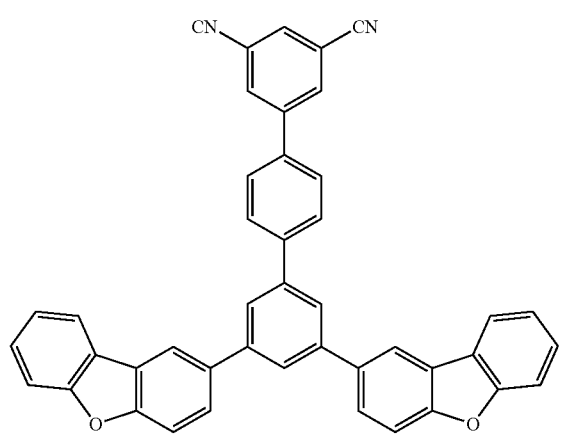
96
94
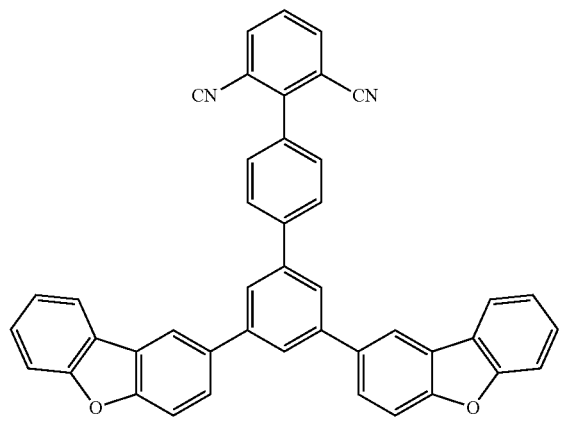
97
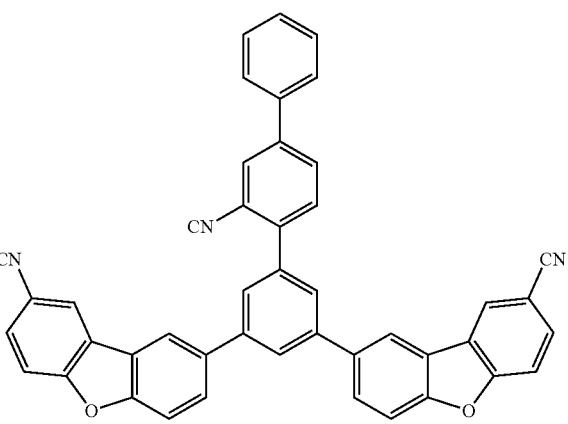

98
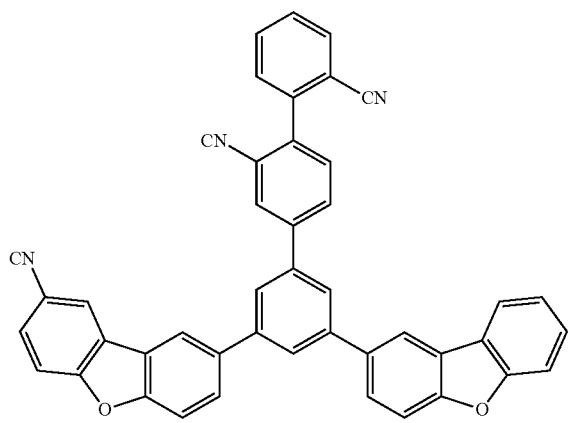
99
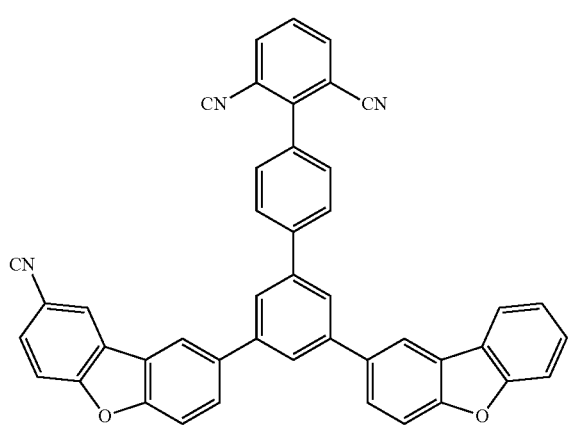
100
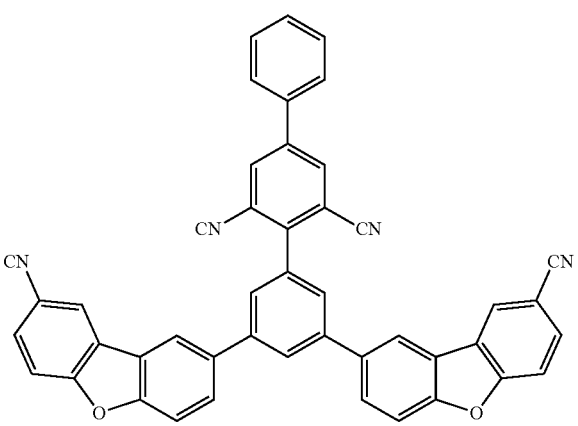
101
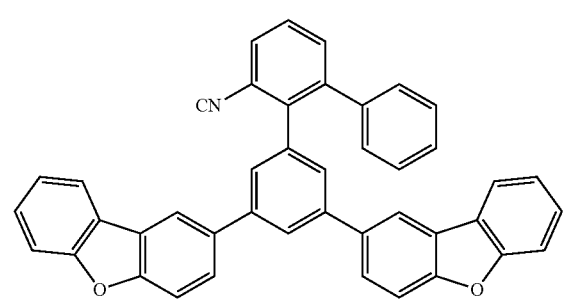
102
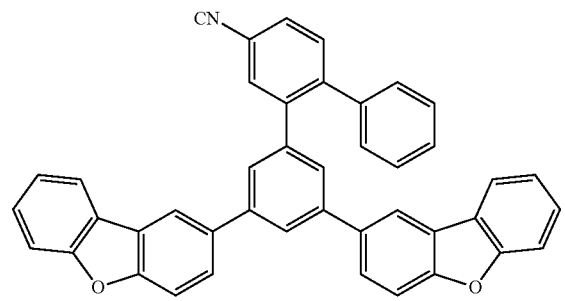
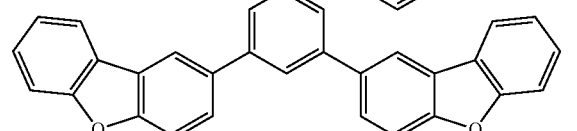
103
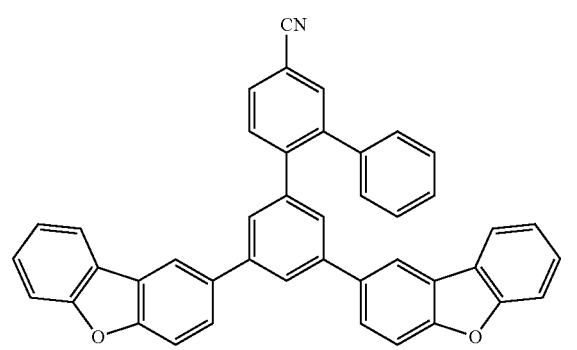
104
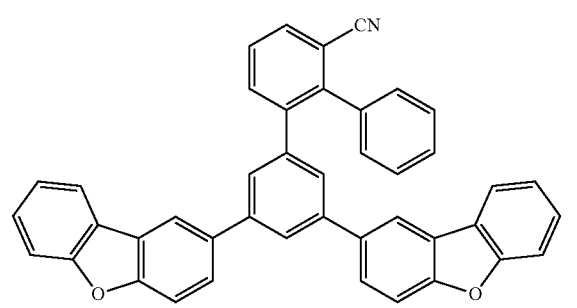
105
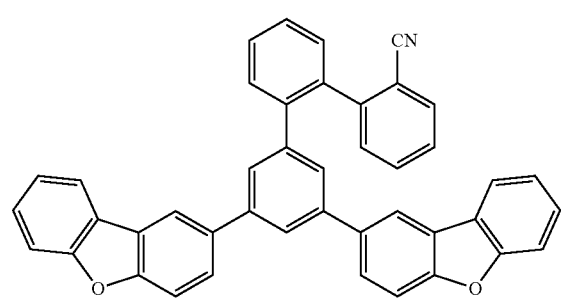
106
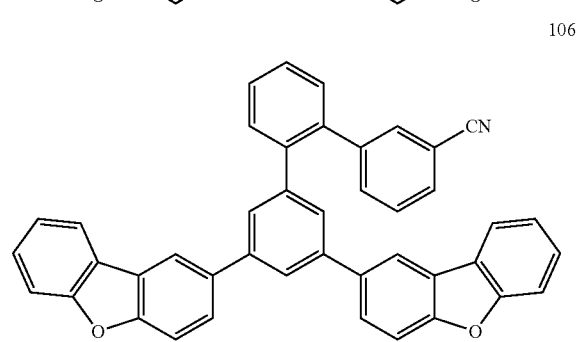

107
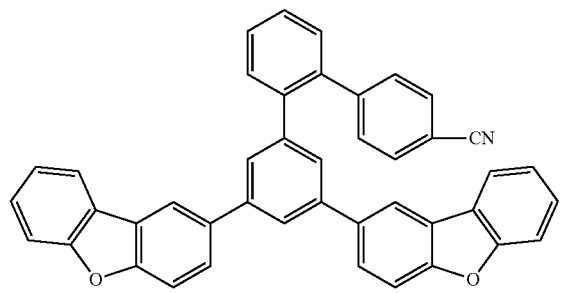
108
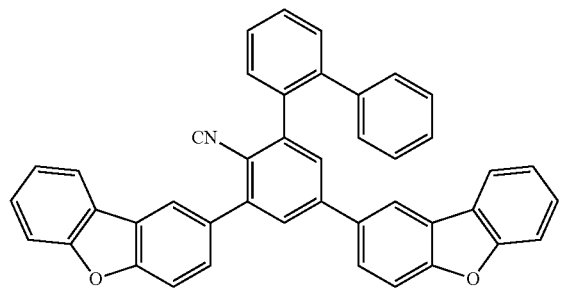
109
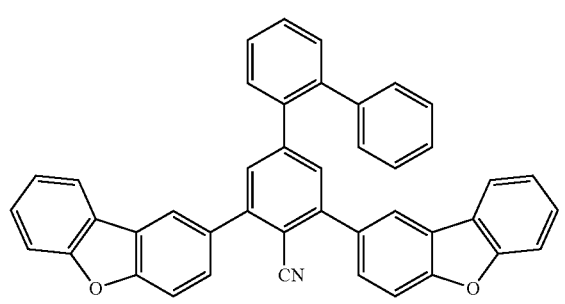
110
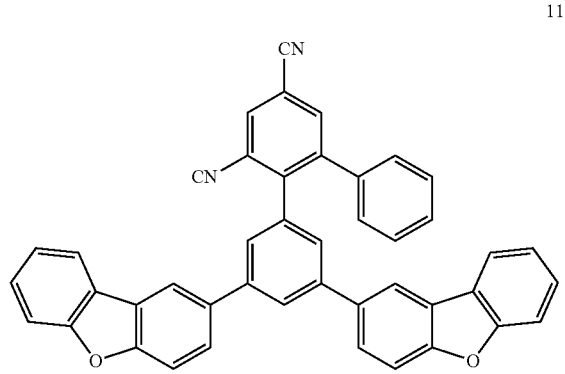
111
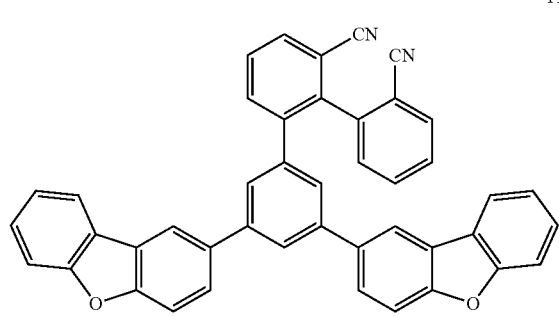
112
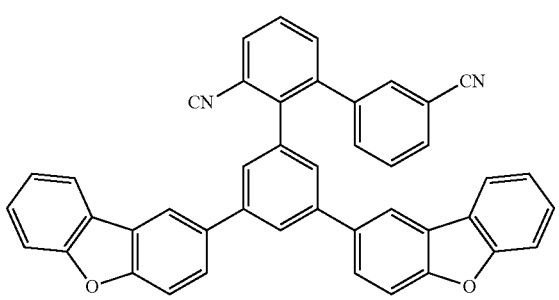
113
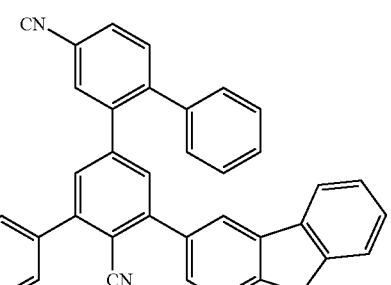
114
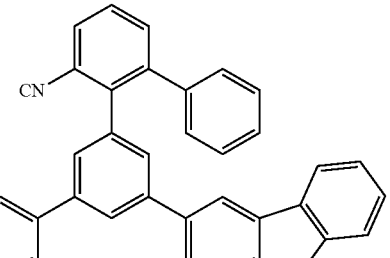
115
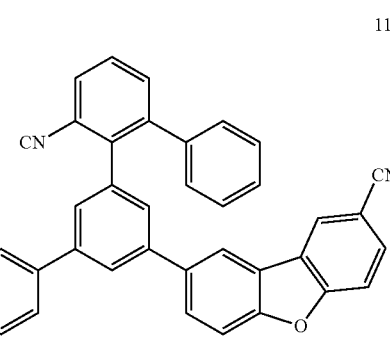
116
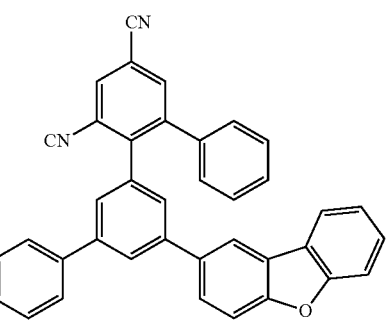

117
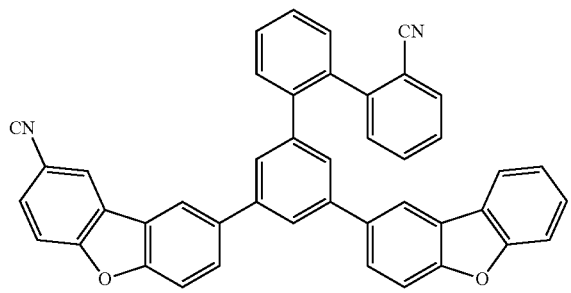
118
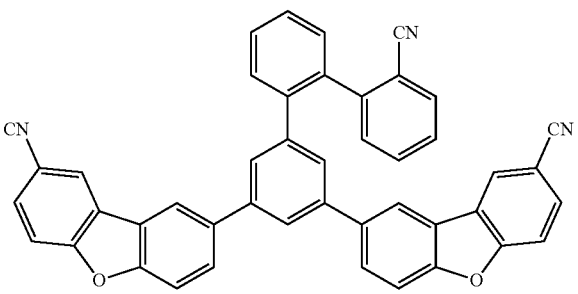
119
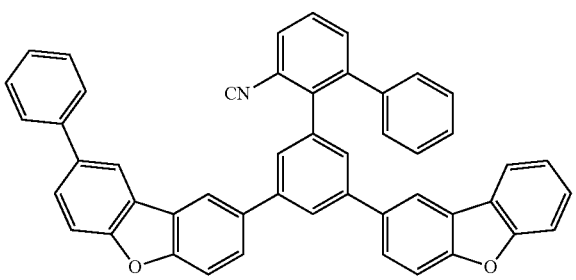
120
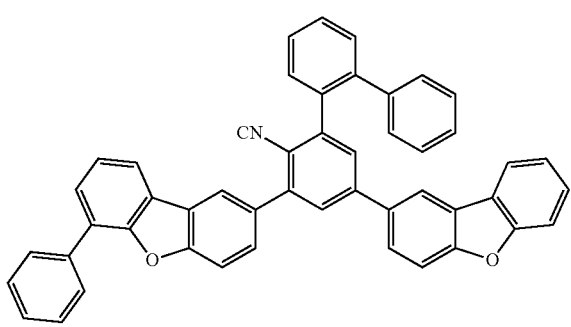
121
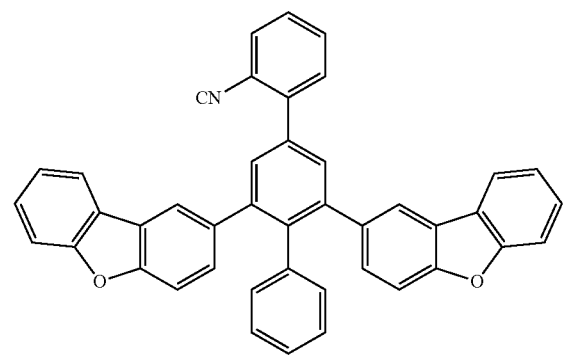
122
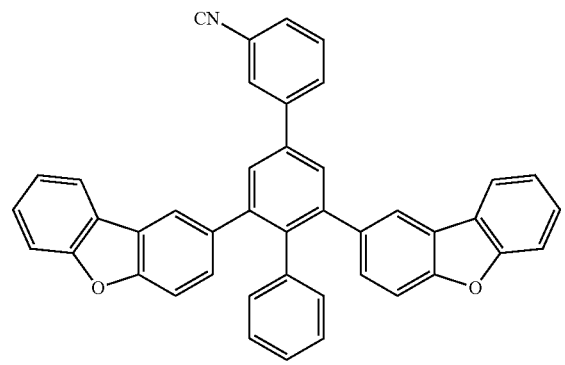
123
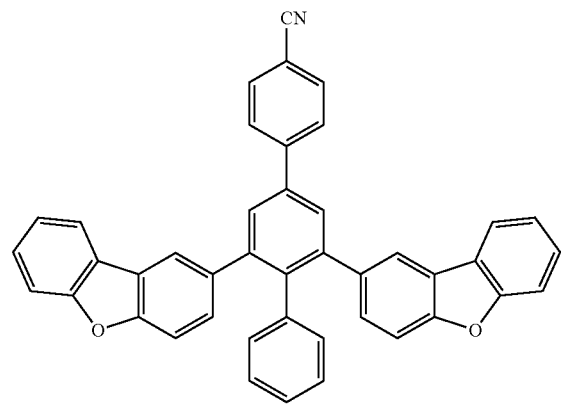
124
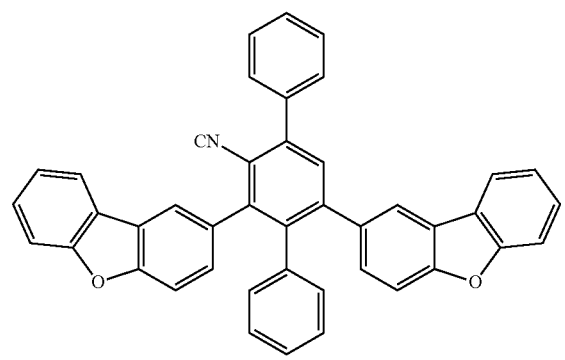
125
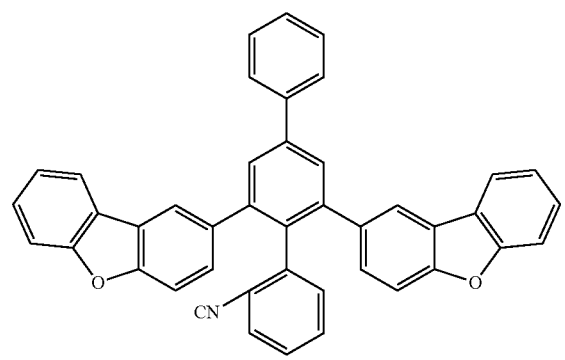

126
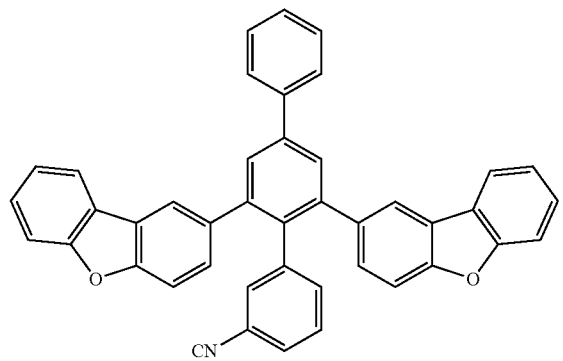
127
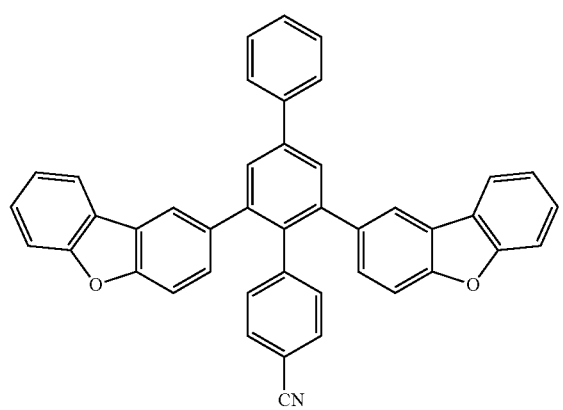
128
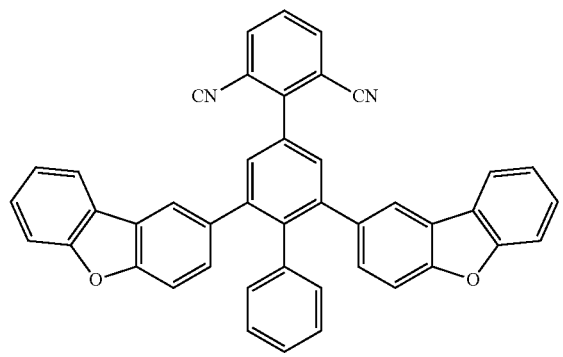
129
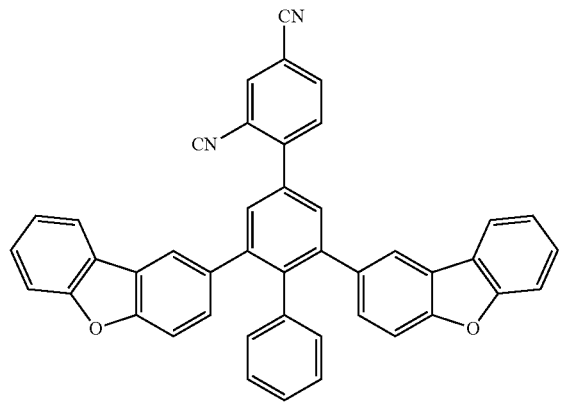
130
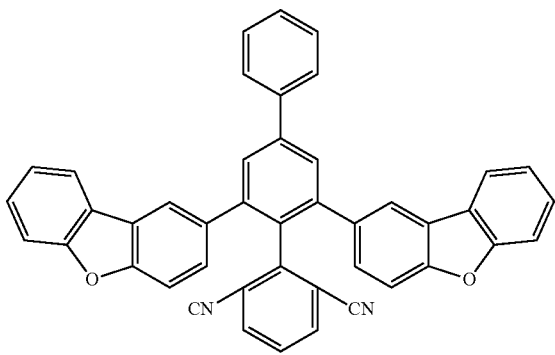
131
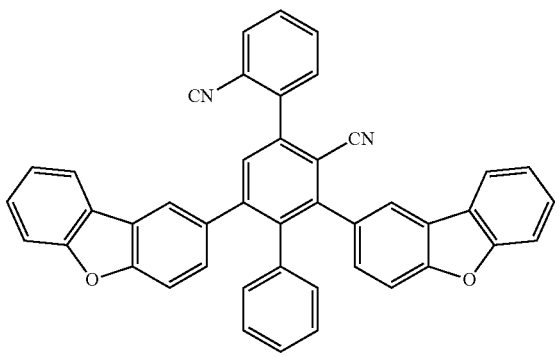
132
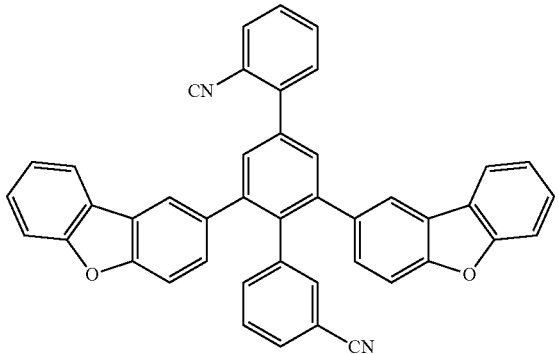
133
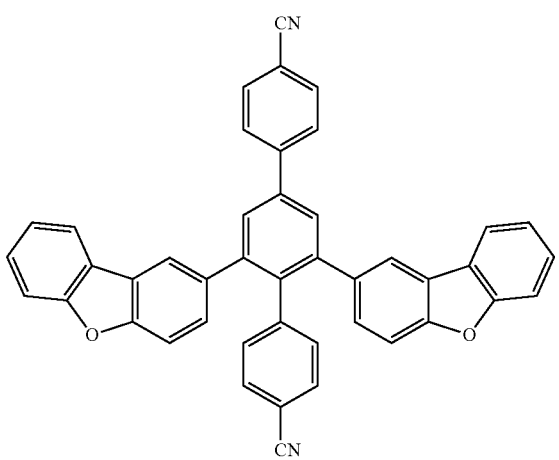

134
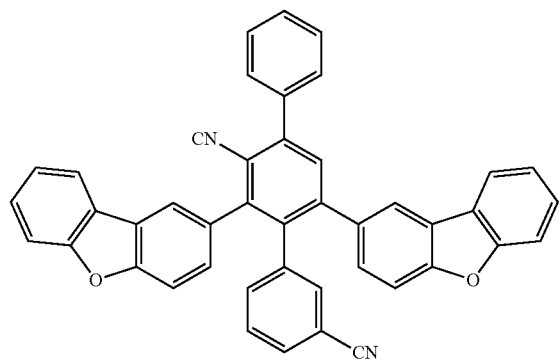
135
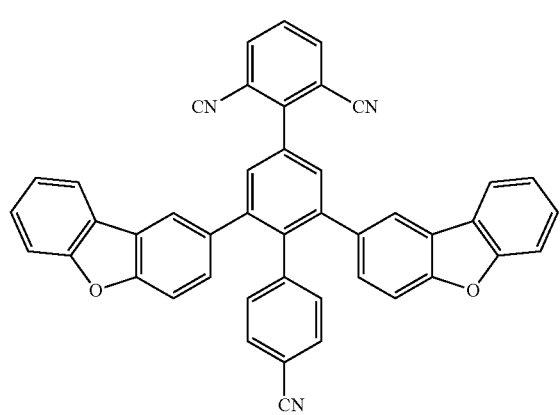
136
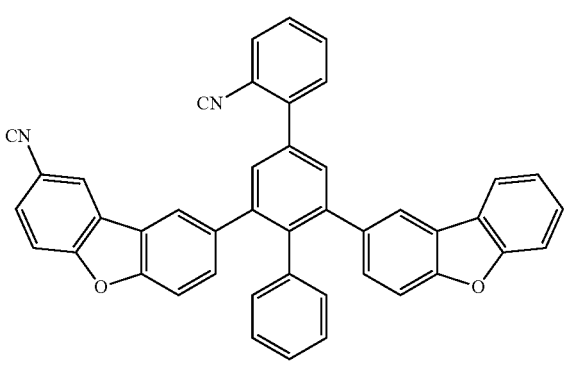
137
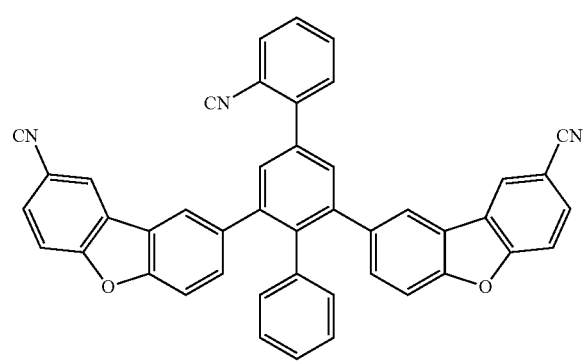
138
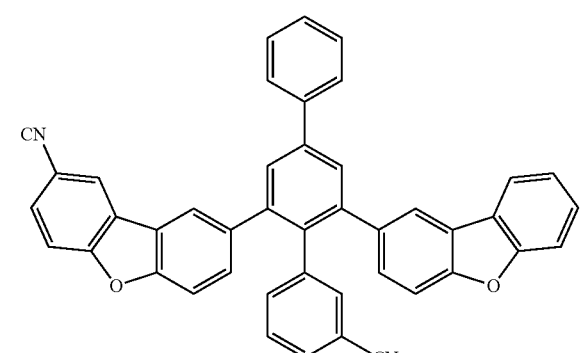
139
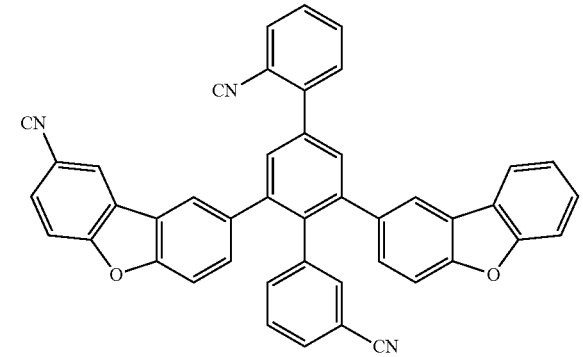
140
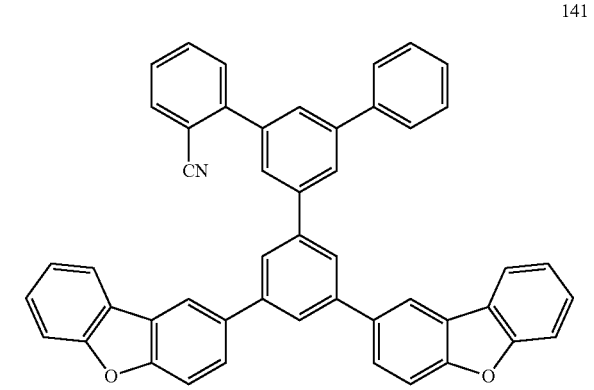
141

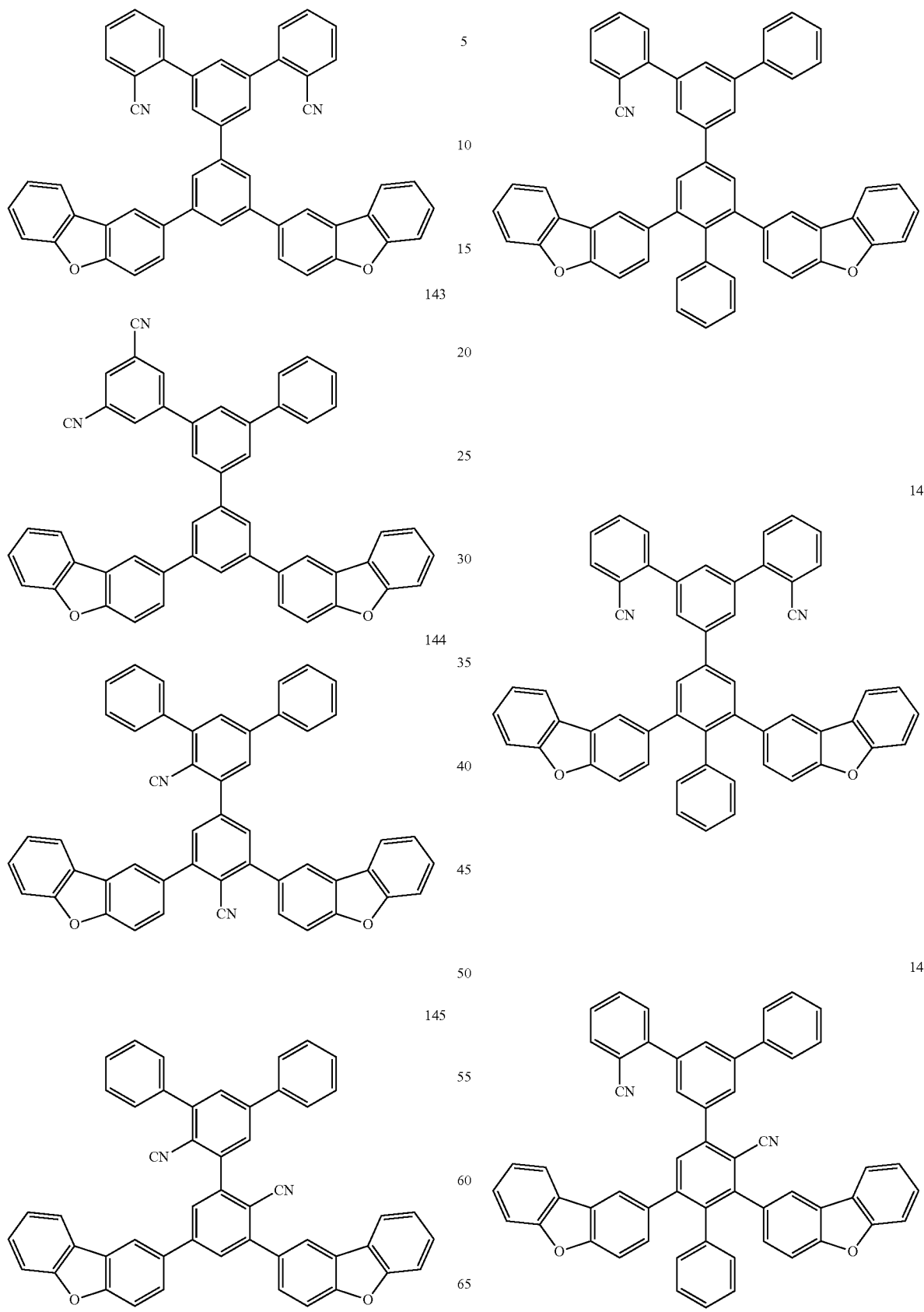

-continued
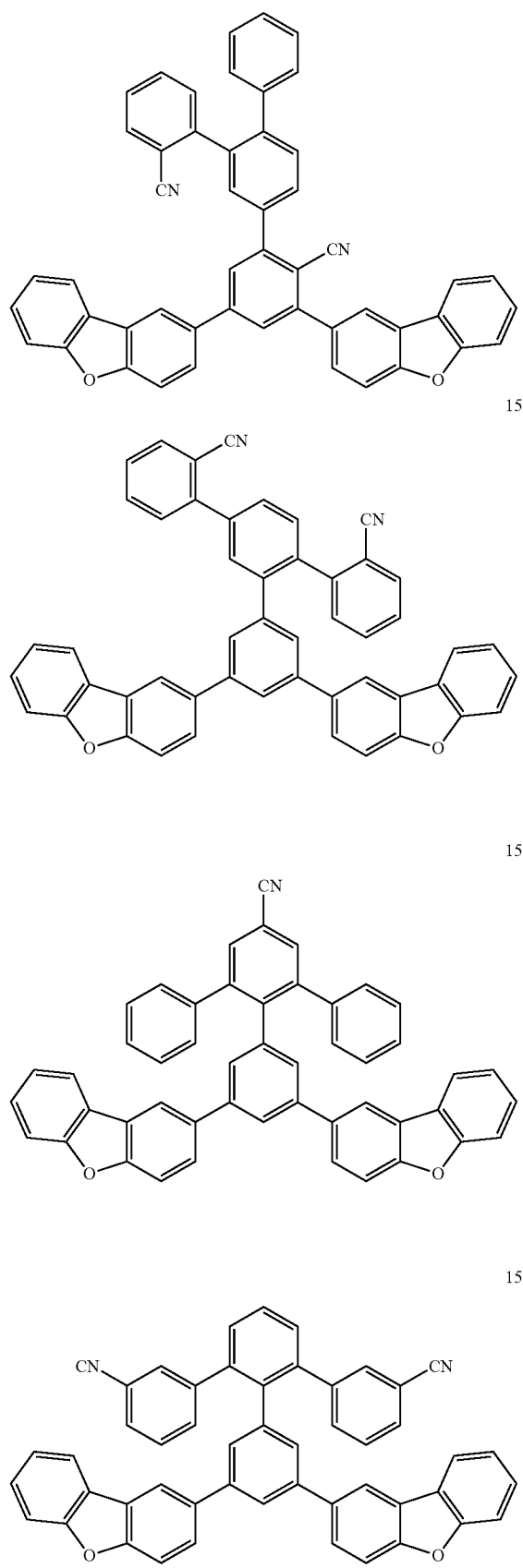
149
150
151
152
-continued
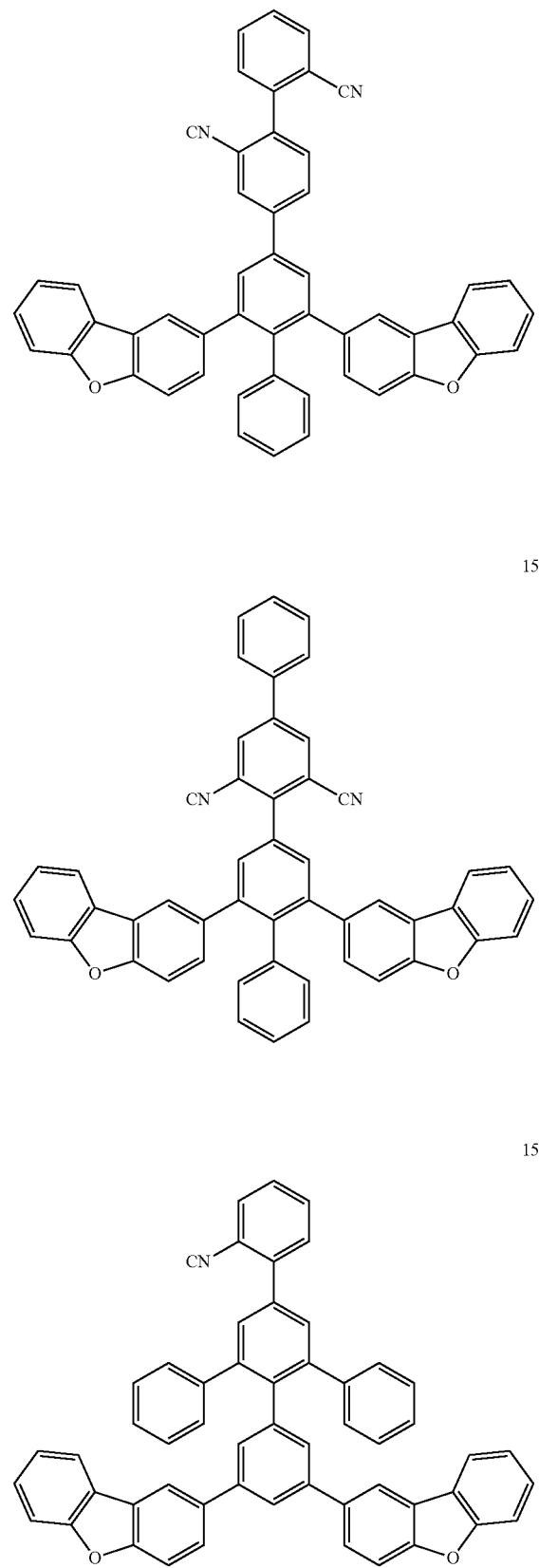
153
154
155

-continued
156
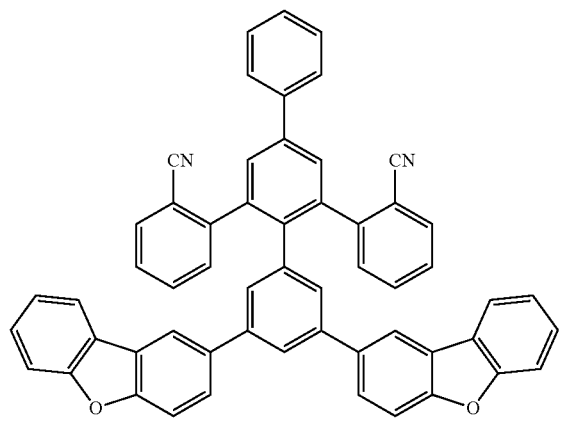
157
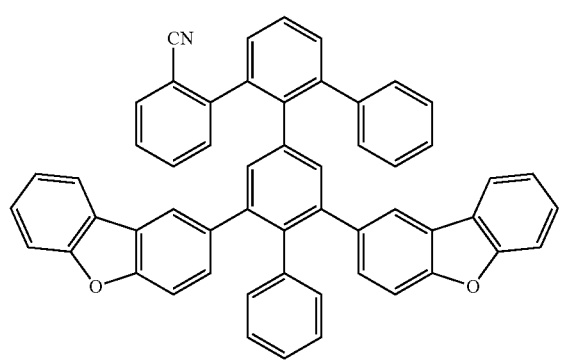
158
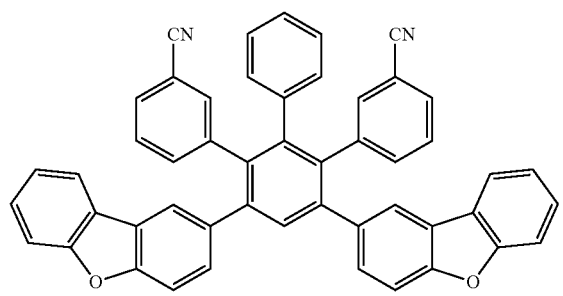
159
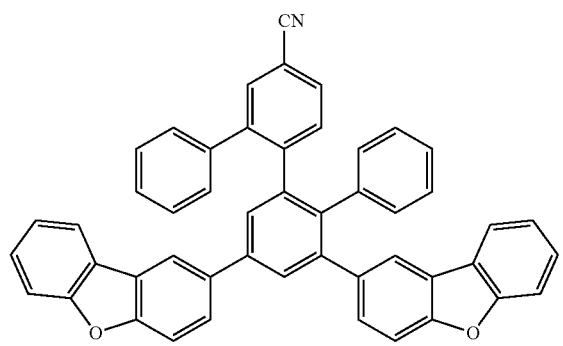
-continued
160
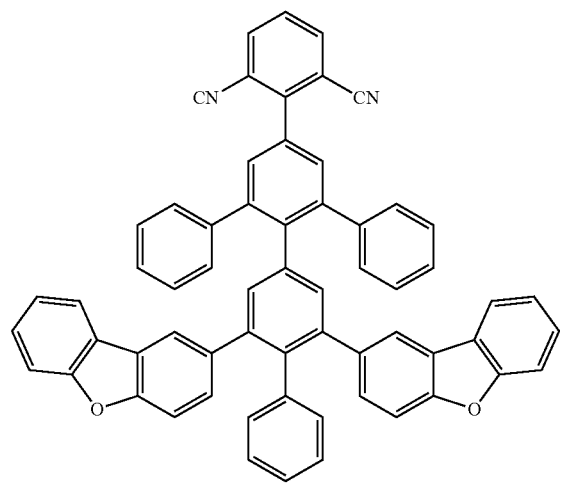
161
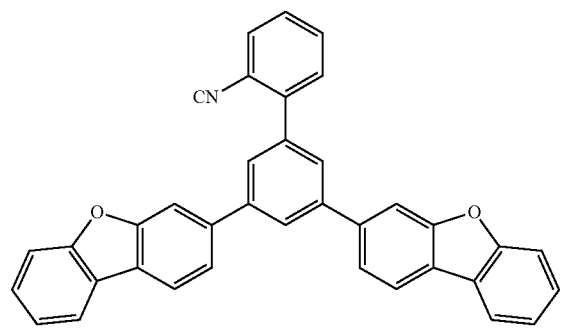
162
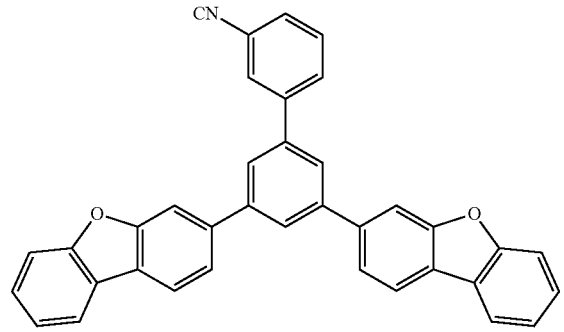
163
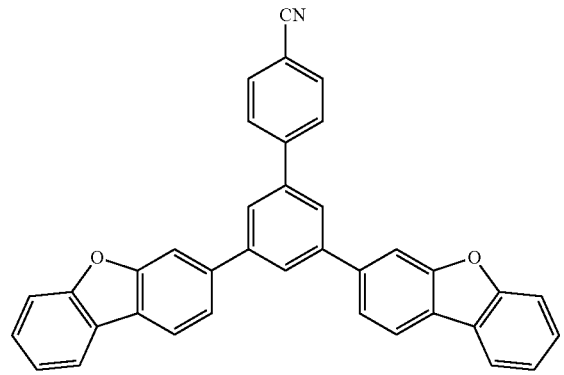

164
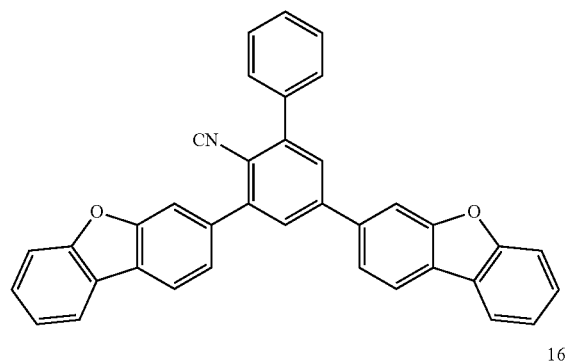
165
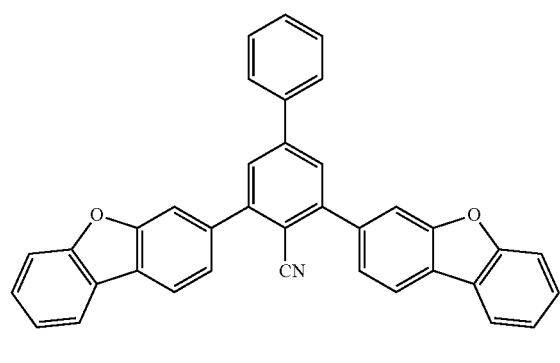
166
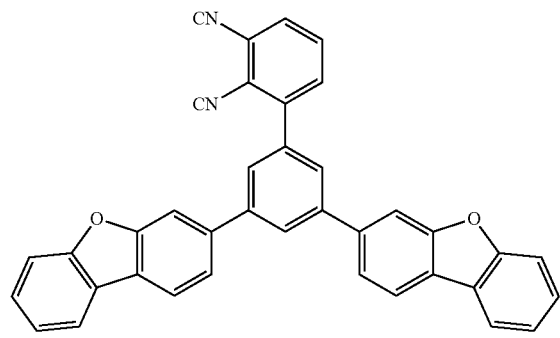
167
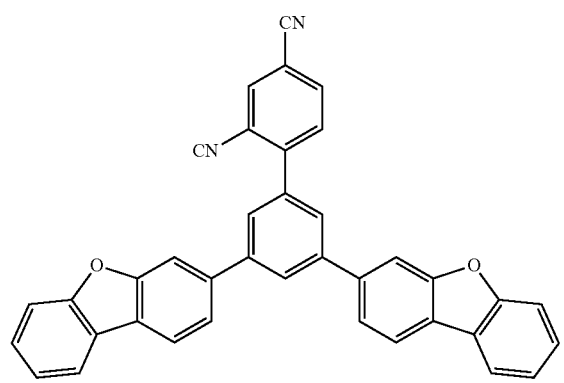
168
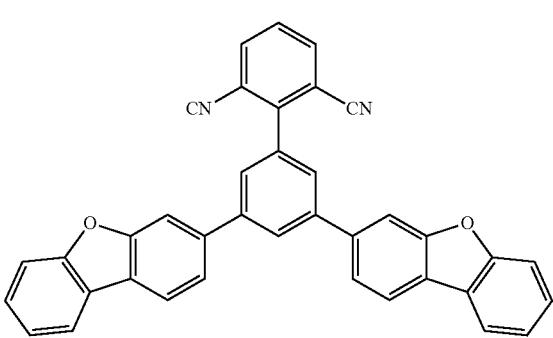
169
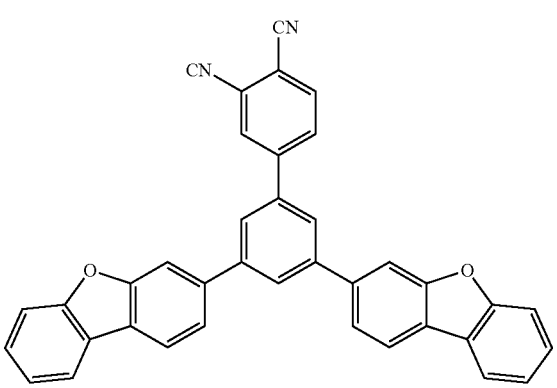
170
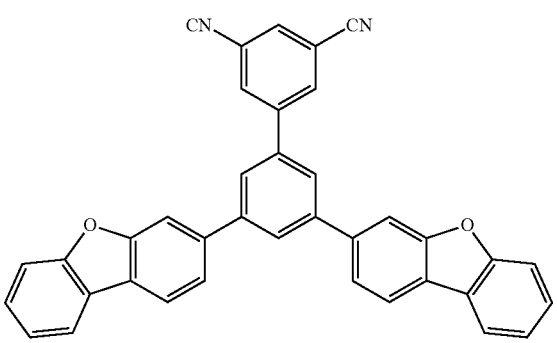
171

172
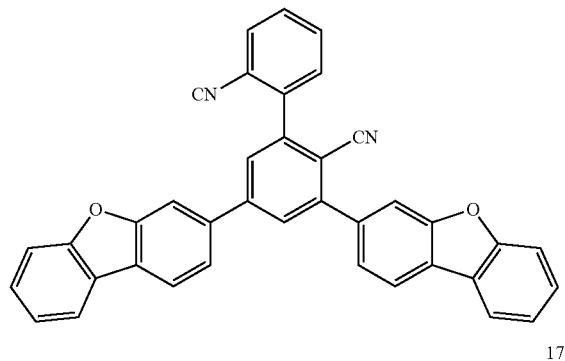
173
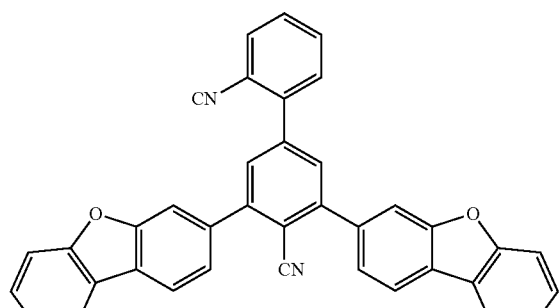
174
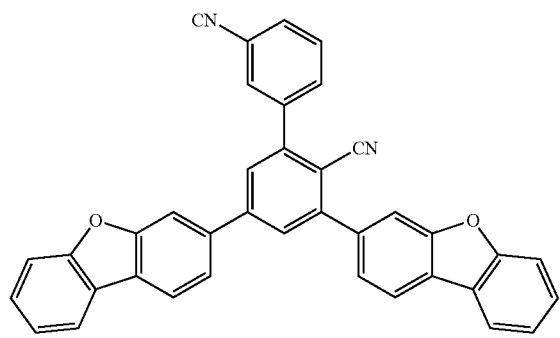
175
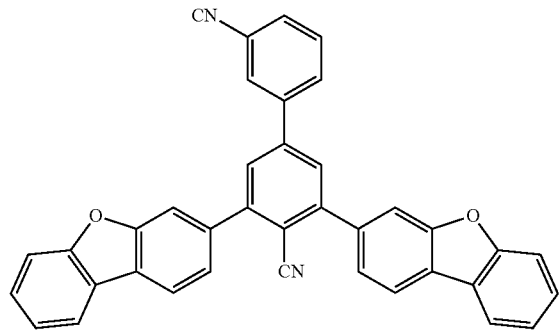
176
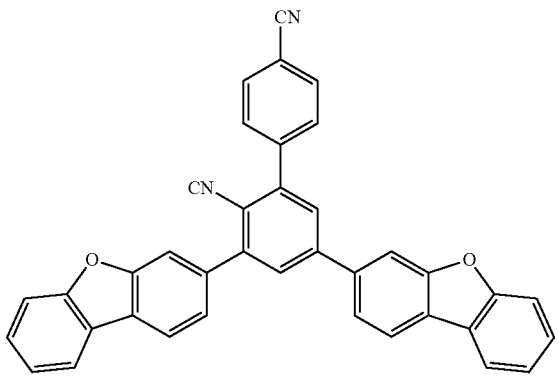
177
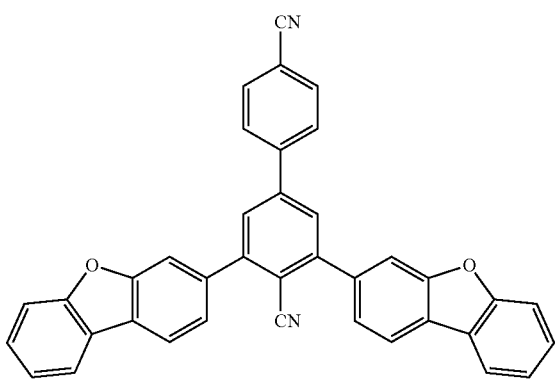
178
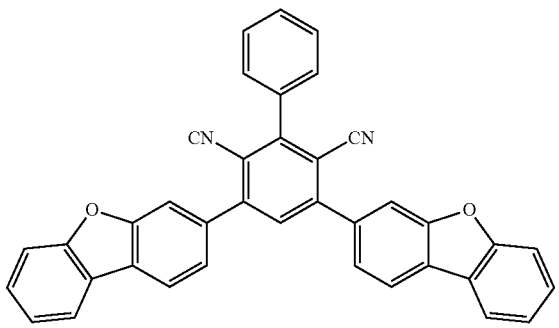
179
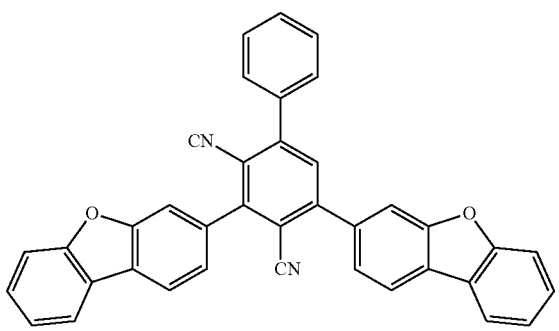

-continued
180
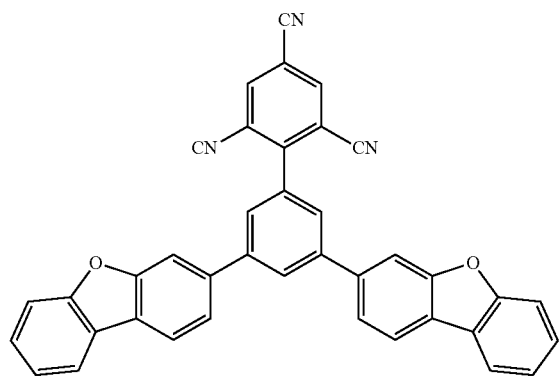
181
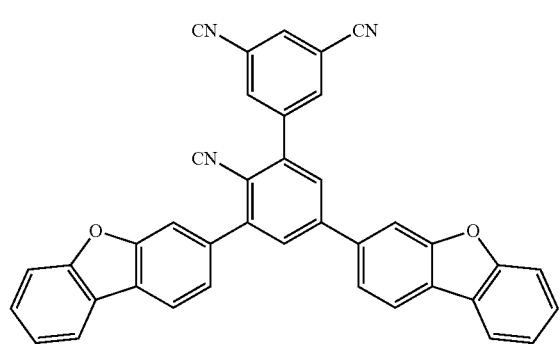
182
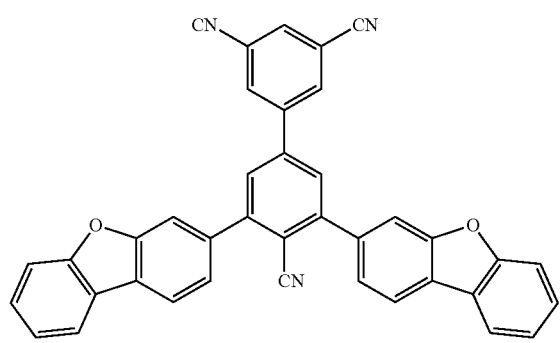
183
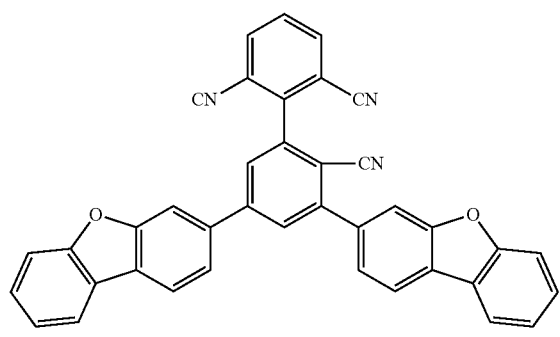
-continued
184
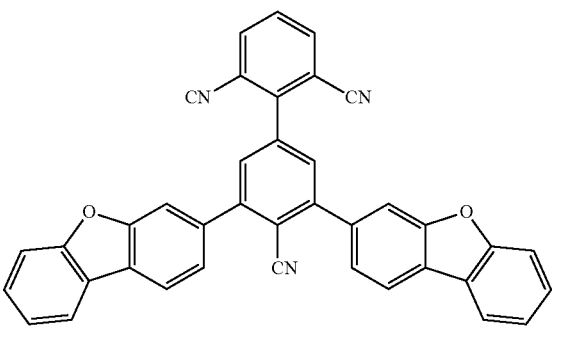
185
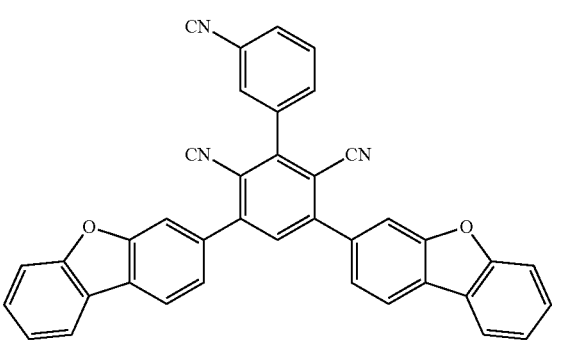
186
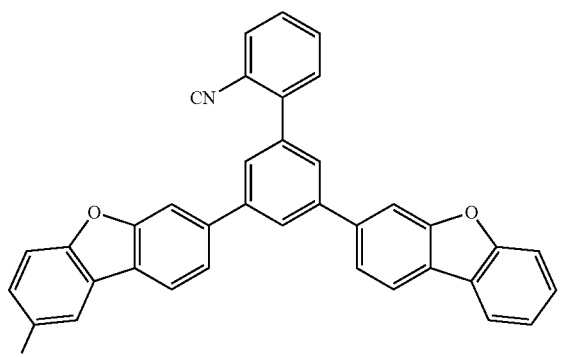
187
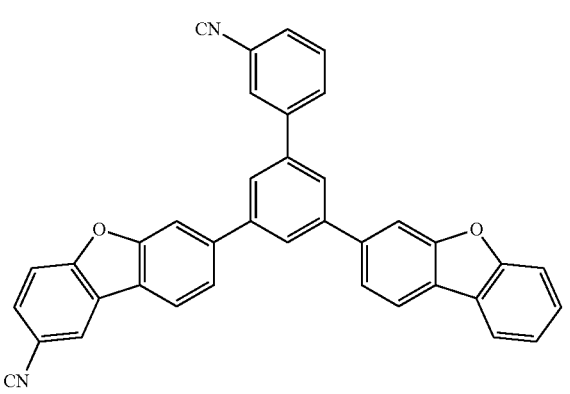

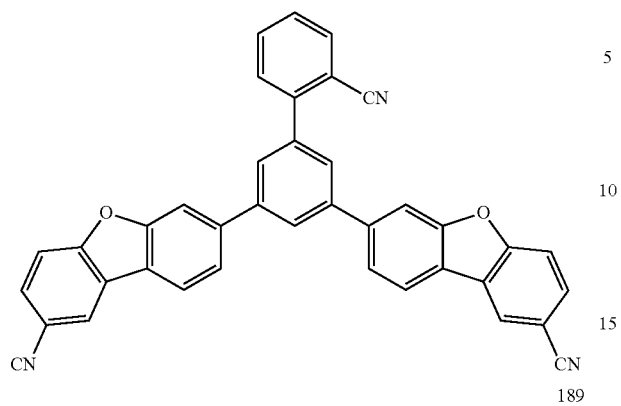
188
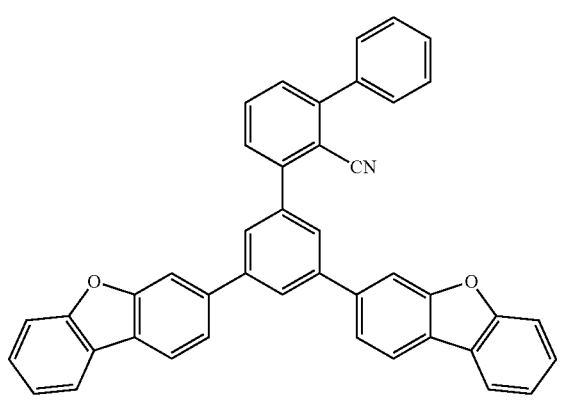
192
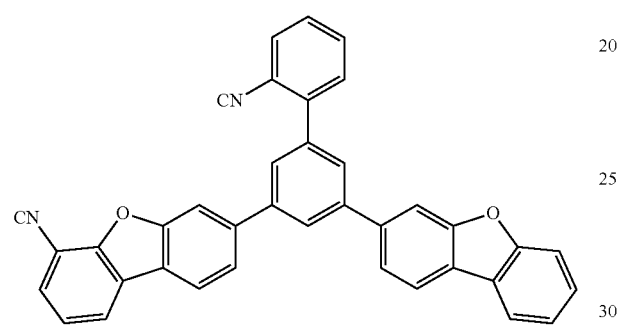
189
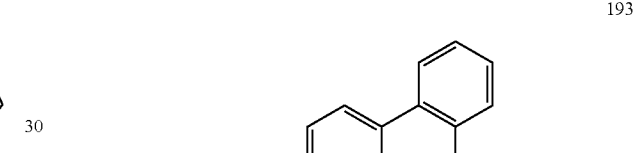
193
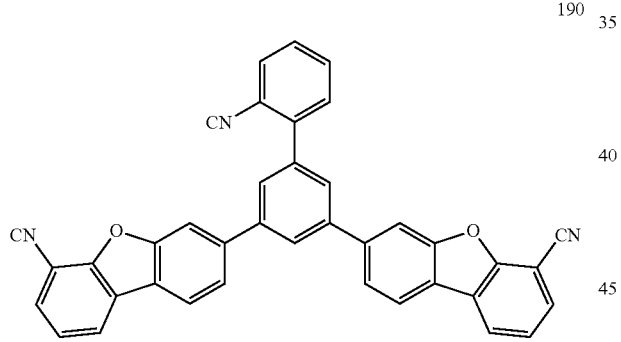
190
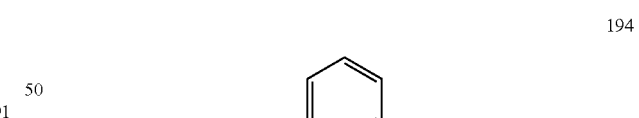
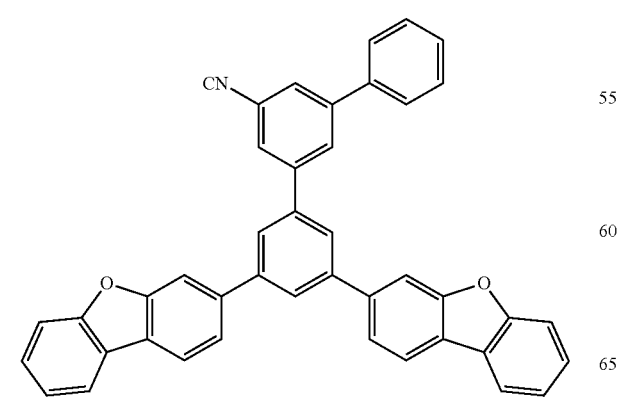
191
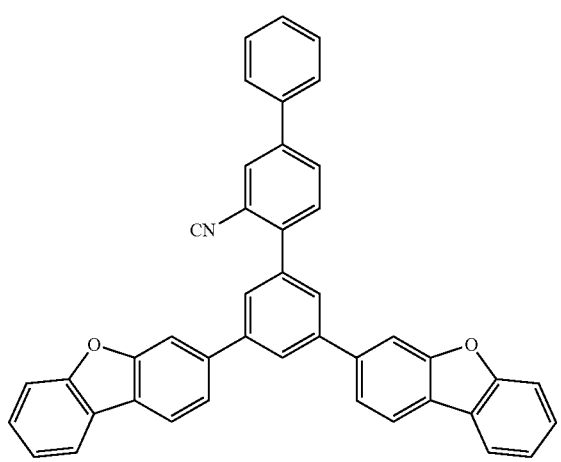
194

-continued
195
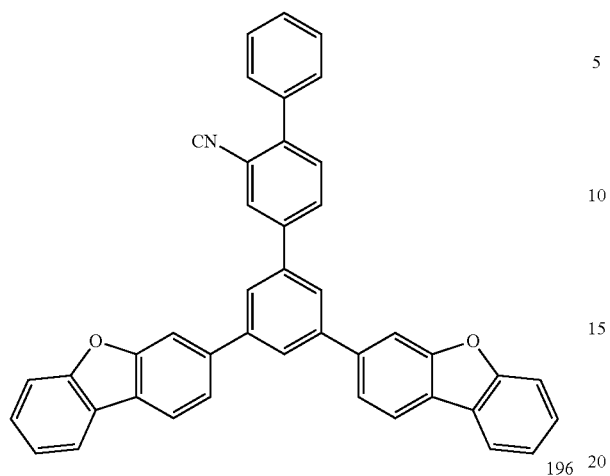
196
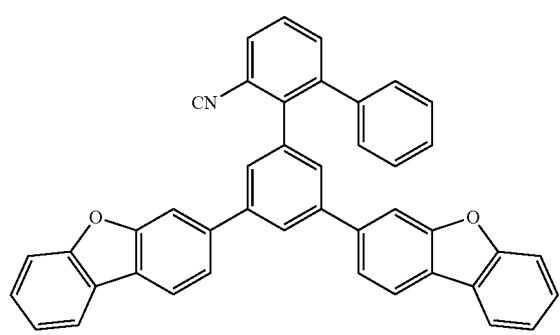
197
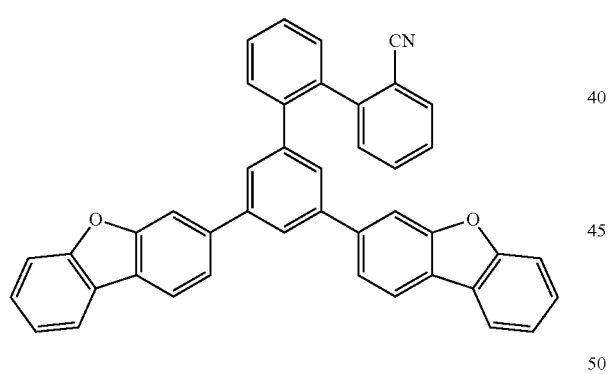
198
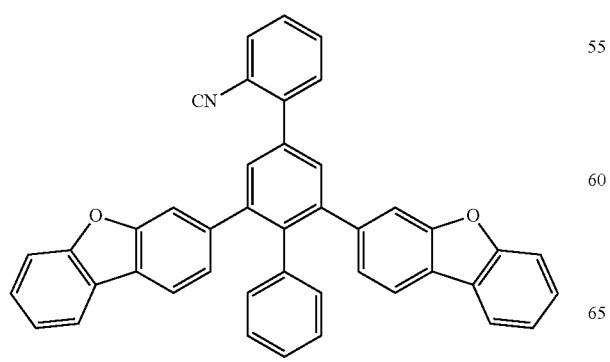
-continued
199
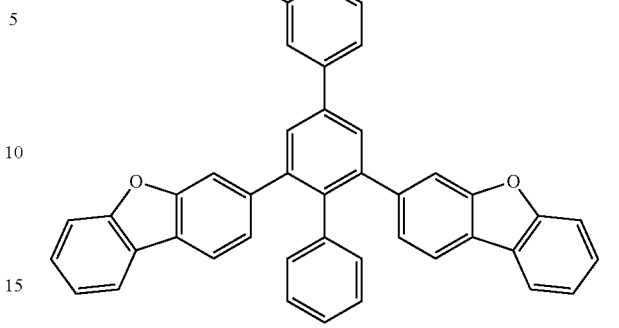
200
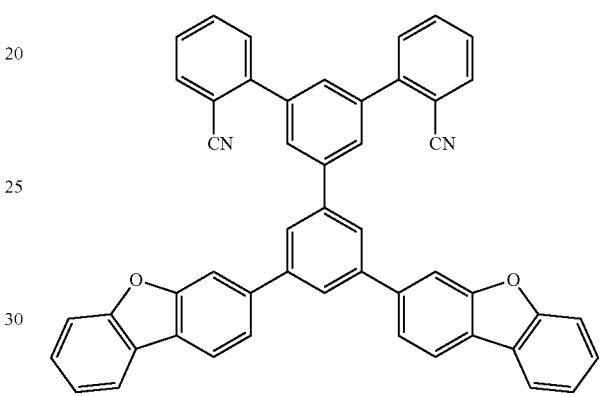
201
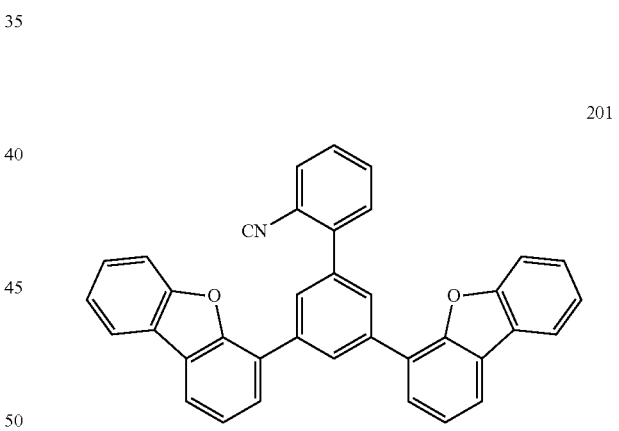
202
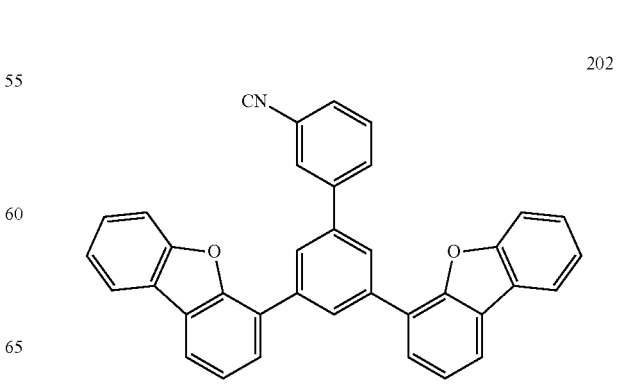

203
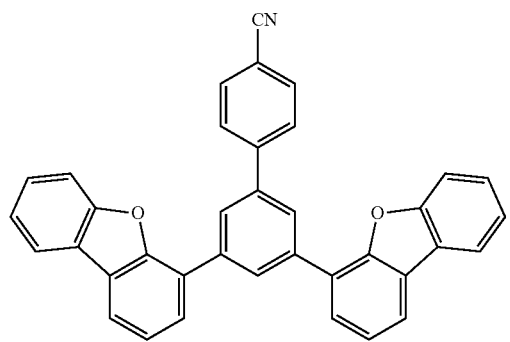
204
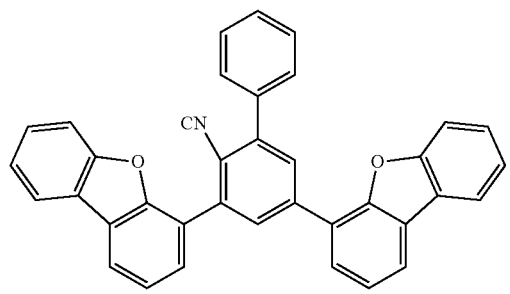
205
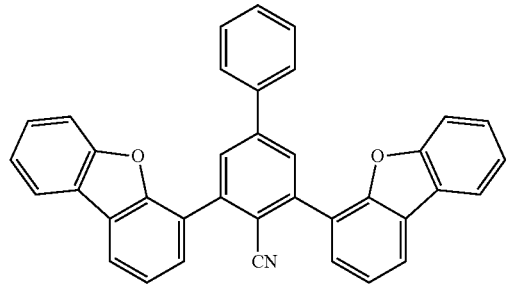
206
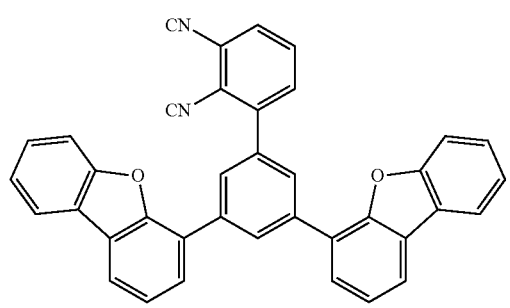
207
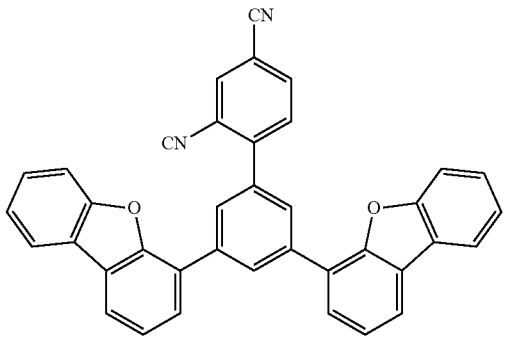
208
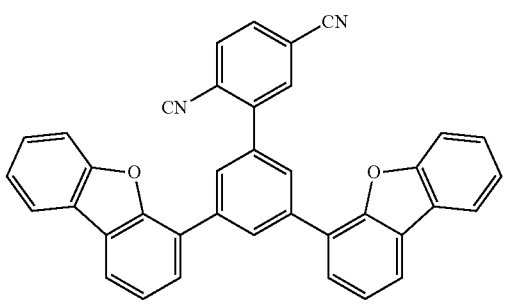
209
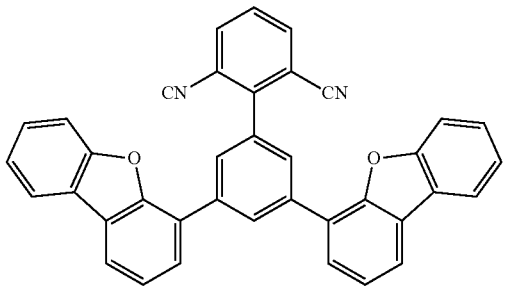
210

-continued
211
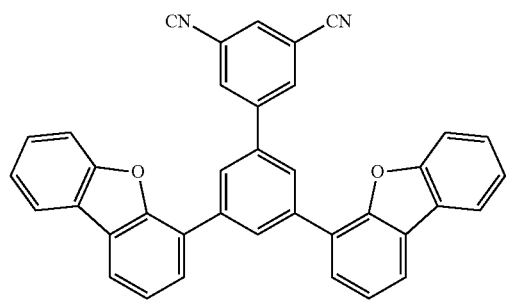
212
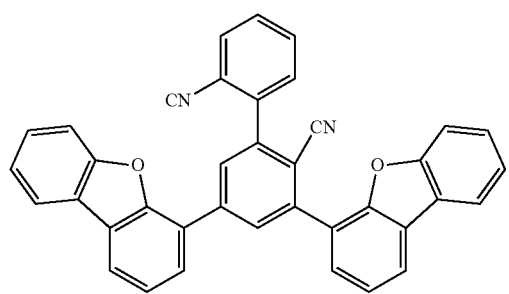
213
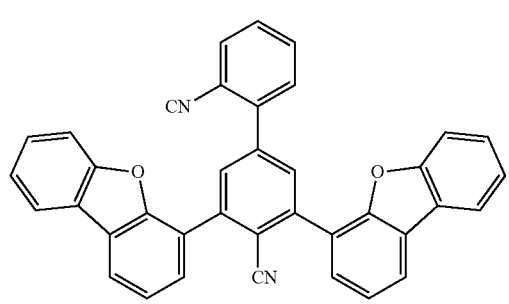
214
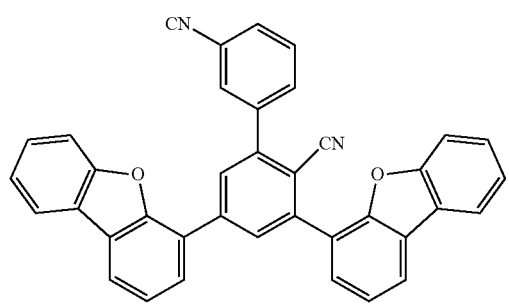
215
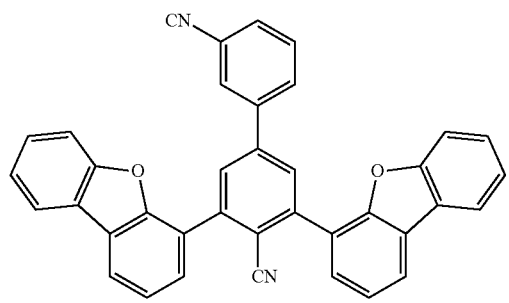
-continued
216
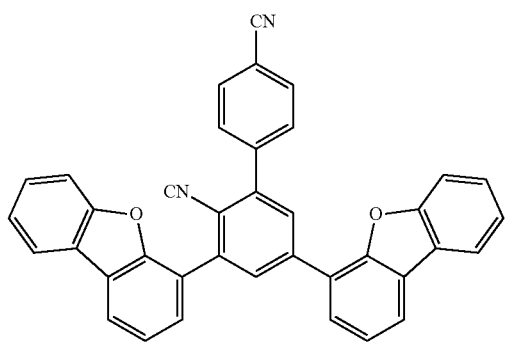
217
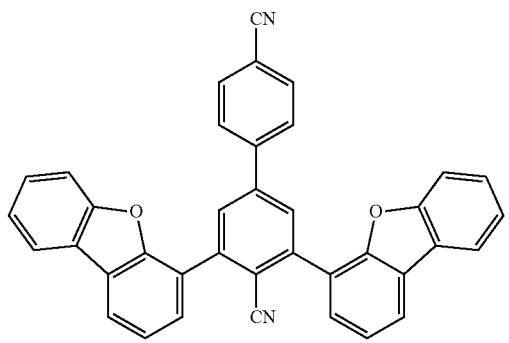
218
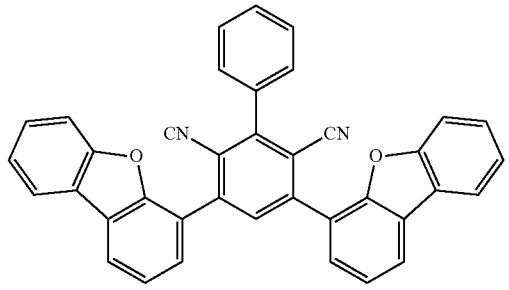
219
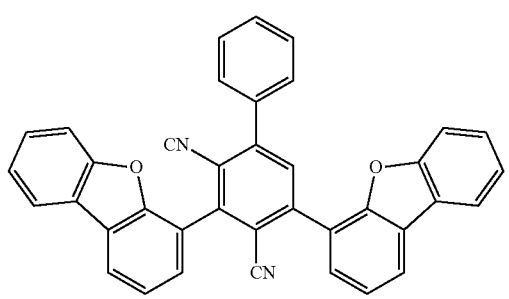

220
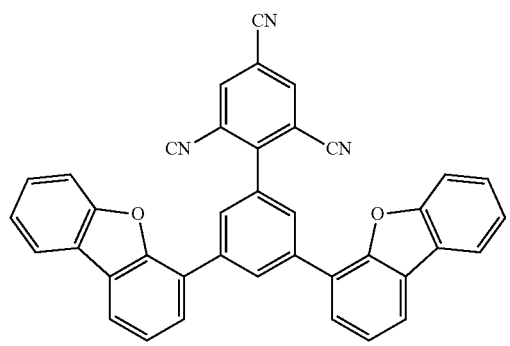
221
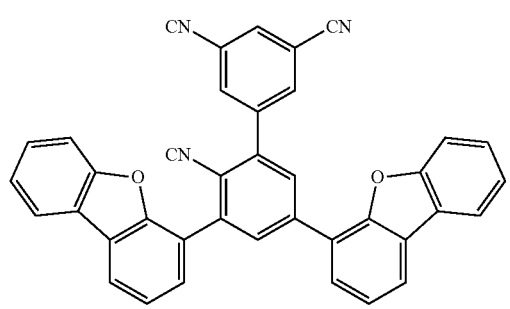
222
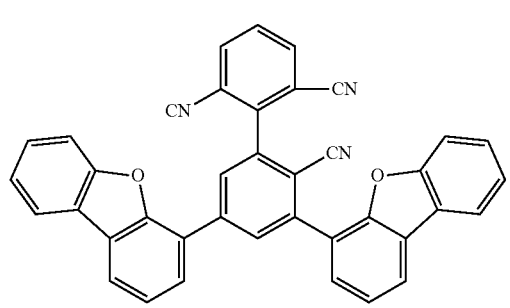
223
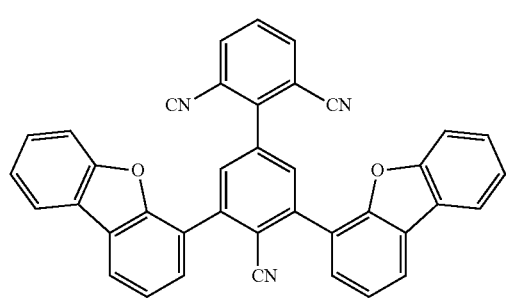
224
225
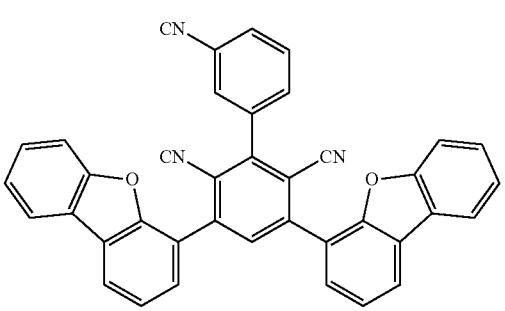
226
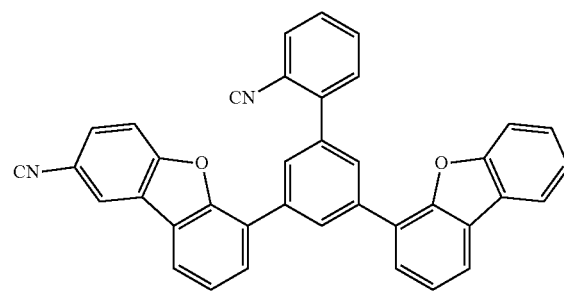
227
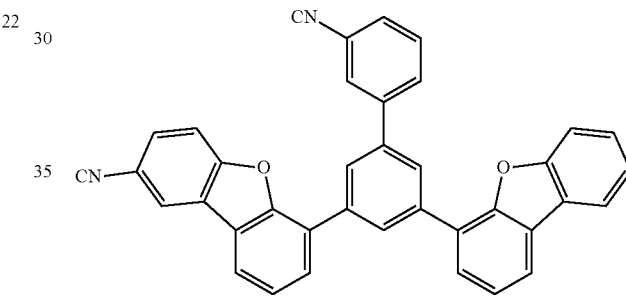
228
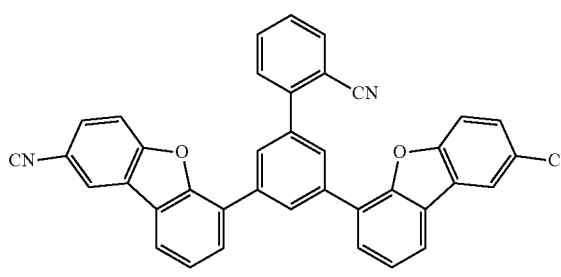
229
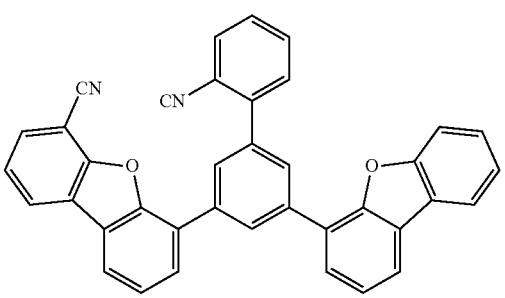

230
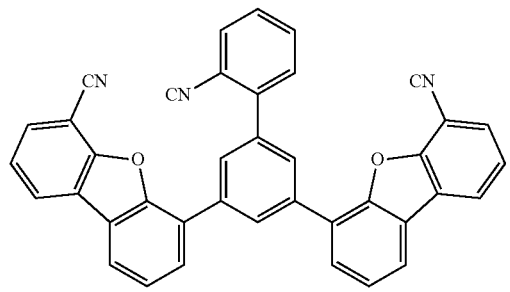
231
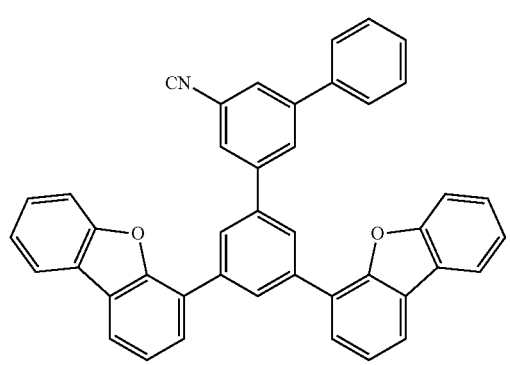
232
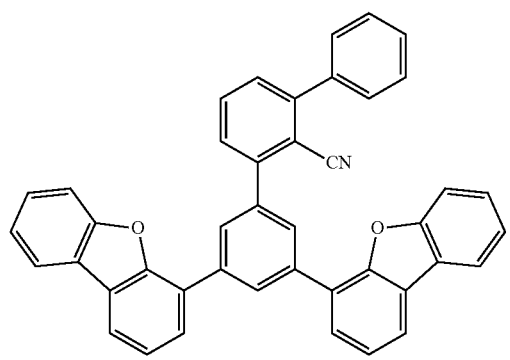
233
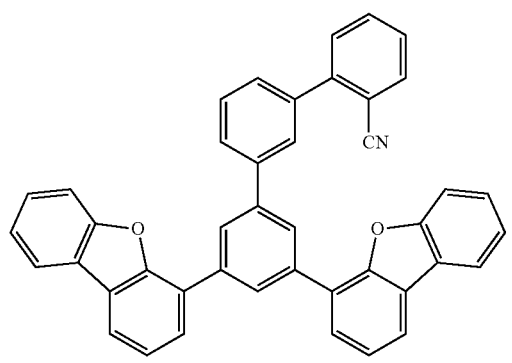
234
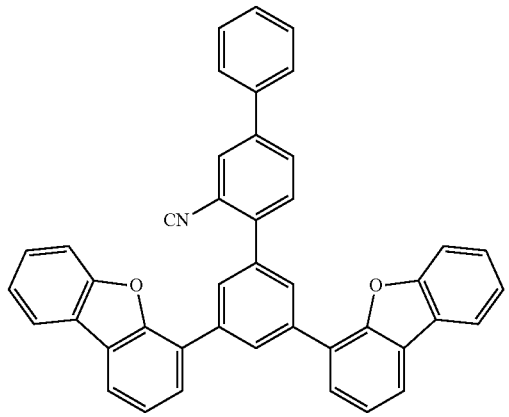
235
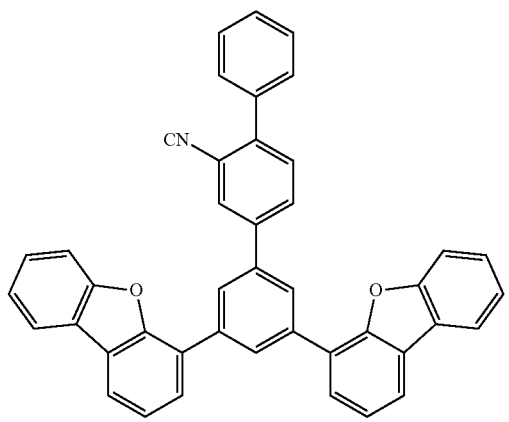
236
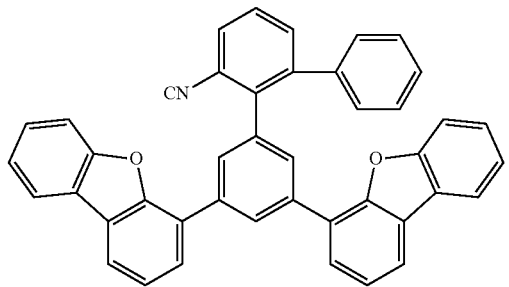
237
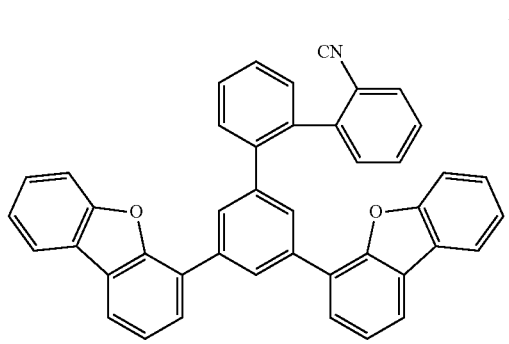

238
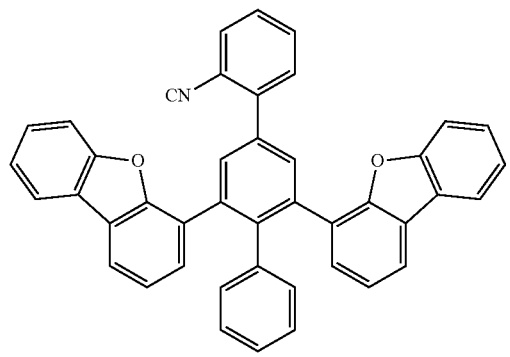
239
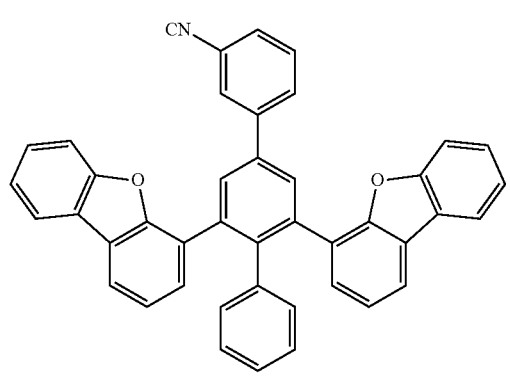
240
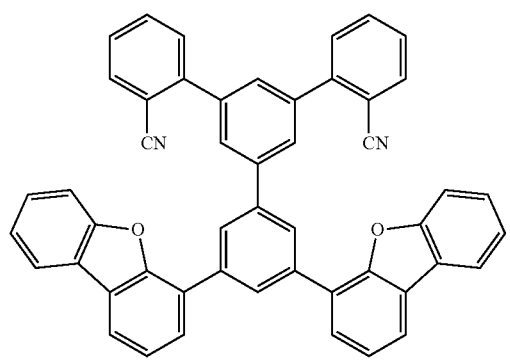
241
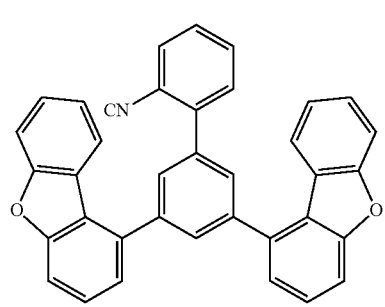
242
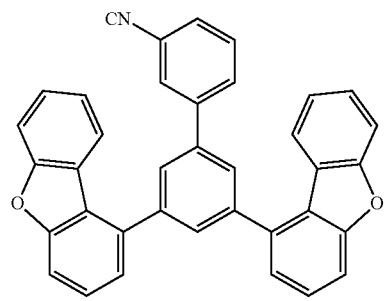
243
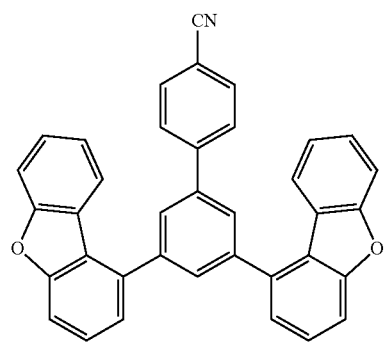
244
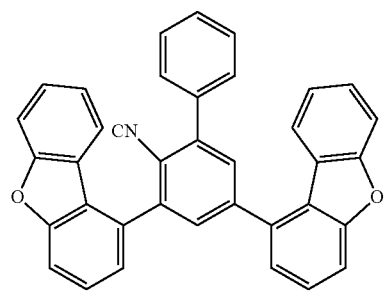
245
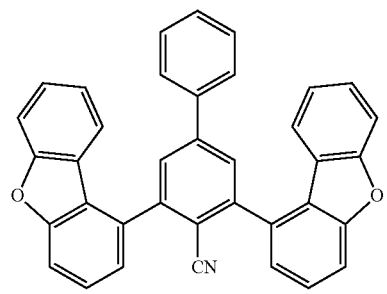
246
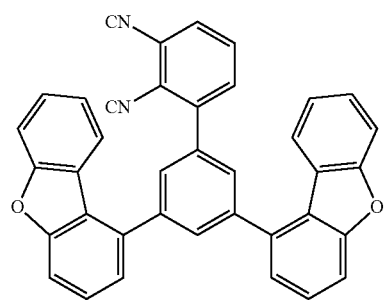

247
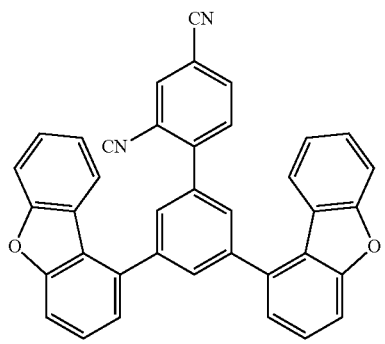
248
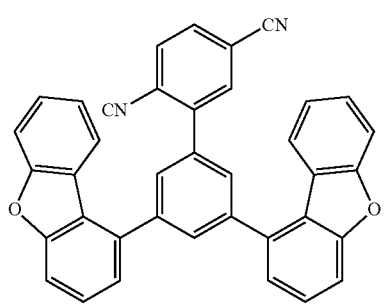
249
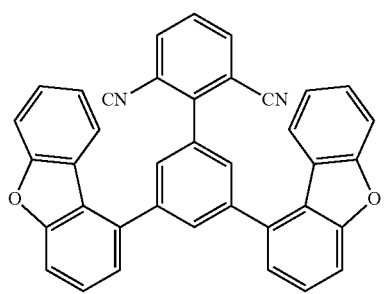
250
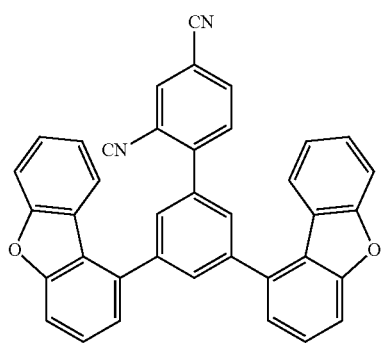
251
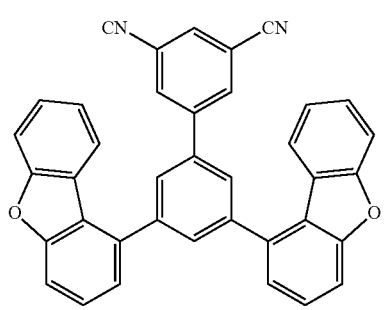
252
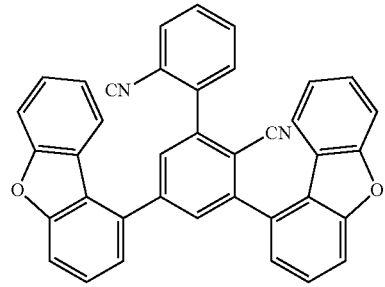
253
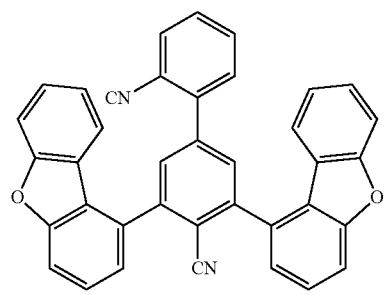
254
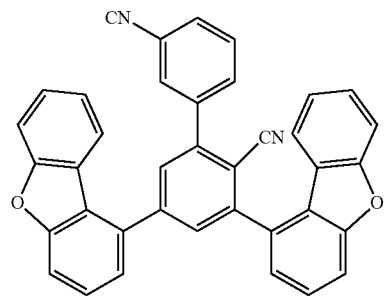
255
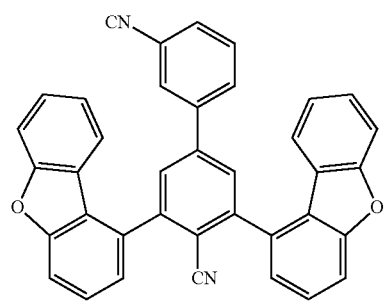
256
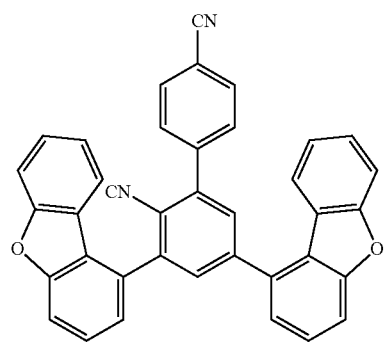

257
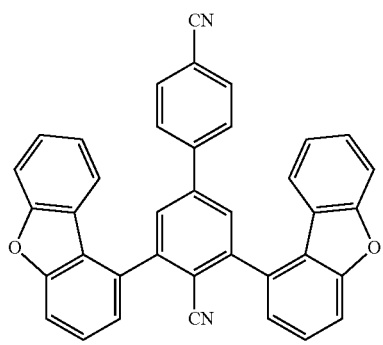
258
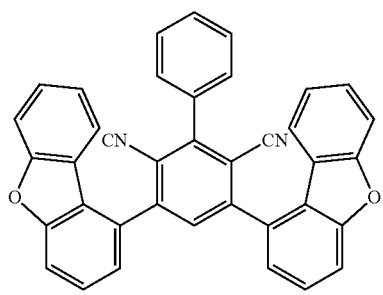
259
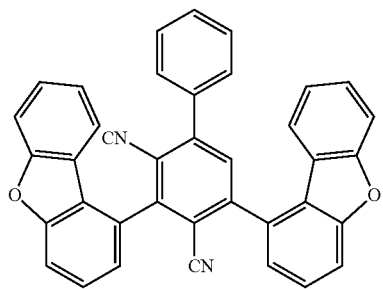
260
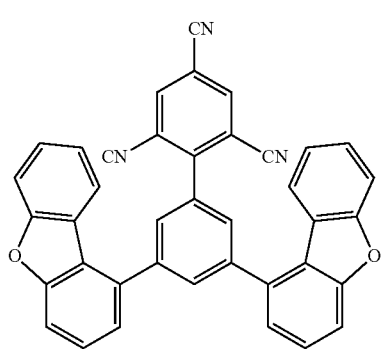
261
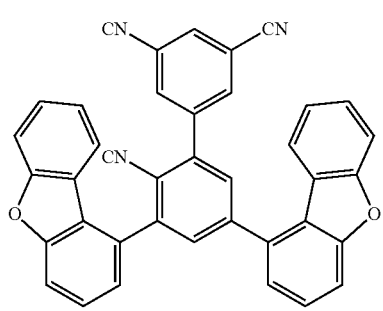
262
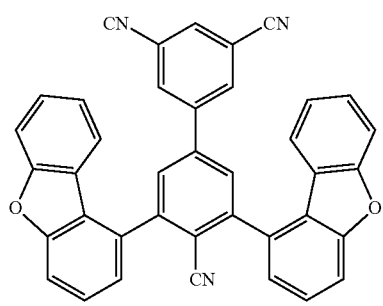
263
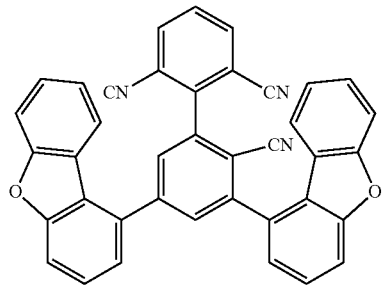
264
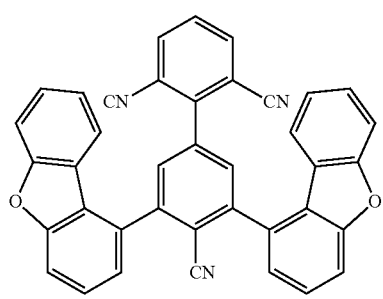
265
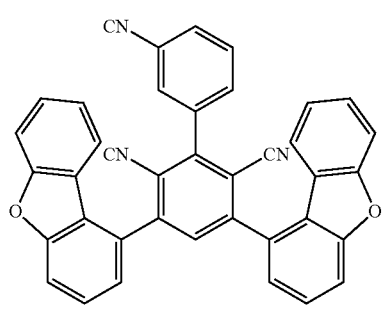
266
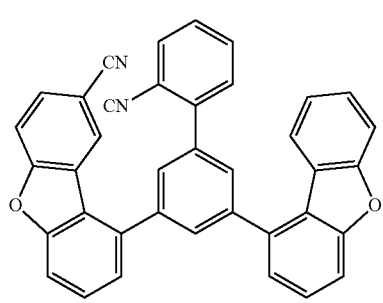

267 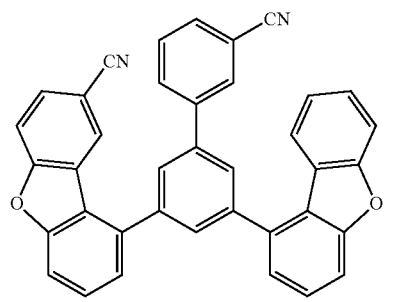
268 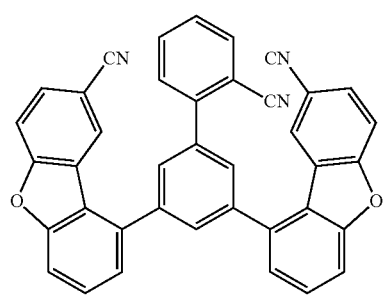
269 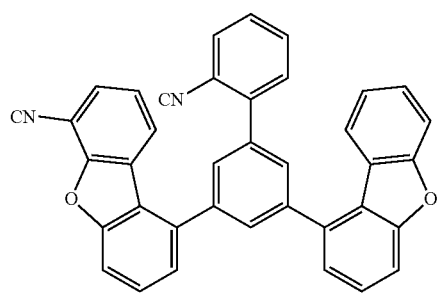
270 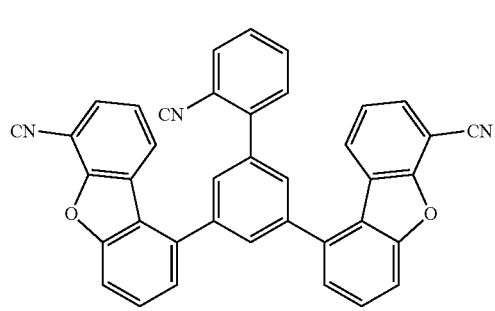
271 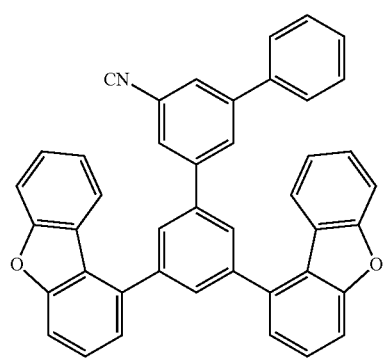
272 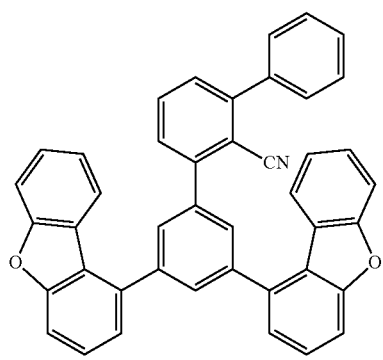
273 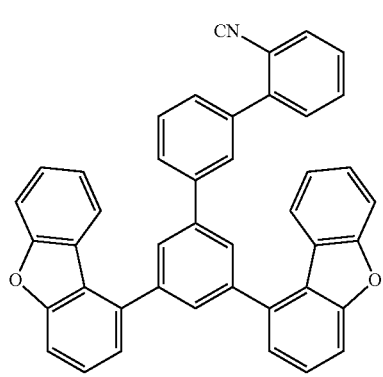
274 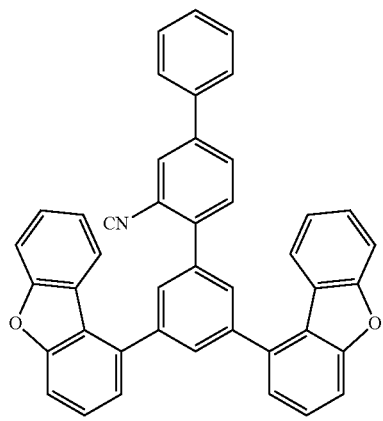
275 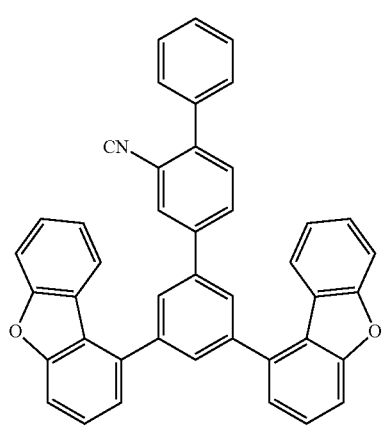

276 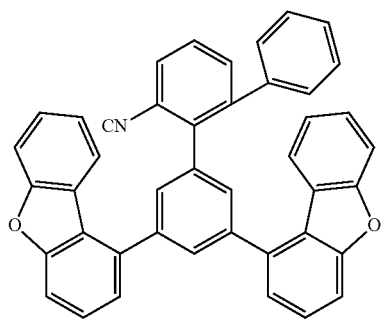
280 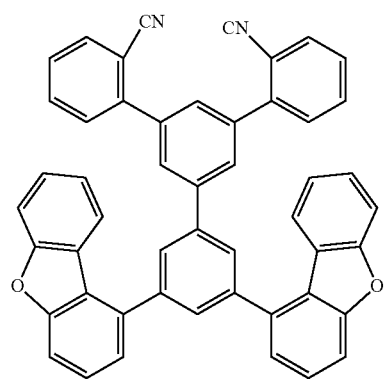
277 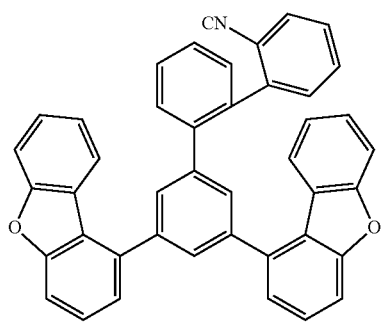
281 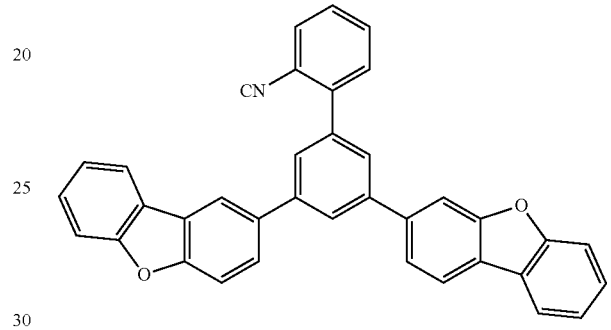
278 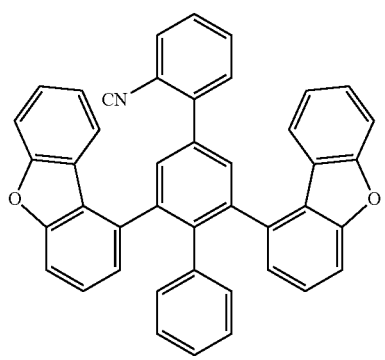
282 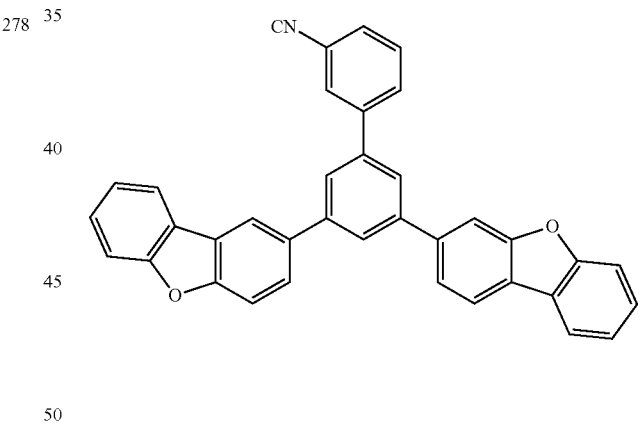
279 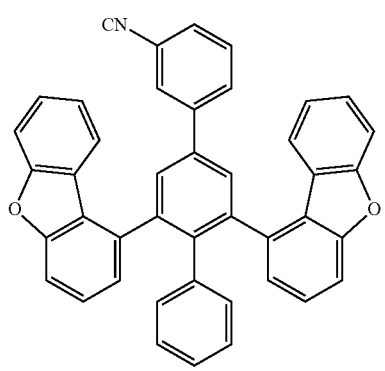
283 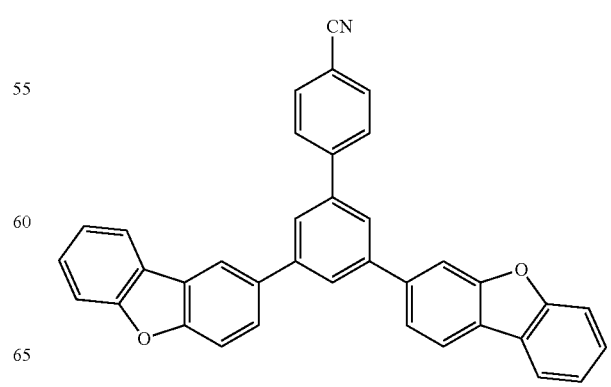

284
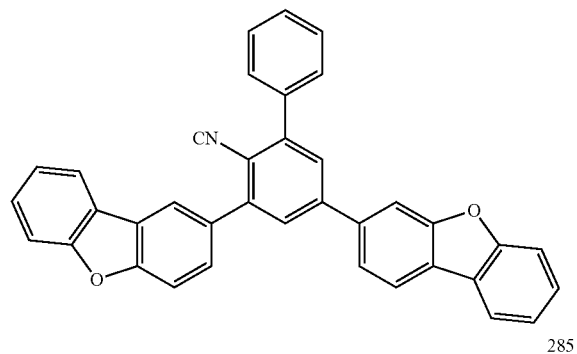
285
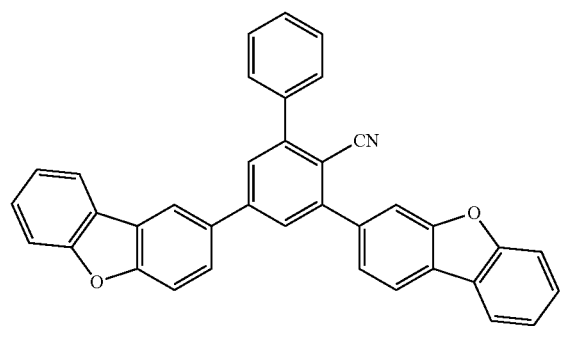
286
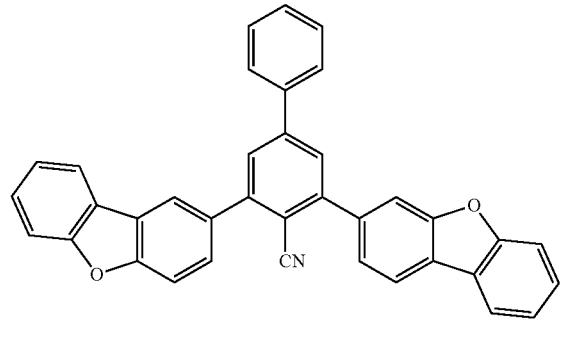
287
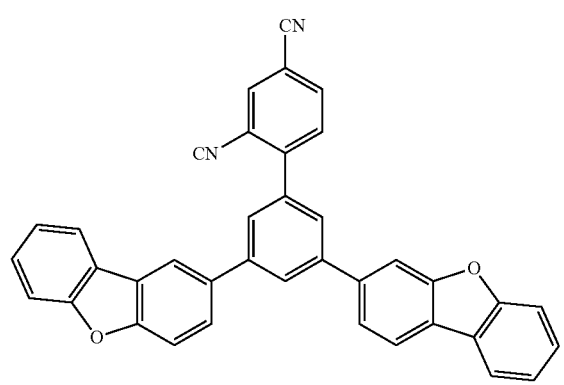
288
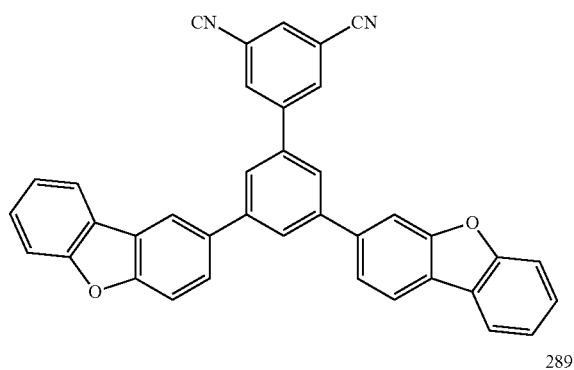
289
290
291
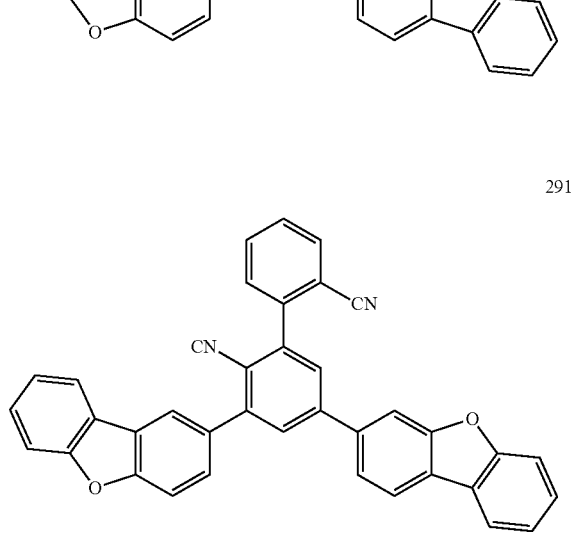

| 107 | 108 |
|---|---|
| -continued | -continued |
292
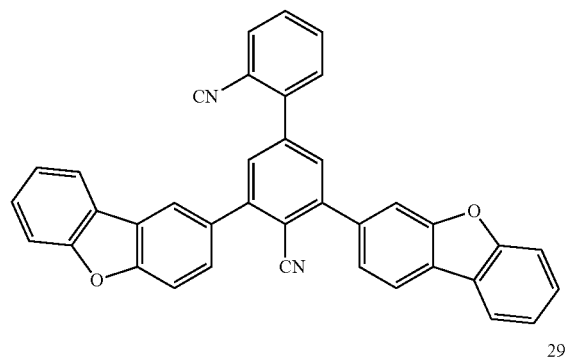
293
296
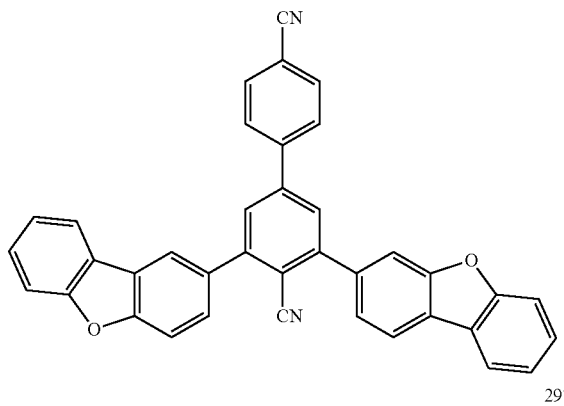
297
294
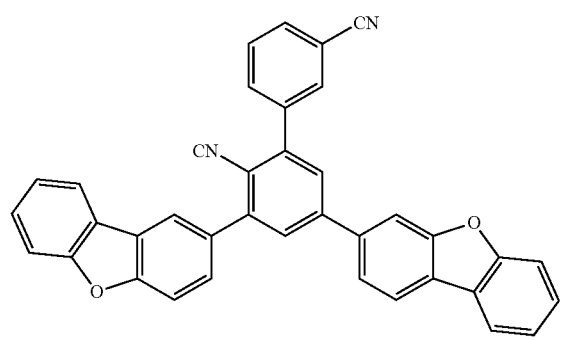
298
295
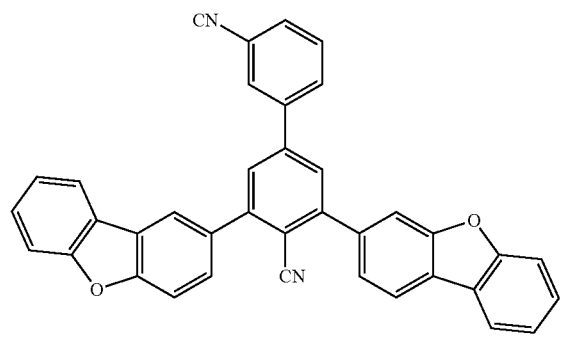
299
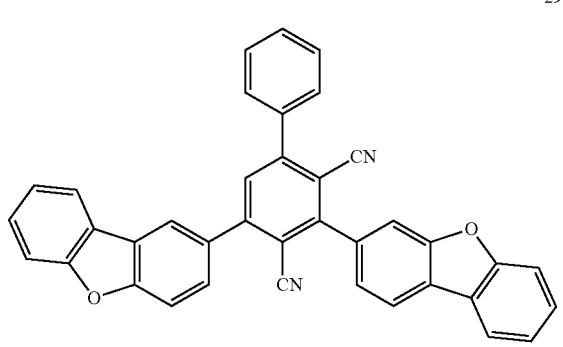

300
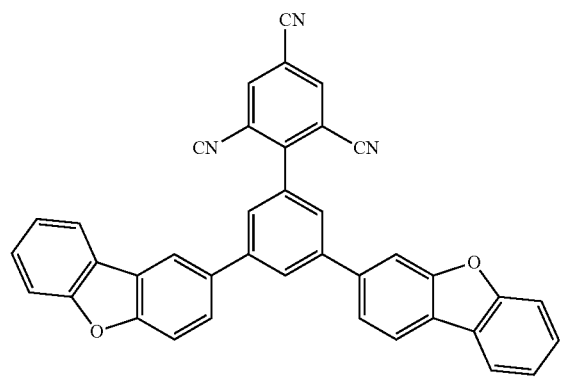
301
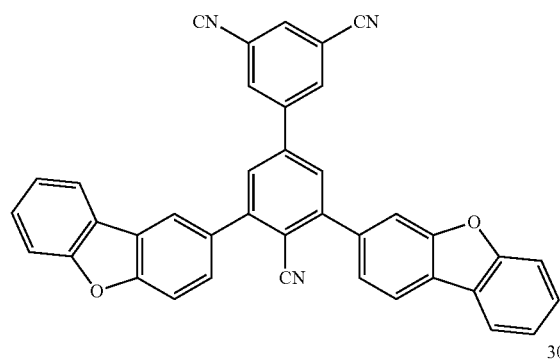
302
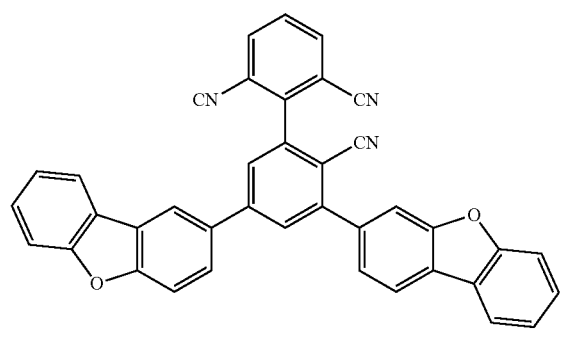
303
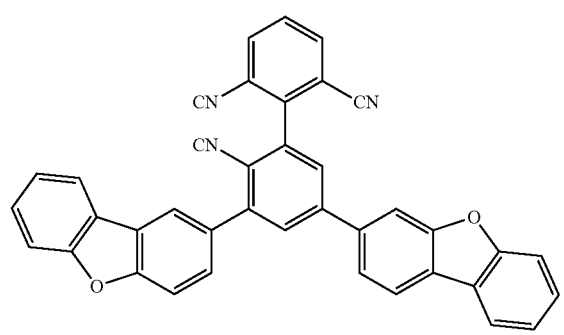
304
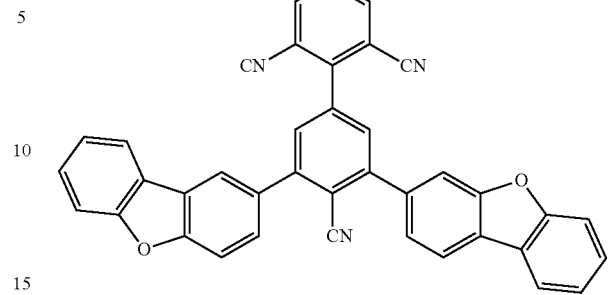
305
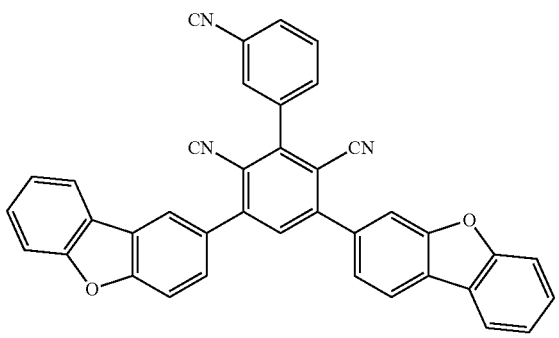
306
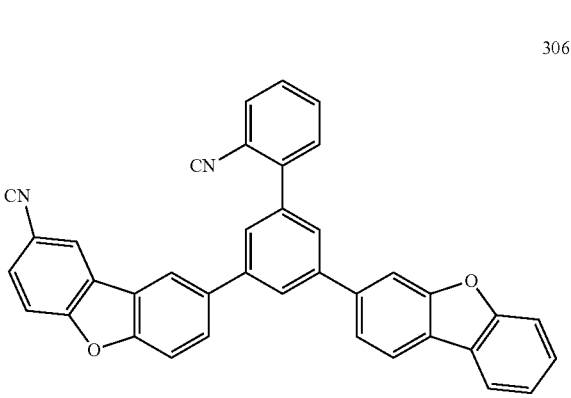
307
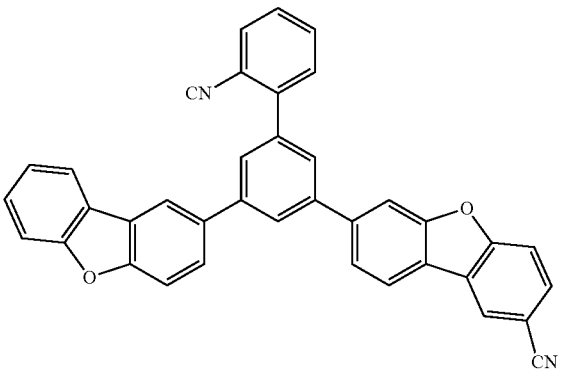

308
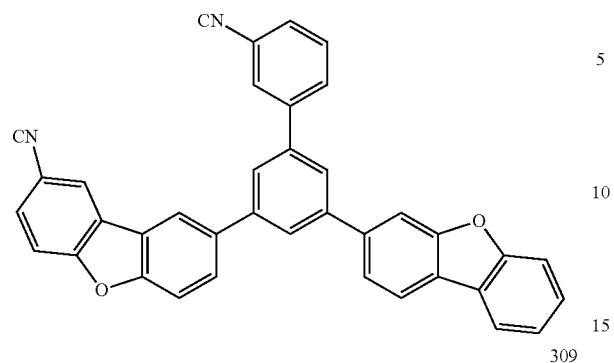
309
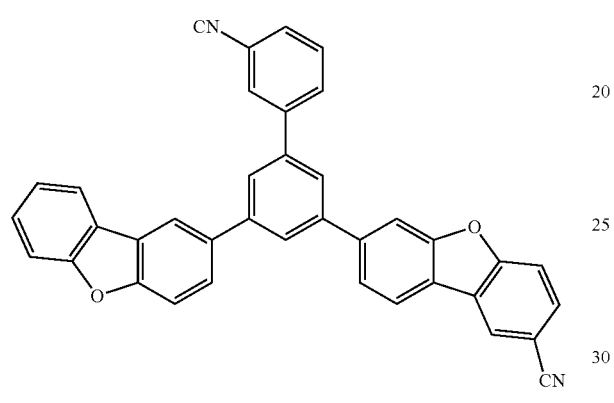
310
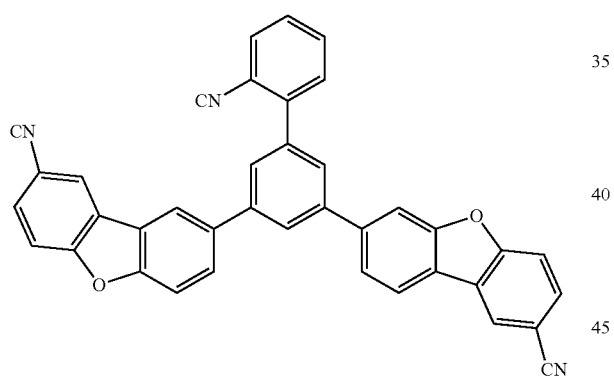
311
312
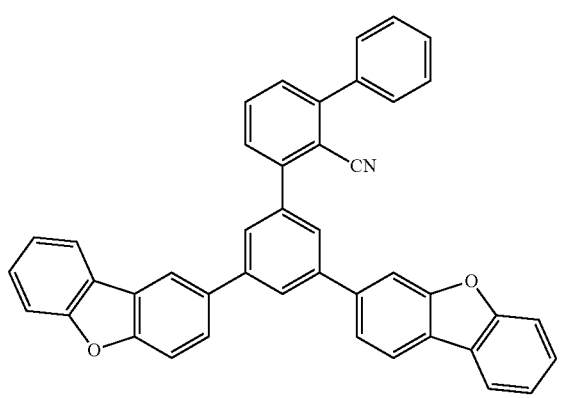
313
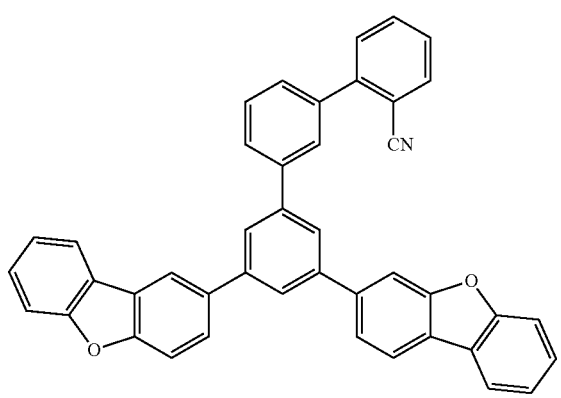
314
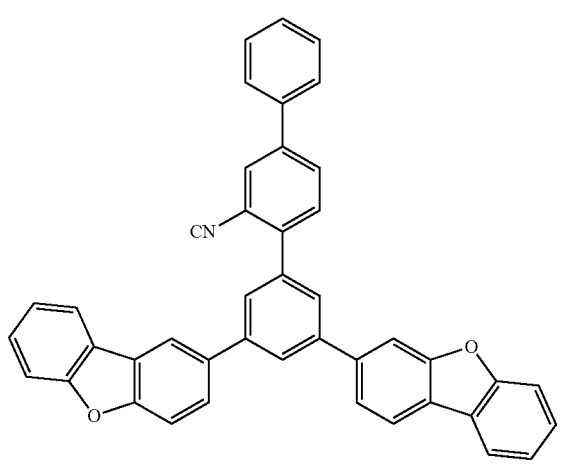

315
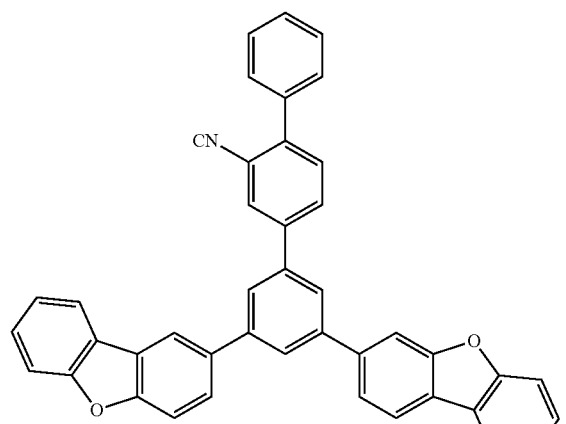
316
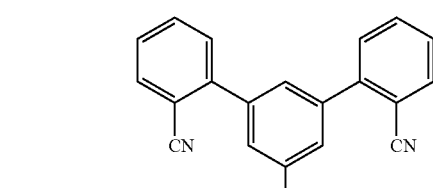
317
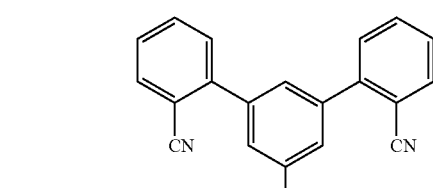
318
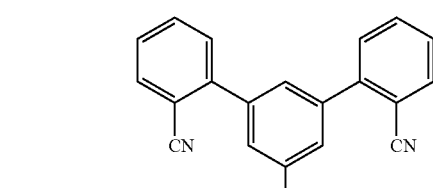
319
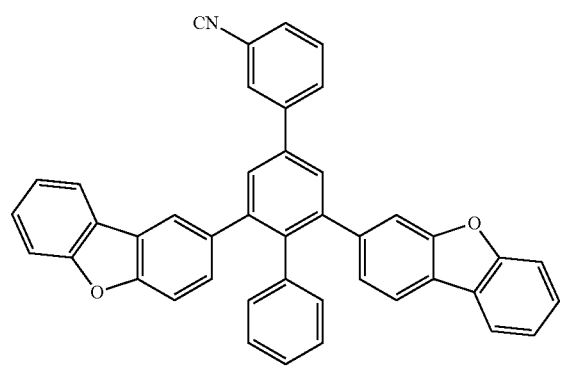
320
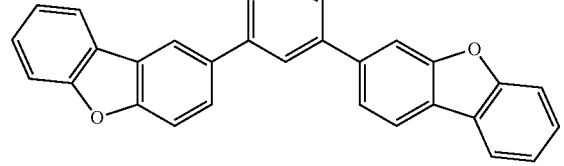
321
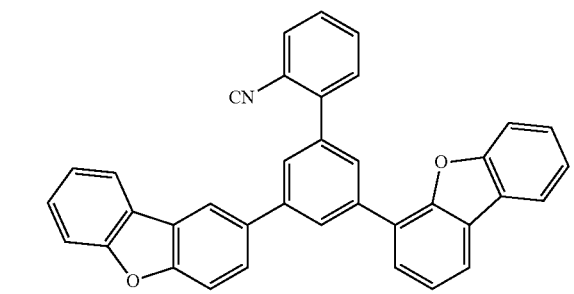
322
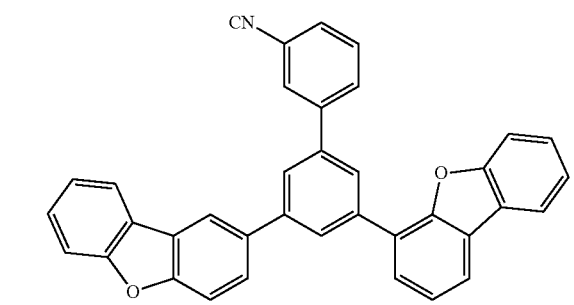

-continued
323
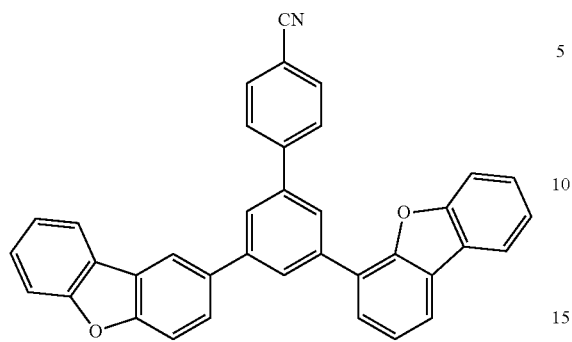
324

325

326
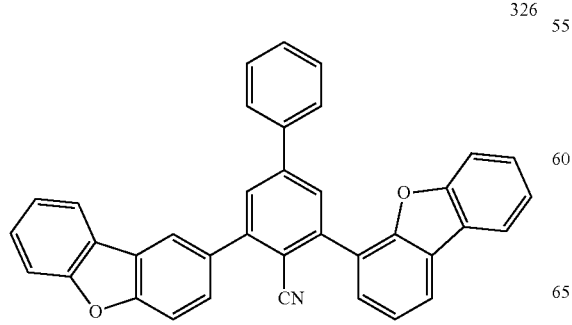
-continued
327
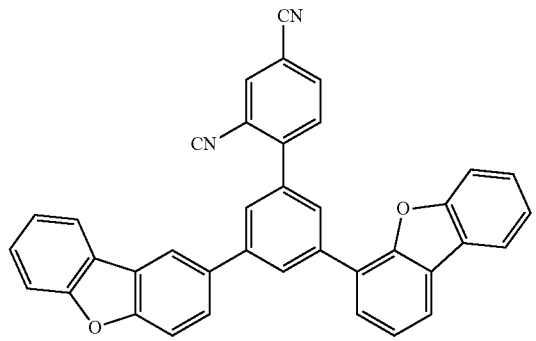
328
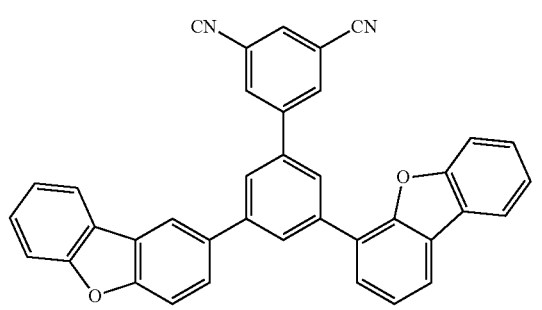
329
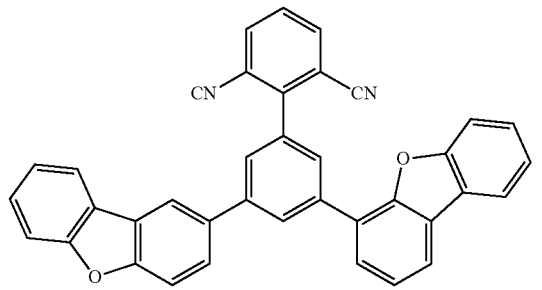
330
331
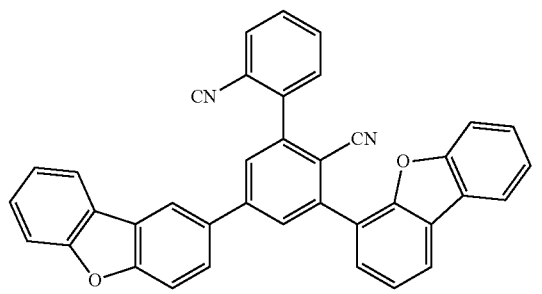

332
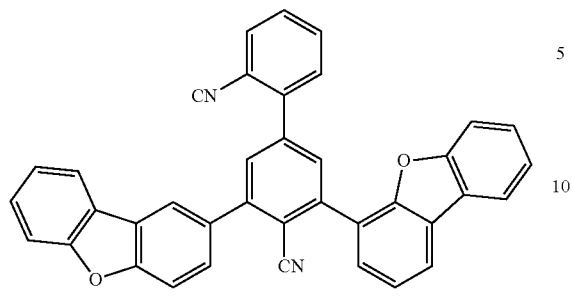
333
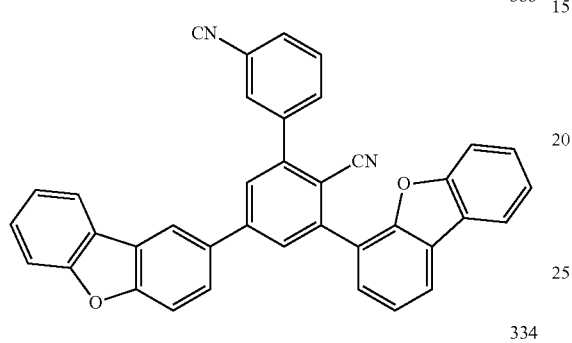
334
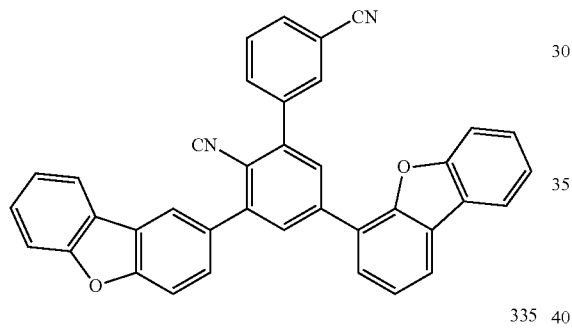
335
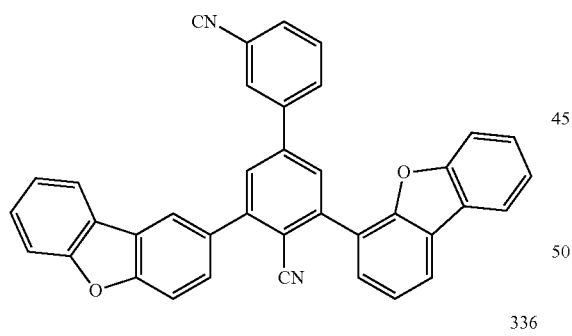
336
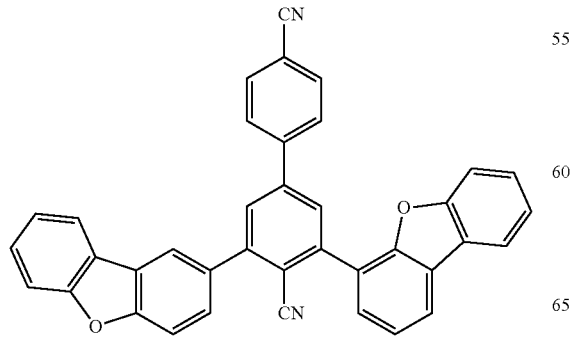
337
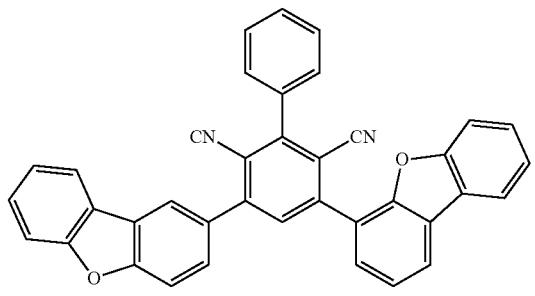
338
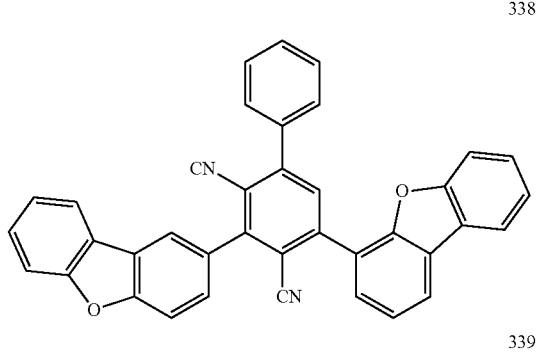
339
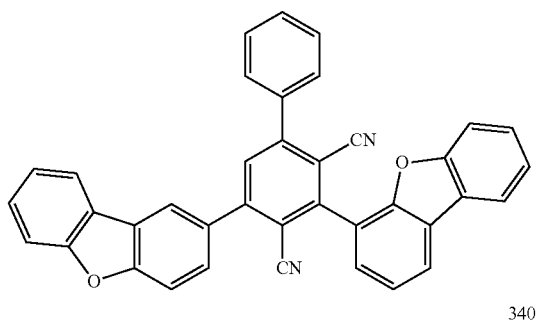
340
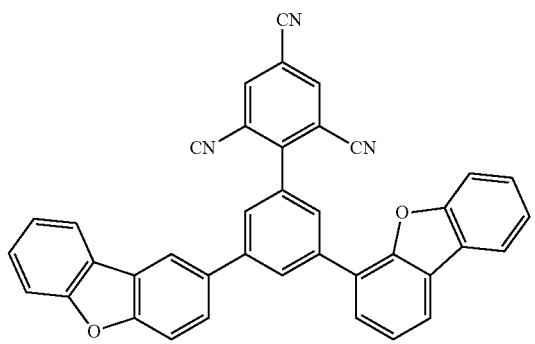
341
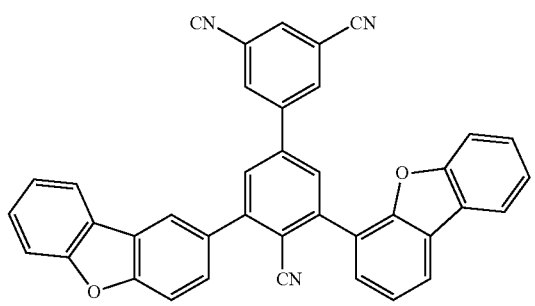

-continued
342
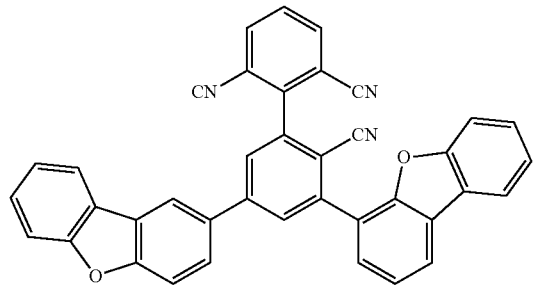
343
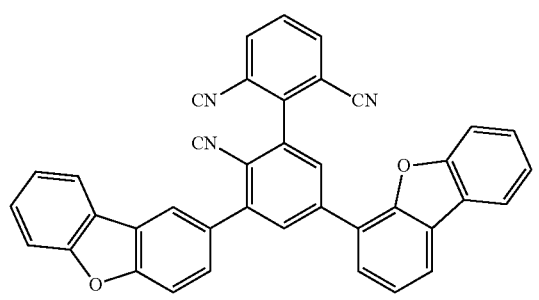
344
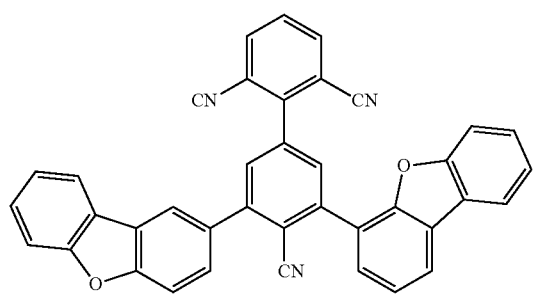
345
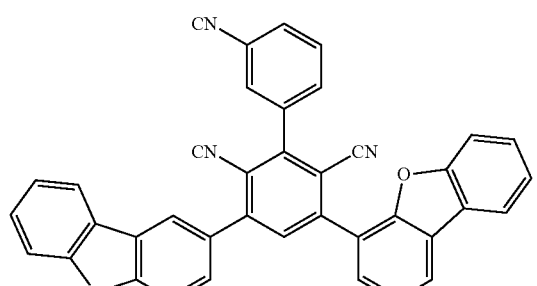
346
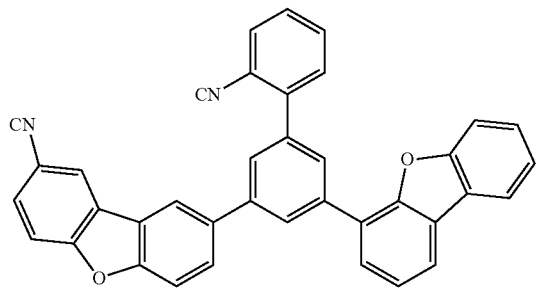
-continued
347
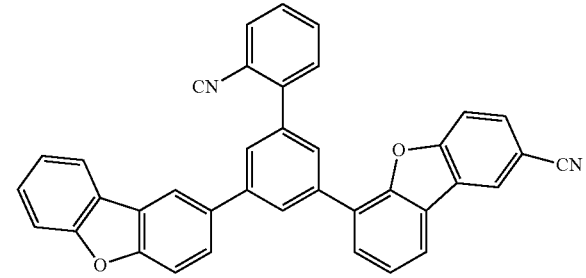
348
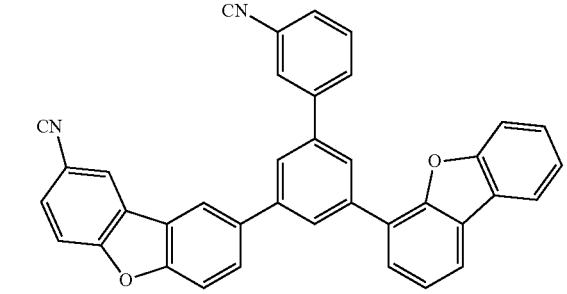
349
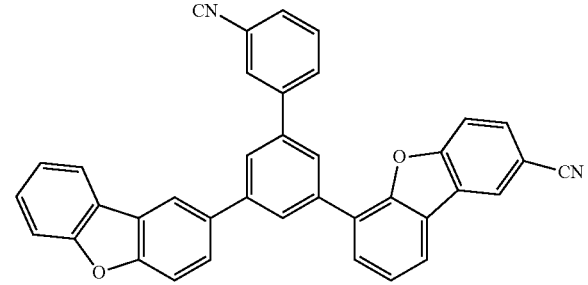
350
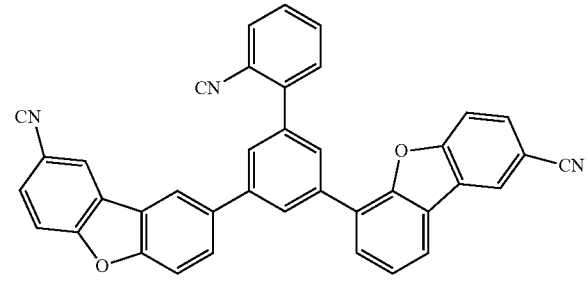
351
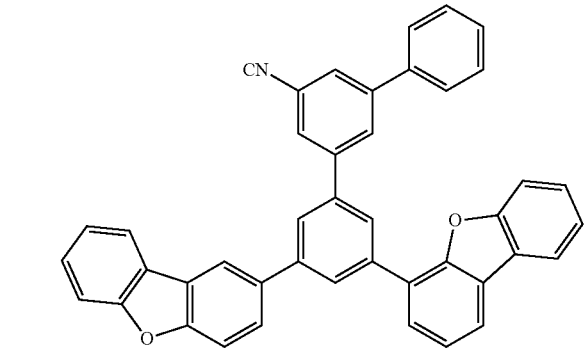

352
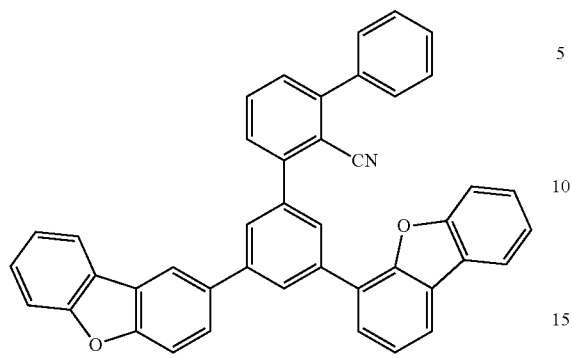
353
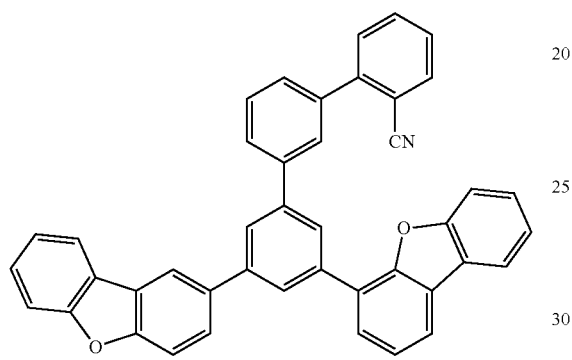
354
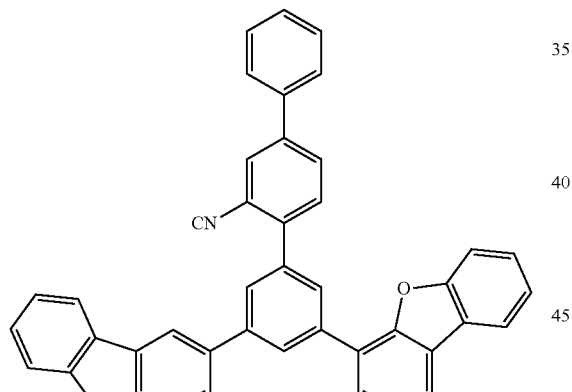
355
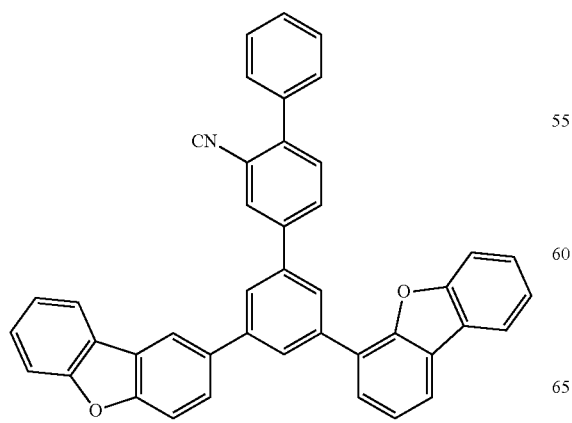
356
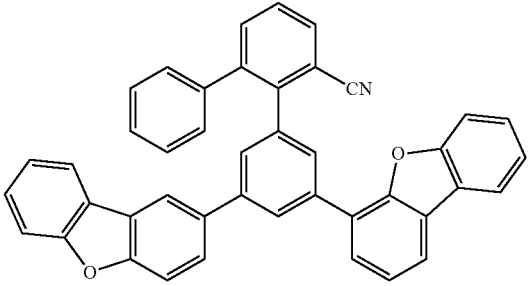
357
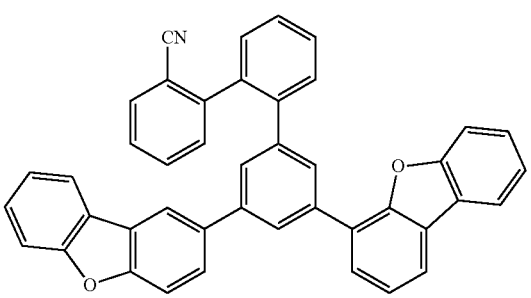
358
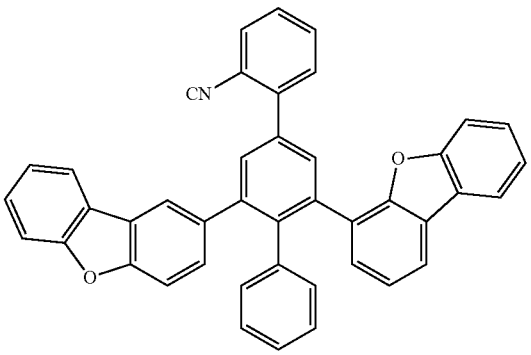
359
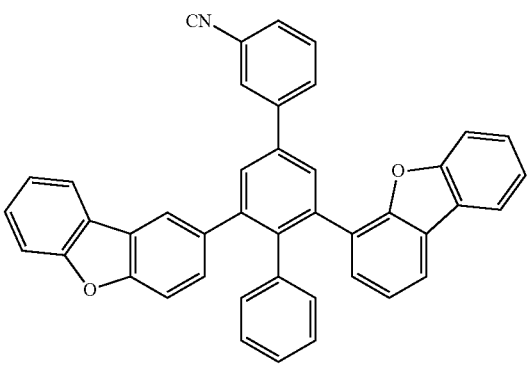

-continued
360
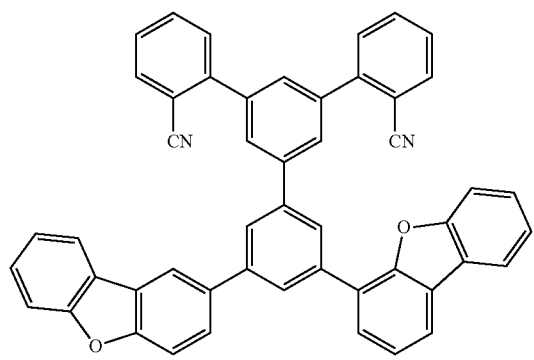
361
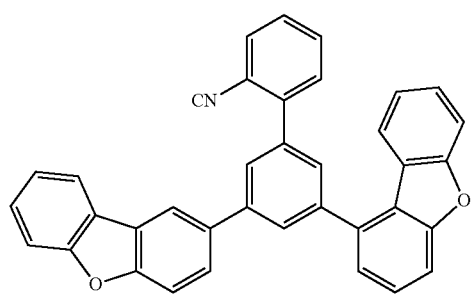
362
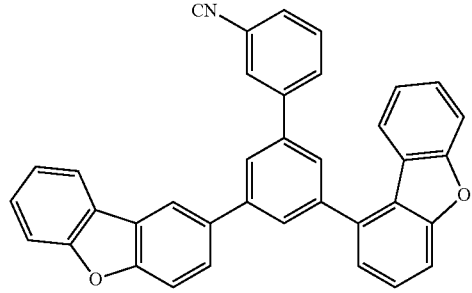
363
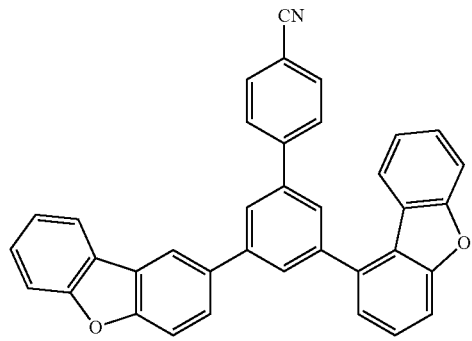
364
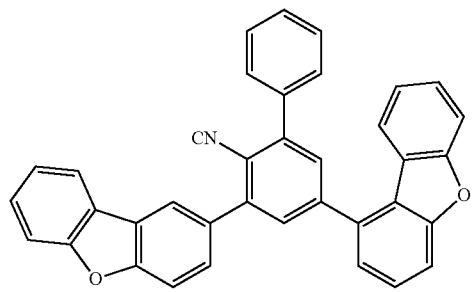
-continued
365
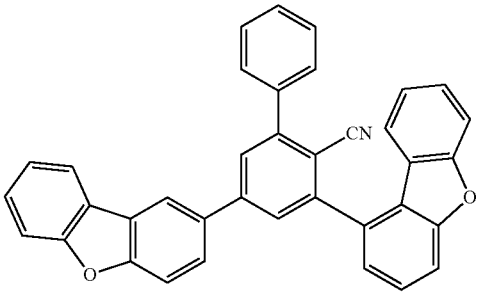
366
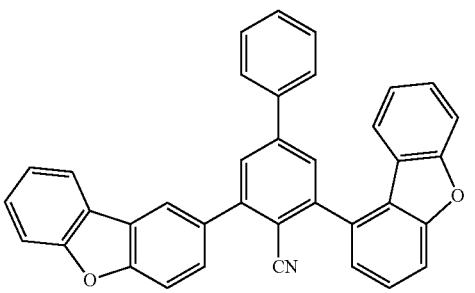
367
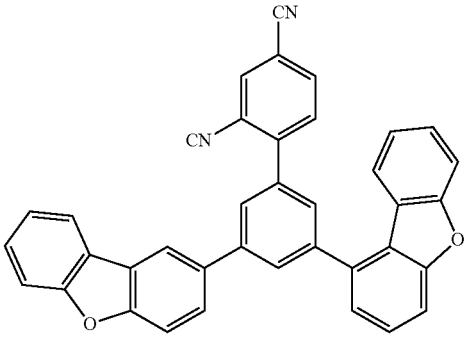
368
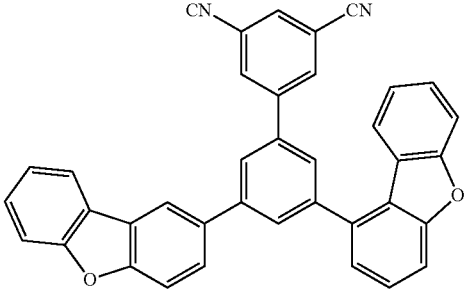
369
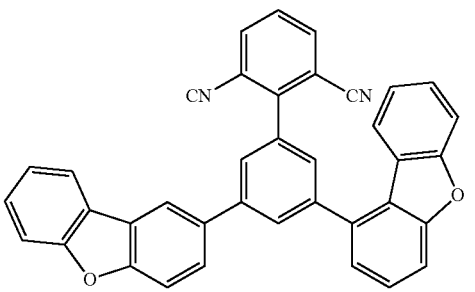

370
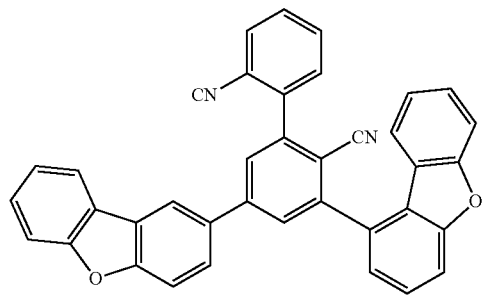
371
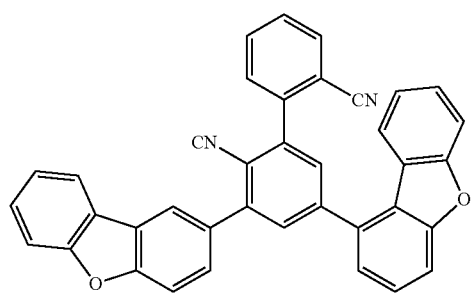
372
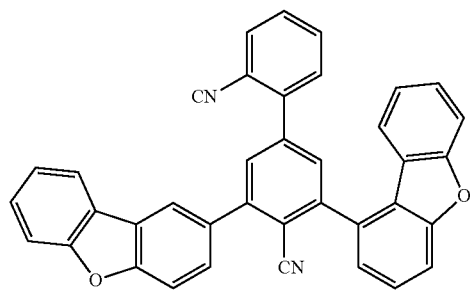
373
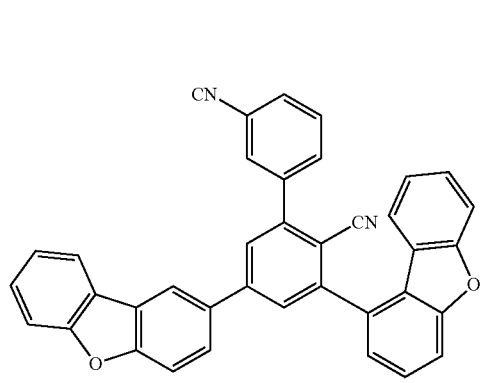
374
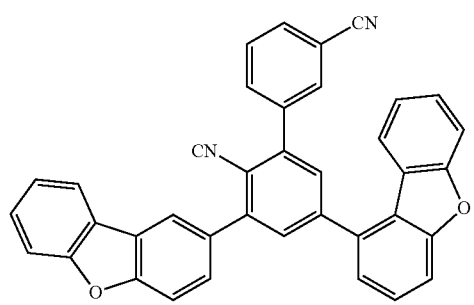
375
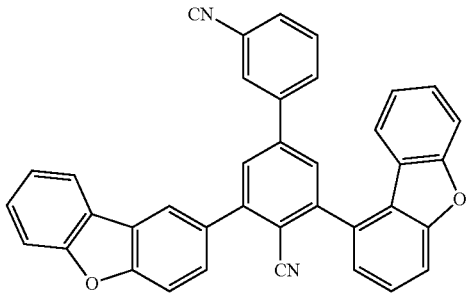
376
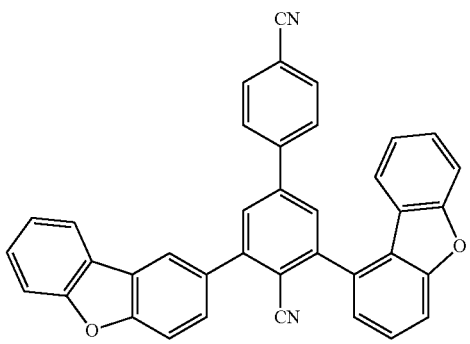
377
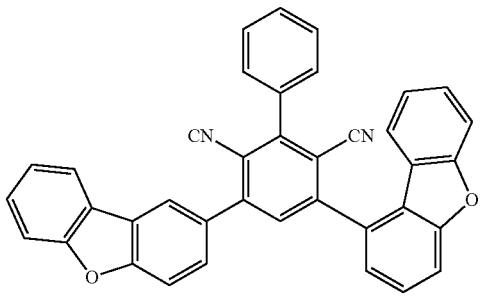
378
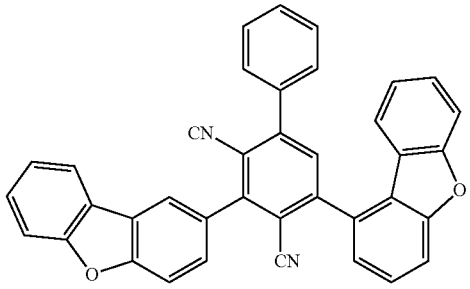
379
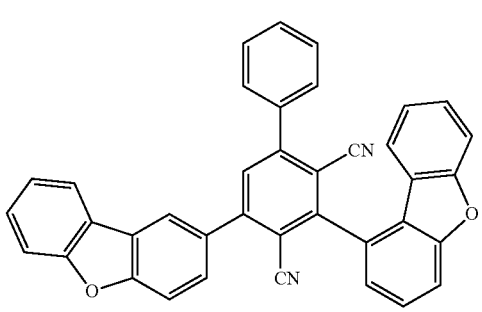

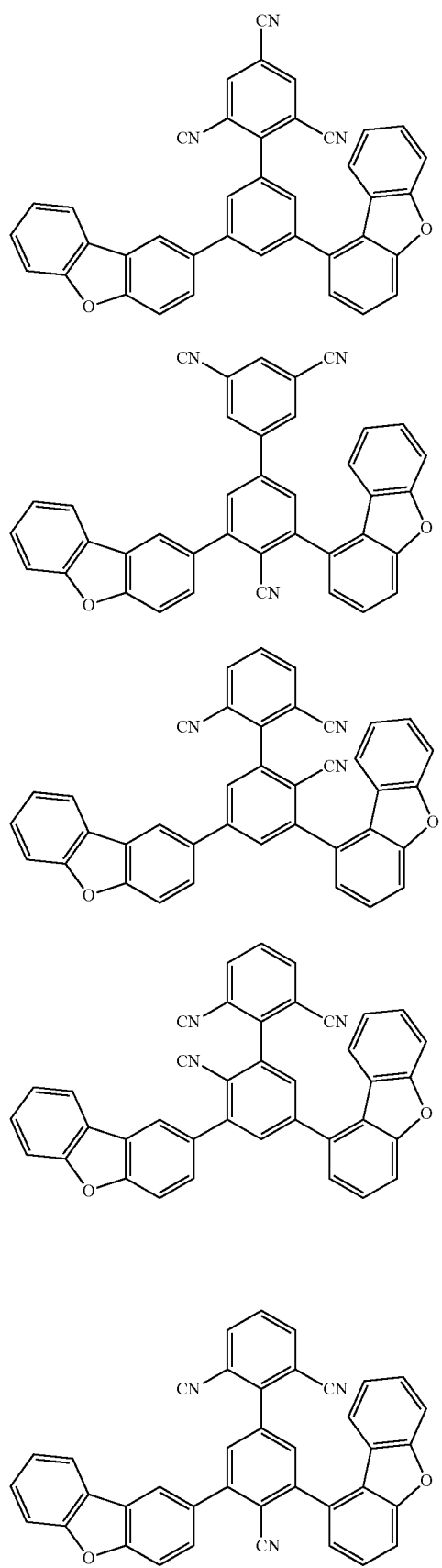
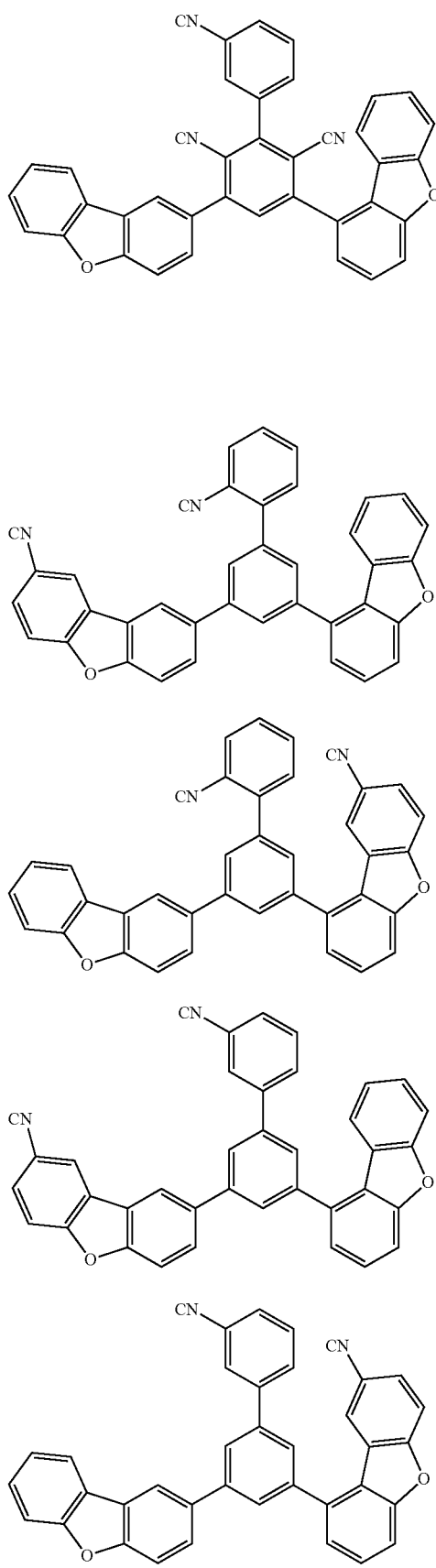

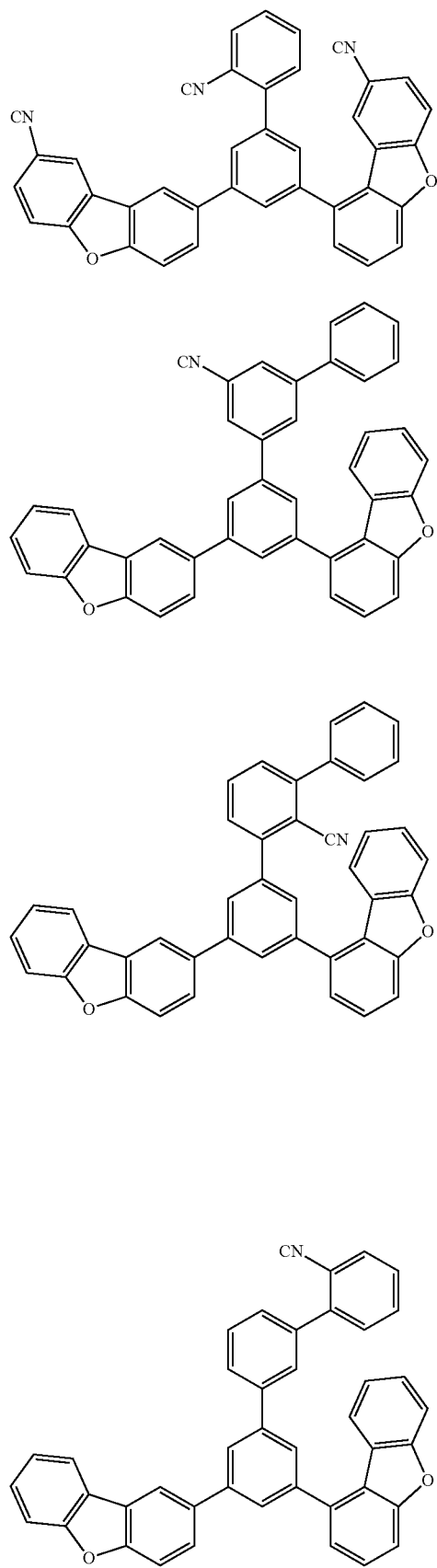
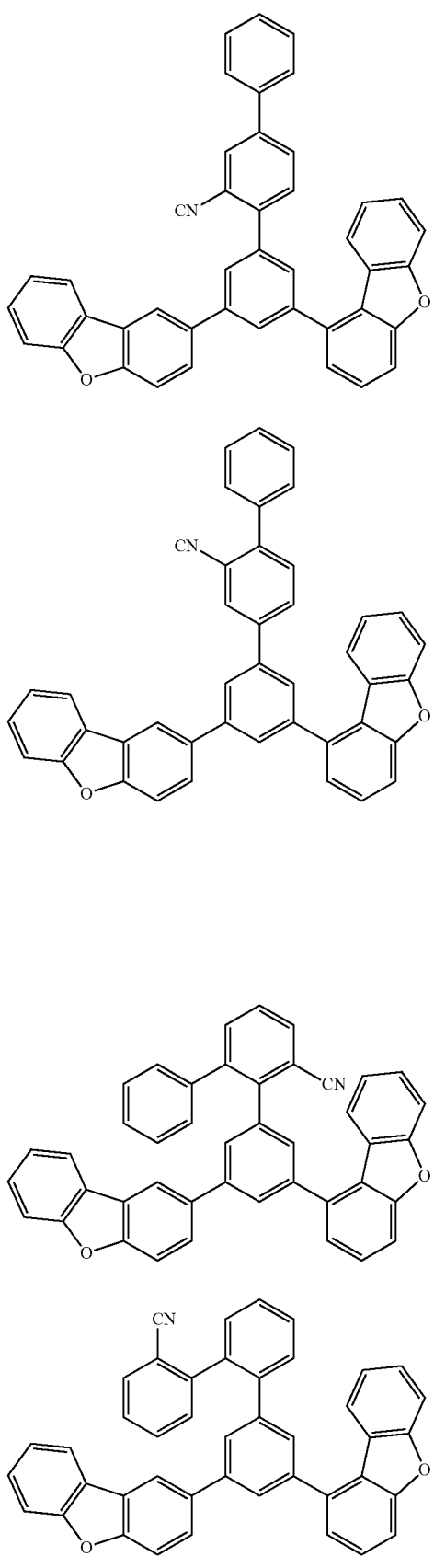

398
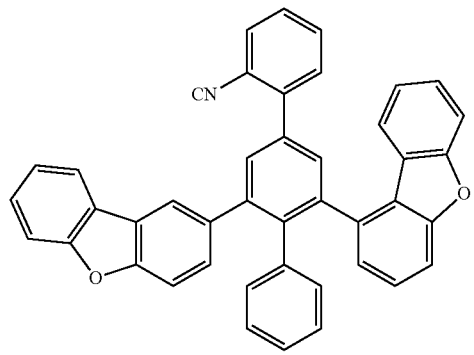
399
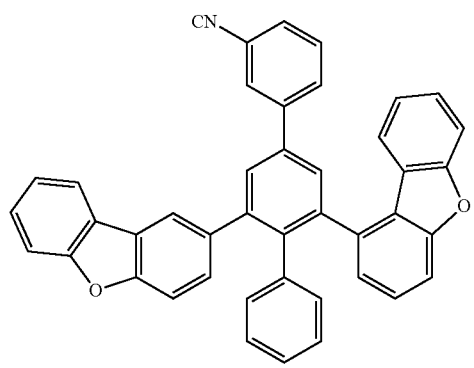
400
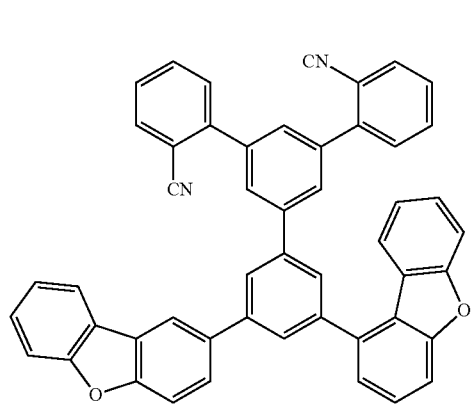
401
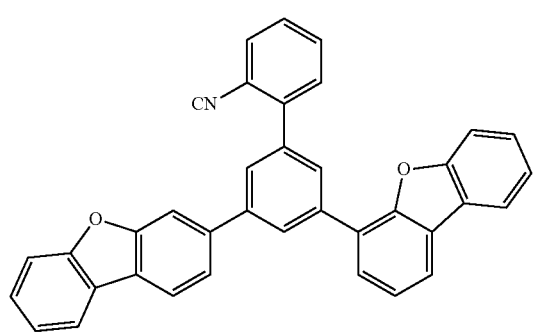
402
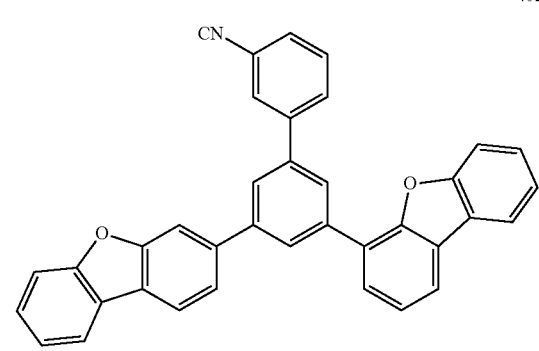
403
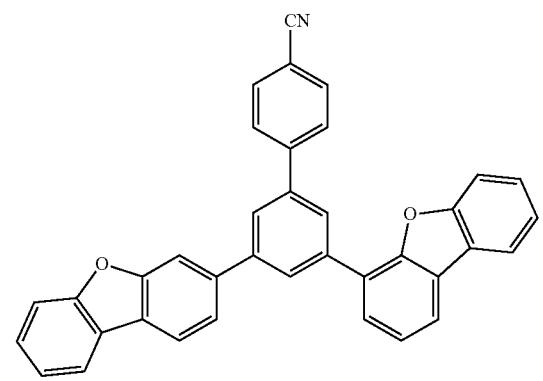
404
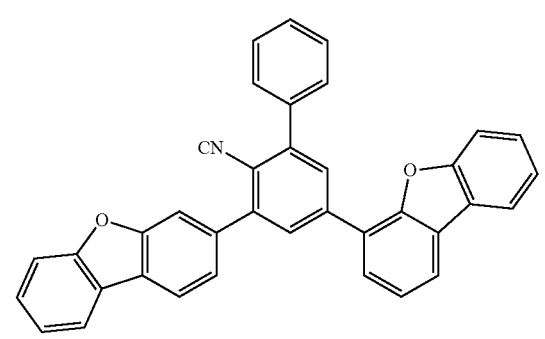
405
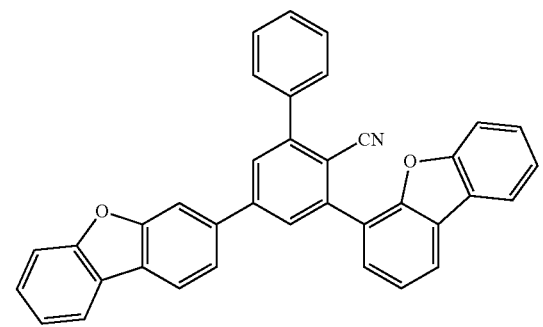

406
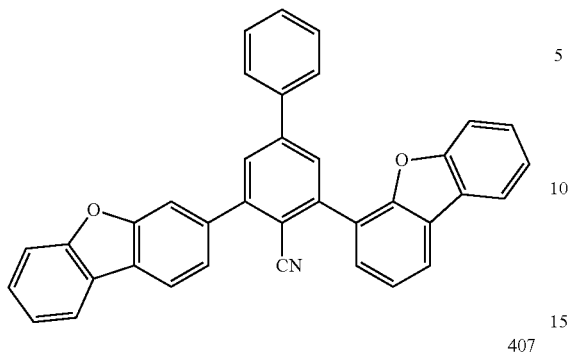
407
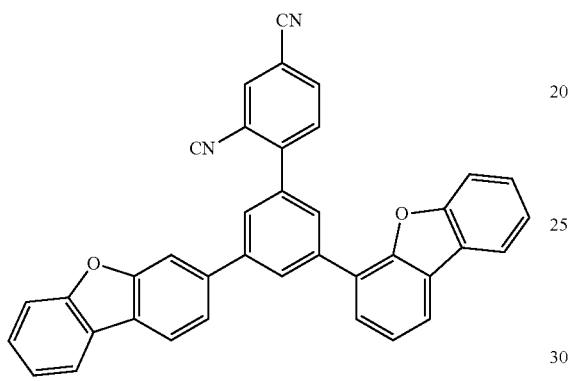
408
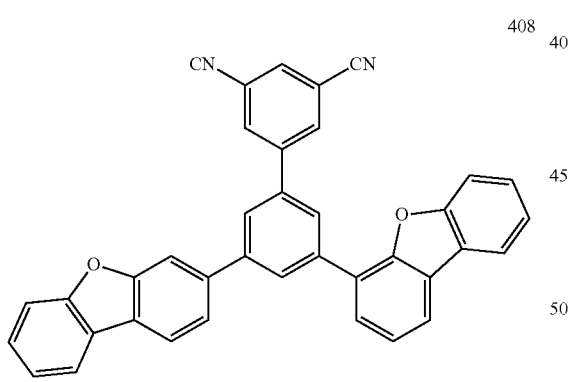
409
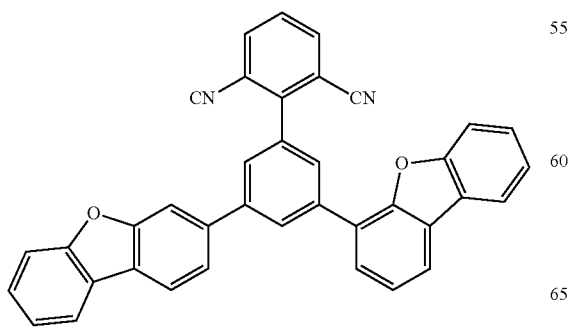
410
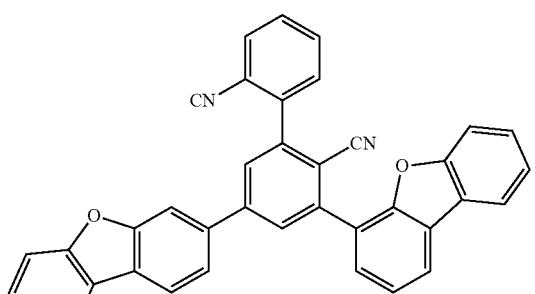
411
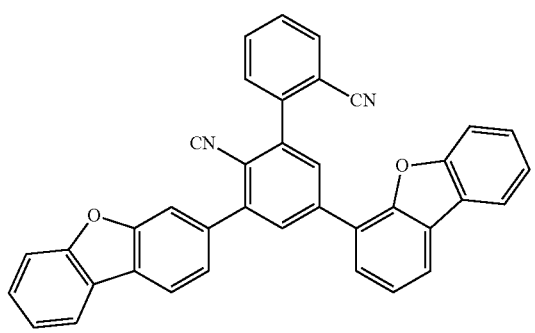
412
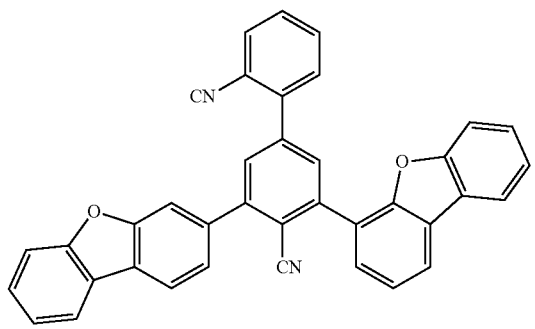
413
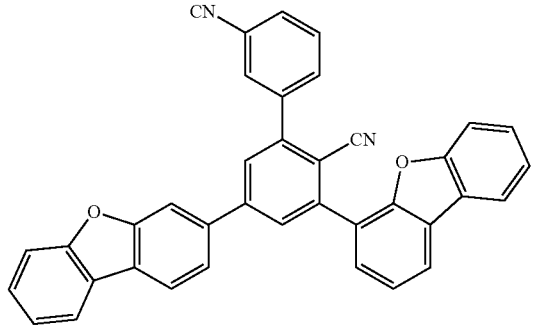

414
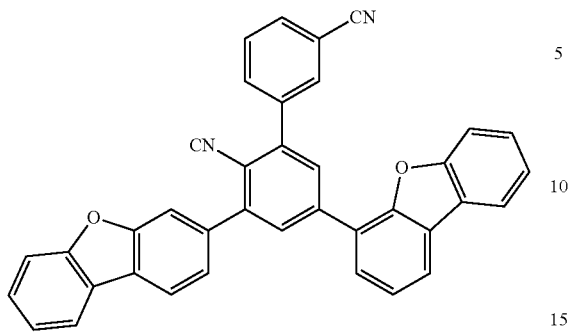
415
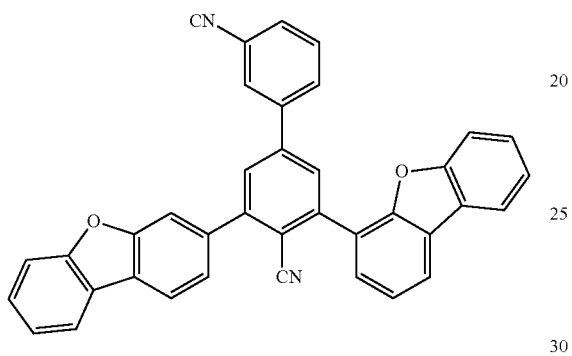
416
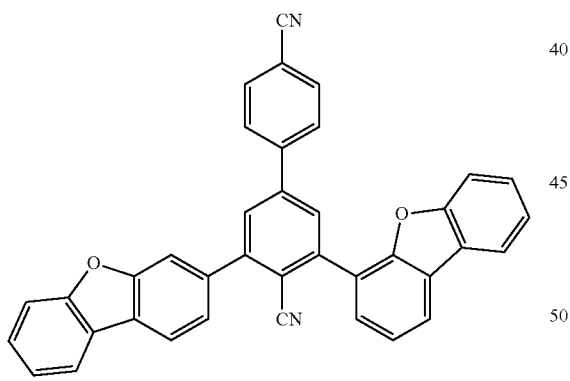
417
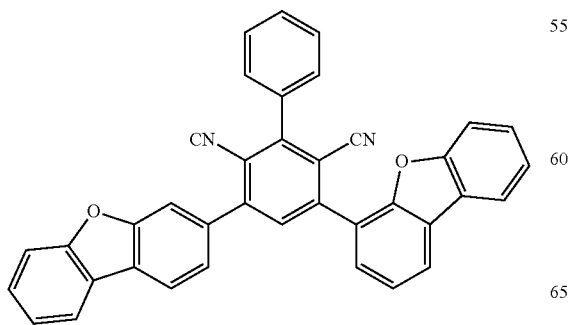
418
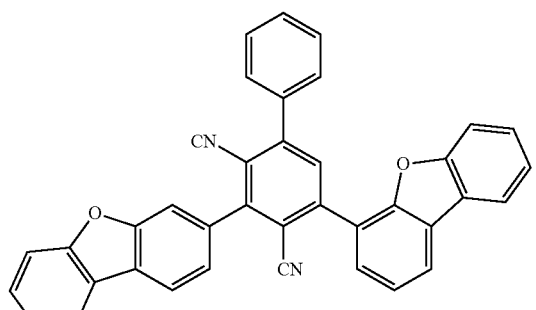
419
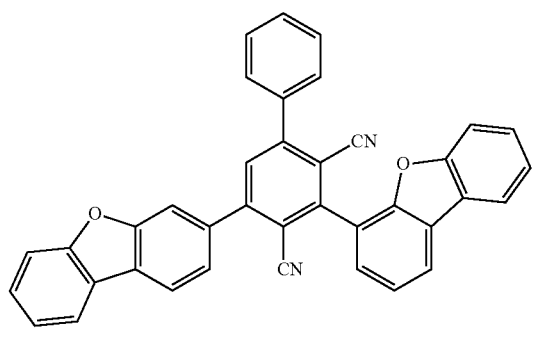
420
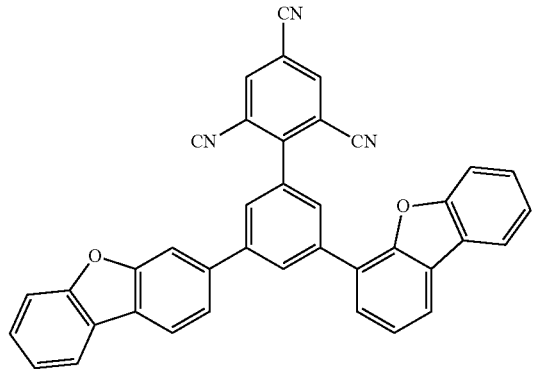
421
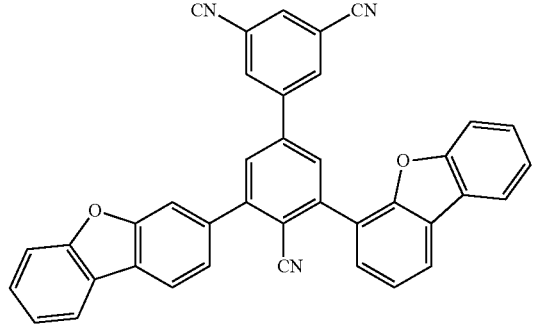

422
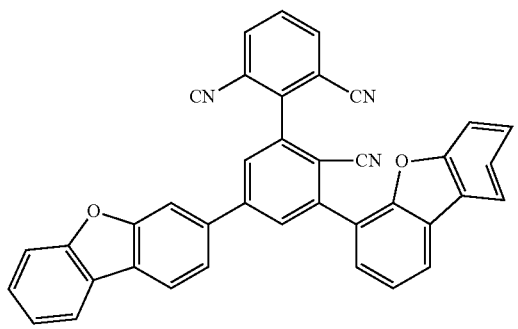
423
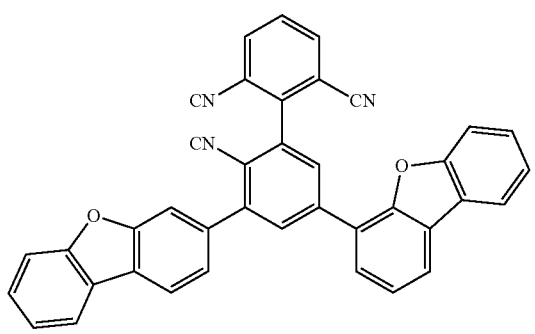
424
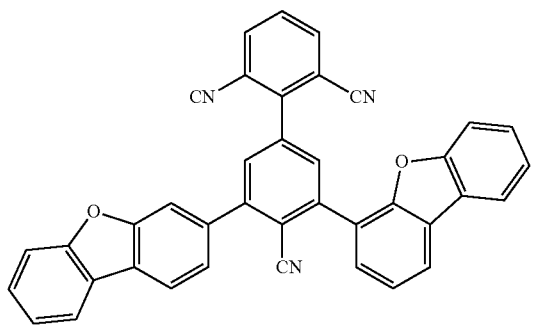
425
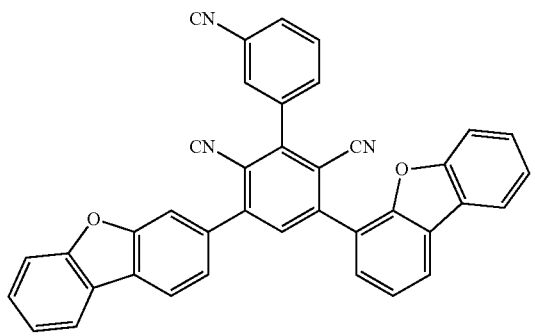
426
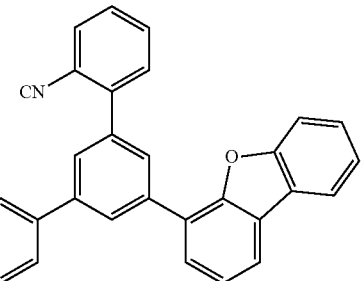
427
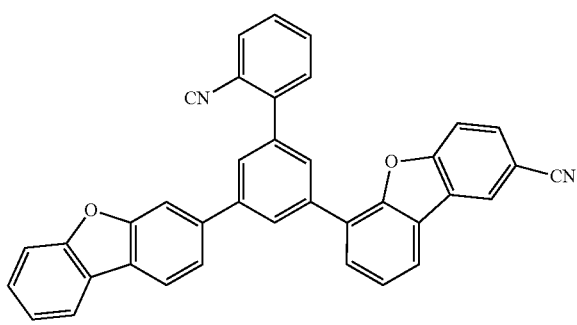
428
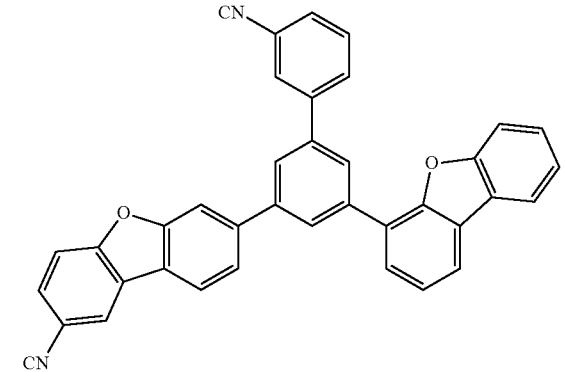
429
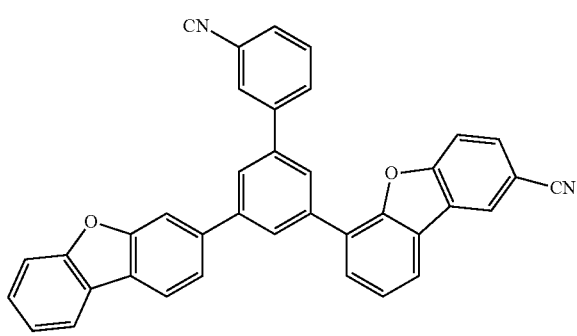

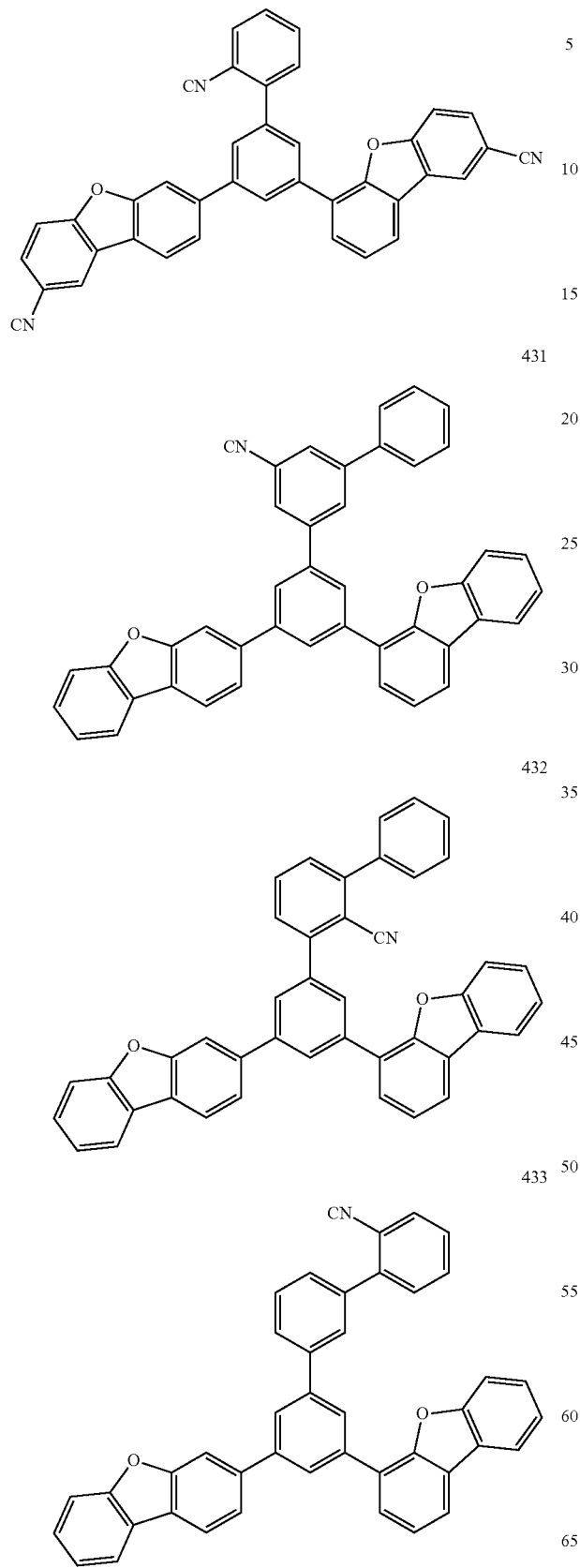

438
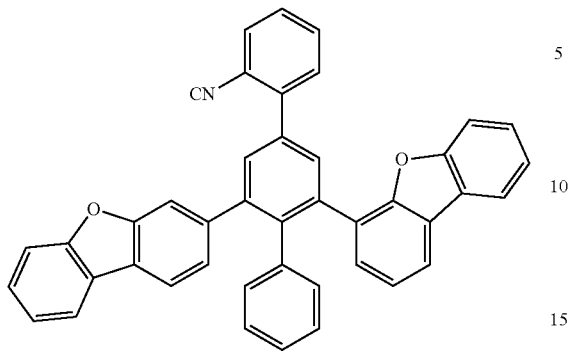
439
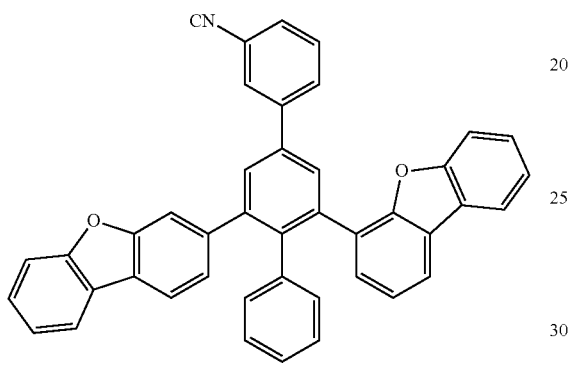
440
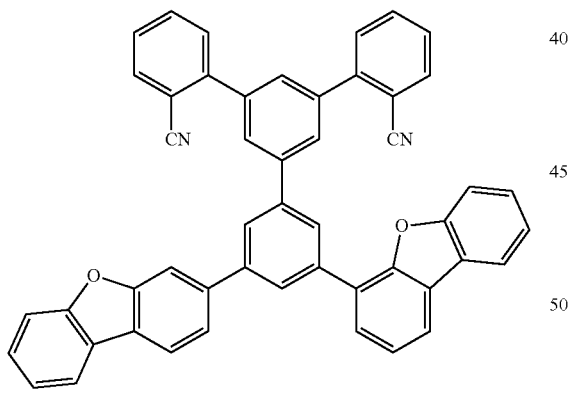
441
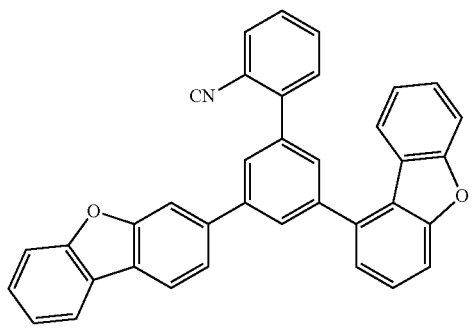
442
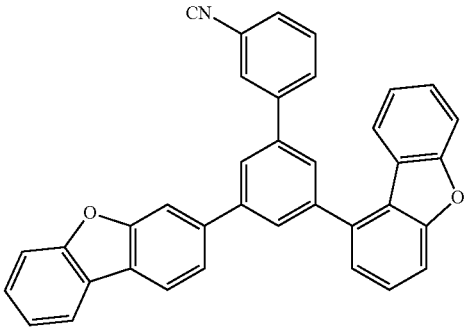
443
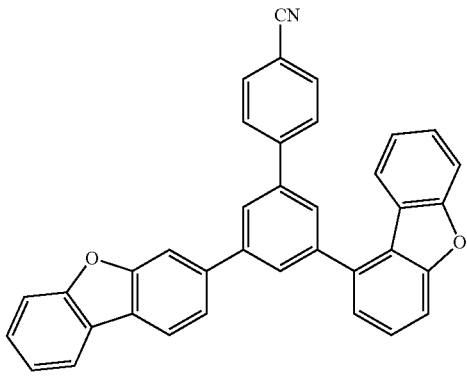
444
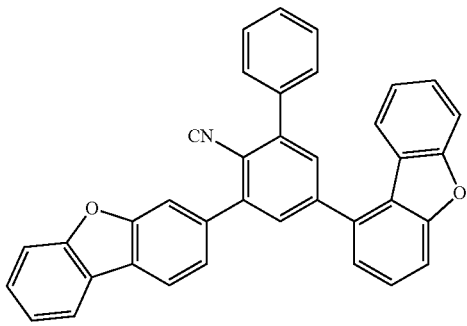
445
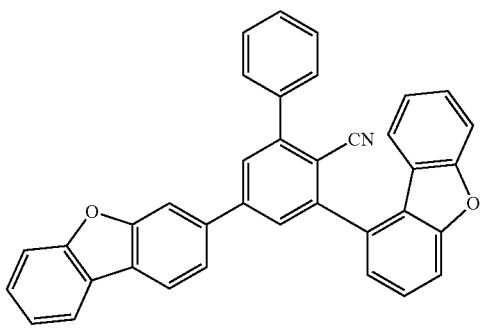

446
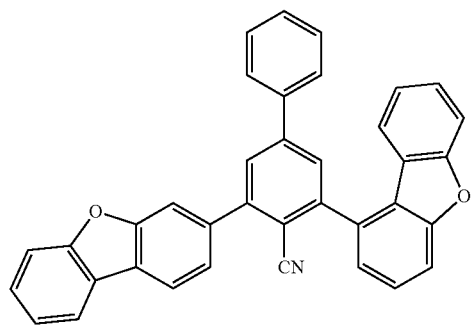
447
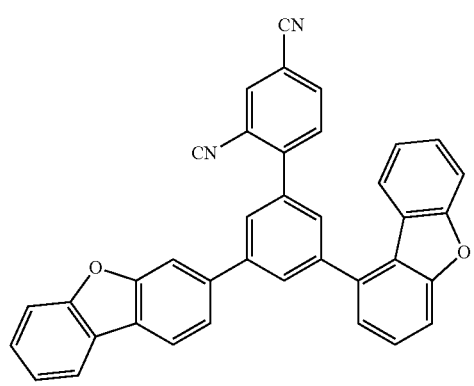
448
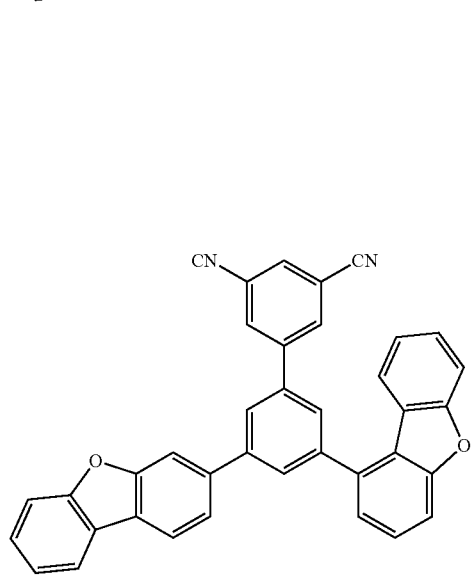
449
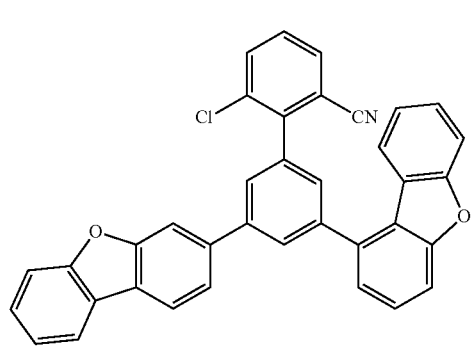
450
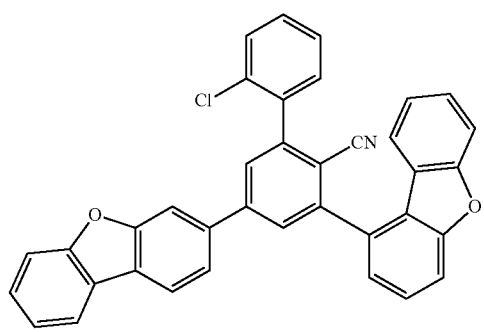
451
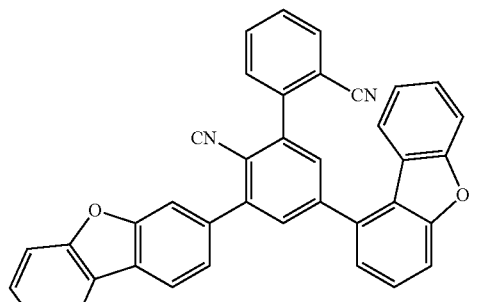
452
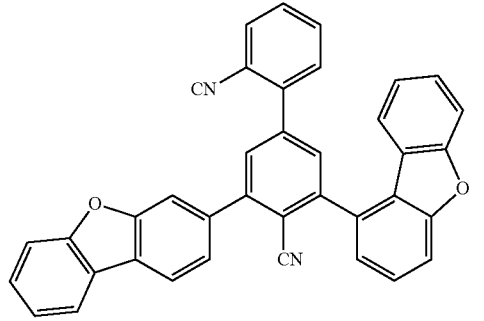
453
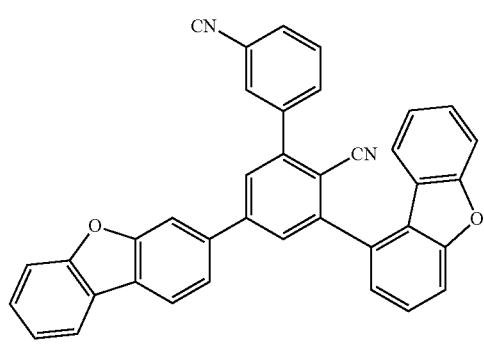

454 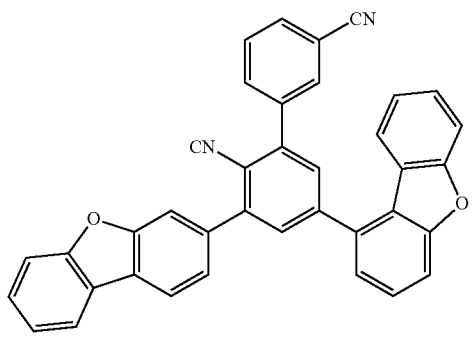
455 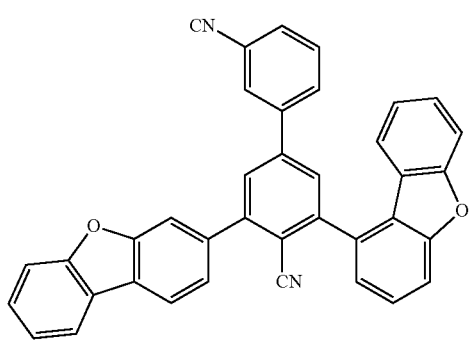
456 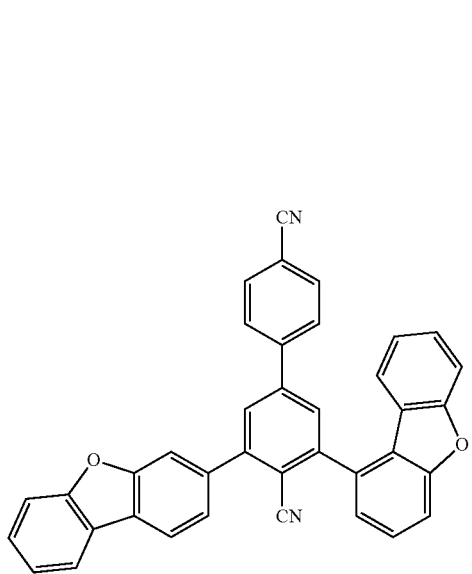
457 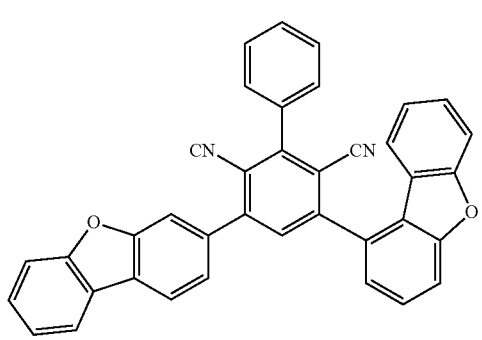
458 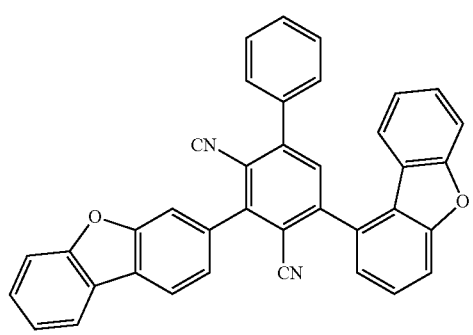
459 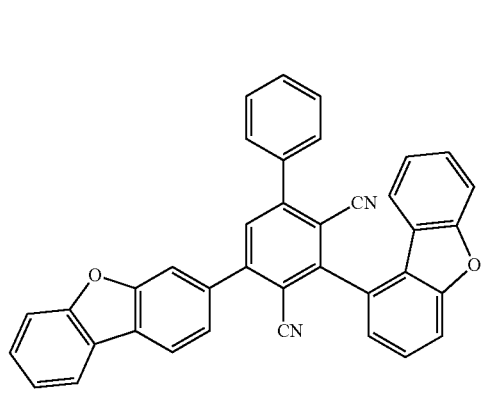
460 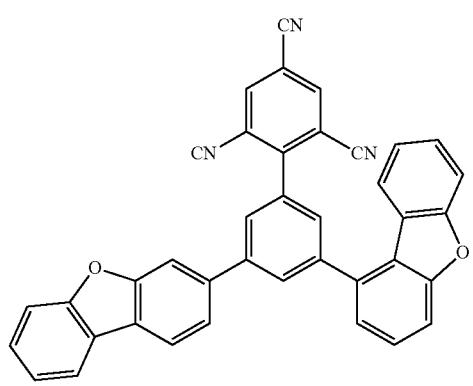
461 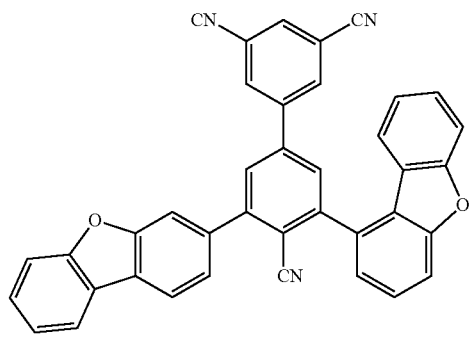

| 462 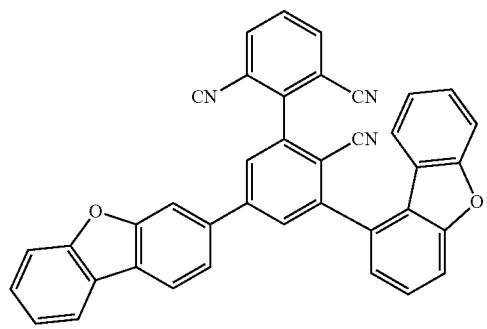 | 466 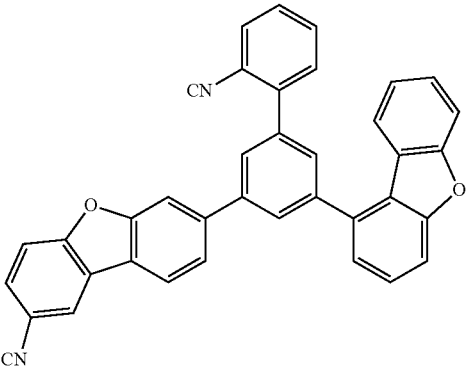 |
| 463 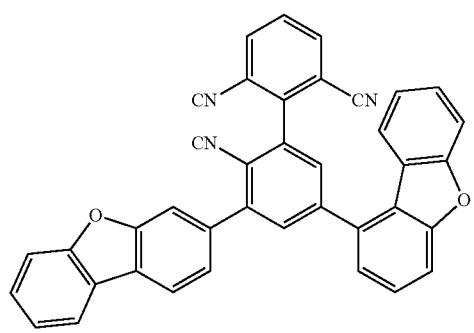 | 467 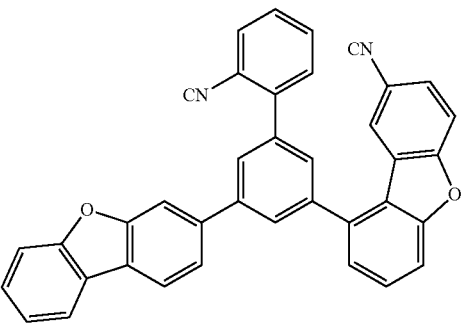 |
| 464 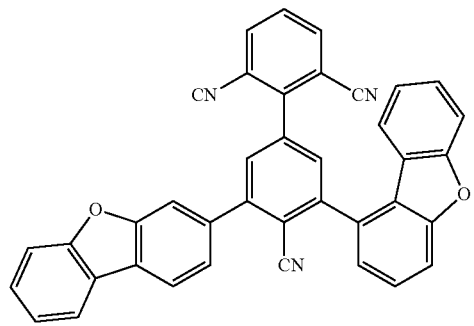 | 468 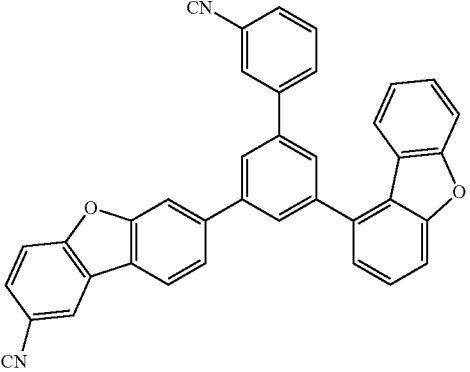 |
| 465 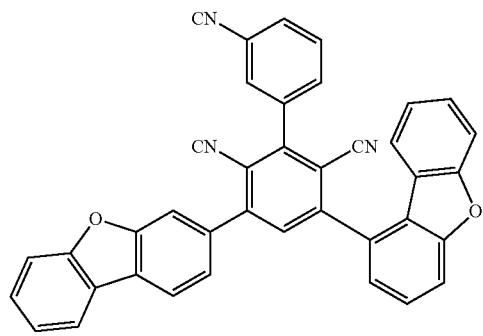 | 469 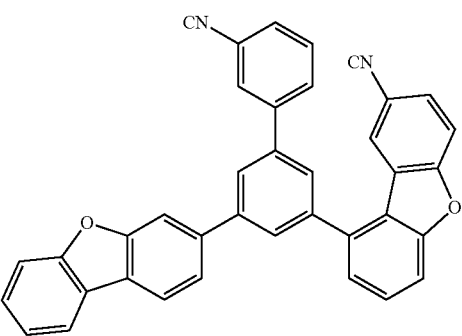 |

149
-continued
470
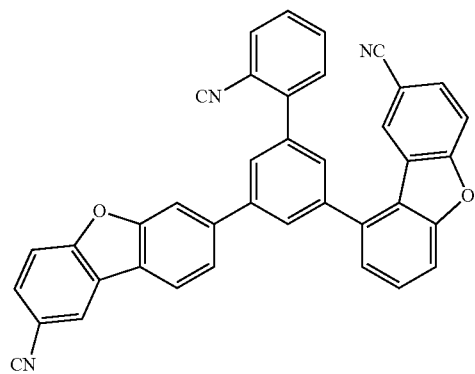
471
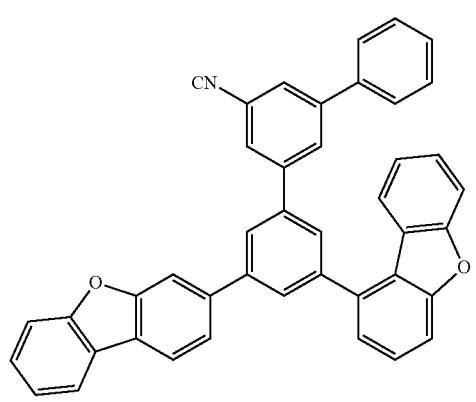
472
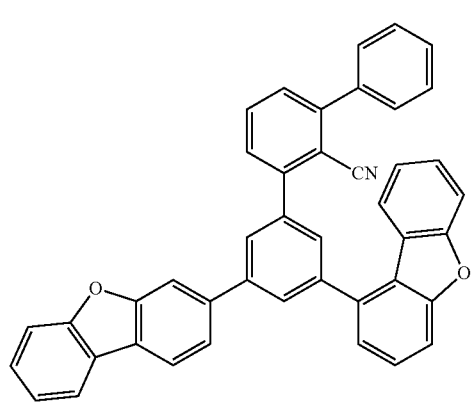
473
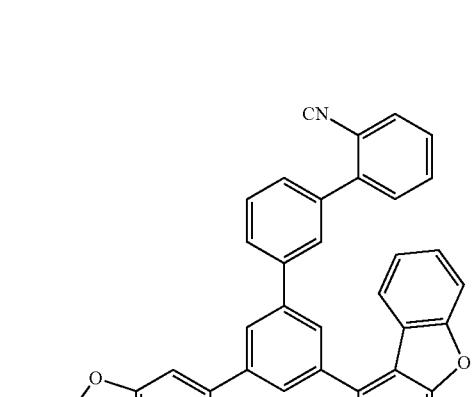
150
-continued
474
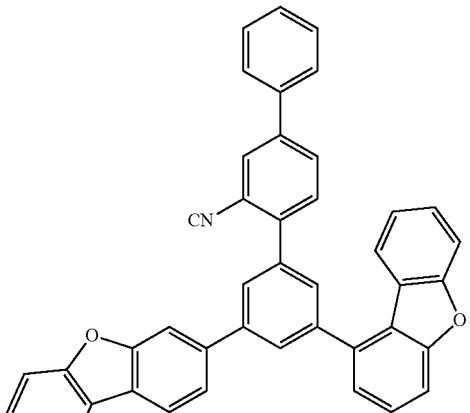
475
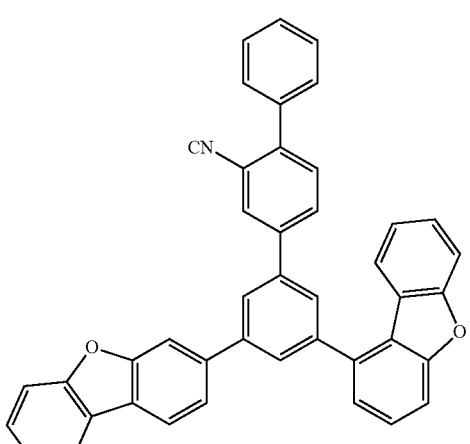
476
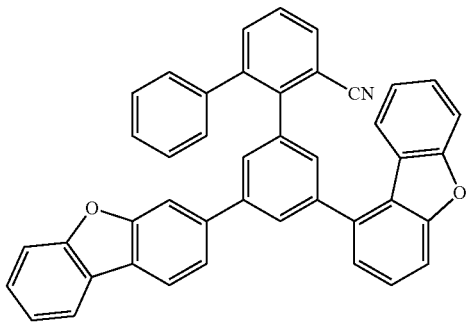
477
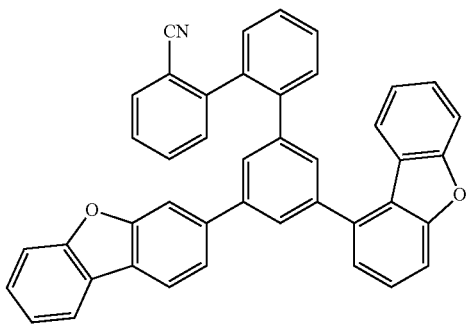

151
-continued
478
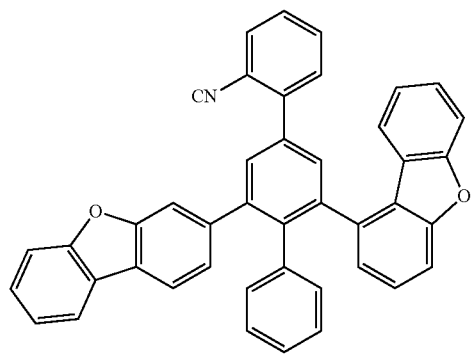
479
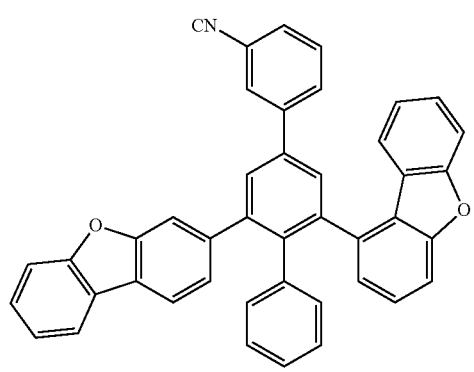
480
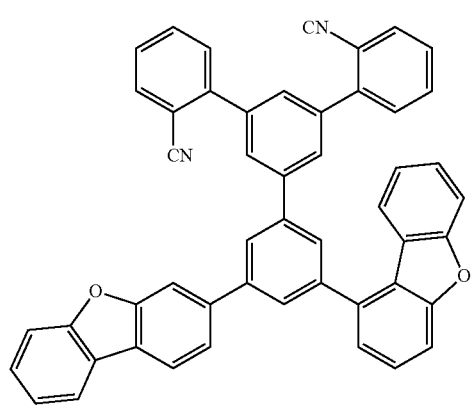
481
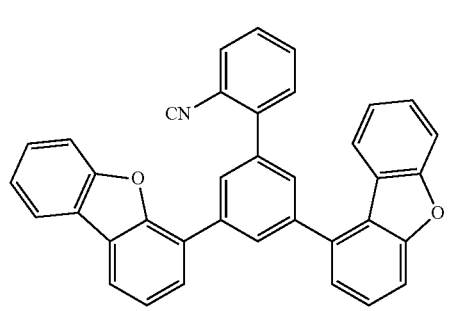
152
-continued
482
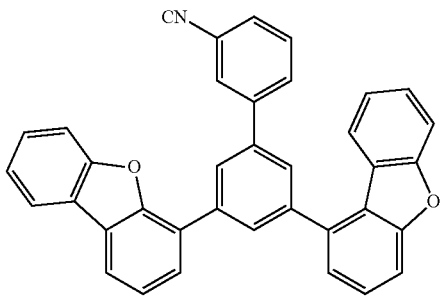
483
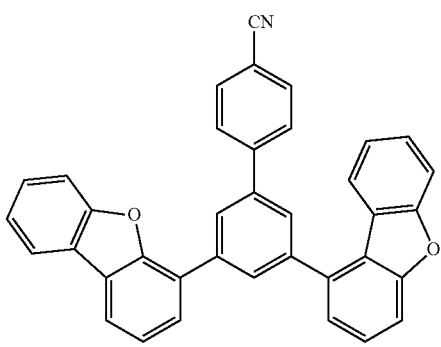
484
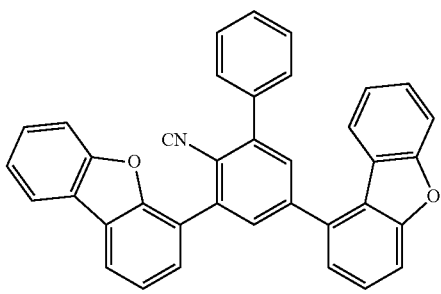
485
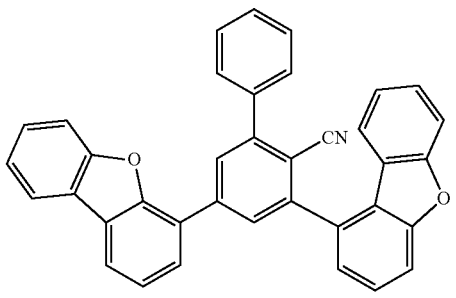
486
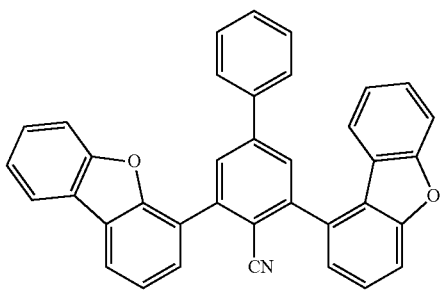

487
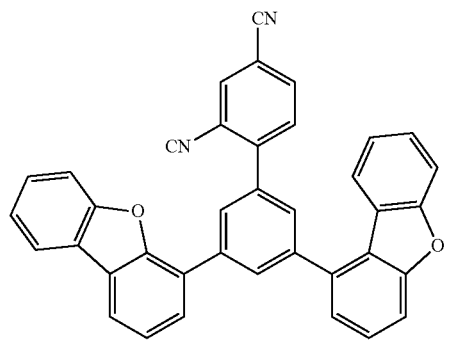
488
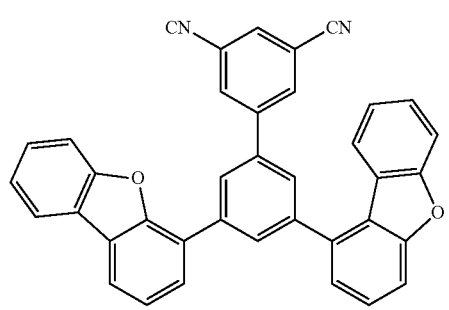
489
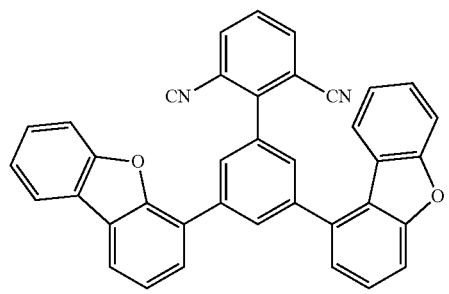
490
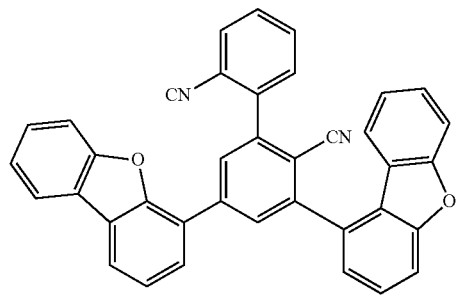
491
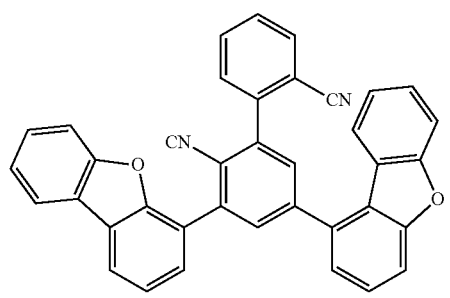
492
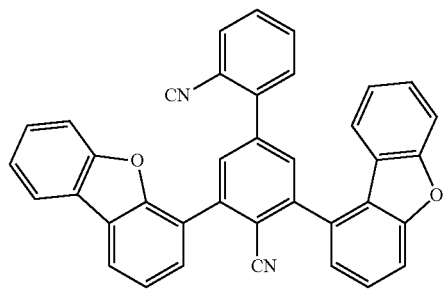
493
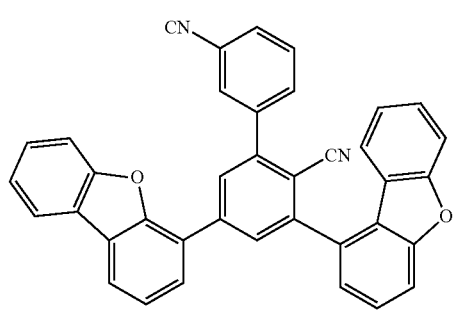
494
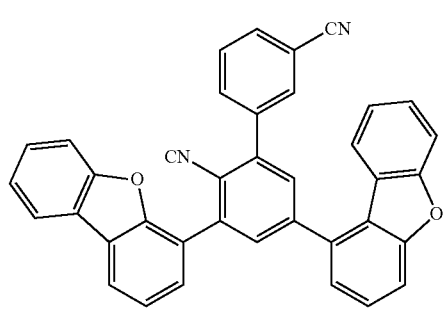
495
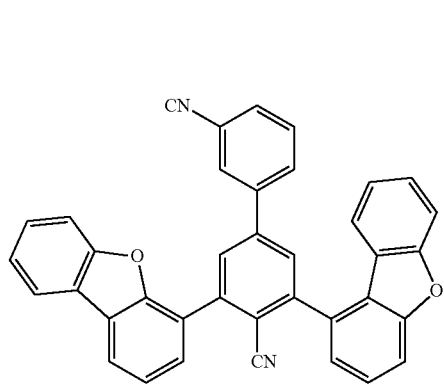
496
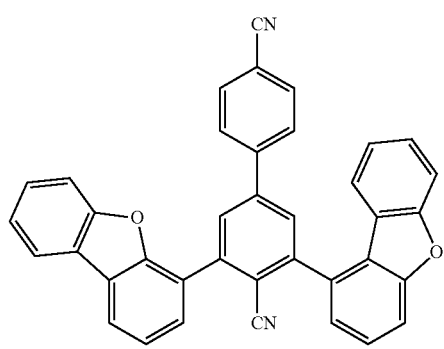

497
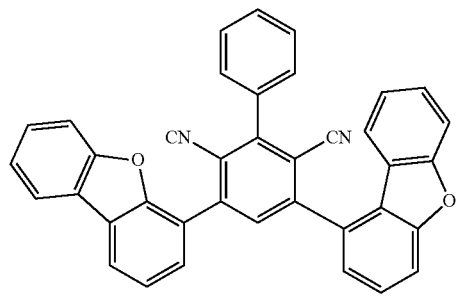
498
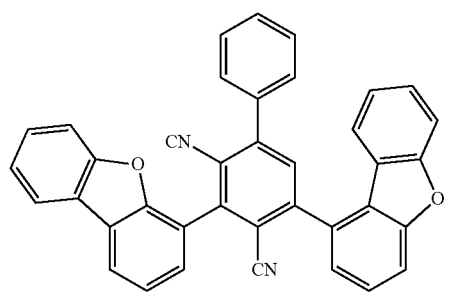
499
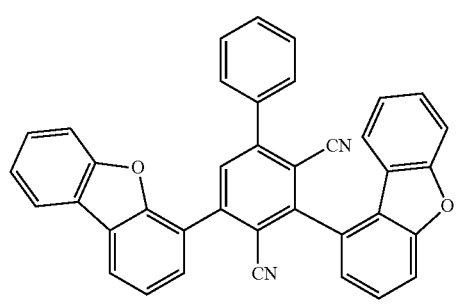
500
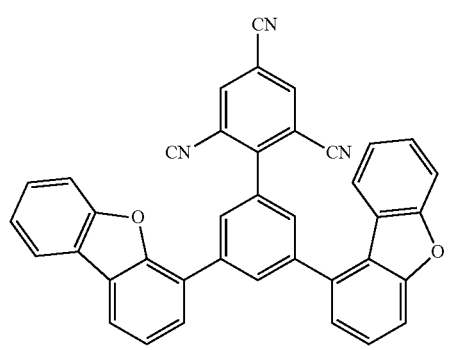
501
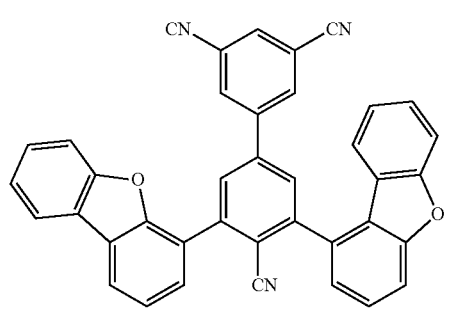
502
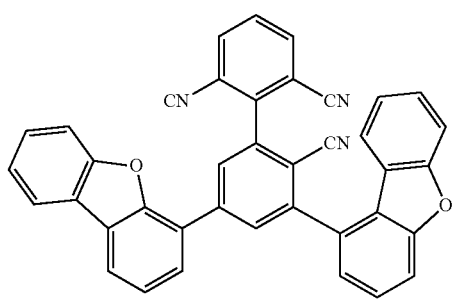
503
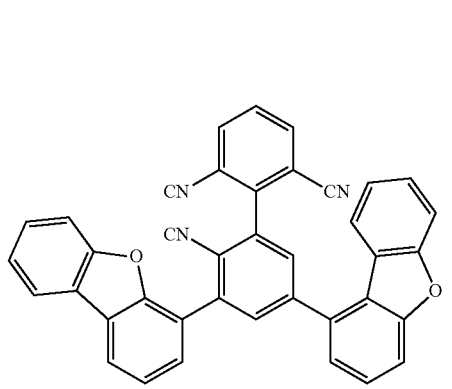
504
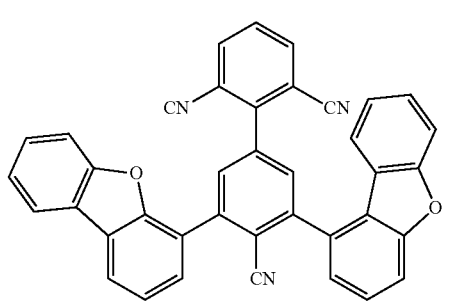
505
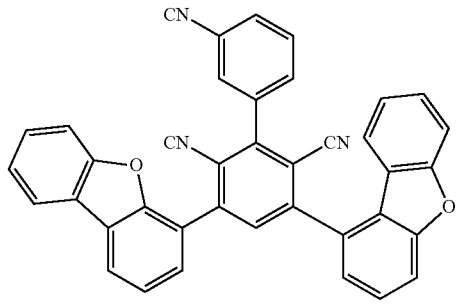
506
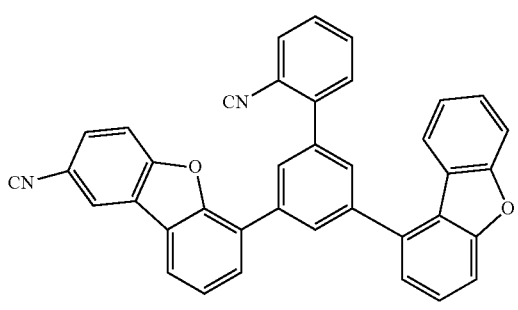

507
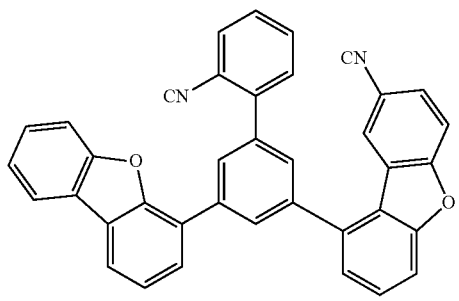
508
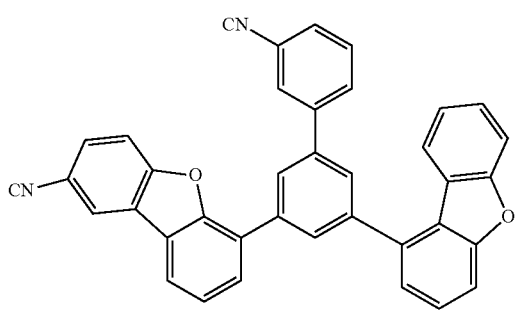
509
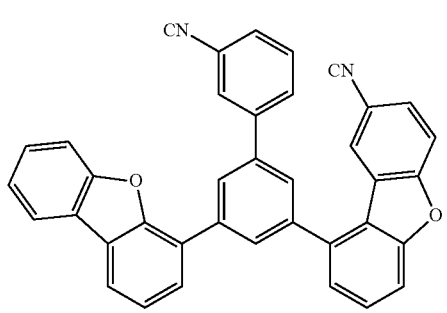
510
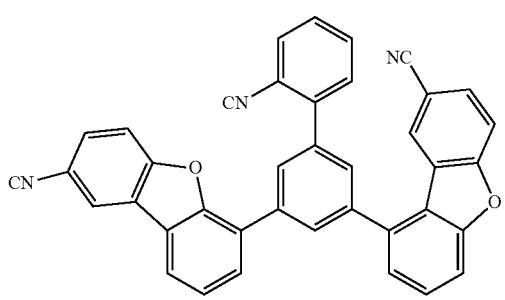
511
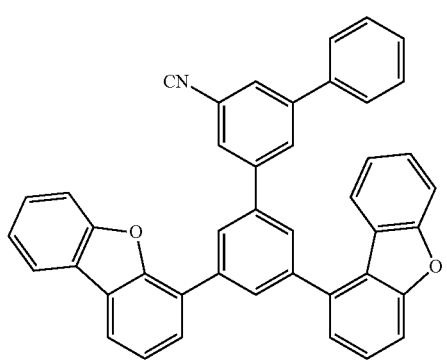
512
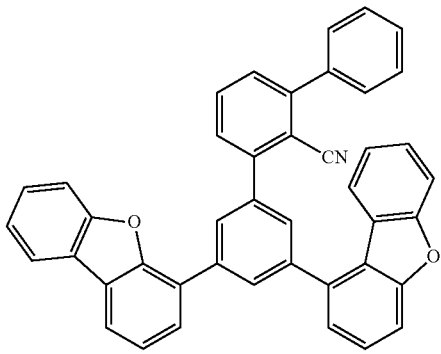
513
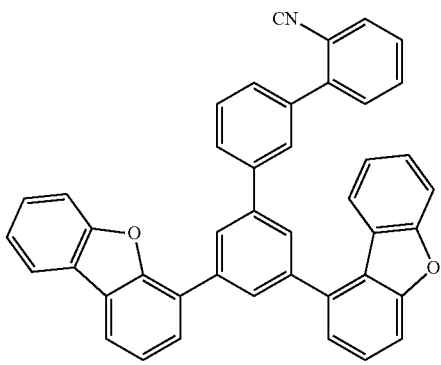
514
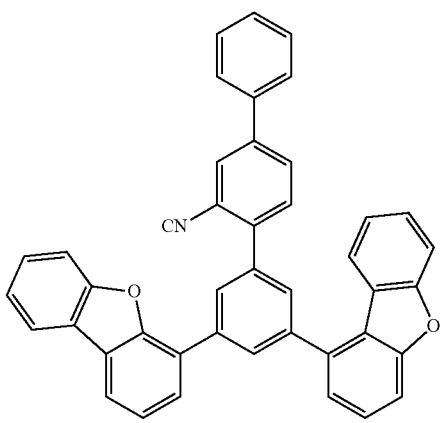
515
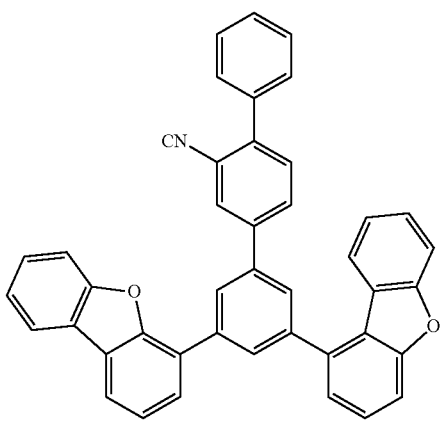

516
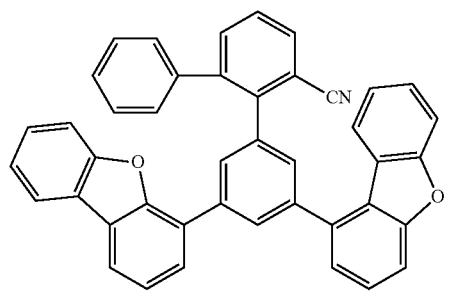
517
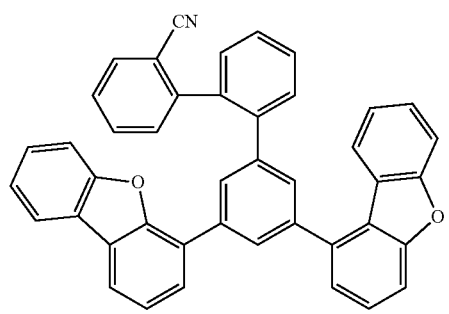
518
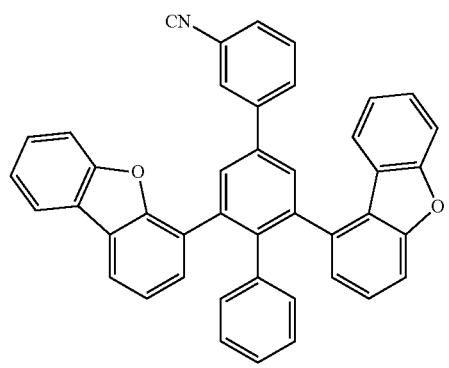
519
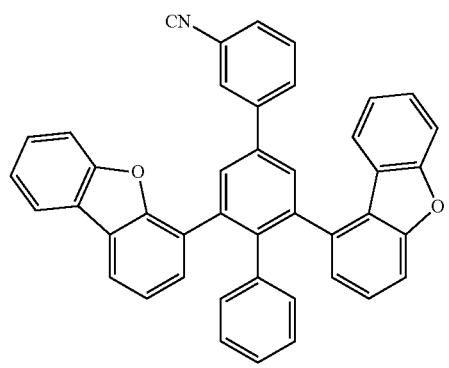
520
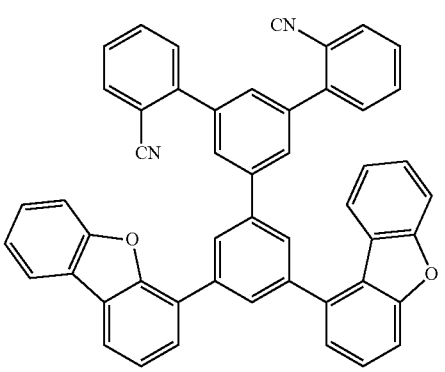
521
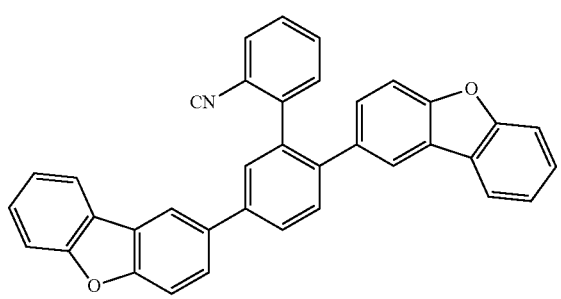
522
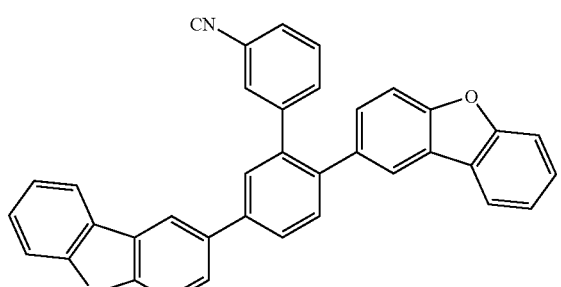
523
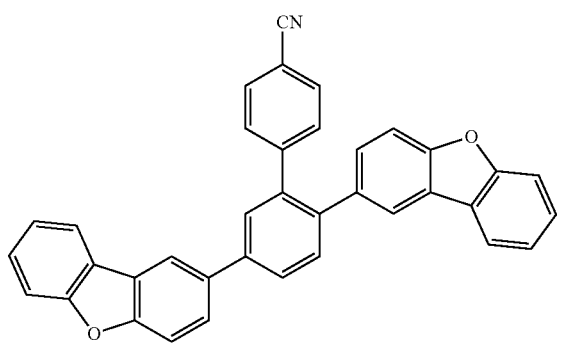

-continued
524
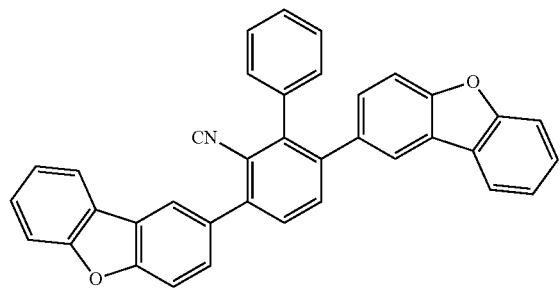
525
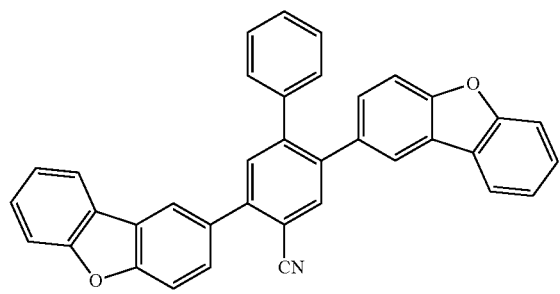
526
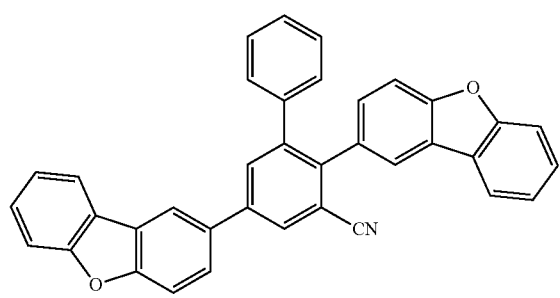
527
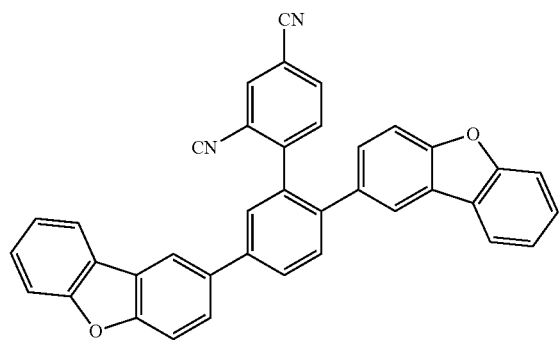
528
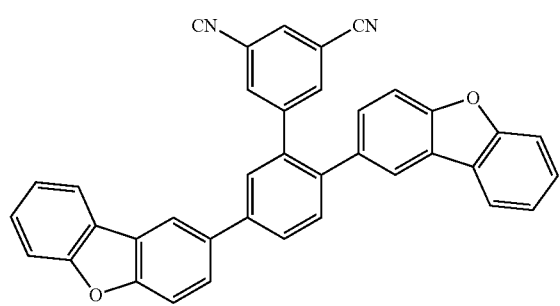
-continued
529
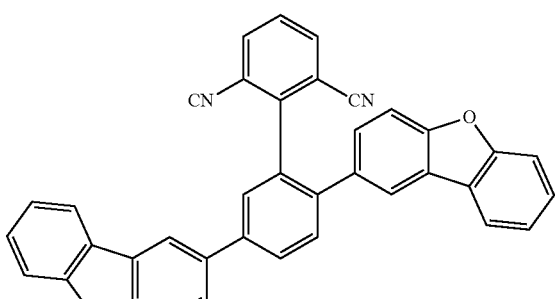
530
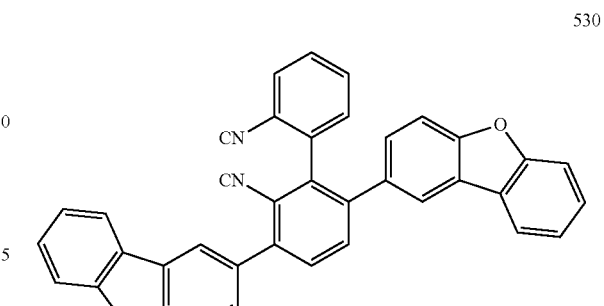
531
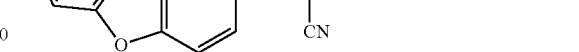
532
533

534
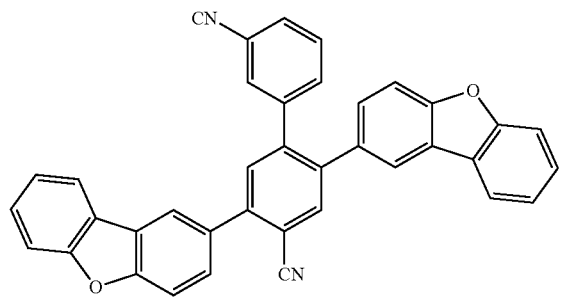
535
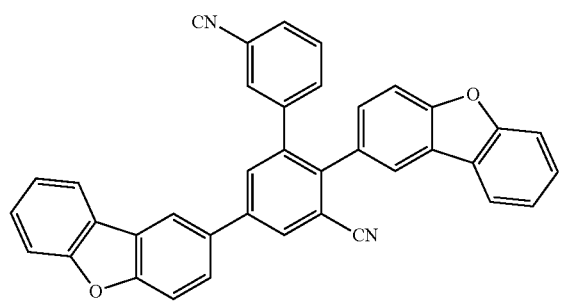
536
537
538
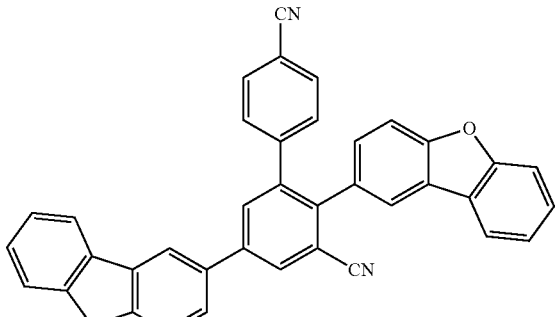
539
540
541
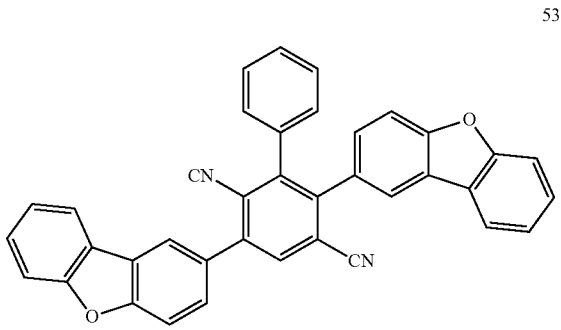
542

543
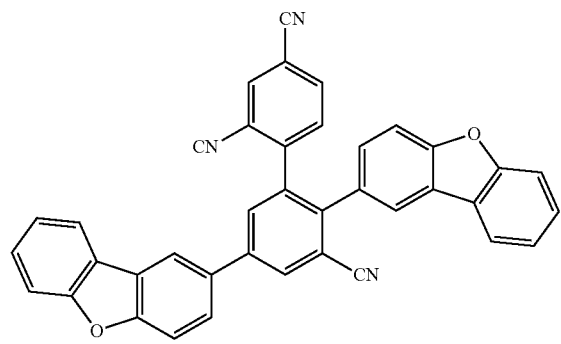
544
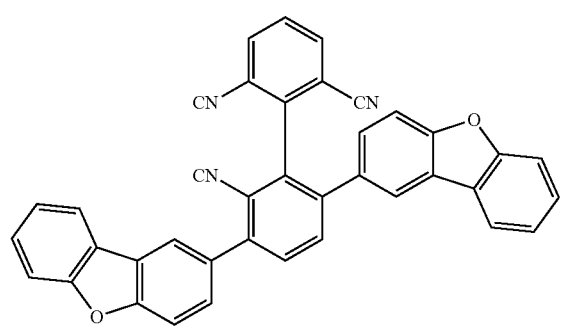
545
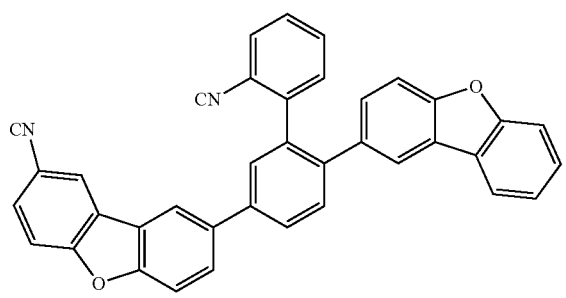
546
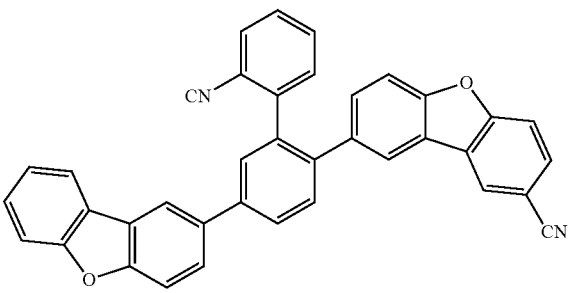
547
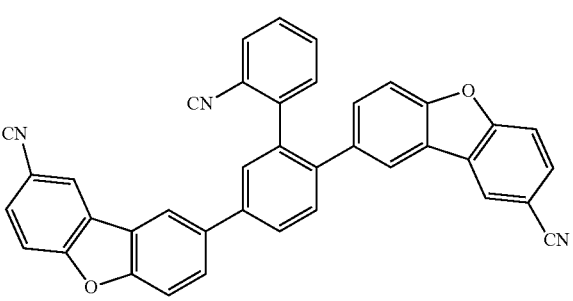
548
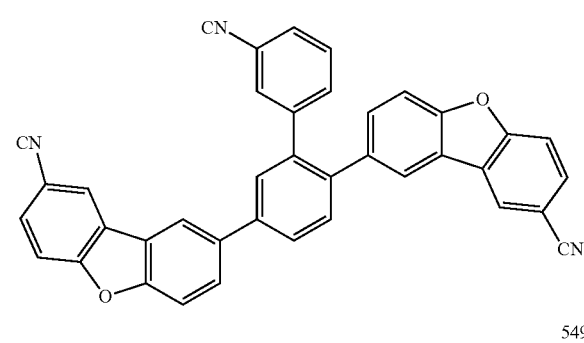
549
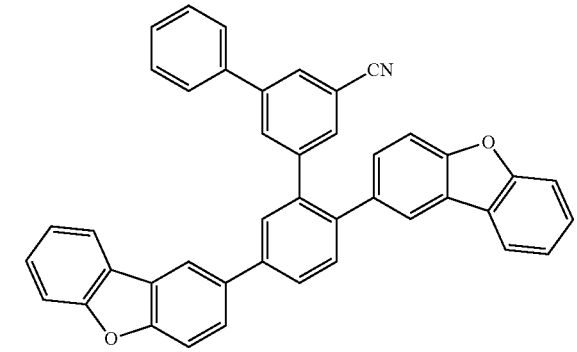
550
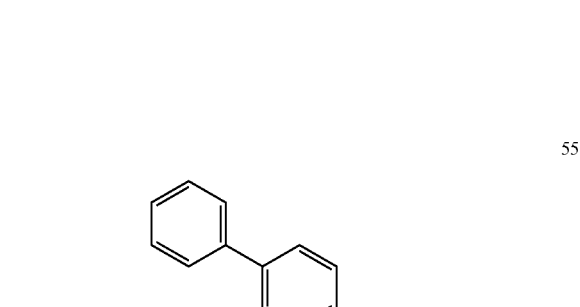
551
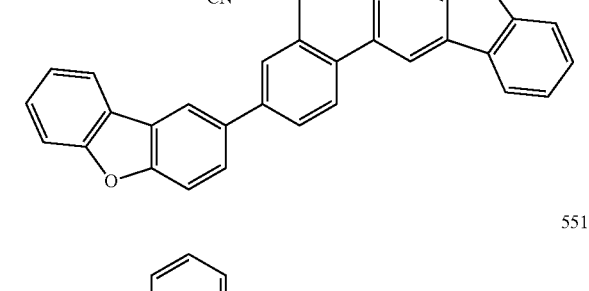
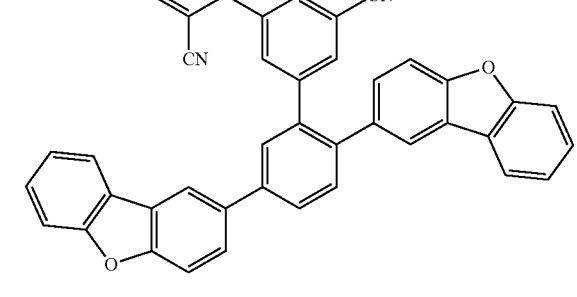

552
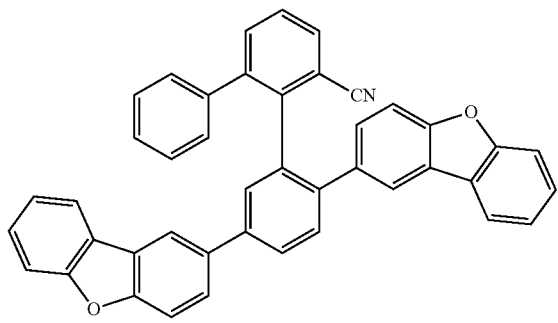
553
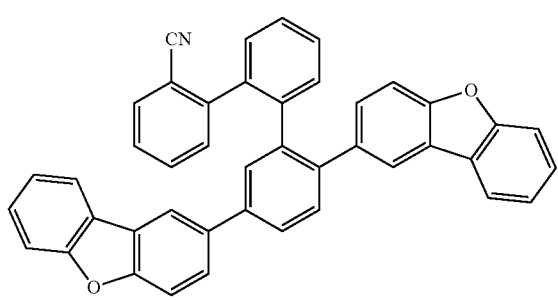
554
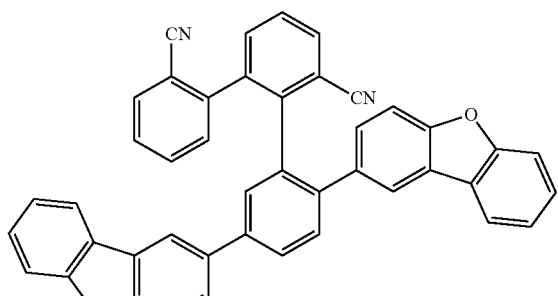
555
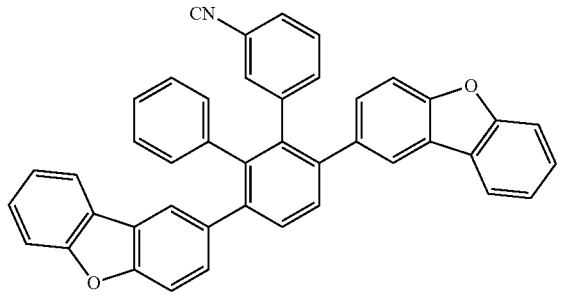
556
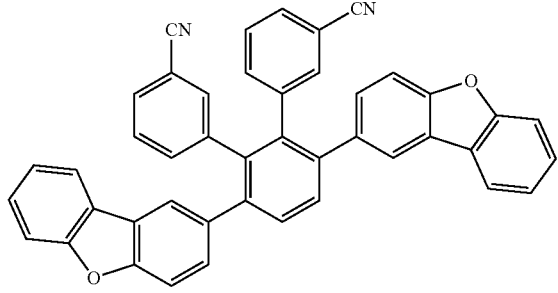
557
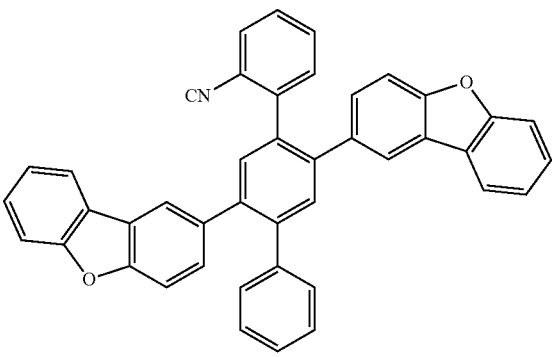
558
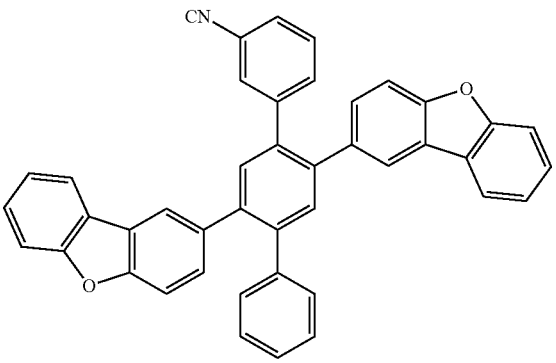
559
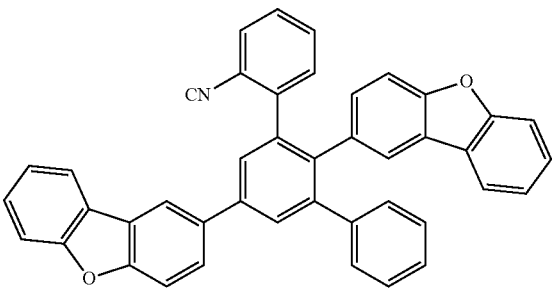
560
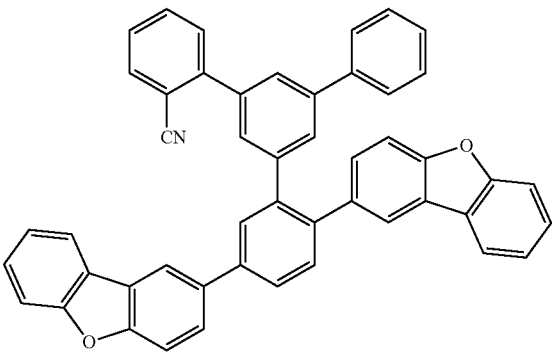

561
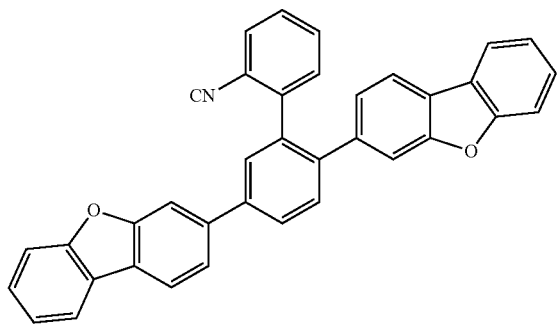
562
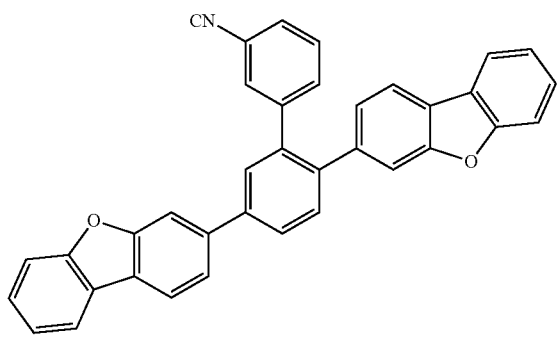
563
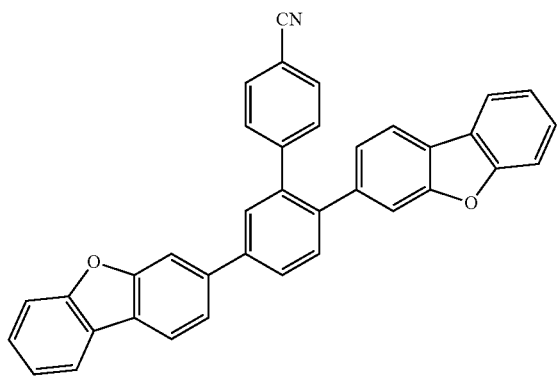
564
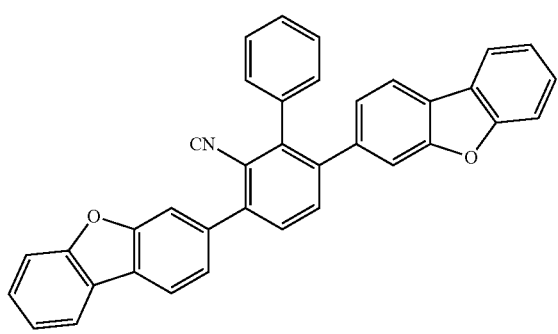
565
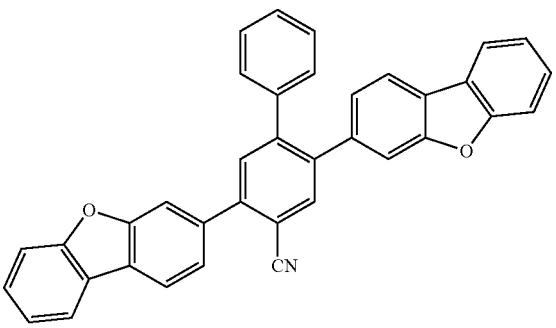
566
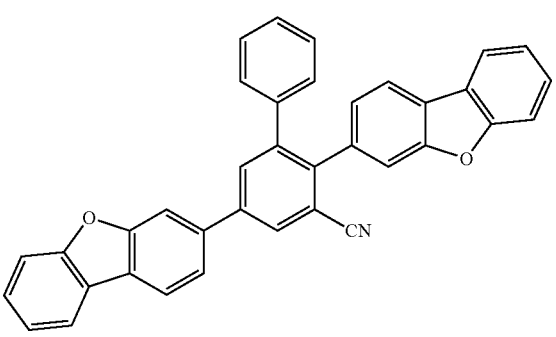
567
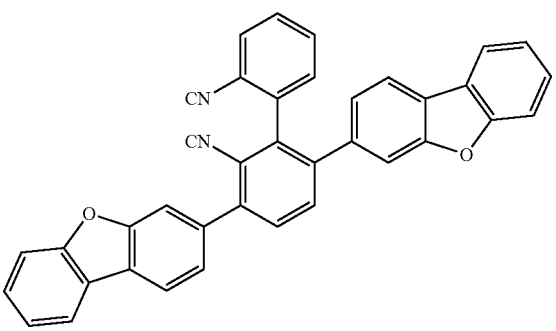
568
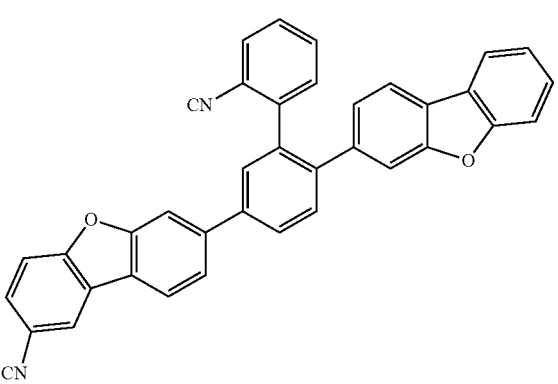

-continued
569
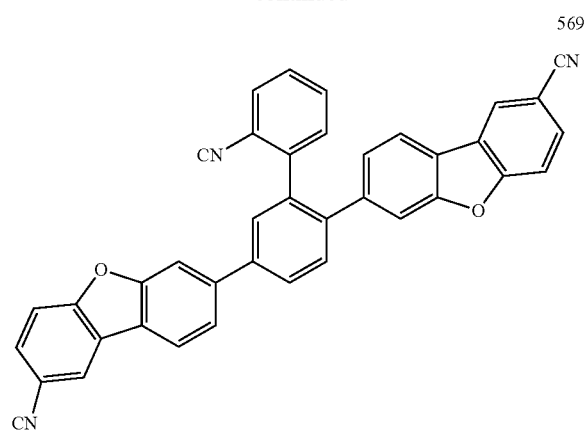
570
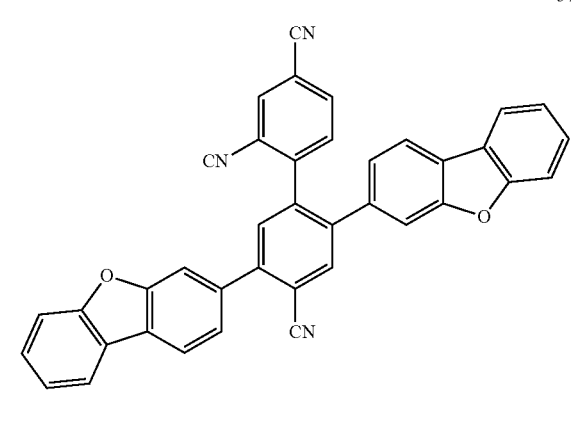
571
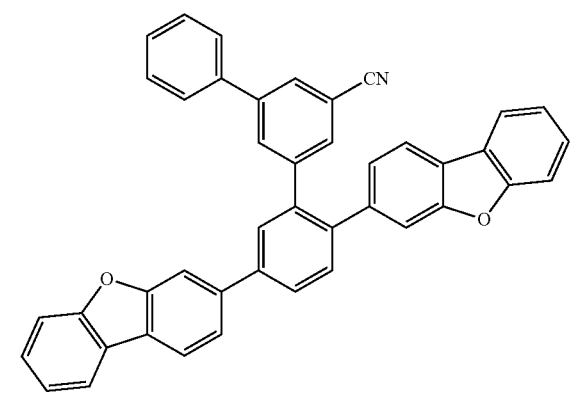
572
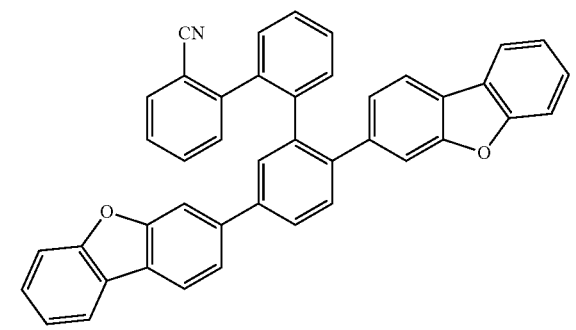
-continued
573
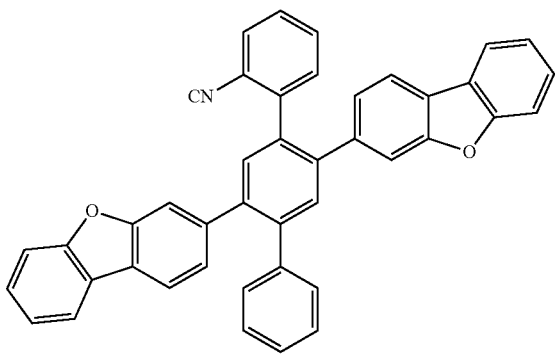
574
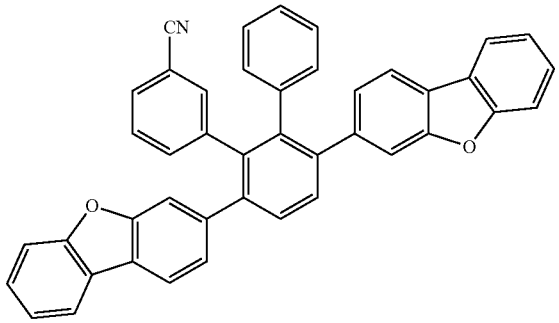
575
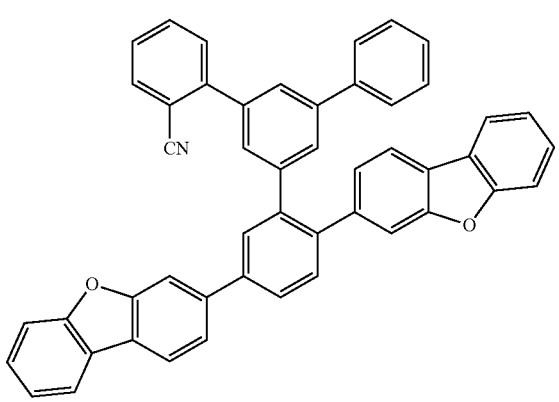
576
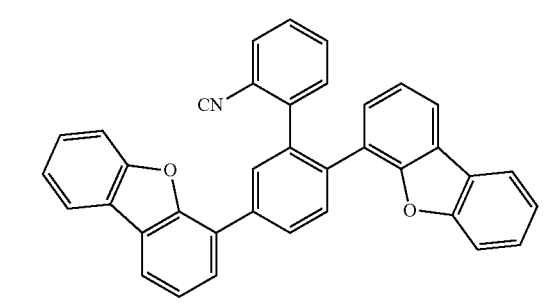

-continued
577
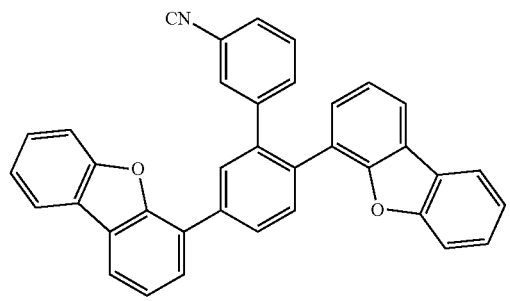
578
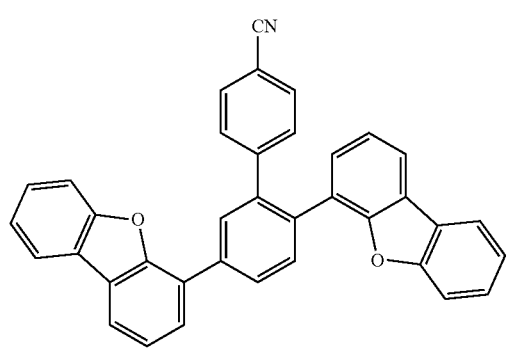
579
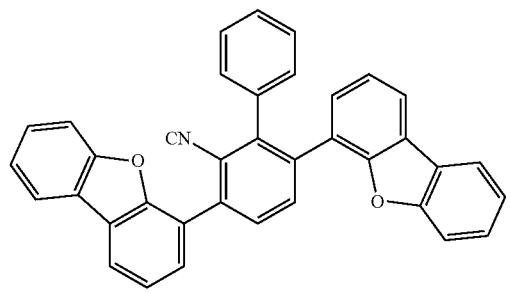
580
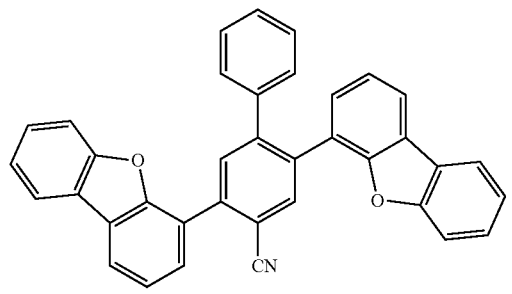
581
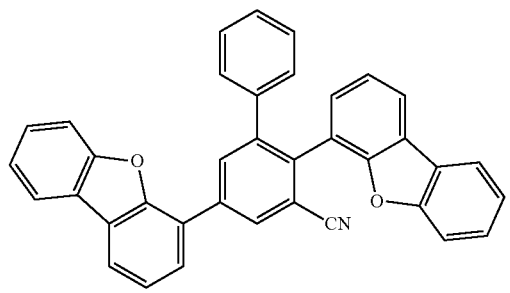
582
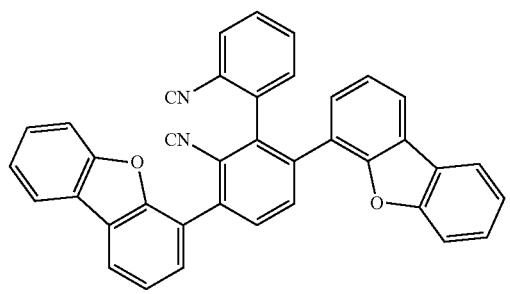
583
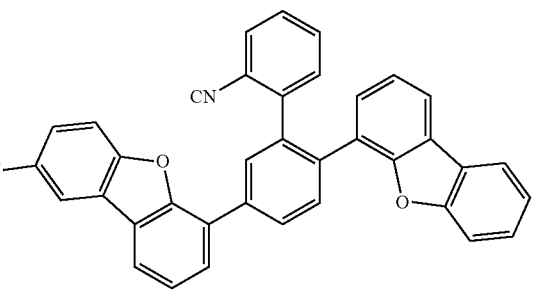
584
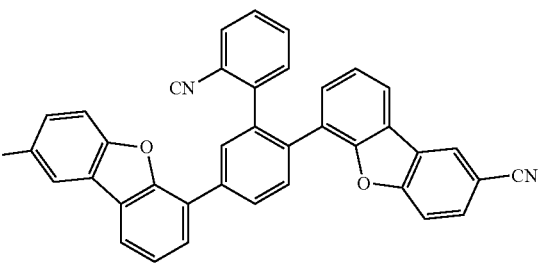
585
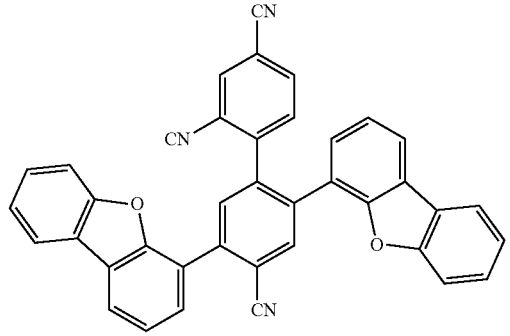

586
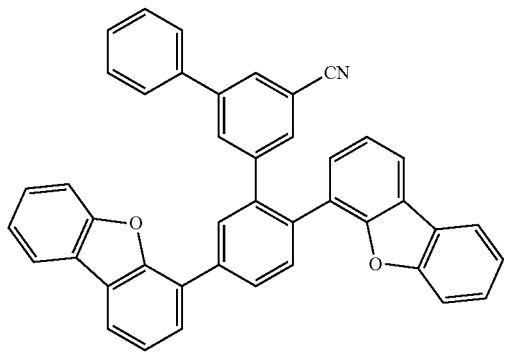
587
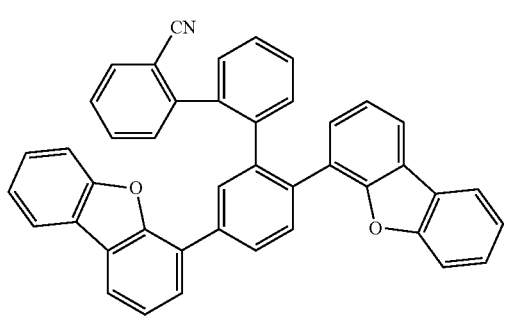
588
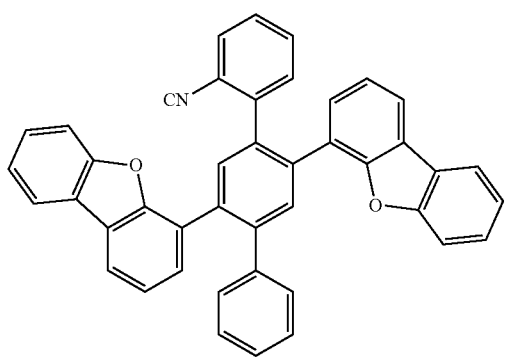
589
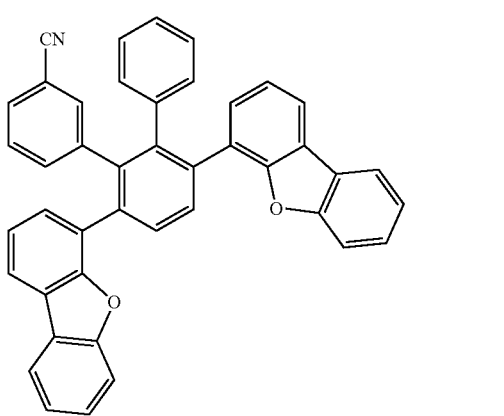
590
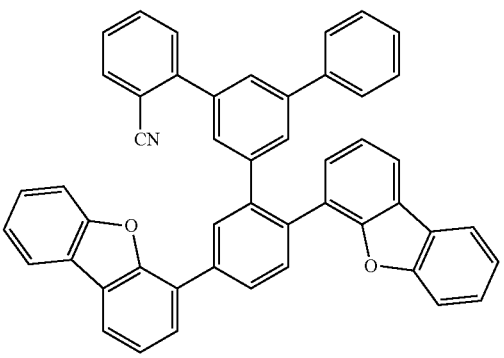
591
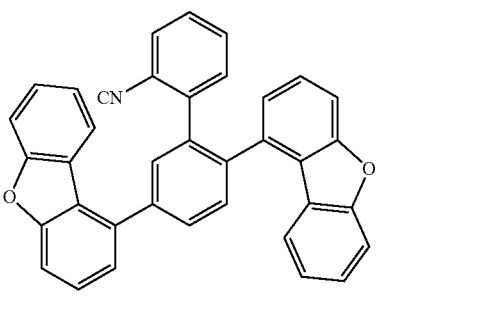
592
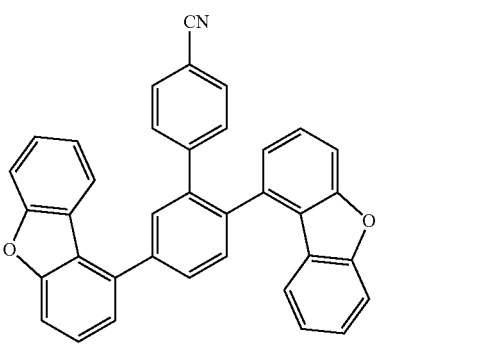
593
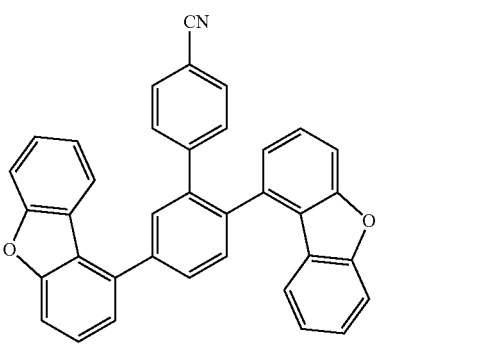
594
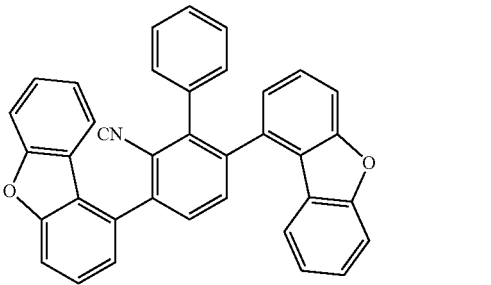

| 595 | 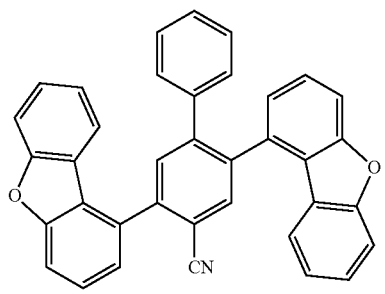 | 600 | 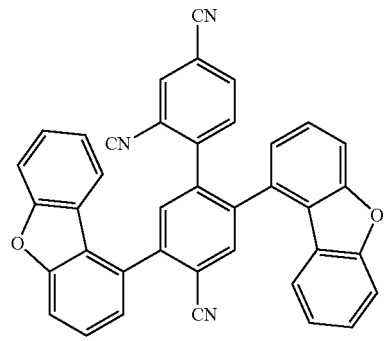 |
| 596 | 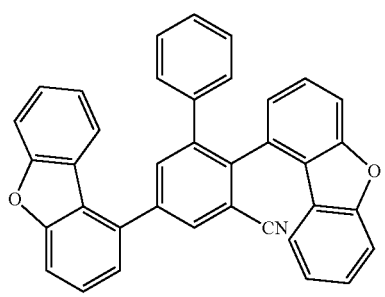 | 601 | 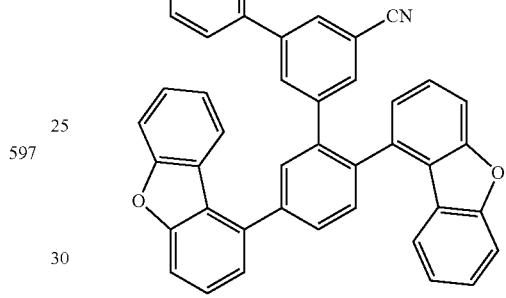 |
| 597 | 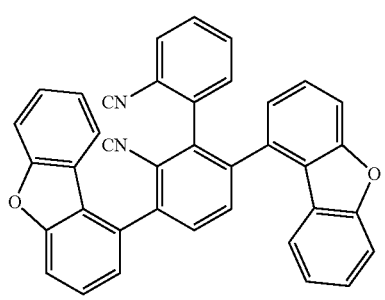 | 602 | 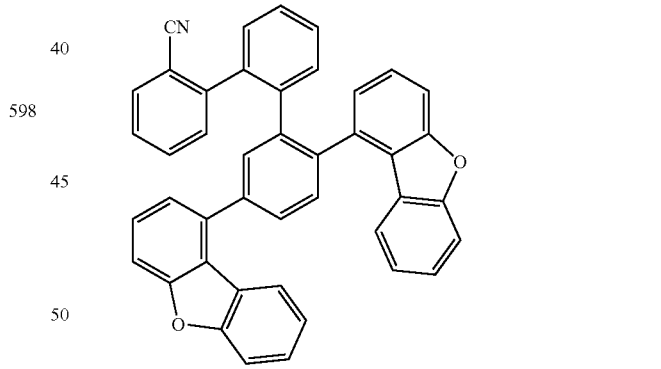 |
| 598 | 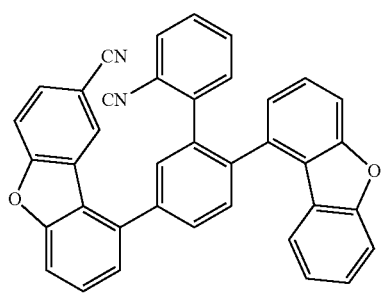 | 603 | 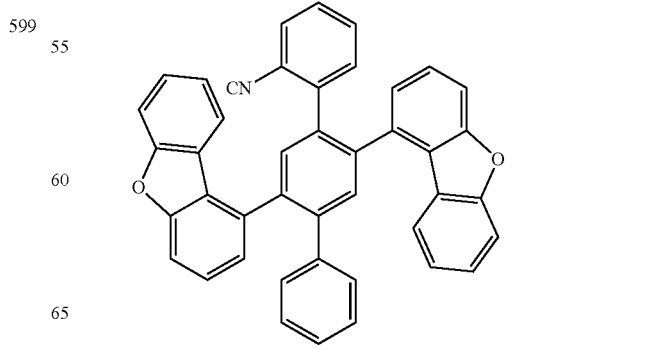 |
| 599 | 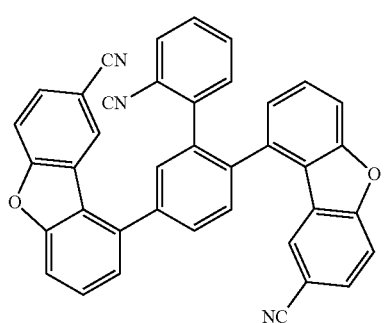 | | |

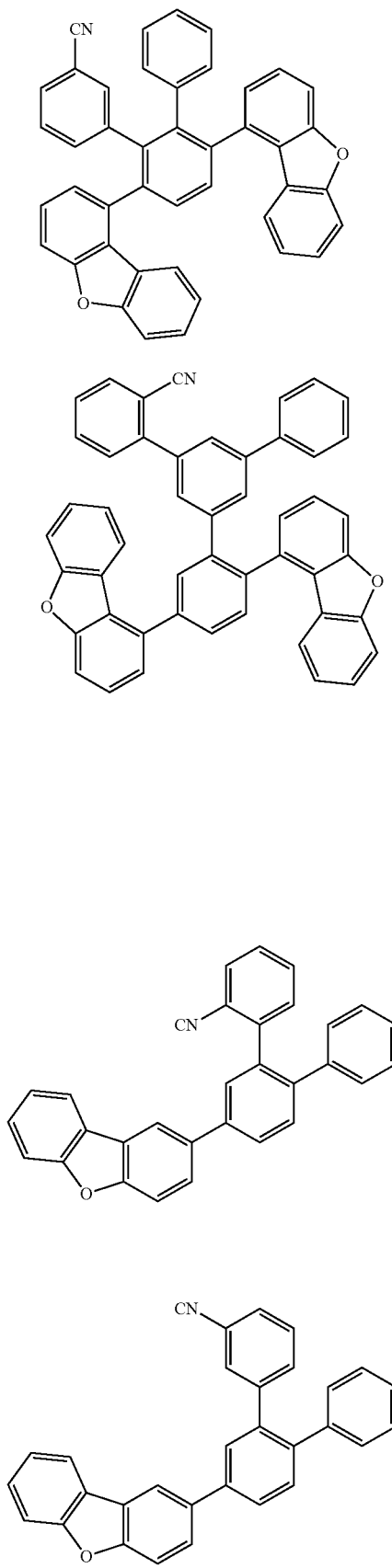
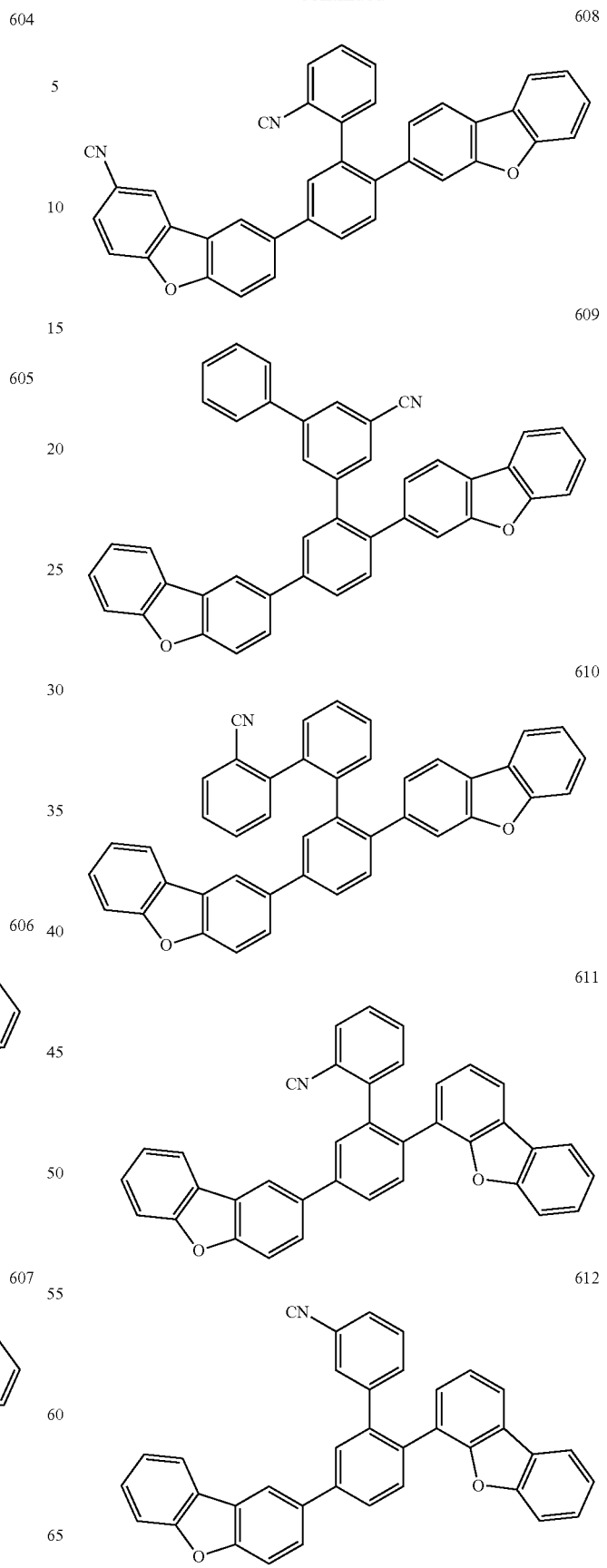

-continued
613
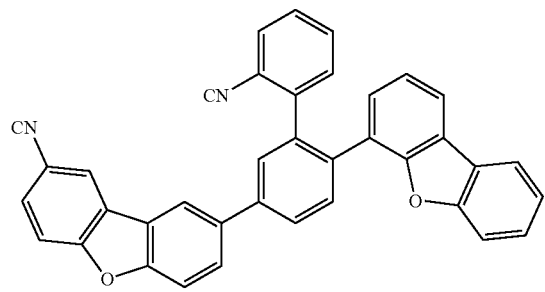
614
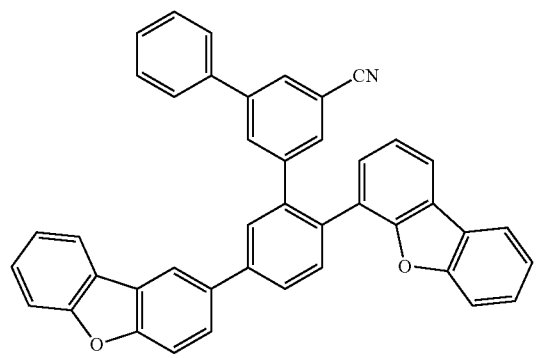
615
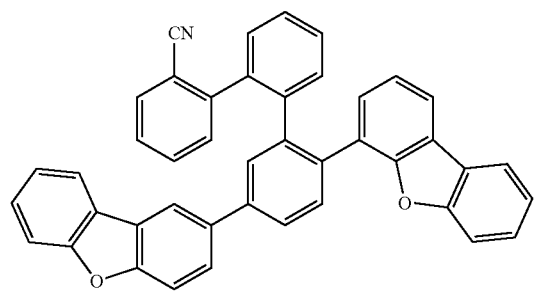
616
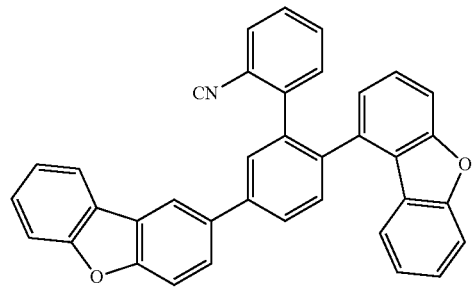
617
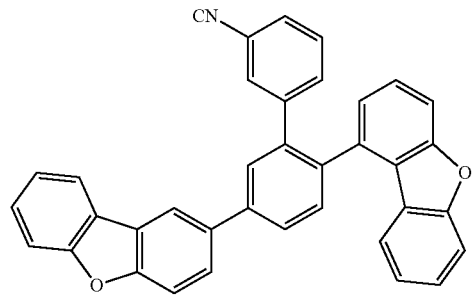
-continued
618
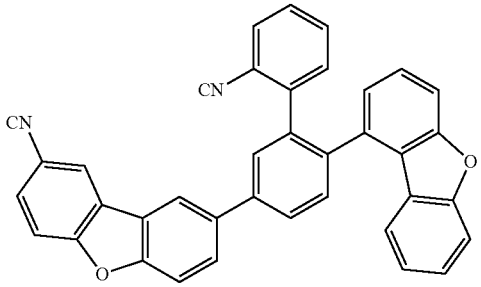
619
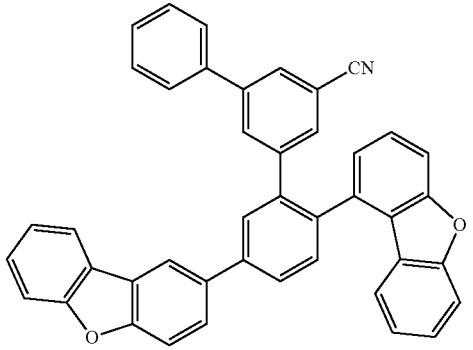
620
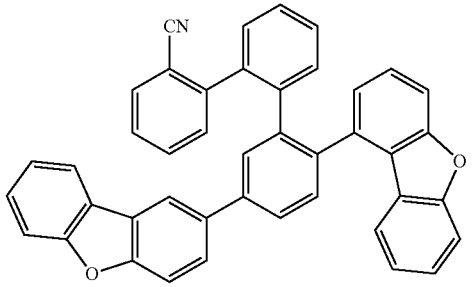
621
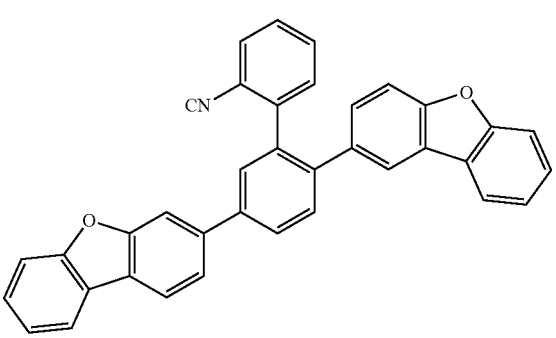
622
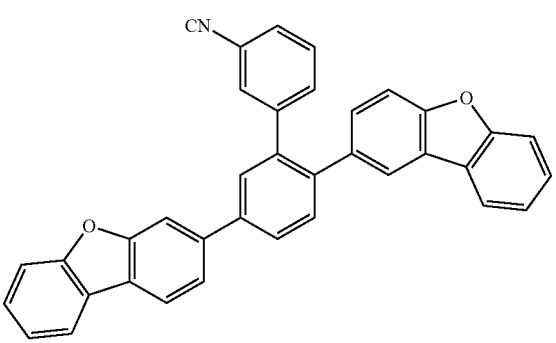

-continued
623
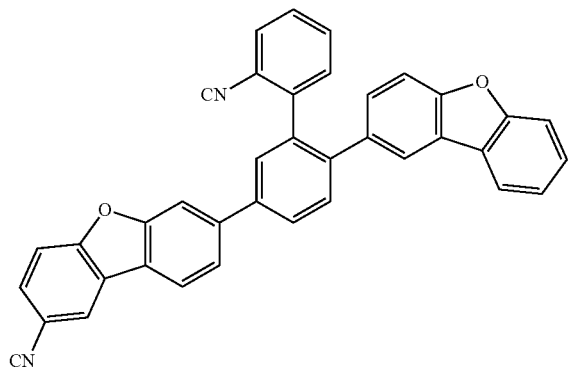
624
625
626
-continued
627
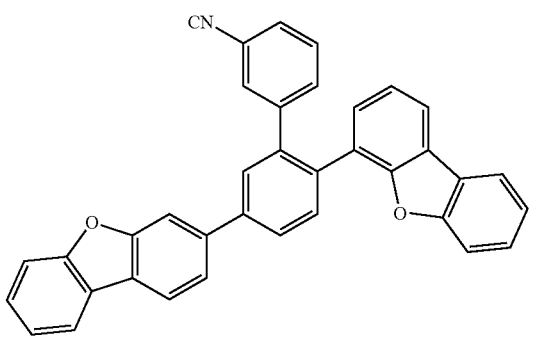
628
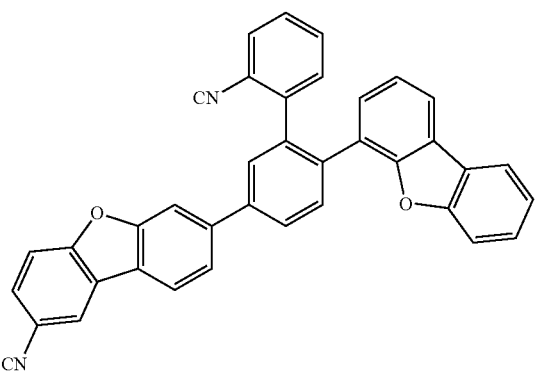
629
630
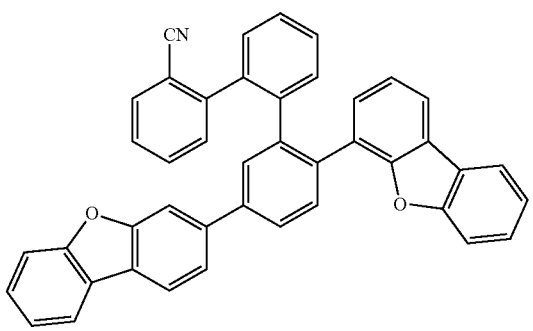

631
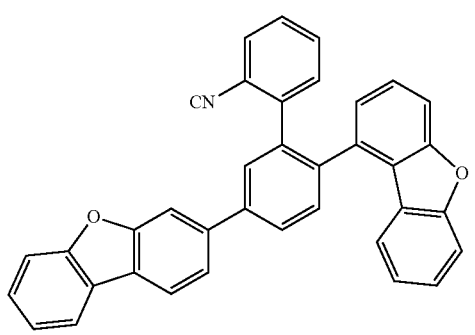
632
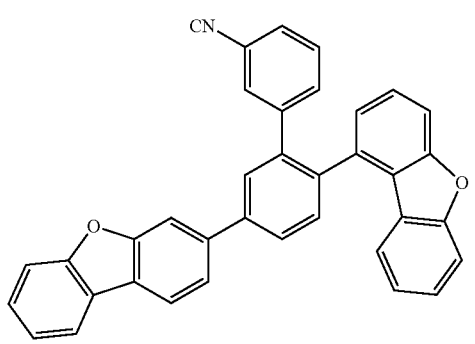
633
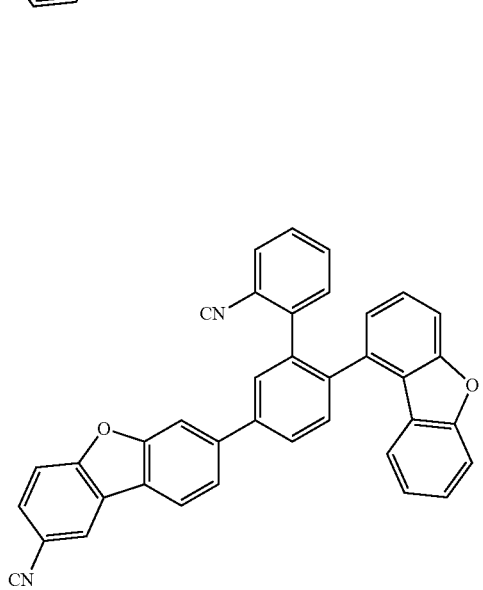
634
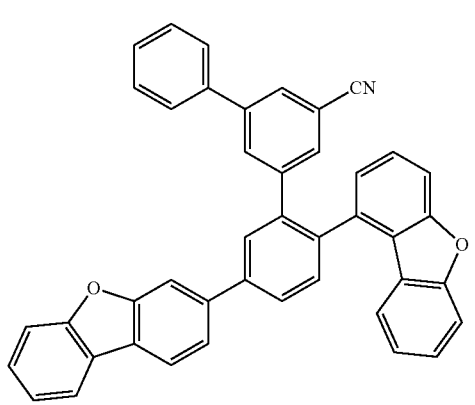
635
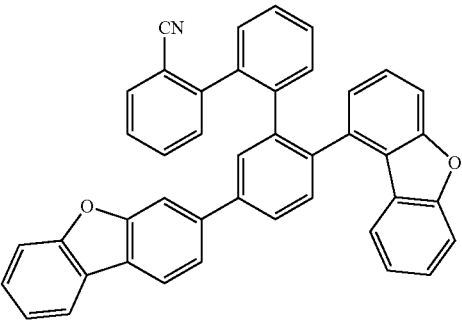
636
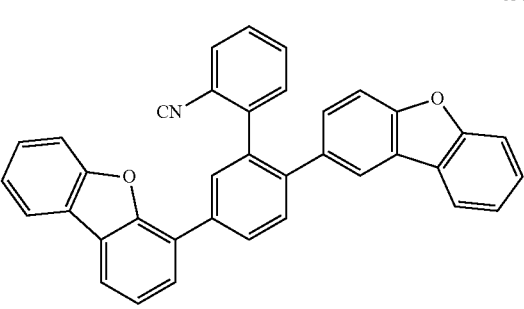
637
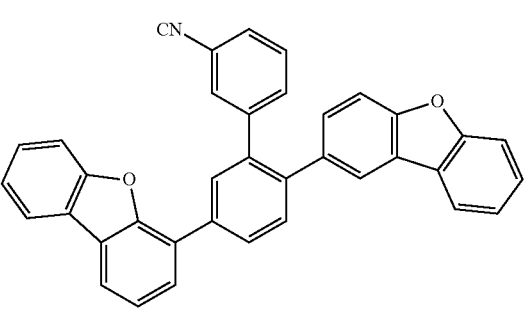
638
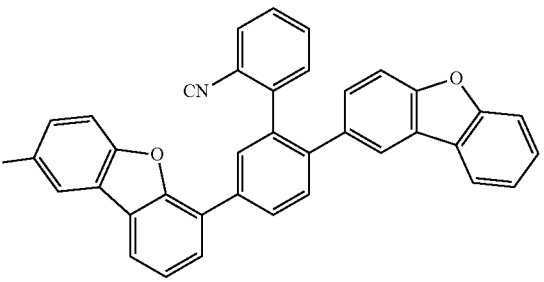
639
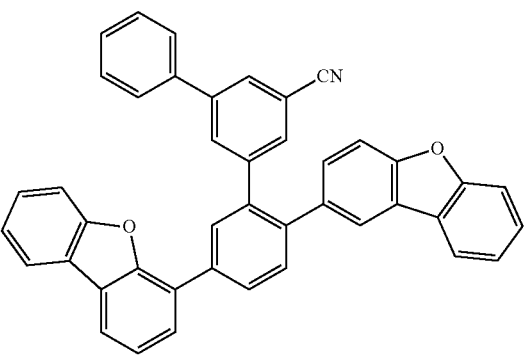

-continued
640
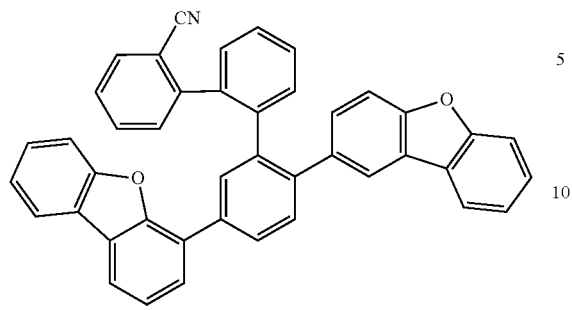
641
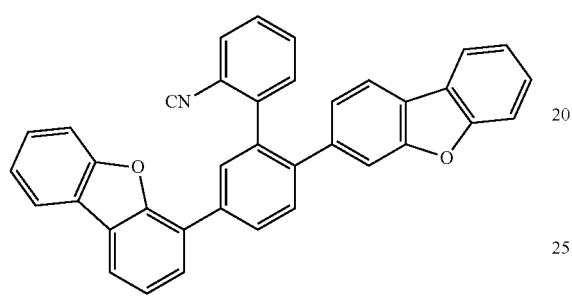
642

643
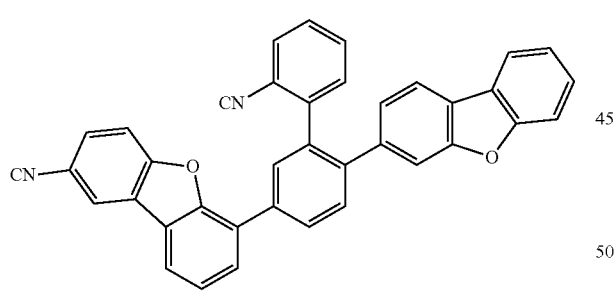
644
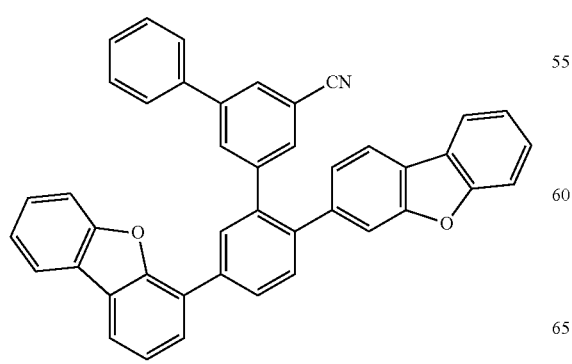
-continued
645
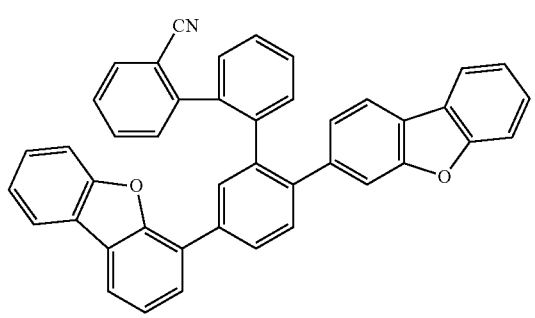
646
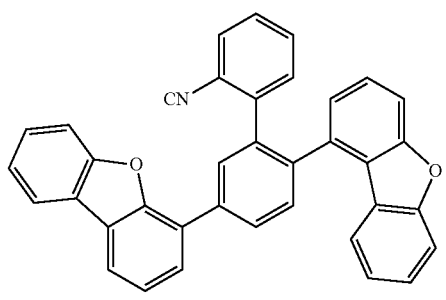
647
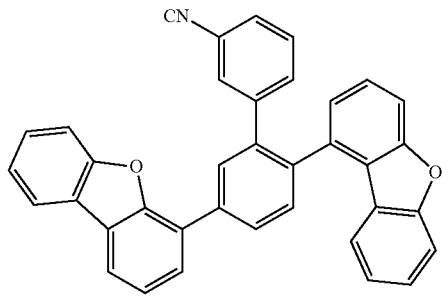
648
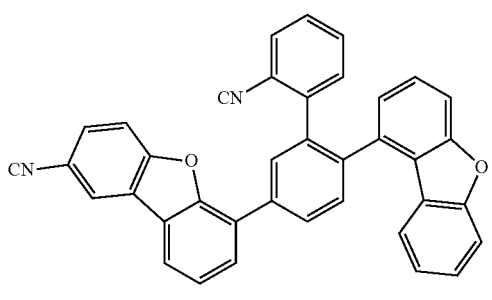
649
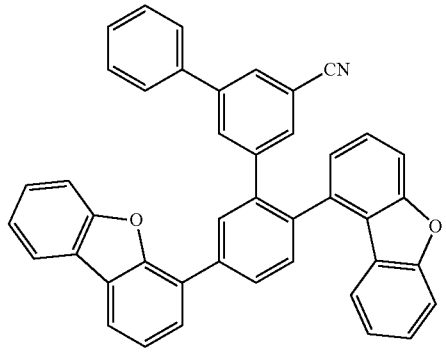

650
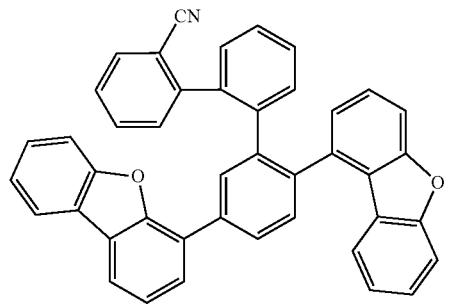
651
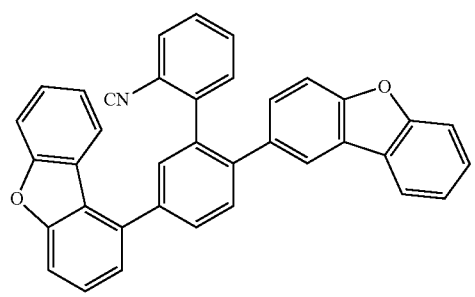
652
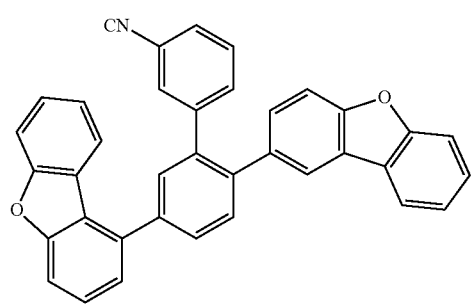
653
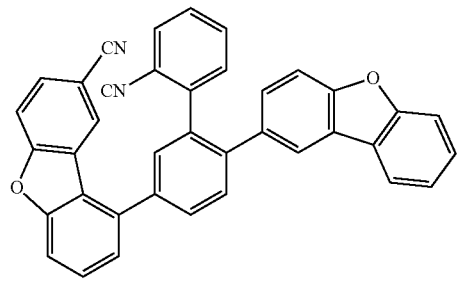
654
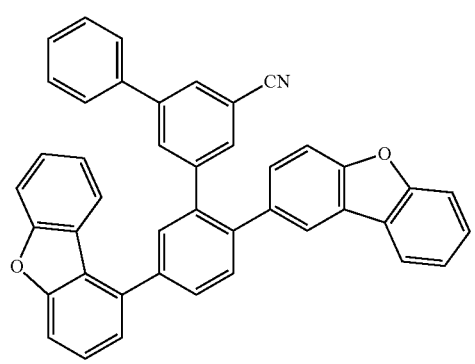
655
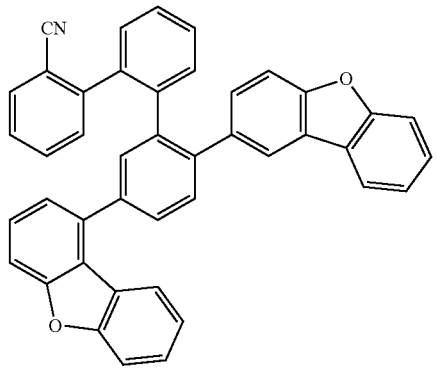
656
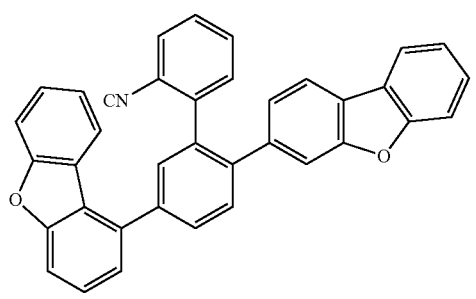
657
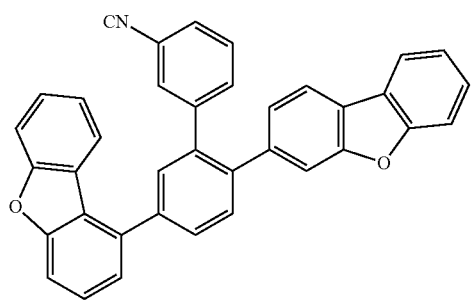
658
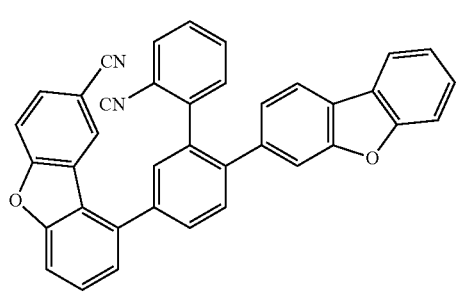
659
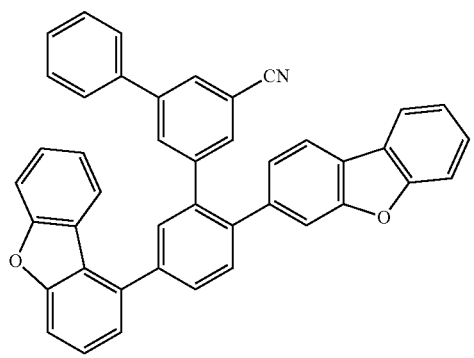

191
-continued
660
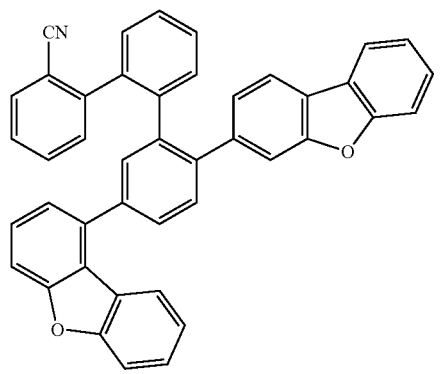
661
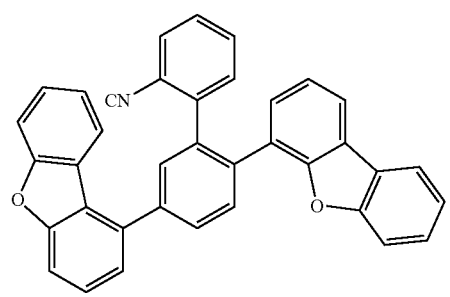
662
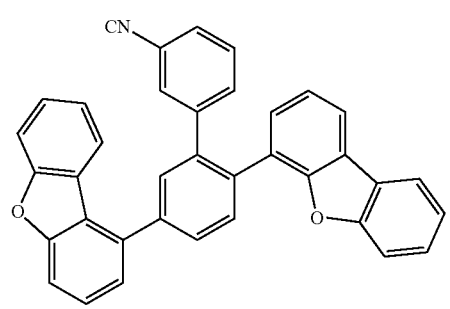
663
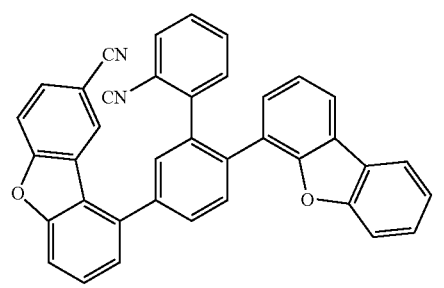
664
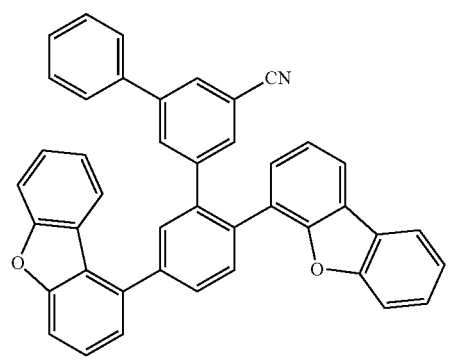
192
-continued
665
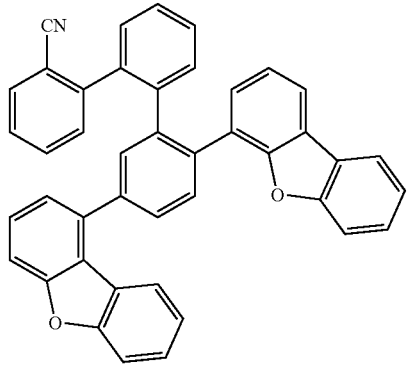
666
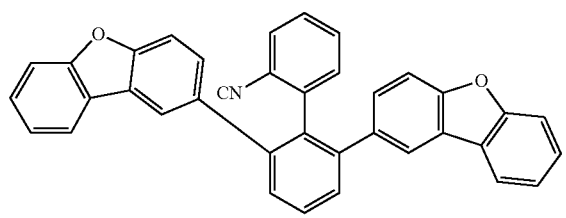
667
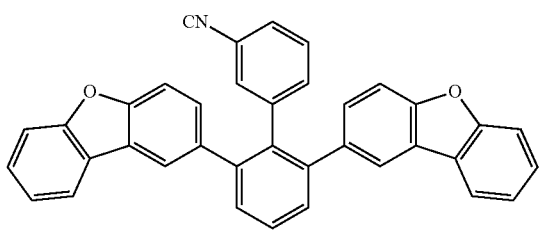
668
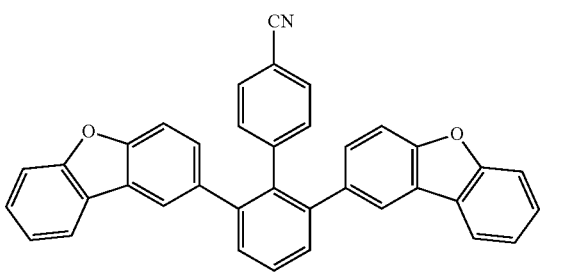
669
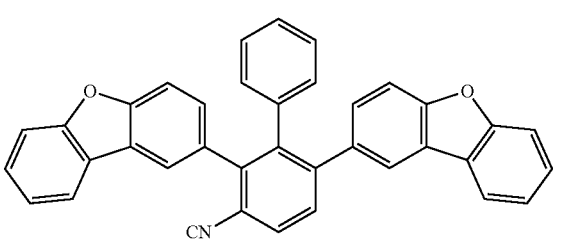

-continued
670
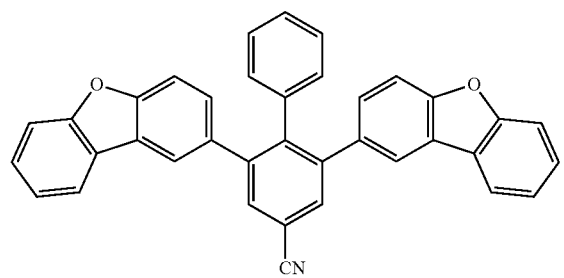
671
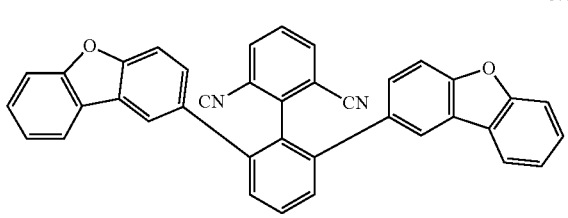
672
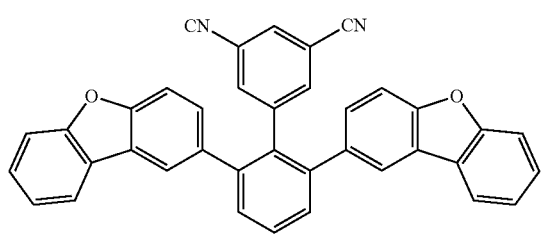
673
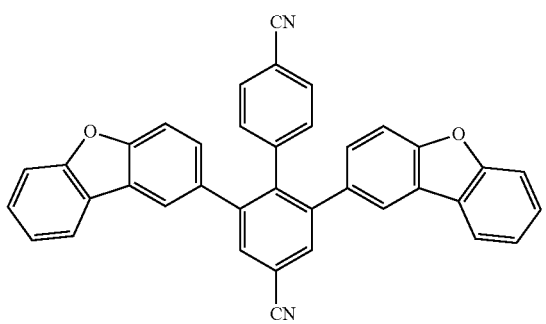
674
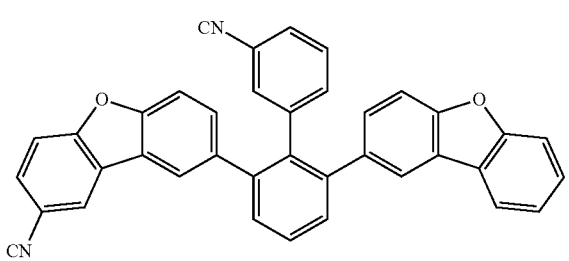
-continued
675
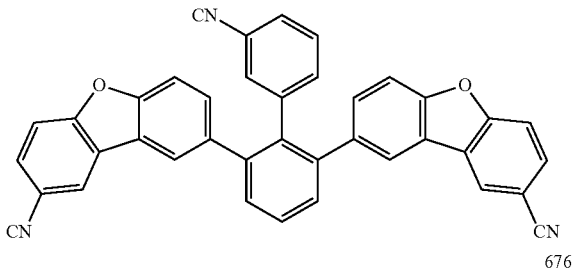
676
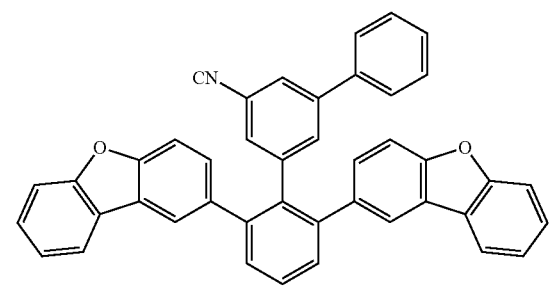
677
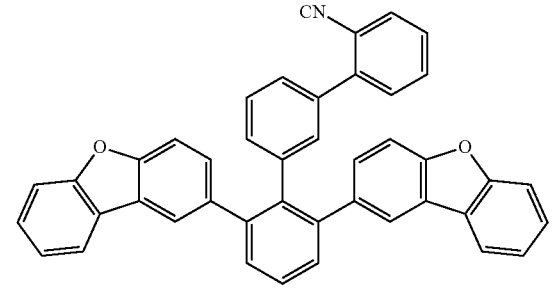
678
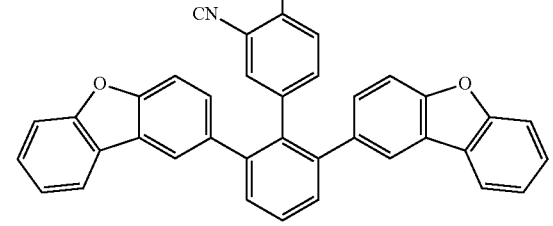
679
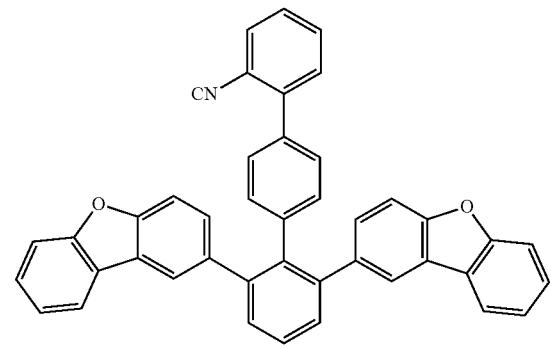

680
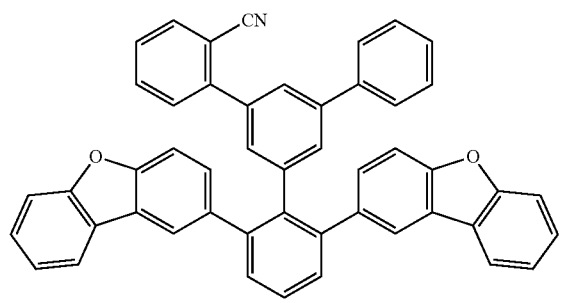
681
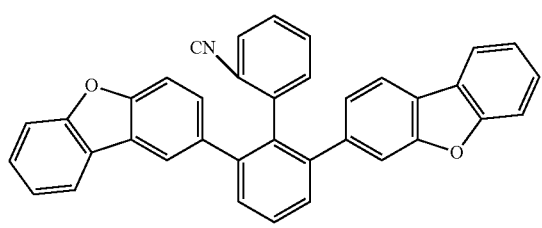
682
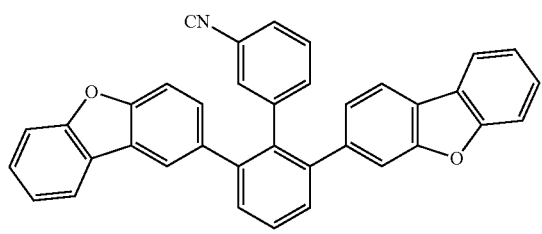
683
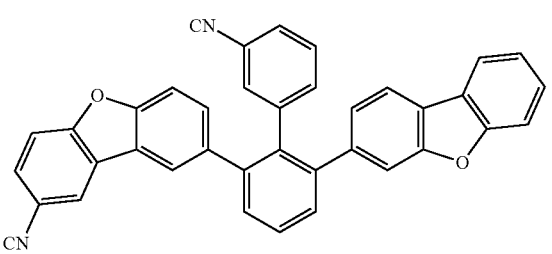
684
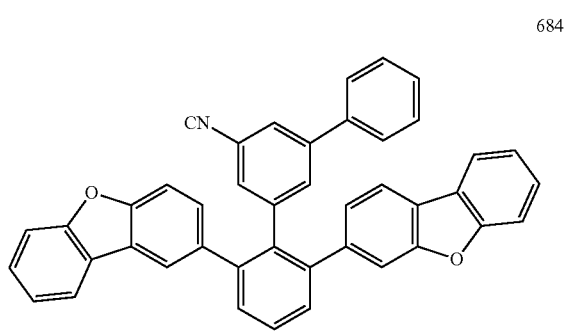
685
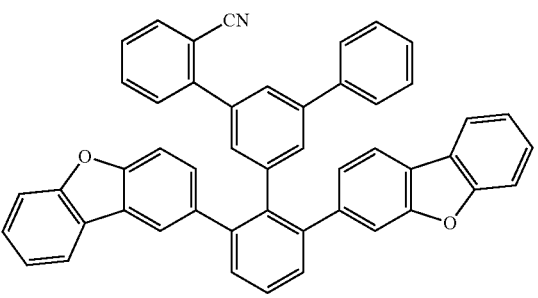
686
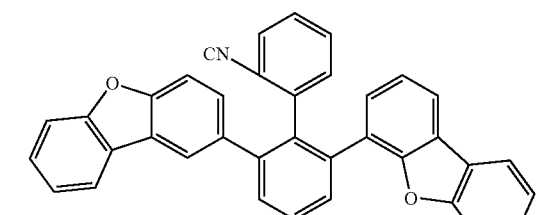
687
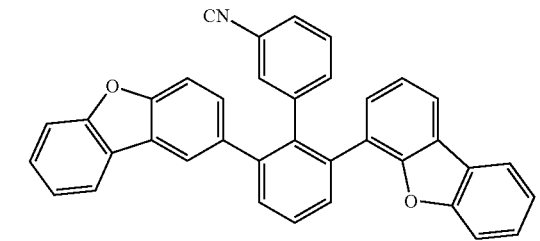
688
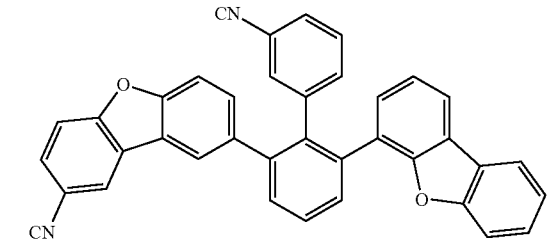
689
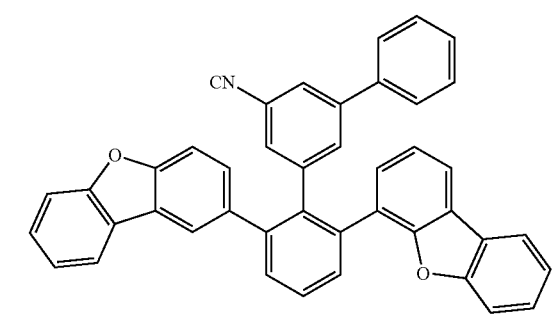

690
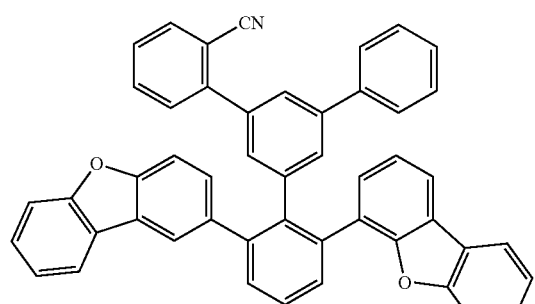
691
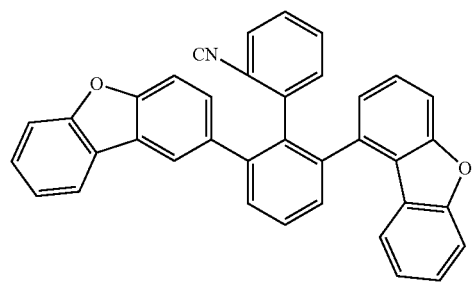
692
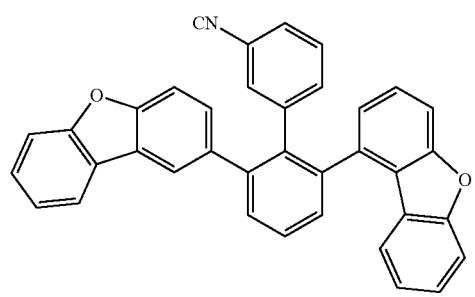
693
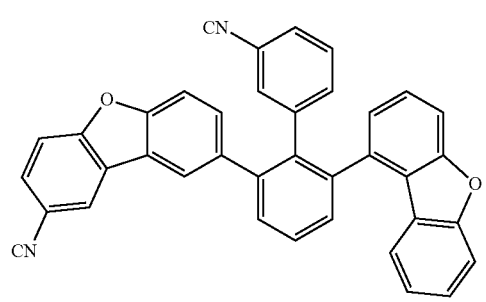
694
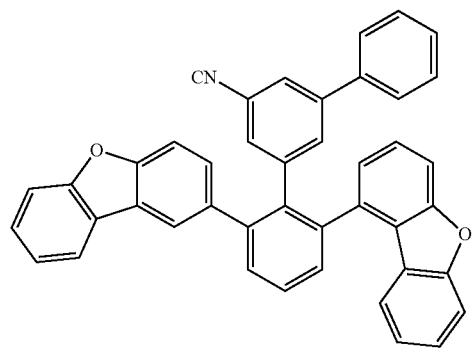
695
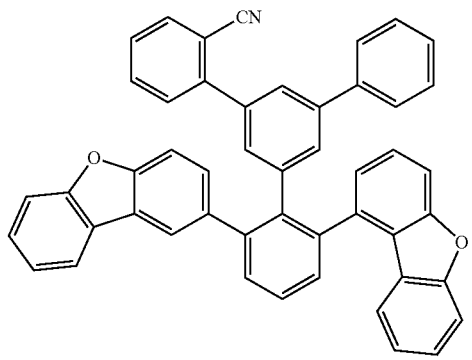
696
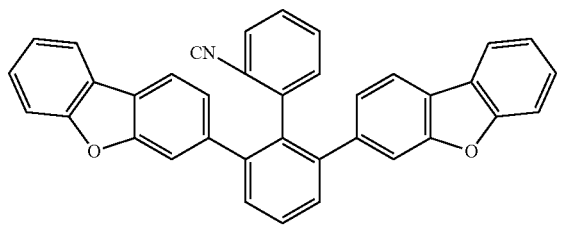
697
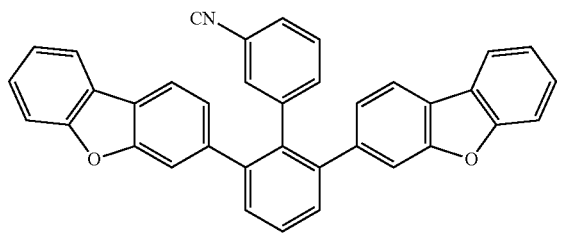
698
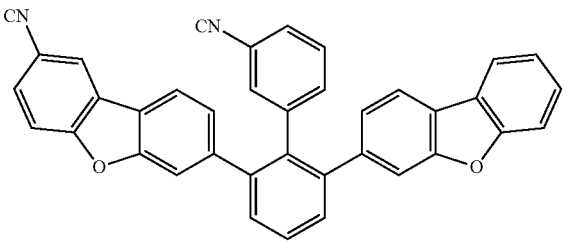
699
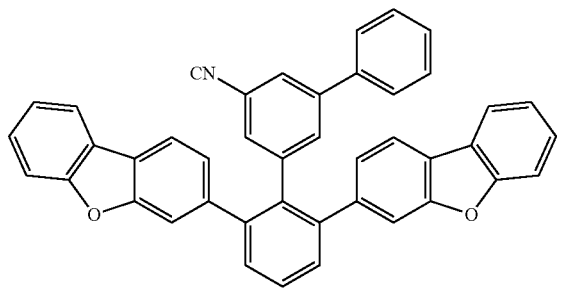

| | |
|---|---|
| 700 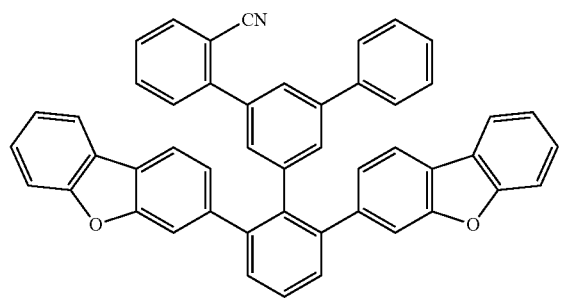 | 705 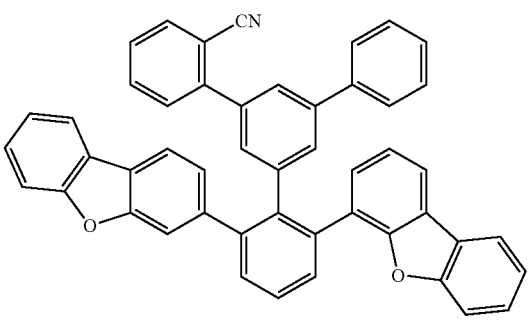 |
| 701 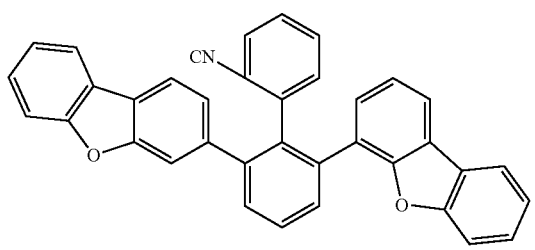 | 706 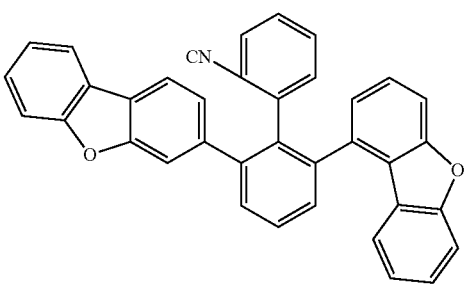 |
| 702 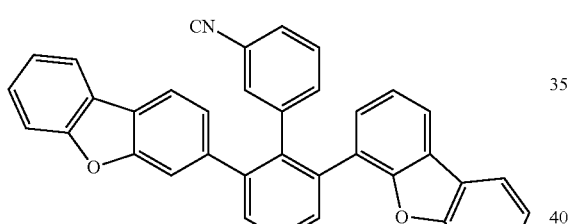 | 707 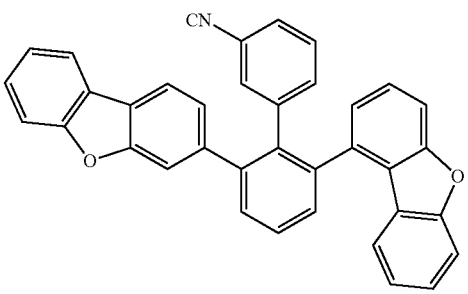 |
| 703 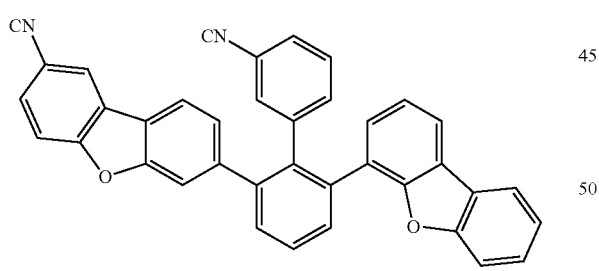 | 708 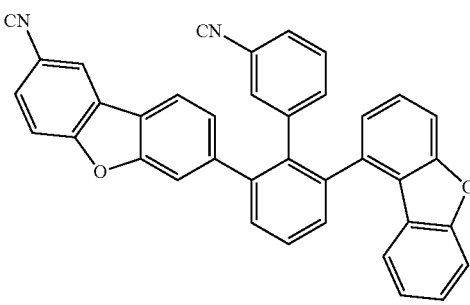 |
| 704 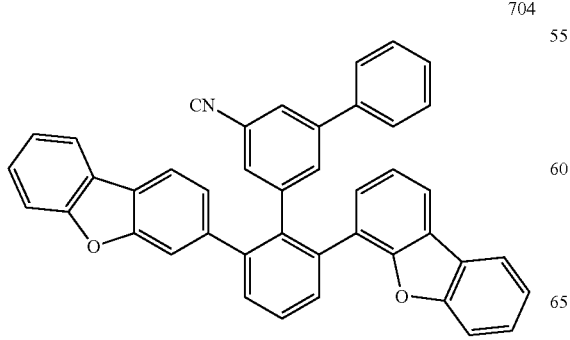 | 709 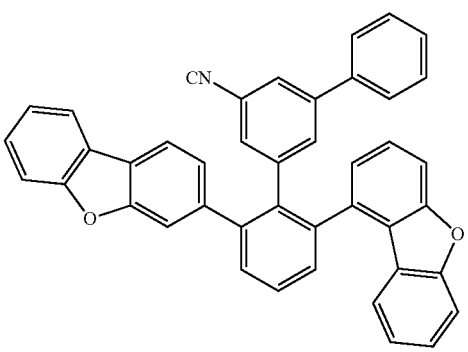 |

710
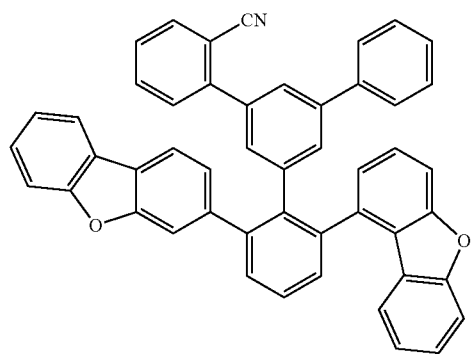
711
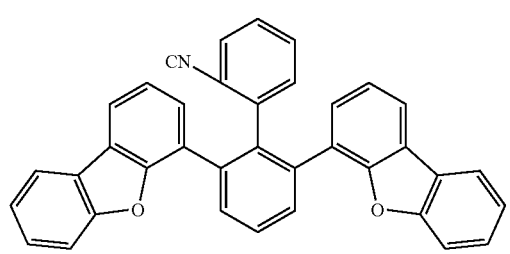
712
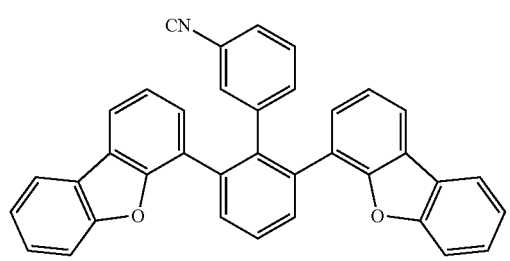
713
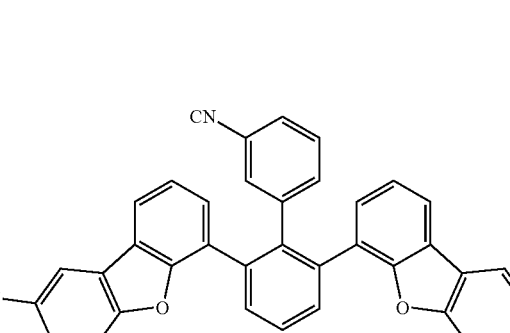
714
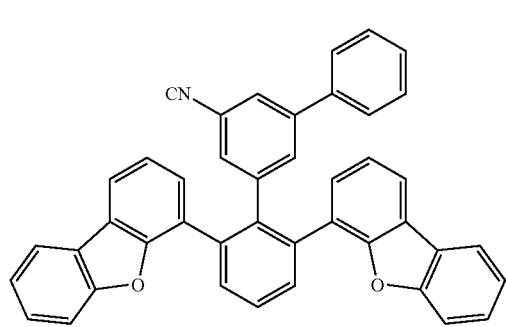
715
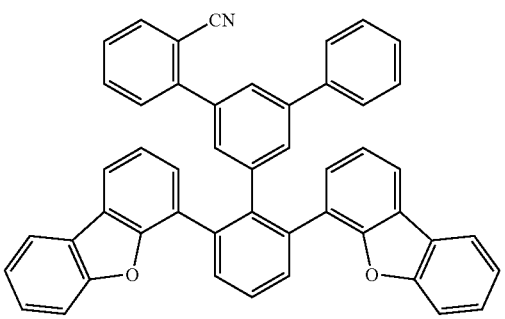
716
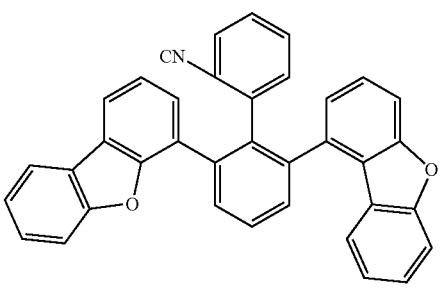
717
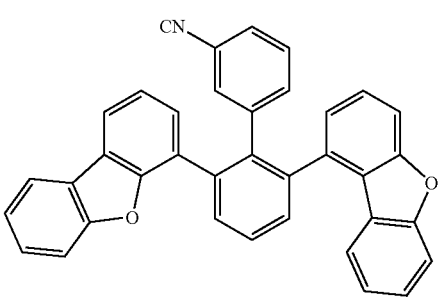
718
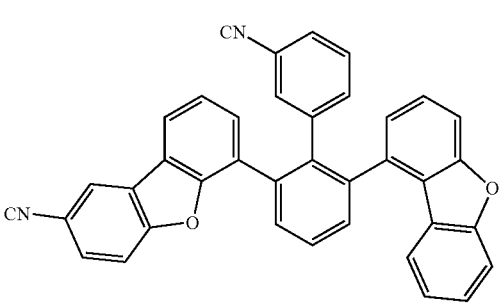
719
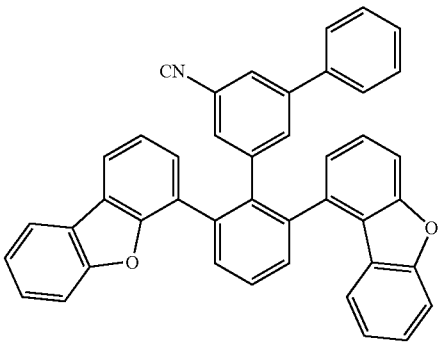

| 720 | 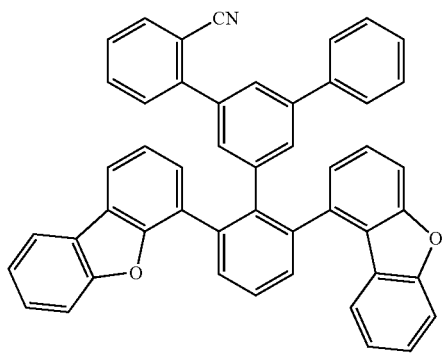 |
| 721 | 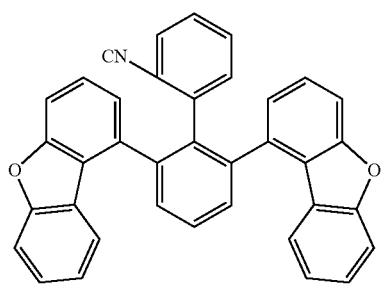 |
| 722 | 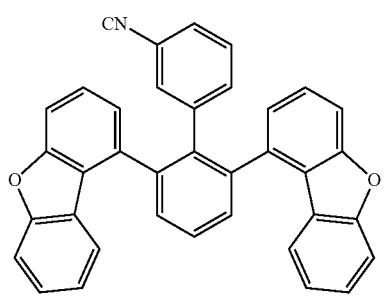 |
| 723 | 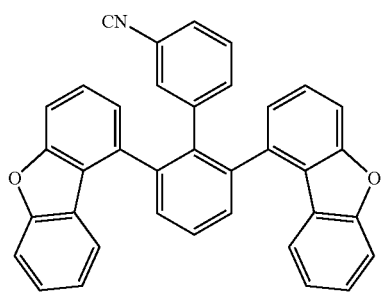 |
| 724 | 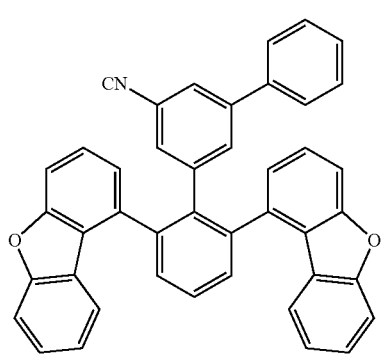 |
| 725 | 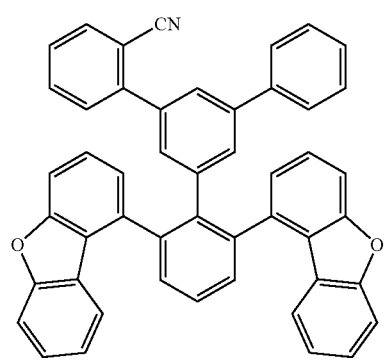 |
| 726 | 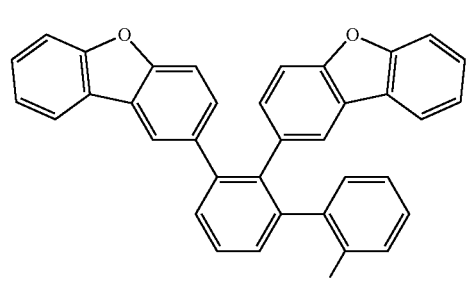 |
| 727 | 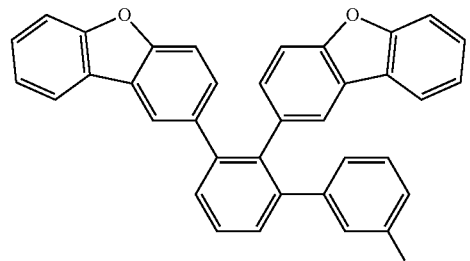 |
| 728 | 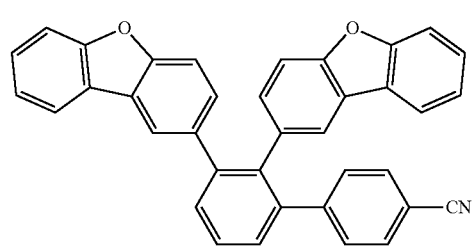 |
| 729 | 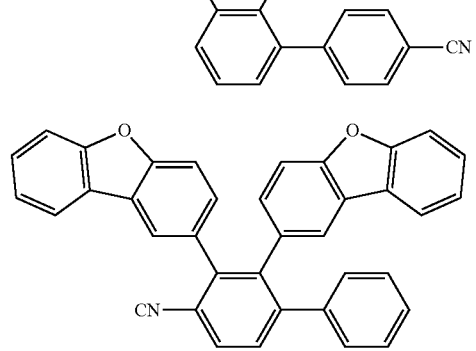 |

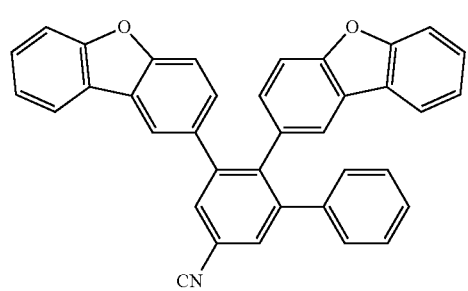
730
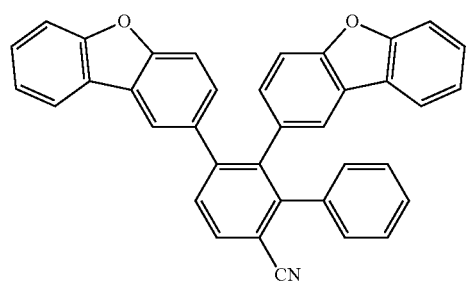
731
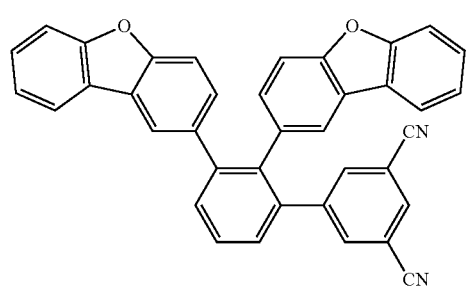
732
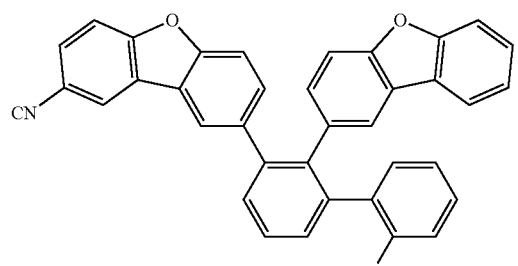
733
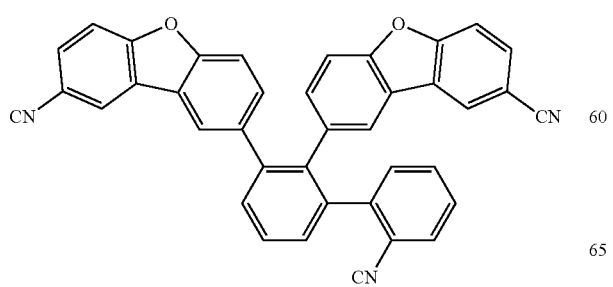
734
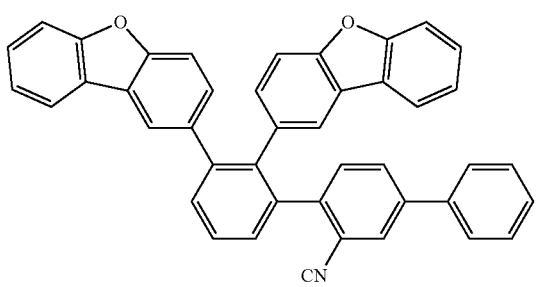
735
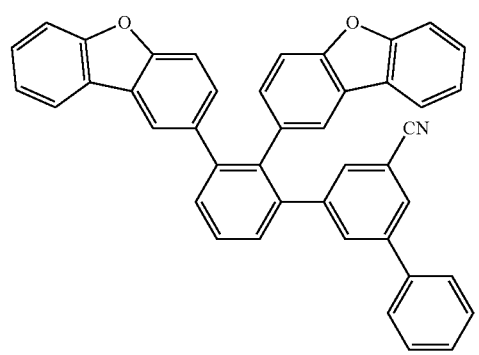
736
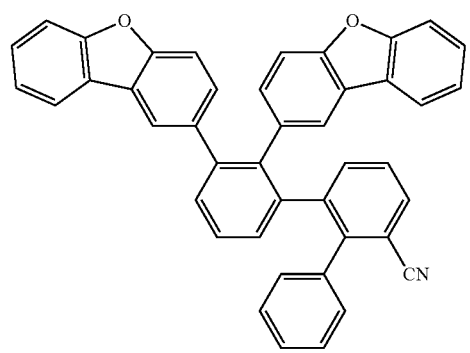
737
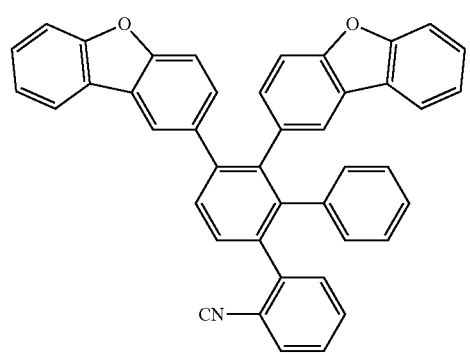
738

-continued
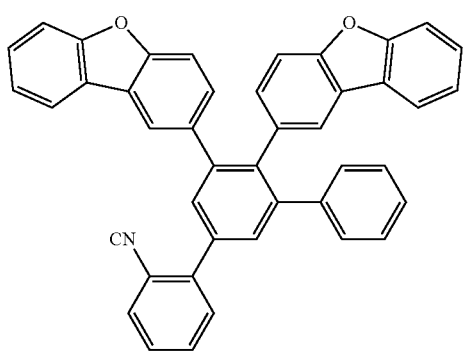 739
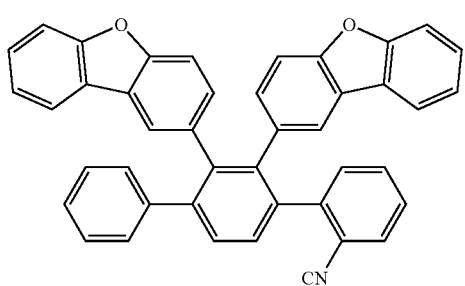 740
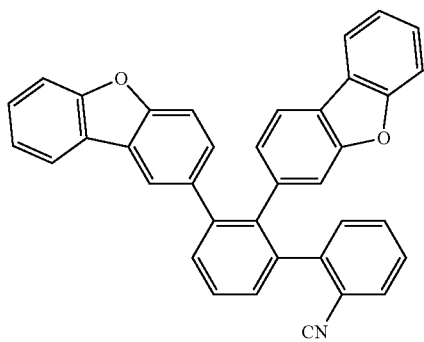 741
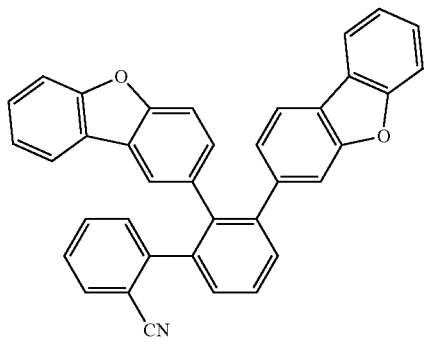 742
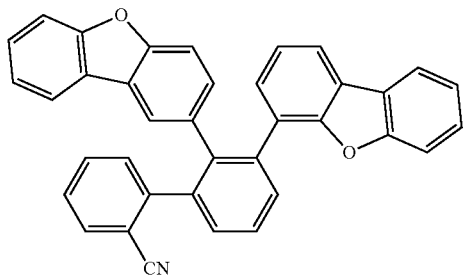 743
-continued
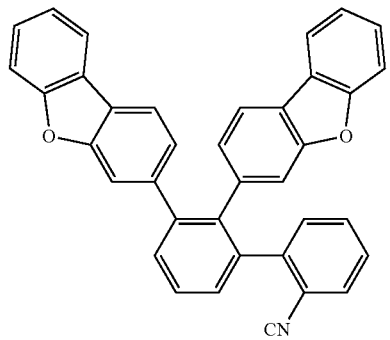 744
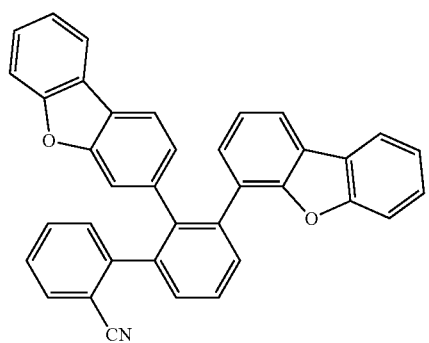 745
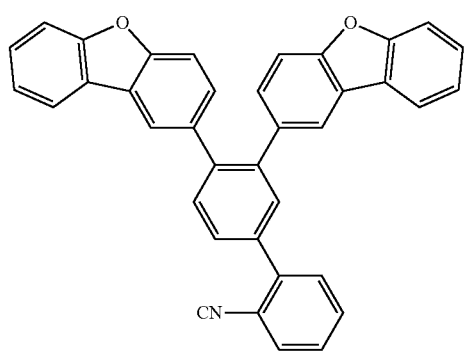 746
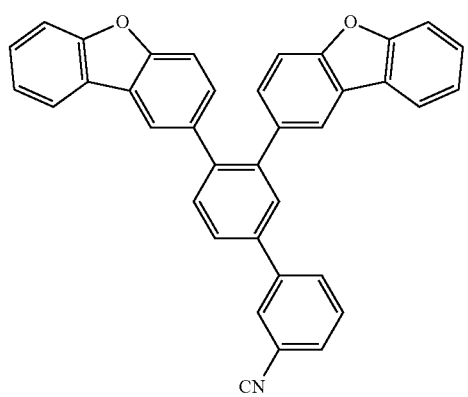 747

-continued
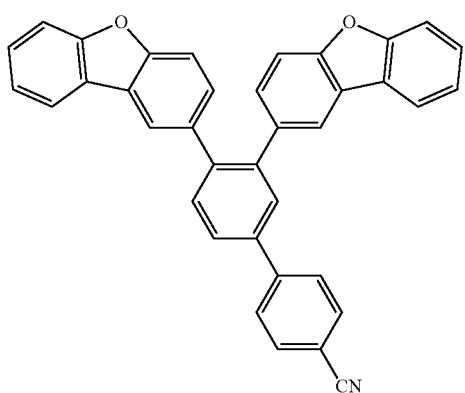
748
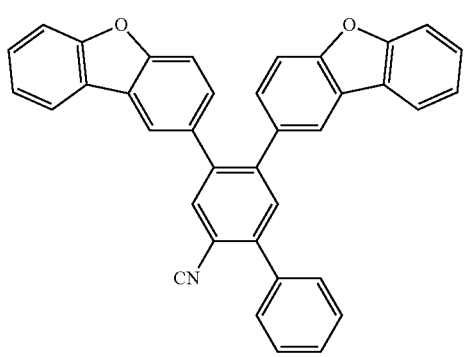
749
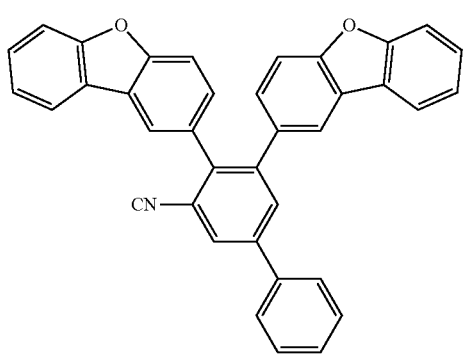
750
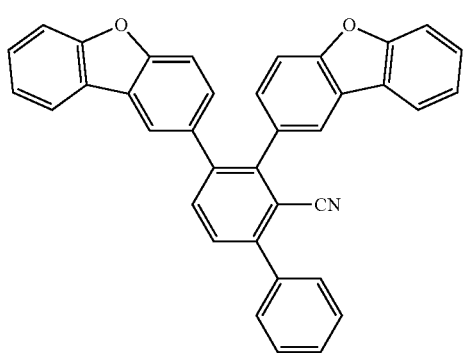
751
-continued
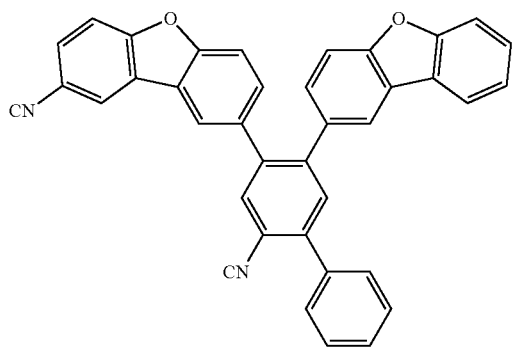
752
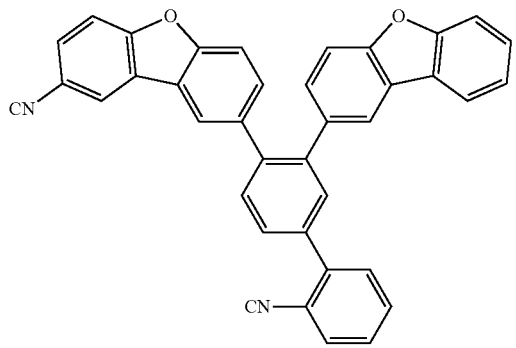
753
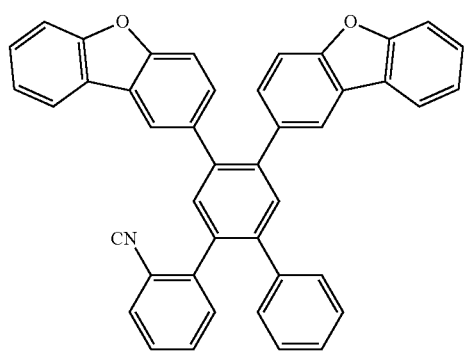
754
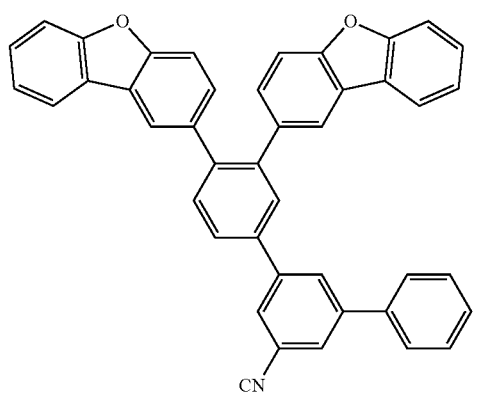
755

211
-continued
756
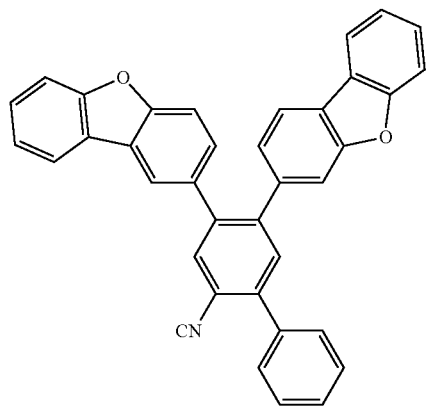
757
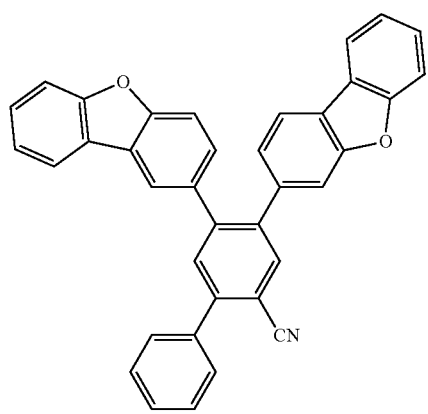
758
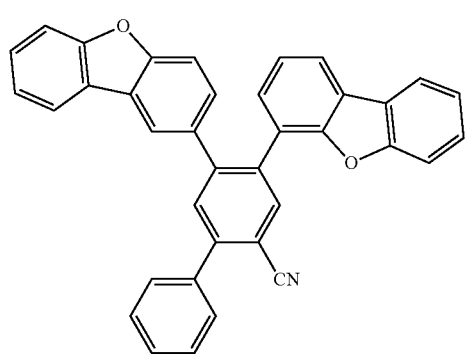
759
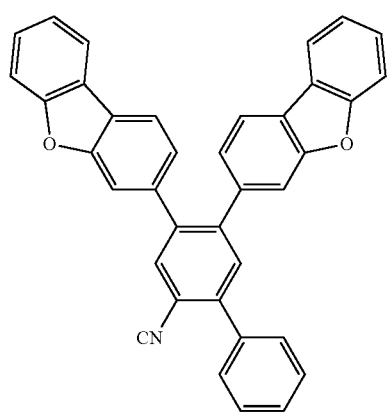
212
-continued
760
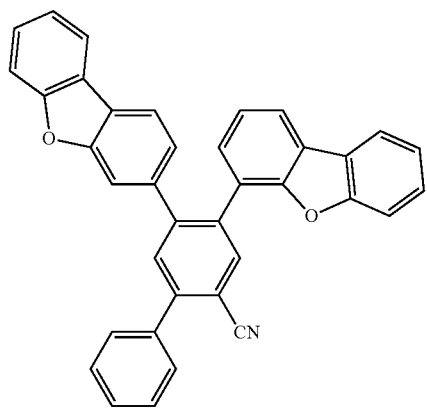
761
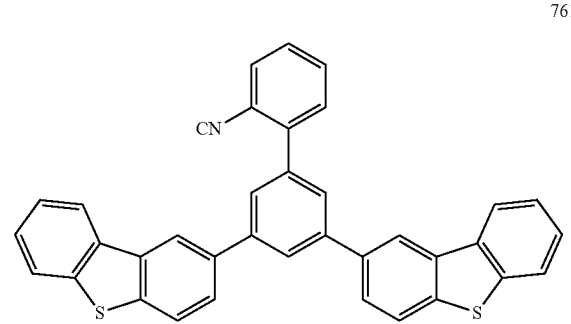
762
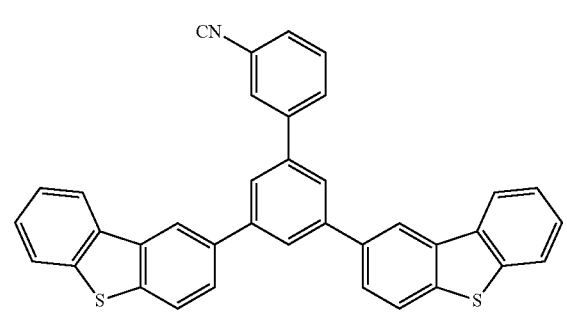
763
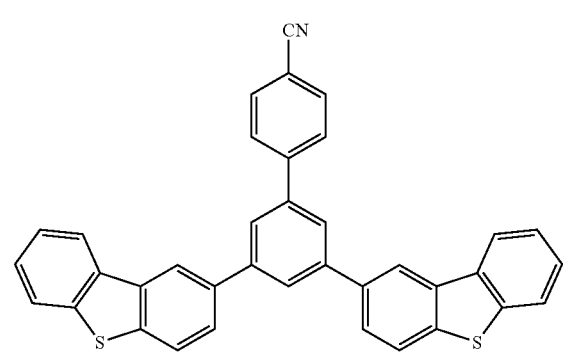

764
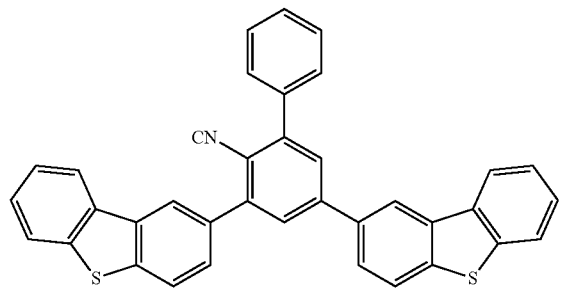
765
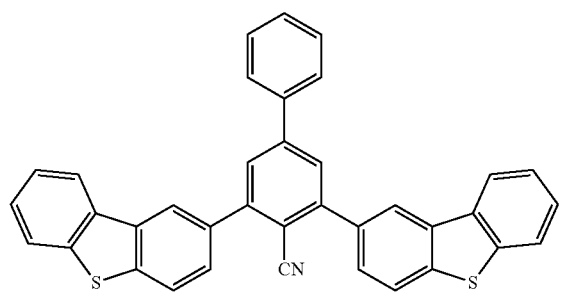
766
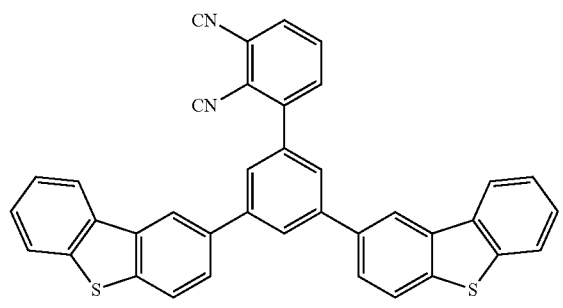
767
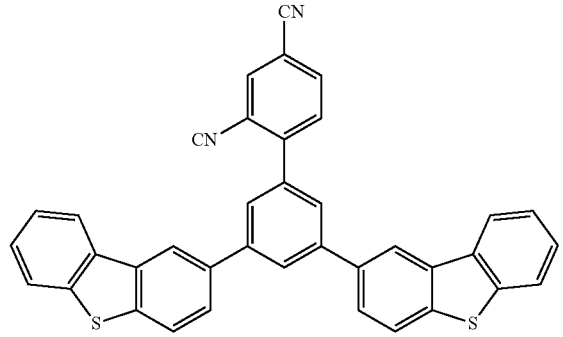
768
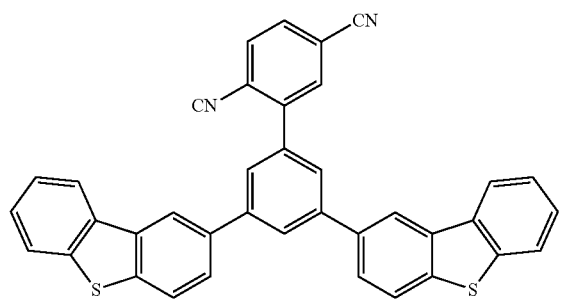
769
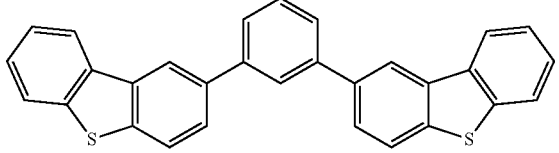
770
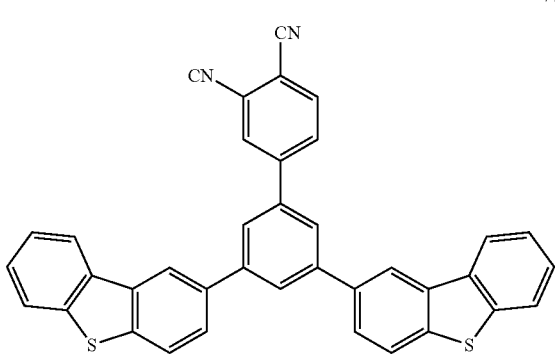
771
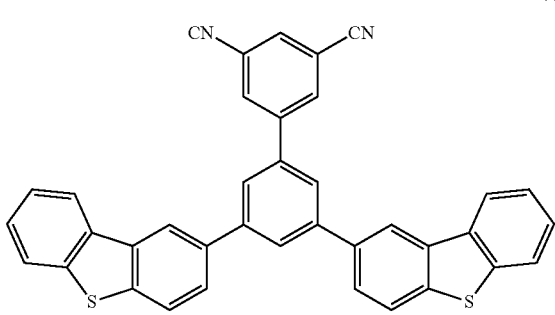
772
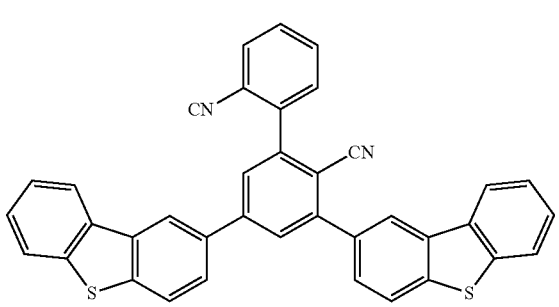
773
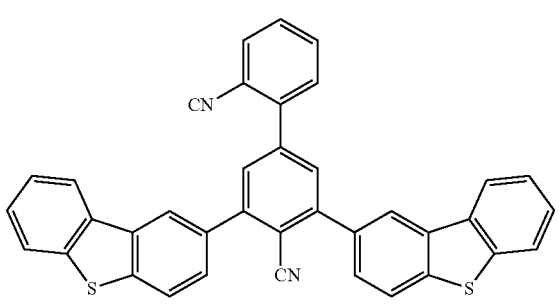

774
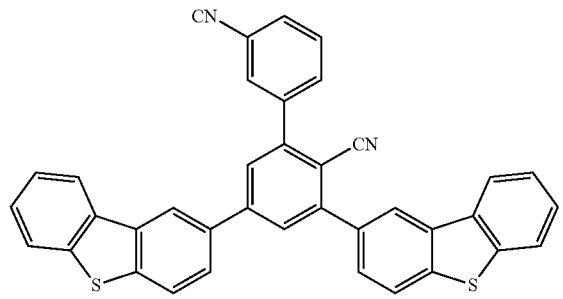
775
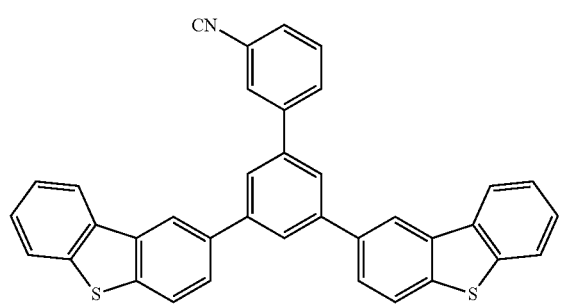
776
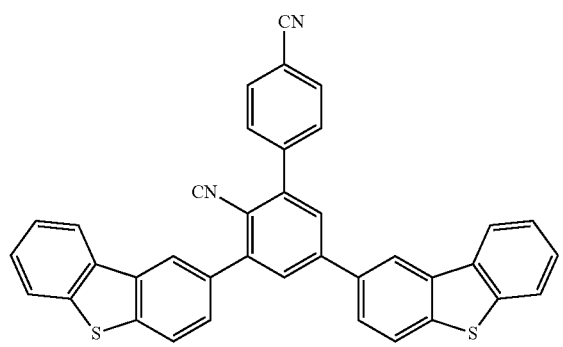
777
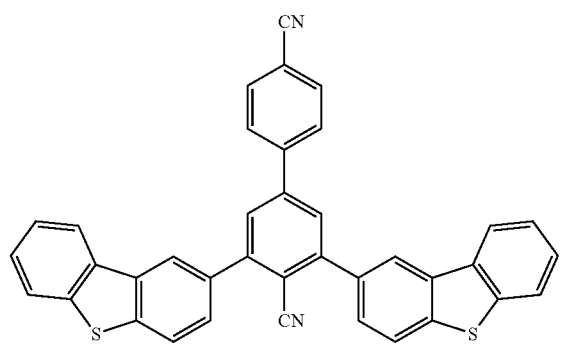
778
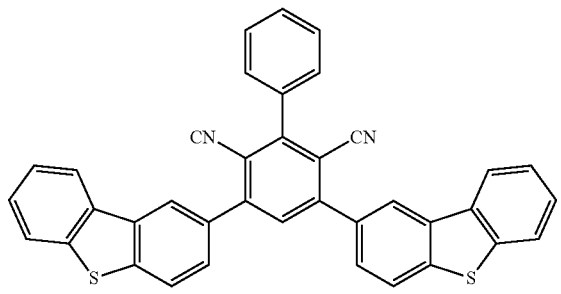
779
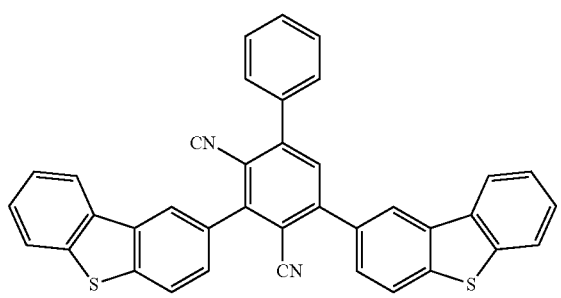
780
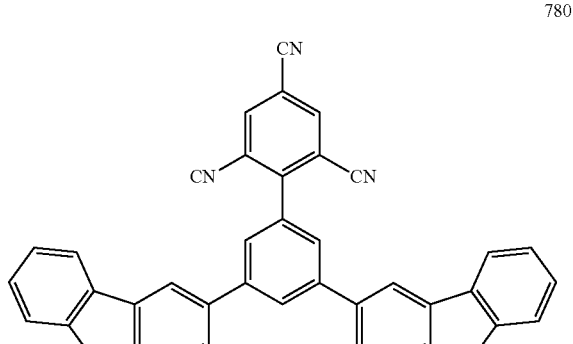
781
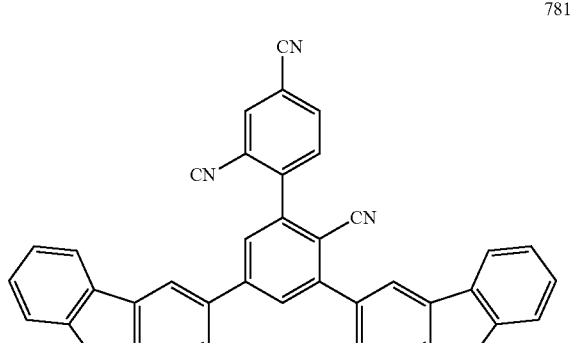

782
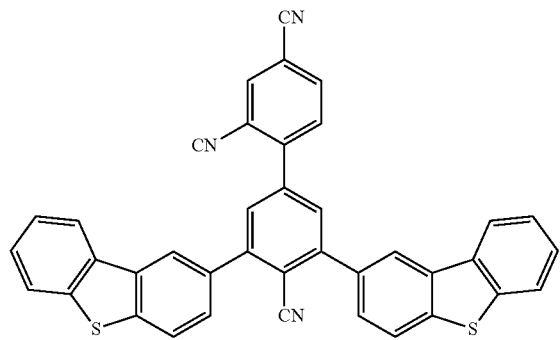
783
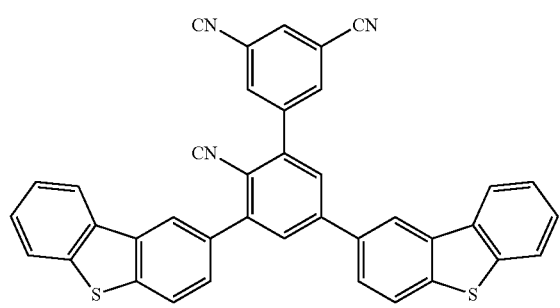
784
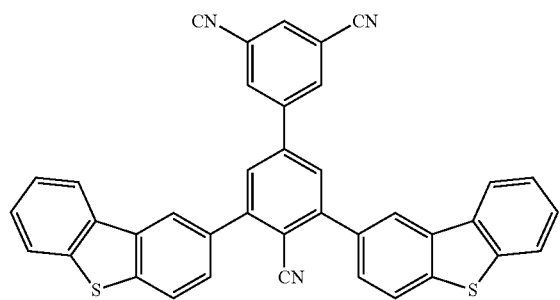
785
786
787
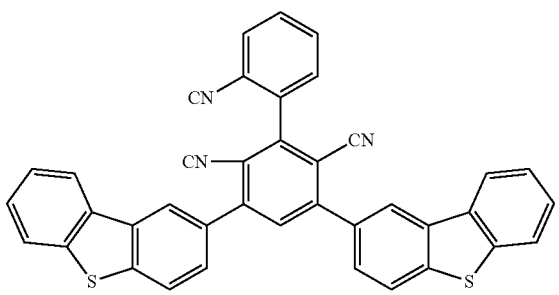
788
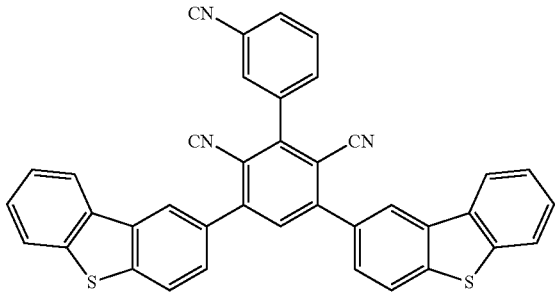
789
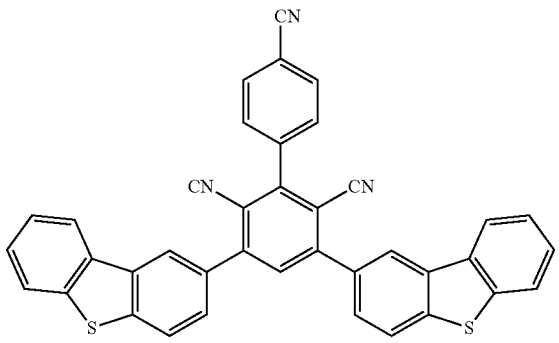
790
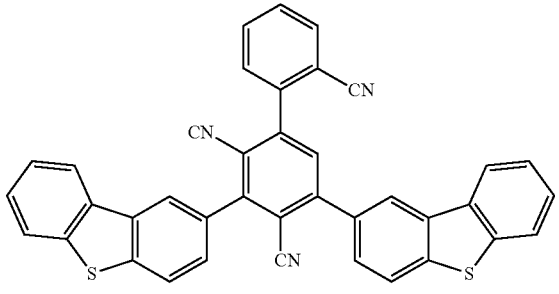
791
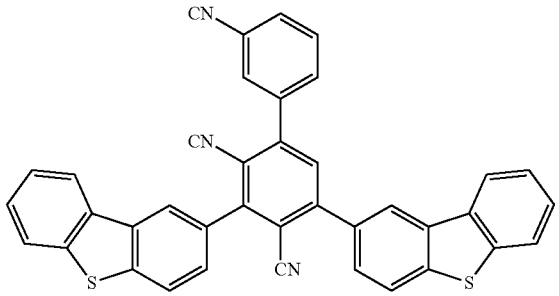

219
-continued
792
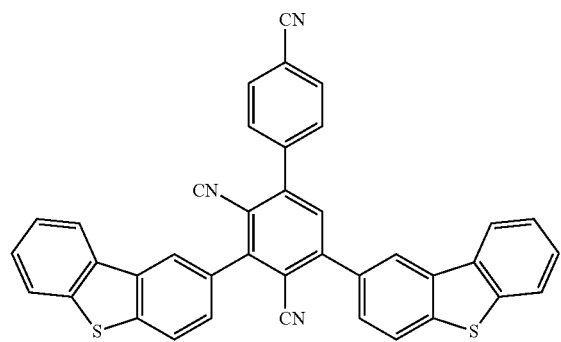
793
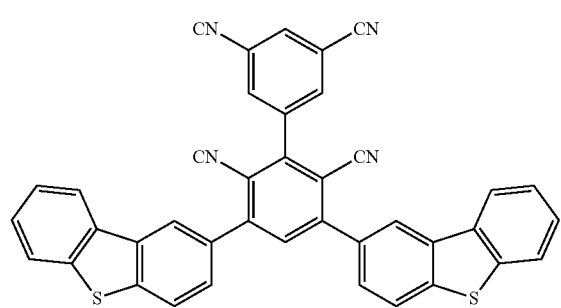
794
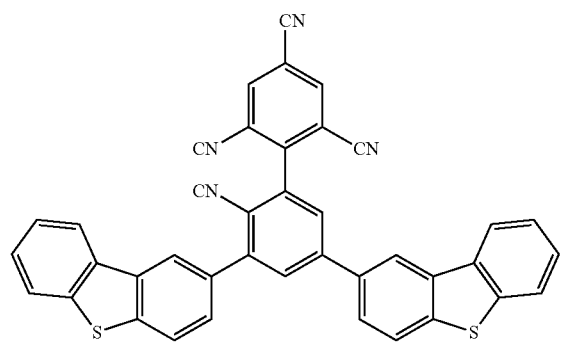
795
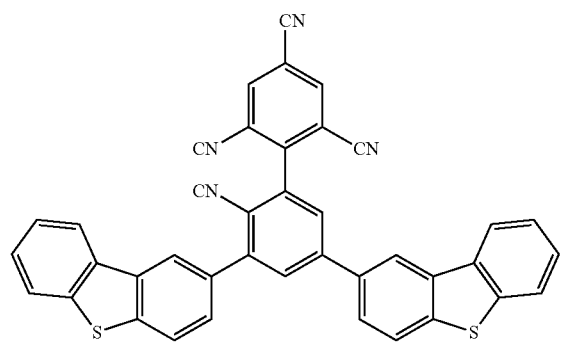
220
-continued
796
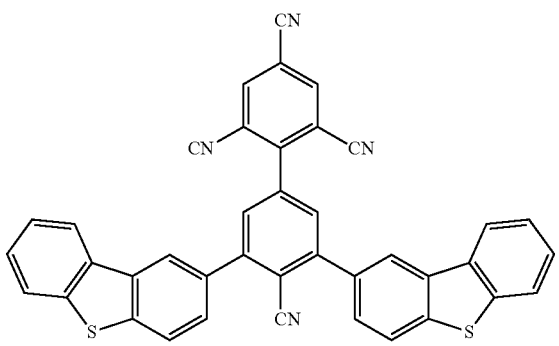
797
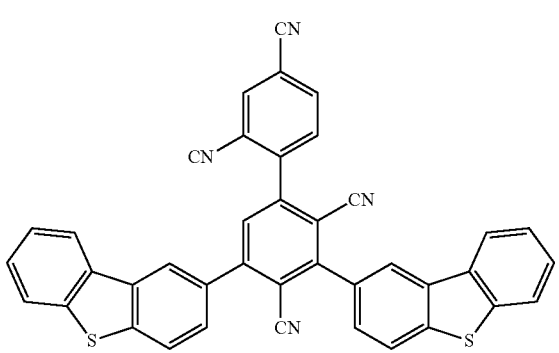
798
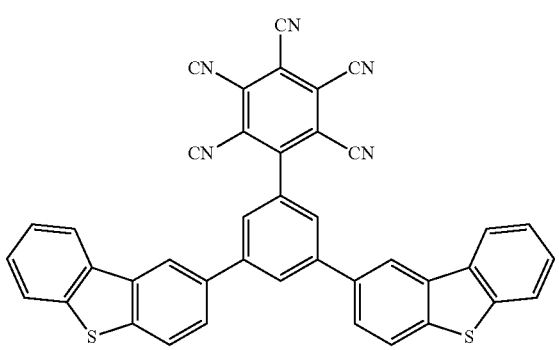
799
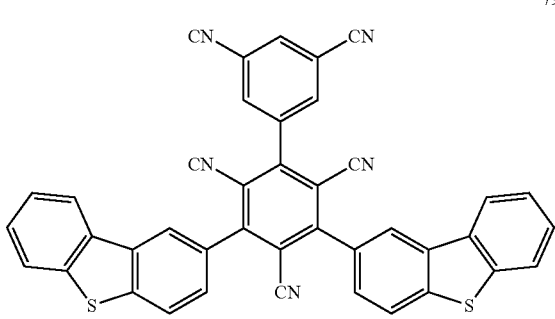

800
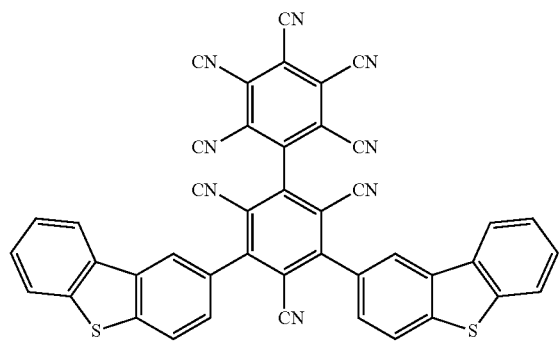
801
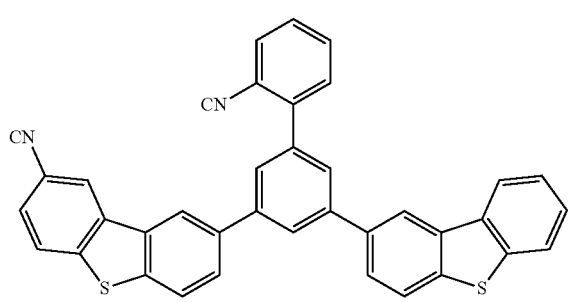
802
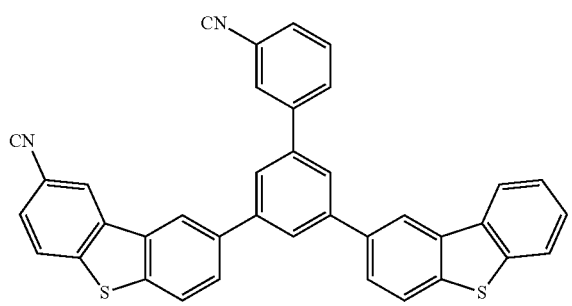
803
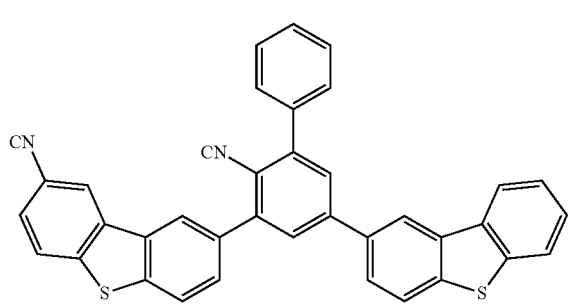
804
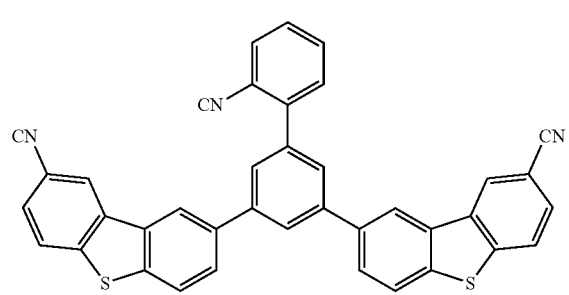
805
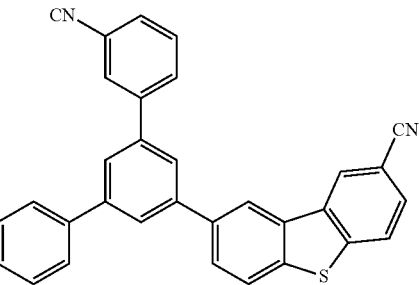
806
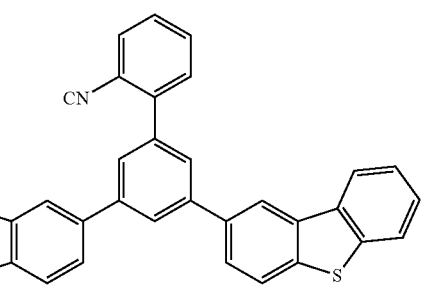
807
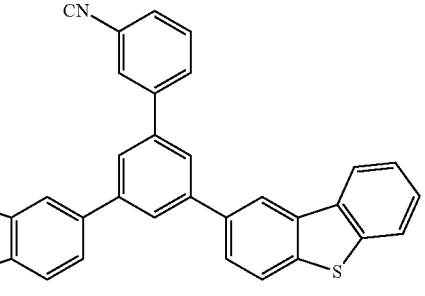
808
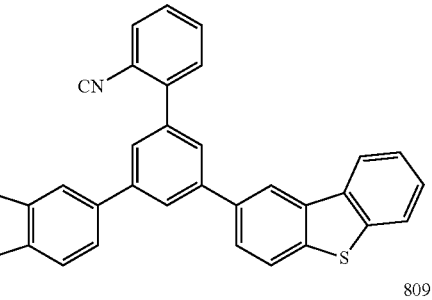
809
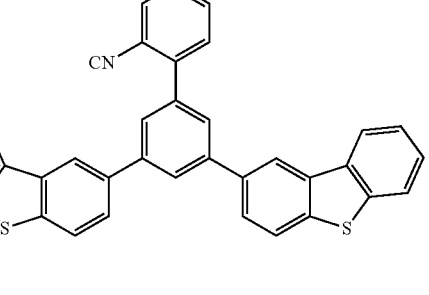

223
-continued
810
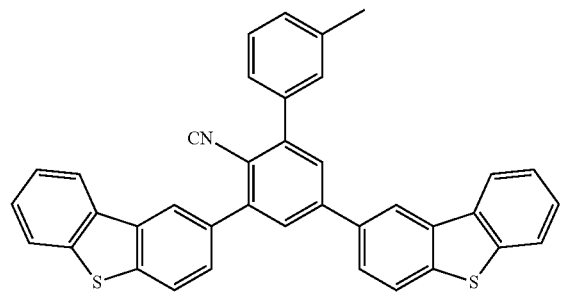
811
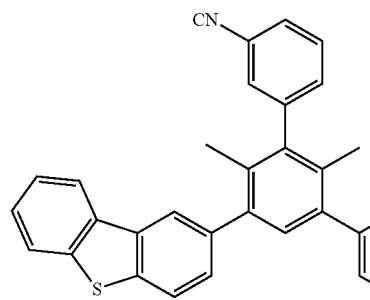
812
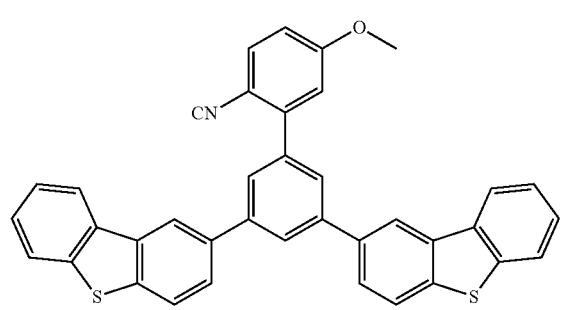
813
814
224
-continued
815
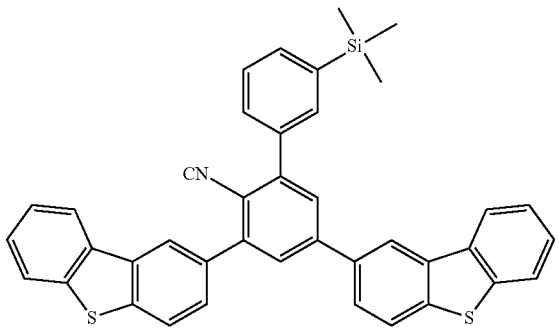
816
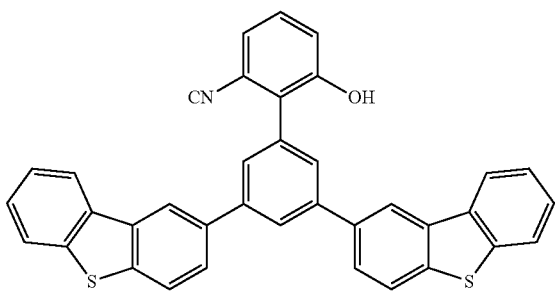
817
818
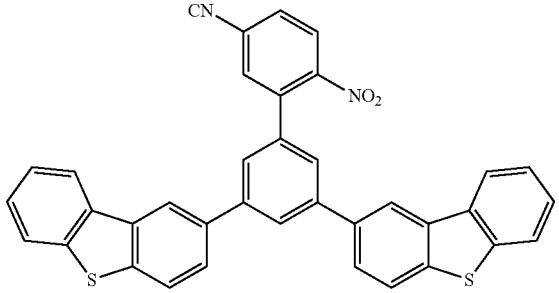
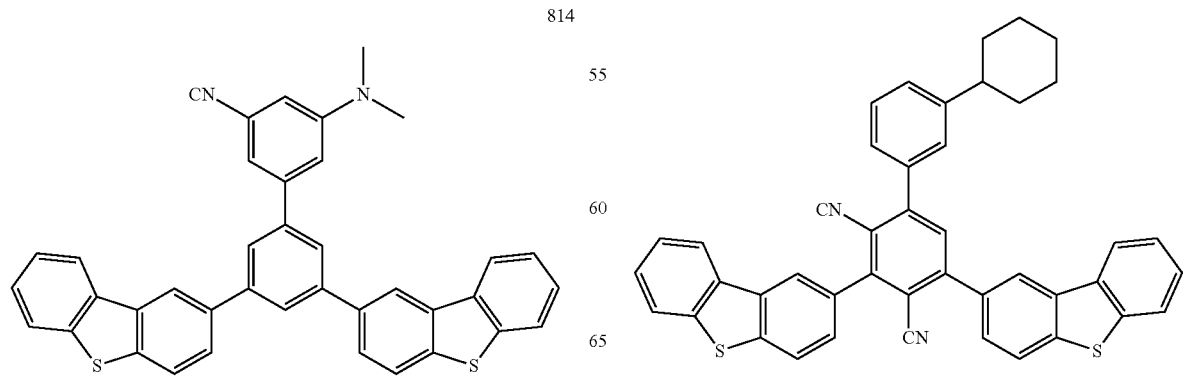

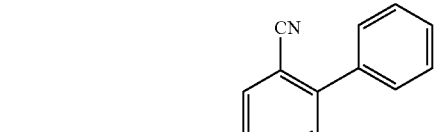
819
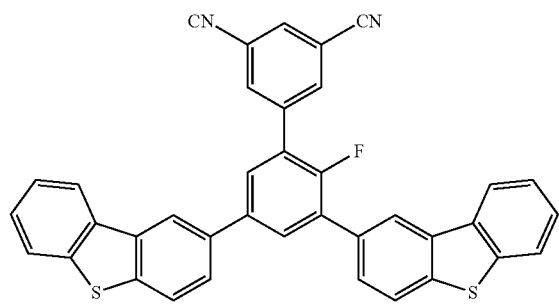
820
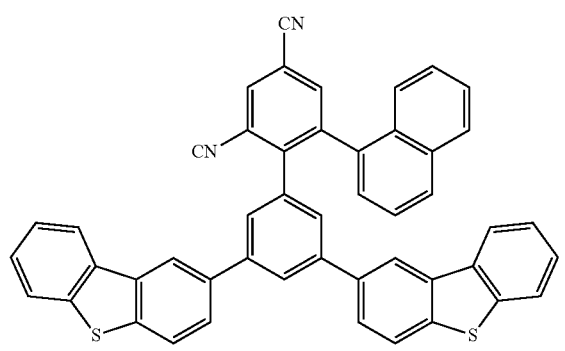
821
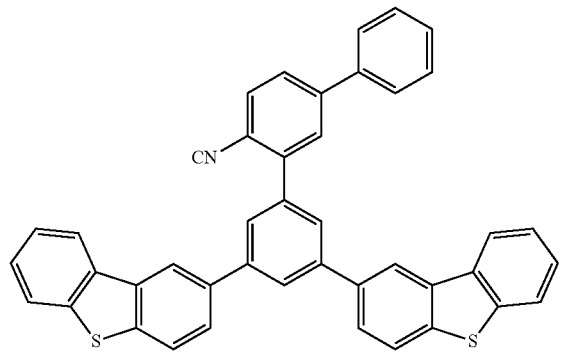
822
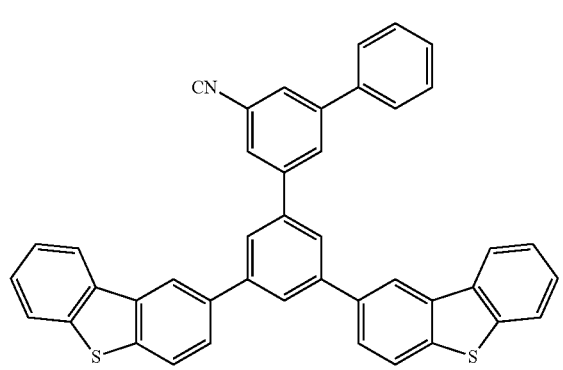
823
824
825
826

227
-continued
828
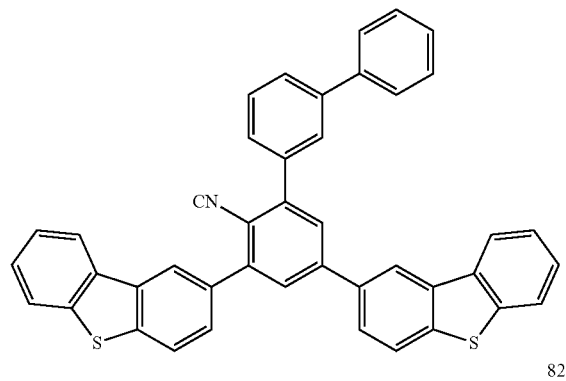
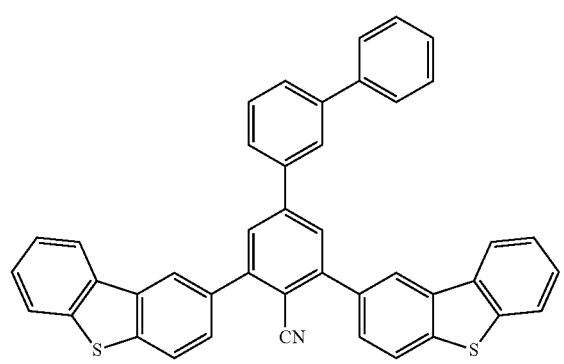
829
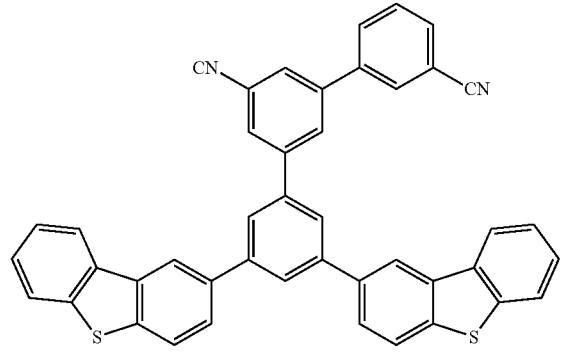
830
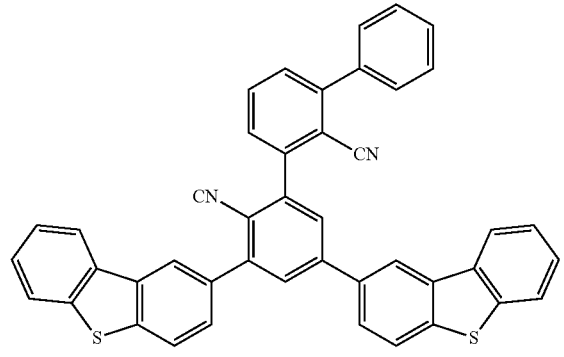
228
-continued
831
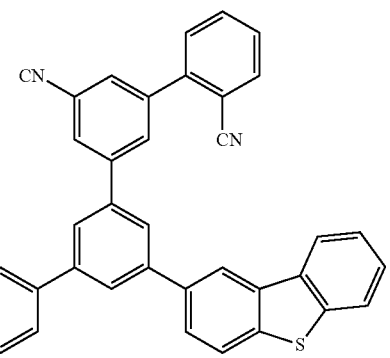
832
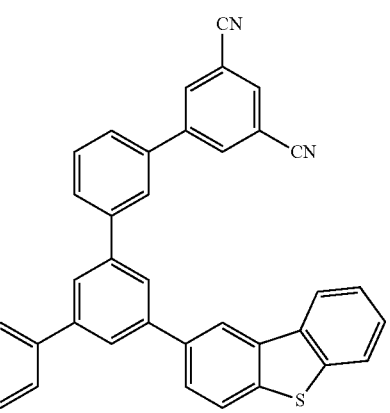
833
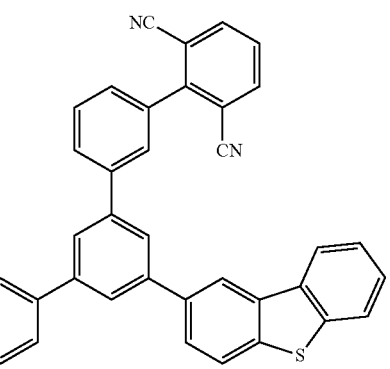
834

835
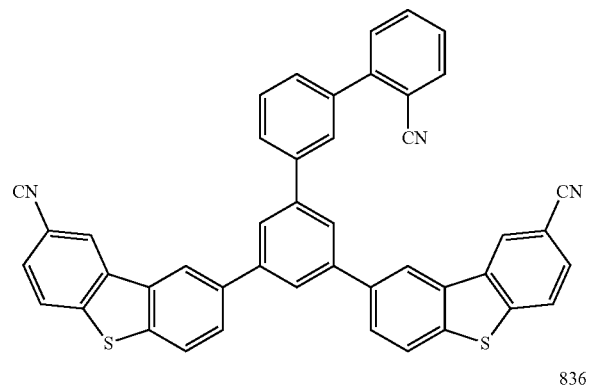
836
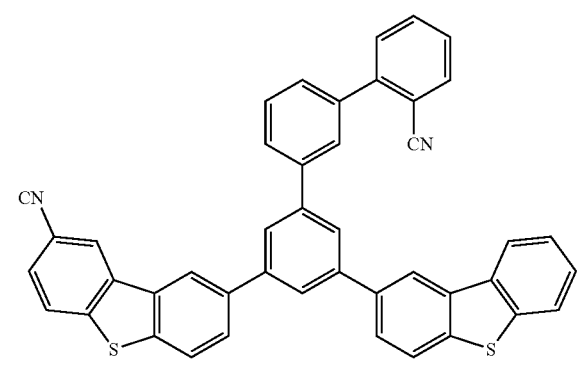
837
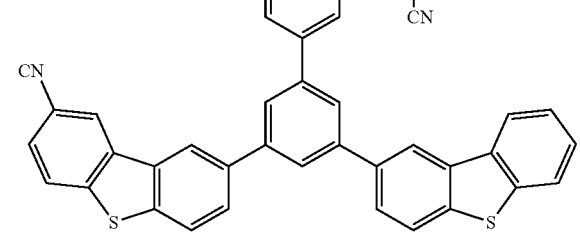
838
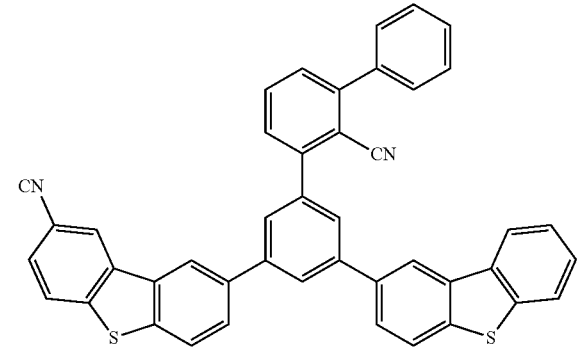
839
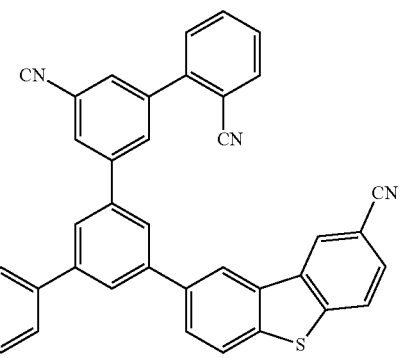
840
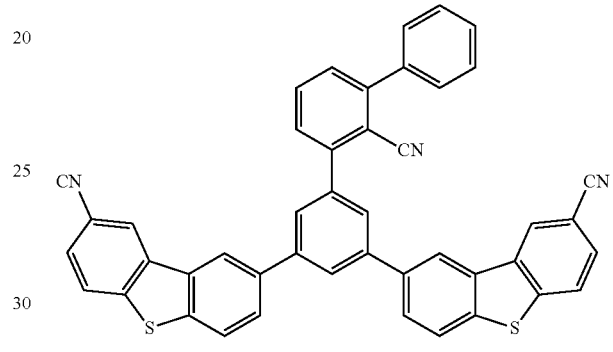
841
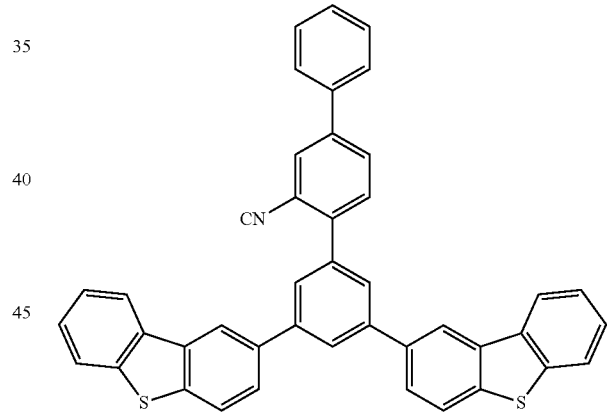
842
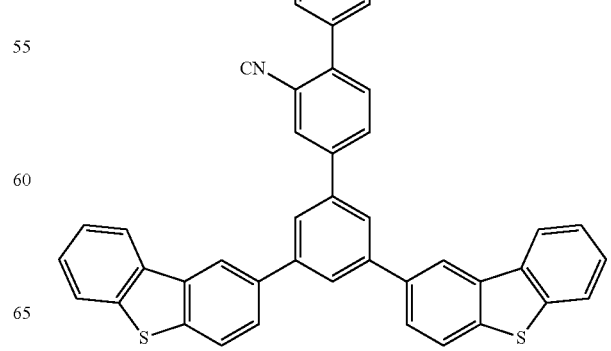

| 843 | 846 |
|---|---|
| 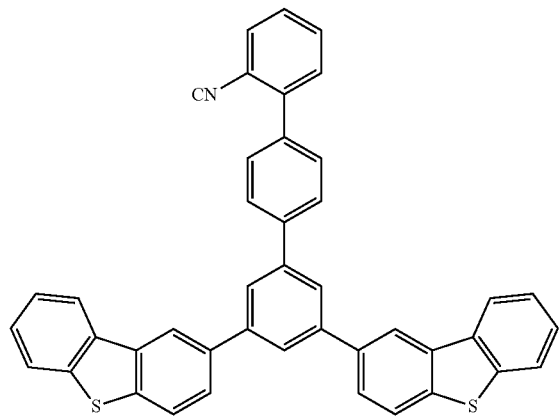 | 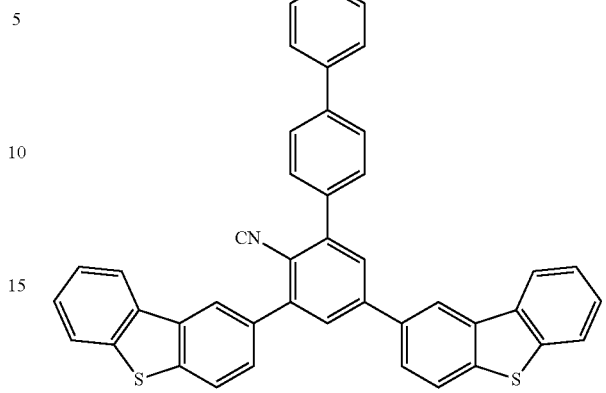 |
| 844 | 847 |
| 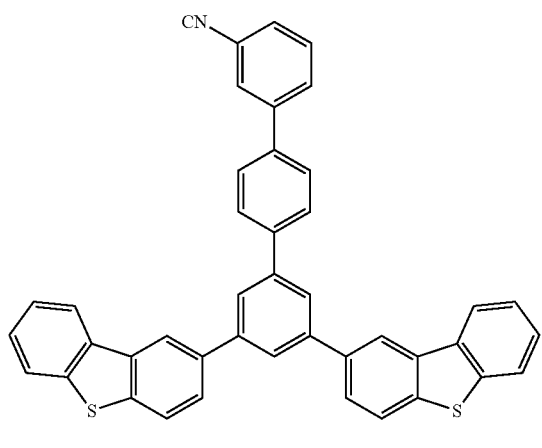 | 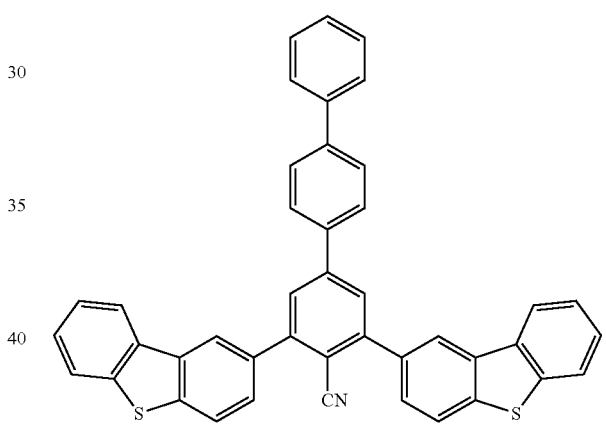 |
| 845 | 848 |
| 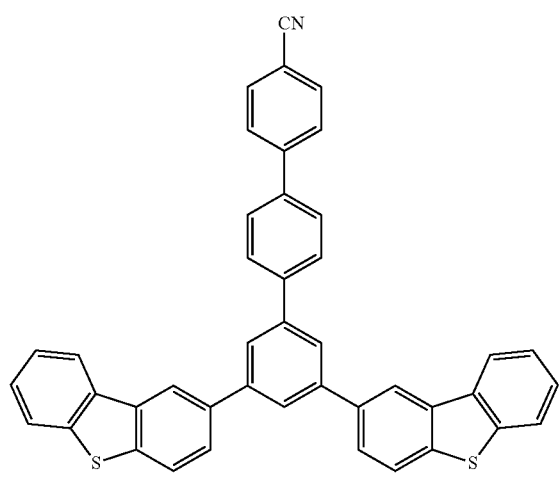 | 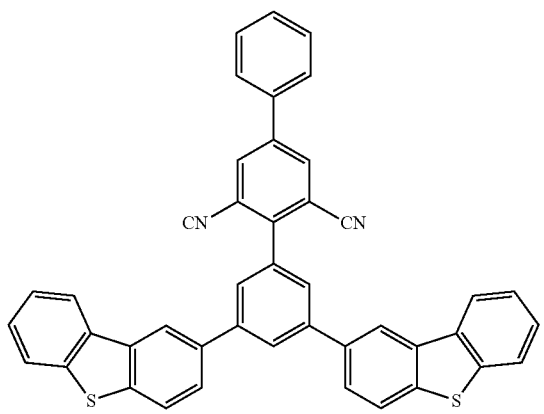 |

233
-continued
849
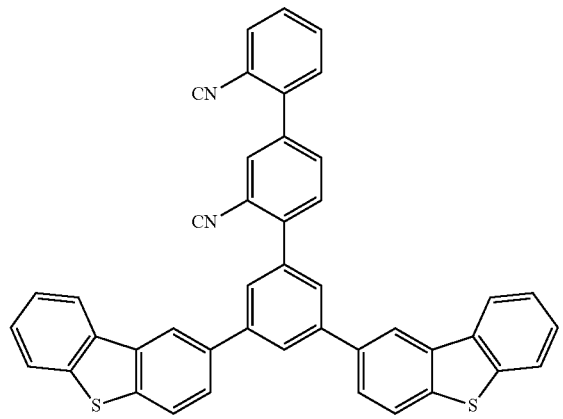
850
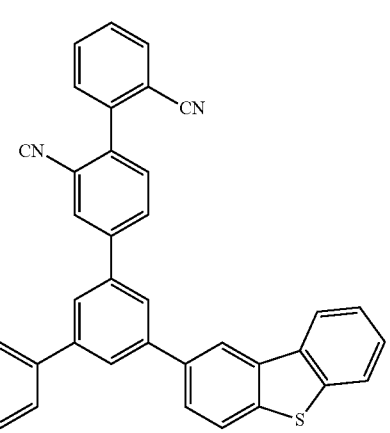
851
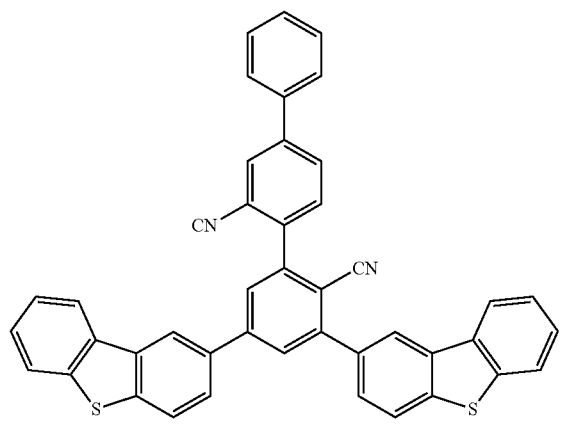
234
-continued
852
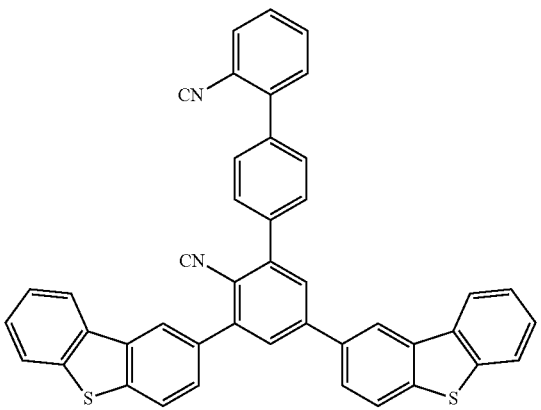
853
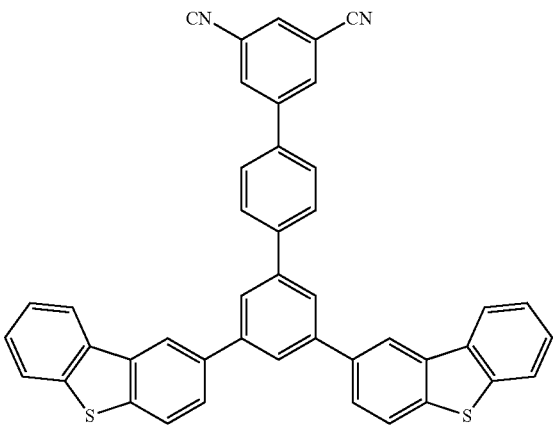
854

235
-continued
855
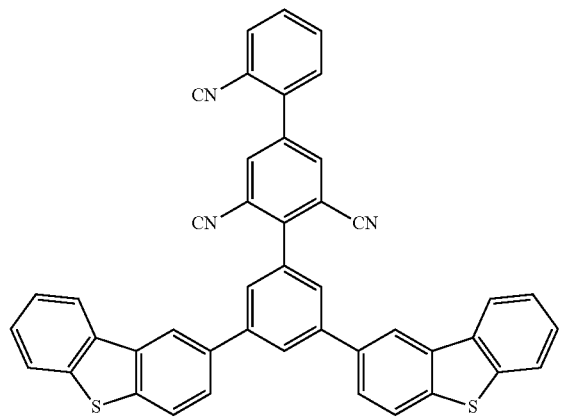
856
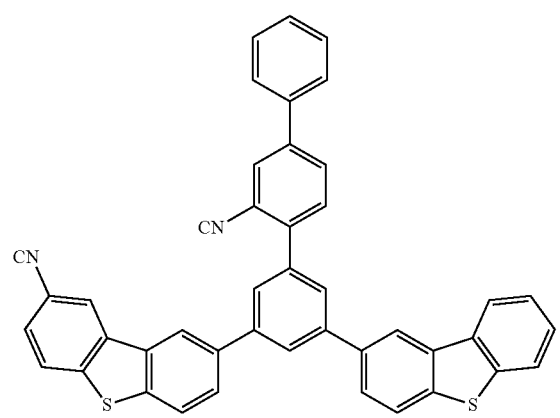
857
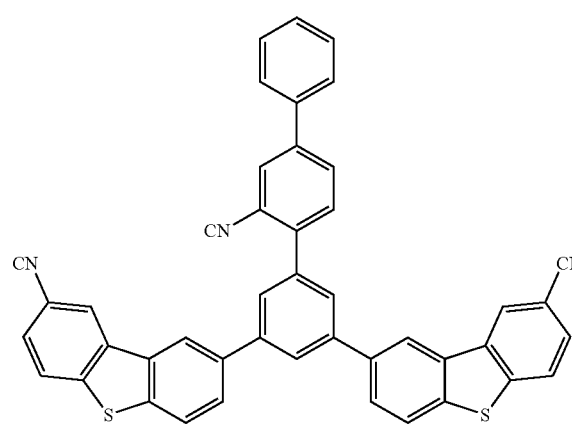
236
-continued
858
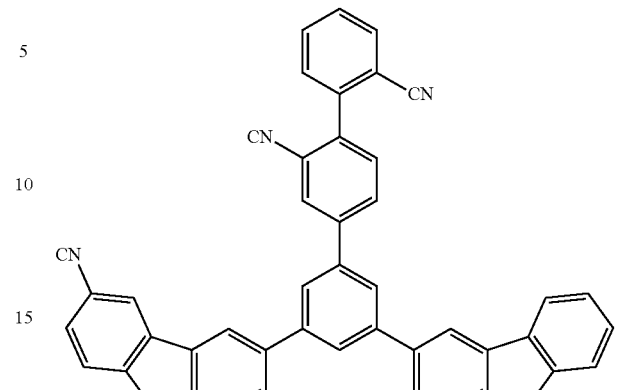
859
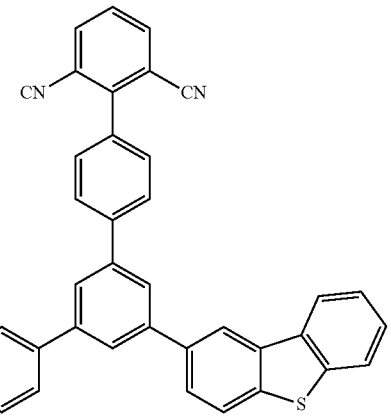
860
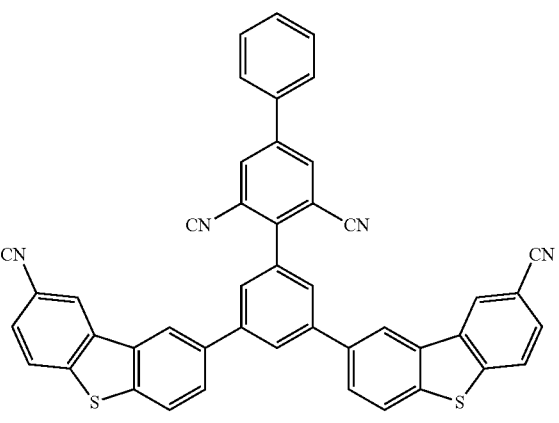

861
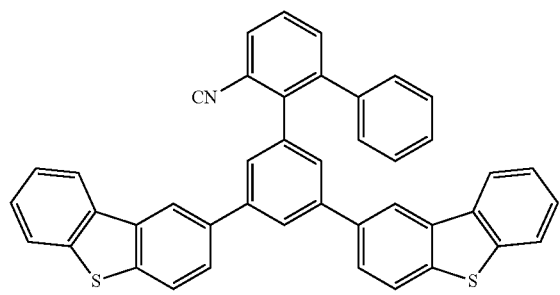
862
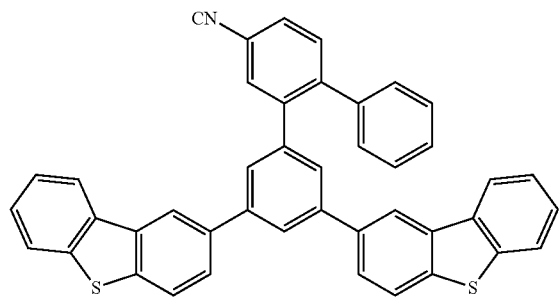
863
864
865
866
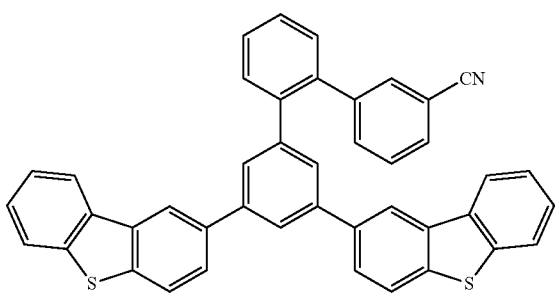
867
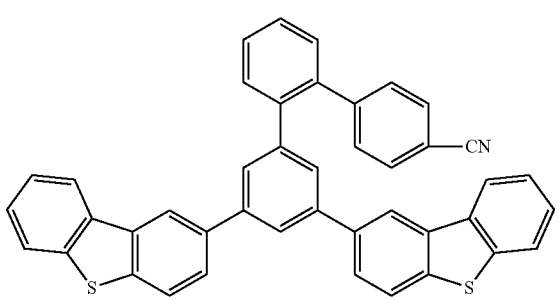
868
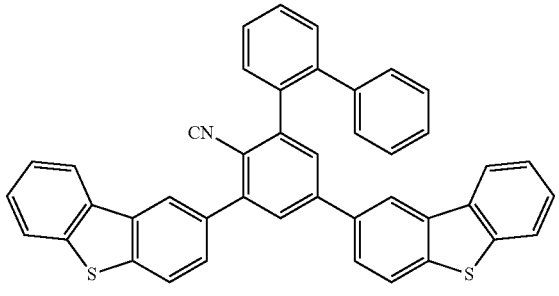
869
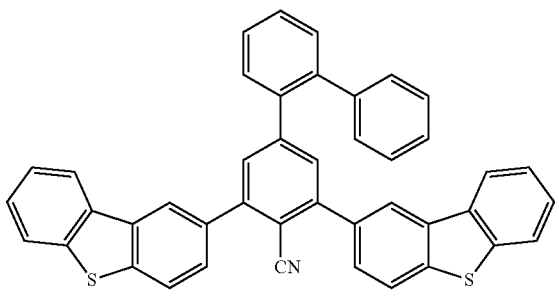
870
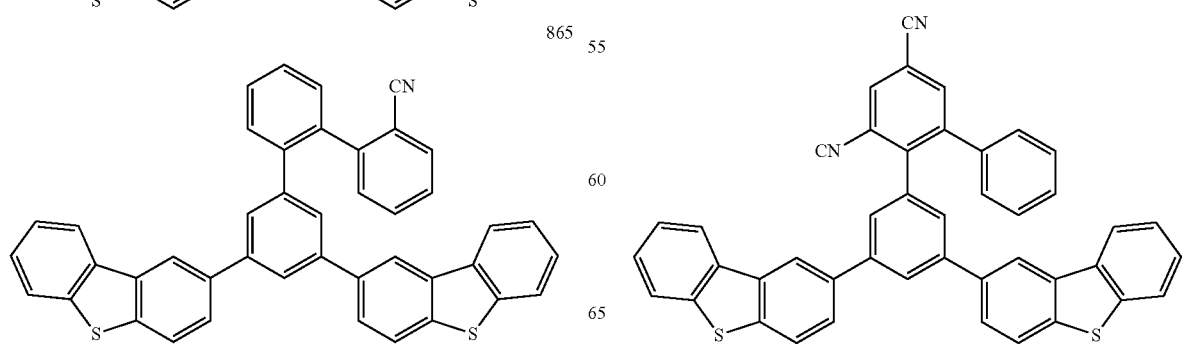

-continued
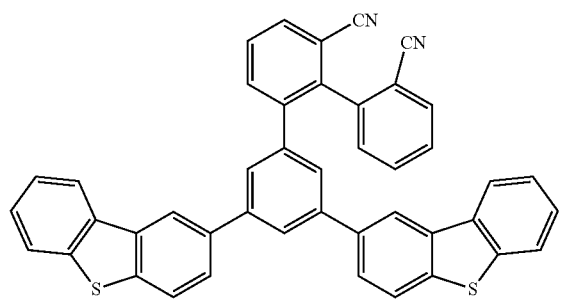
871
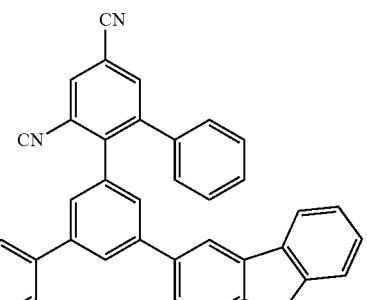
876
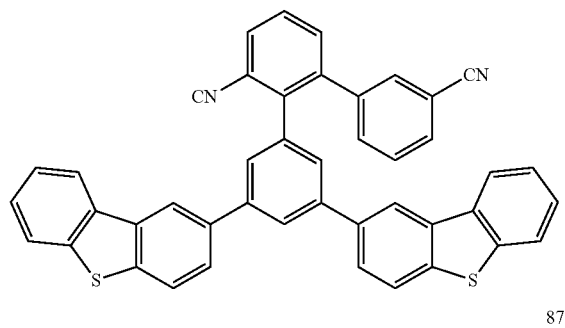
872
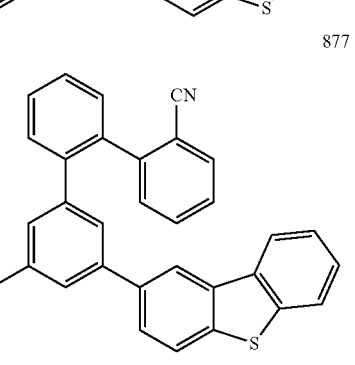
877
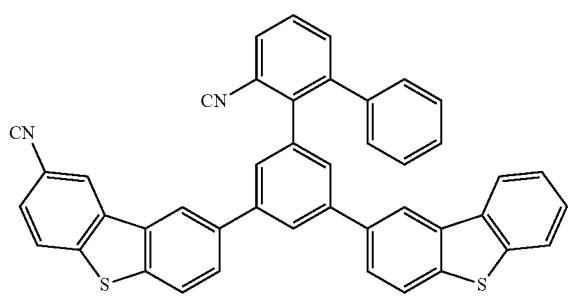
873
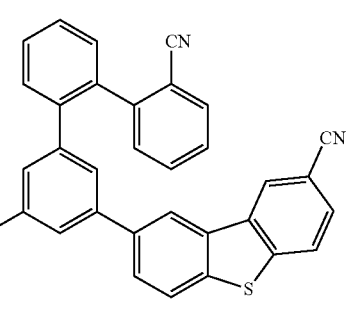
878
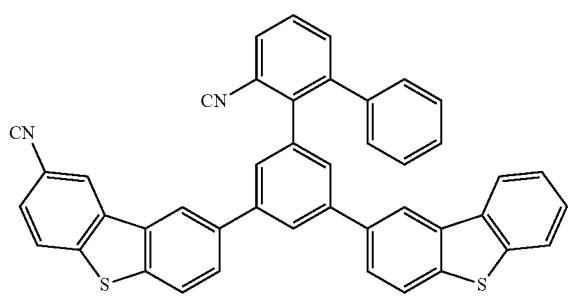
874
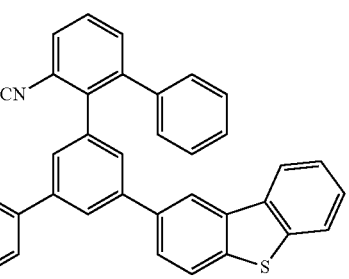
879
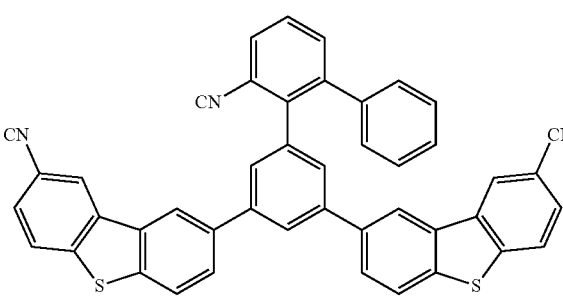
875
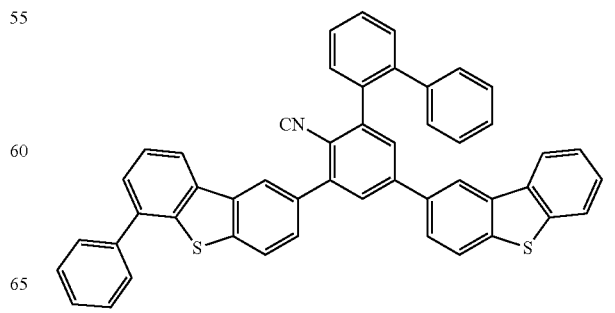
880

-continued
881
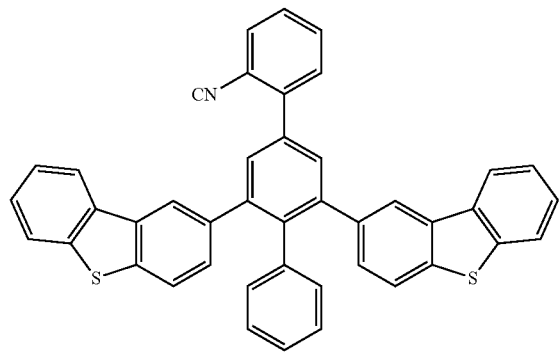
882
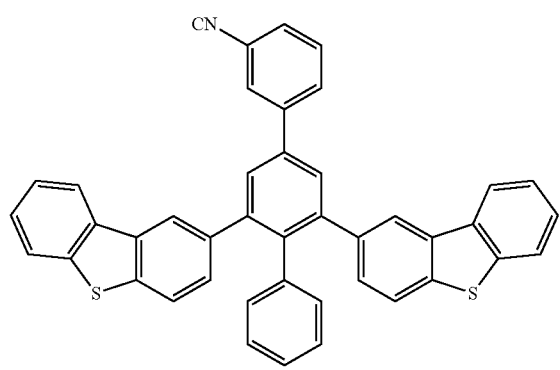
883
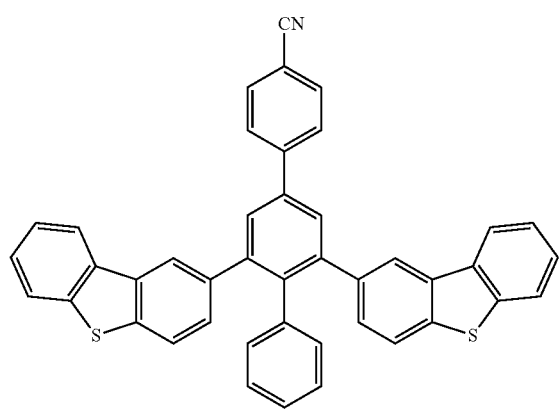
884
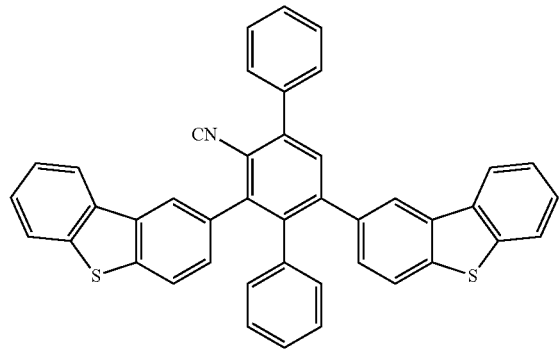
-continued
885
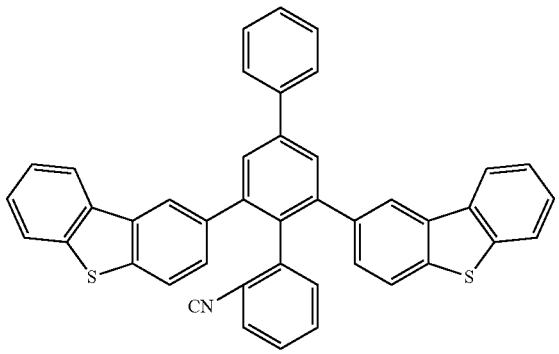
886
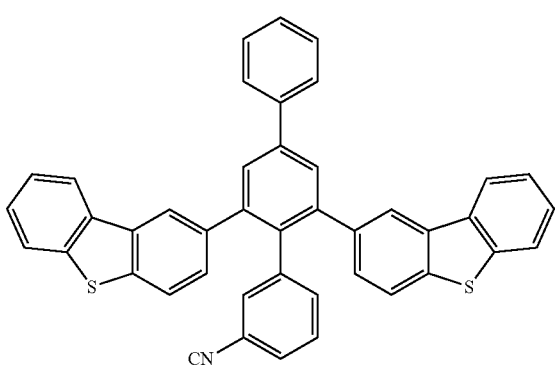
887
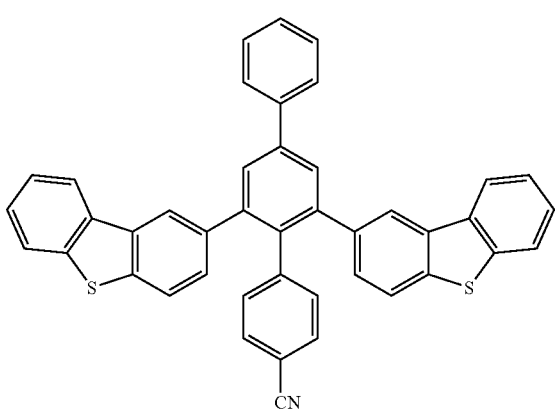
888
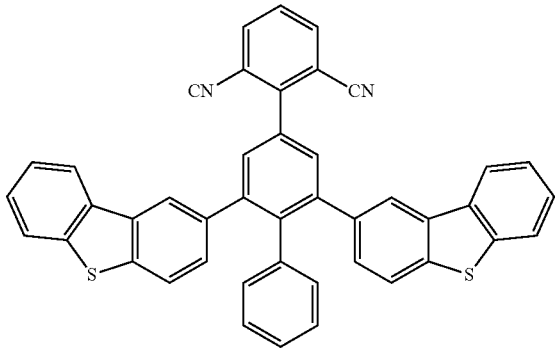

889
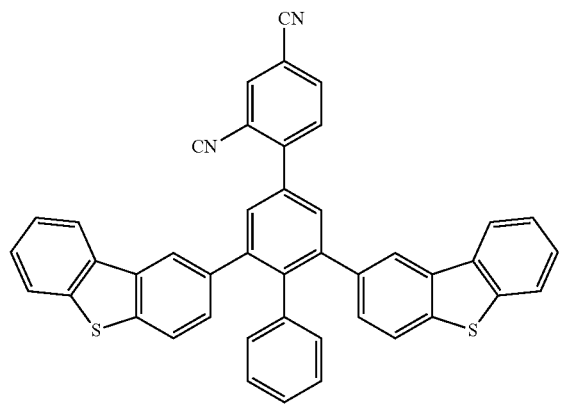
890
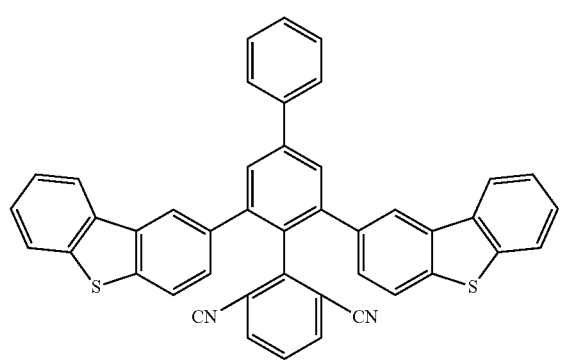
891
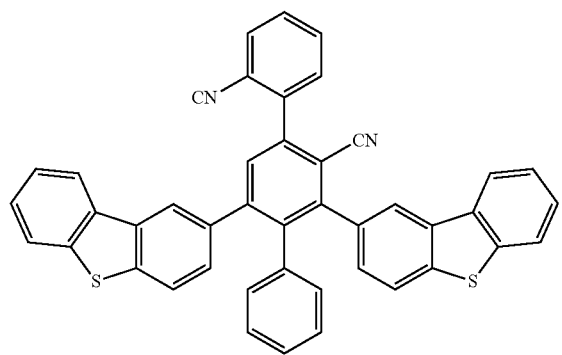
892
893
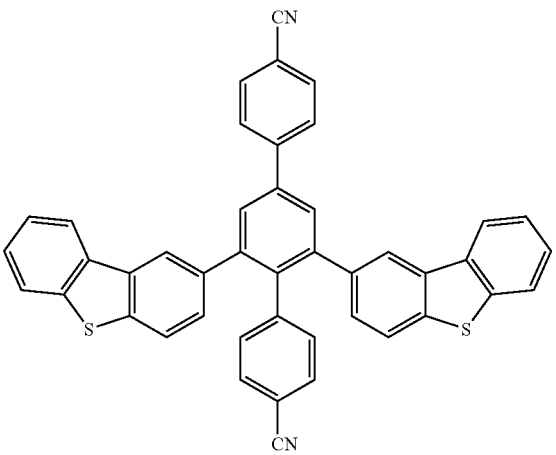
894
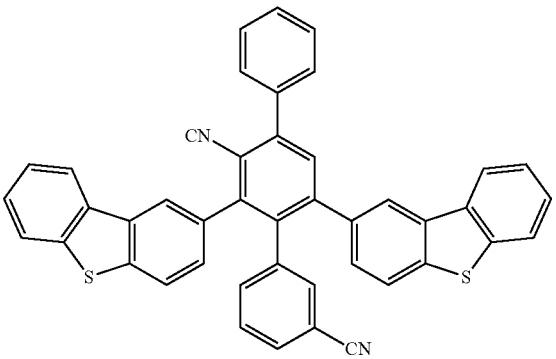
895
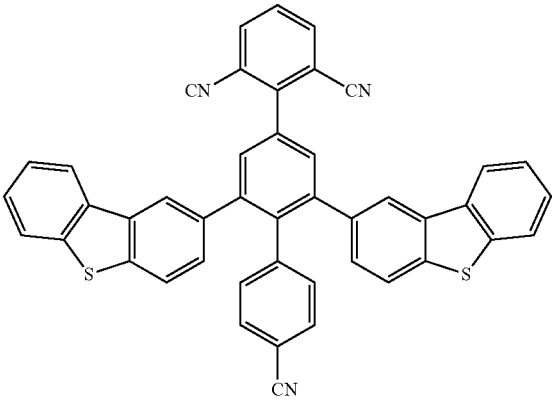
896
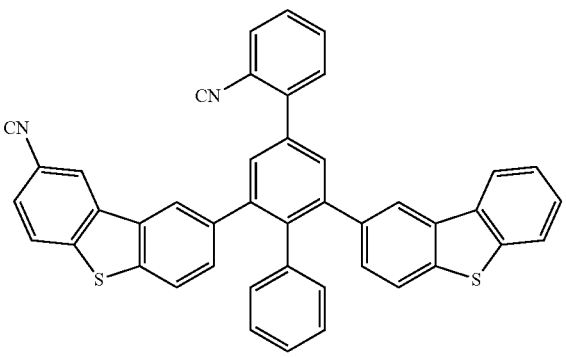

245
-continued
897
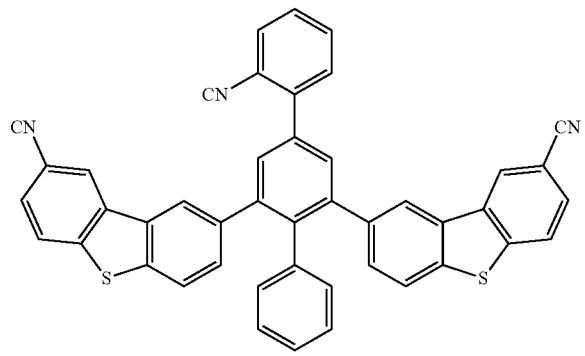
898
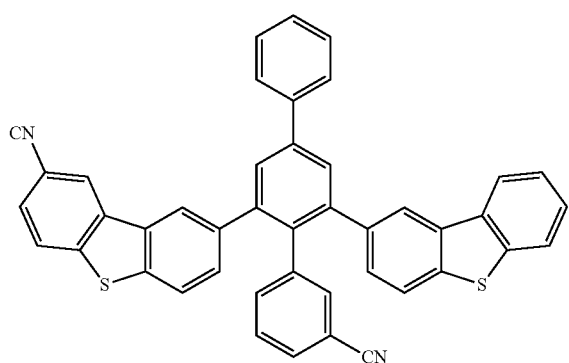
899
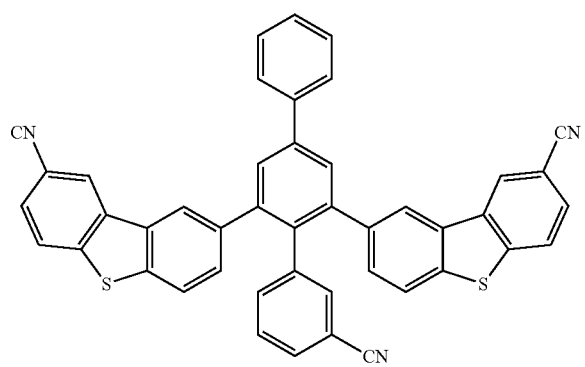
900
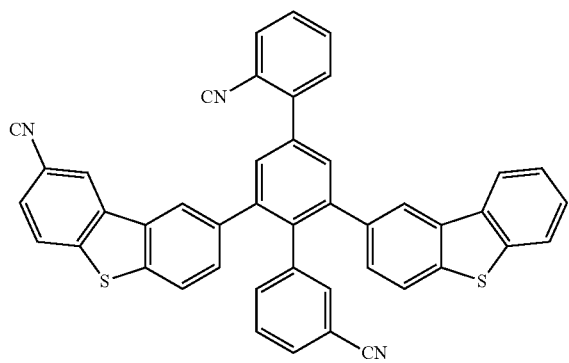
246
-continued
901
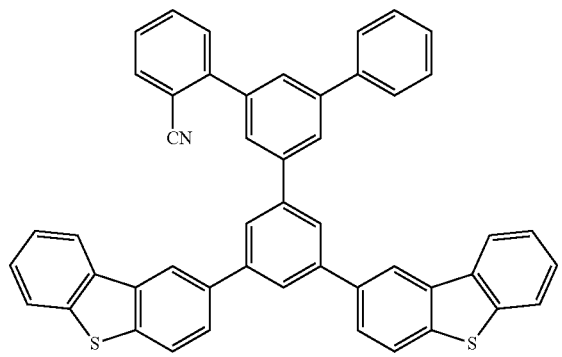
902
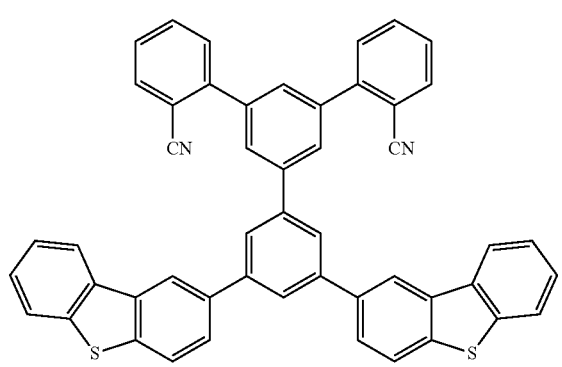
903
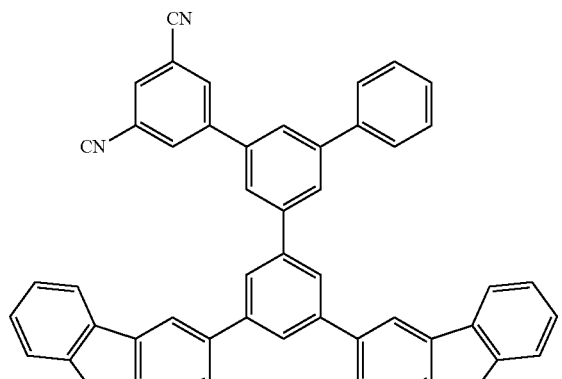
904
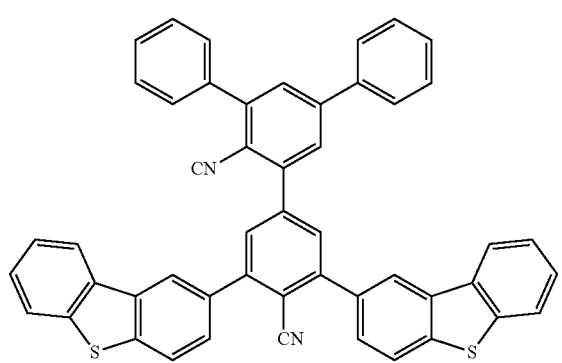

905
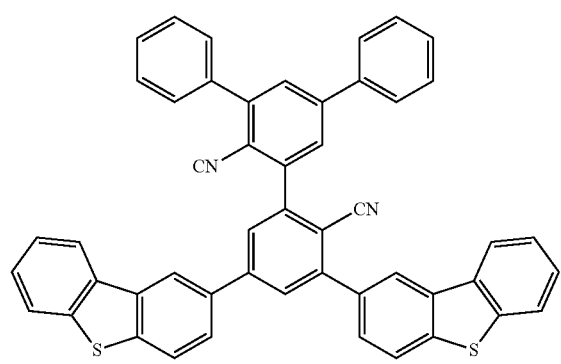
906
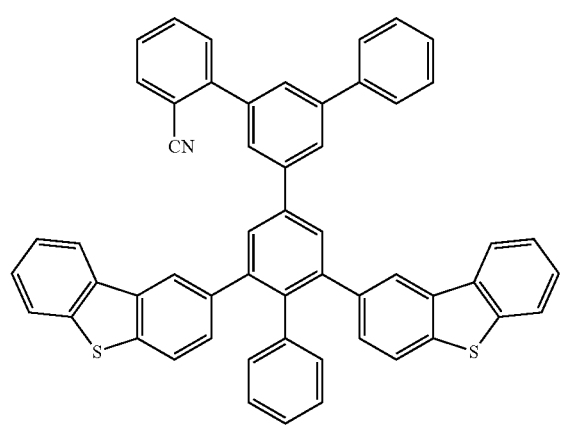
907
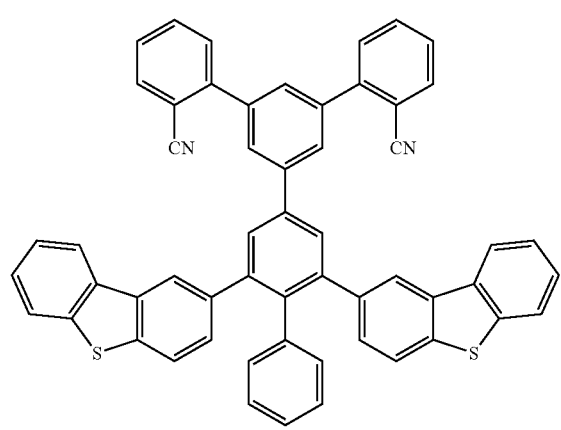
908
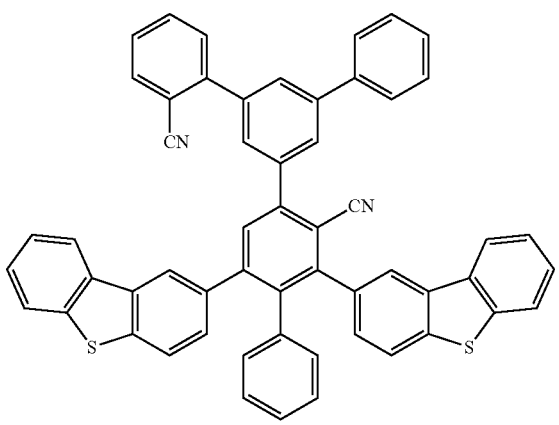
909
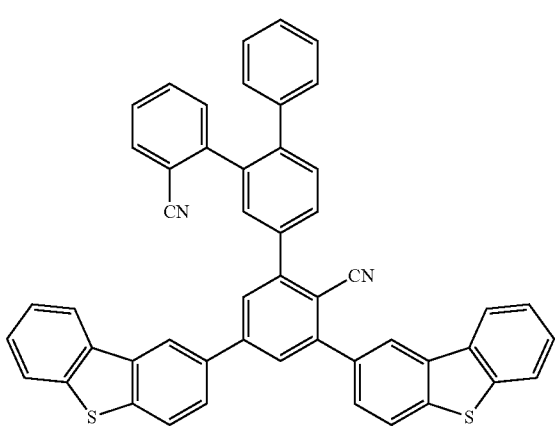
910
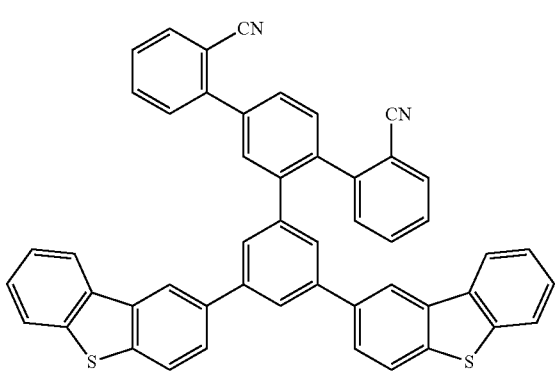
911
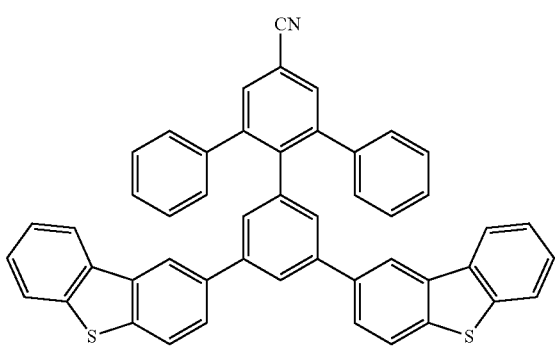

-continued
912
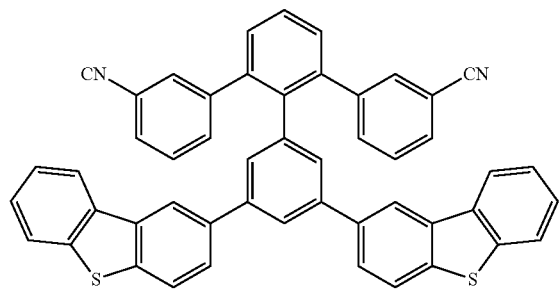
913
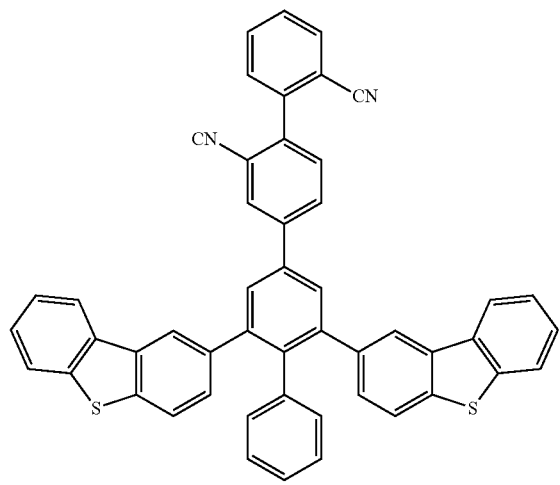
914
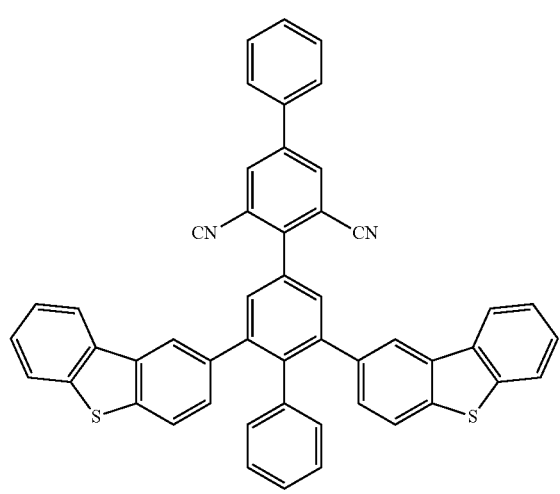
-continued
915
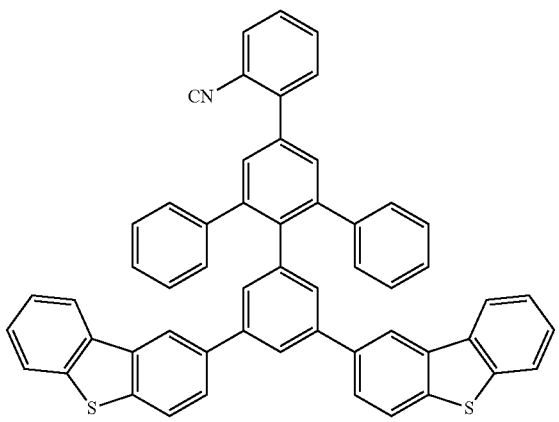
916
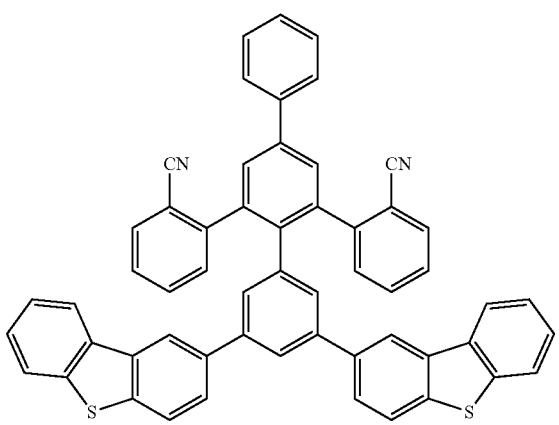
917
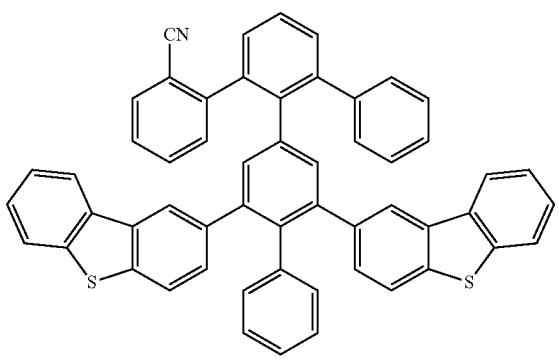
918
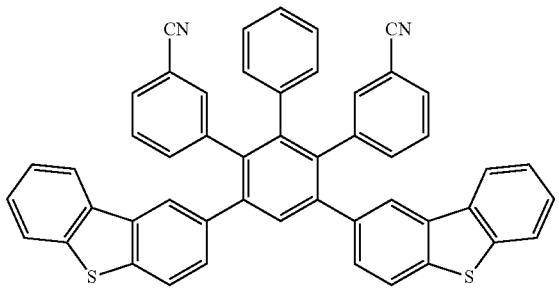

919
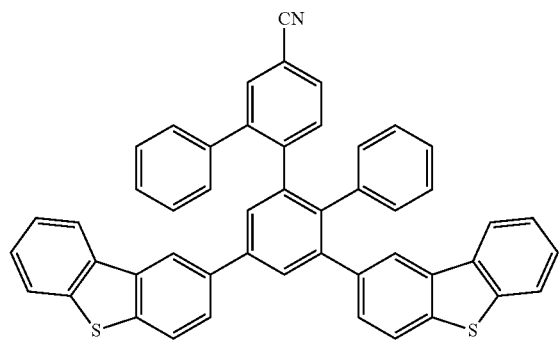
920
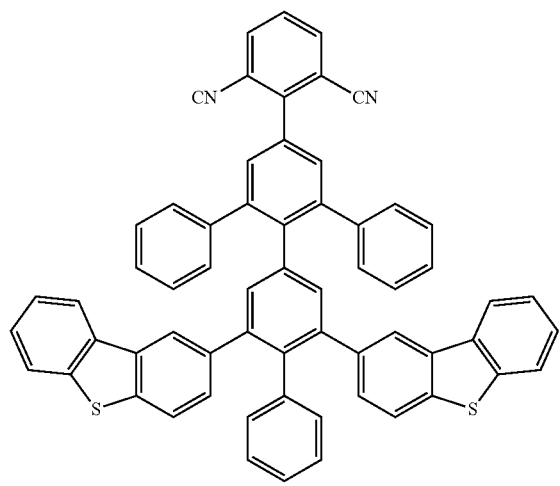
921
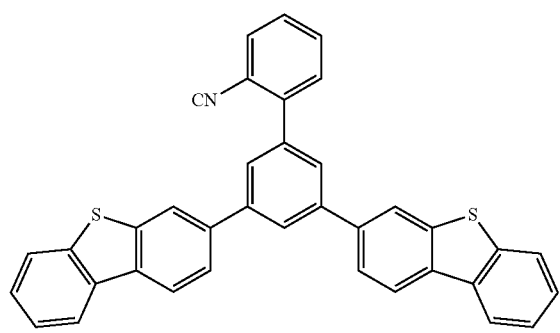
922
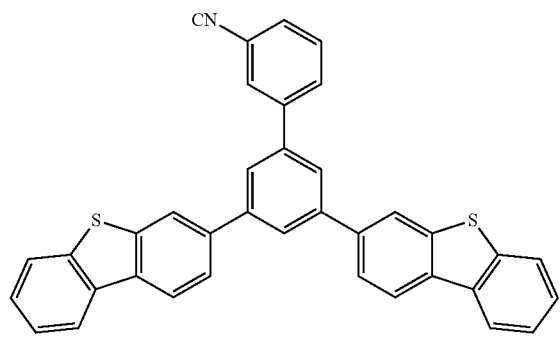
923
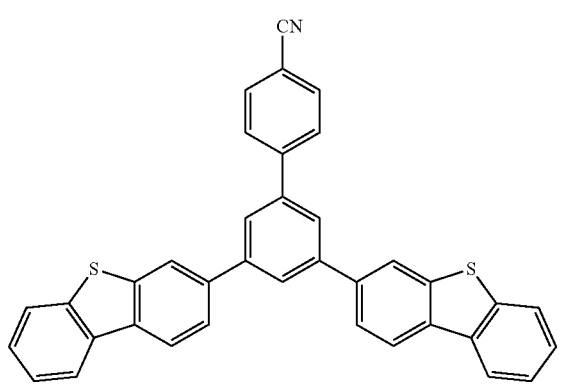
924
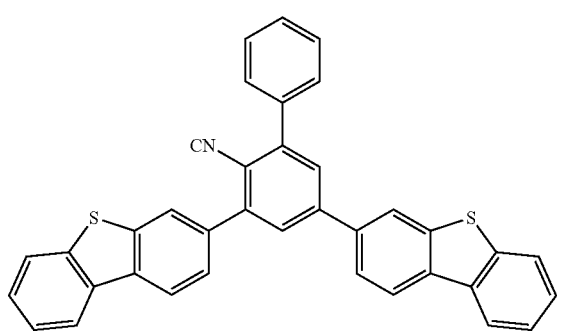
925
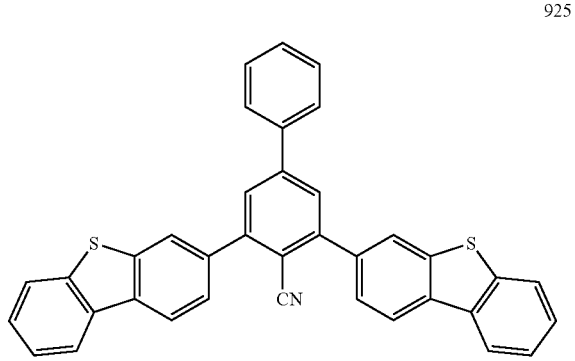
926
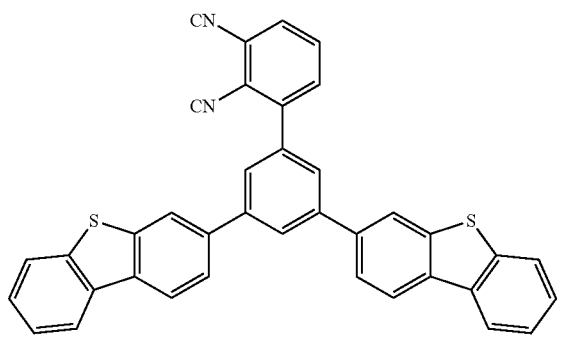

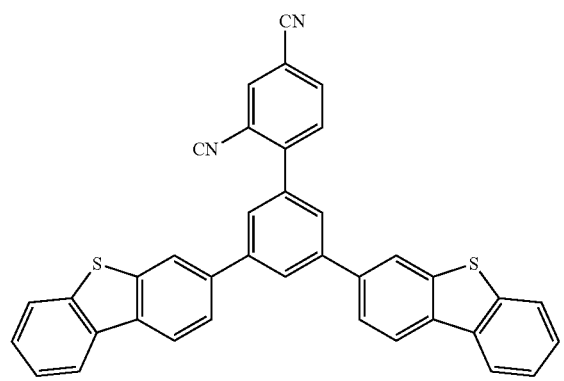
927
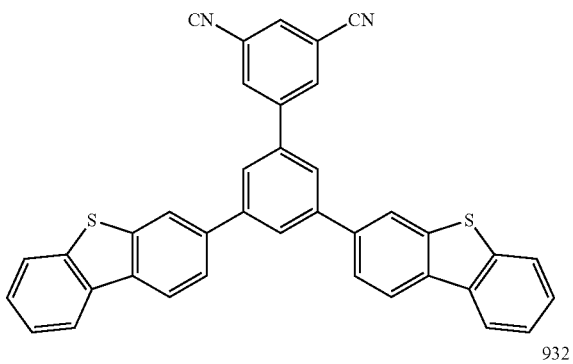
931
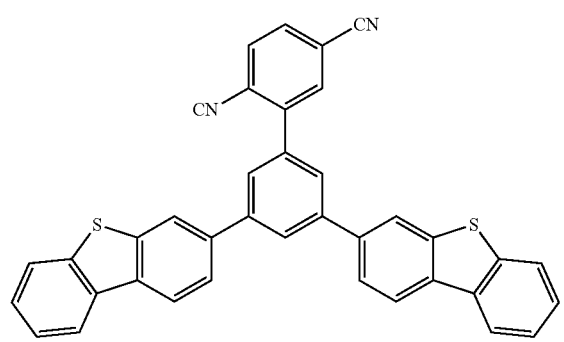
928
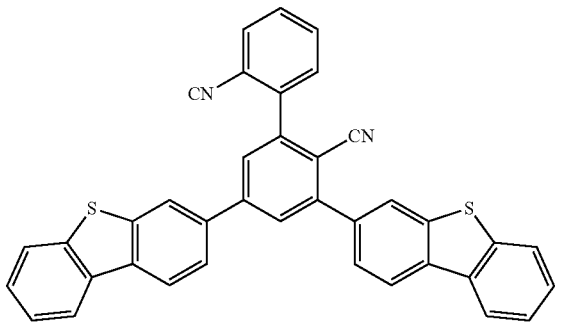
932
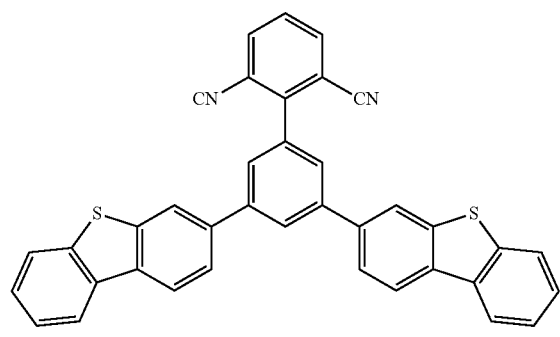
929
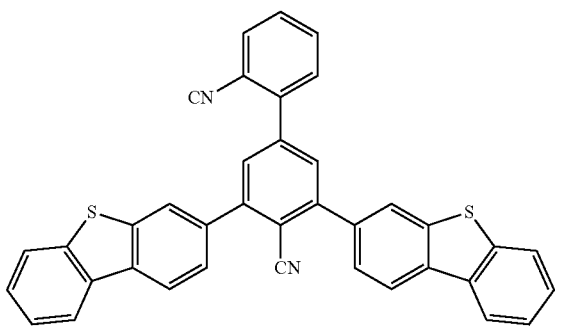
933
930
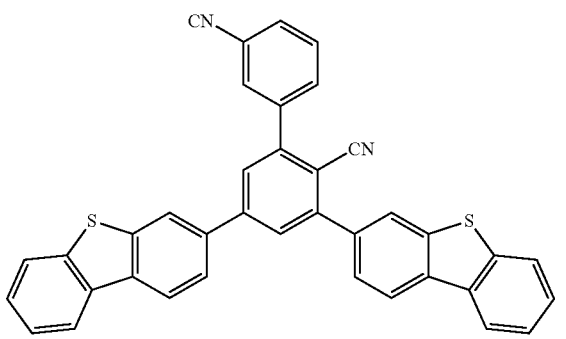
934

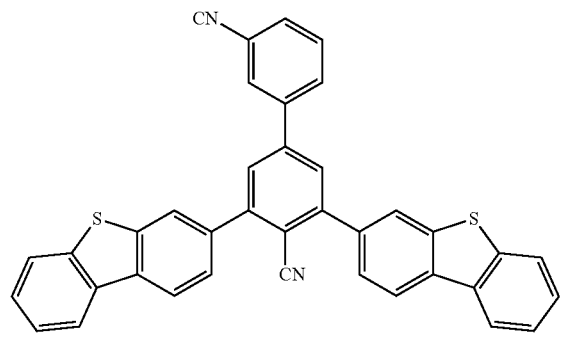
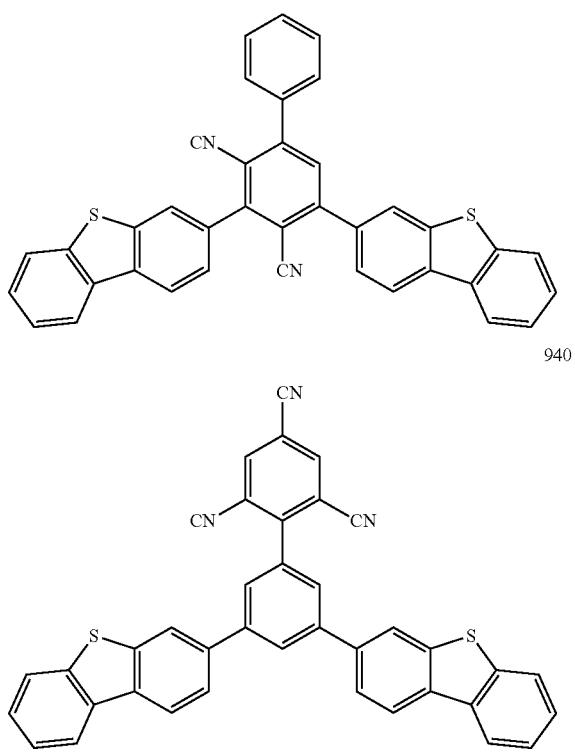
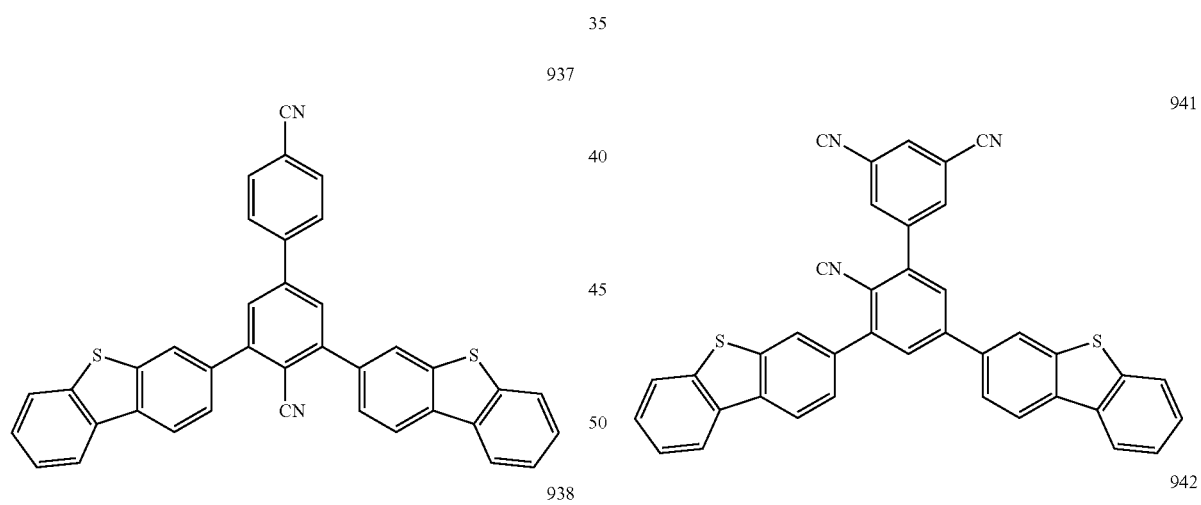
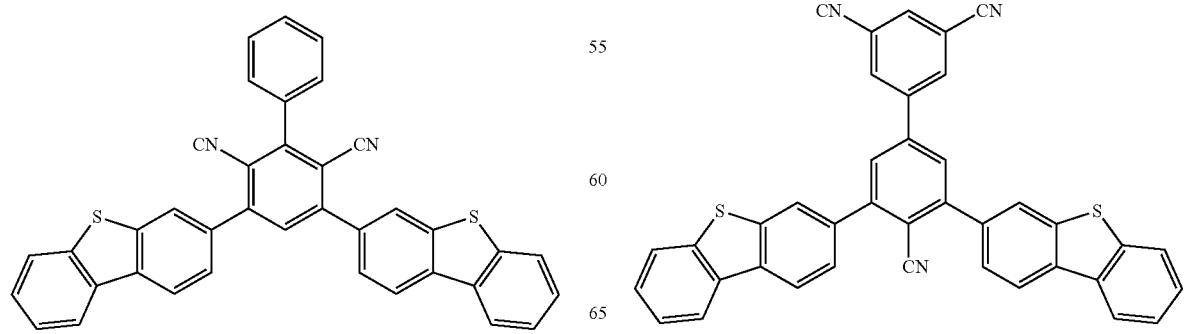

943
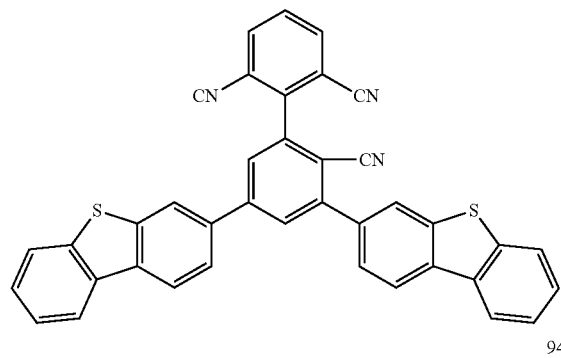
944
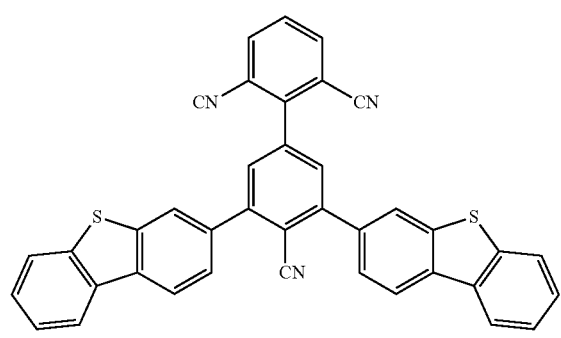
945
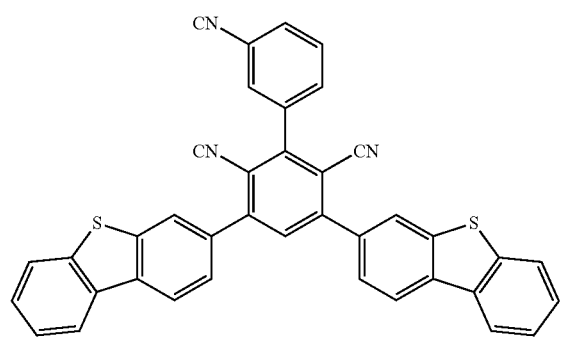
946
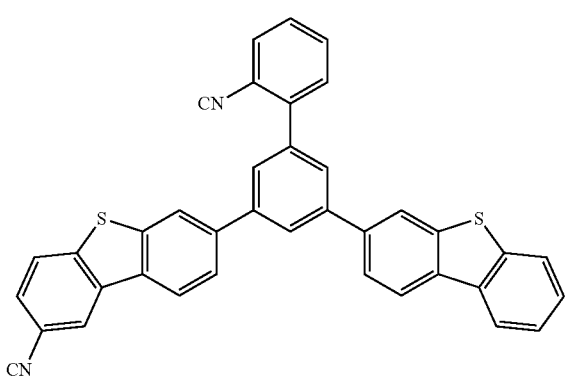
947
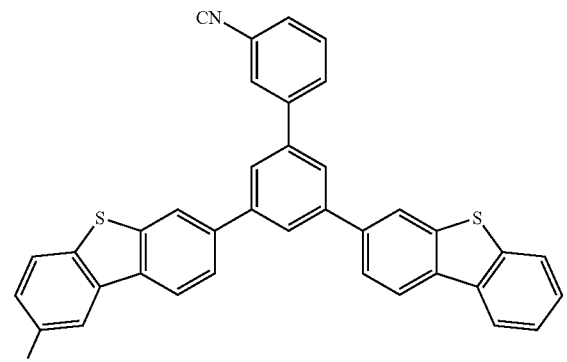
948
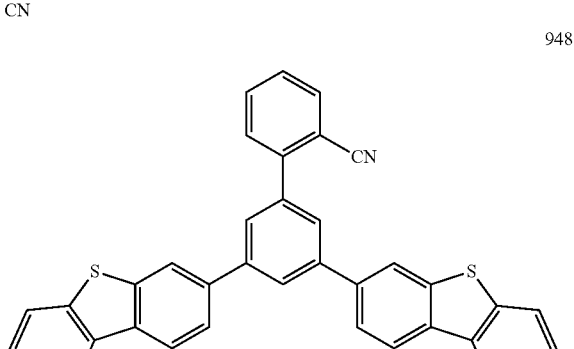
949
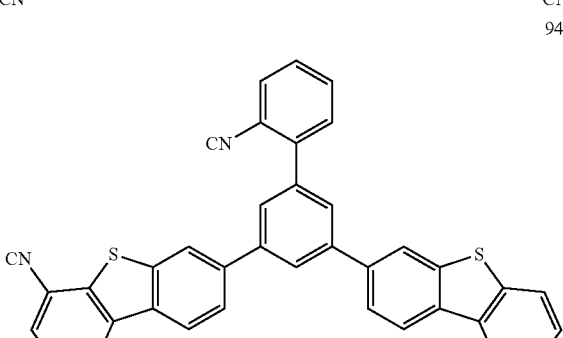
950
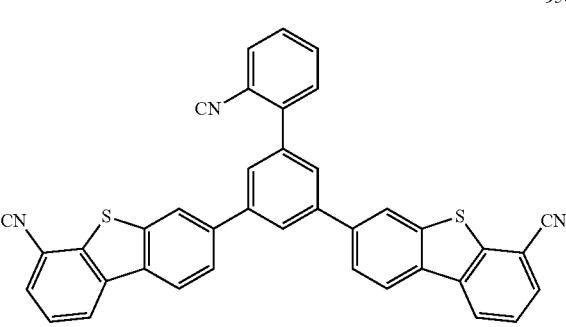

259
-continued
260
-continued
951
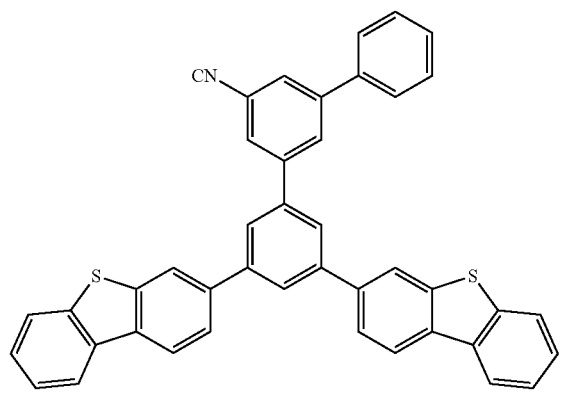
954
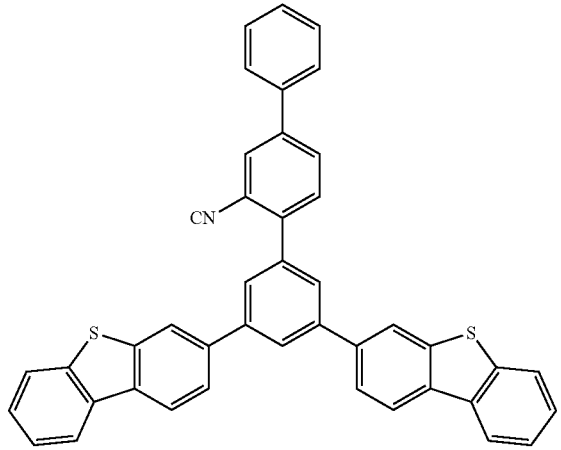
952
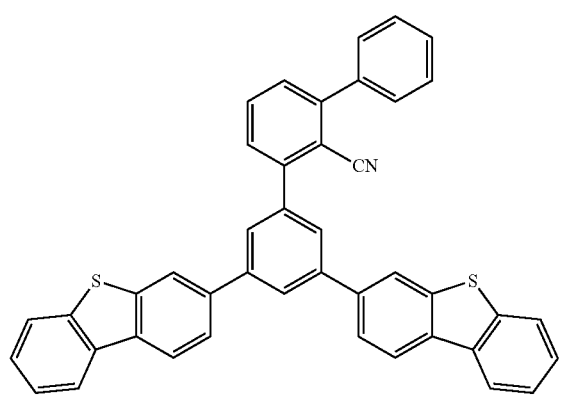
955
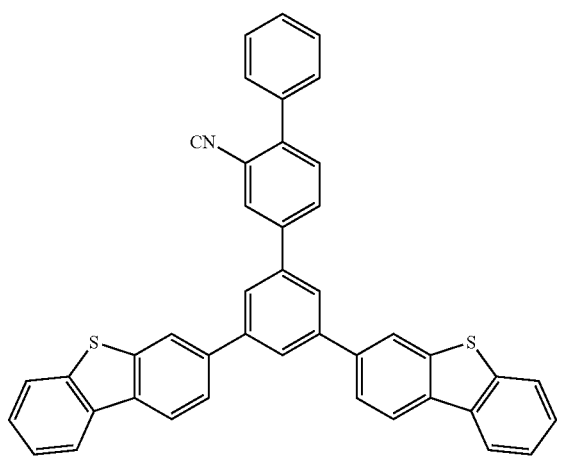
953
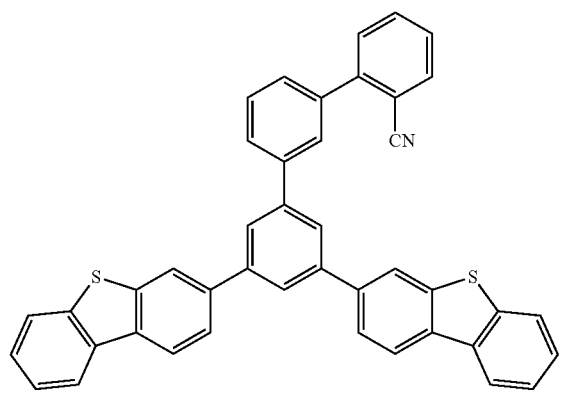
956
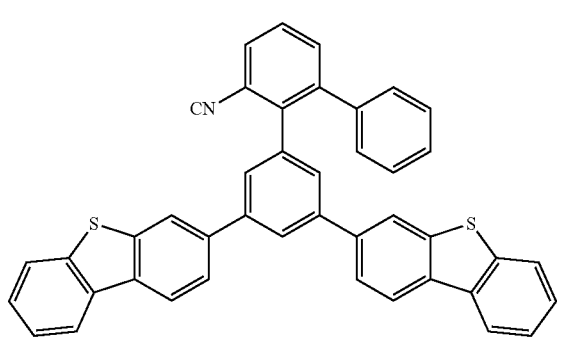
957
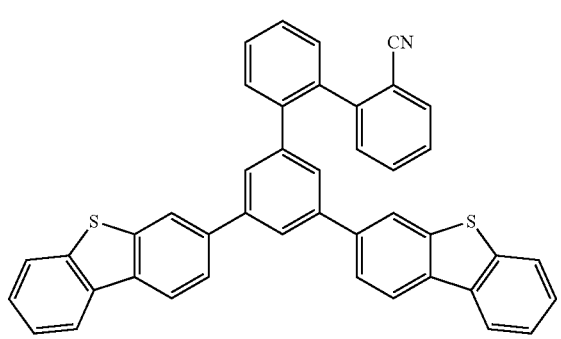

958
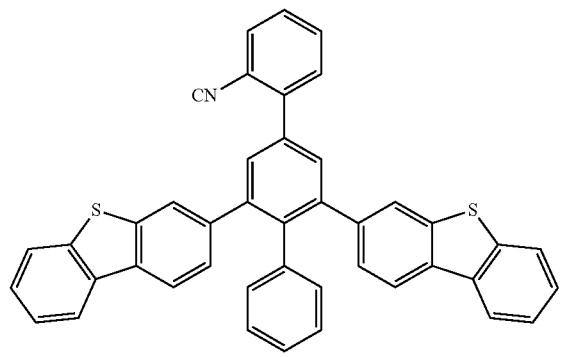
959
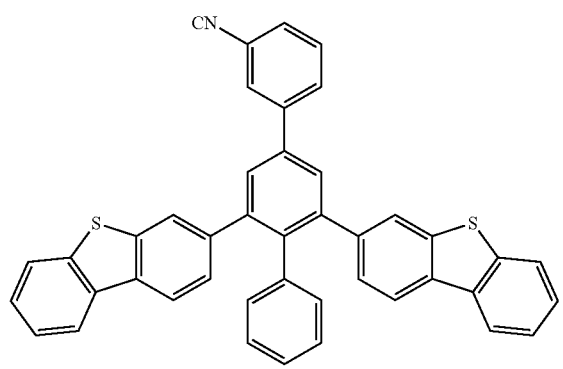
960
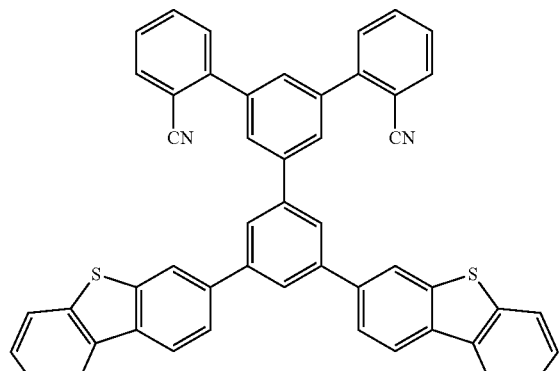
961
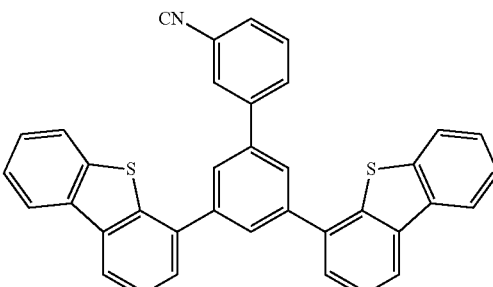
962
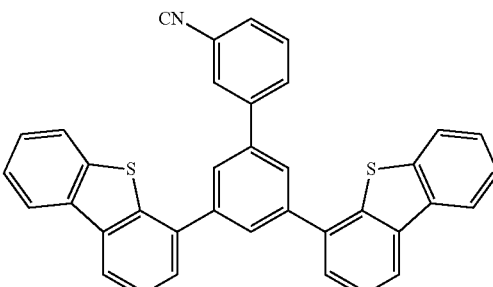
963
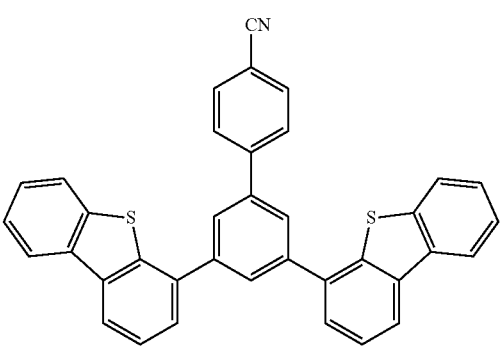
964
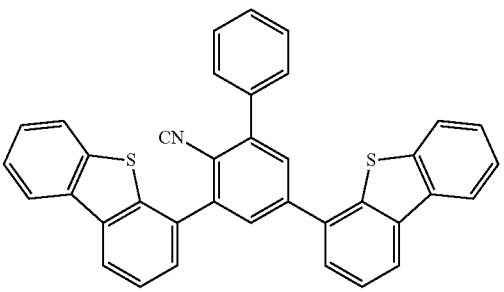
965
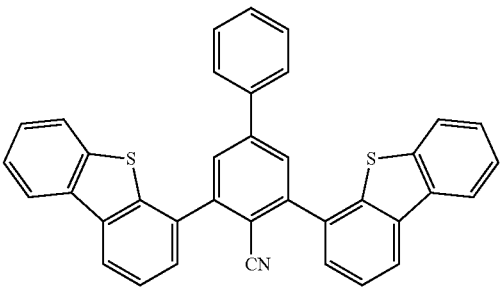
966
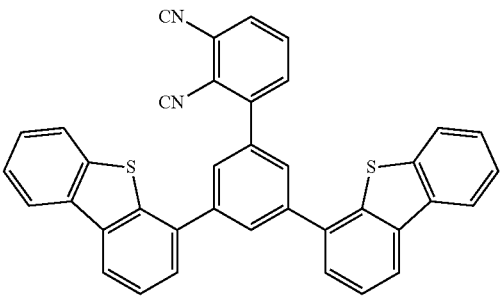

263
-continued
967
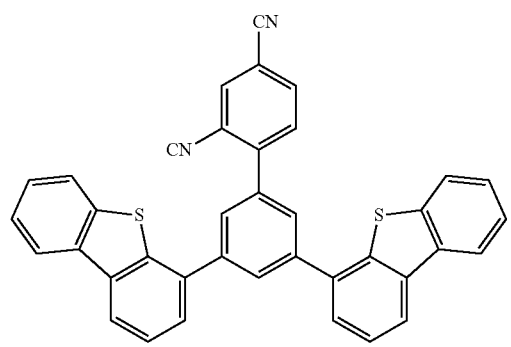
968
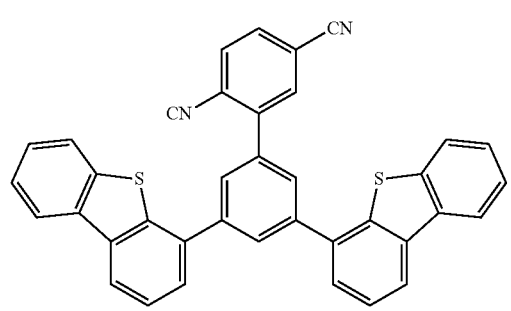
969
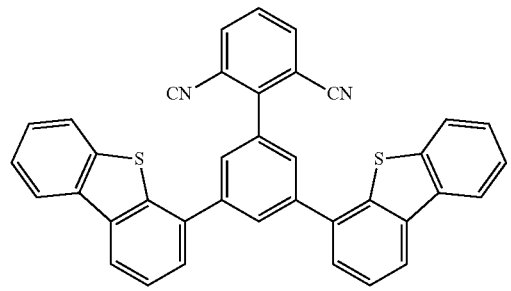
970
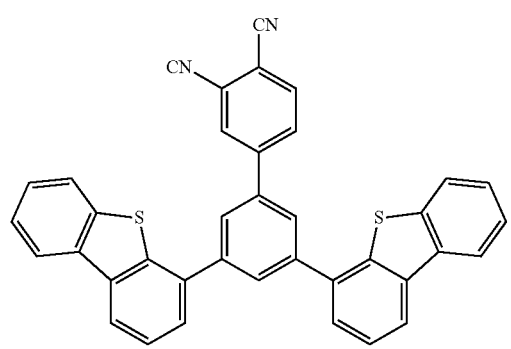
264
-continued
971
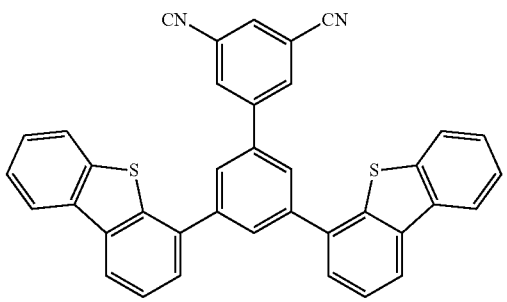
972
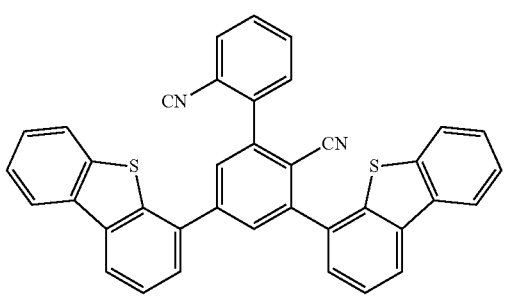
973
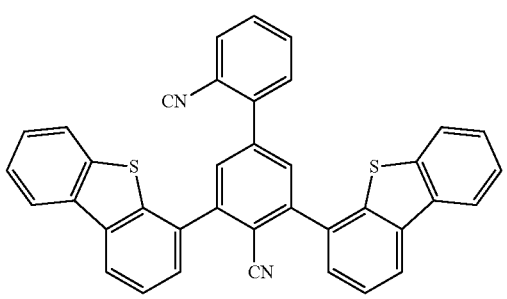
974
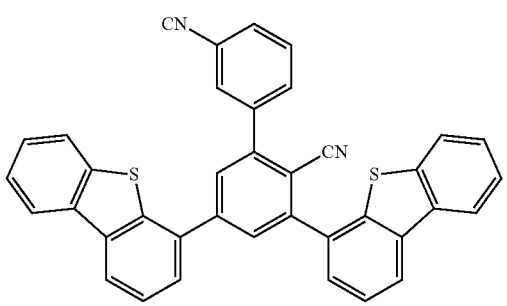
975
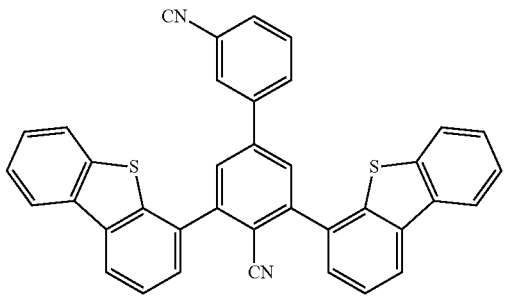

976
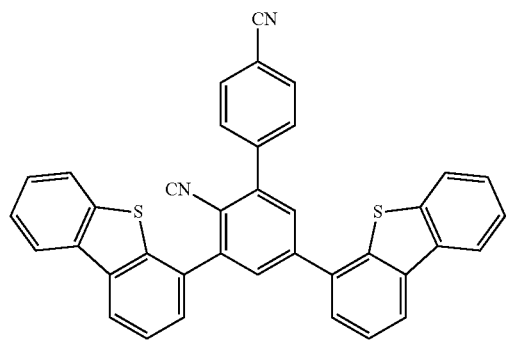
977
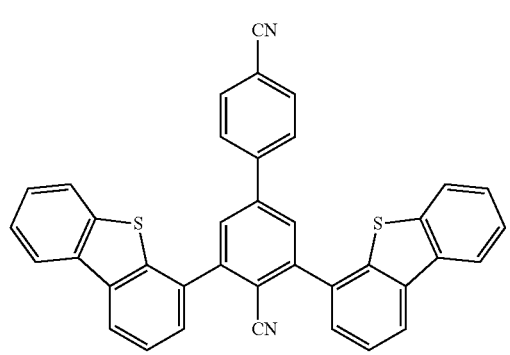
978
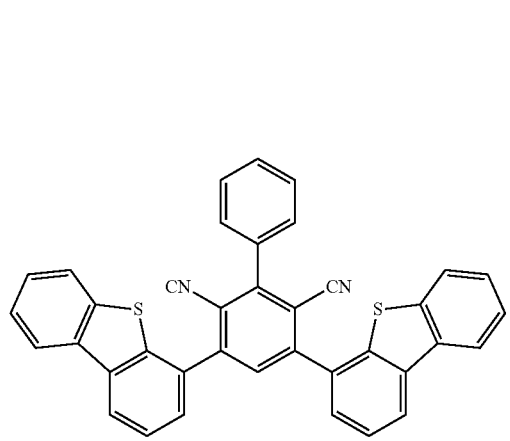
979
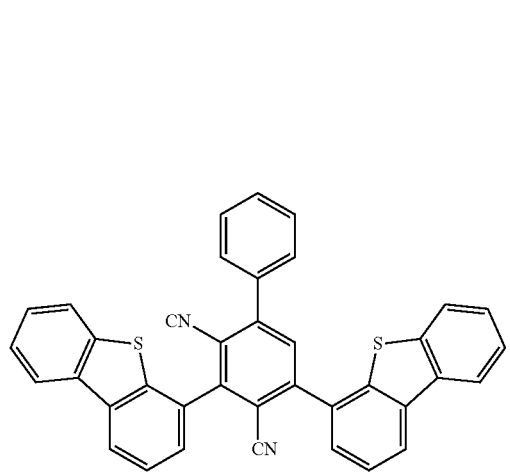
980
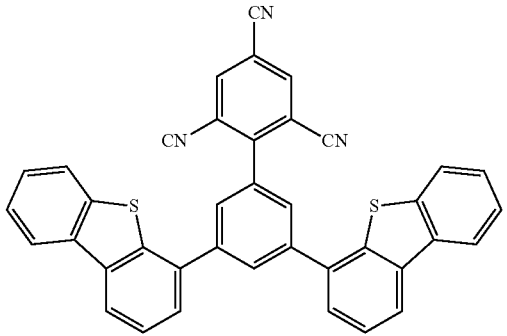
981
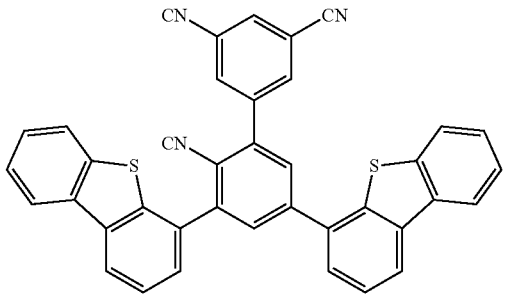
982
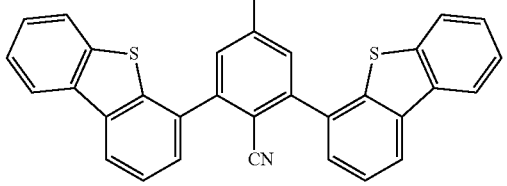
983
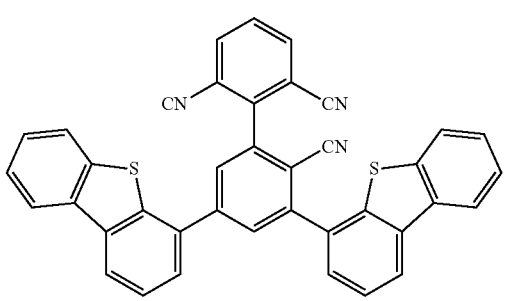
984
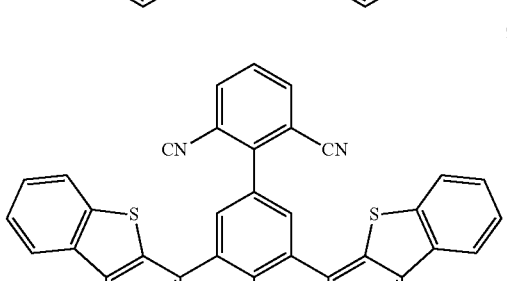

267
-continued
985
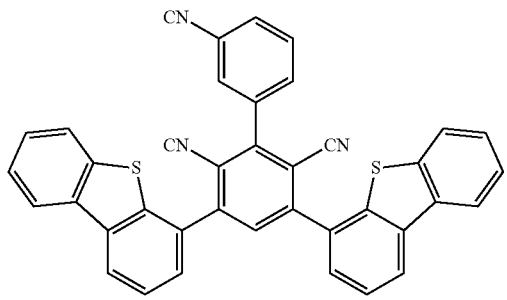
986
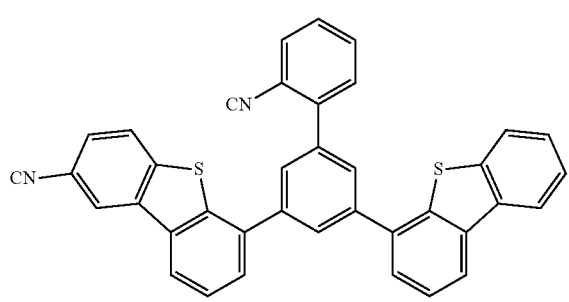
987
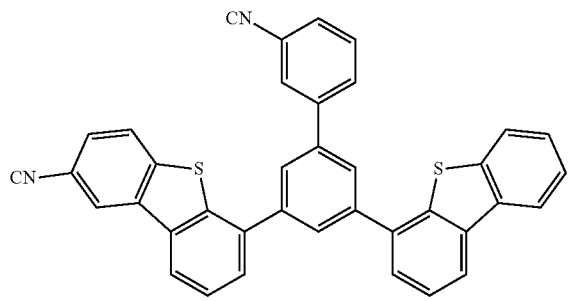
988
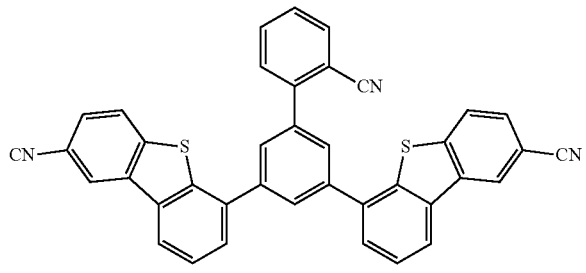
989
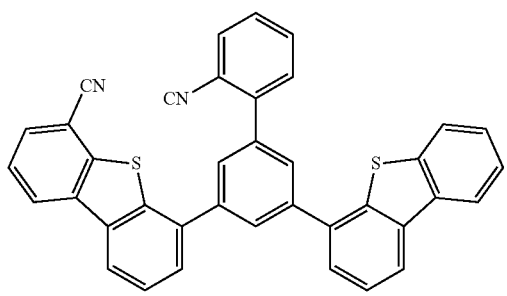
268
-continued
990
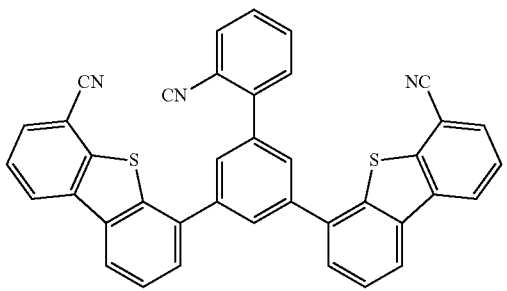
991
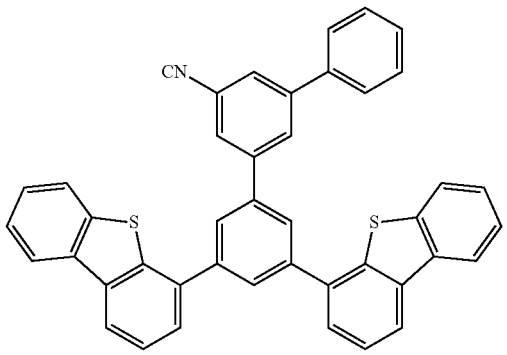
992
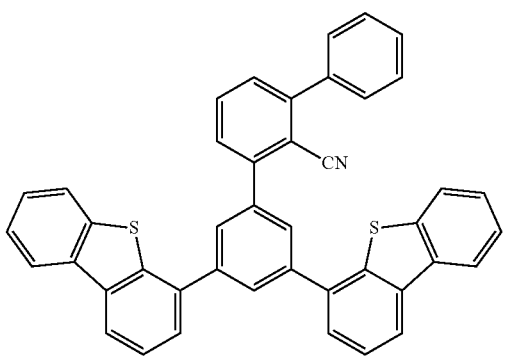
993
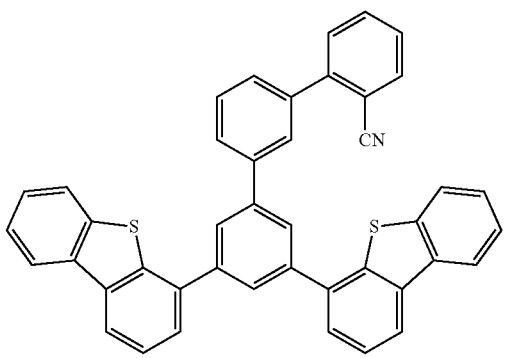

994
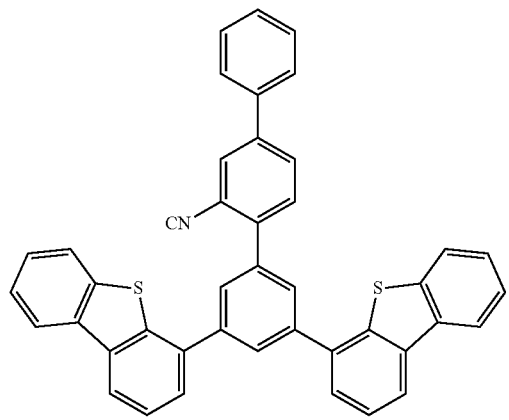
995
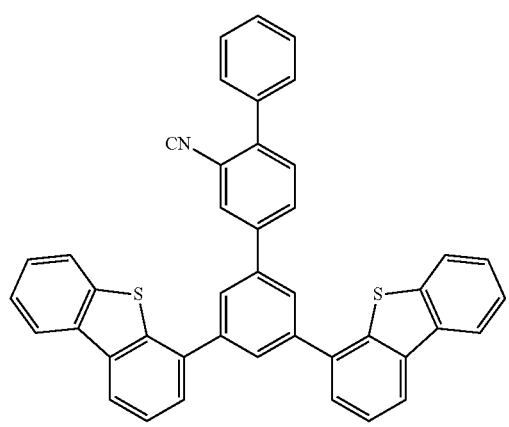
996
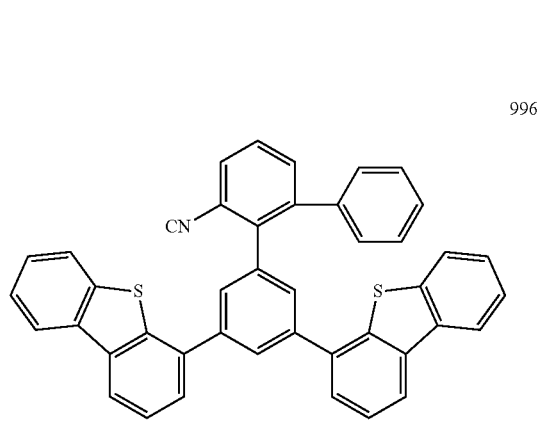
997
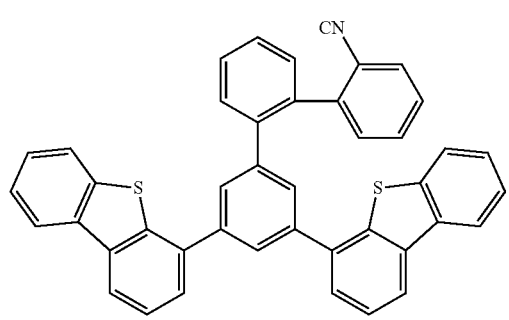
998
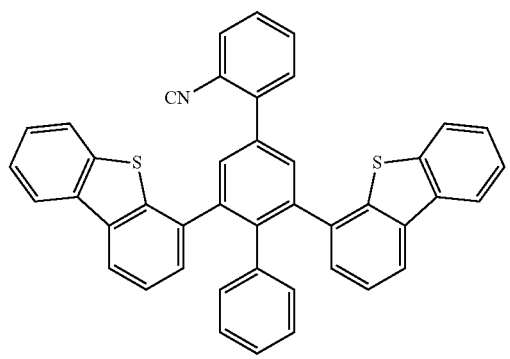
999
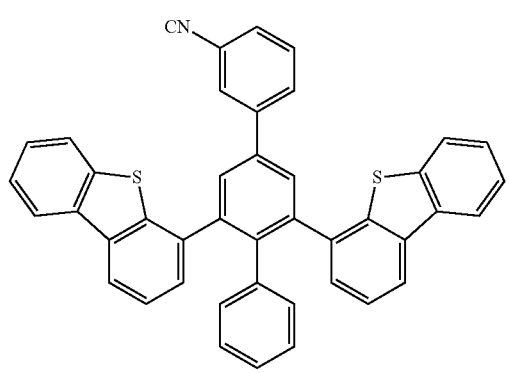
1000
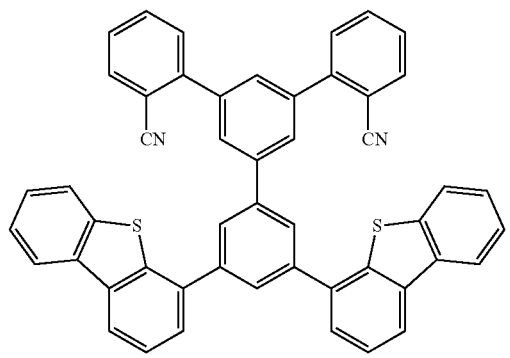
1001
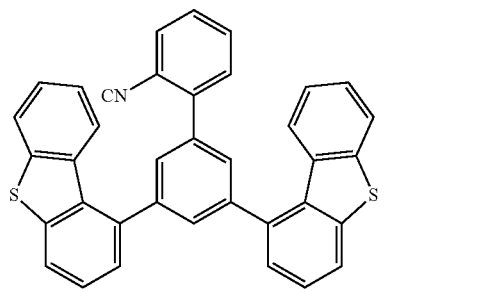

| | |
|---|---|
| 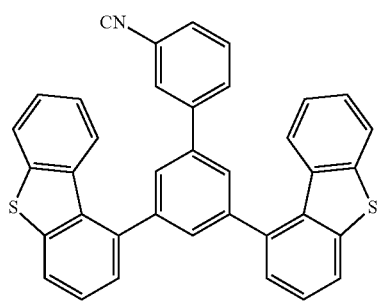 1002 | 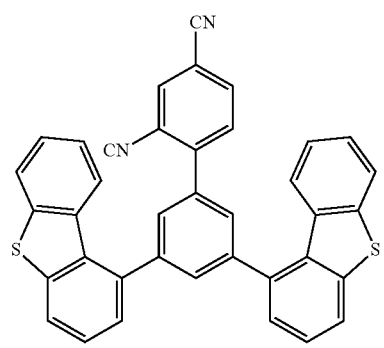 1007 |
| 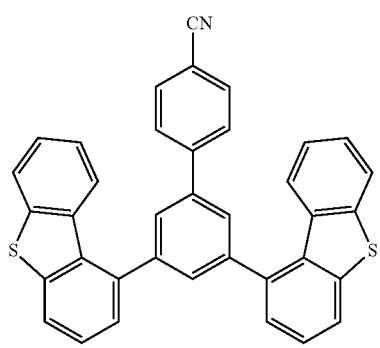 1003 | 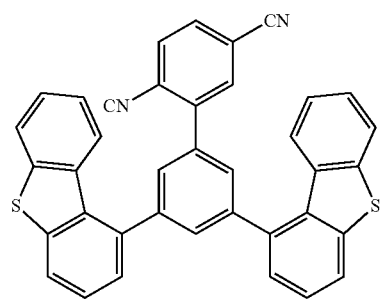 1008 |
| 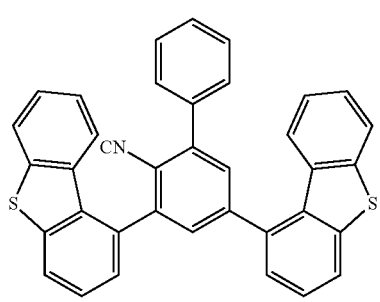 1004 | 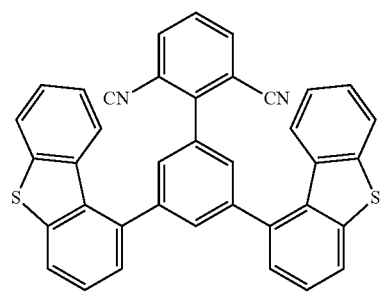 1009 |
| 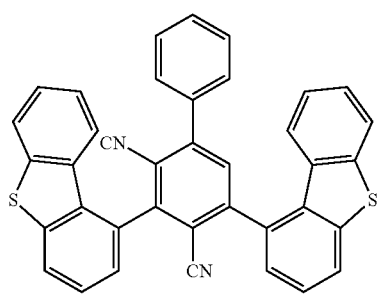 1005 | 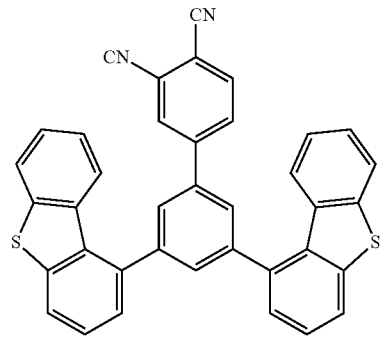 1010 |
| 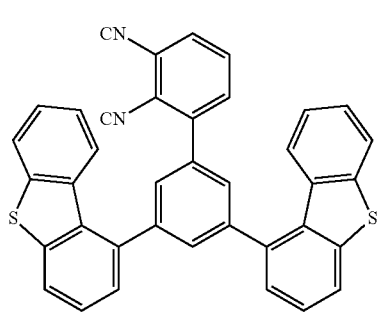 1006 | 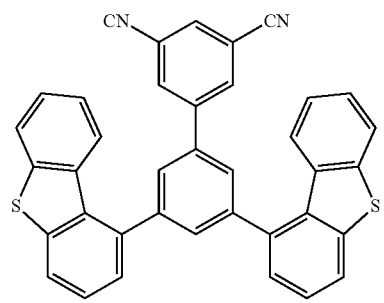 1011 |

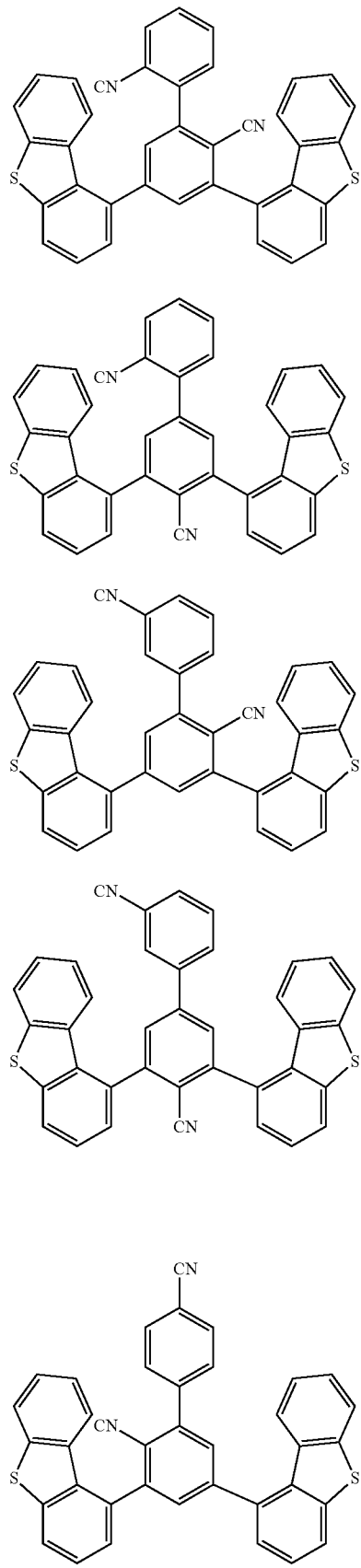
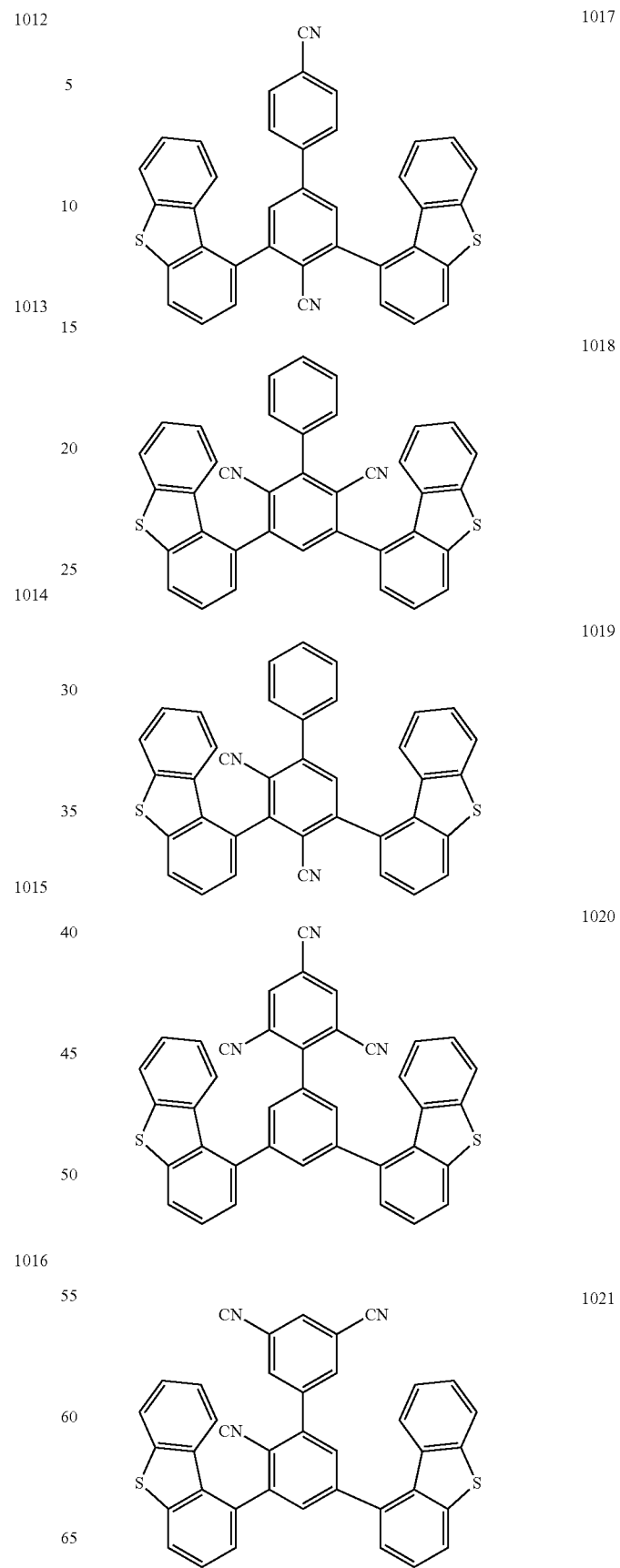

| 1022 | 1027 |
|---|---|
| 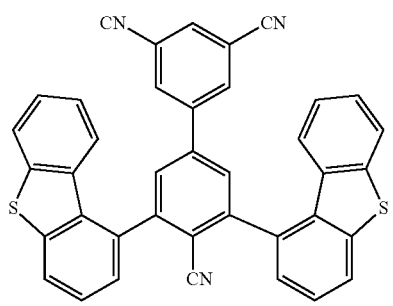 | 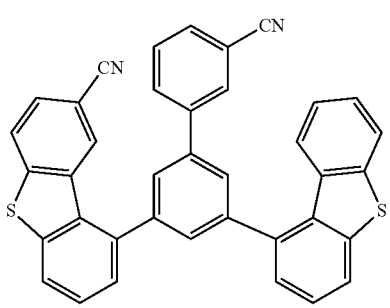 |
| 1023 | 1028 |
| 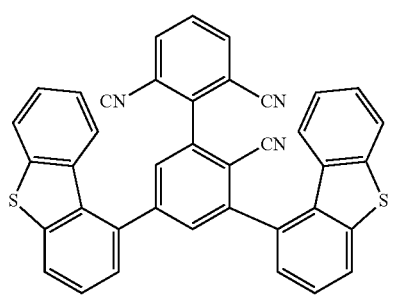 | 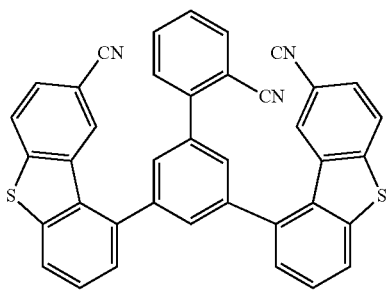 |
| 1024 | 1029 |
| 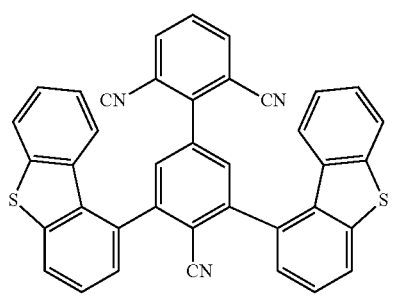 | 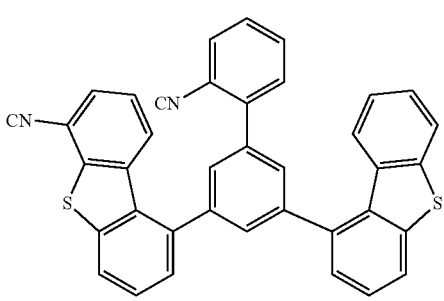 |
| 1025 | 1030 |
| 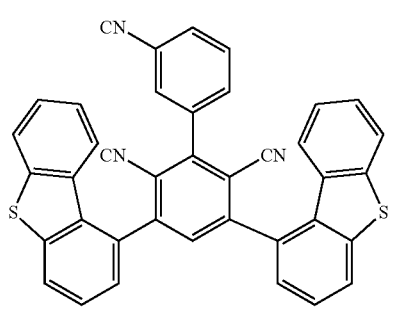 | 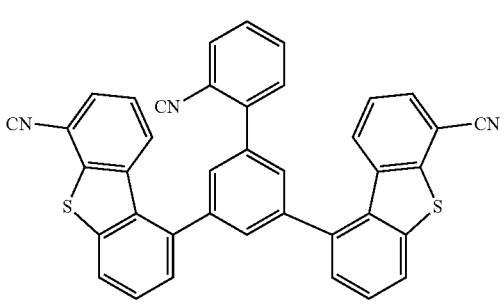 |
| 1026 | 1031 |
| 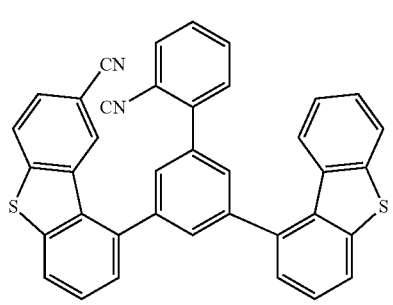 | 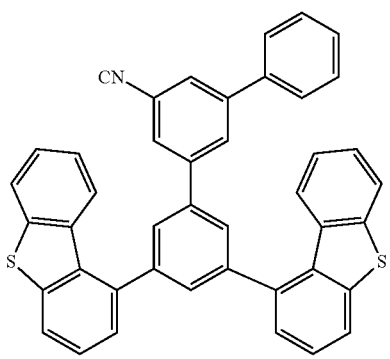 |

-continued
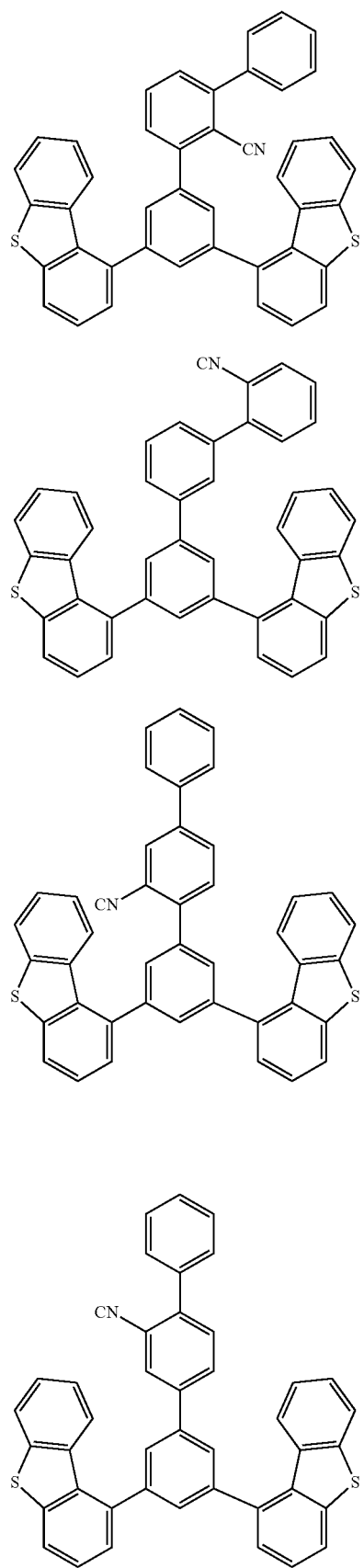
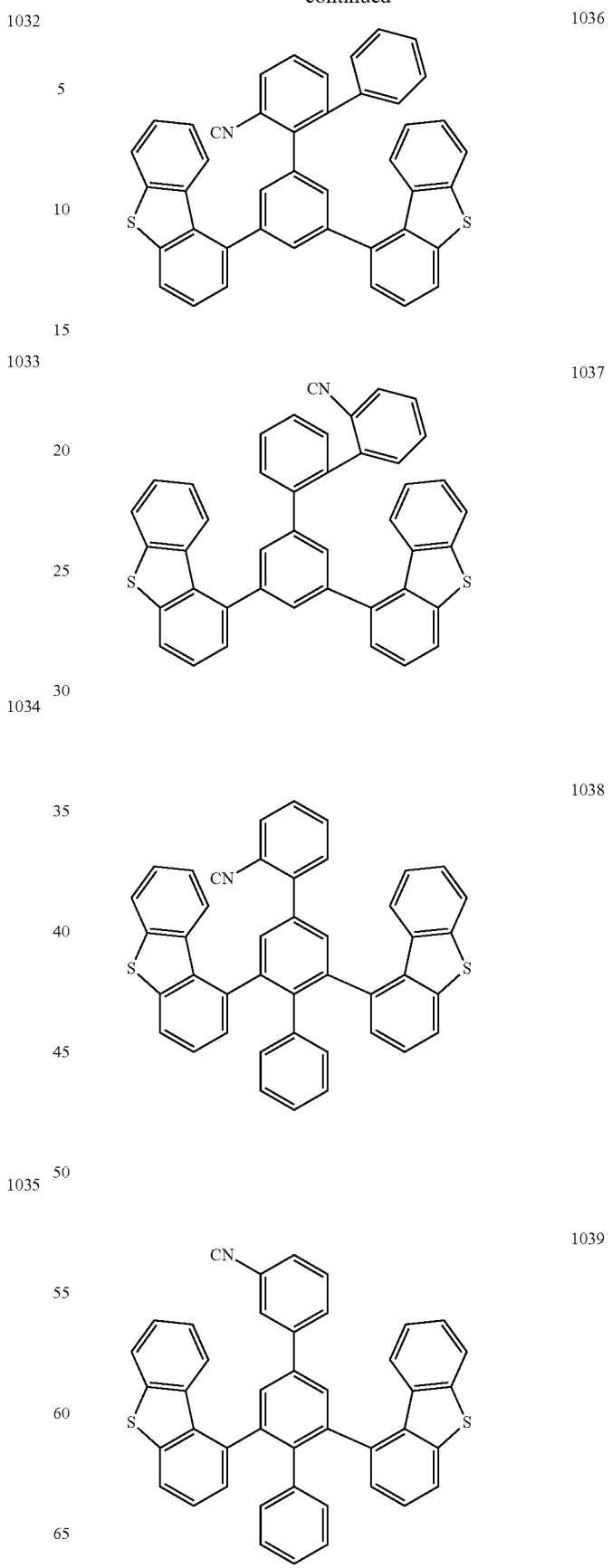

1040
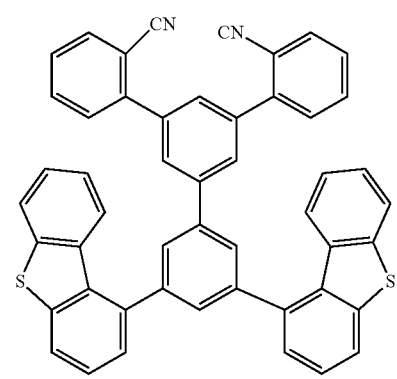
1041
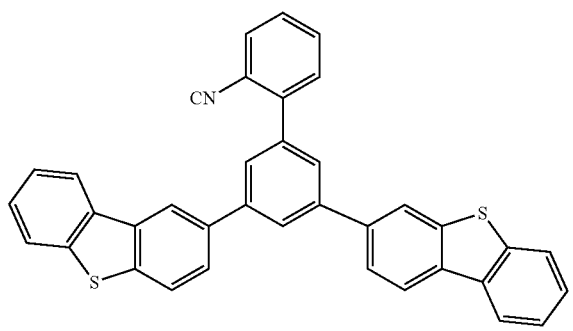
1042
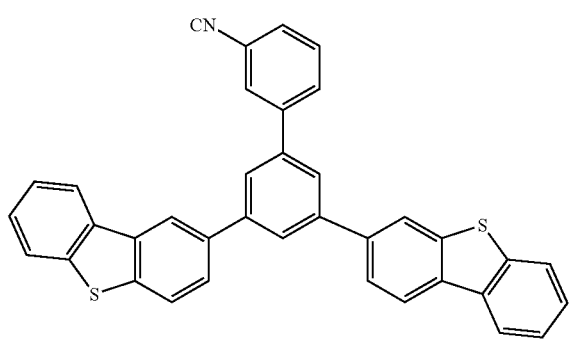
1043
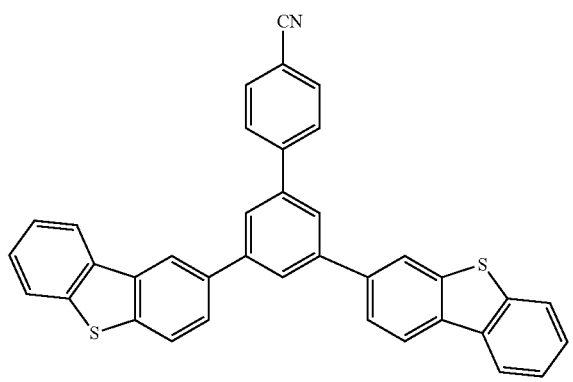
1044
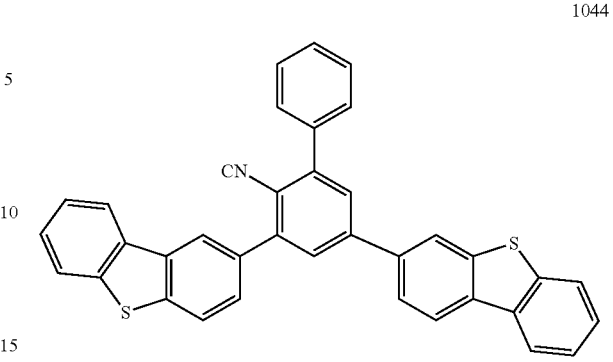
1045
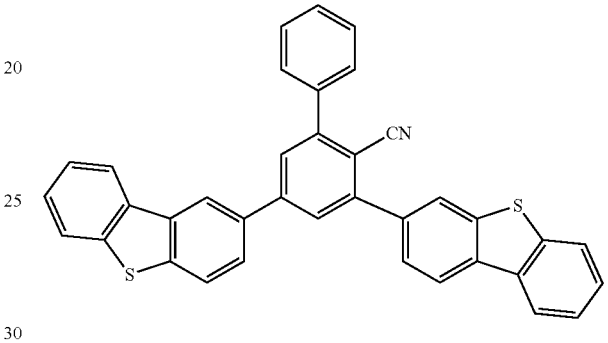
1046
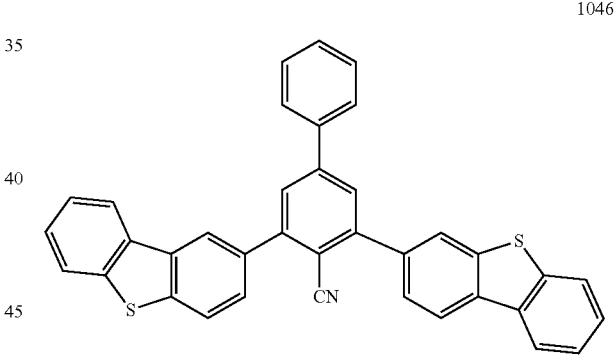
1047

-continued
1048
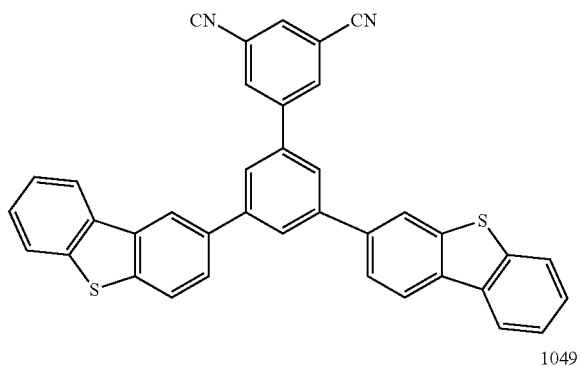
1049
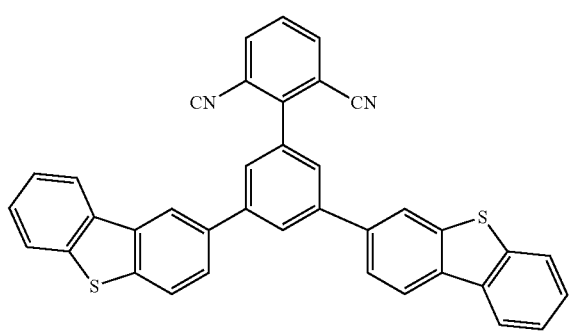
1050
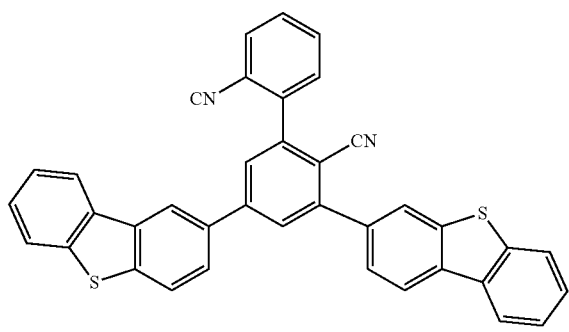
1051
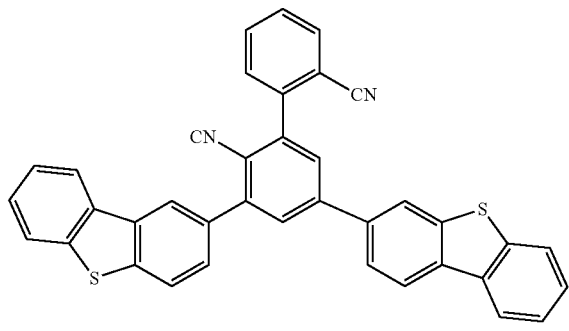
-continued
1052
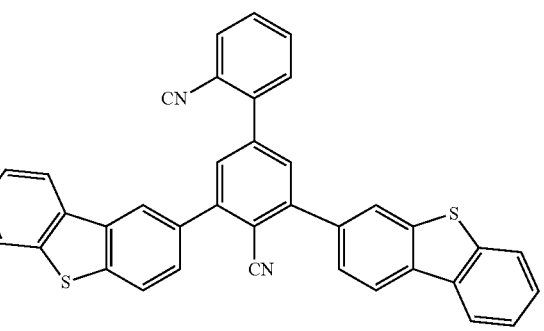
1053
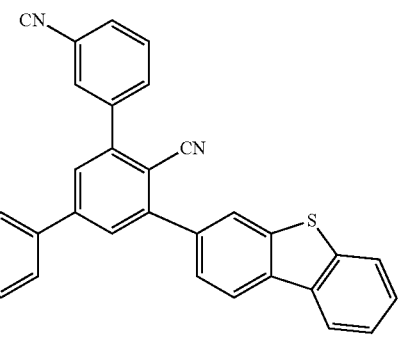
1054
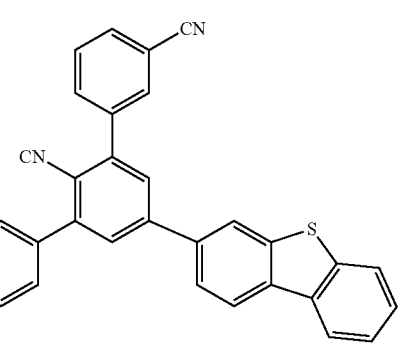
1055
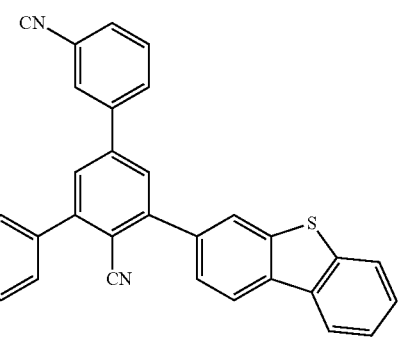

1056
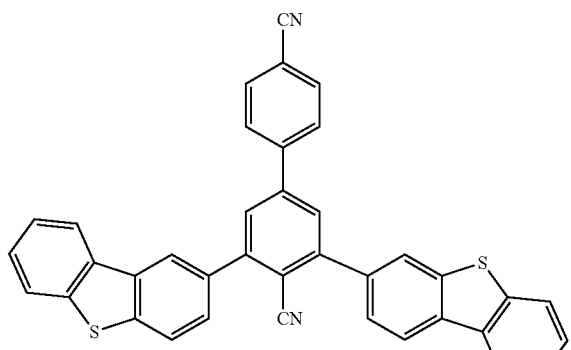
1057
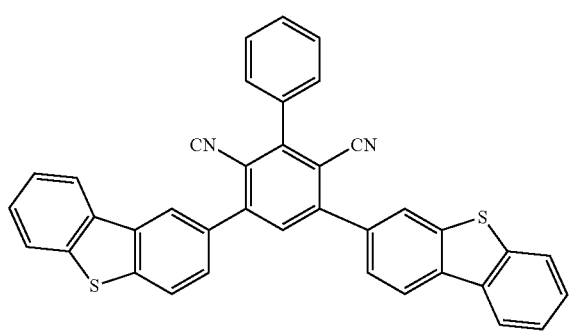
1058
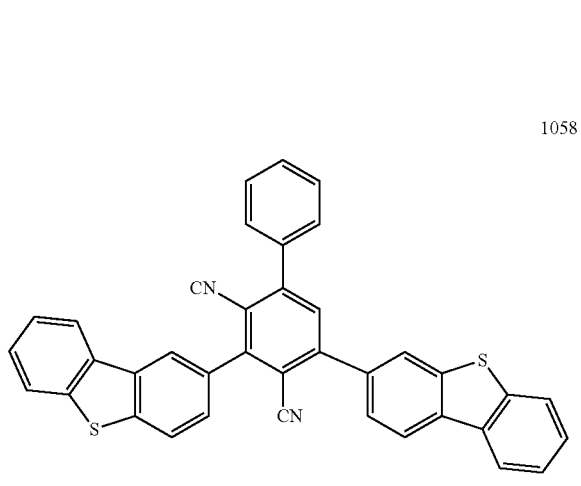
1059
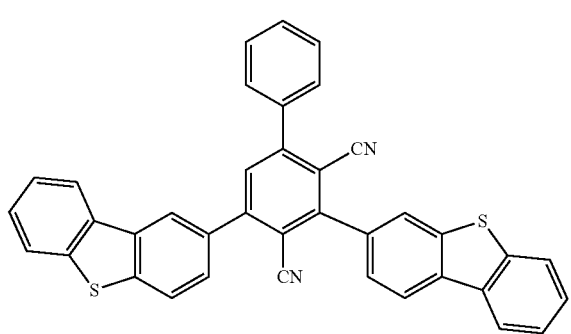
1060
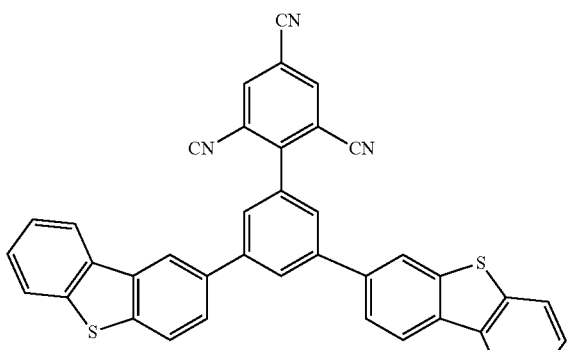
1061
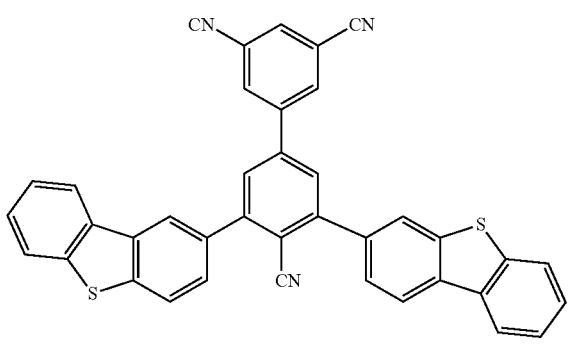
1062
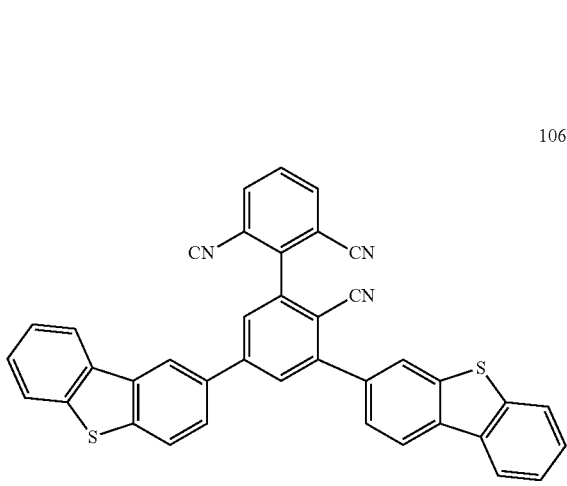
1063
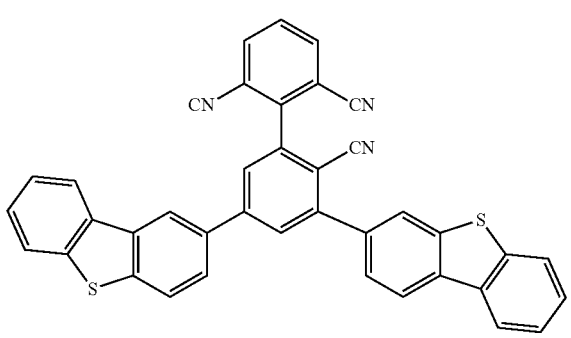

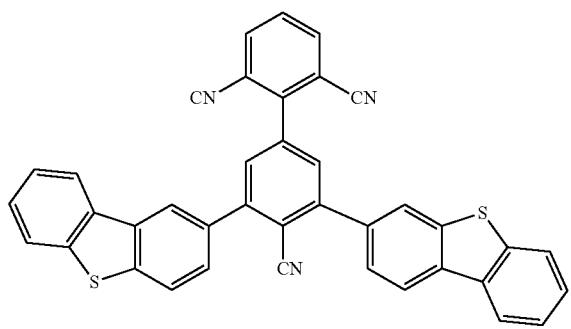
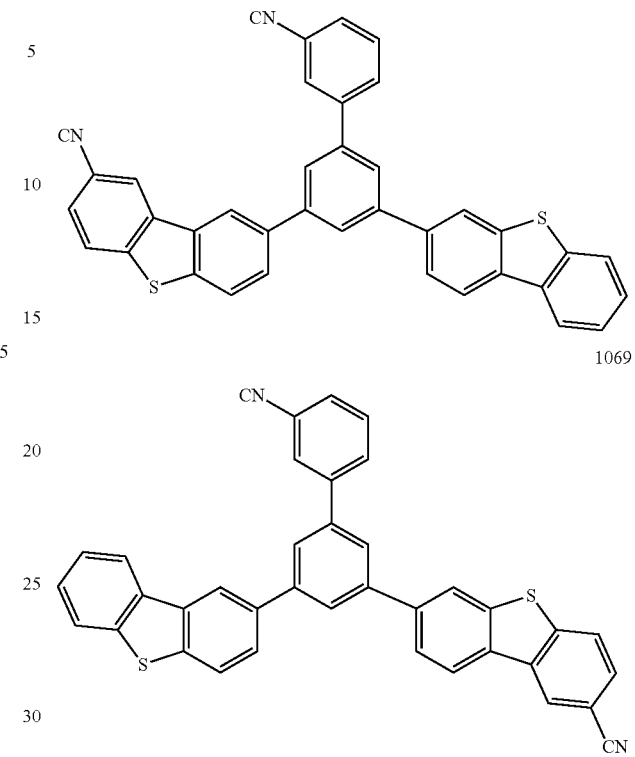
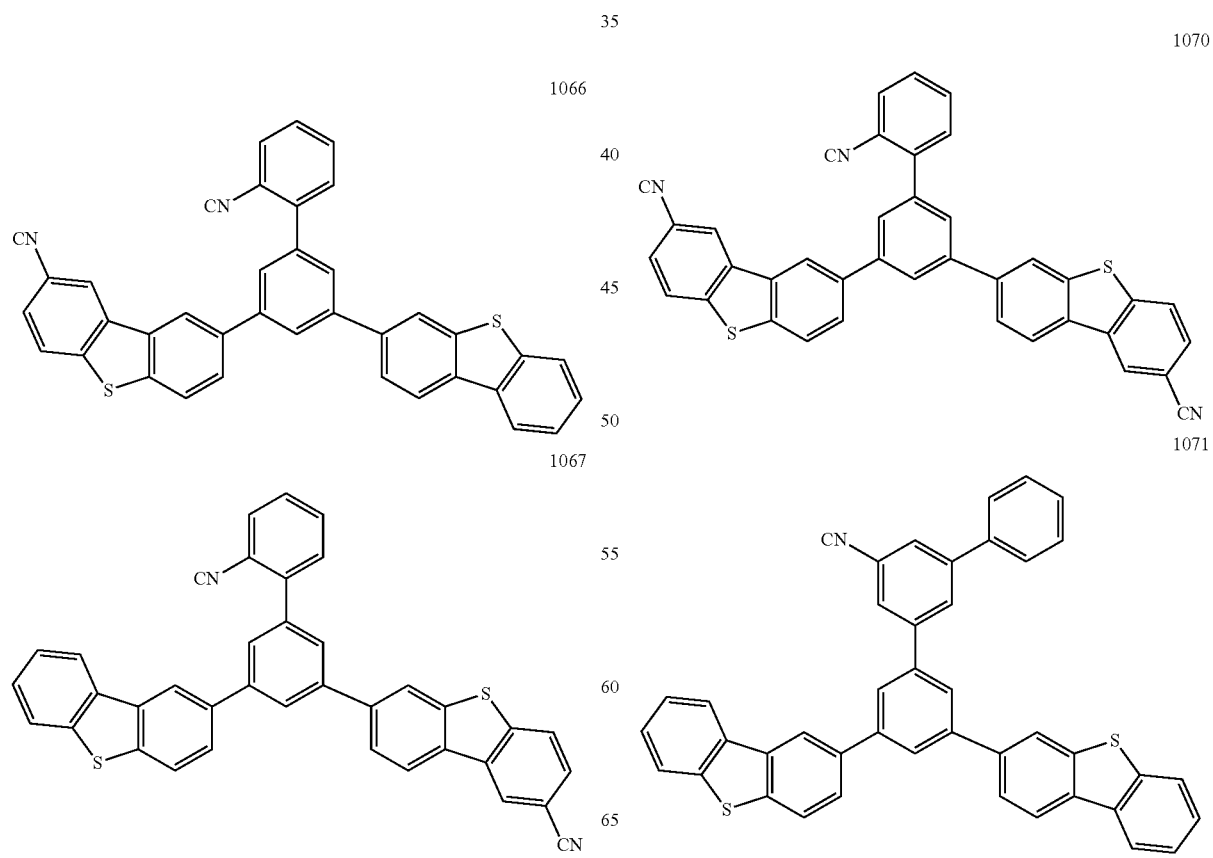

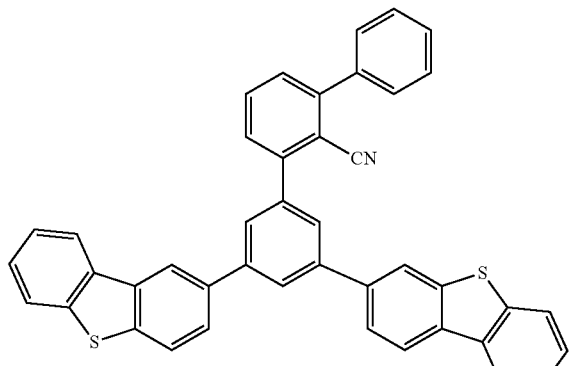
1072
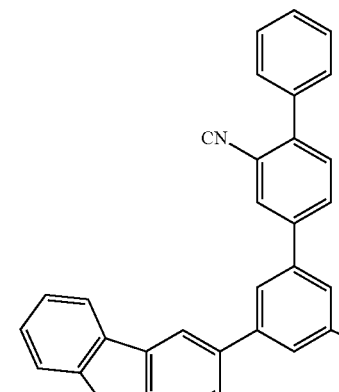
1075
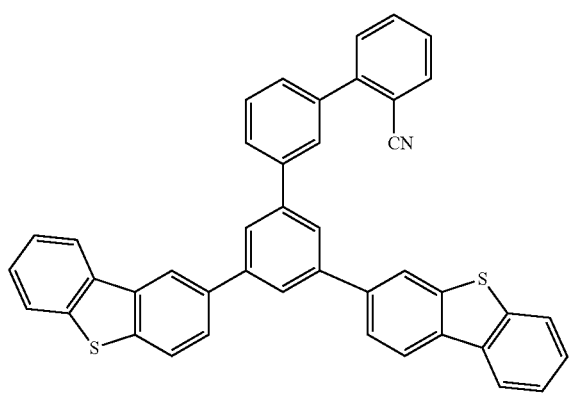
1073
1076
1077
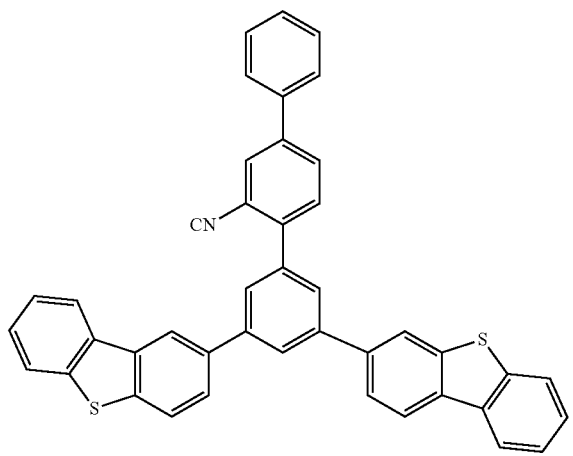
1074
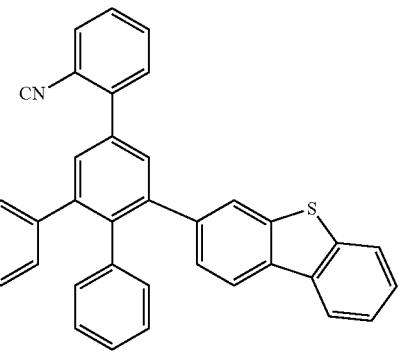
1078

| 289 | 290 |
|---|---|
| 1079 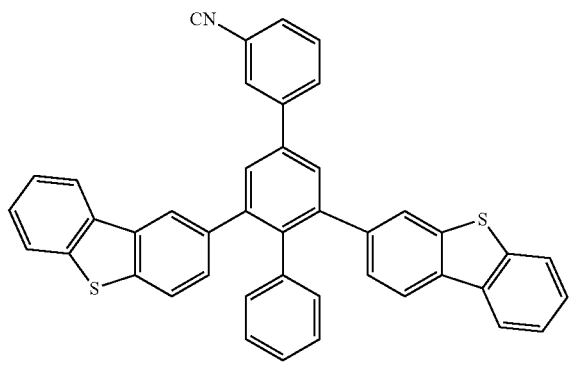 | 1083 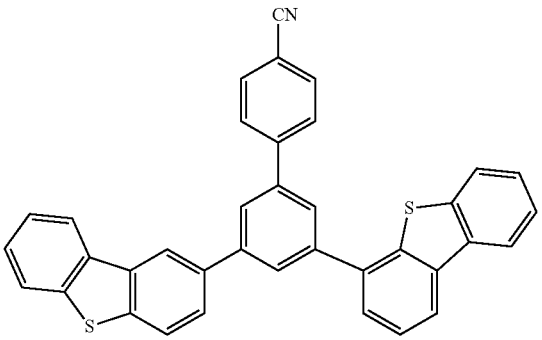 |
| 1080 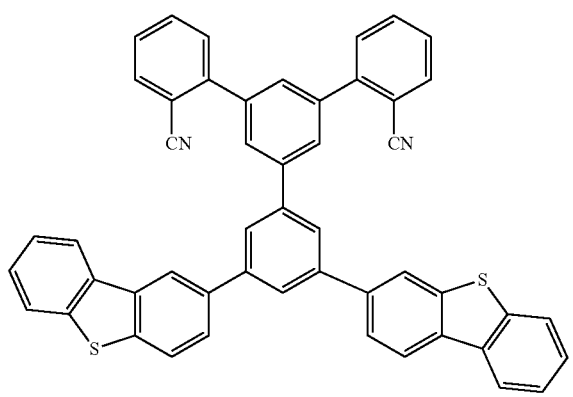 | 1084 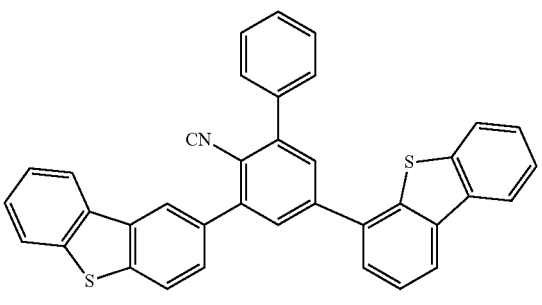 |
| 1081 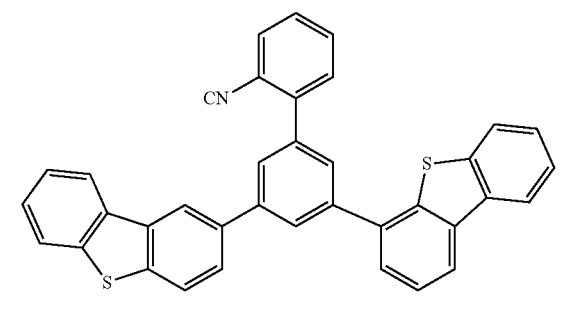 | 1085 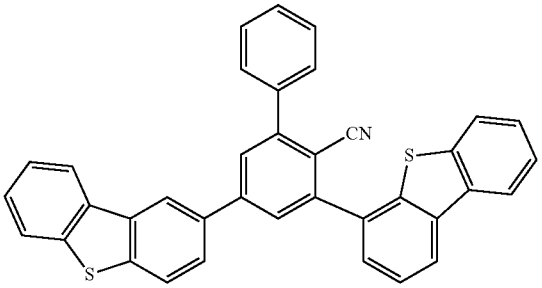 |
| 1082 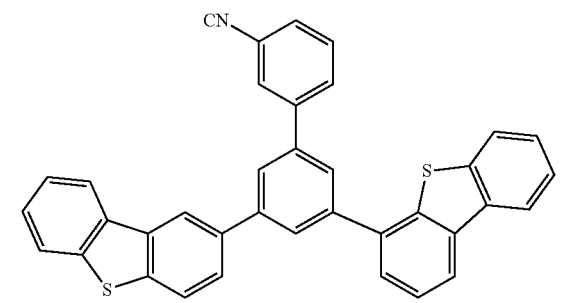 | 1086 |

1087
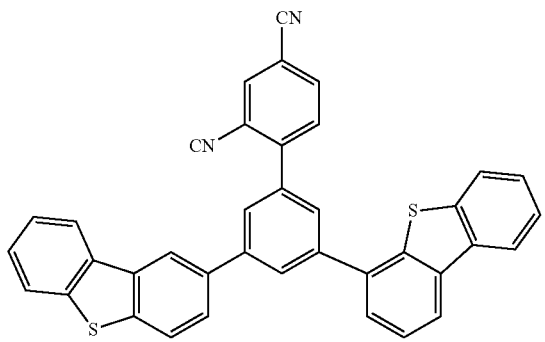
1088
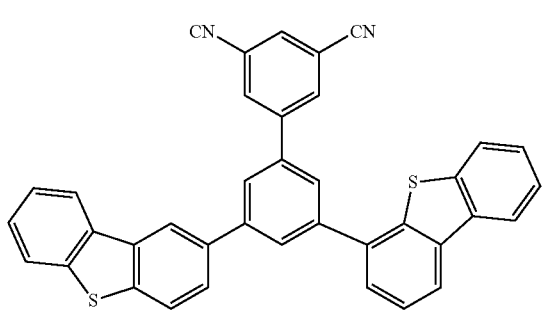
1089
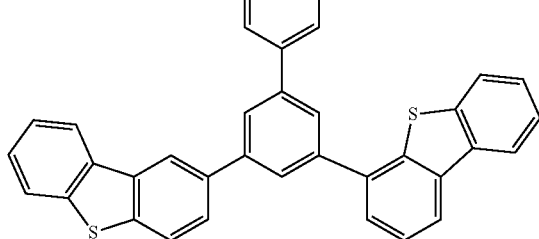
1090
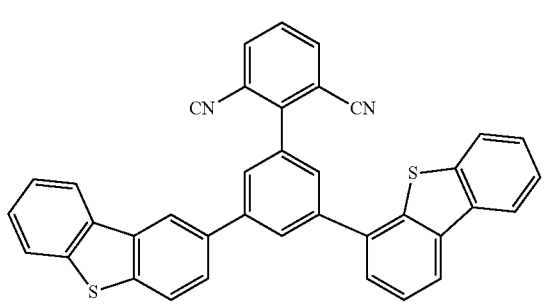
1091
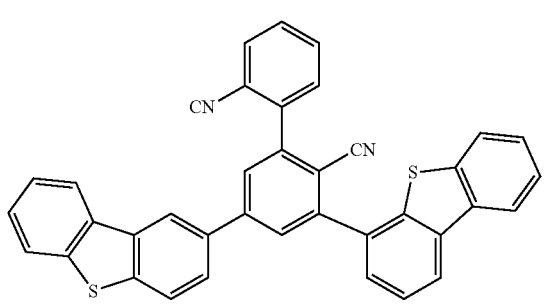
1092
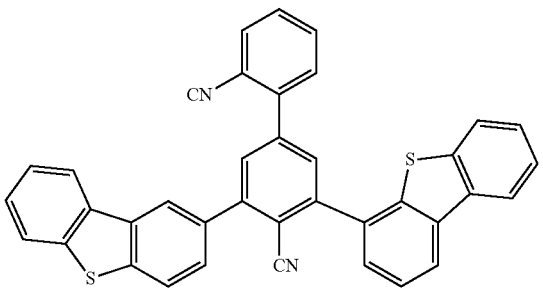
1093
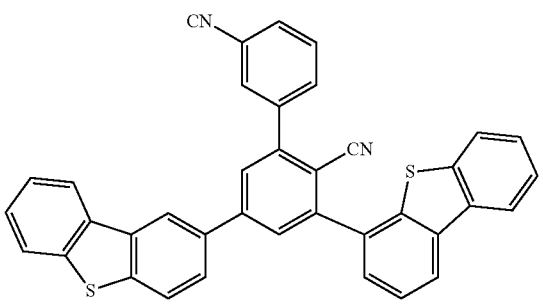
1094
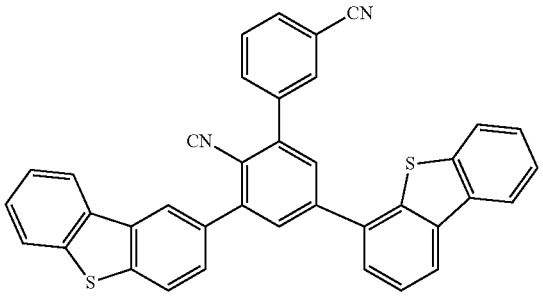
1095
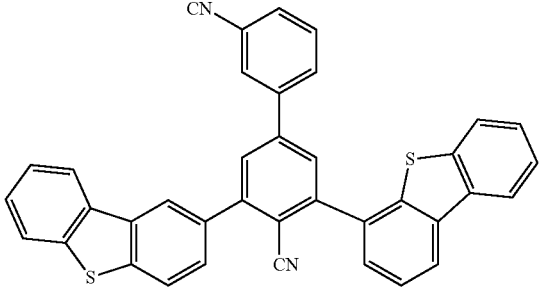
1096
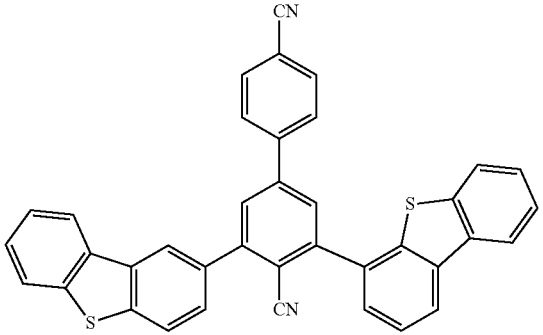

-continued
1097
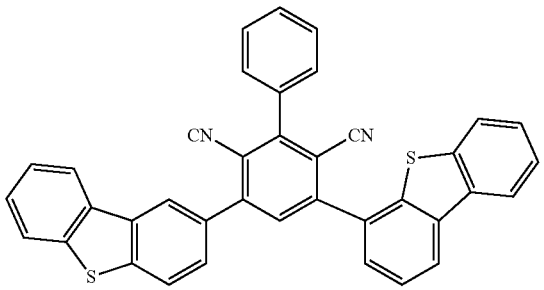
1098
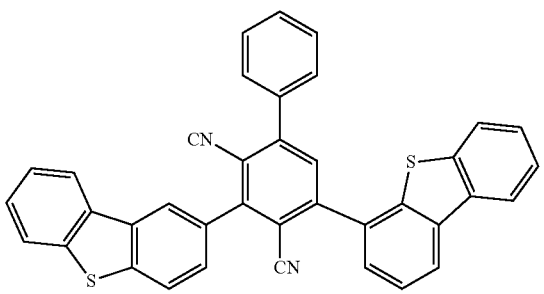
1099
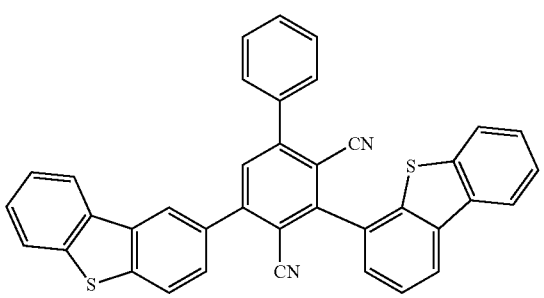
1100
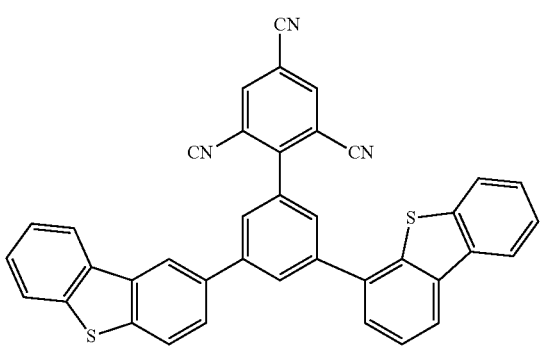
1101
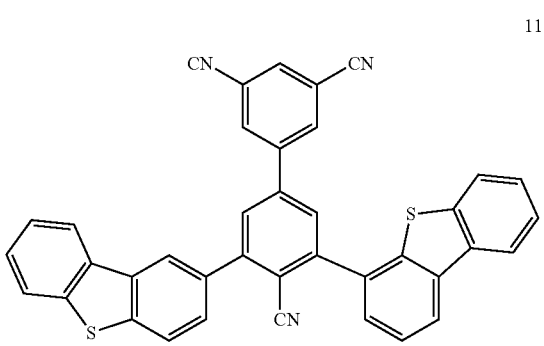
-continued
1102
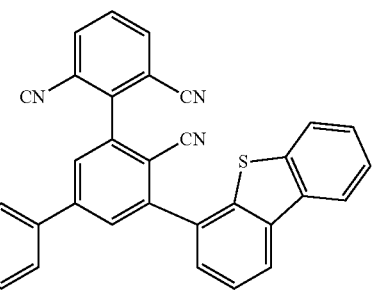
1103
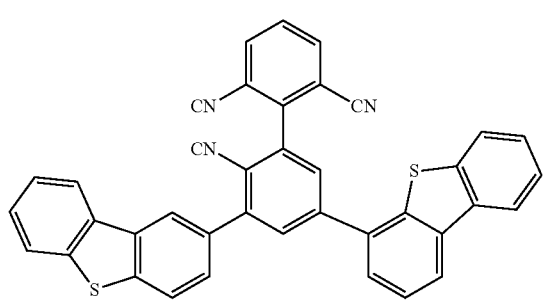
1104
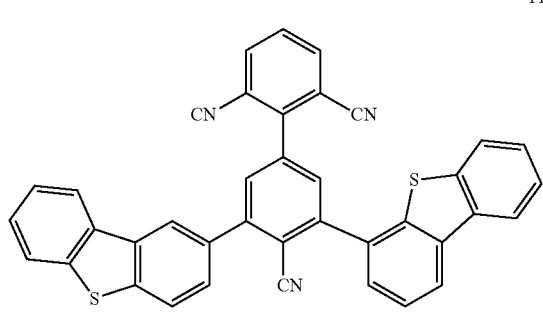
1105
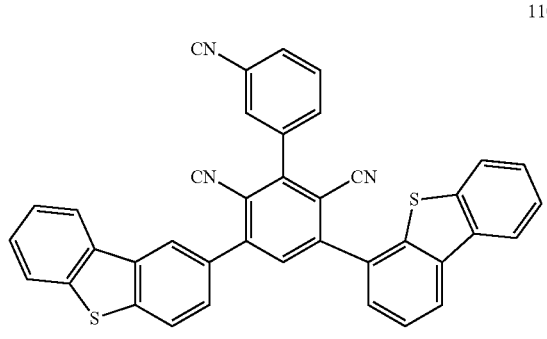
1106
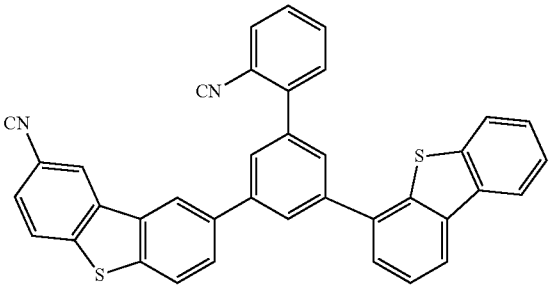

1107
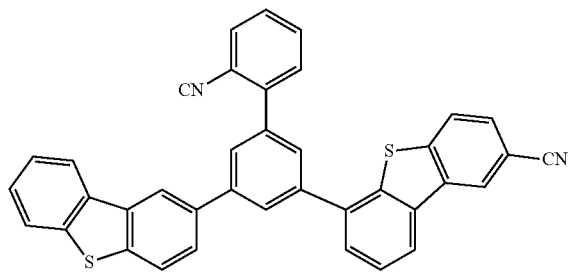
1108
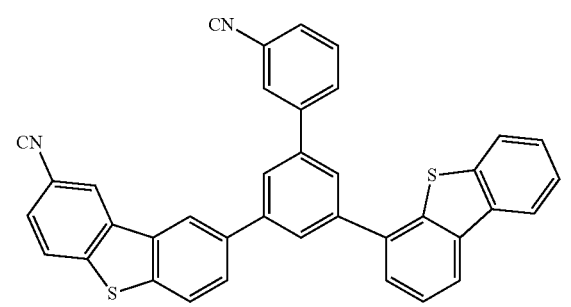
1109
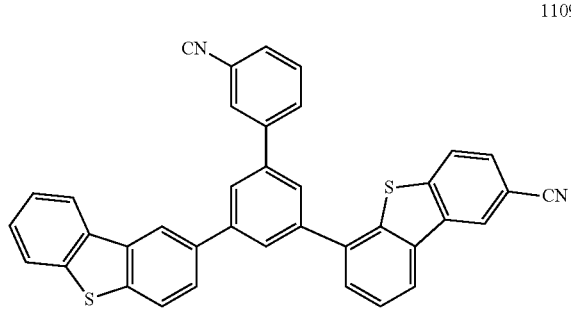
1110
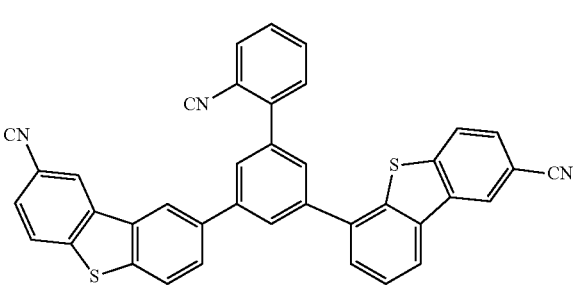
1111
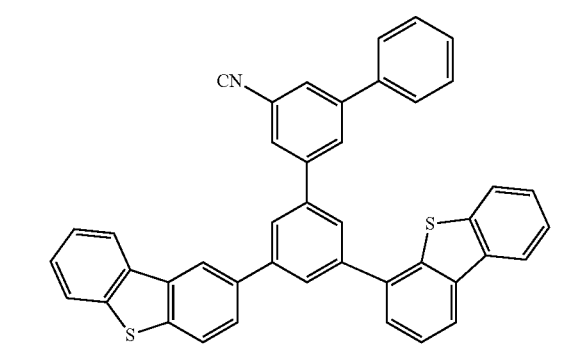
1112
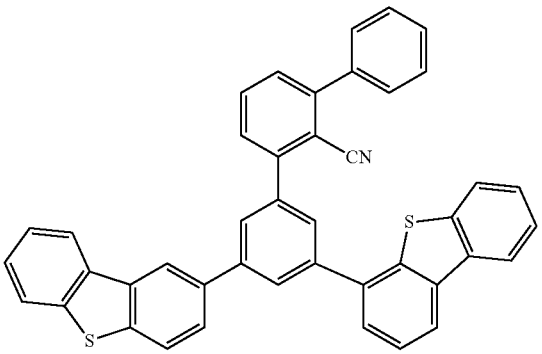
1113
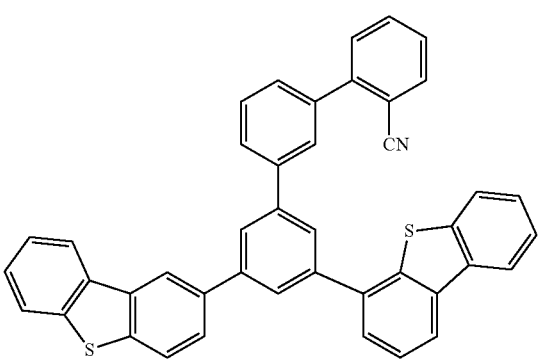
1114
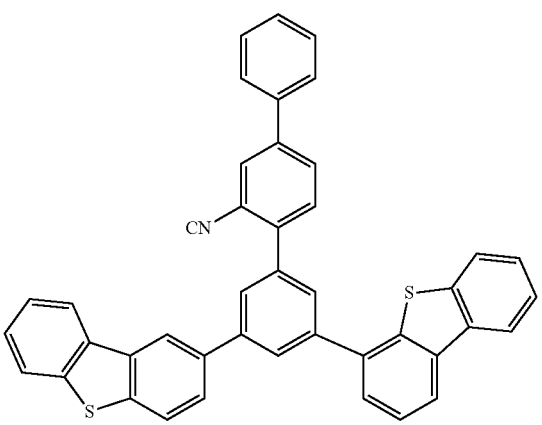
1115
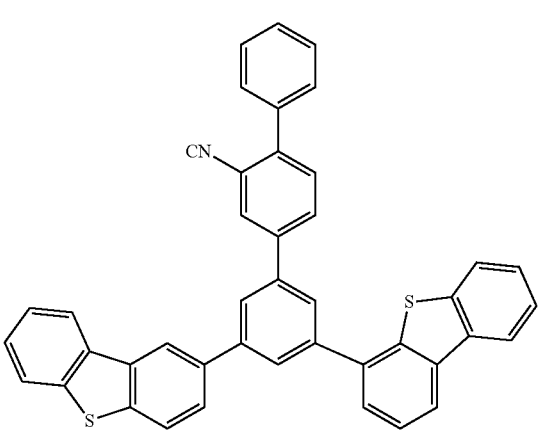

1116
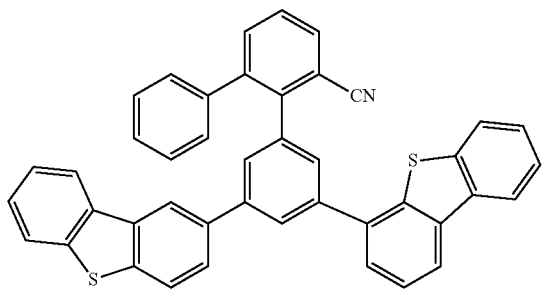
1117
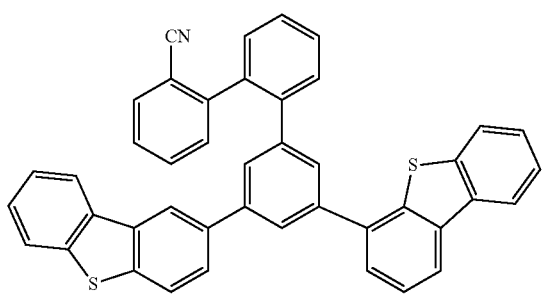
1118
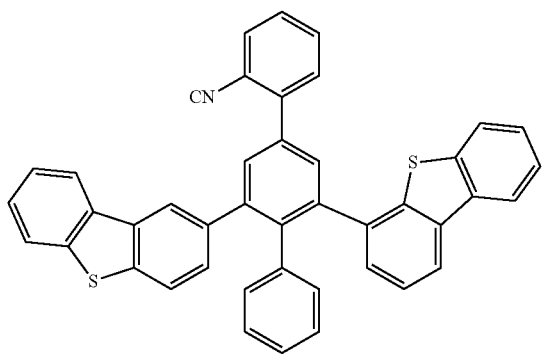
1119
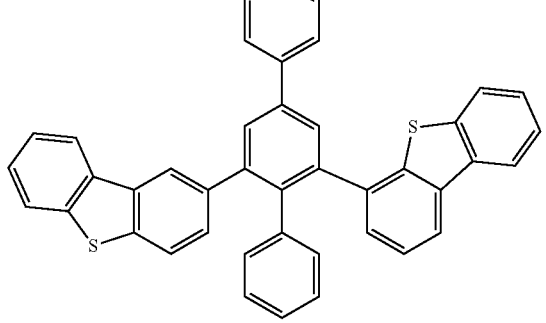
1120
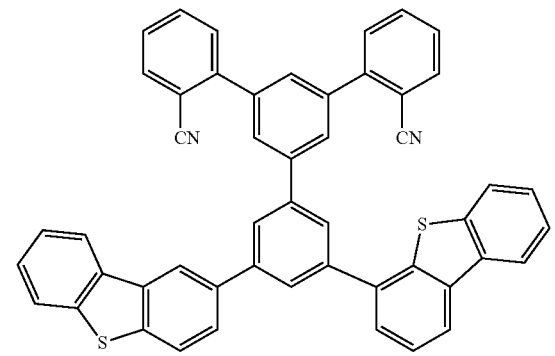
1121
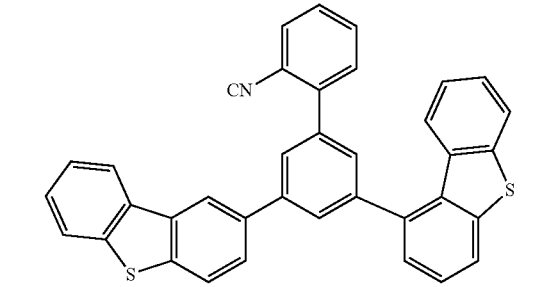
1122
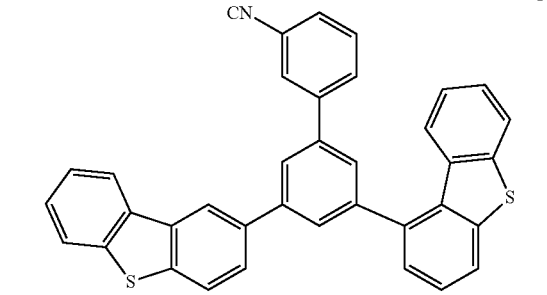
1123
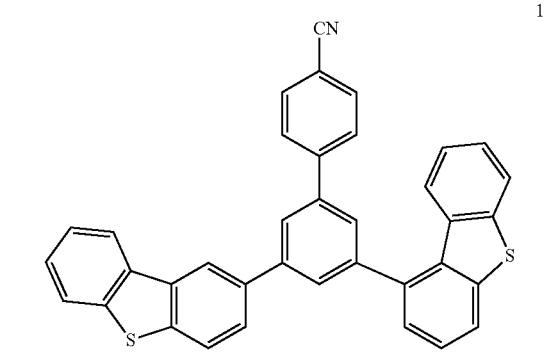
1124
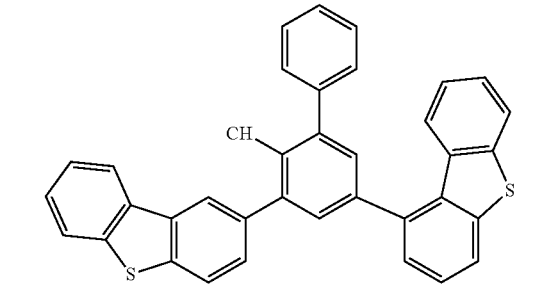

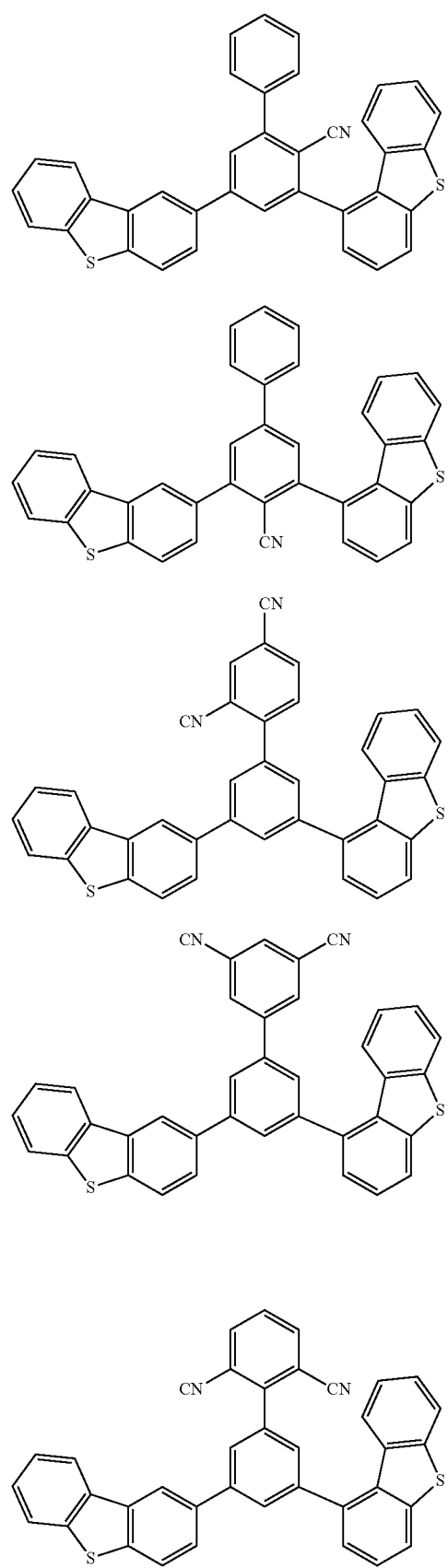
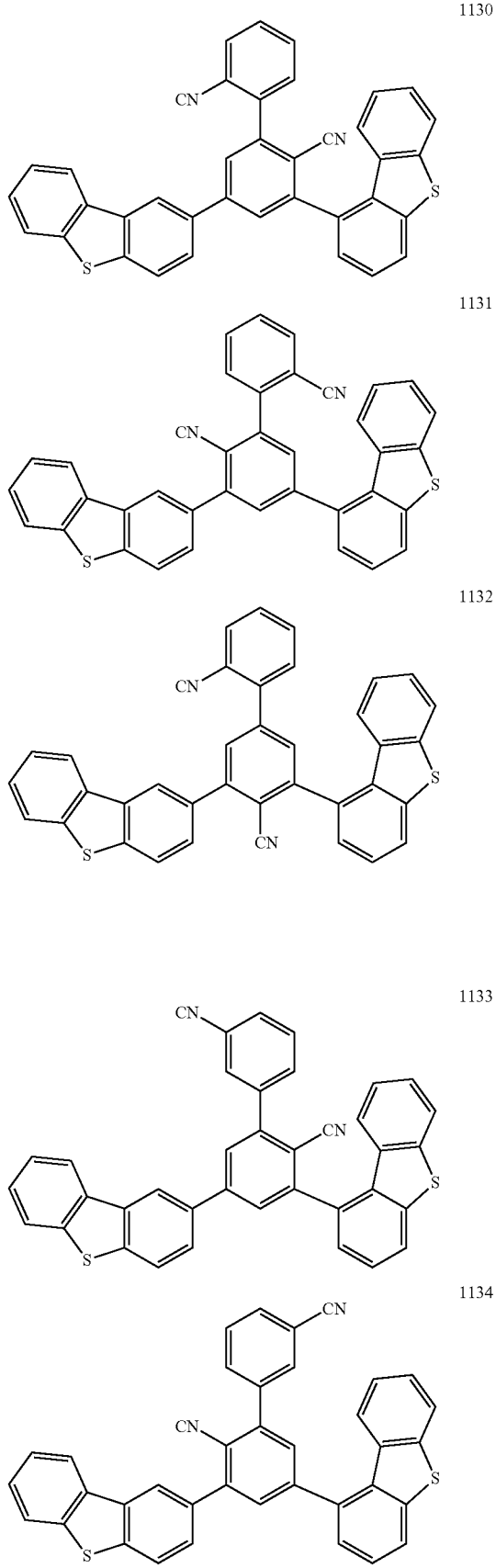

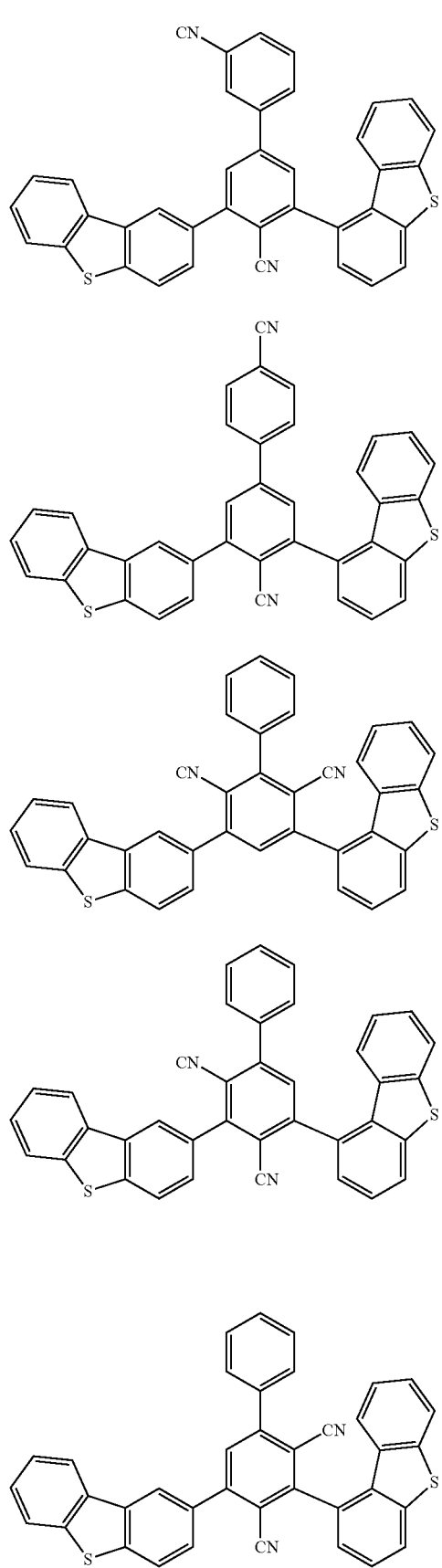
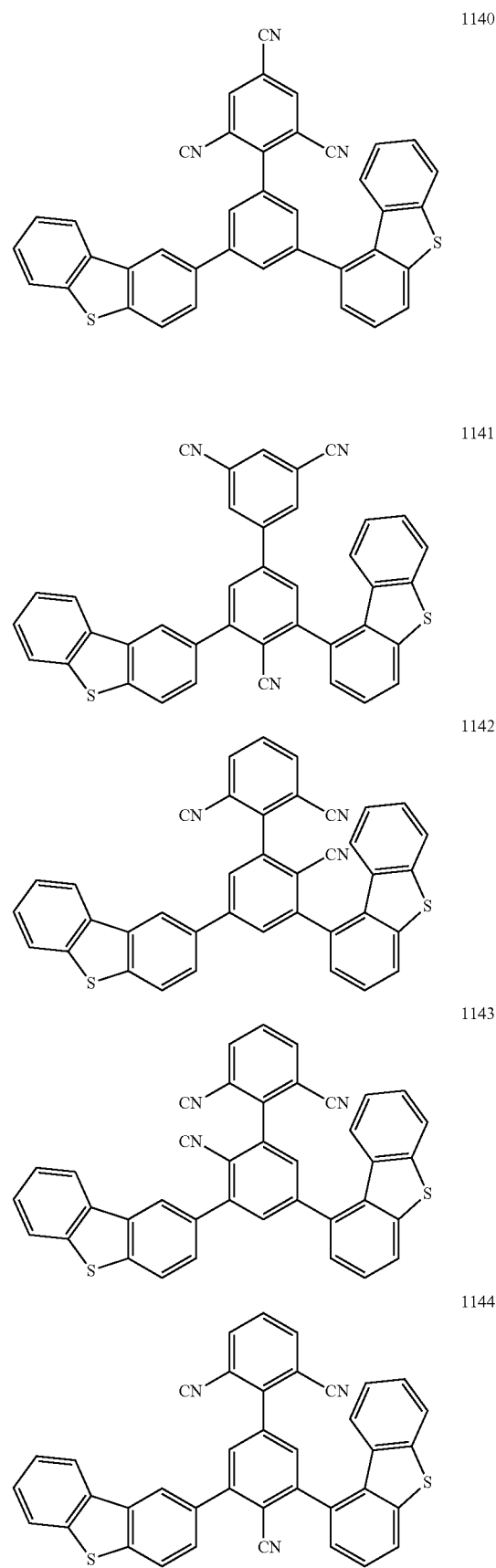

303
-continued
| | |
|---|---|
| 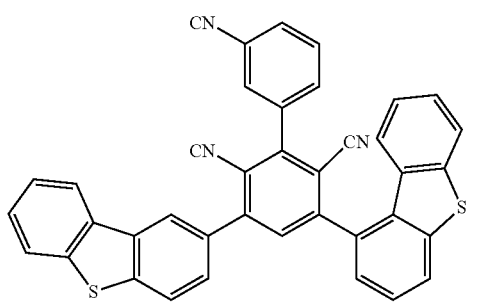 | 1145 |
| 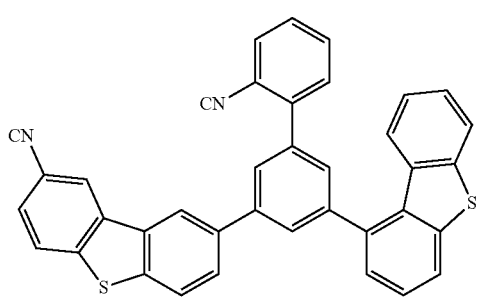 | 1146 |
| 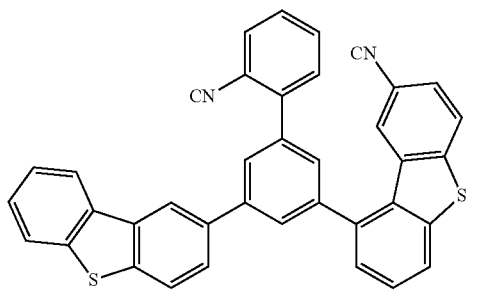 | 1147 |
| 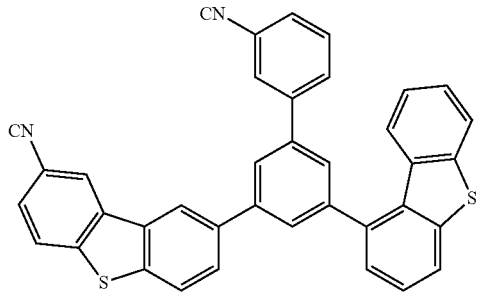 | 1148 |
| 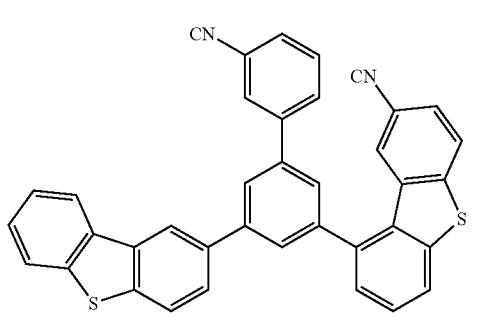 | 1149 |
304
-continued
| | |
|---|---|
| 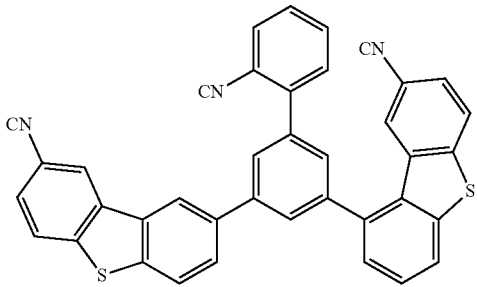 | 1150 |
| 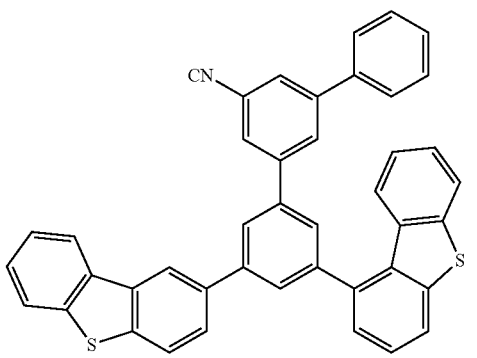 | 1151 |
| 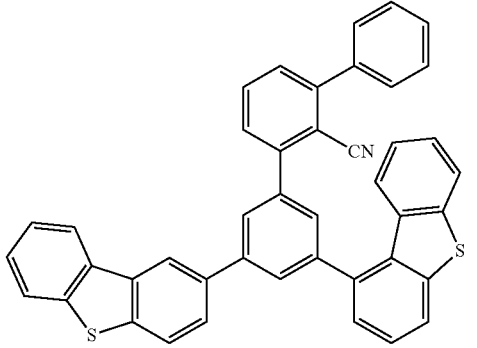 | 1152 |
| 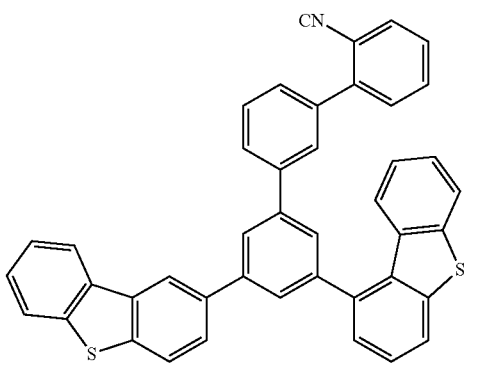 | 1153 |

1154
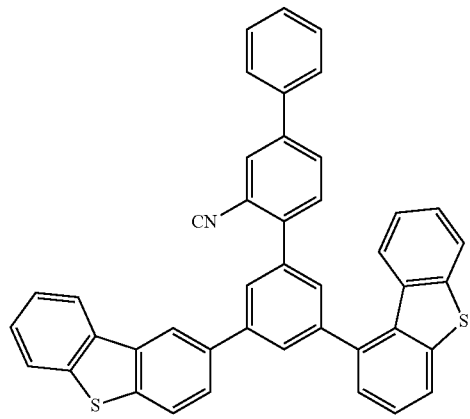
1155
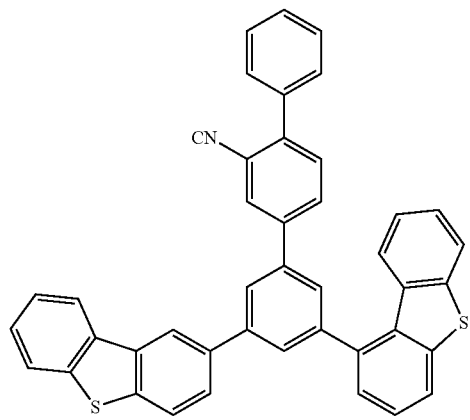
1156
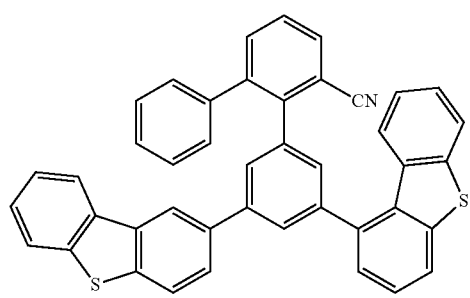
1157
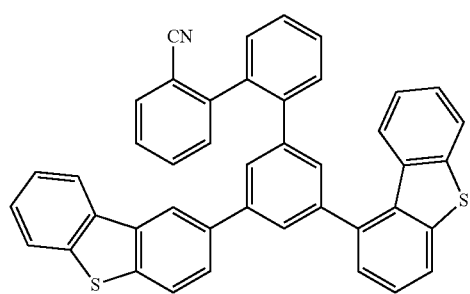
1158
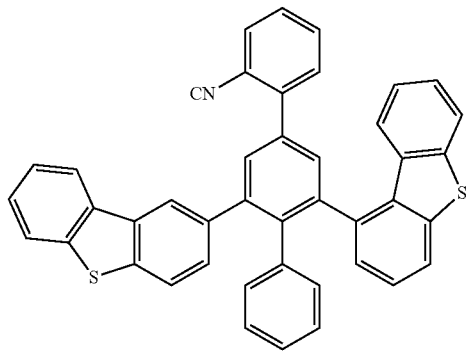
1159
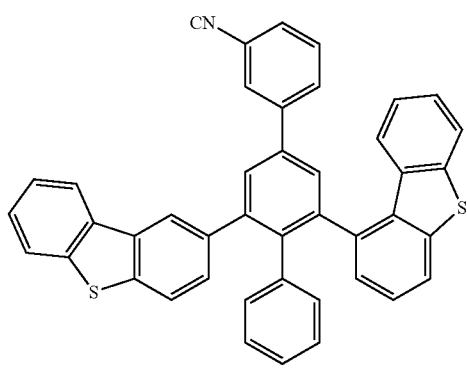
1160
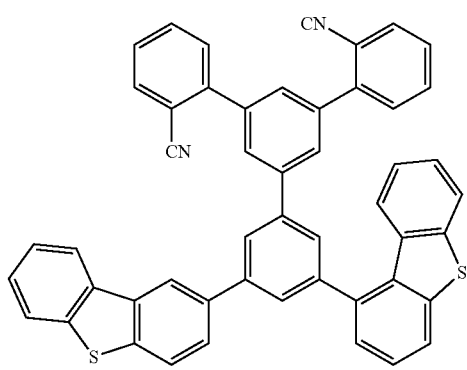
1161
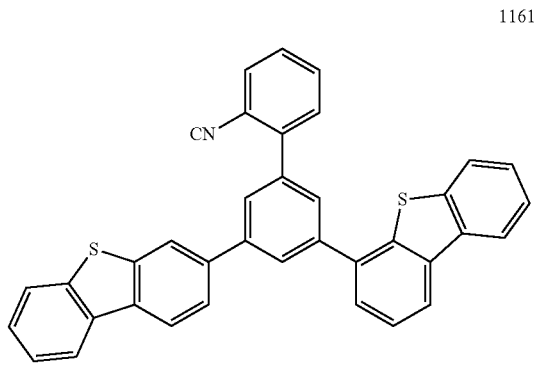

| 307 -continued | 308 -continued |
|---|---|
| 1162 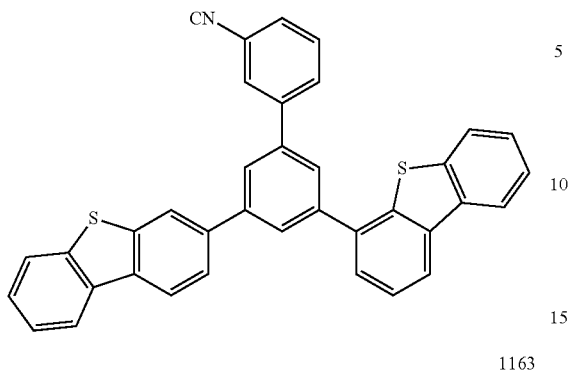 | 1166 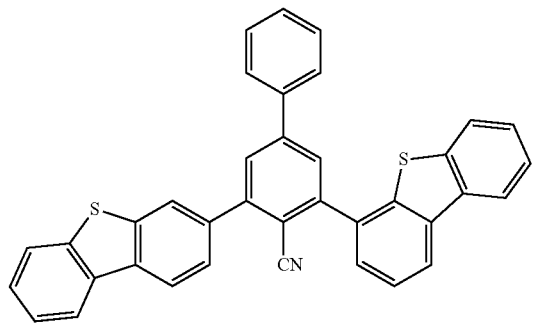 |
| 1163 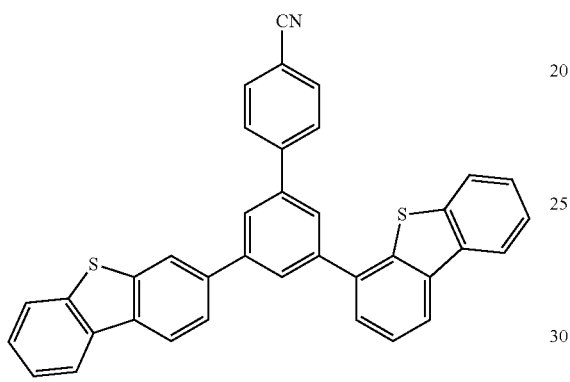 | 1167 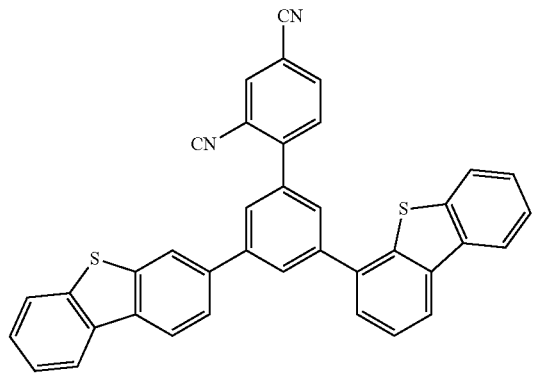 |
| 1164 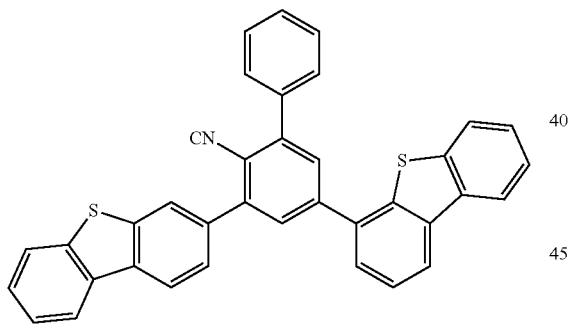 | 1168 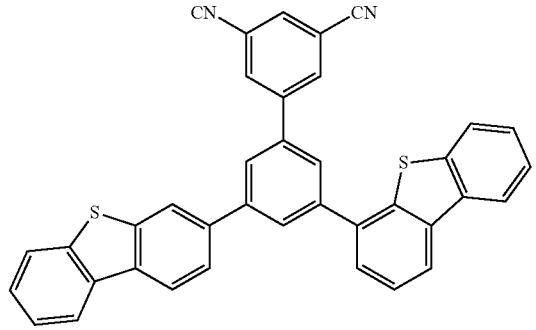 |
| 1165 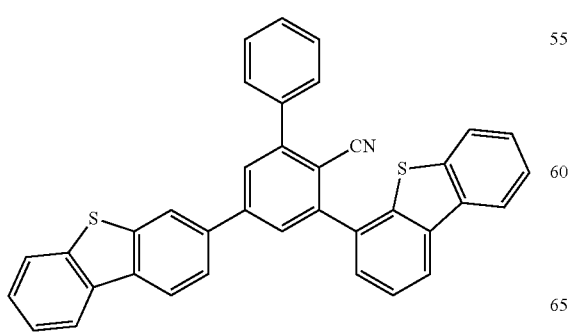 | 1169 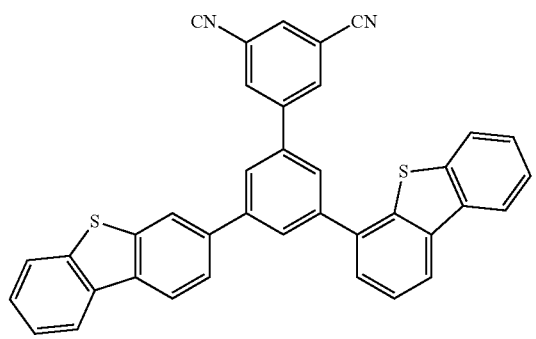 |

309
-continued
1170
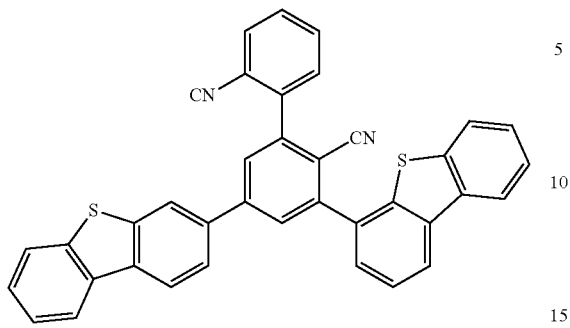
1171
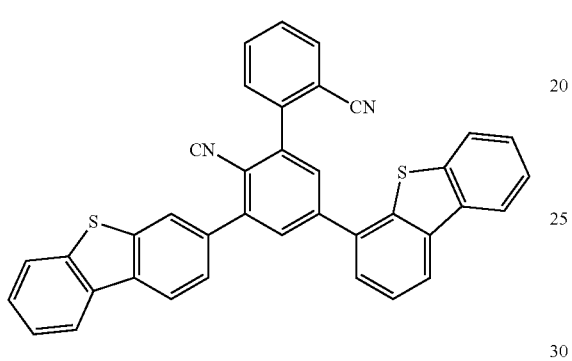
1172
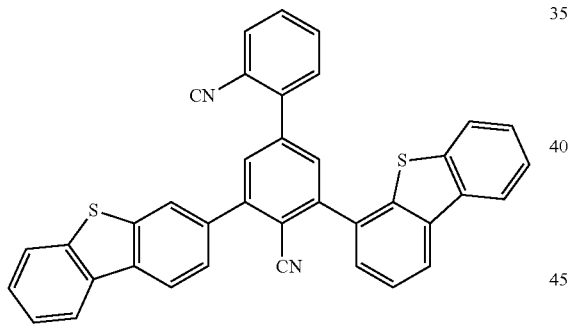
1173
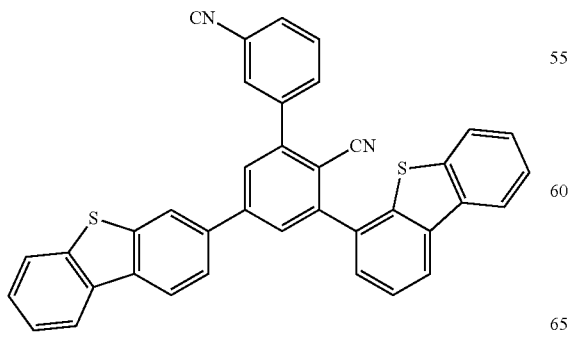
310
-continued
1174
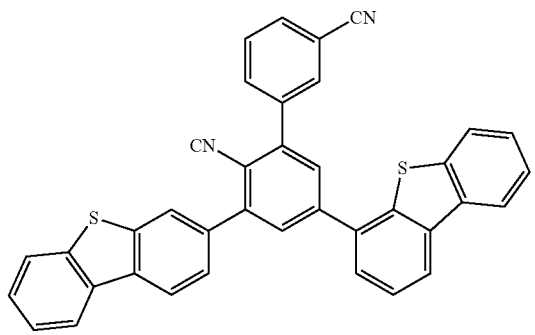
1175
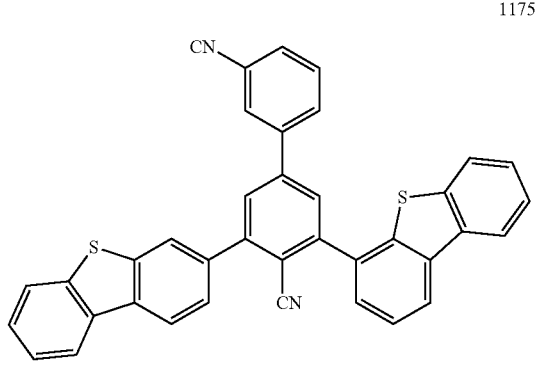
1176
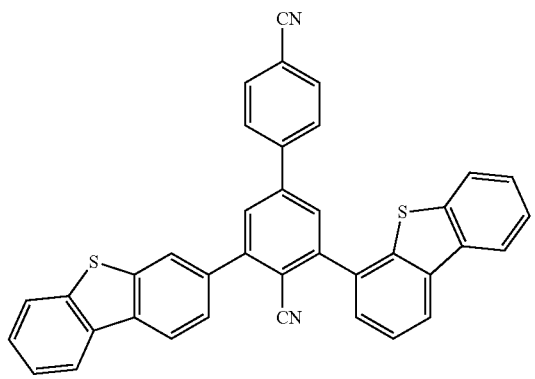
1177
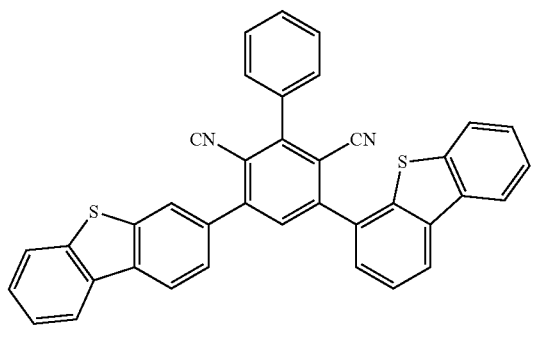

| 311 -continued | 312 -continued |
|---|---|
| 1178 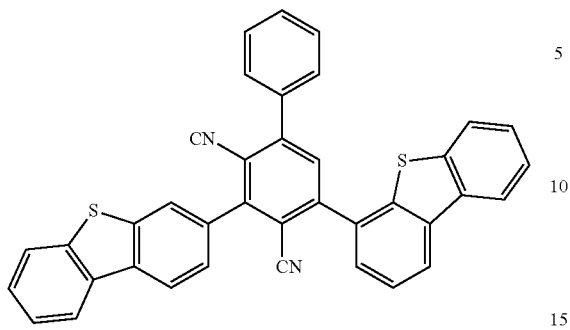 | 1182 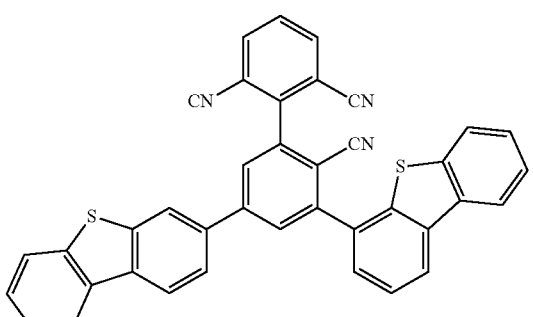 |
| 1179 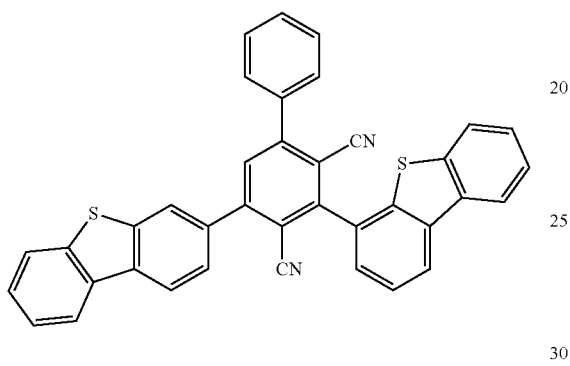 | 1183 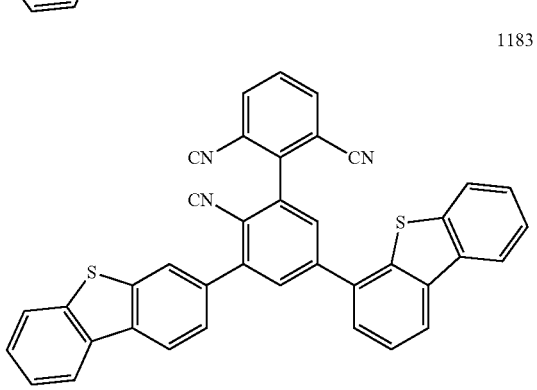 |
| 1180 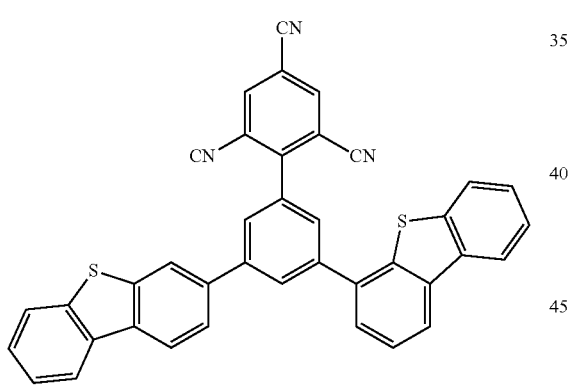 | 1184 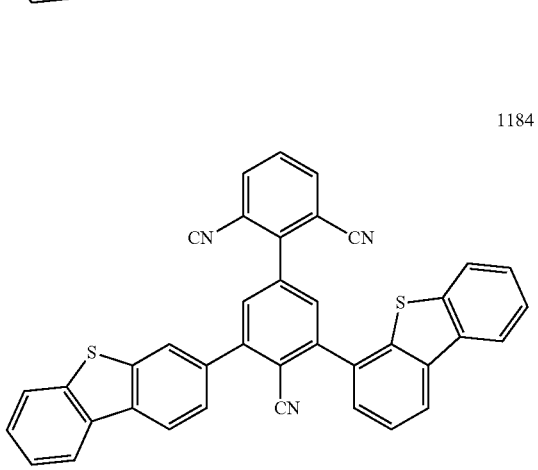 |
| 1181 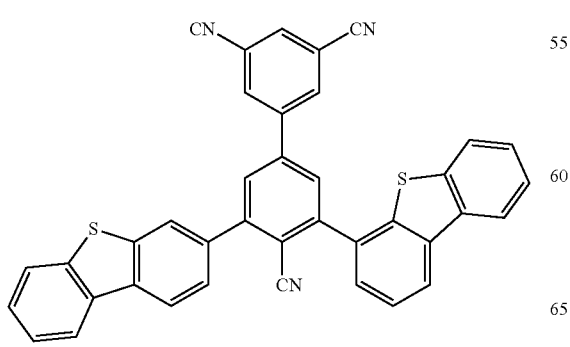 | 1185 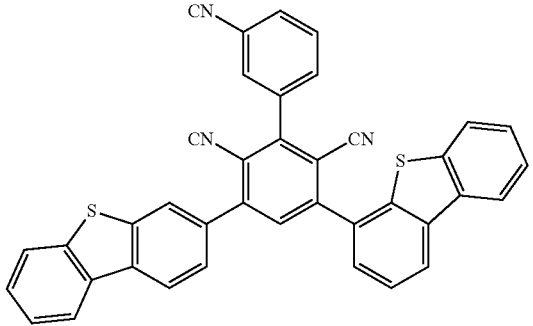 |

| 1186 | 1190 |
|---|---|
| 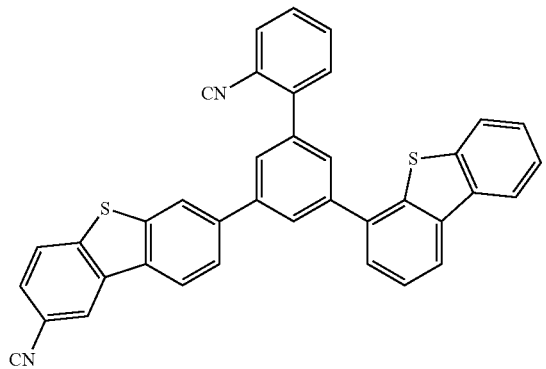 | 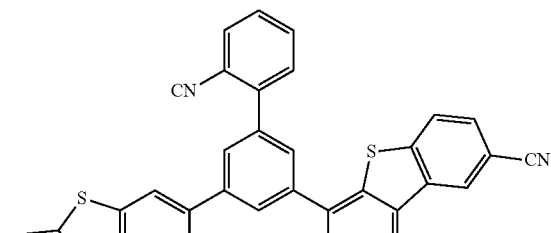 |
| 1187 | 1191 |
| 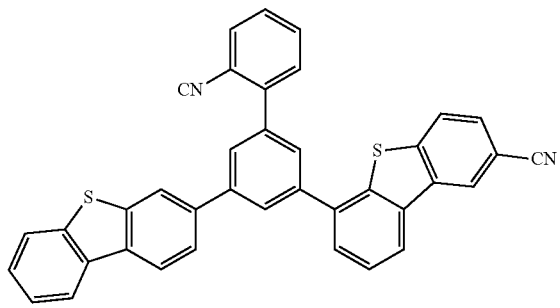 | 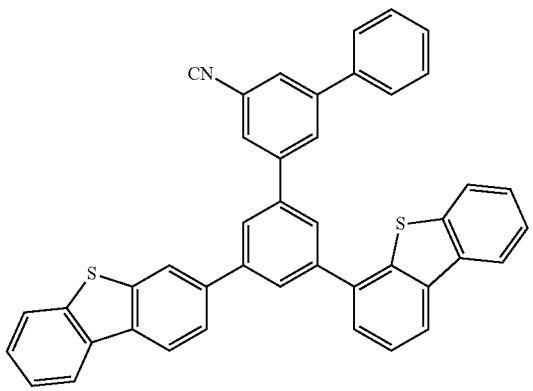 |
| 1188 | 1192 |
| 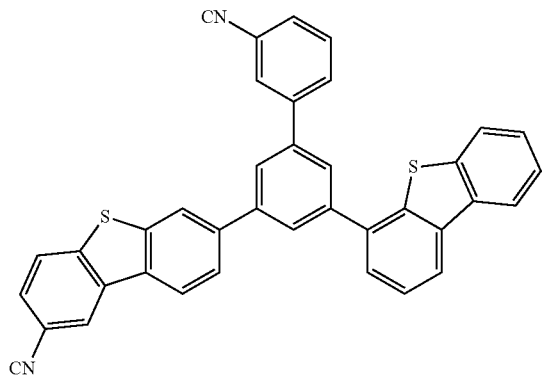 | 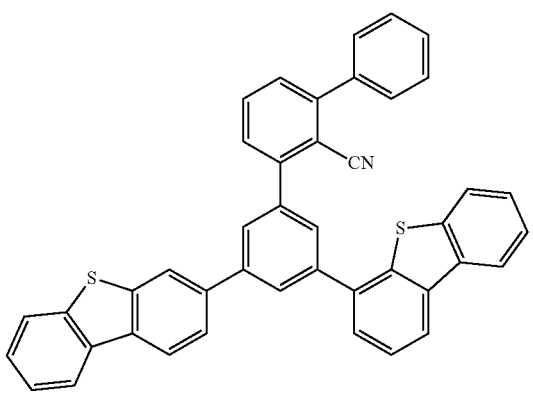 |
| 1189 | 1193 |
| 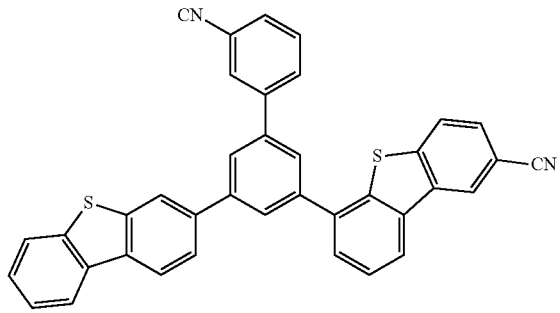 | 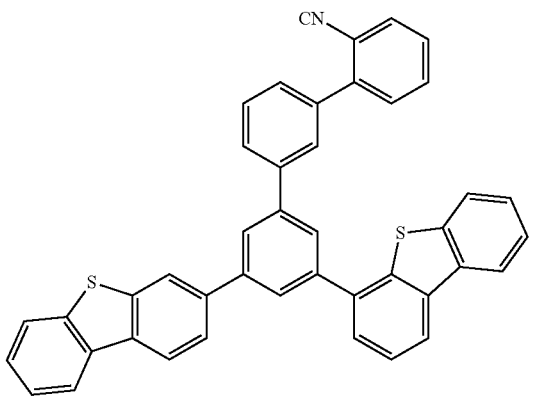 |

315
-continued
1194
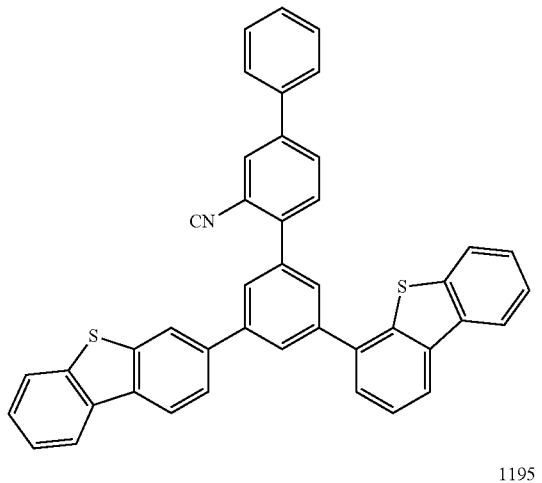
1195
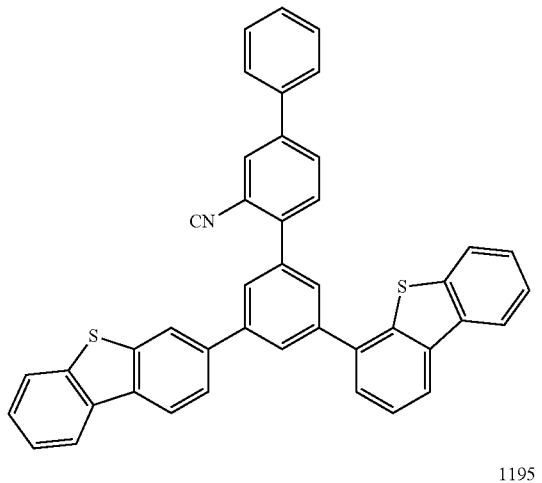
1196
1197
316
-continued
1198
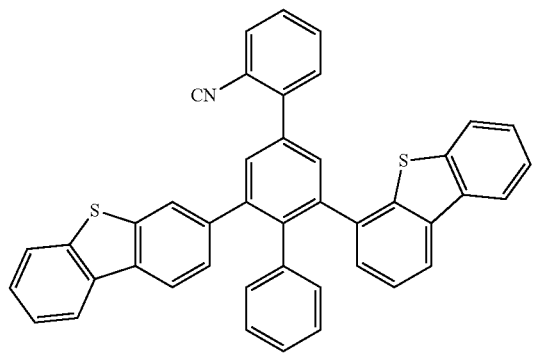
1199
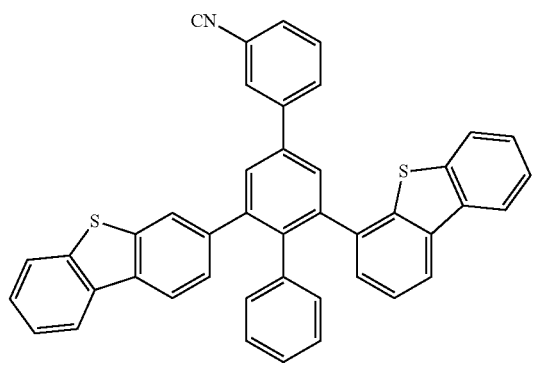
1200
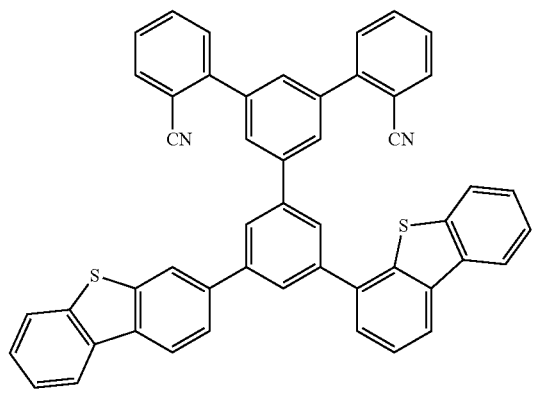
1201
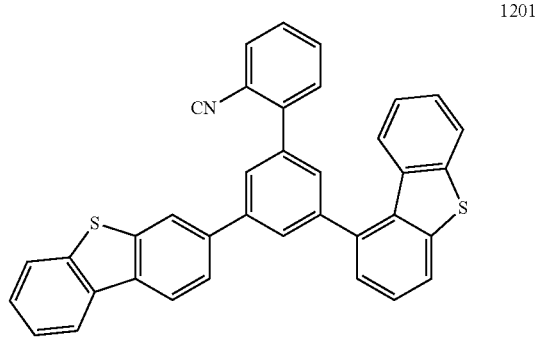
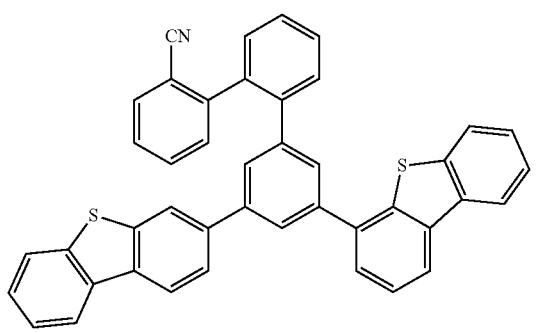

| 1202 | 1206 |
|---|---|
| 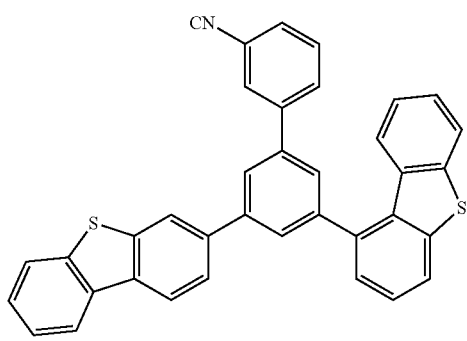 | 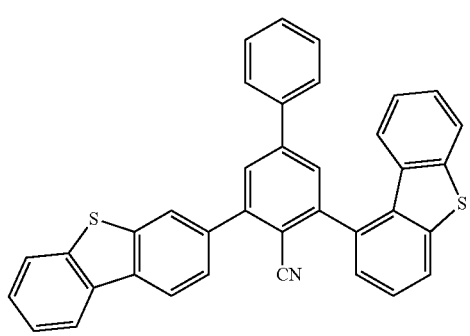 |
| 1203 | 1207 |
| 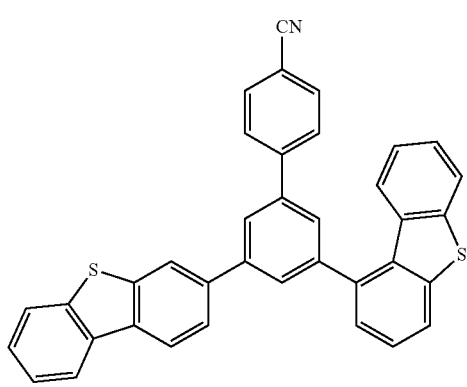 | 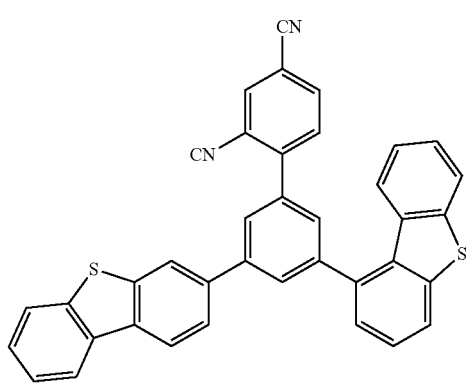 |
| 1204 | 1208 |
| 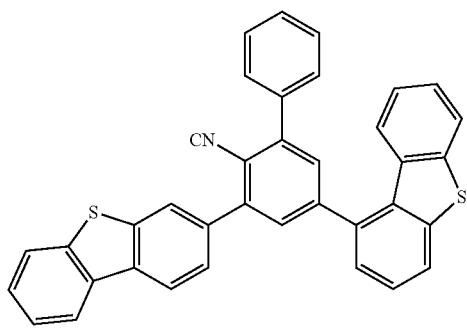 | 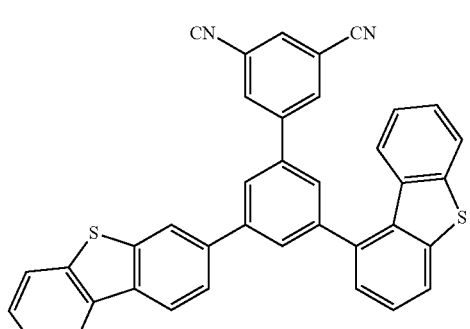 |
| 1205 | 1209 |
| 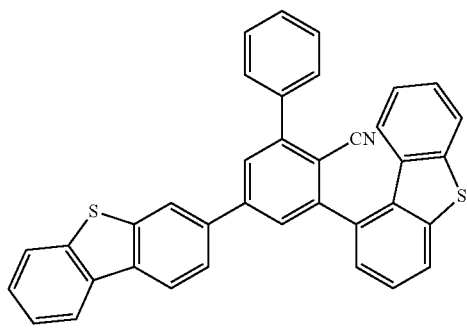 | 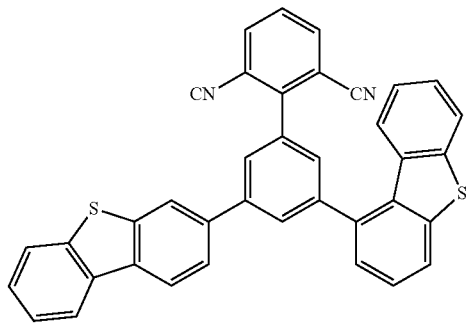 |

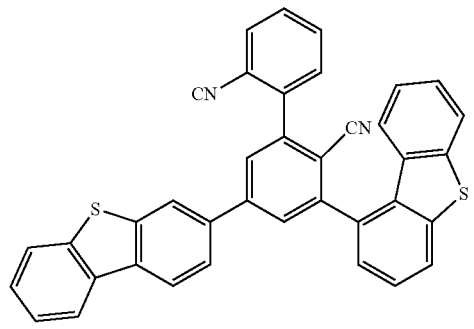
1210
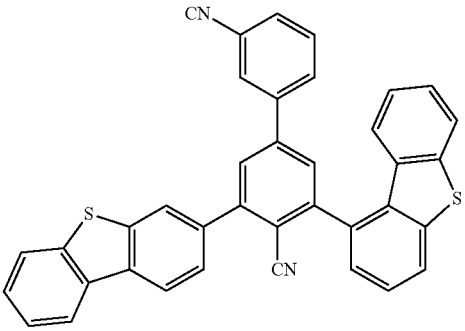
1215

1211
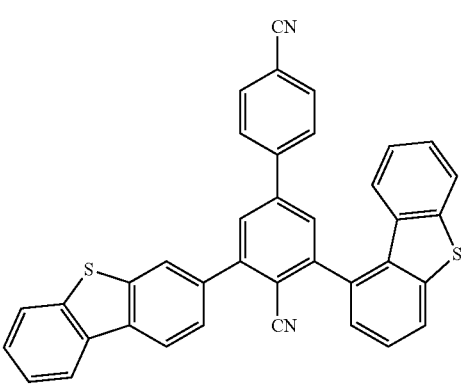
1216
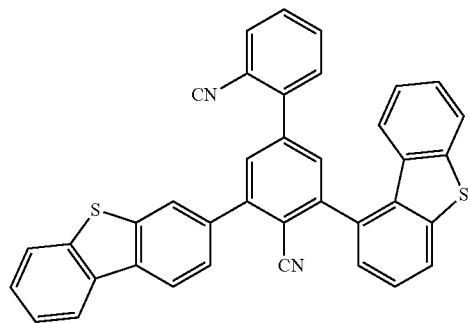
1212

1213
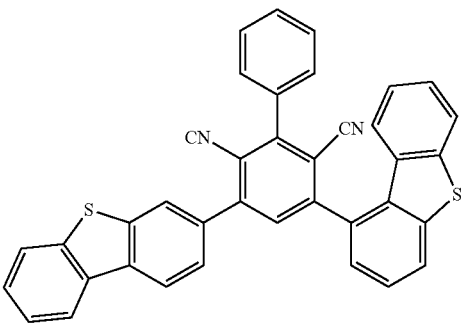
1217
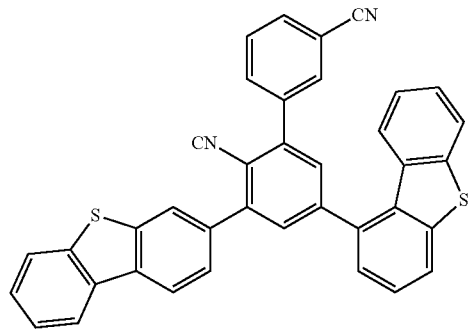
1214
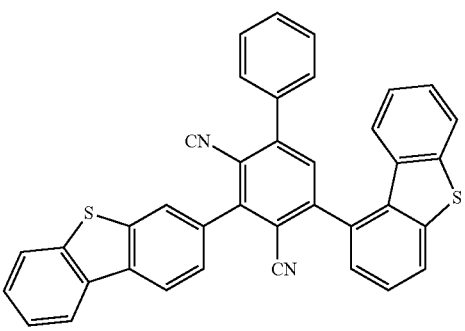
1218

1219 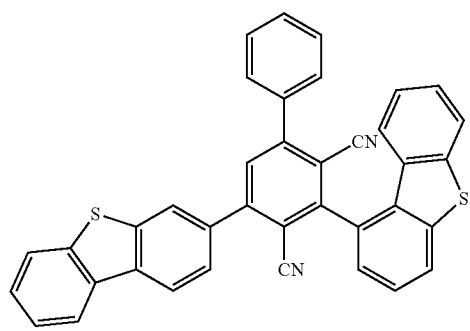
1220 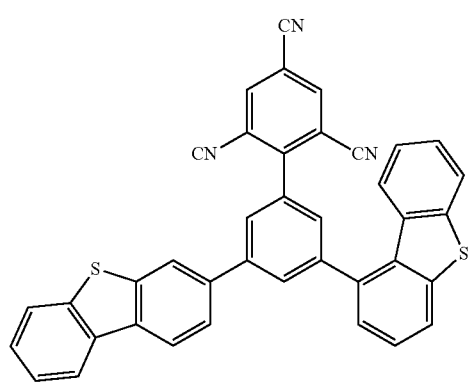
1221 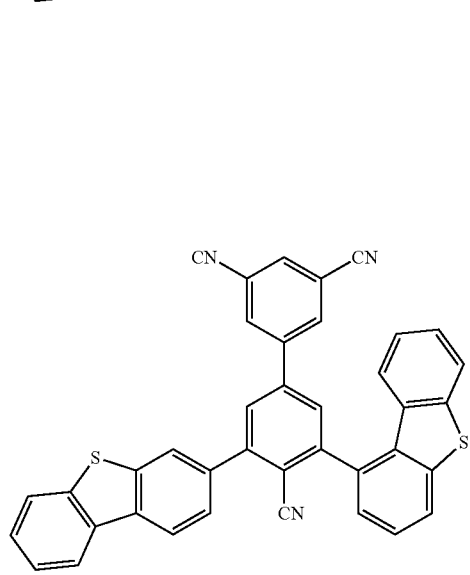
1222 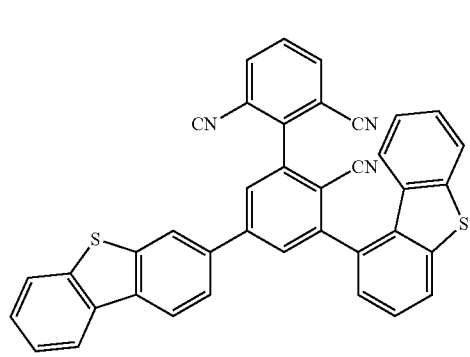
1223 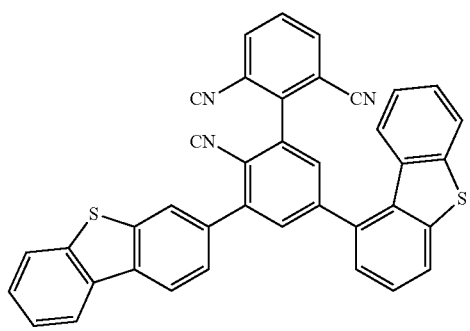
1224 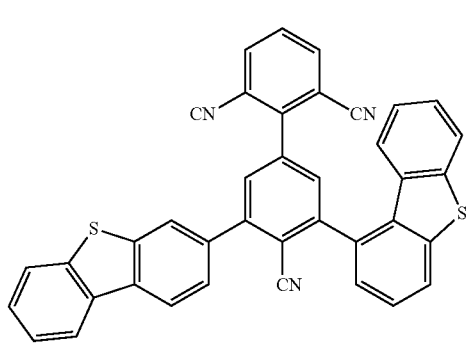
1225 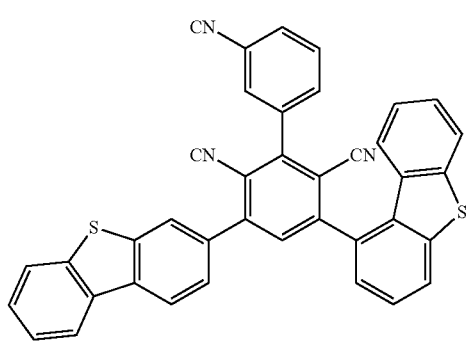
1226 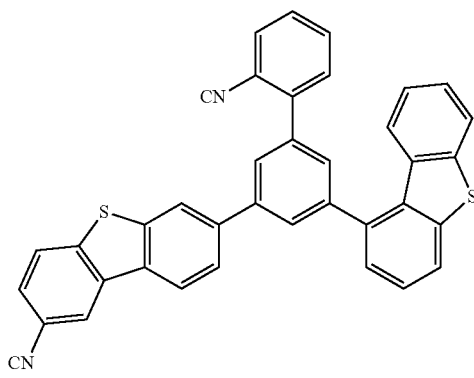

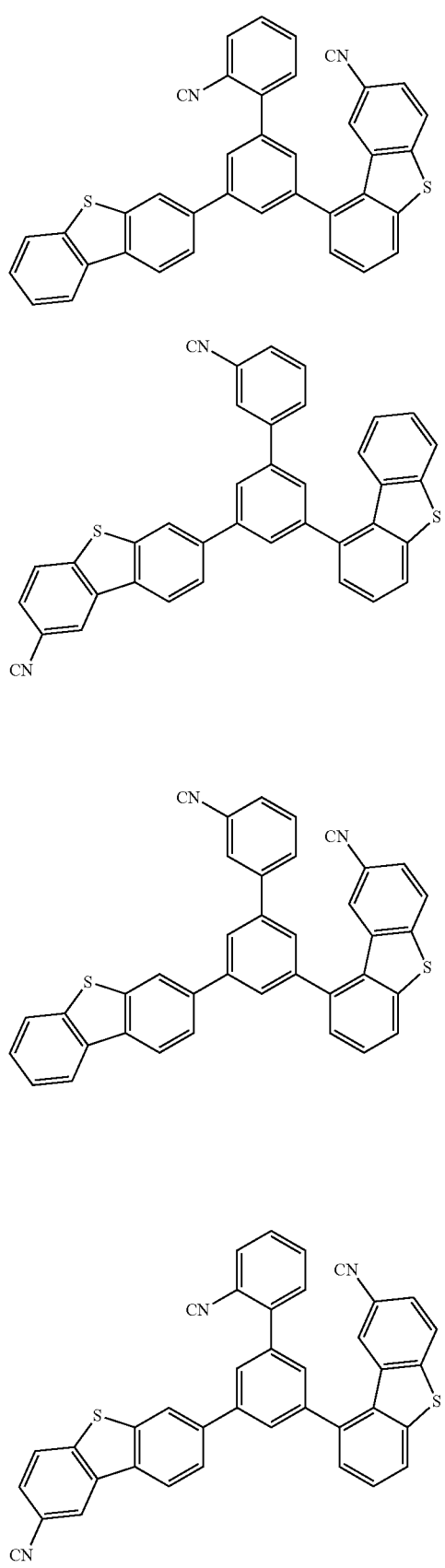
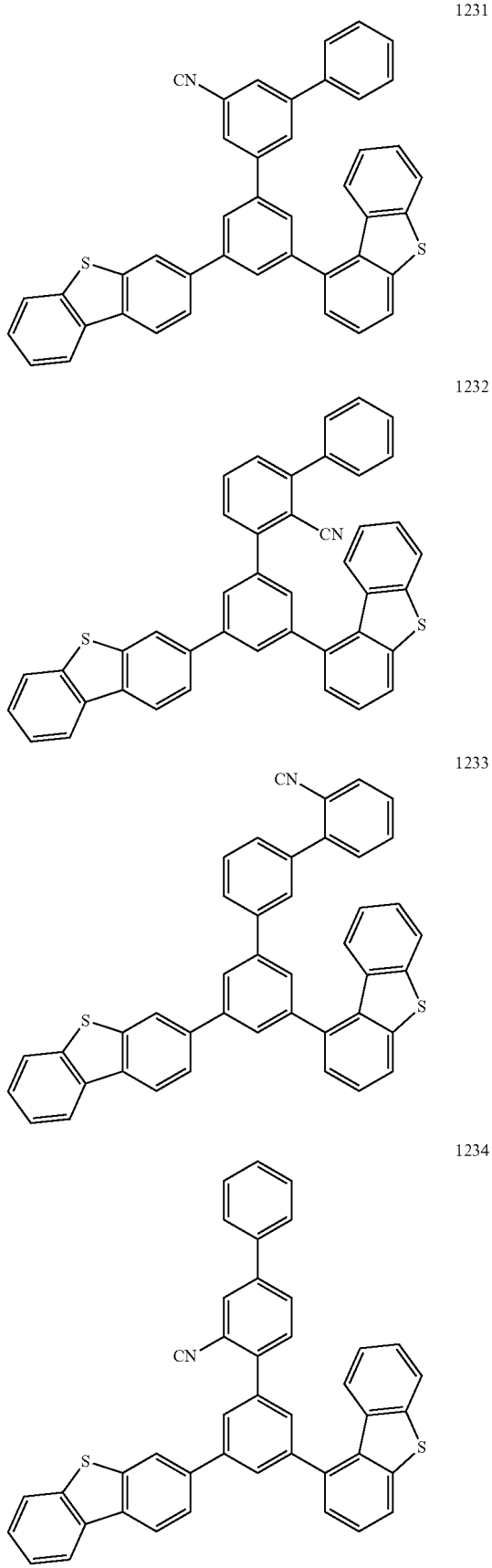

1235
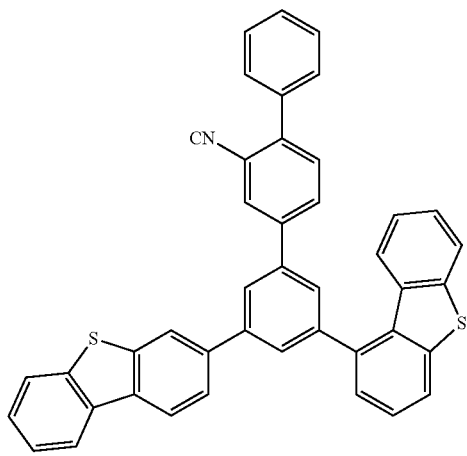
1236
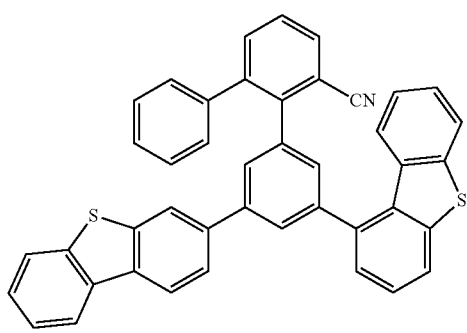
1237
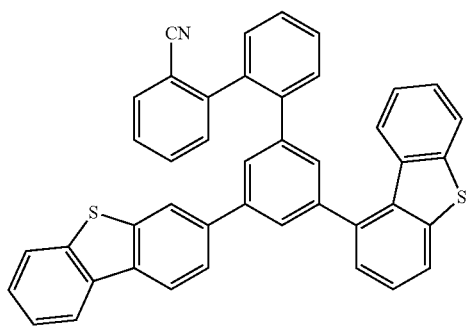
1238
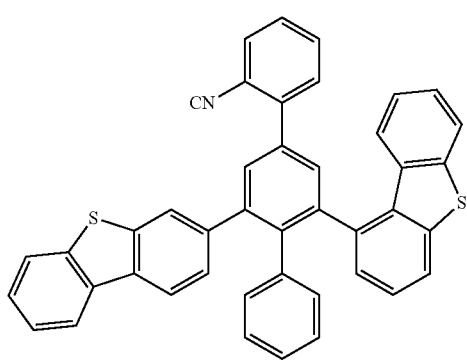
1239
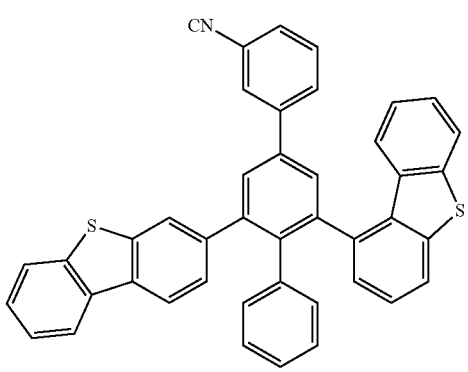
1240
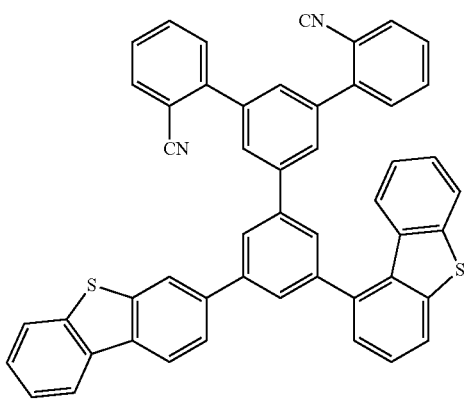
1241
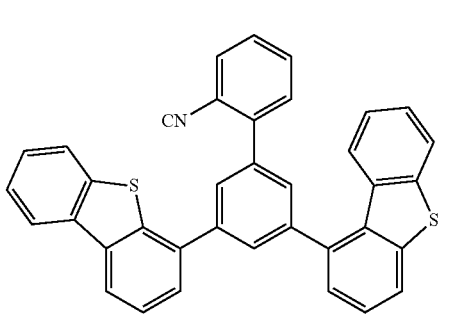
1242
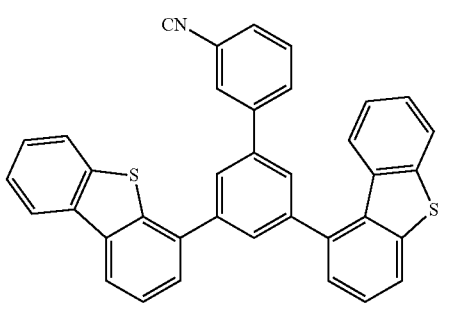

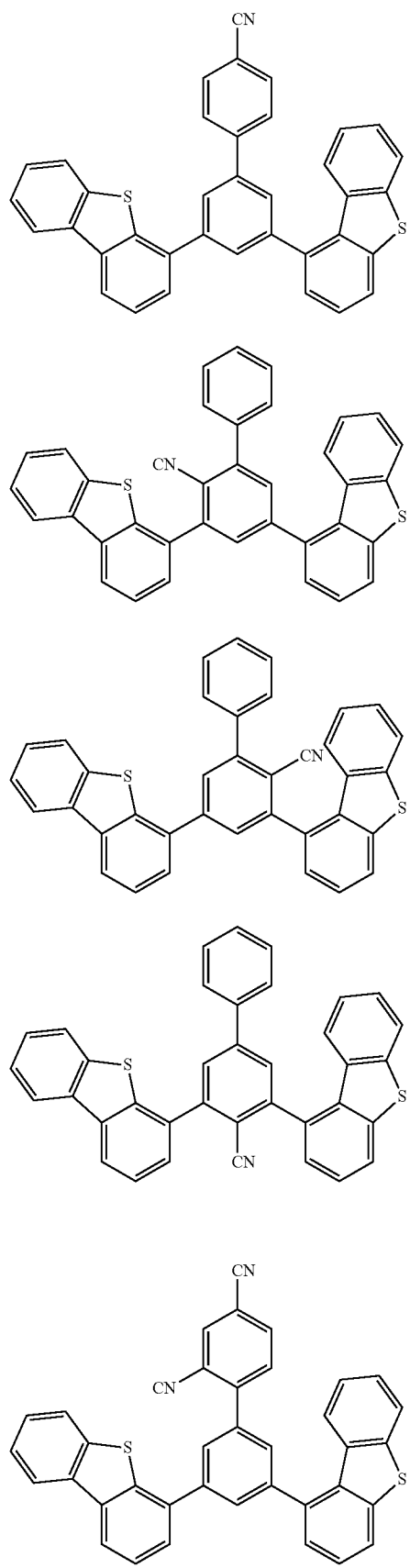

329
-continued
330
-continued
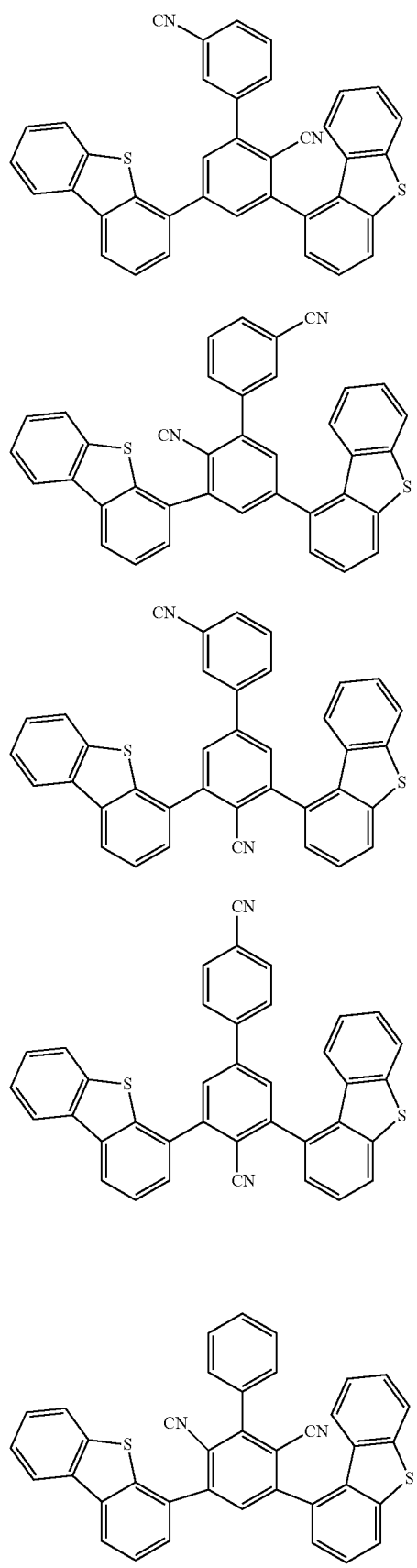
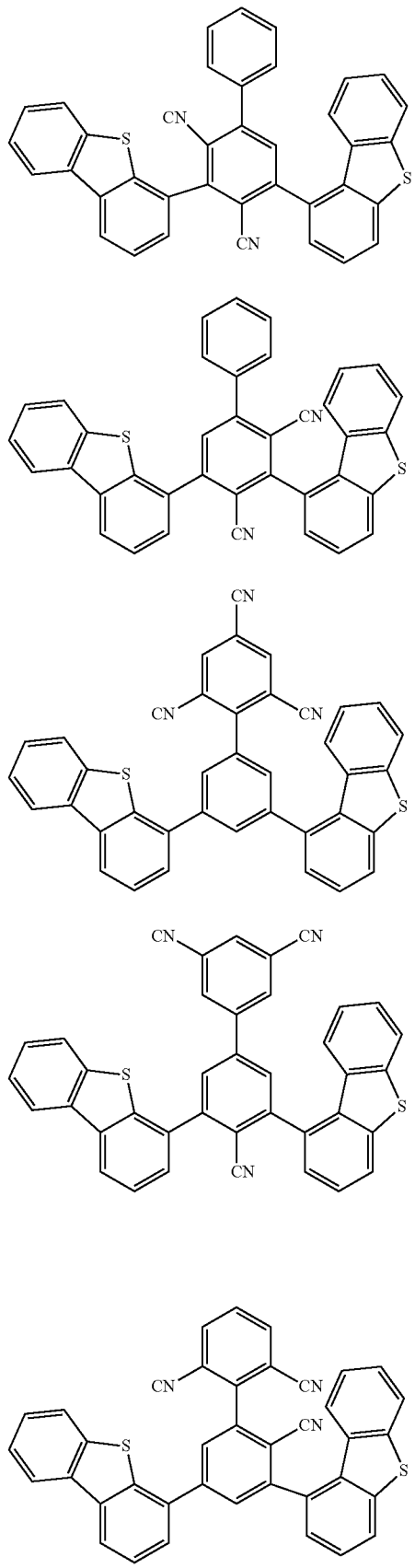

1263
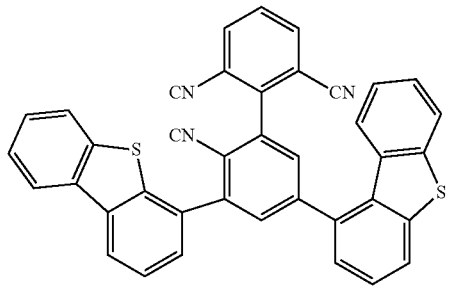
1264
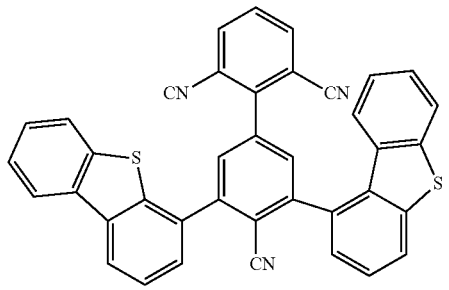
1265
1266
1267
1268
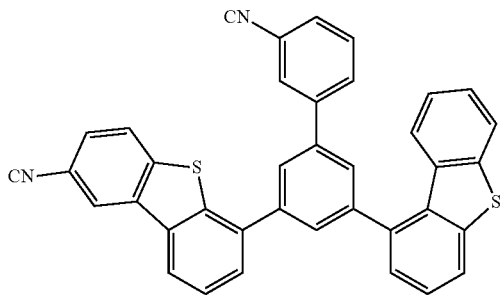
1269
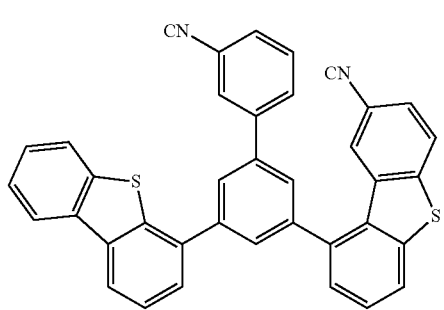
1270
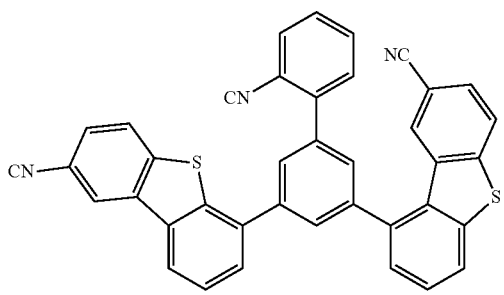
1271
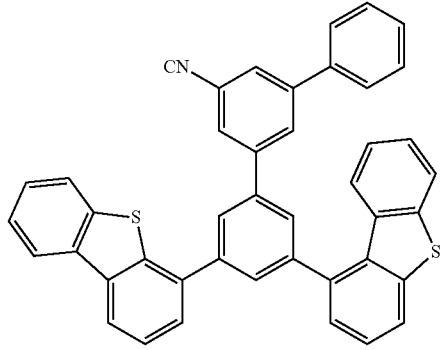
1272
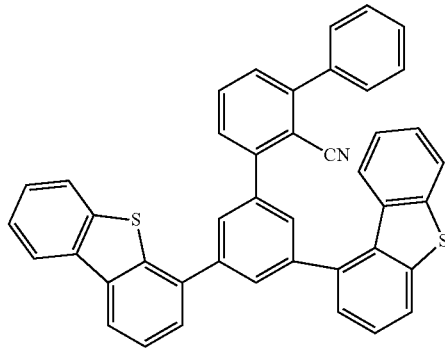

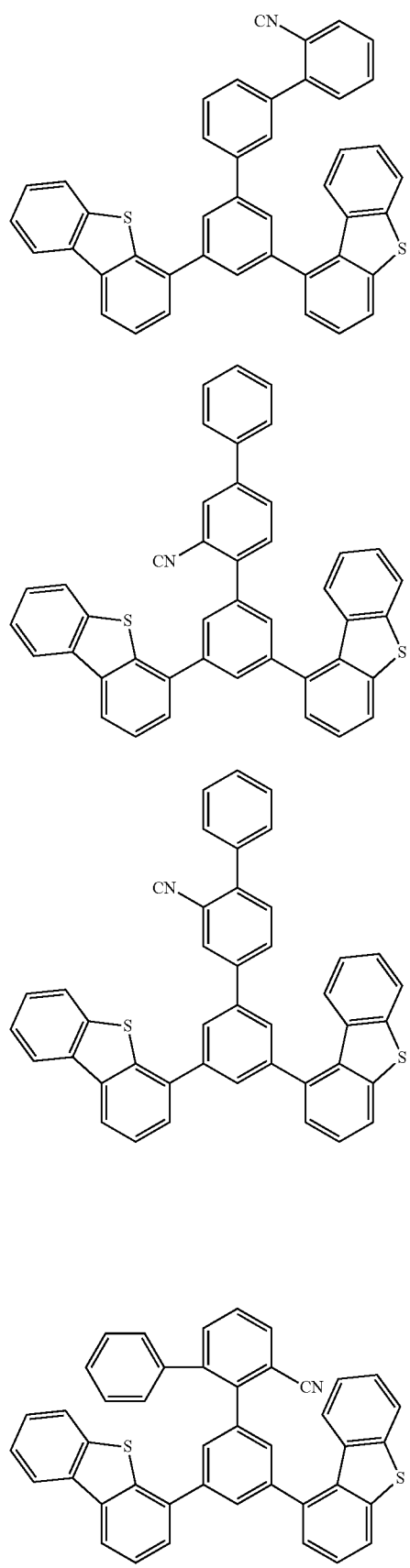
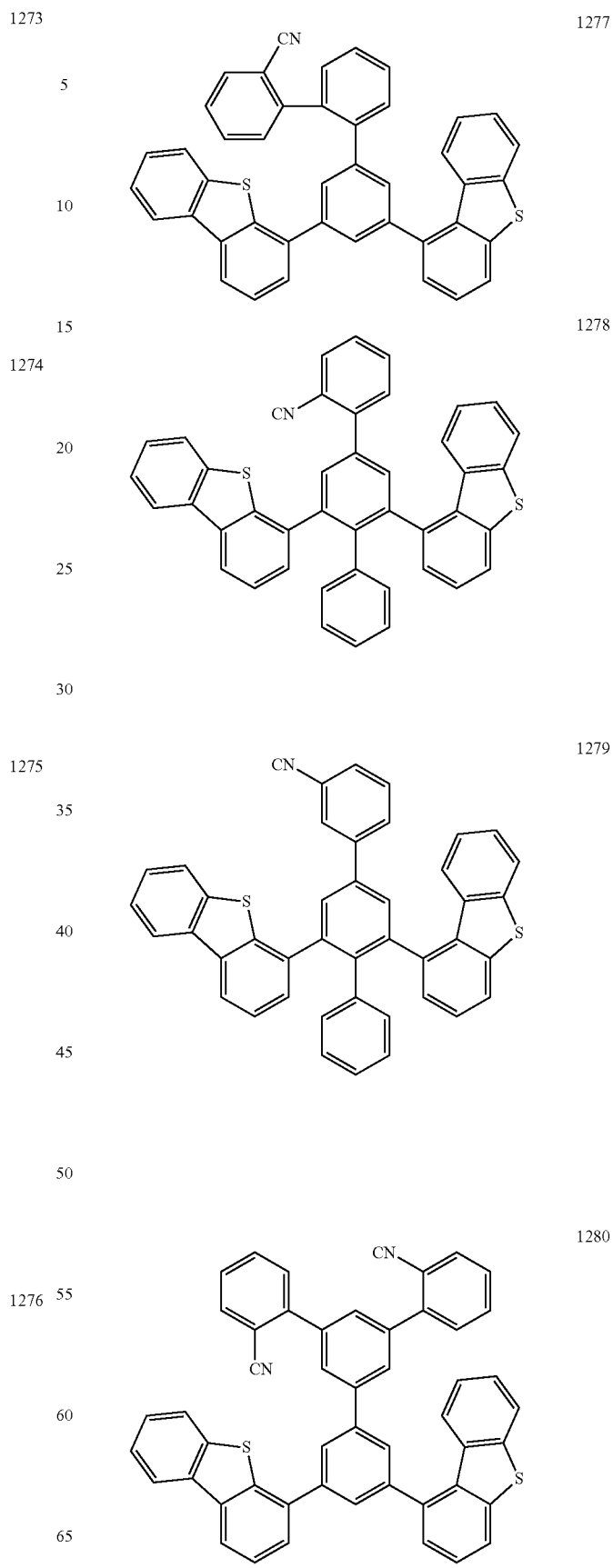

335
-continued
1281
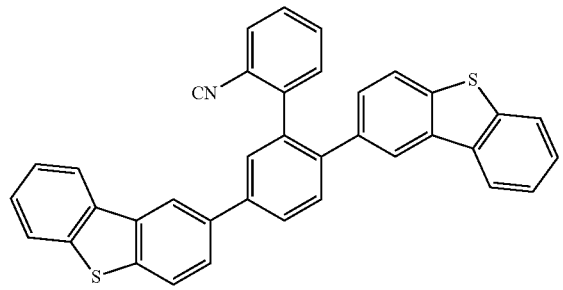
1282
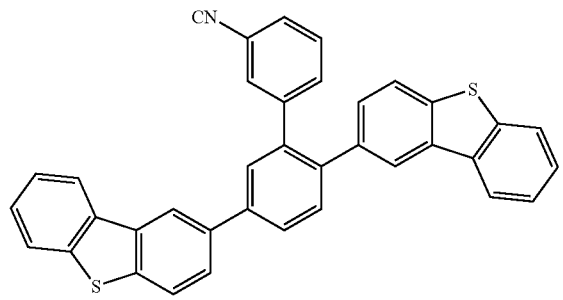
1283
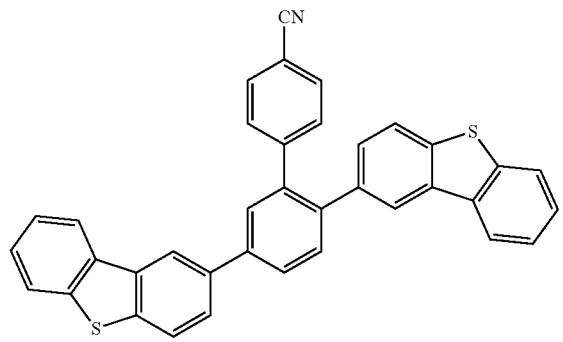
1284
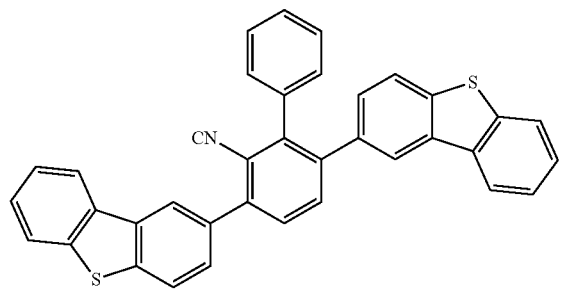
1285
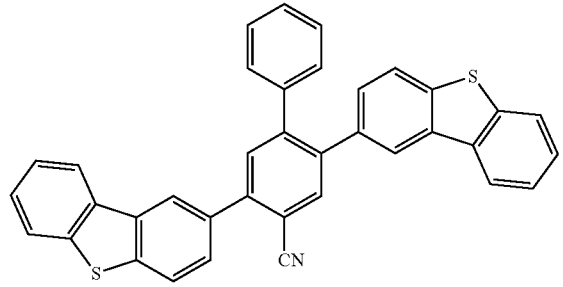
336
-continued
1286
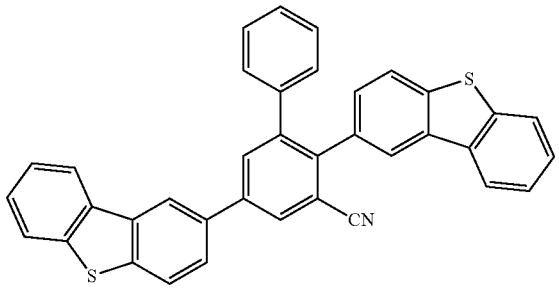
1287
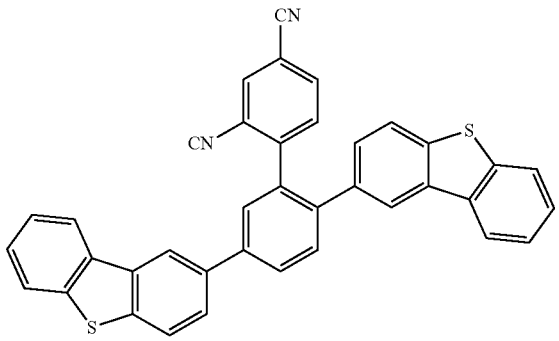
1288
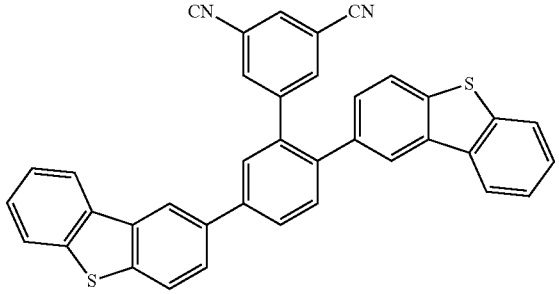
1289
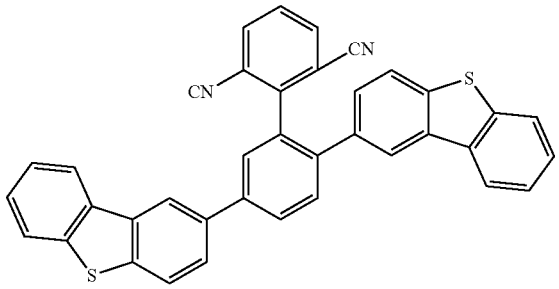
1290
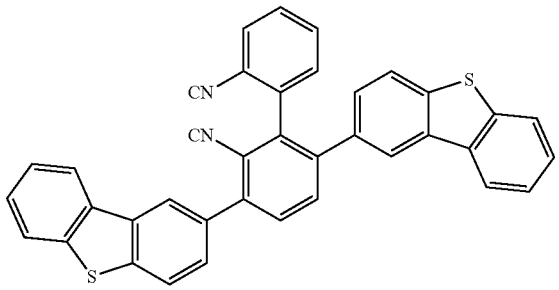

1291
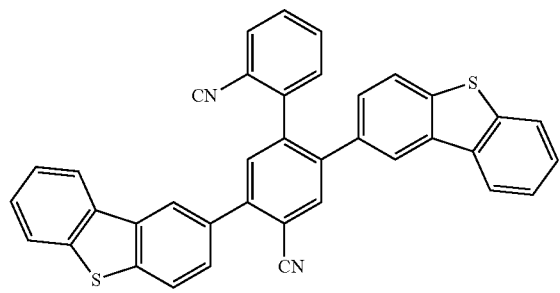
1292
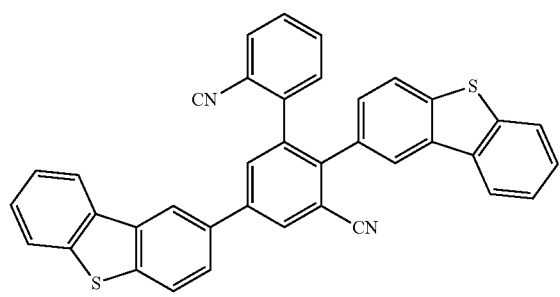
1293
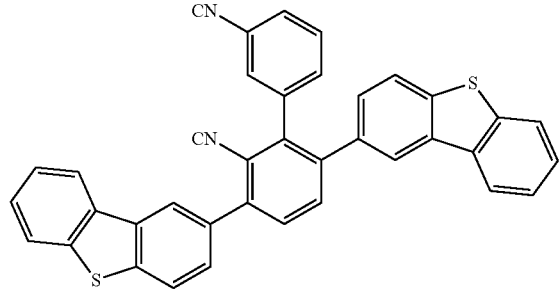
1294
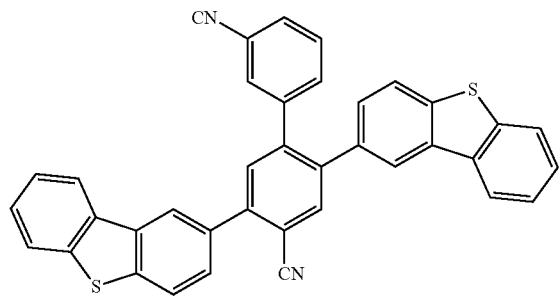
1295
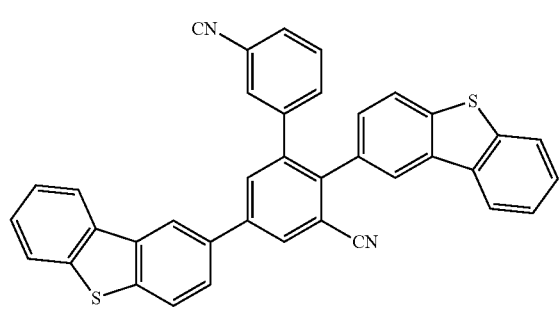
1296
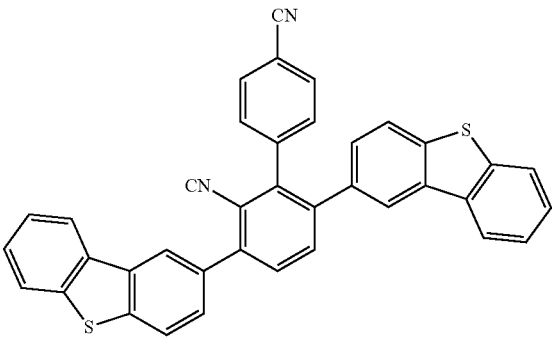
1297
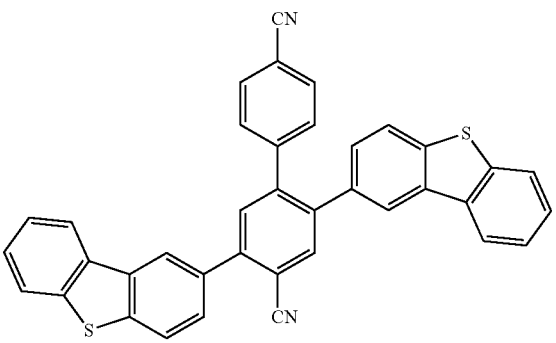
1298
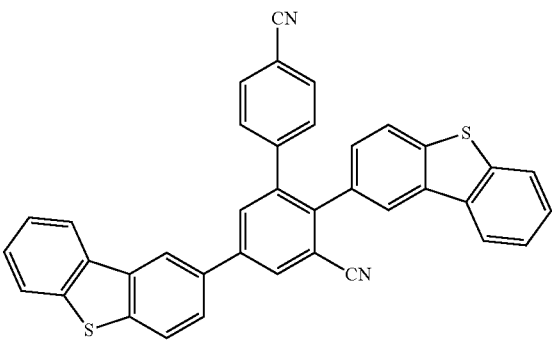
1299
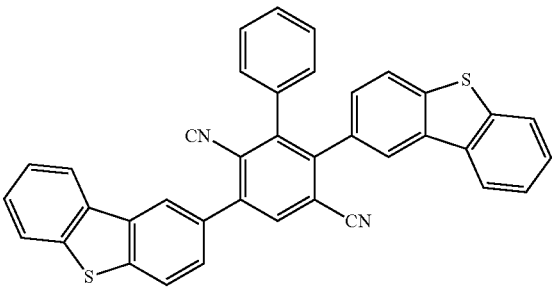

1300
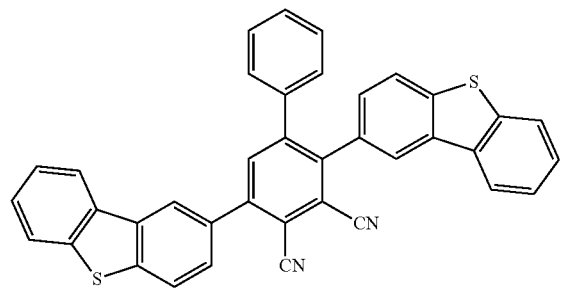
1301
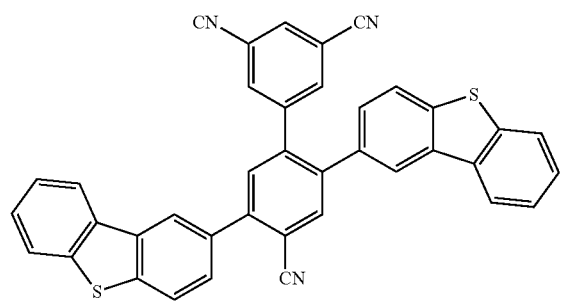
1302
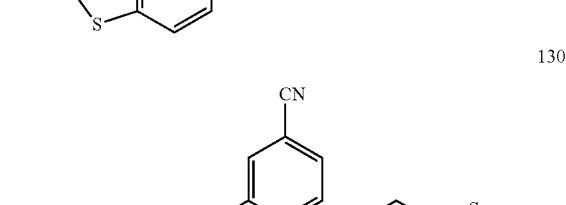
1303
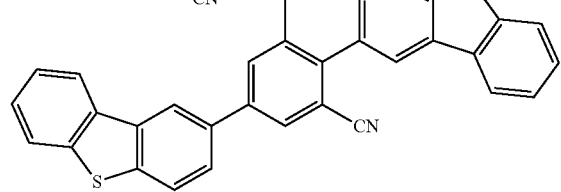
1304
1305
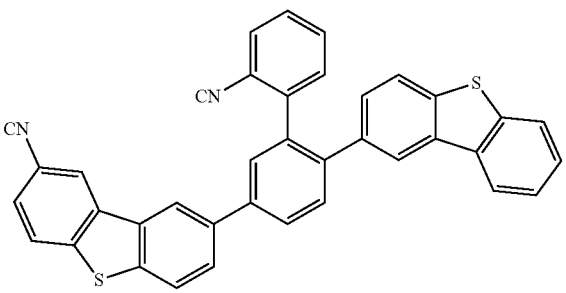
1306
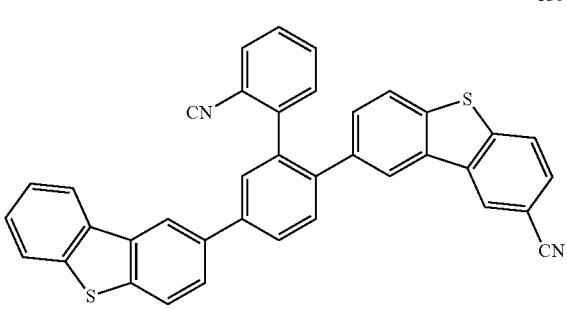
1307
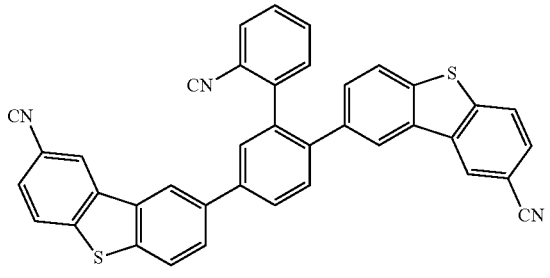
1308
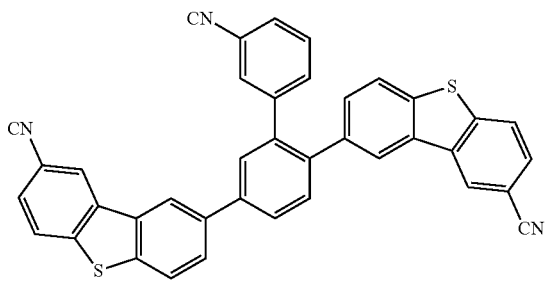
1309
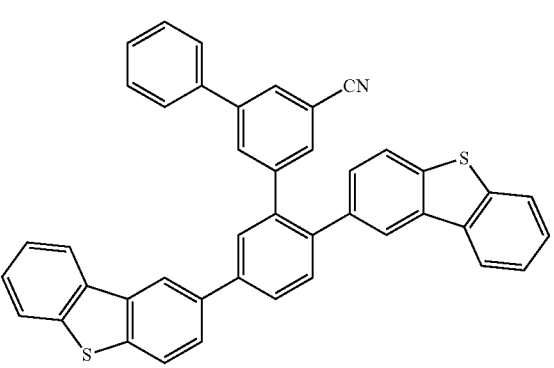

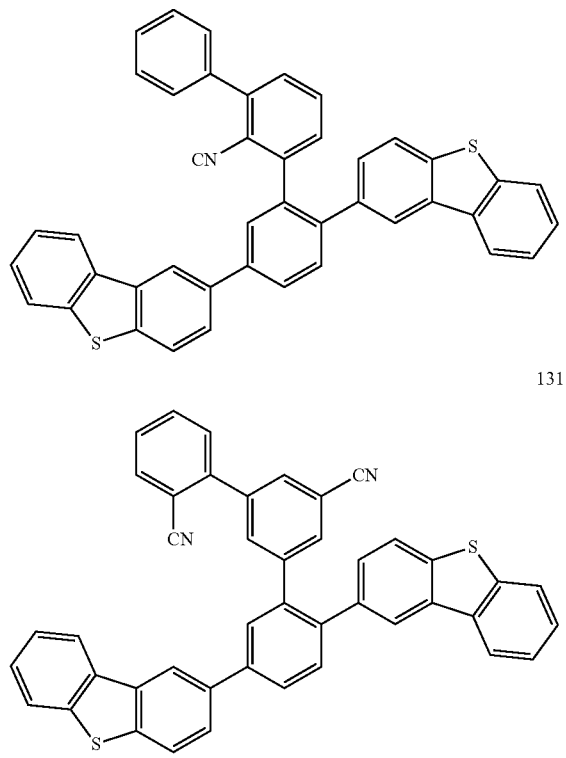
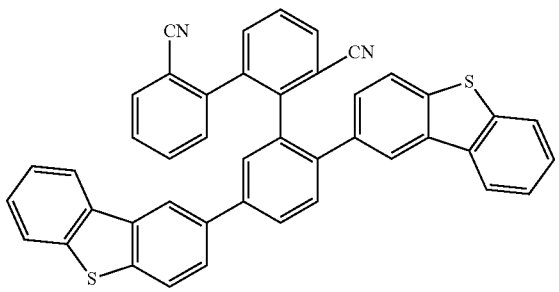
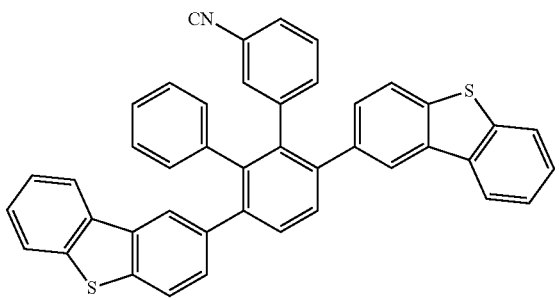
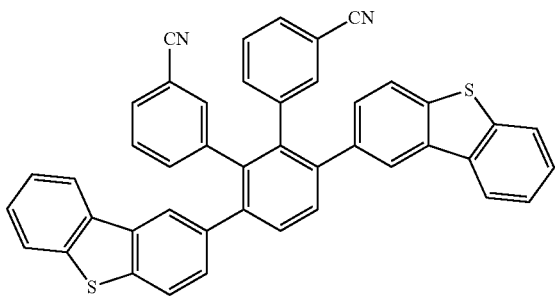
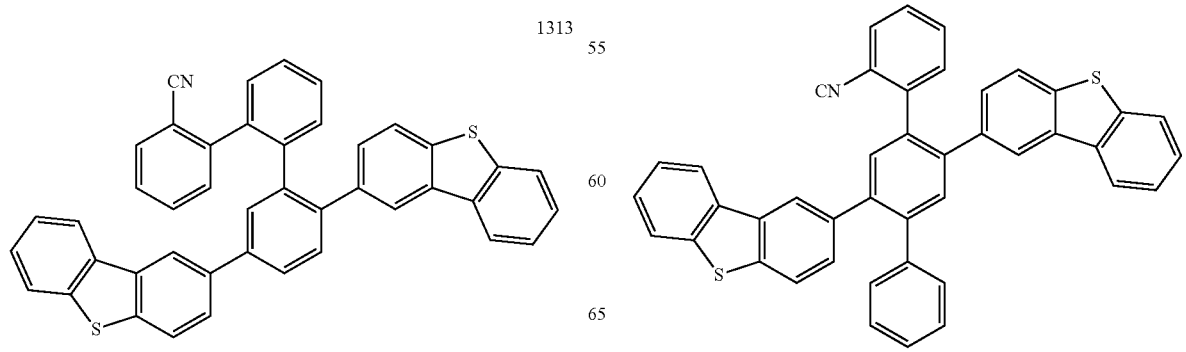

343
-continued
1318
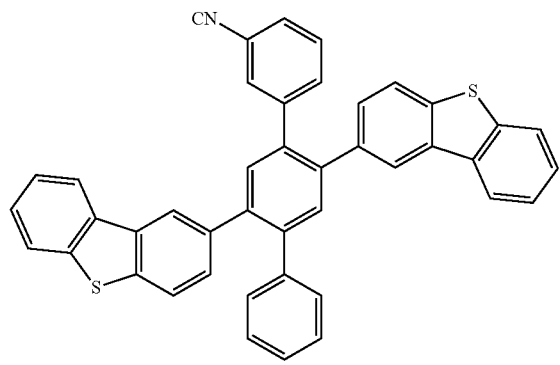
1319
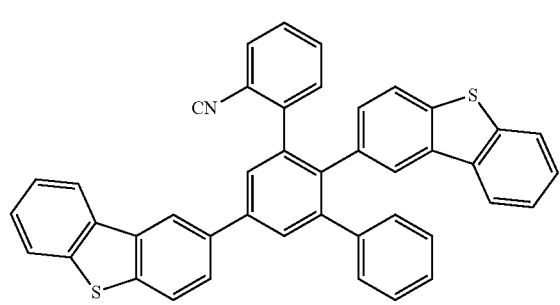
1320
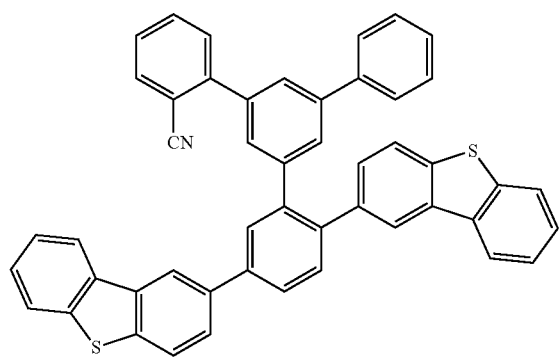
1321
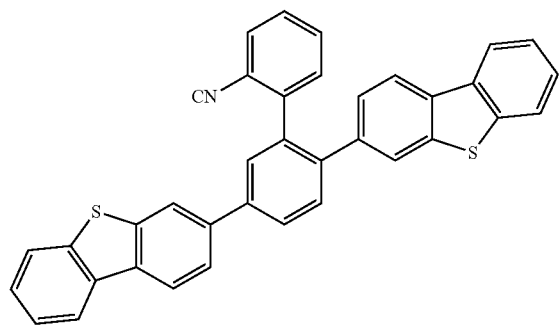
344
-continued
1322
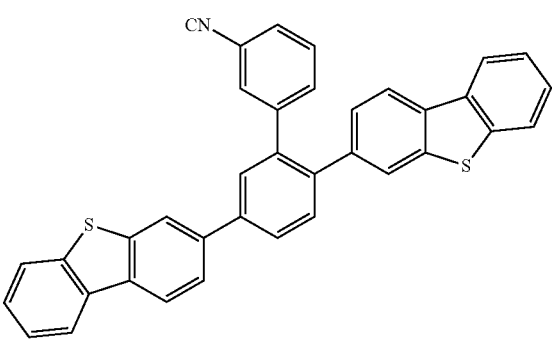
1323
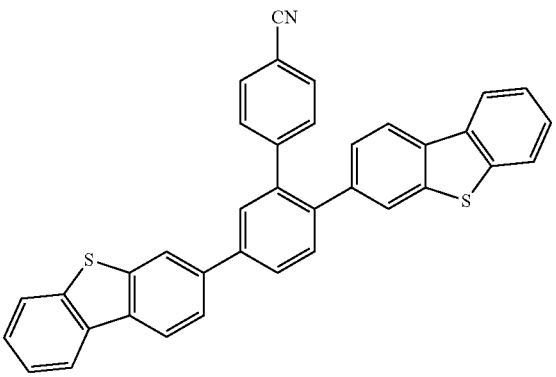
1324
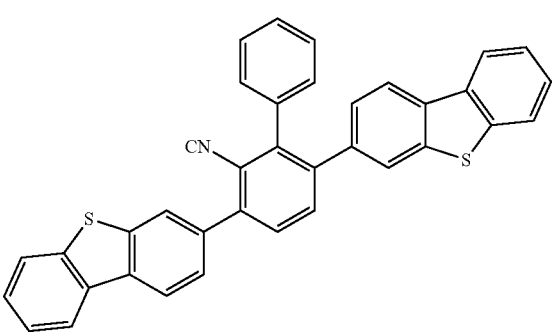
1325
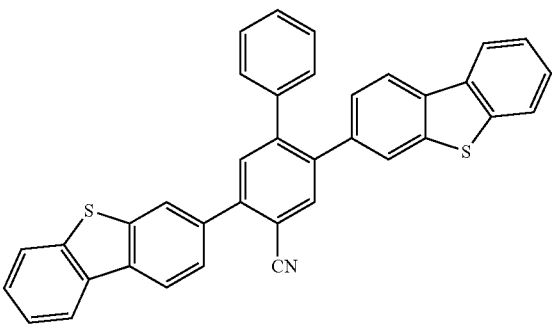

| | |
|---|---|
| 1326 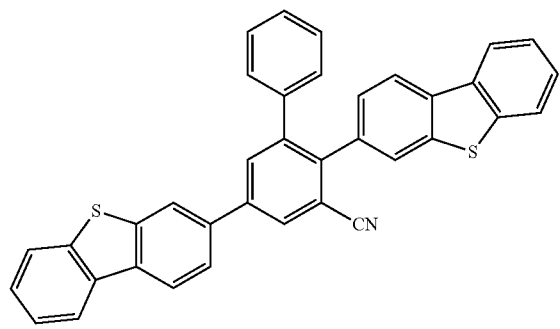 | 1330 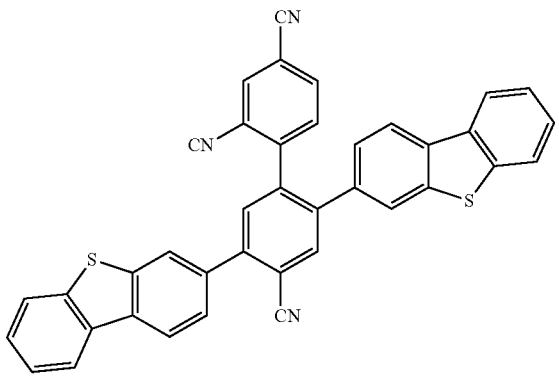 |
| 1327 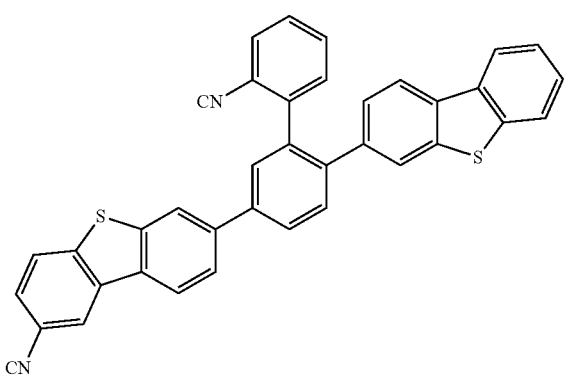 | 1331 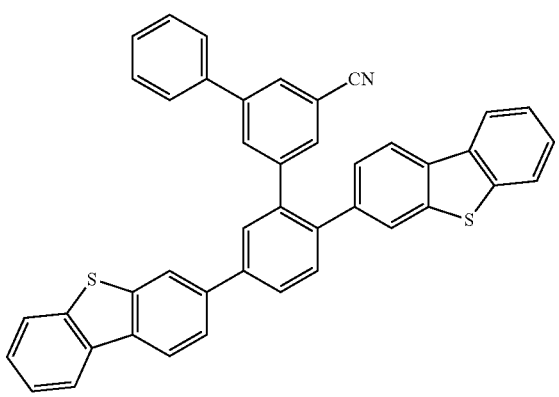 |
| 1328 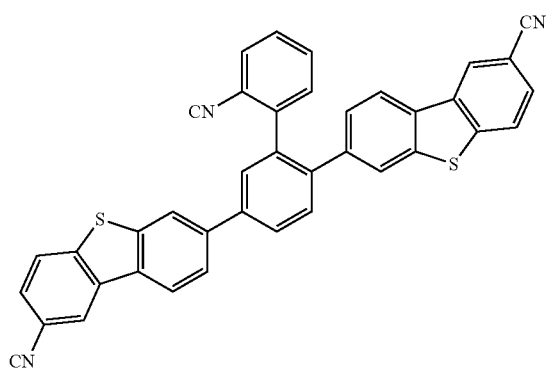 | 1332 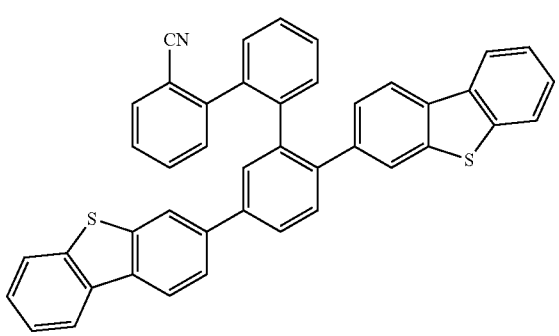 |
| 1329 | 1333 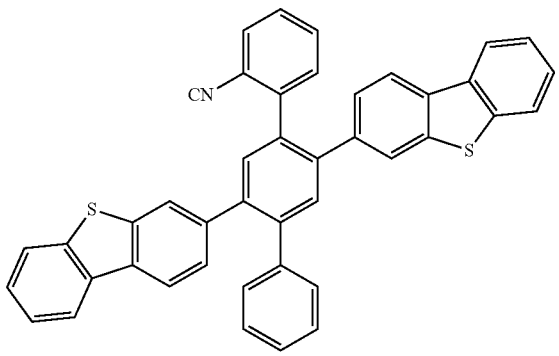 |

1334
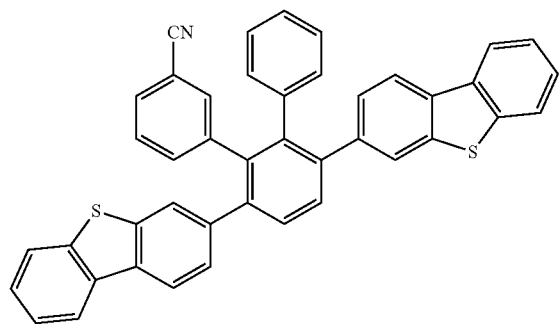
1335
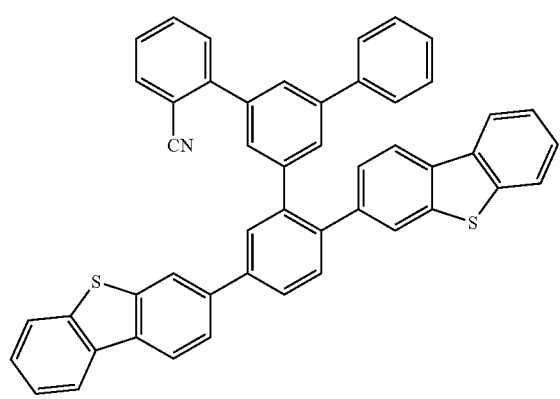
1336
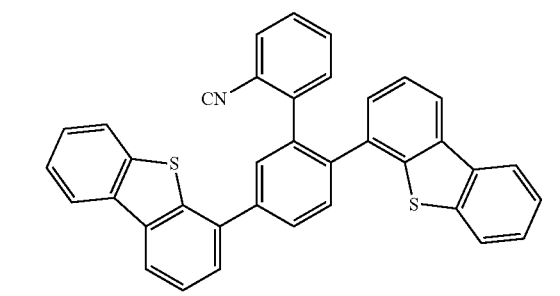
1337
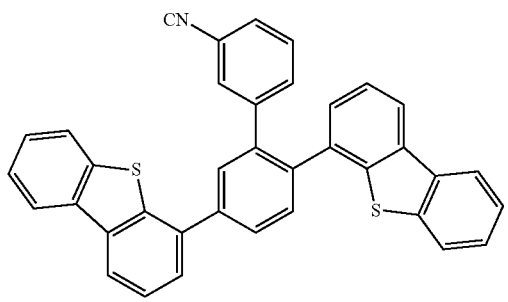
1338
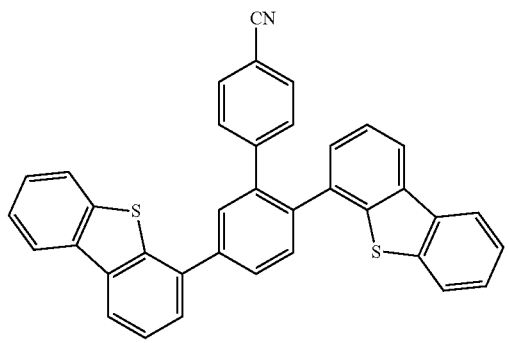
1339
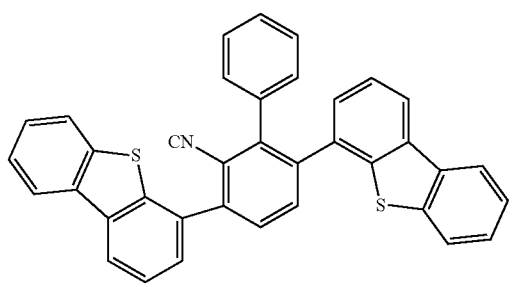
1340
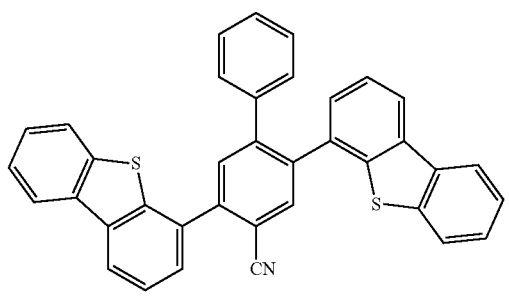
1341
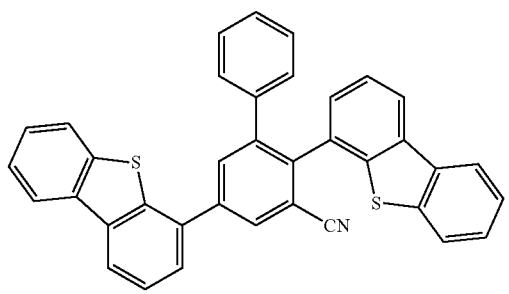
1342
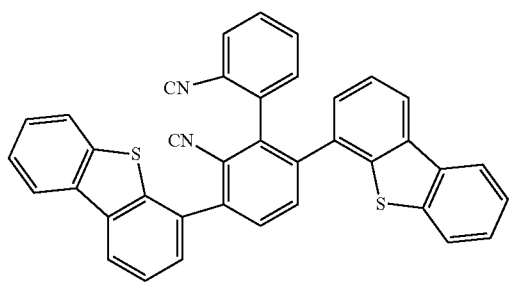

1343
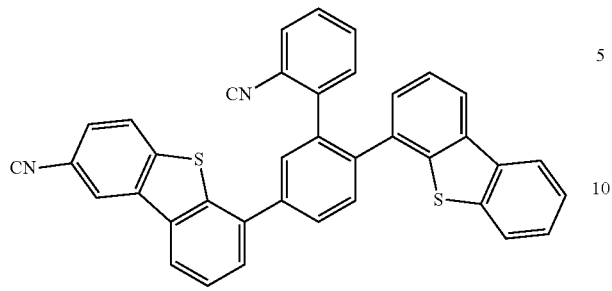
1344
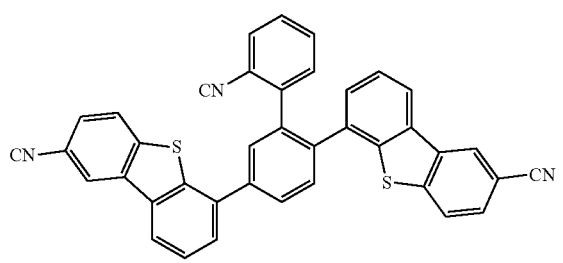
1345
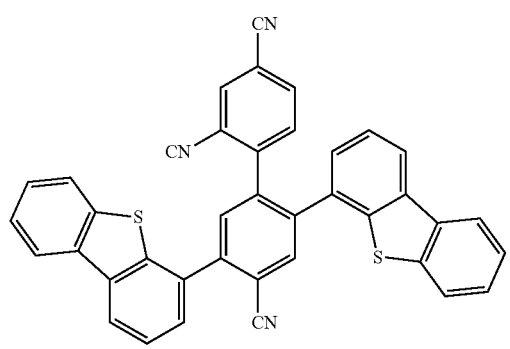
1346
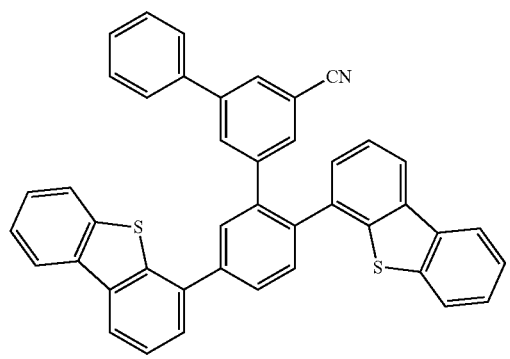
1347
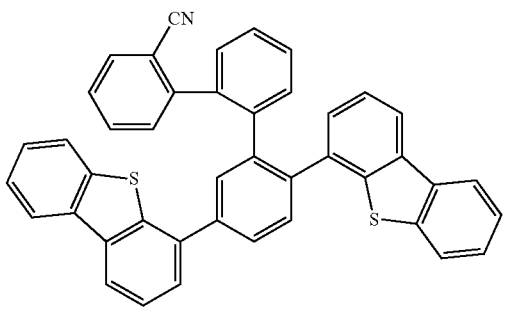
1348
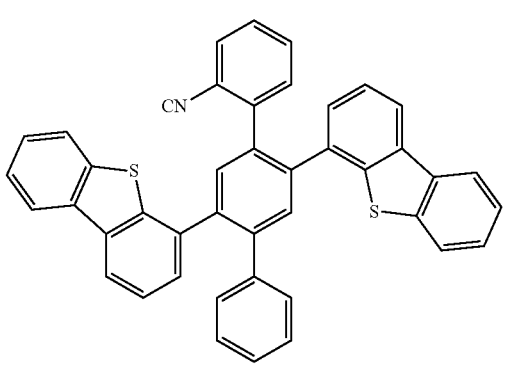
1349
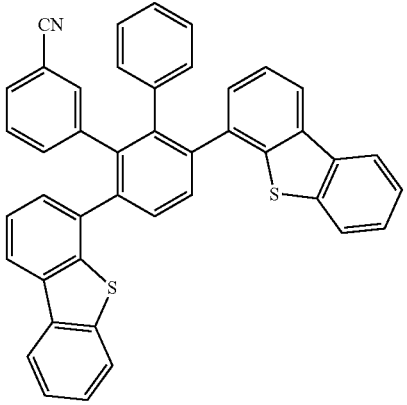
1350
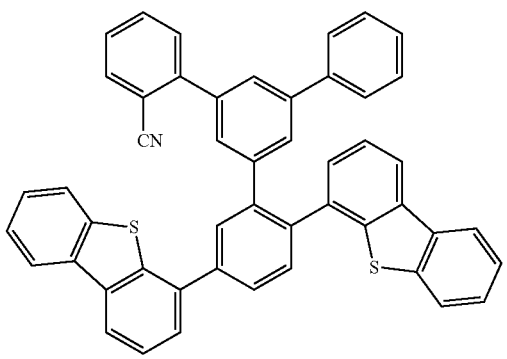

1351 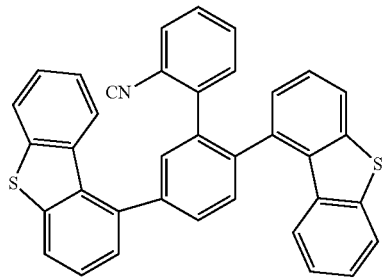
1352 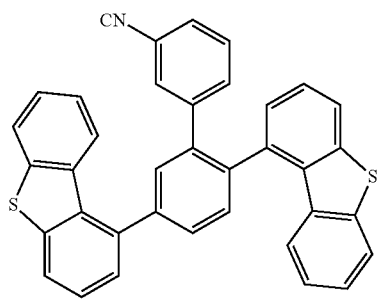
1353 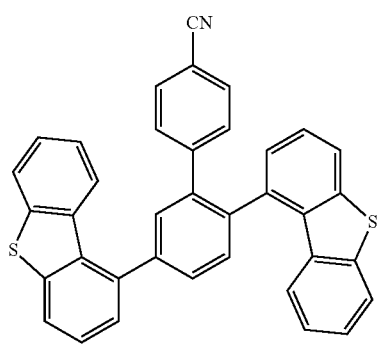
1354 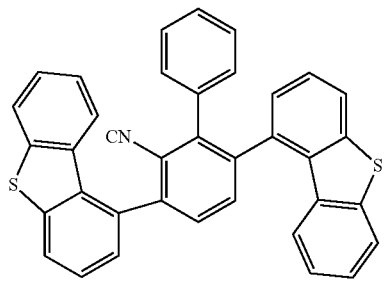
1355 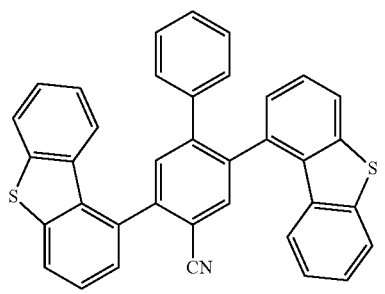
1356 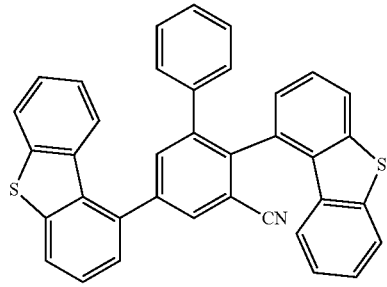
1357 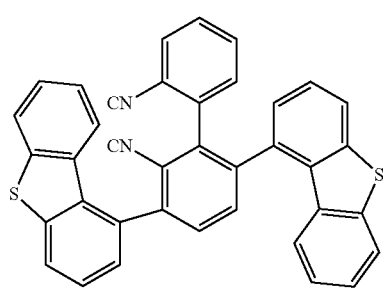
1358 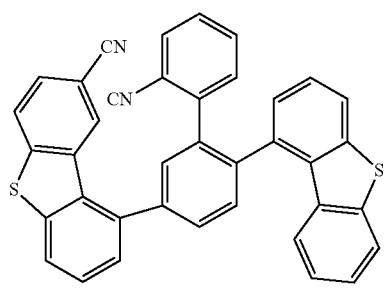
1359 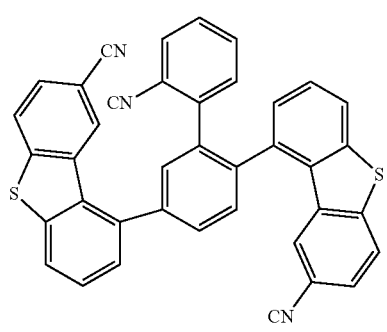
1360 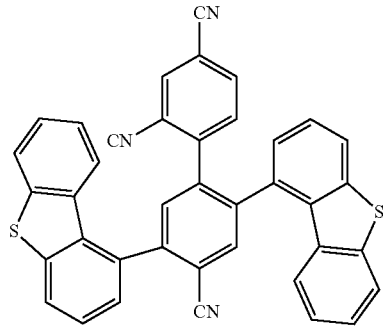

-continued
1361
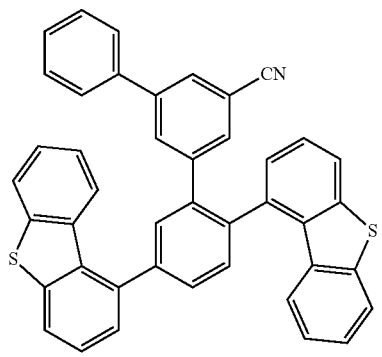
1362
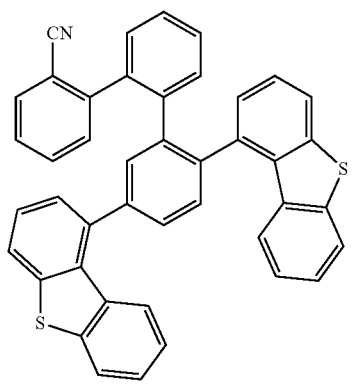
1363
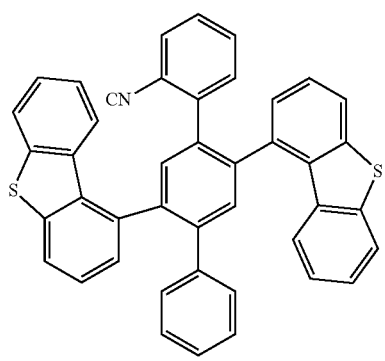
1364
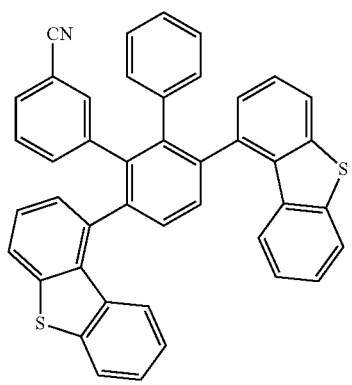
-continued
1365
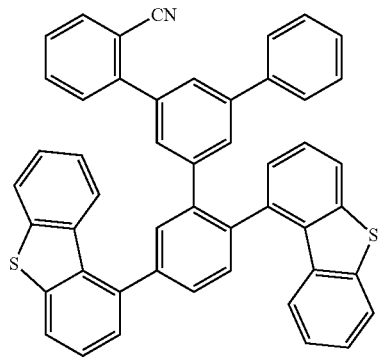
1366
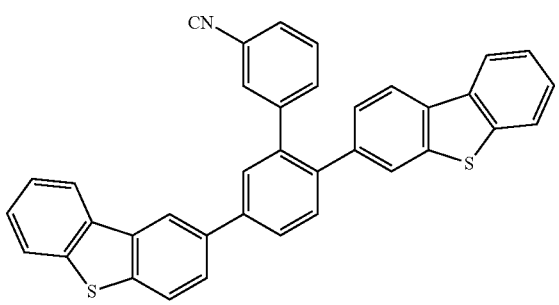
1367
1368
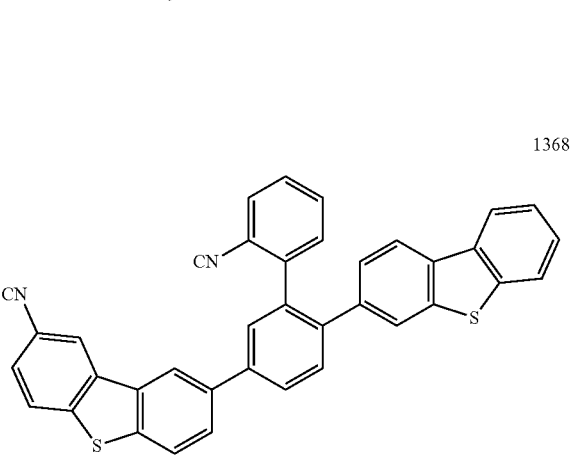

-continued
1369
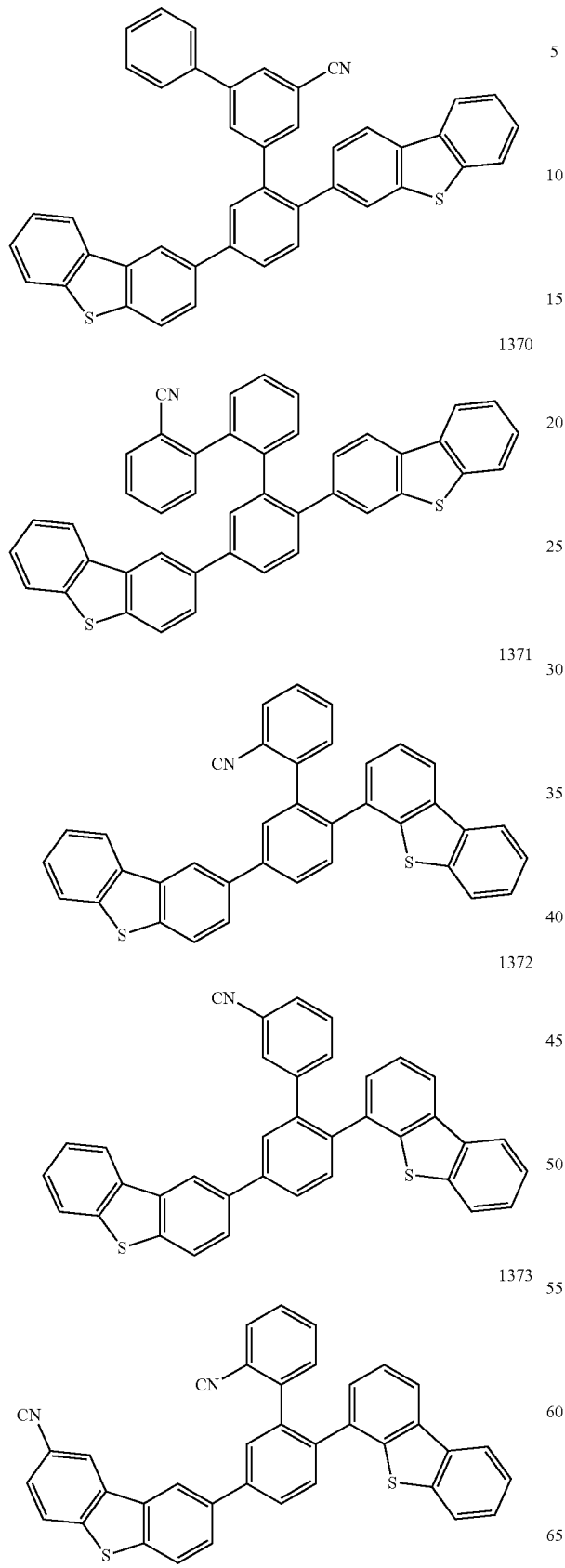
1370
1371
1372
1373
-continued
1374
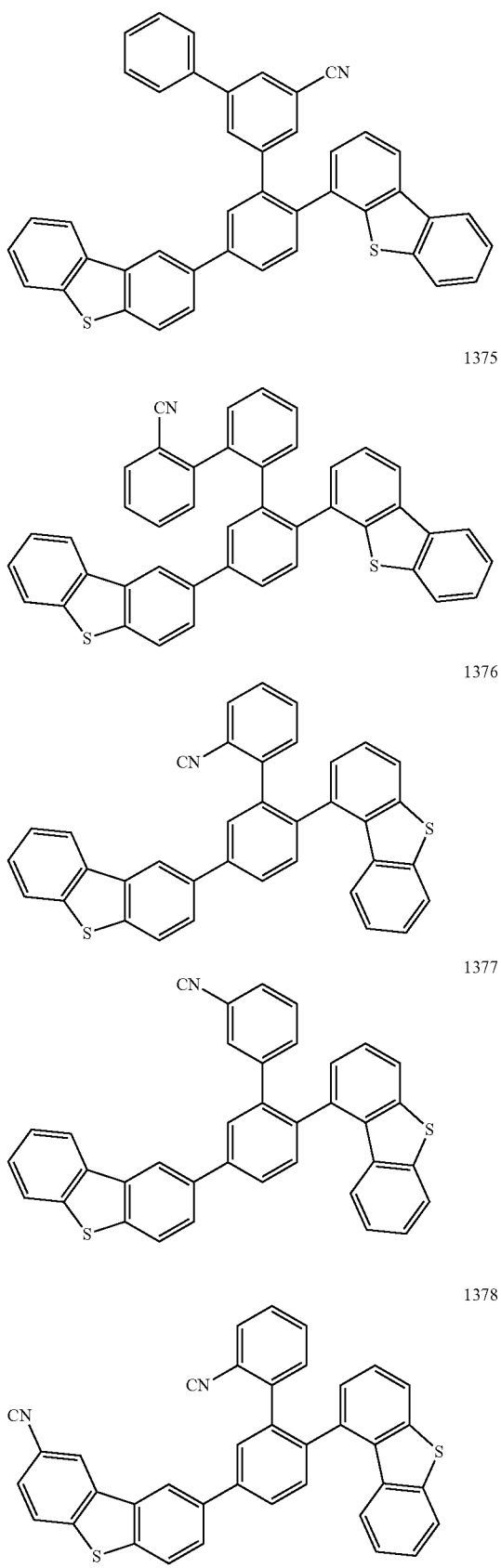
1375
1376
1377
1378

1379
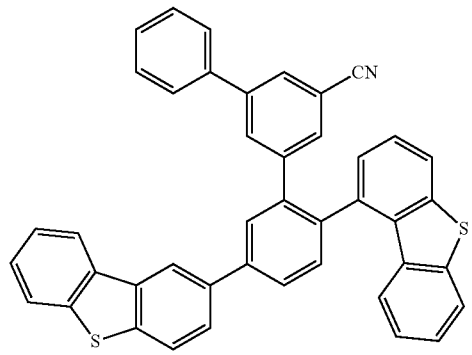
1380
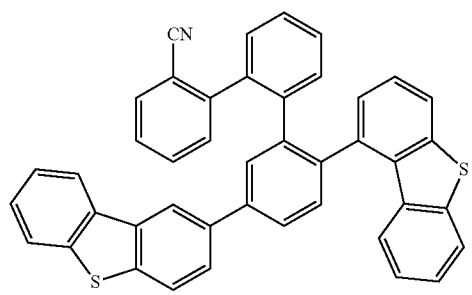
1381
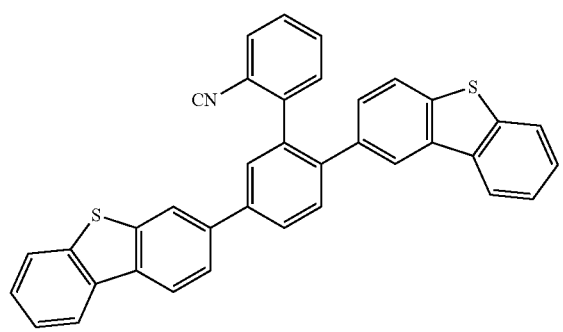
1382
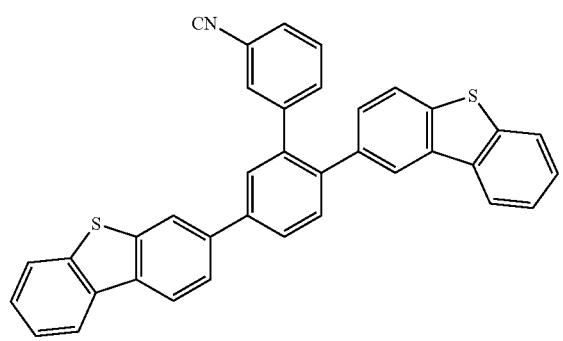
1383
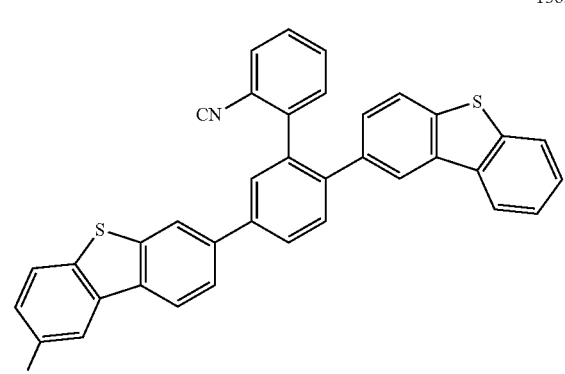
1384
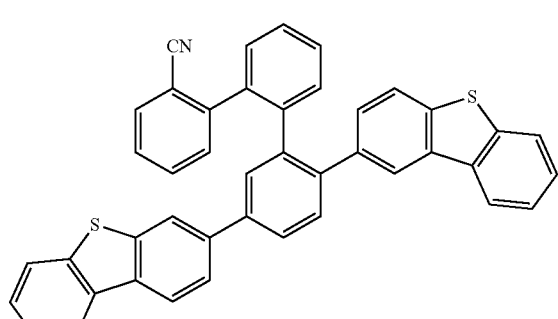
1385
1386
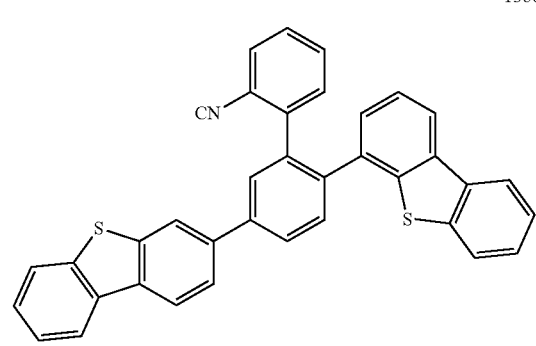

359
-continued
1387
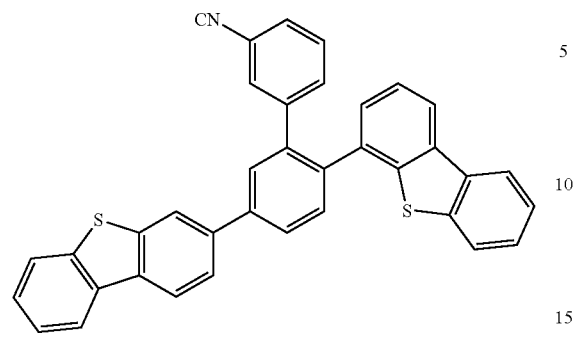
1388
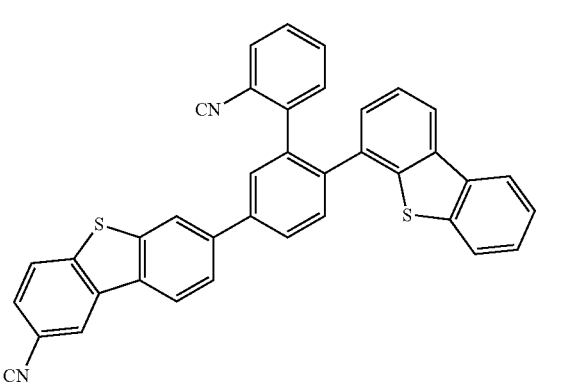
1389
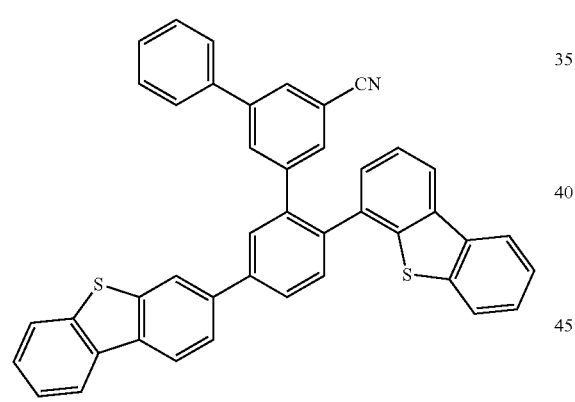
1390
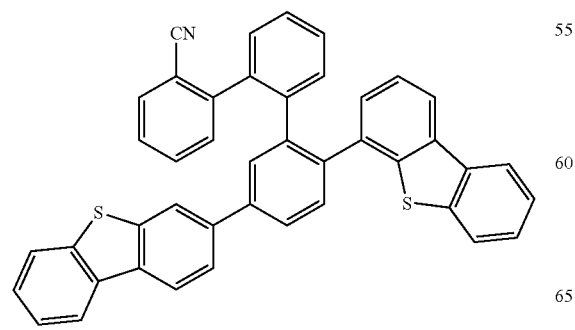
360
-continued
1391
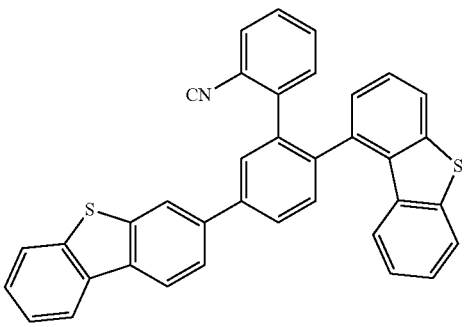
1392
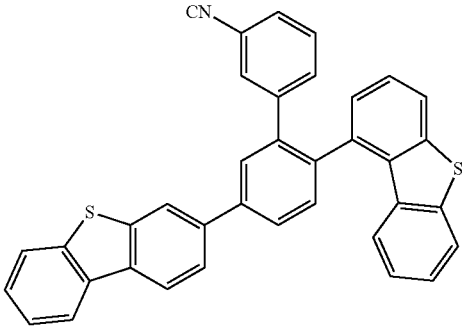
1393
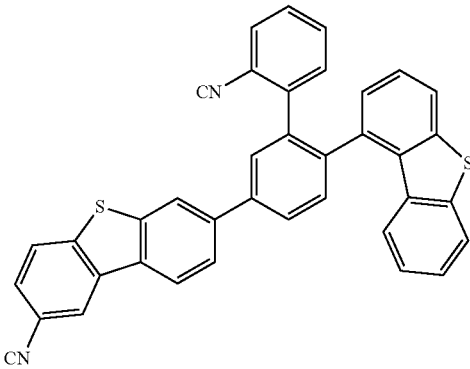
1394
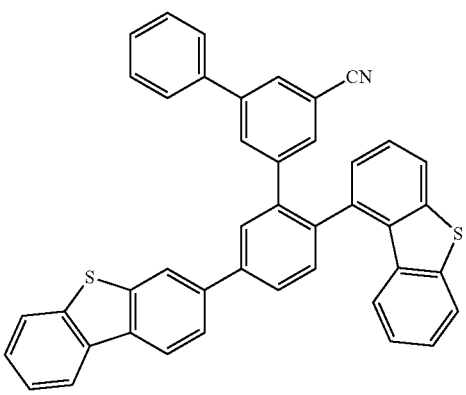

-continued
1395
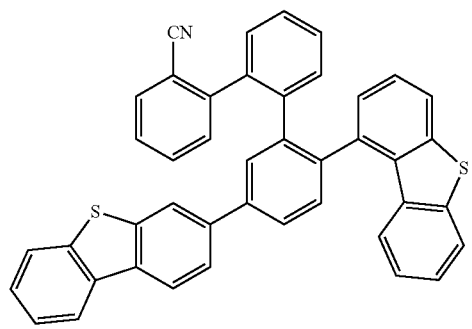
1396
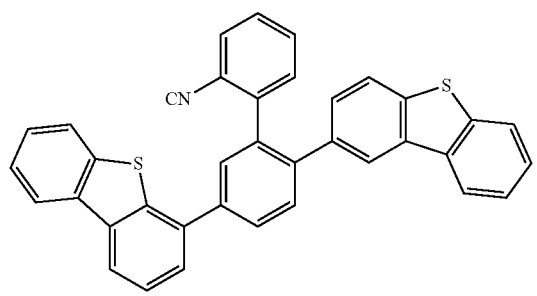
1397
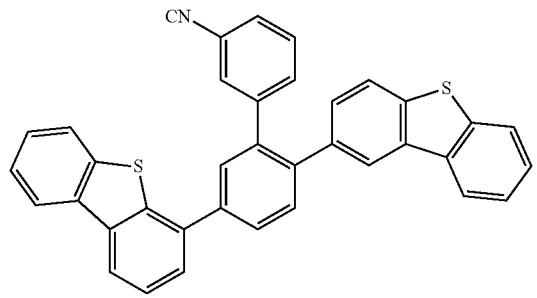
1398
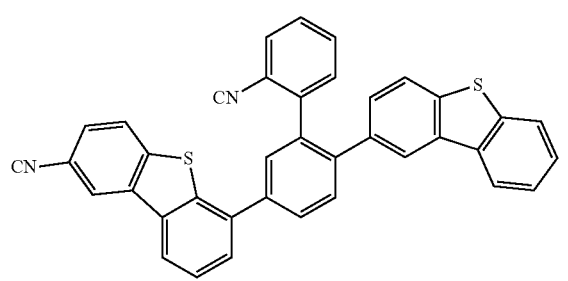
1399
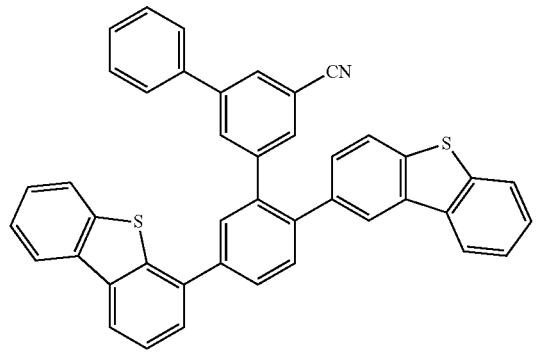
-continued
1400
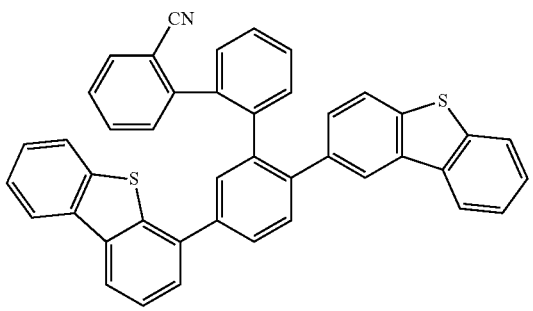
1401
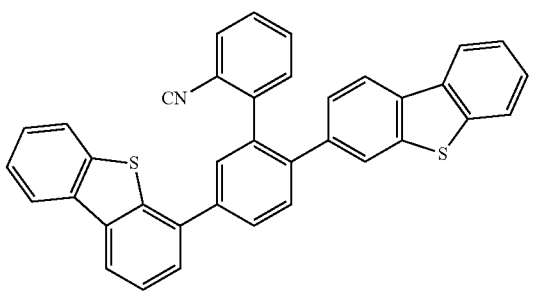
1402
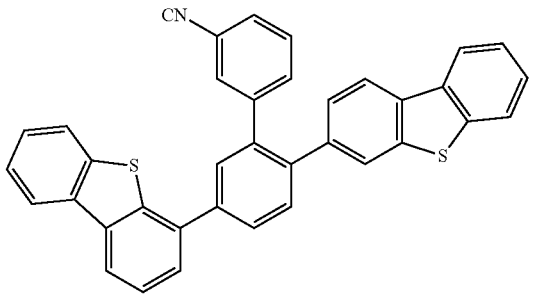
1403
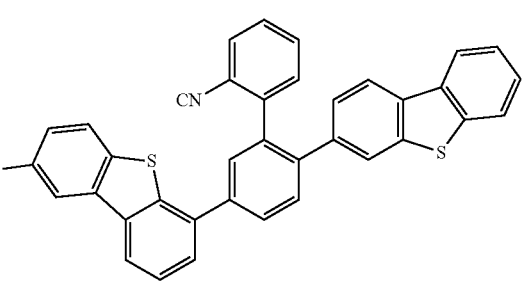
1404
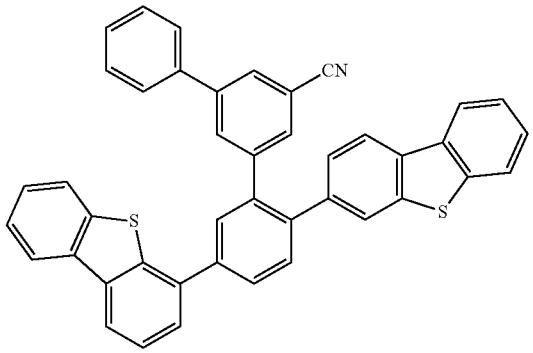

1405
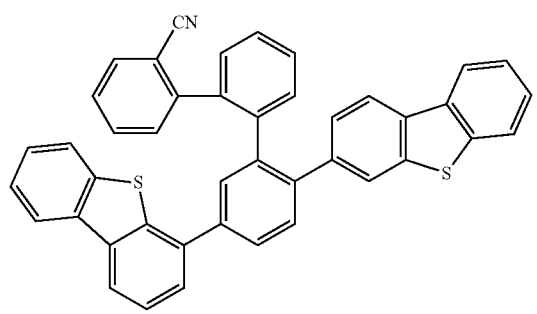
1406
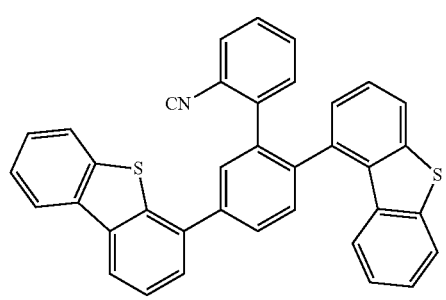
1407
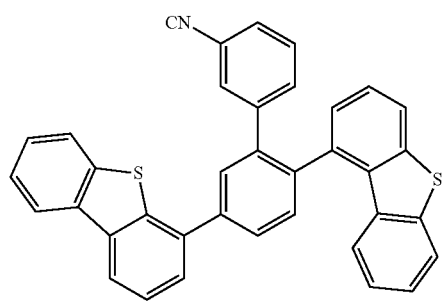
1408
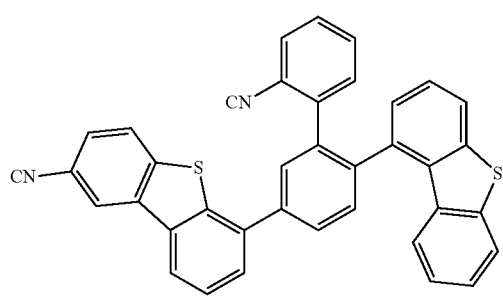
1409
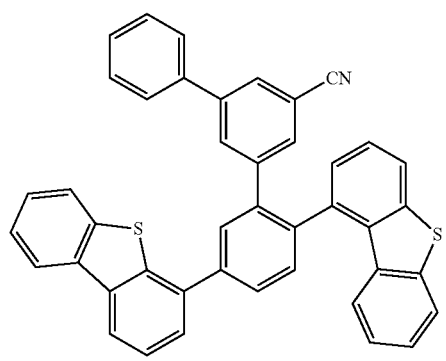
1410
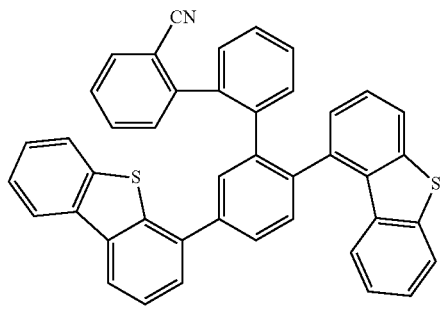
1411
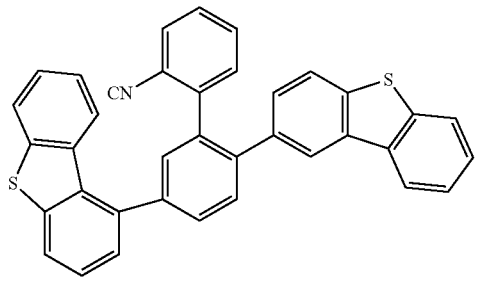
1412
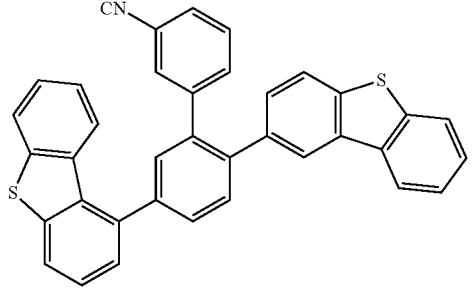
1413
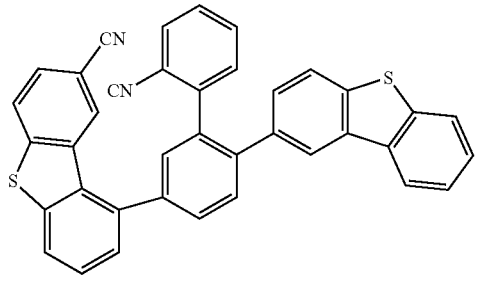
1415
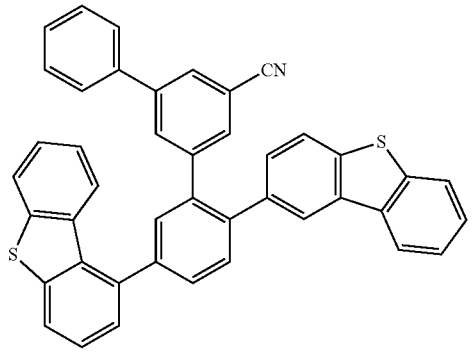

| 1415 | 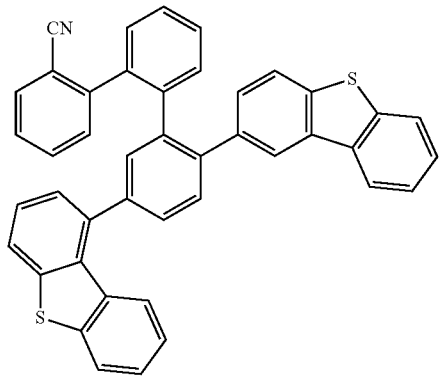 | 1420 | 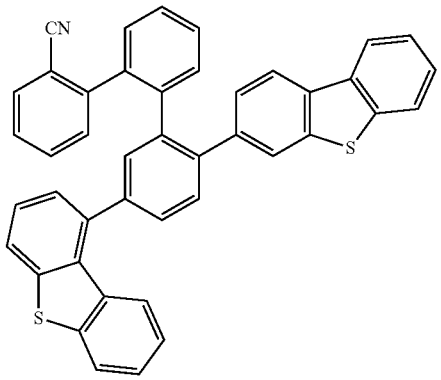 |
| 1416 | 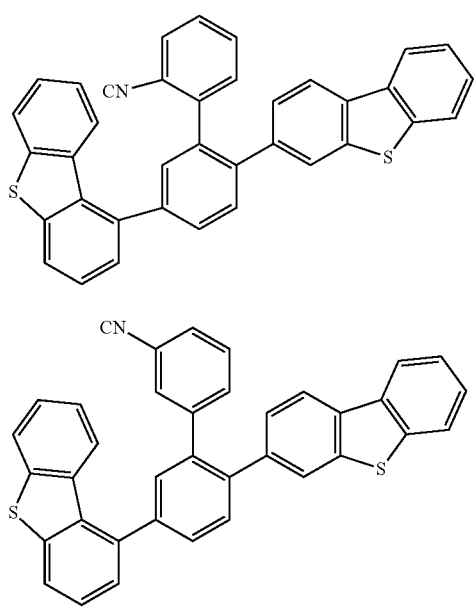 | 1421 | 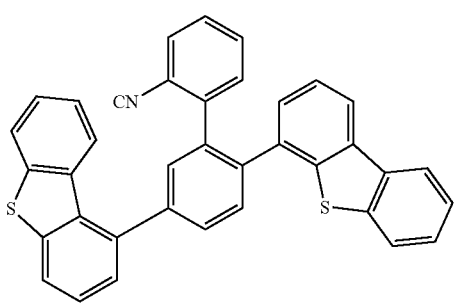 |
| 1417 | | 1422 | 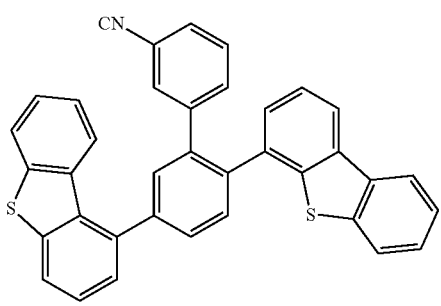 |
| 1418 | 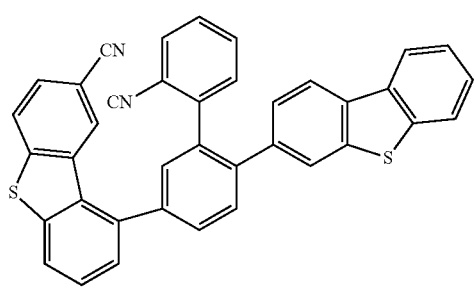 | 1423 | 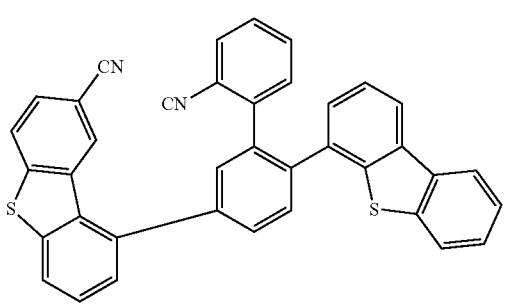 |
| 1419 | 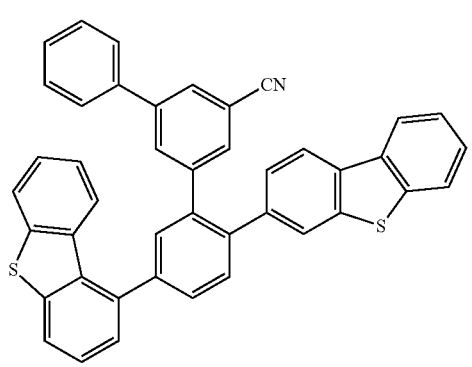 | | |

1424
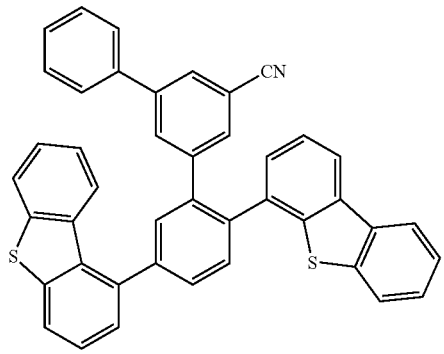
1425
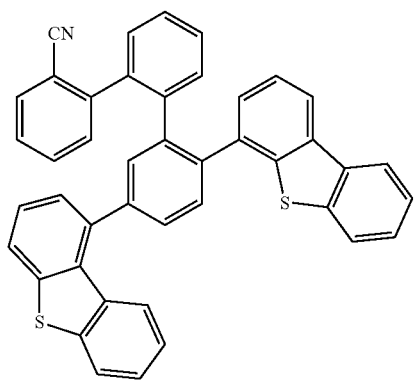
1426
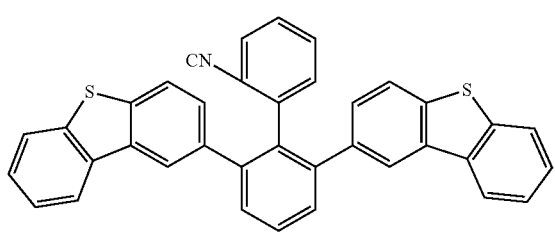
1427
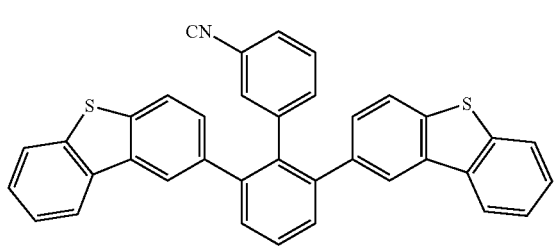
1428
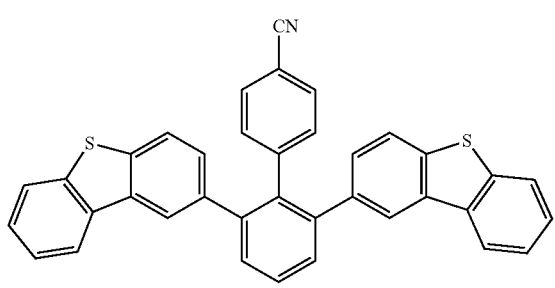
1429
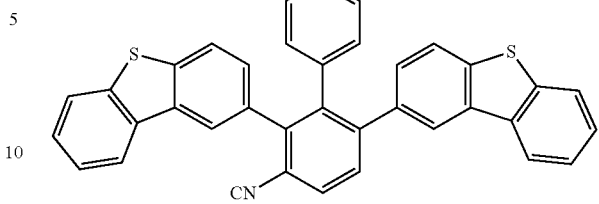
1430
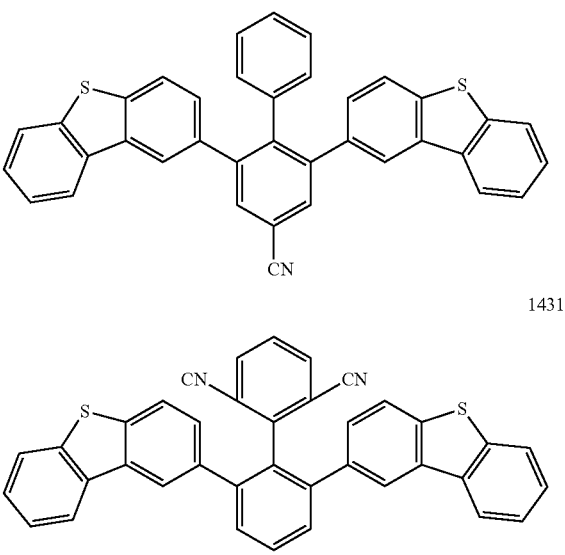
1431
1432
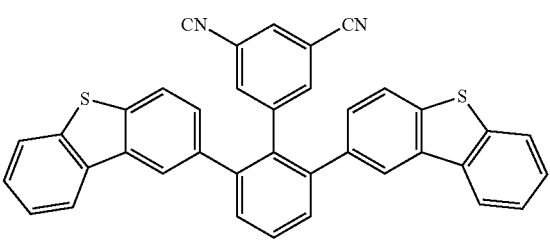
1433
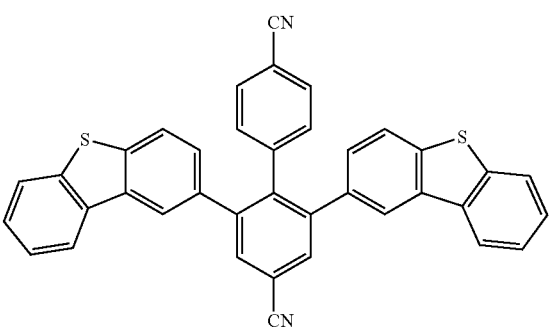

-continued
1434
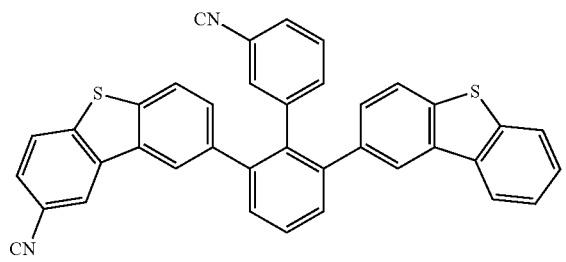
1435
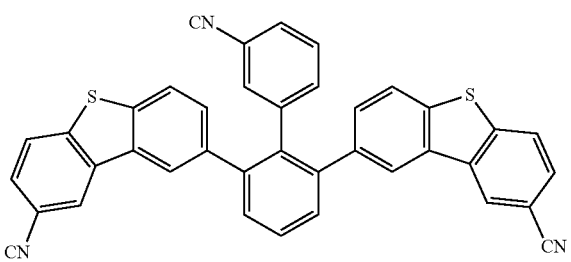
1436
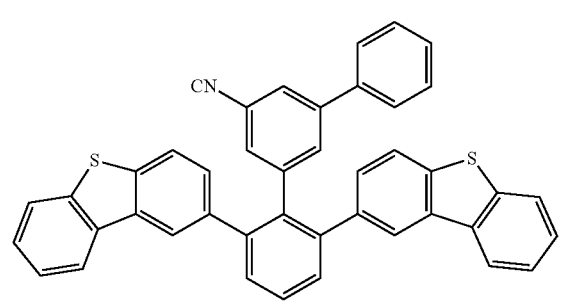
1437
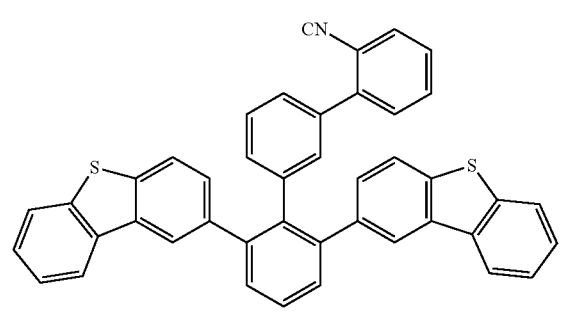
1438
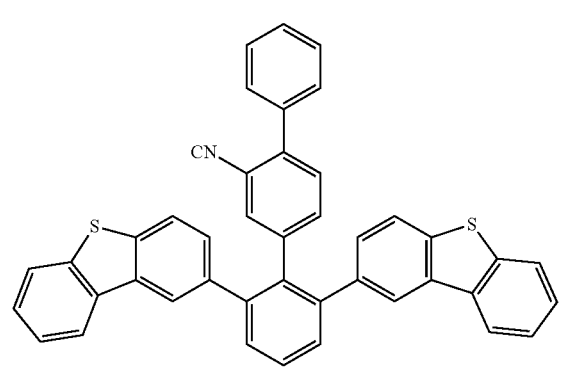
-continued
1439
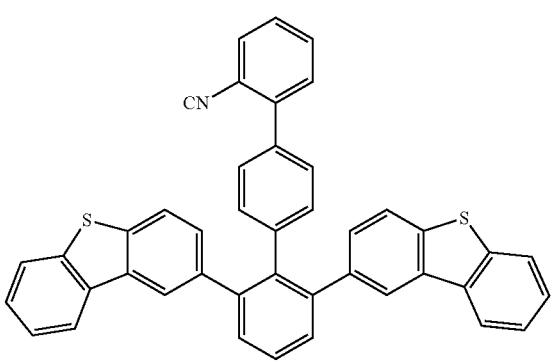
1440
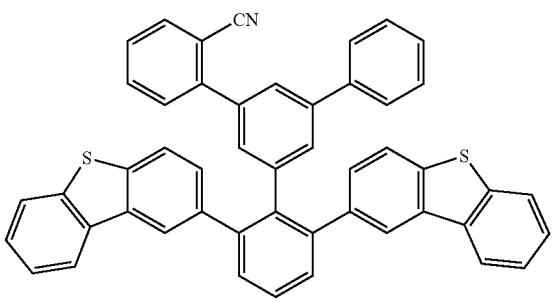
1441
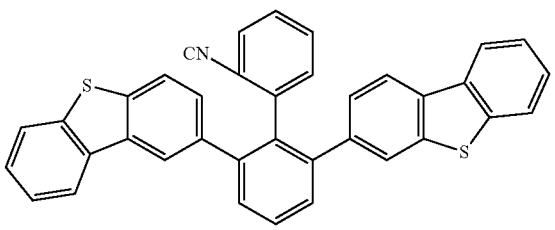
1442
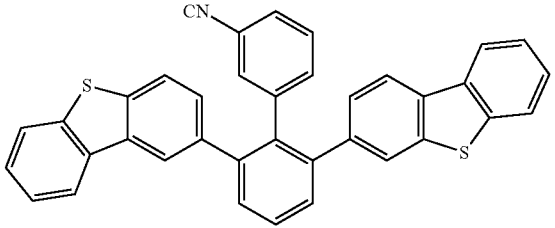
1443
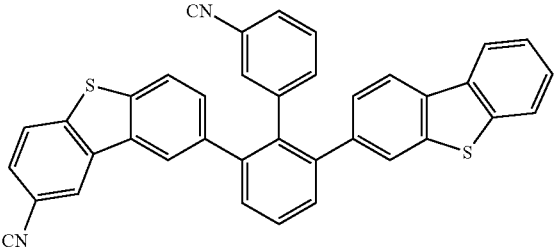

371
-continued
1444
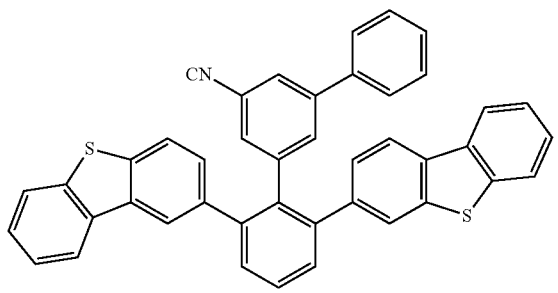
1445
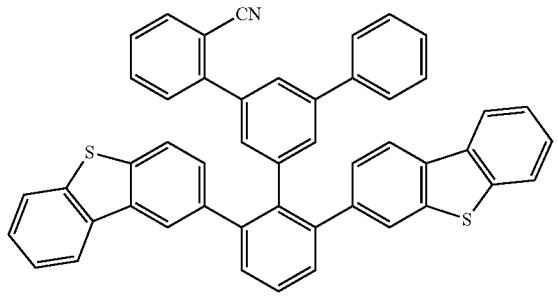
1446
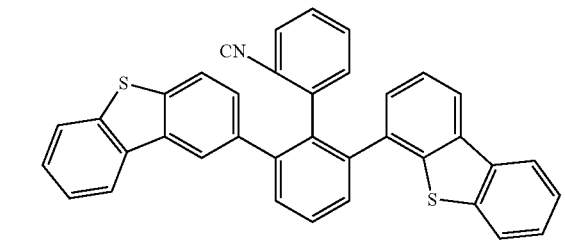
1447
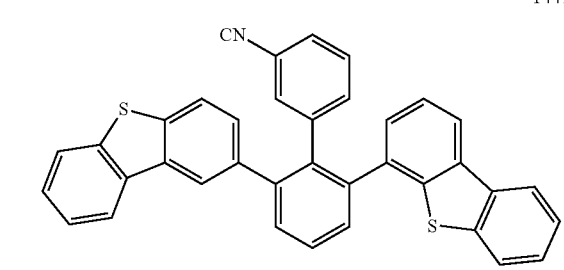
1448
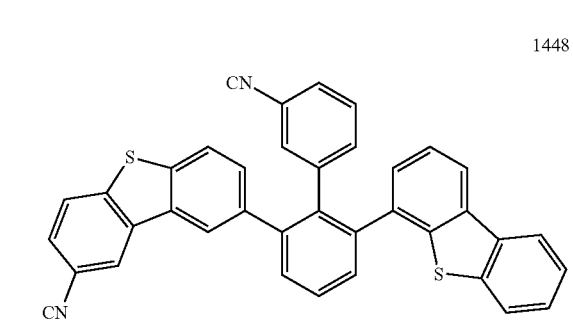
372
-continued
1449
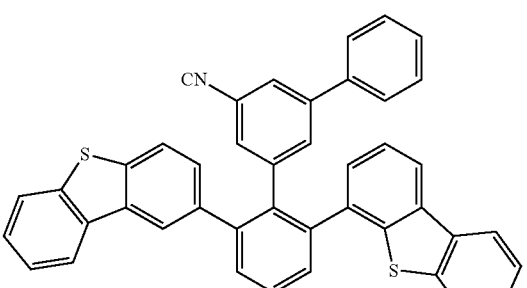
1450
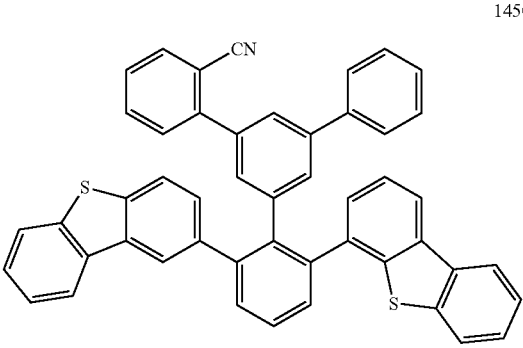
1451
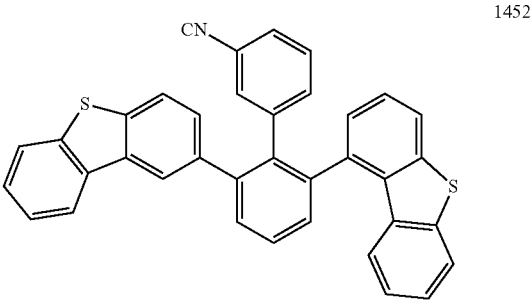
1452
1453
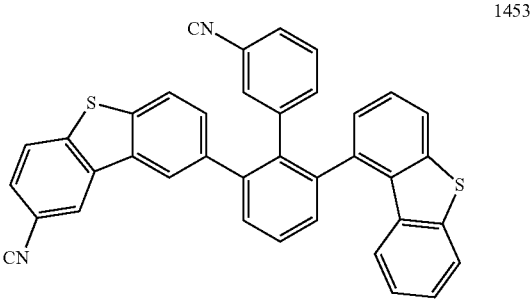

373
-continued
1454
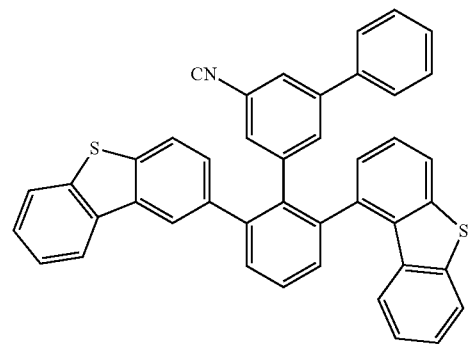
1455
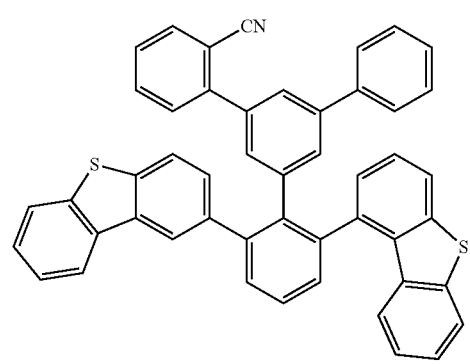
1456
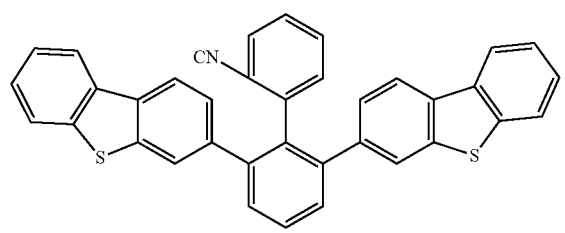
1457
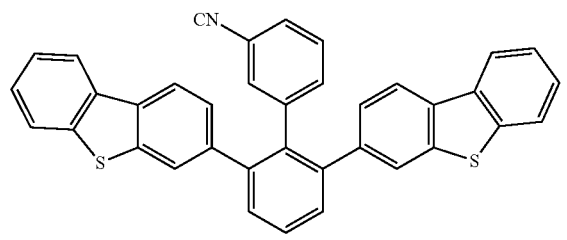
1458
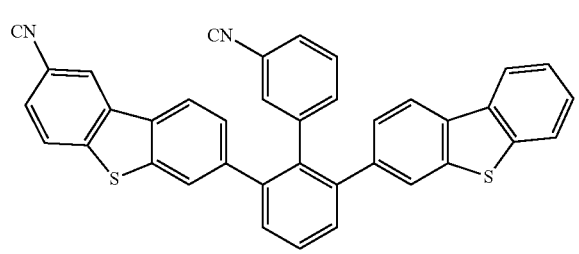
374
-continued
1459
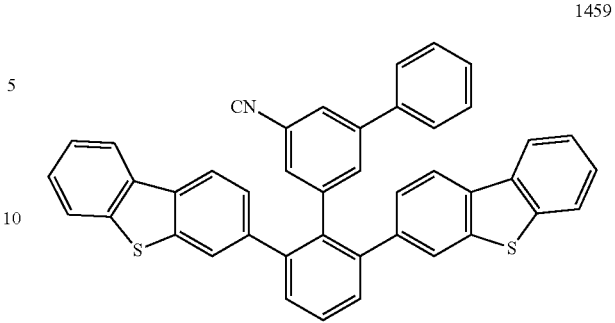
1460
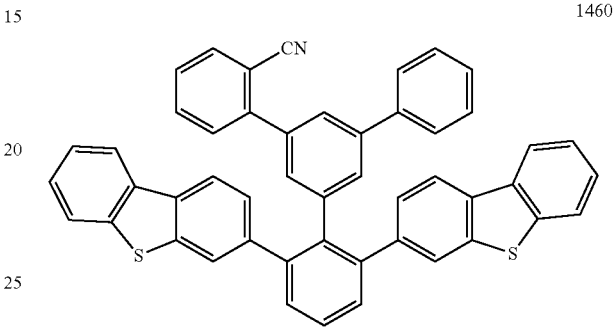
1461
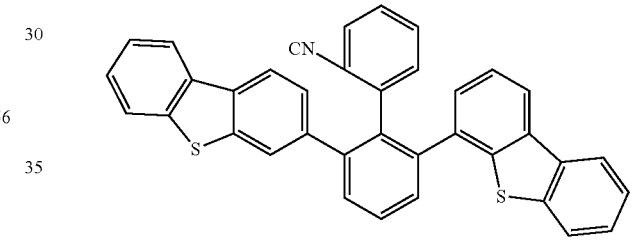
1462
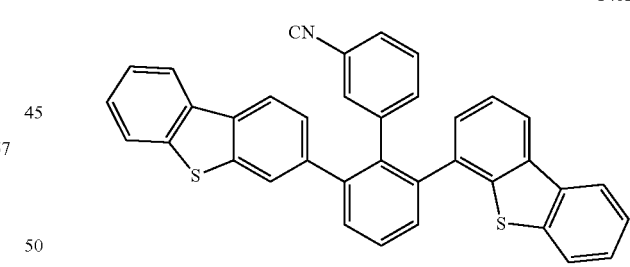
1463
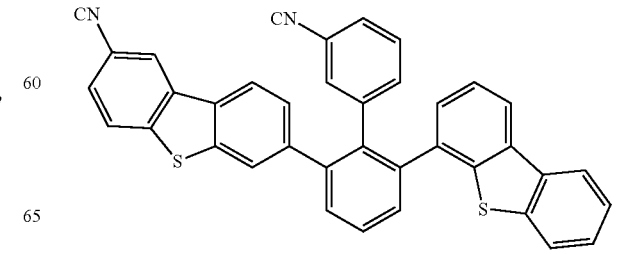

| 375 -continued | 376 -continued |
|---|---|
| 1464 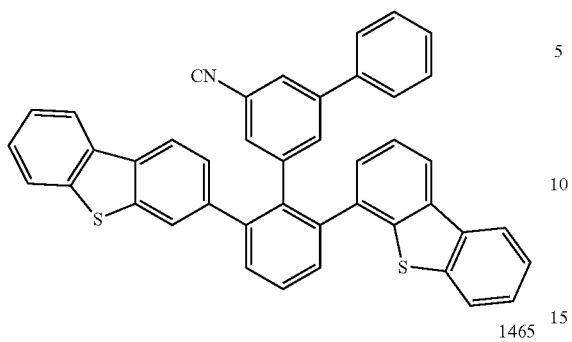 | 1469 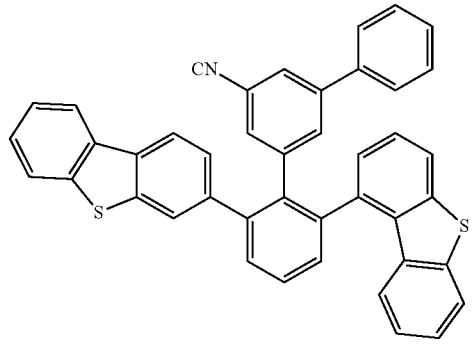 |
| 1465 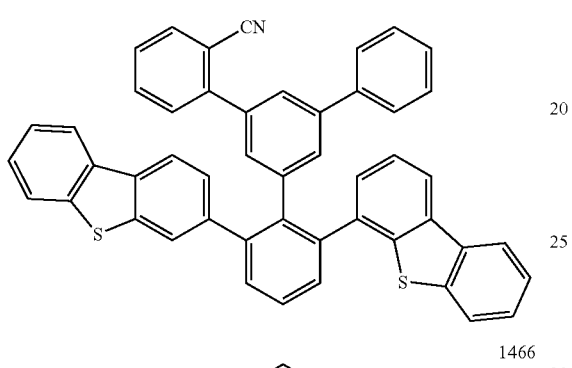 | 1470 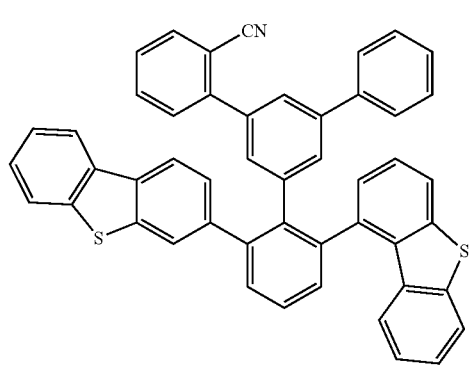 |
| 1466 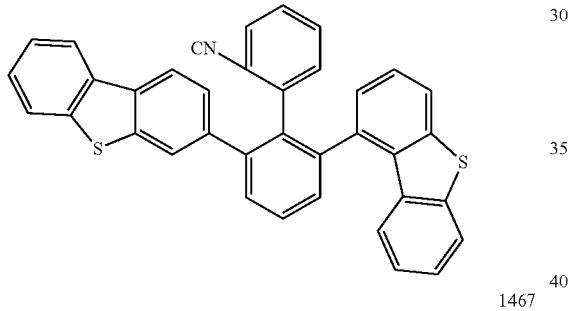 | 1471 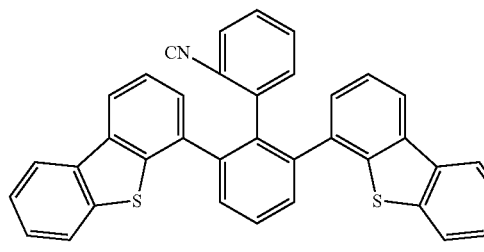 |
| 1467 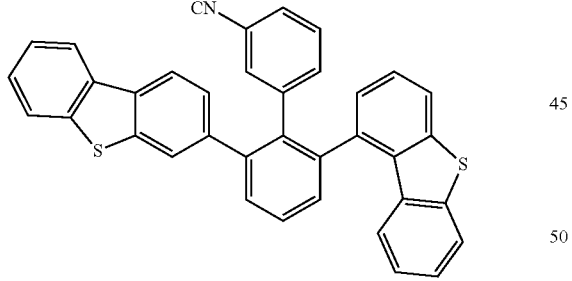 | 1472 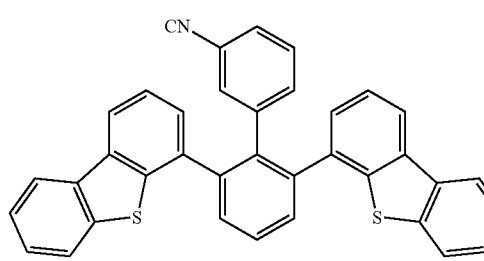 |
| 1468 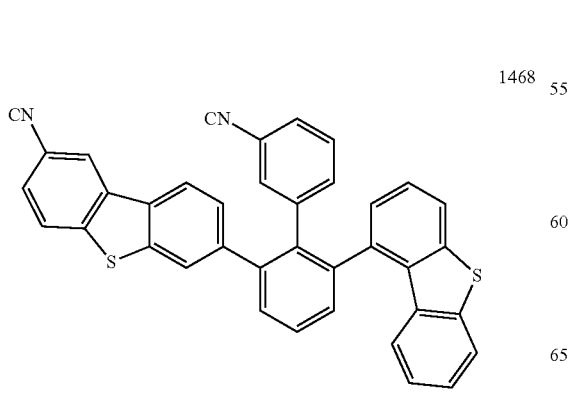 | 1473 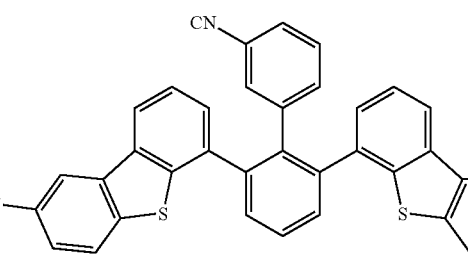 |

| 1474 | 1479 |
|---|---|
| 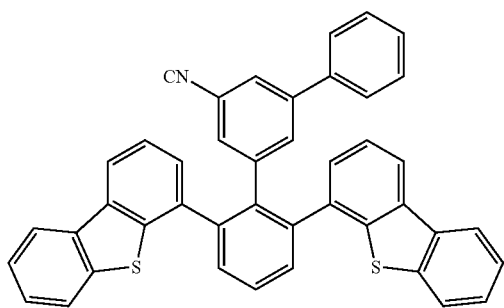 | 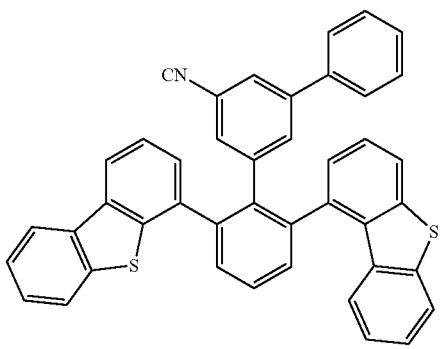 |
| 1475 | 1480 |
| 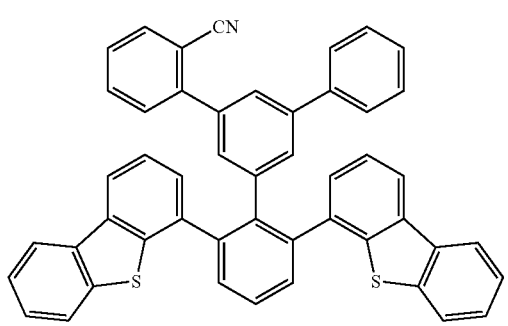 | 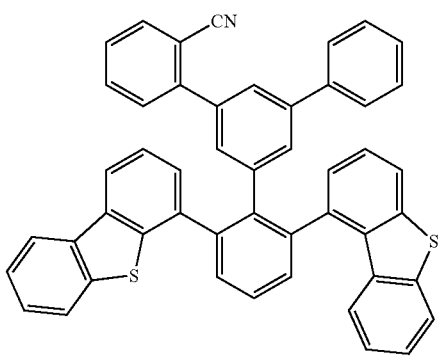 |
| 1476 | 1481 |
| 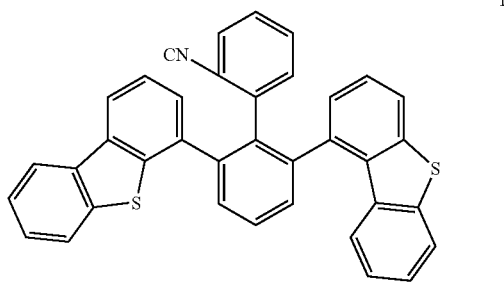 | 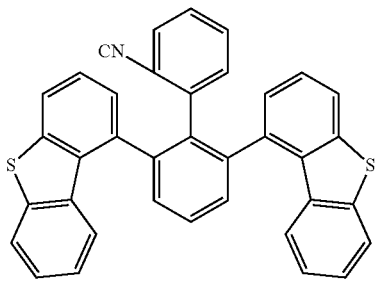 |
| 1477 | 1482 |
| 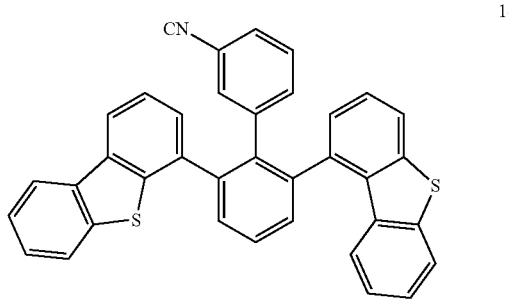 | 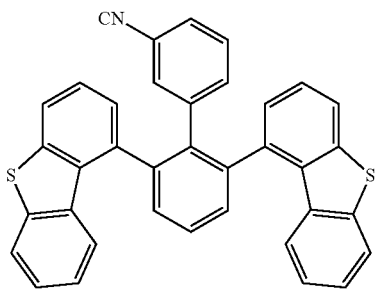 |
| 1478 | 1483 |
| 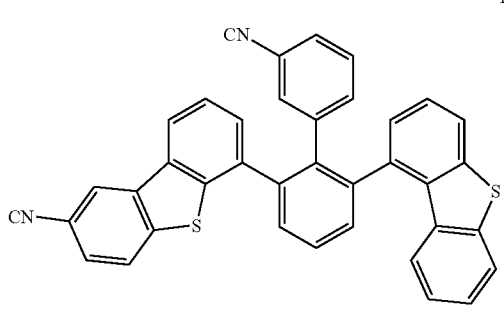 | 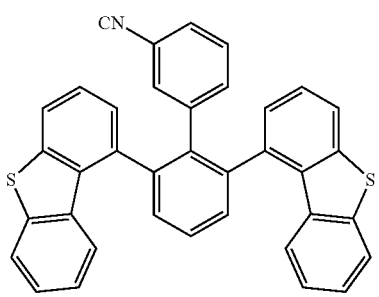 |

379
-continued
1484
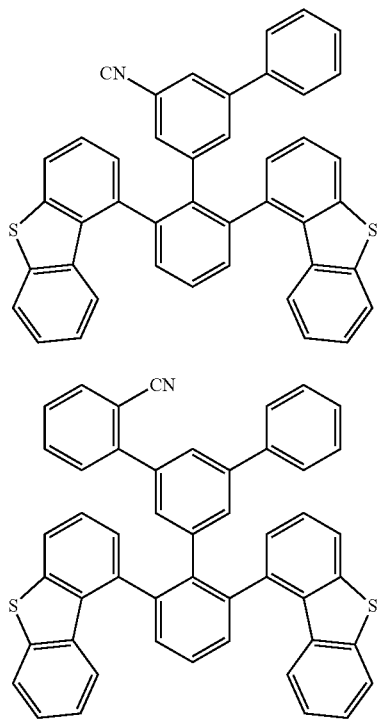
1485
1486
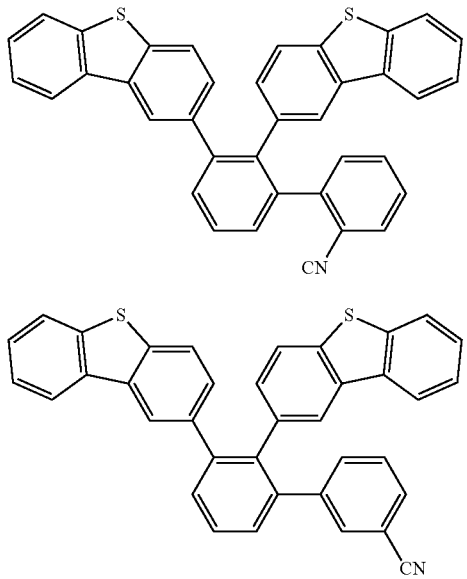
1487
1488
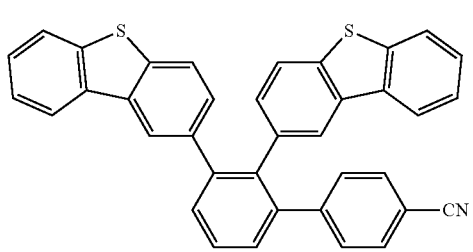
380
-continued
1489
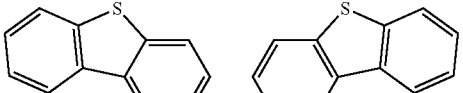
1490
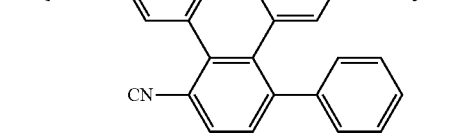
1491
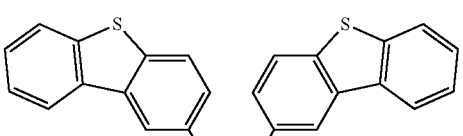
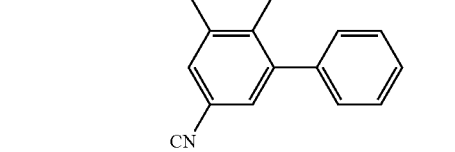
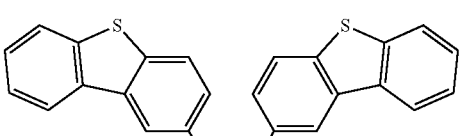
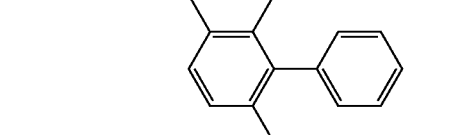
1492
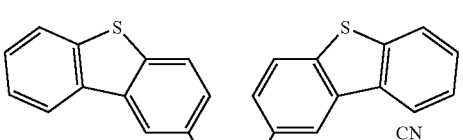
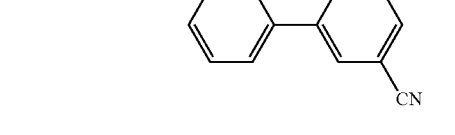
1493
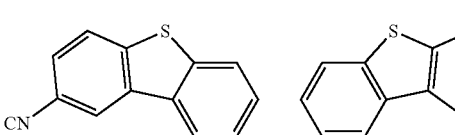
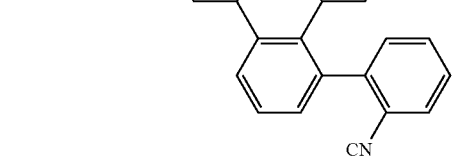

381
-continued
1494
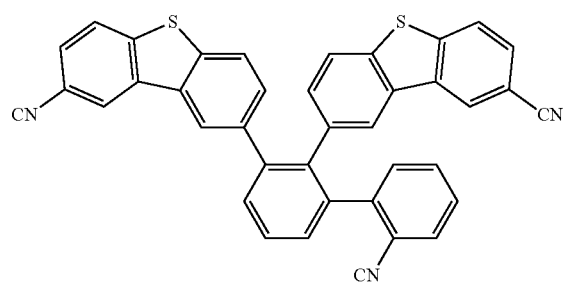
1495
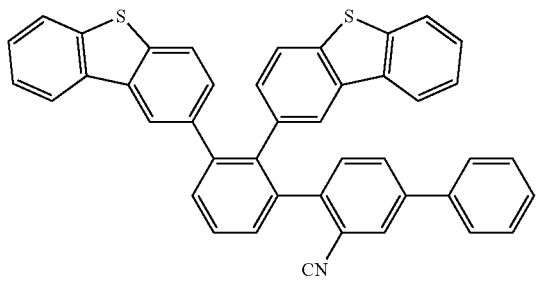
1496
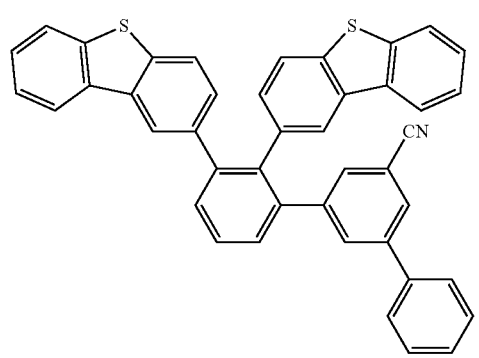
1497
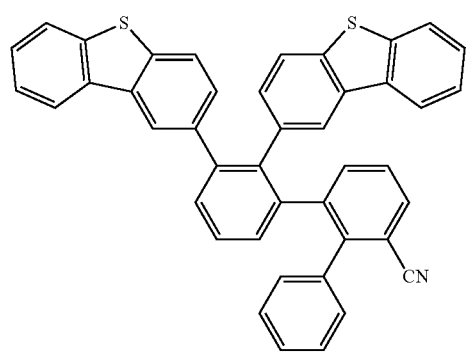
1498
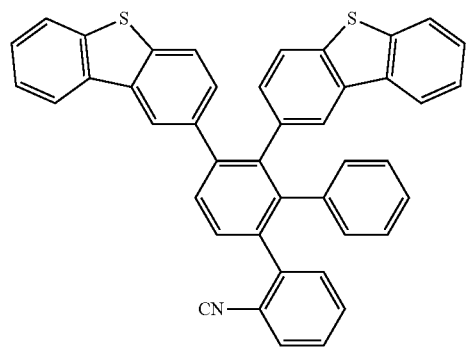
382
-continued
1499
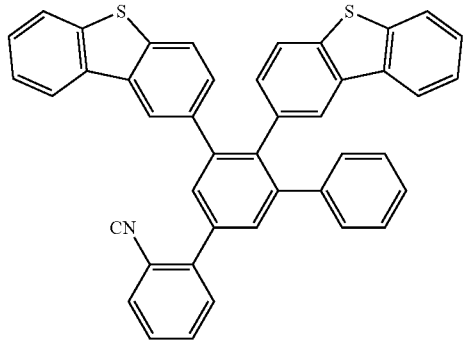
1500
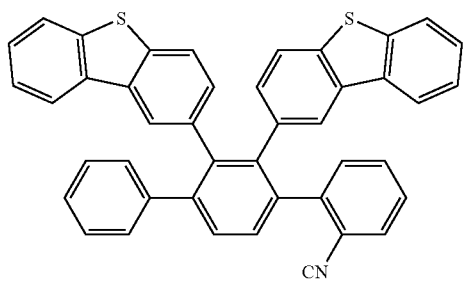
1501
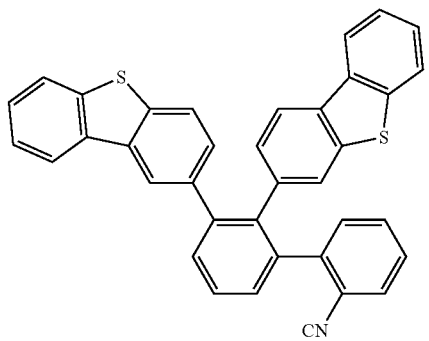
1502
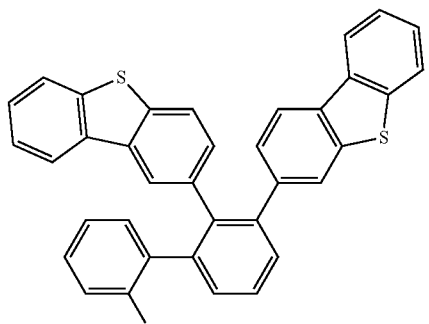
1503
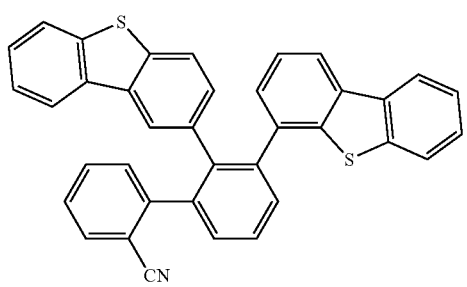

| | |
|---|---|
| 1504 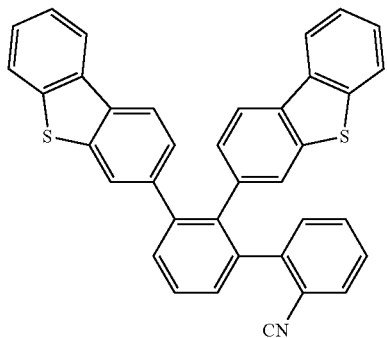 | 1508 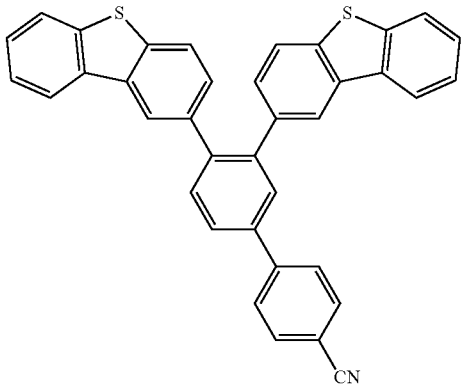 |
| 1505  | 1509 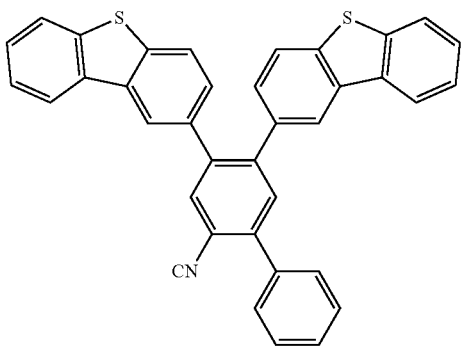 |
| 1506 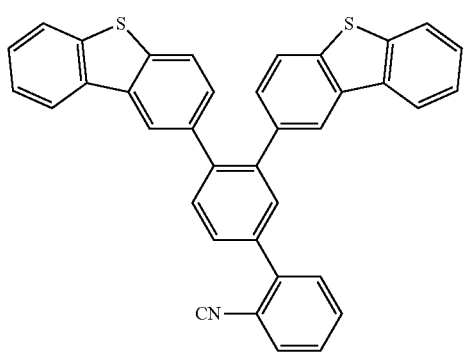 | 1510 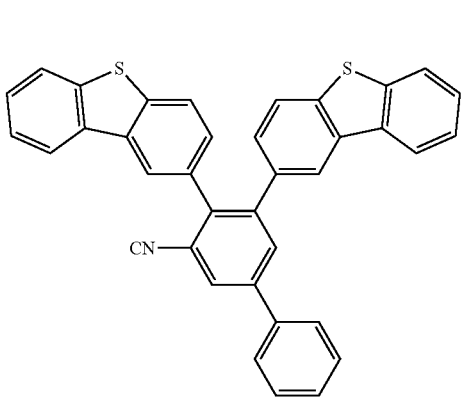 |
| 1507 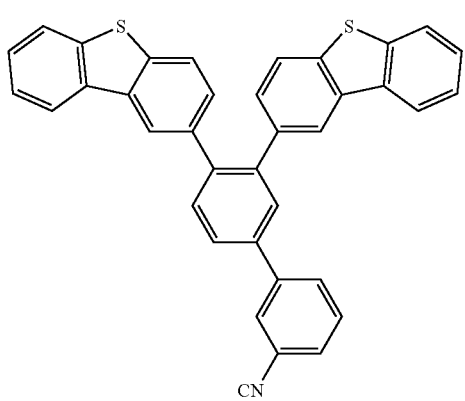 | 1511 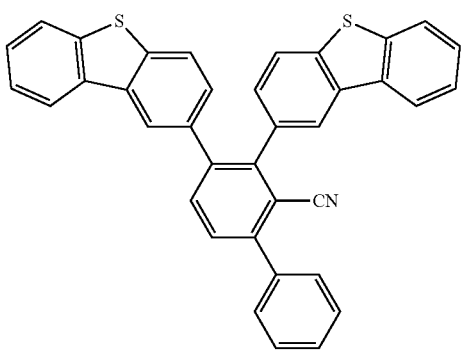 |

385
-continued
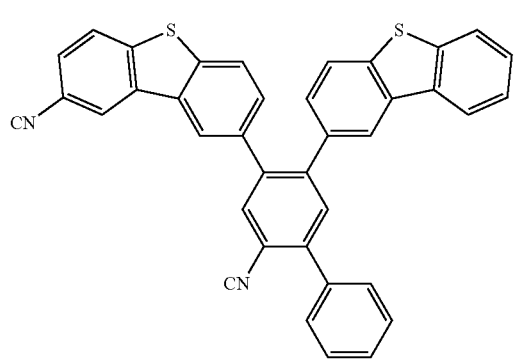
1512
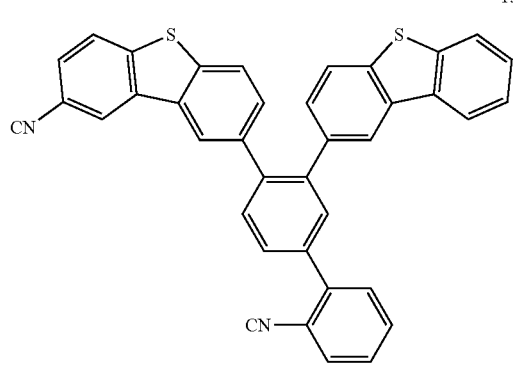
1513
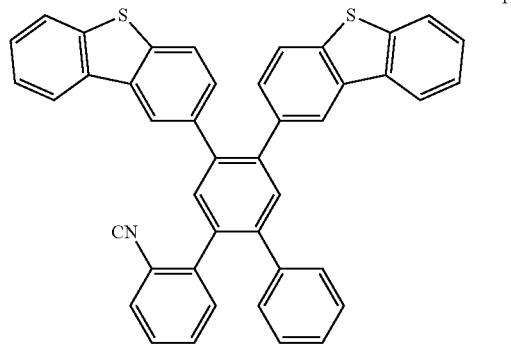
1514
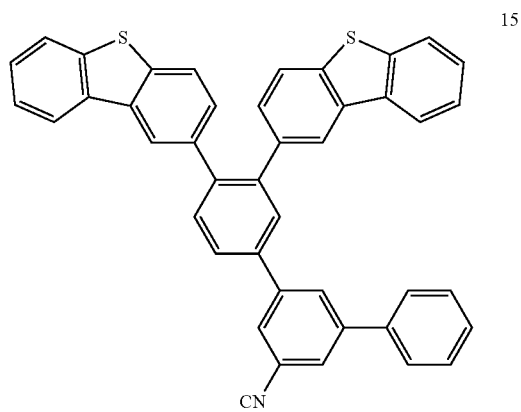
1515
386
-continued
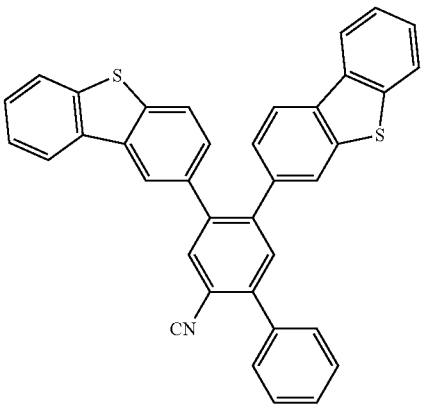
1516
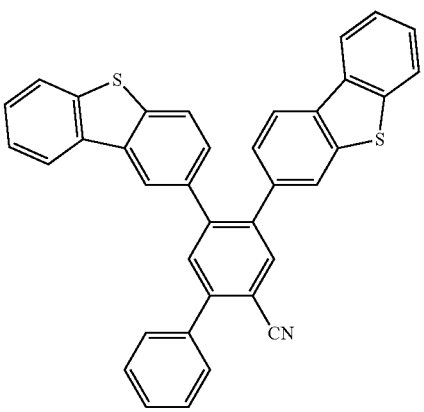
1517
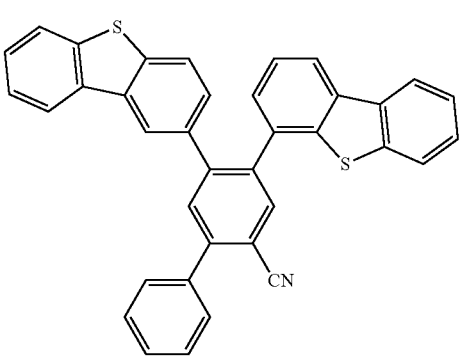
1518
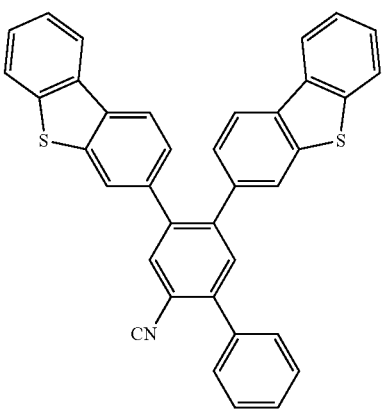
1519

387
-continued
1520
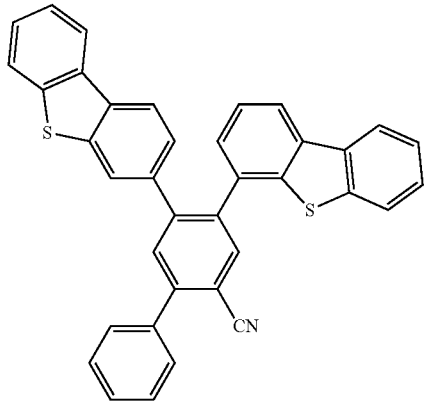
1521
1522
1523
388
-continued
1524
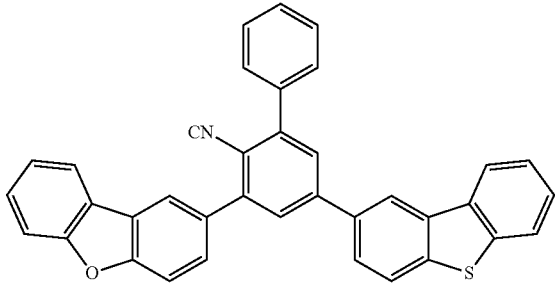
1525
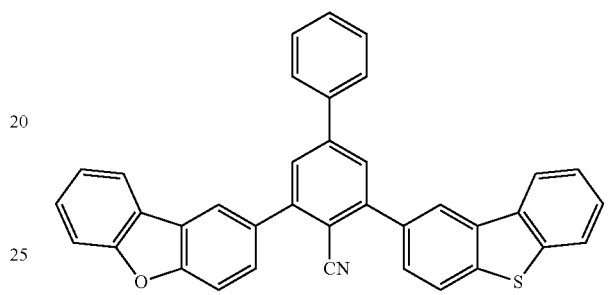
1526
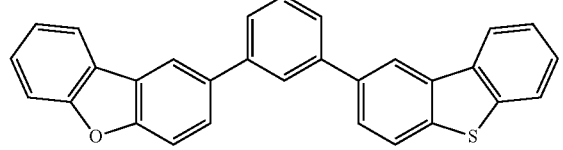
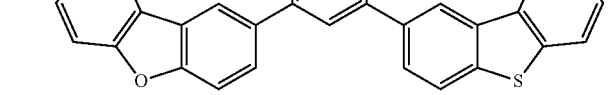
1527
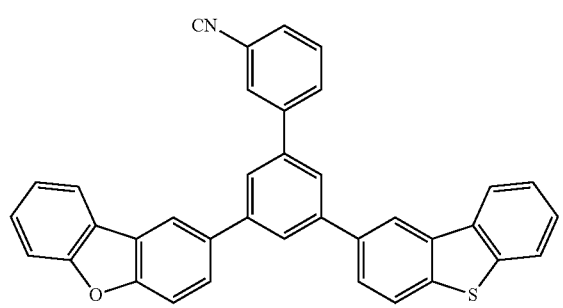
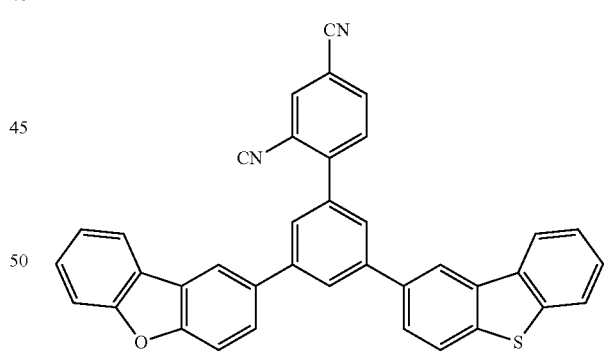
1528
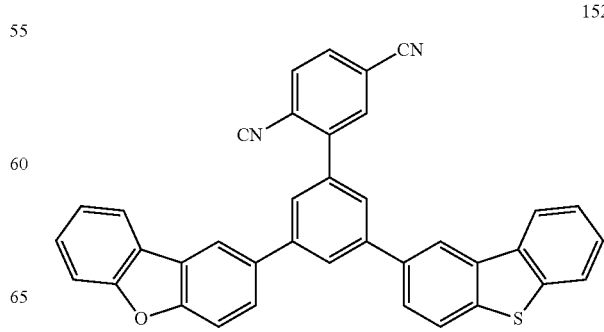

1529
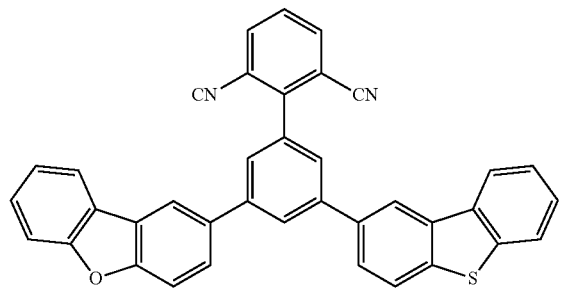
1530
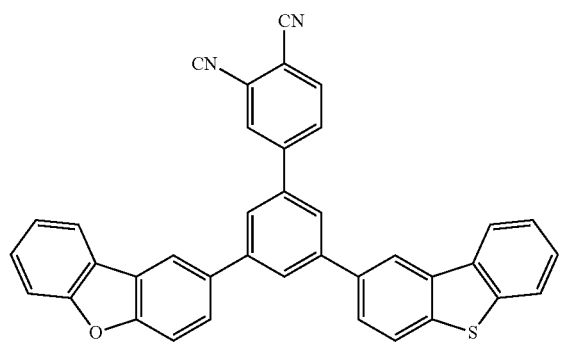
1531
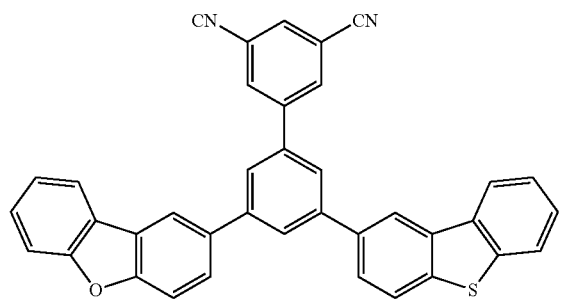
1532
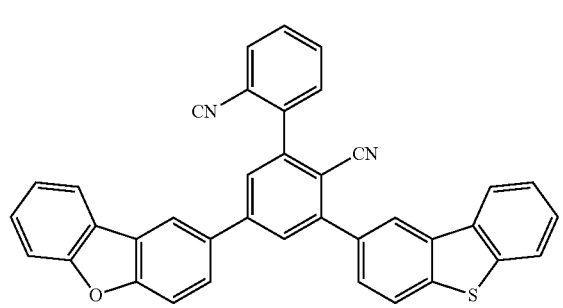
1533
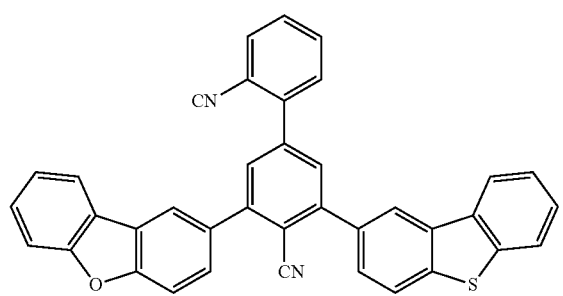
1534
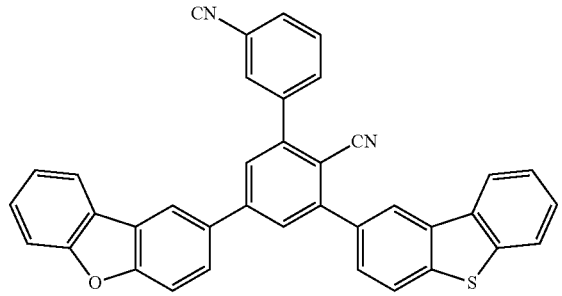
1535
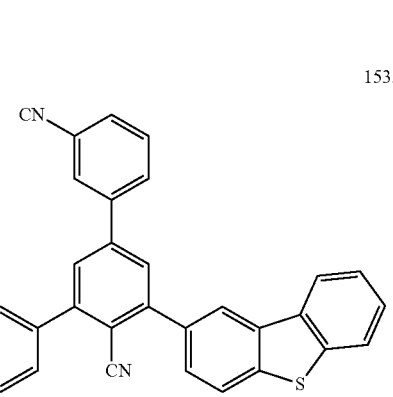
1356
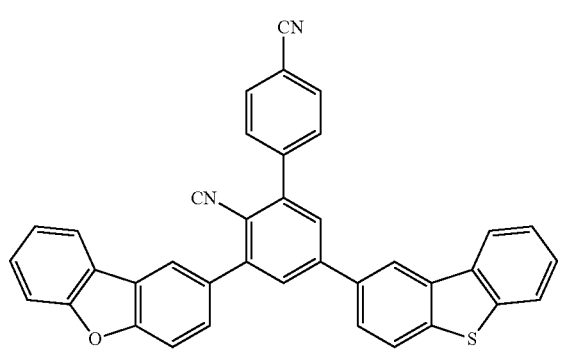
1537
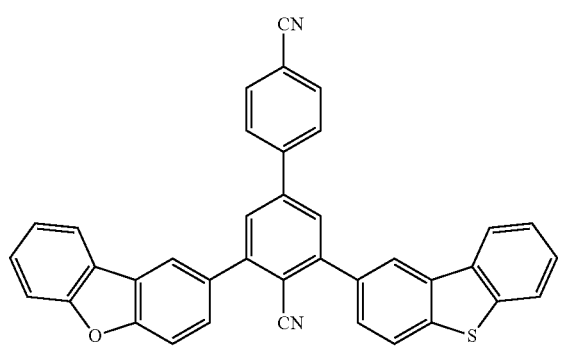

| 391 -continued | 392 -continued |
|---|---|
| 1538 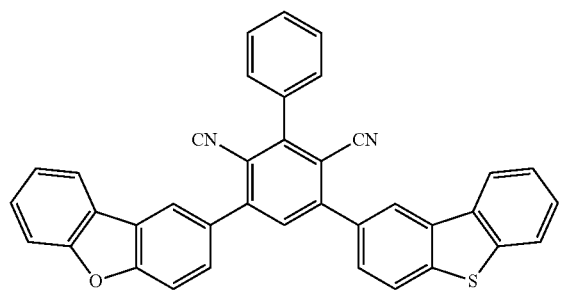 | 1542 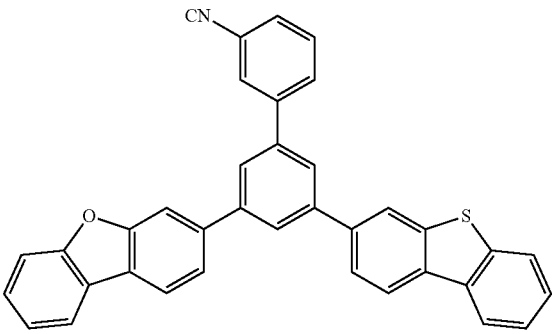 |
| 1539 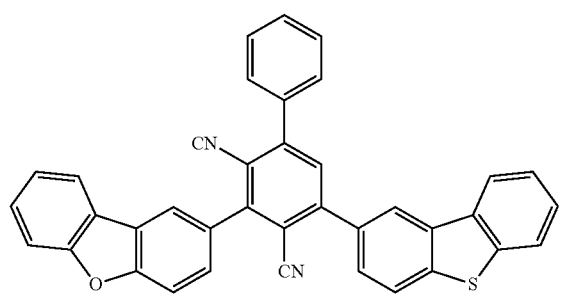 | 1543 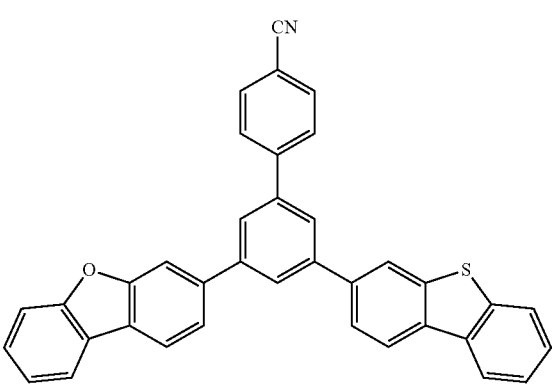 |
| 1540 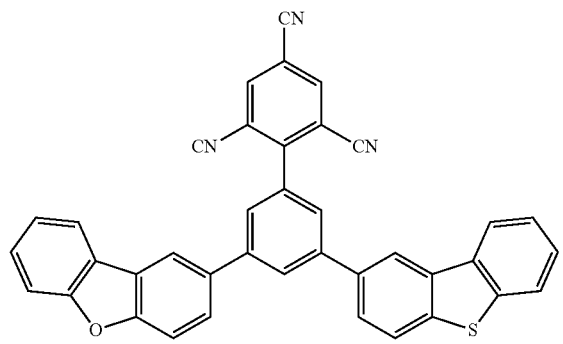 | 1544 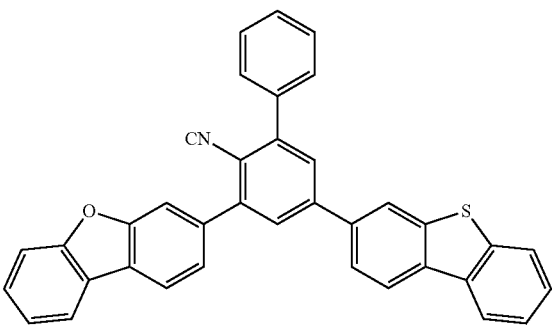 |
| 1541 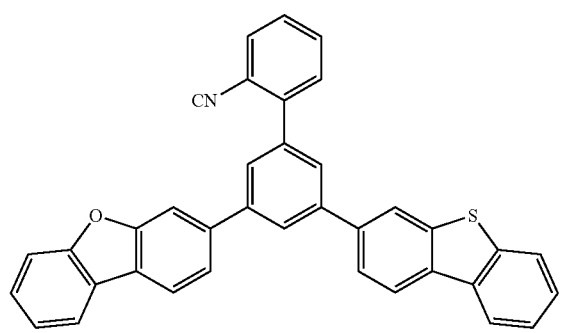 | 1545 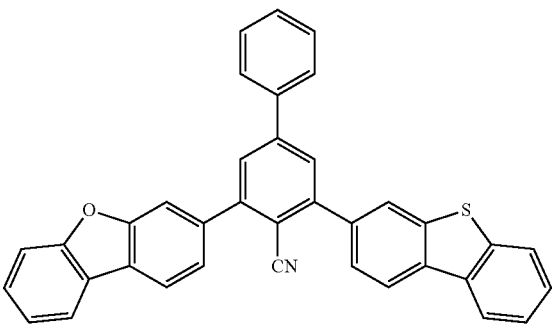 |

393
-continued
1546
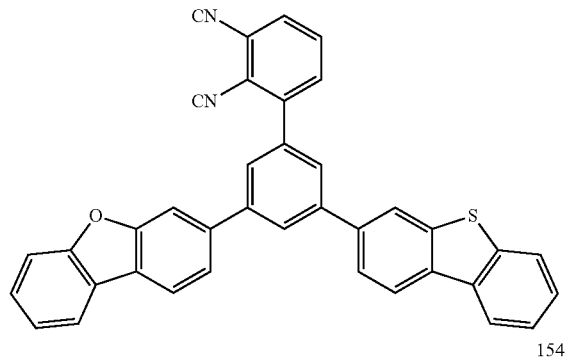
1547
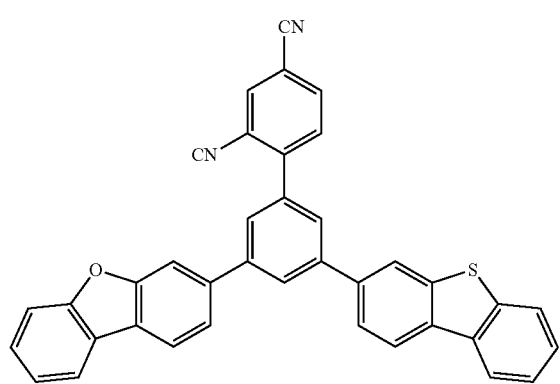
1548
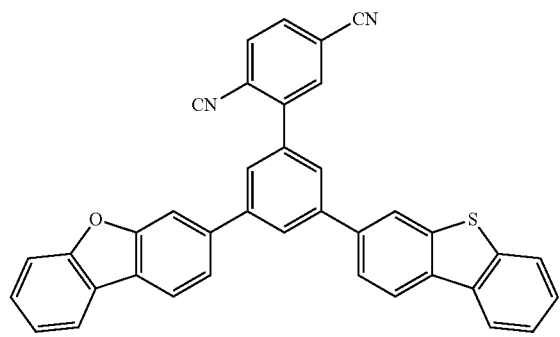
1549
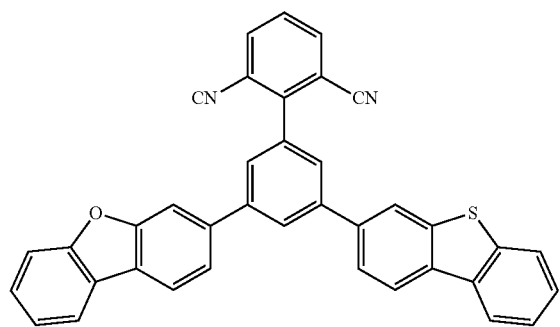
394
-continued
1550
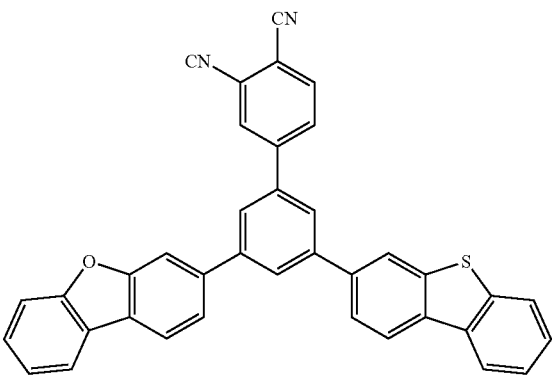
1551
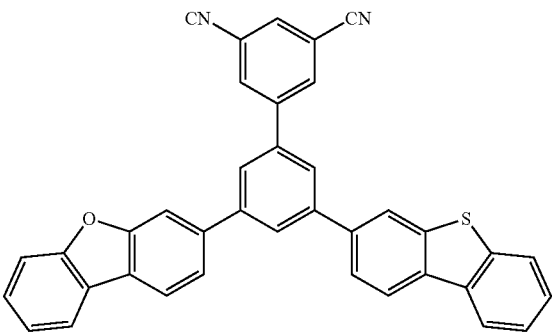
1552
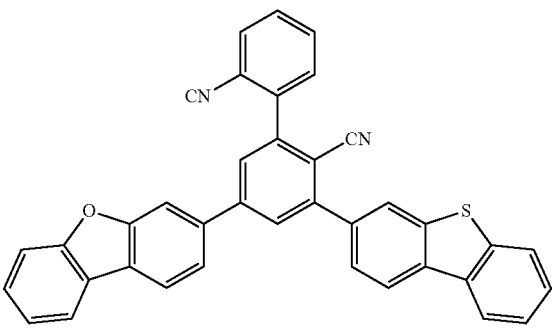
1553
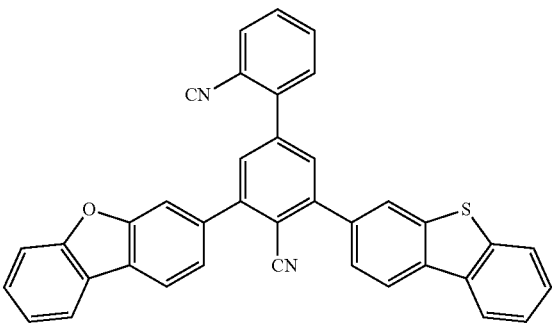

395
-continued
1554
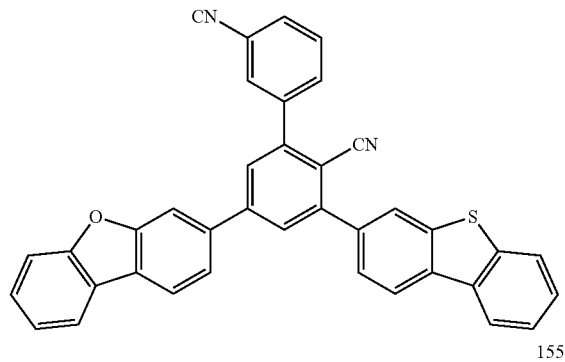
1555
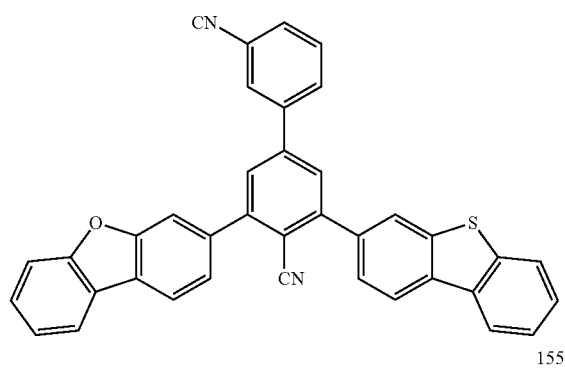
1556
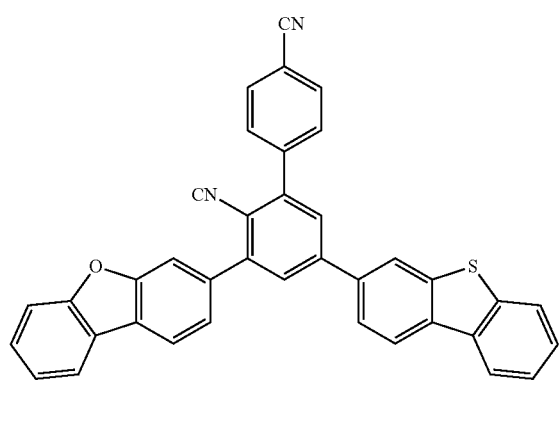
1557
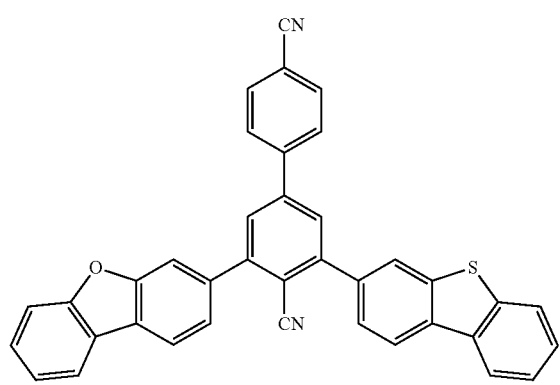
396
-continued
1558
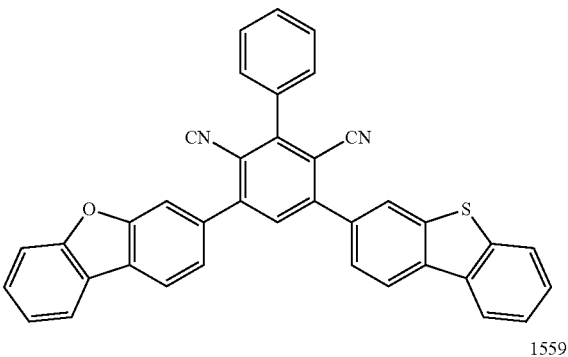
1559
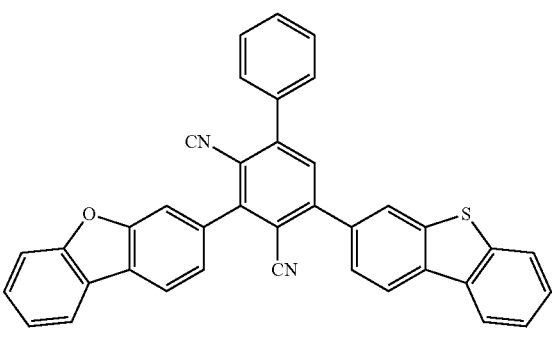
1560
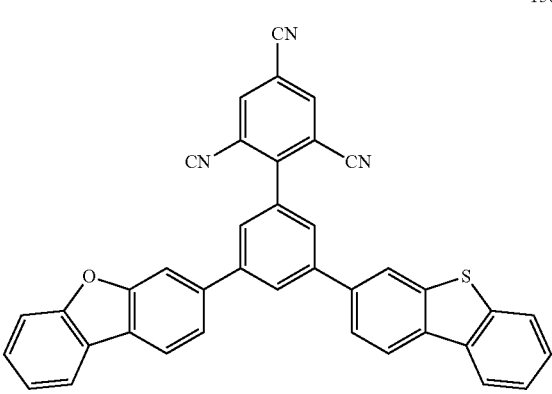
1561

1562 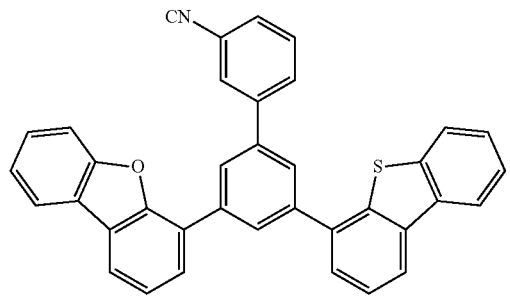
1563 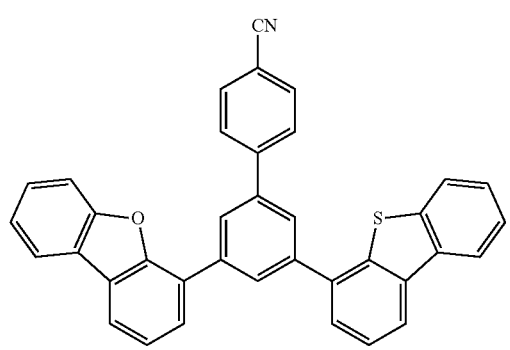
1564 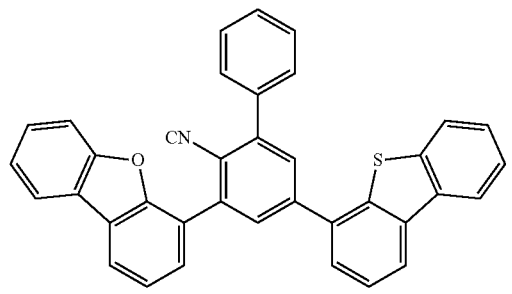
1565 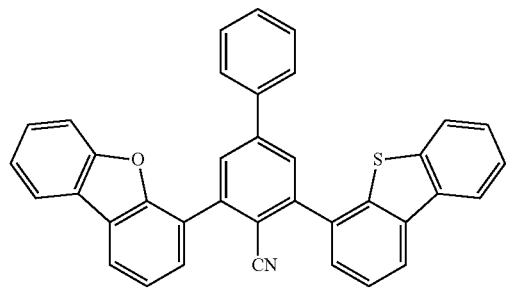
1566 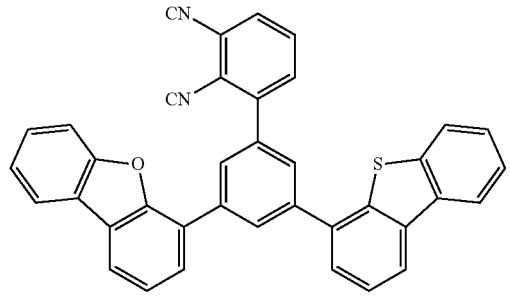
1567 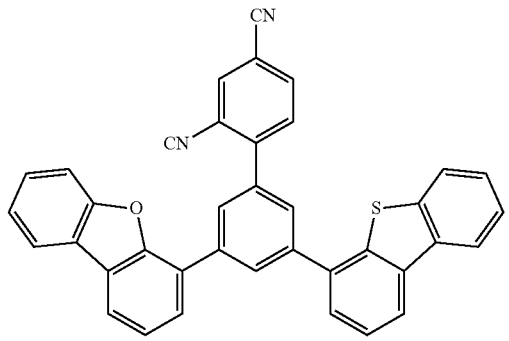
1568 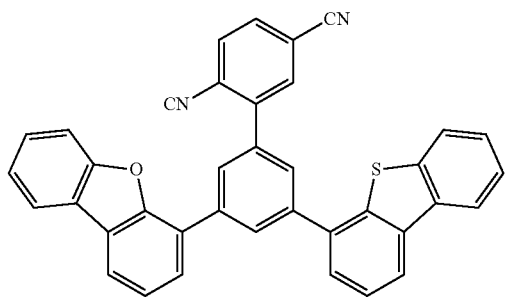
1569 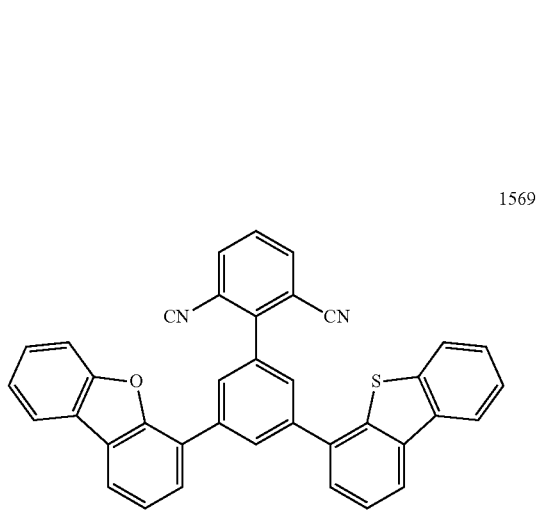
1570 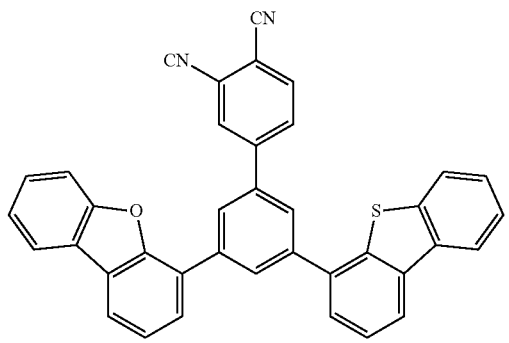

399-continued
1571
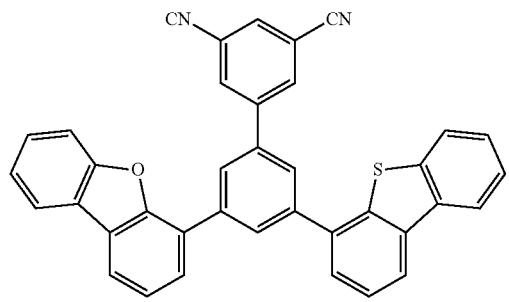
1572
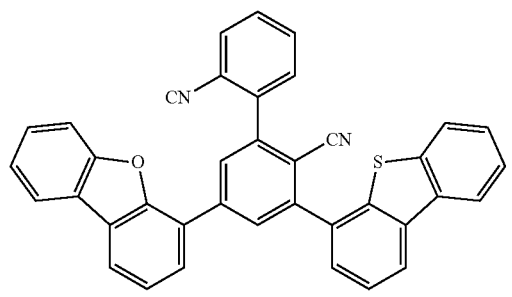
1573
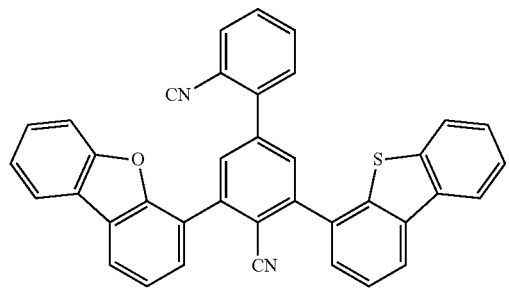
1574
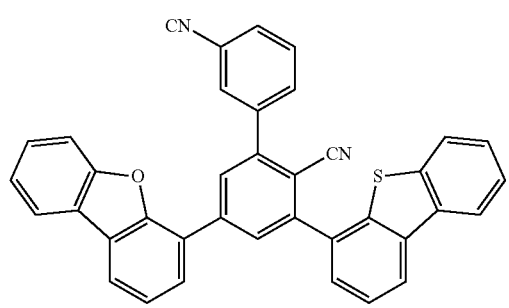
1575
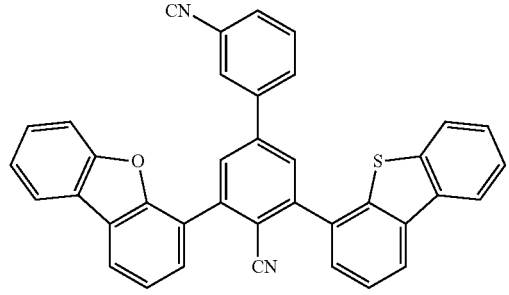
400-continued
1576
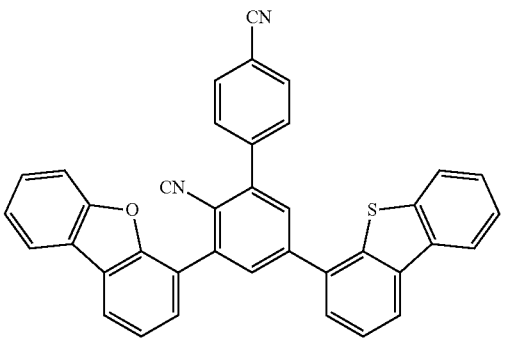
1577
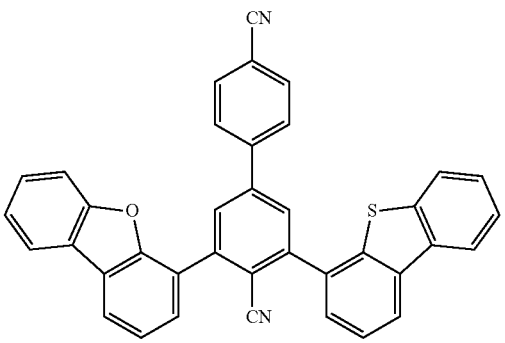
1578
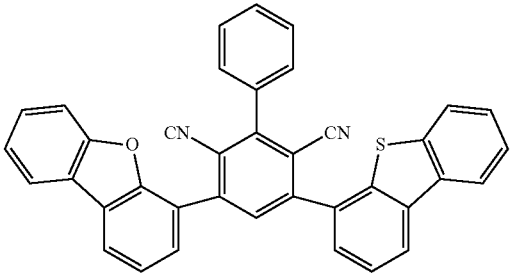
1579
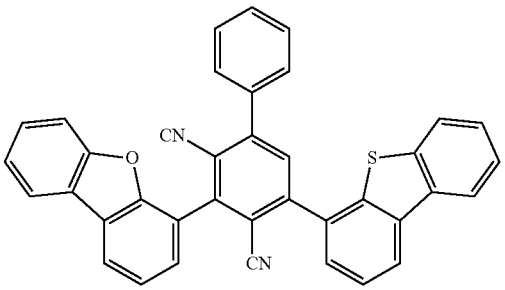

-continued
1580
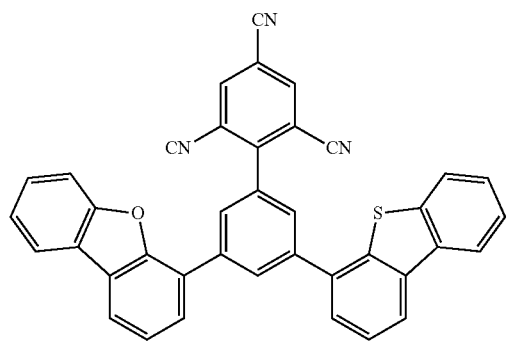
1581
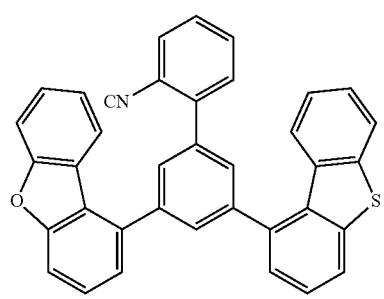
1582
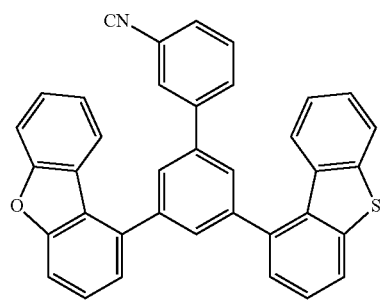
1583
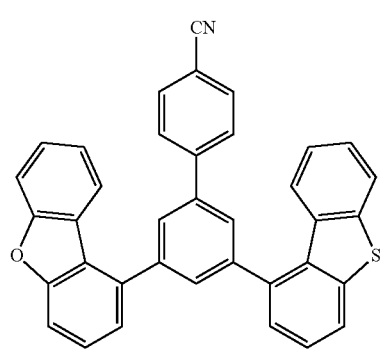
1584
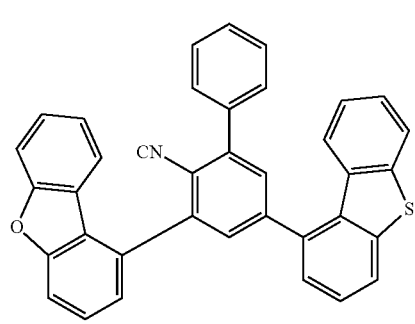
-continued
1585
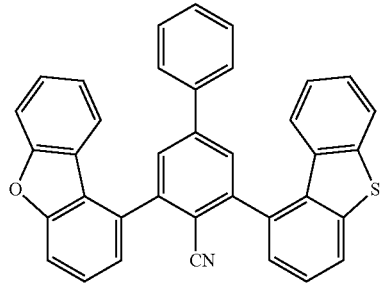
1586
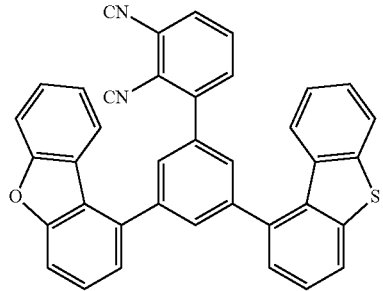
1587
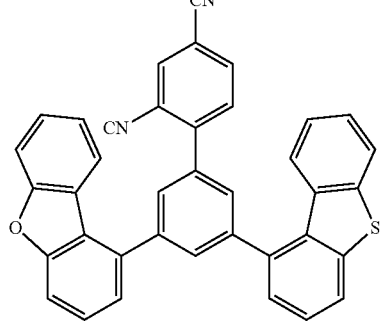
1588
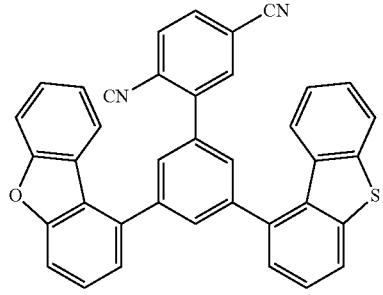
1589
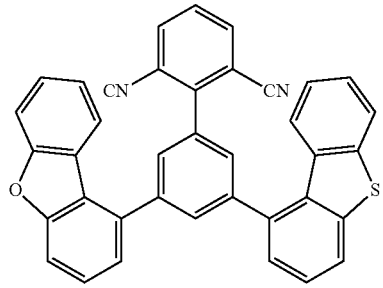

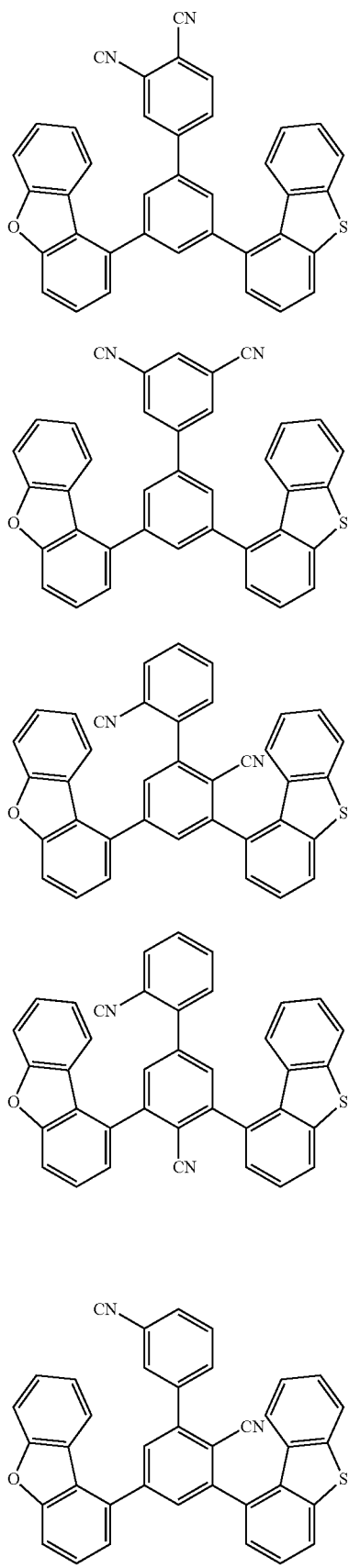
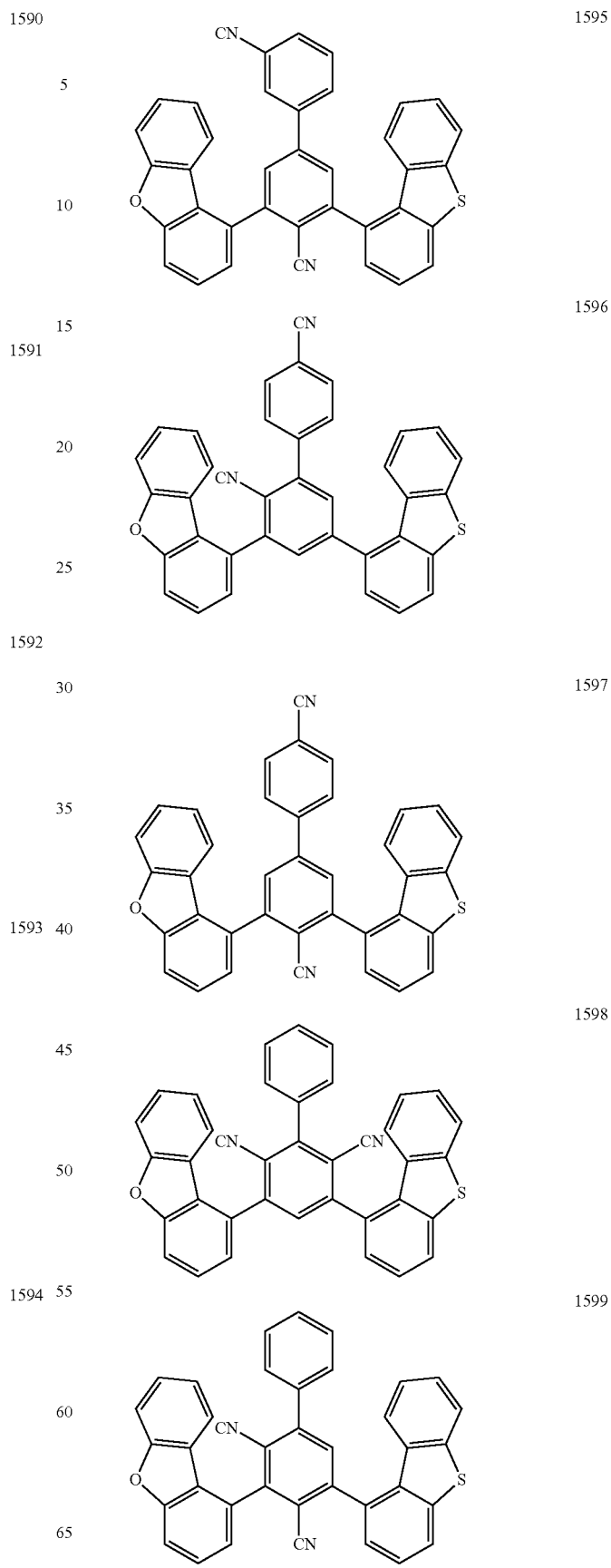

1600
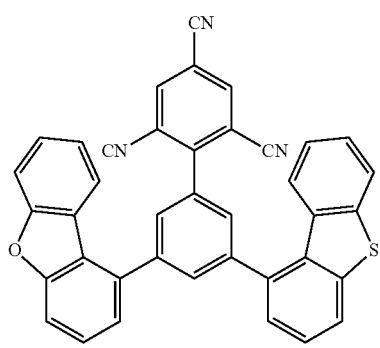
1601
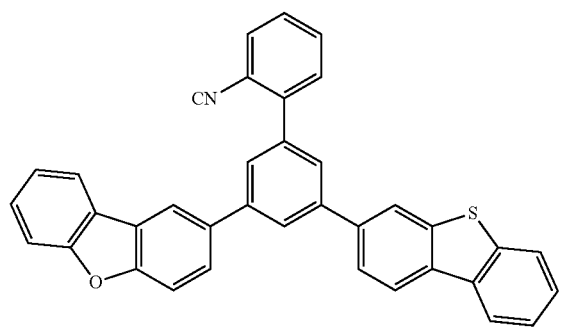
1602
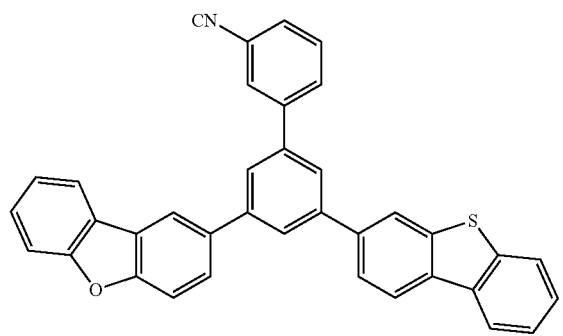
1603
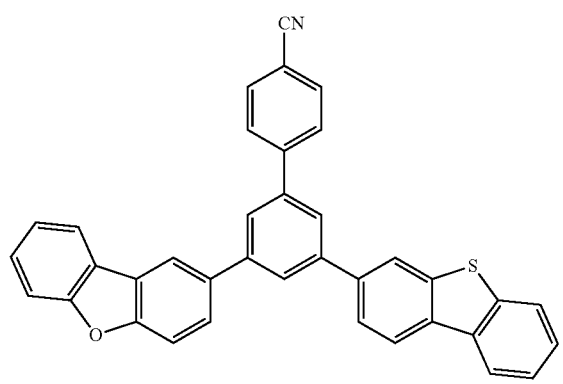
1604
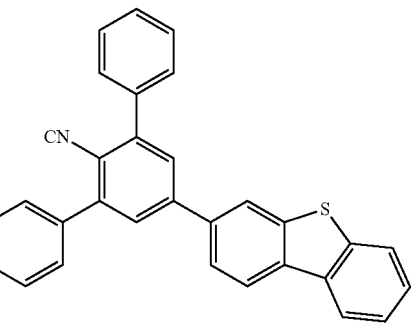
1605
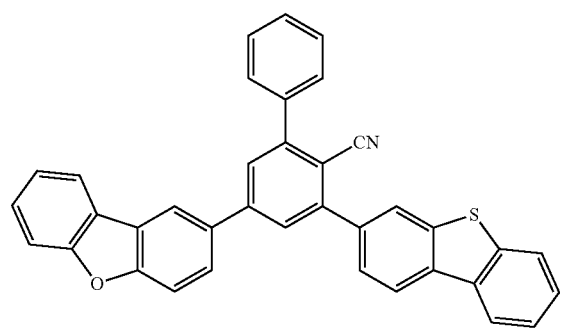
1606
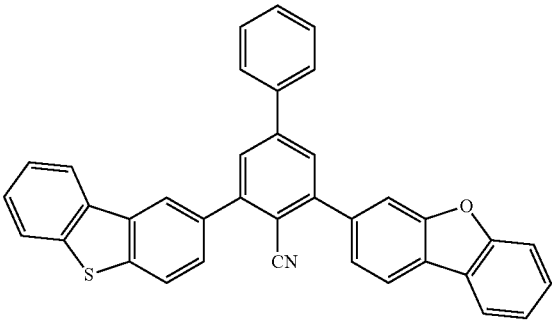
1607
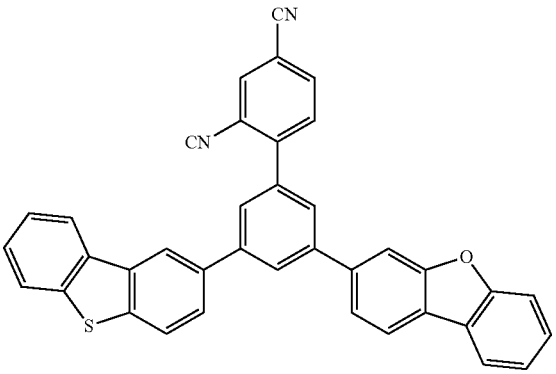

407
-continued
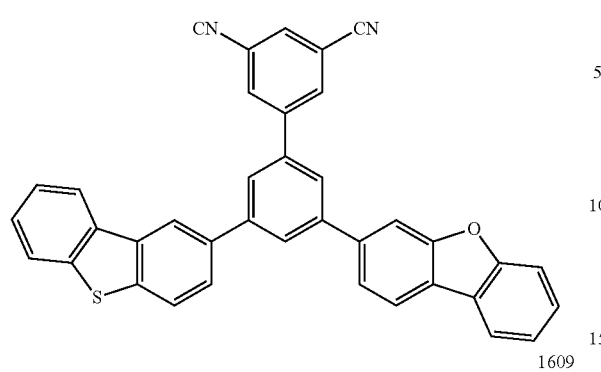
408
-continued
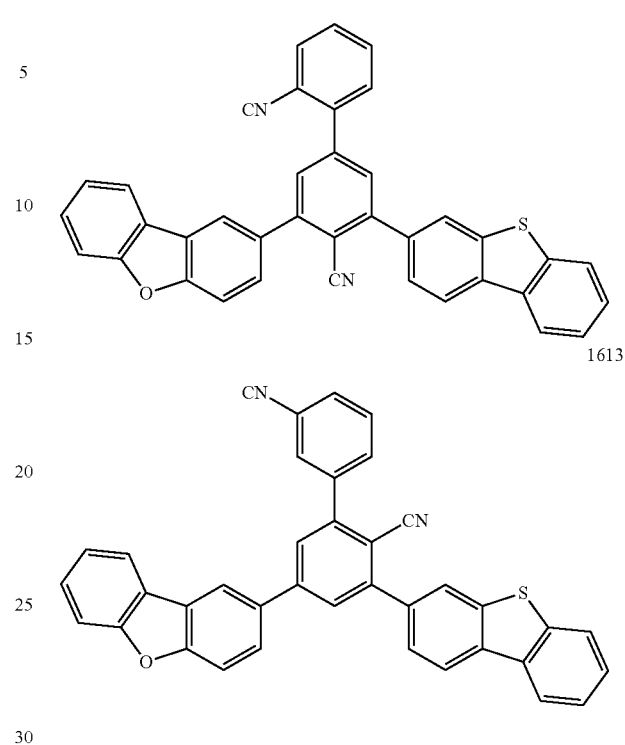
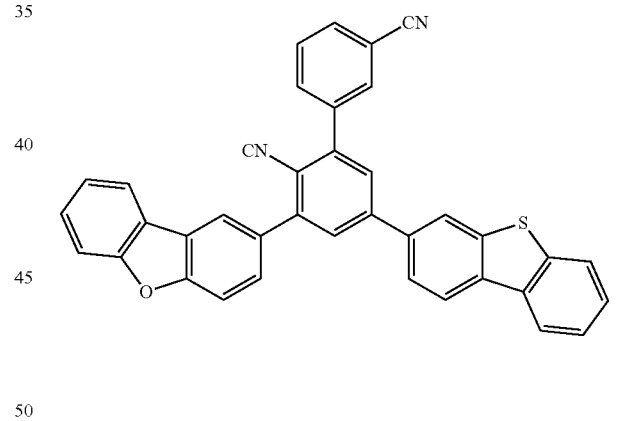
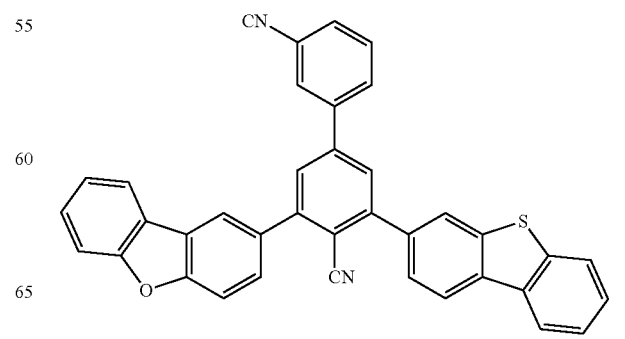

409
-continued
1616
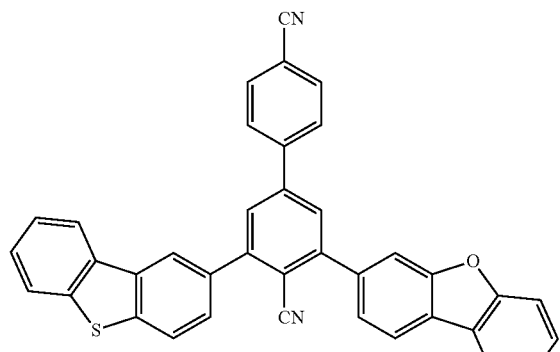
1617
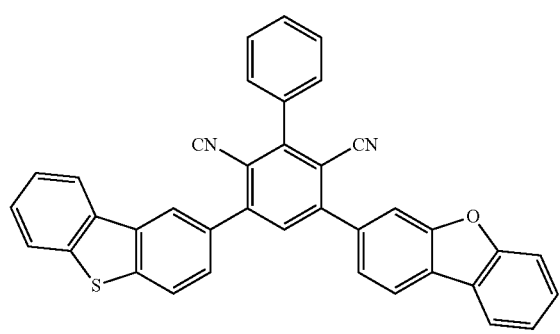
1618
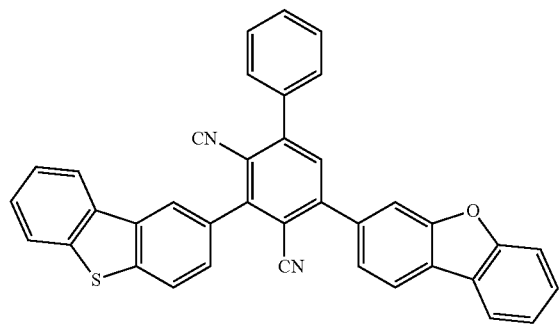
1619
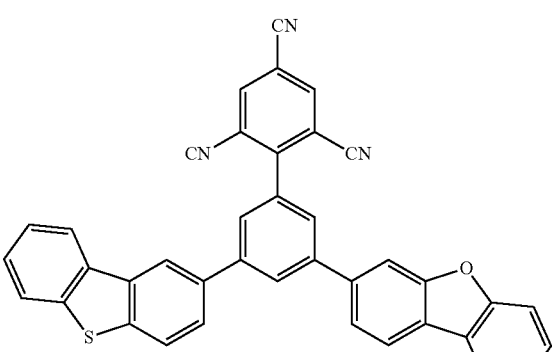
410
-continued
1620
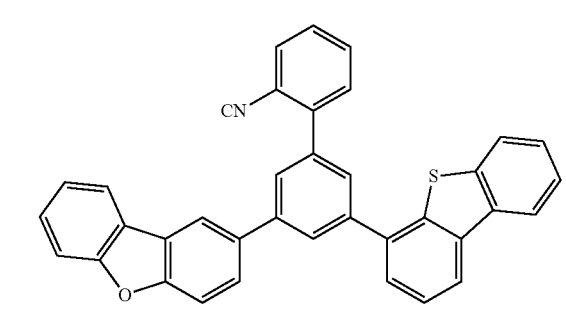
1621
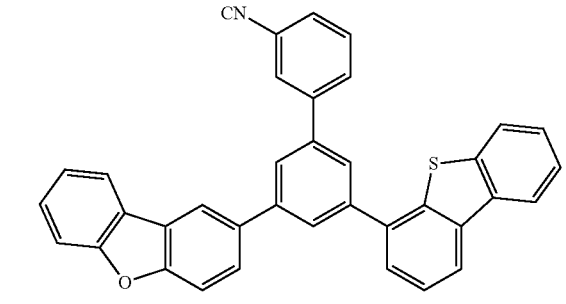
1622
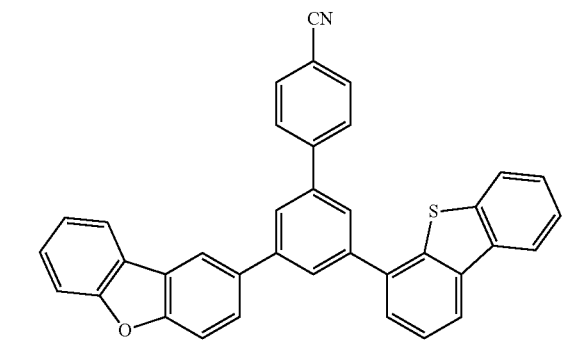
1623

| 411 -continued | 412 -continued |
|---|---|
| 1624 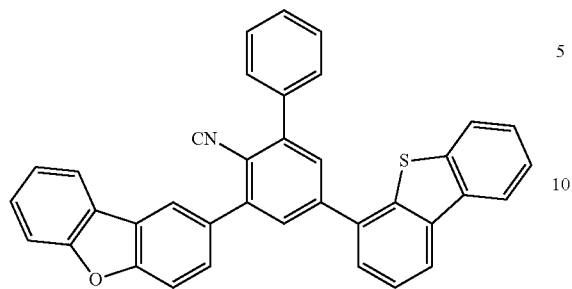 | 1629 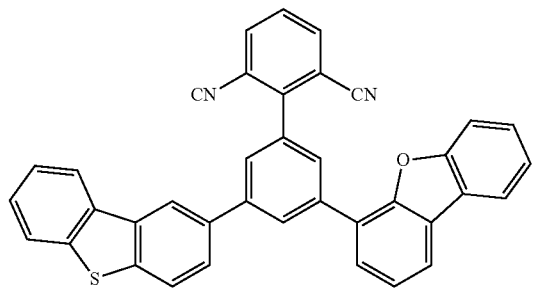 |
| 1625 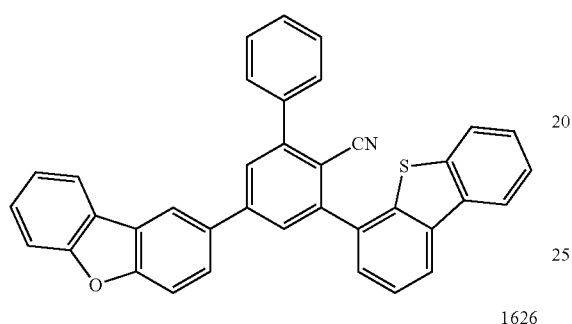 | 1630 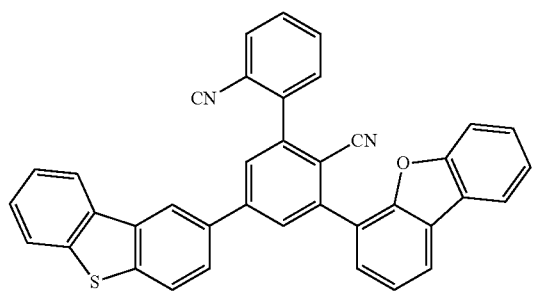 |
| 1626 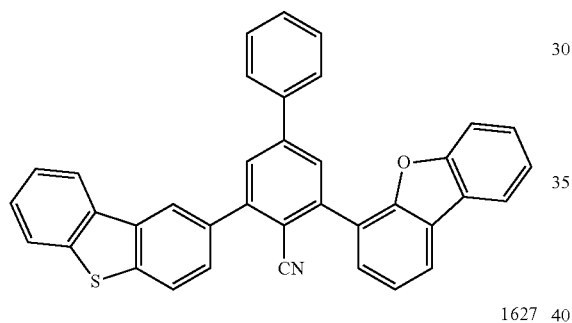 | 1631 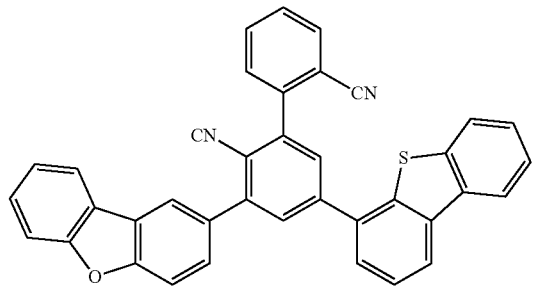 |
| 1627 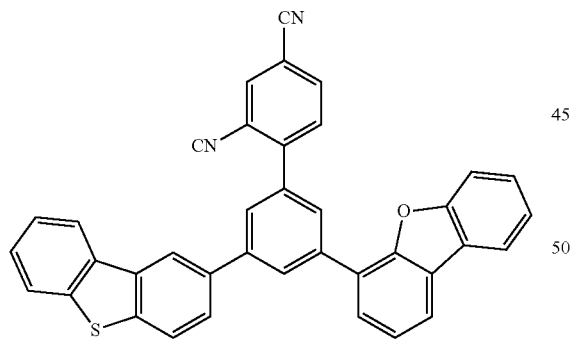 | 1632 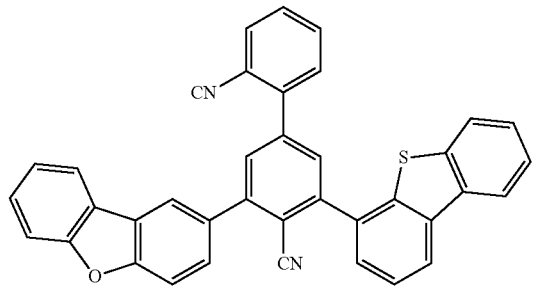 |
| 1628 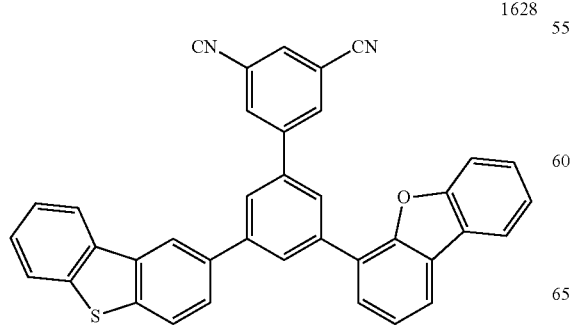 | 1633 |

413
-continued
414
-continued
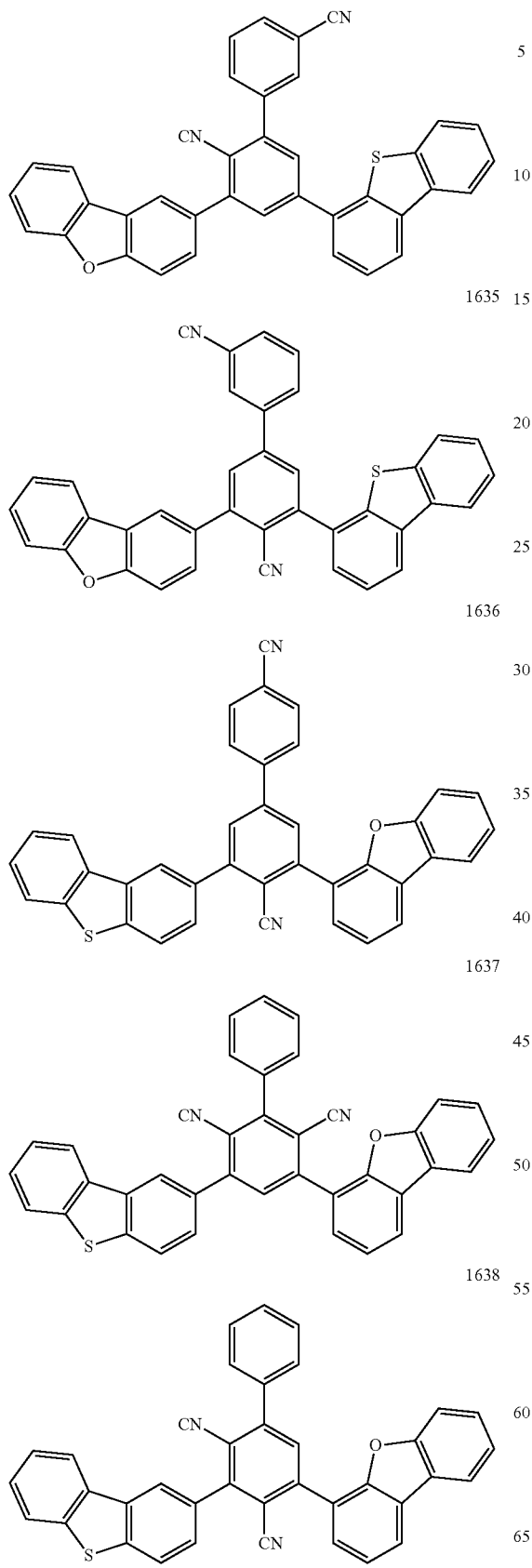
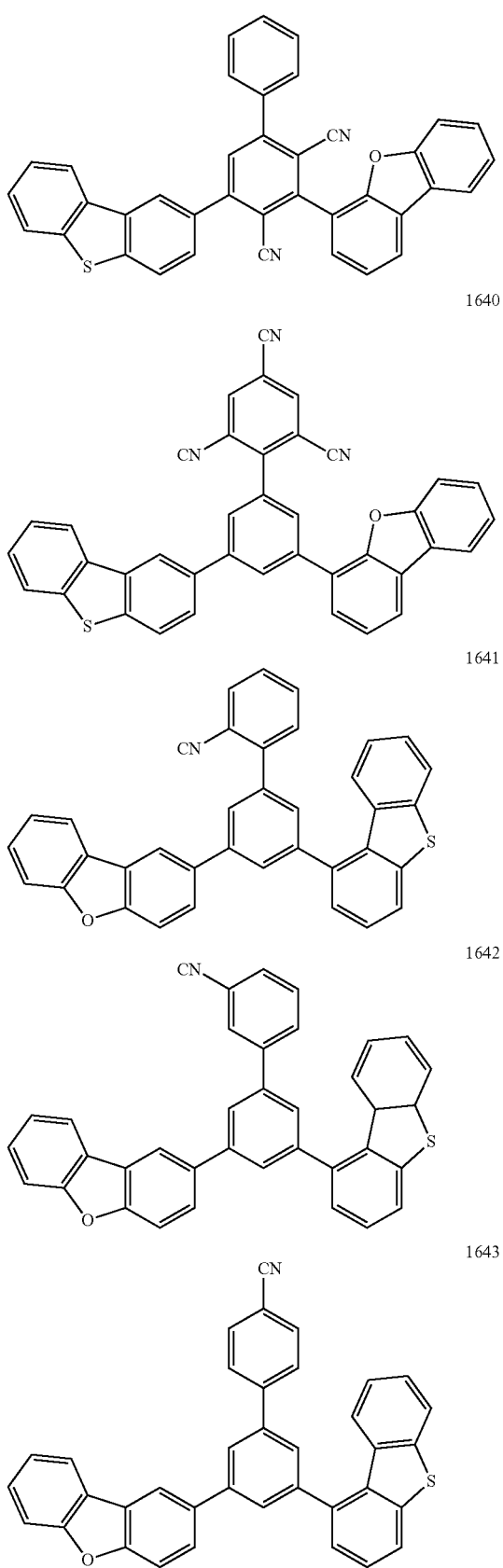

415
-continued
1644
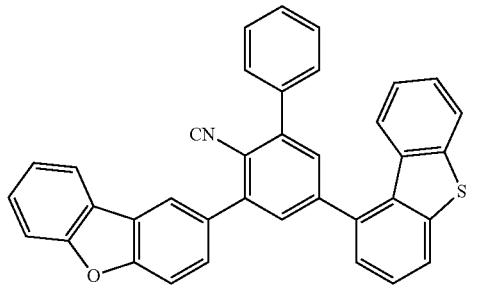
1645
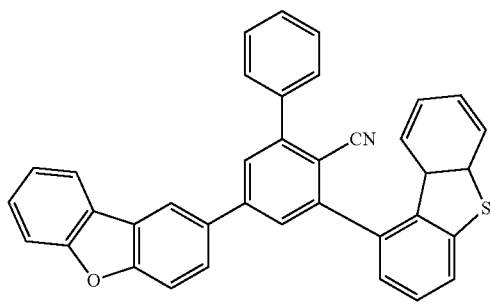
1646
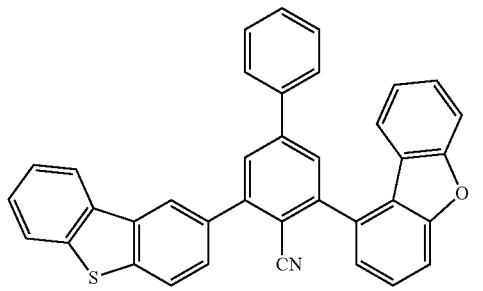
1647
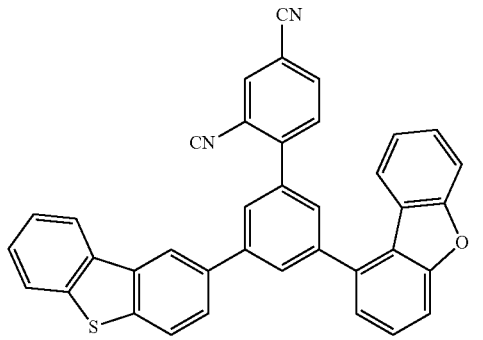
1648
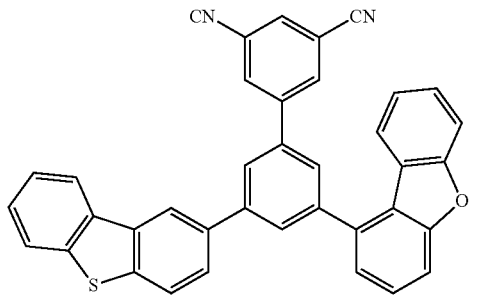
416
-continued
1649
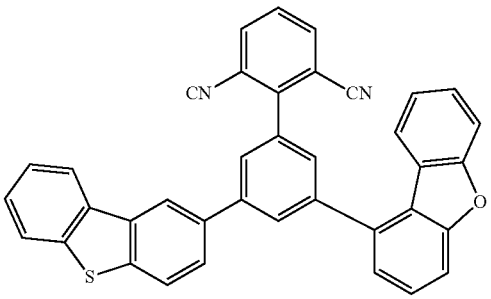
1650
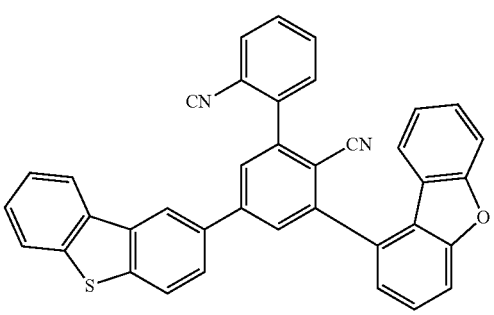
1651
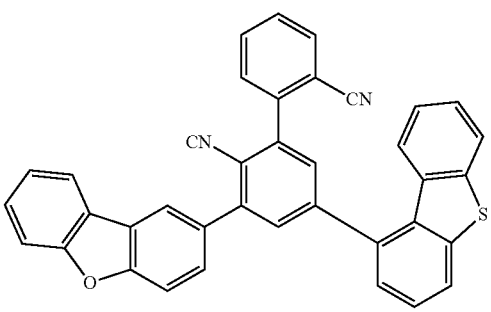
1652
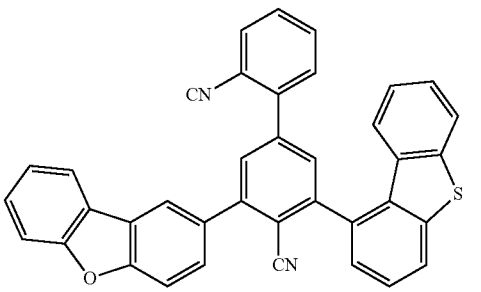
1653
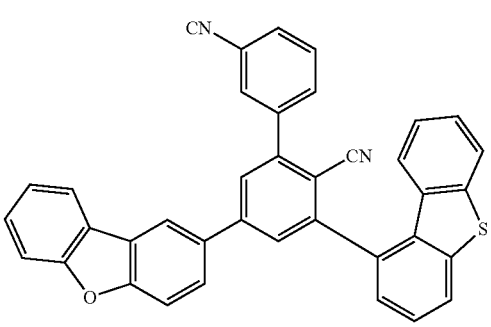

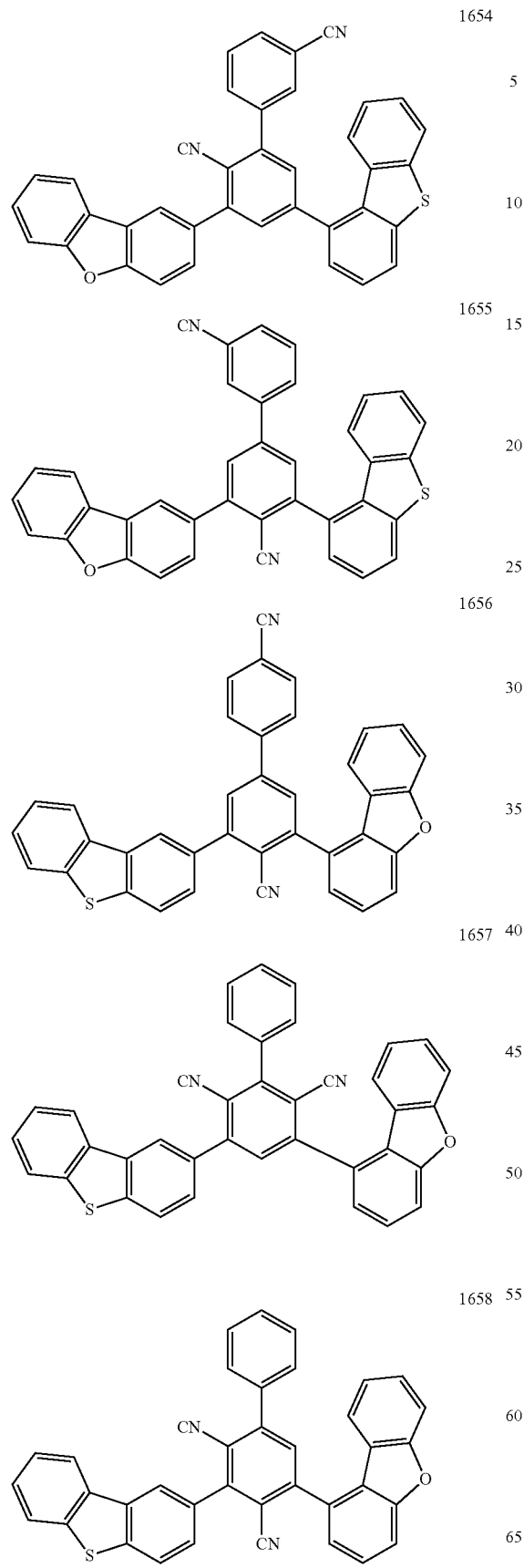
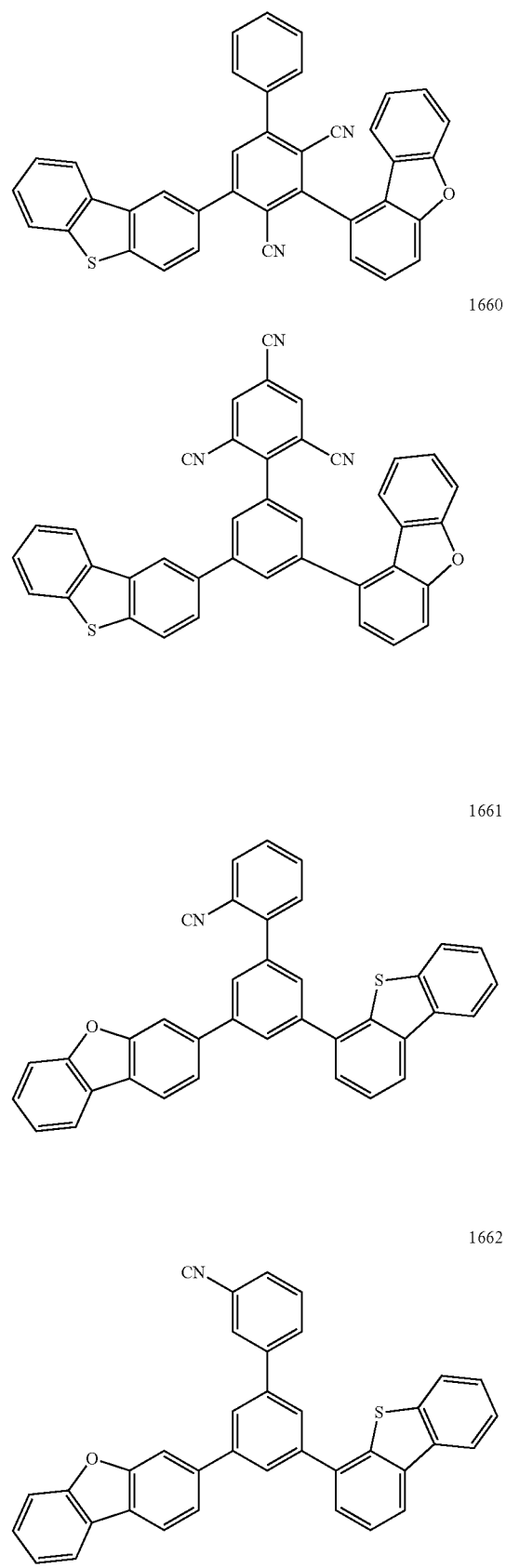

-continued
1663
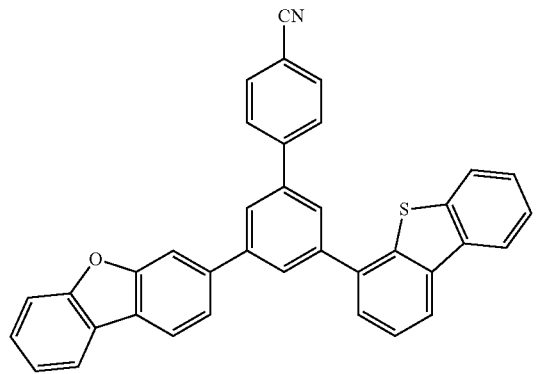
1664
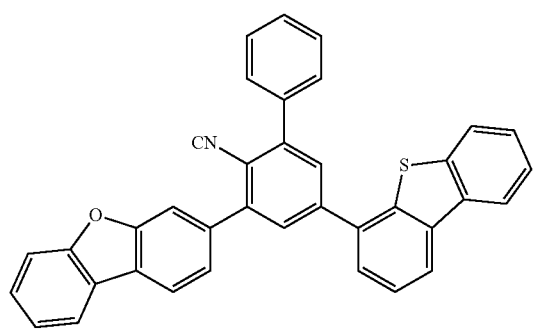
1665
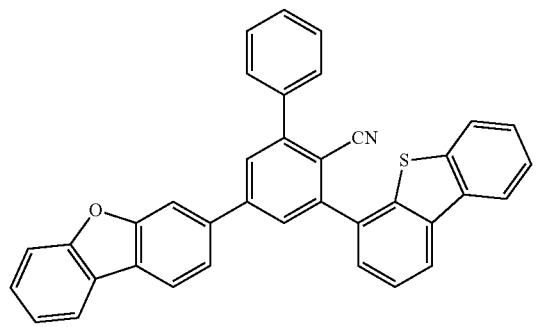
1666
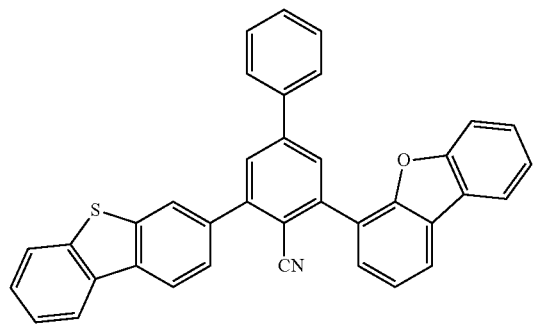
-continued
1667
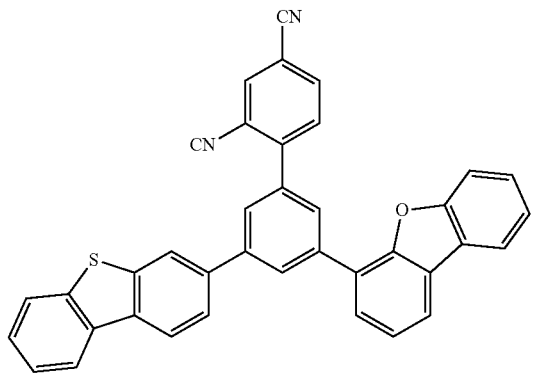
1668
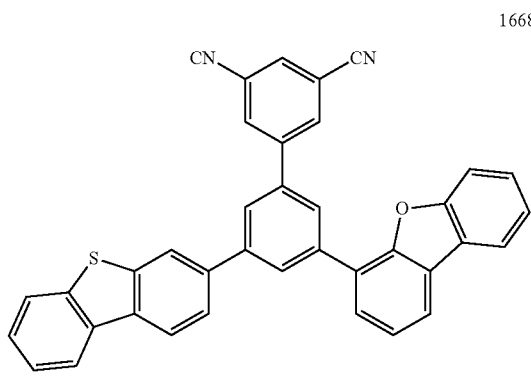
1669
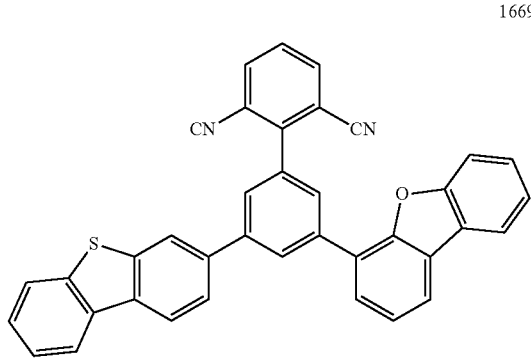
1670
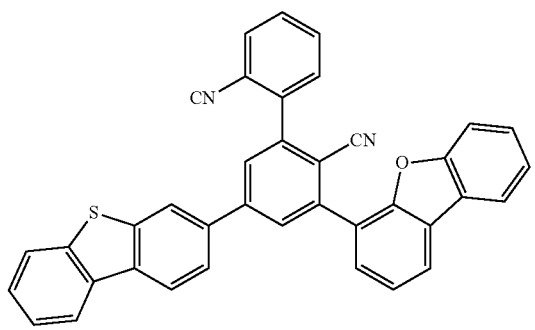

421
-continued
1671
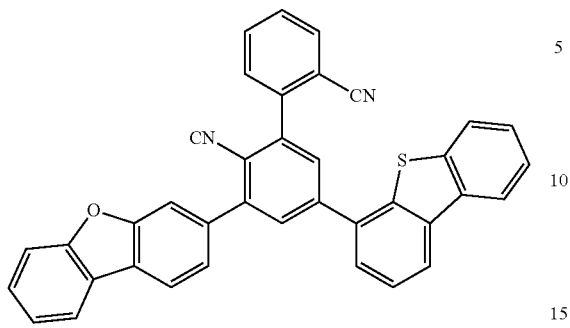
1672
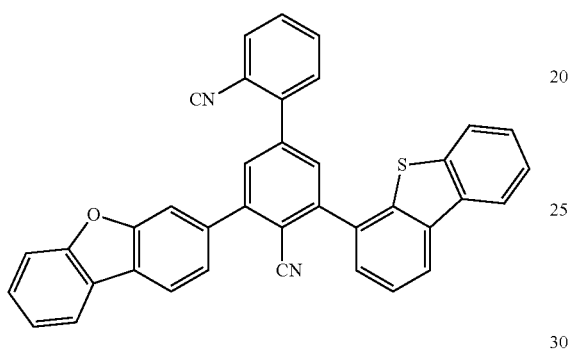
1673
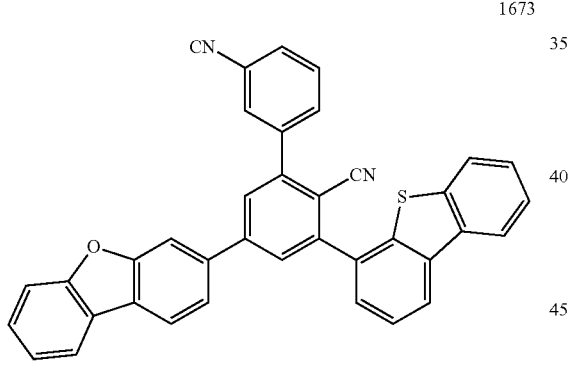
1674
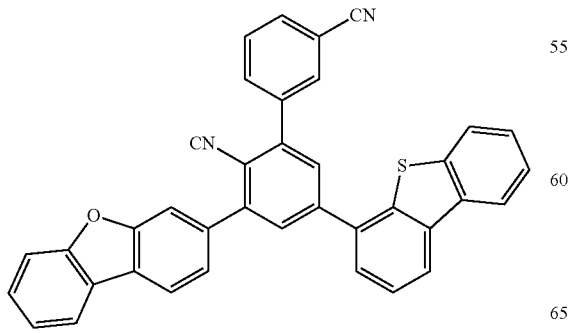
422
-continued
1675
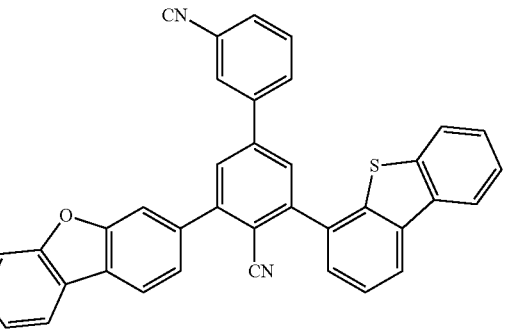
1676
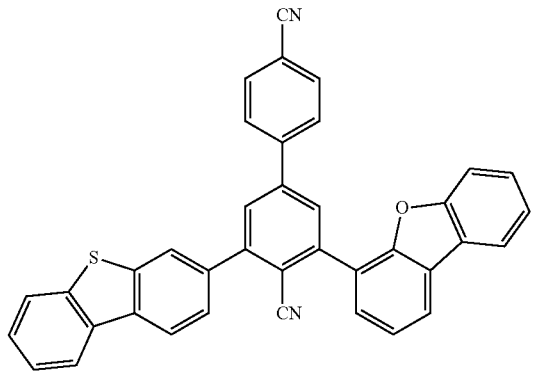
1677
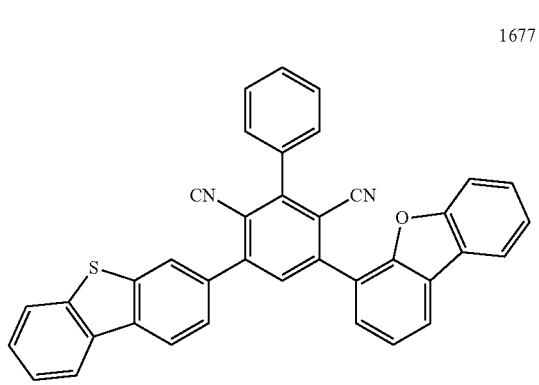
1678
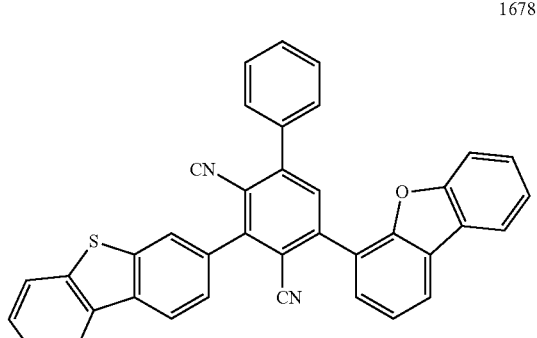

1679
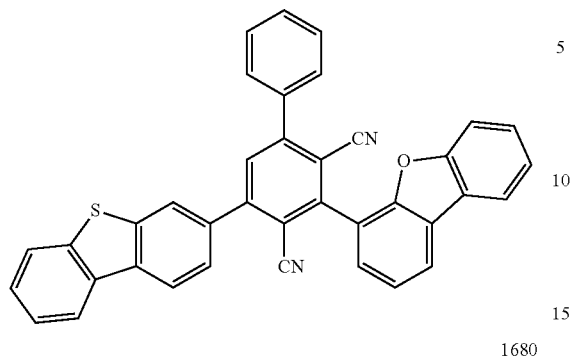
1683
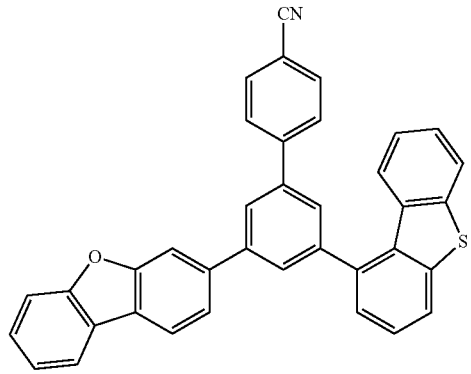
1680
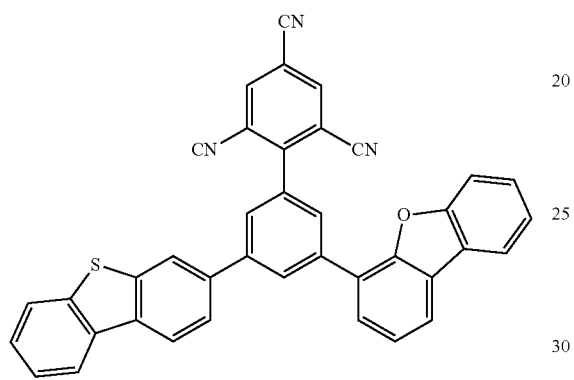
1684
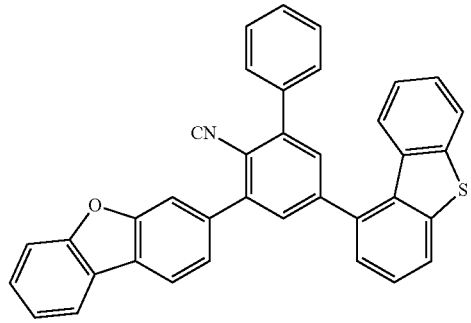
1681
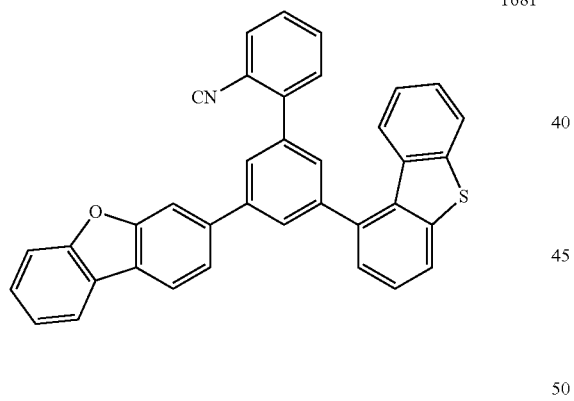
1685
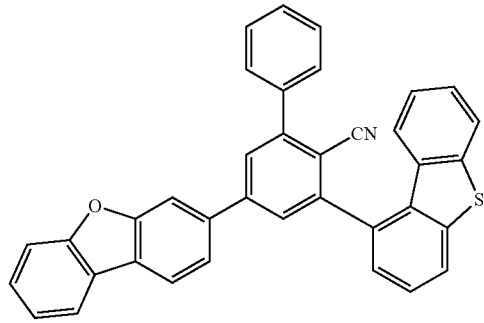
1682
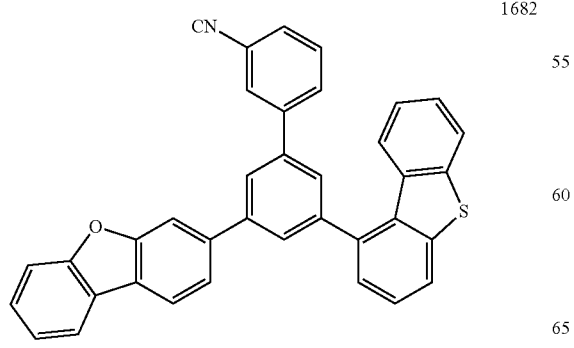
1686
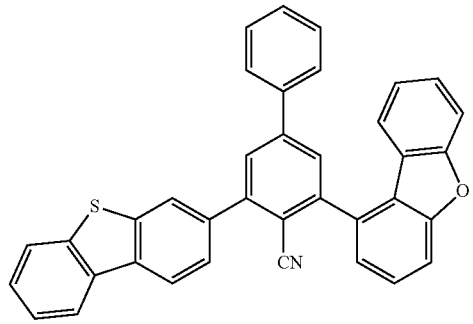

-continued
1687
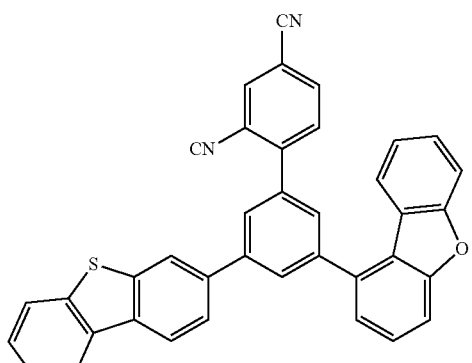
1688
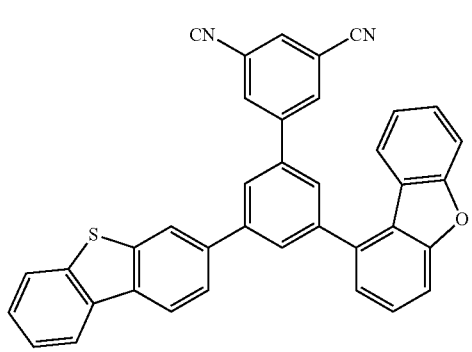
1689
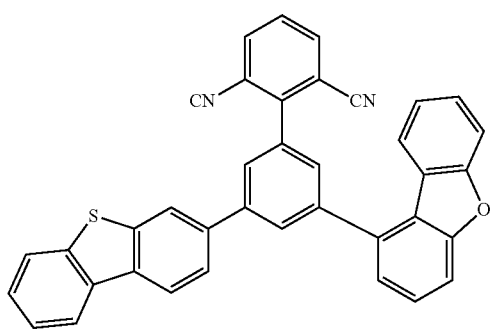
1690
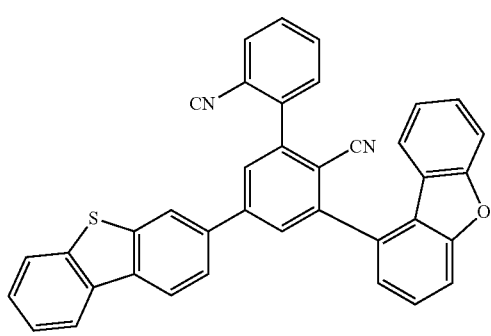
-continued
1691
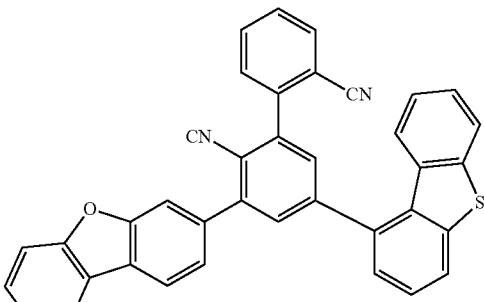
1692
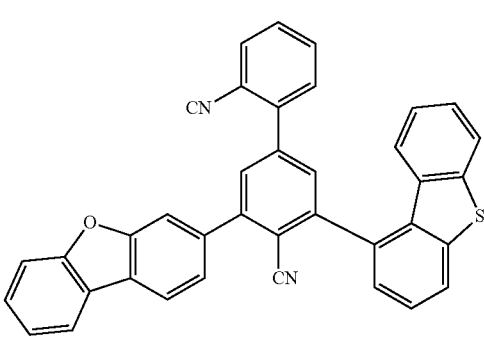
1993
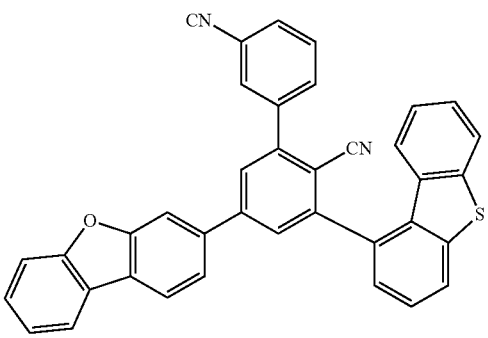
1694
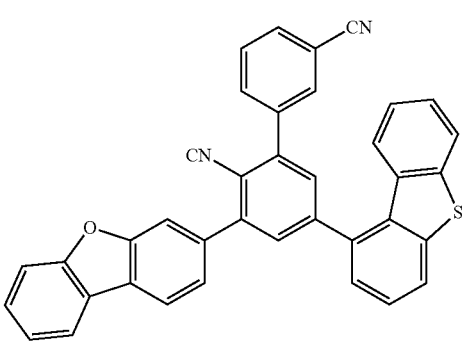

427
-continued
1695
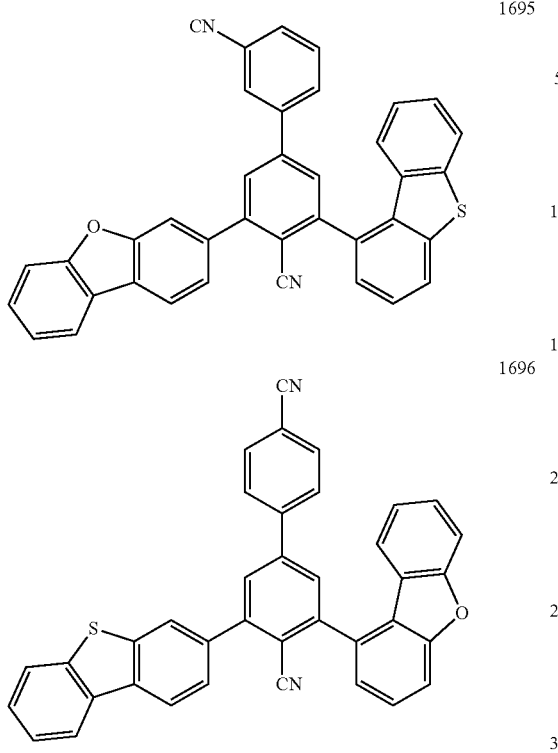
1696
1697
1698
428
-continued
1699
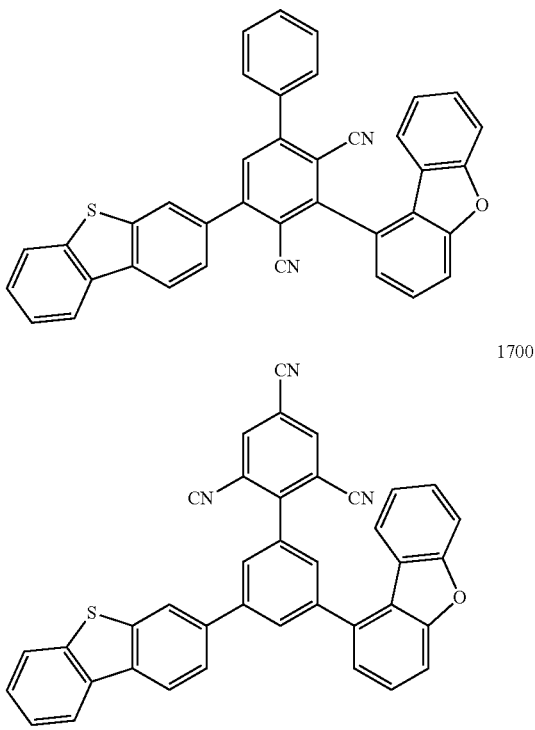
1700
1701
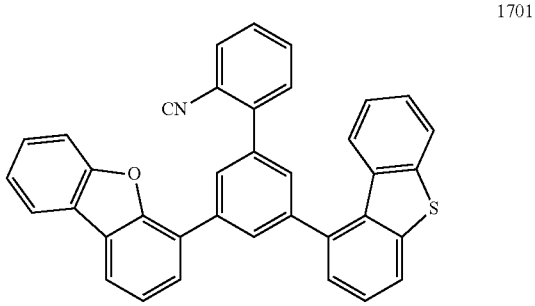
1702

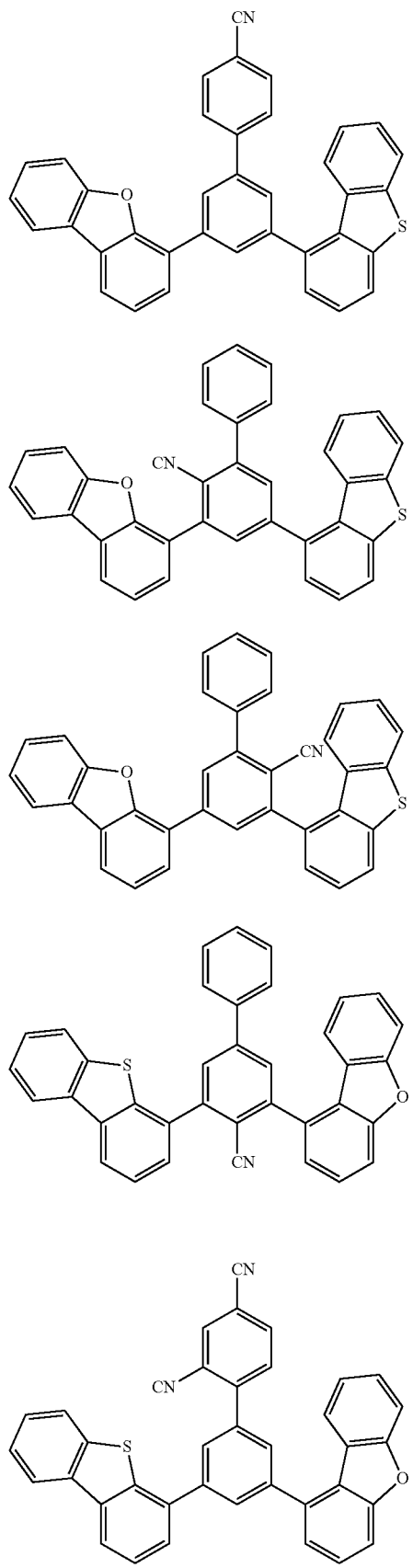
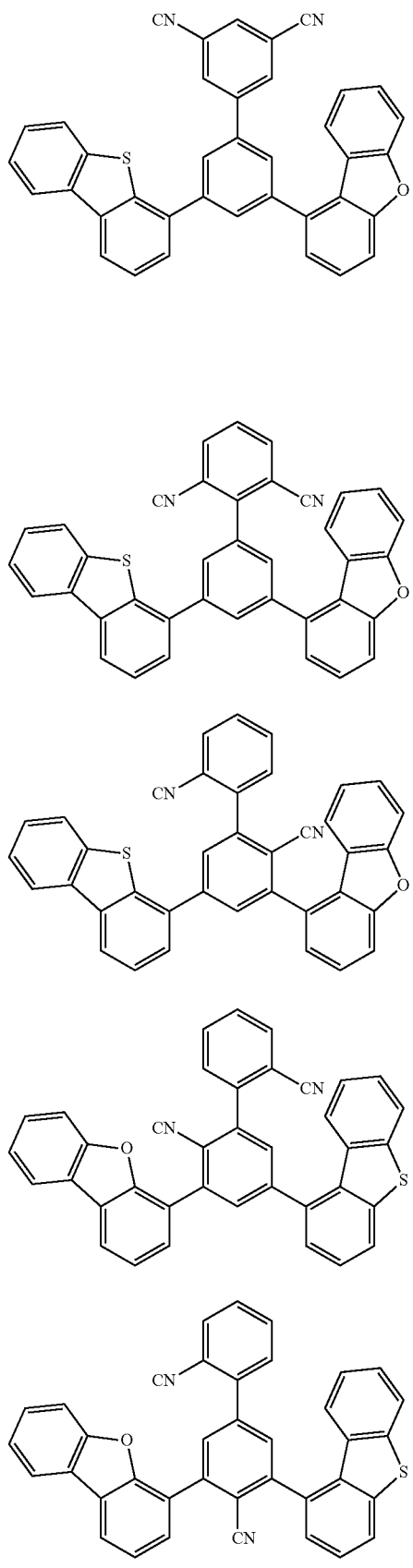

431
-continued
1713
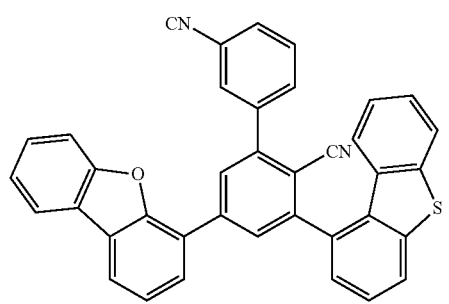
1714
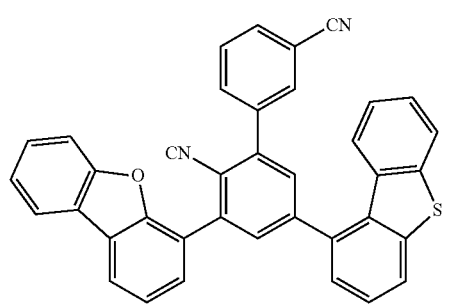
1715
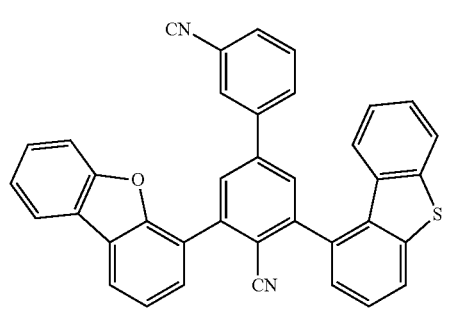
1716
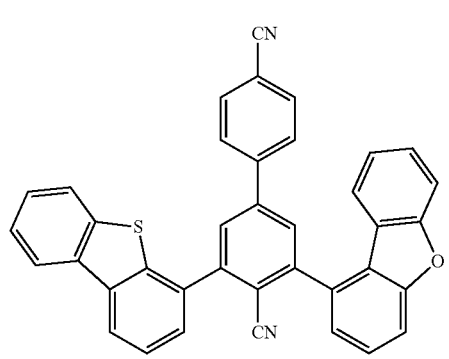
1717
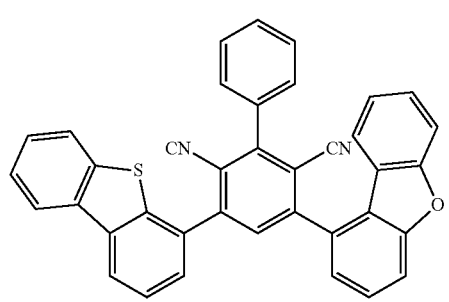
432
-continued
1718
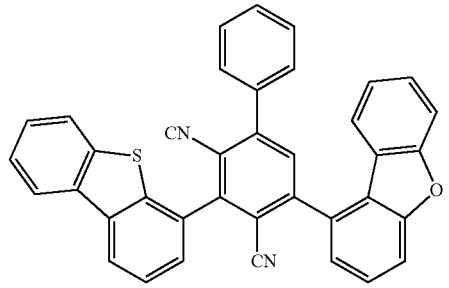
1719
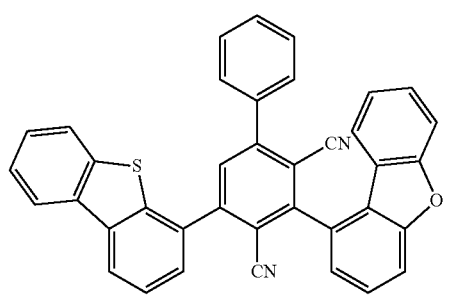
1720
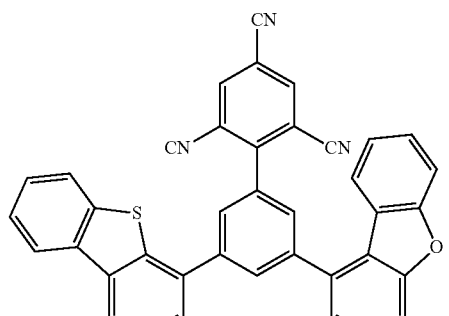
1721
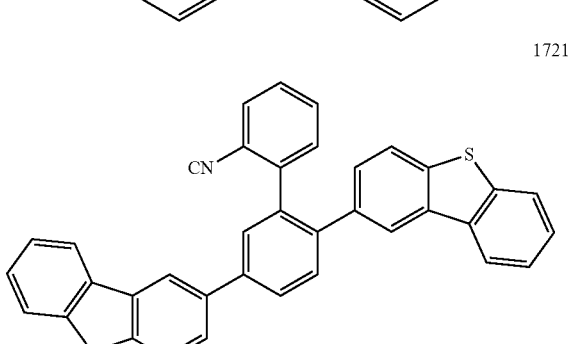
1722
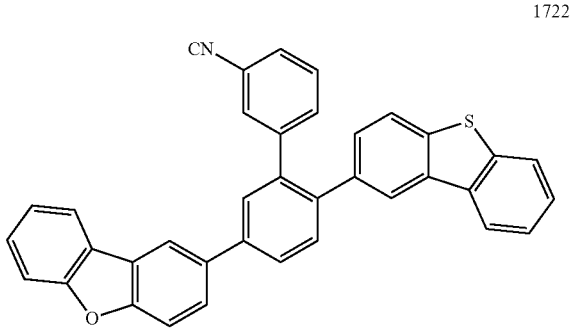

-continued
1723
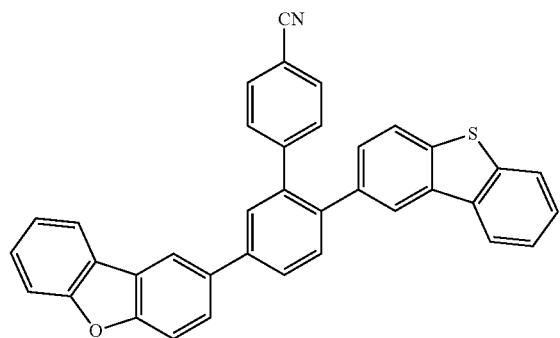
1724
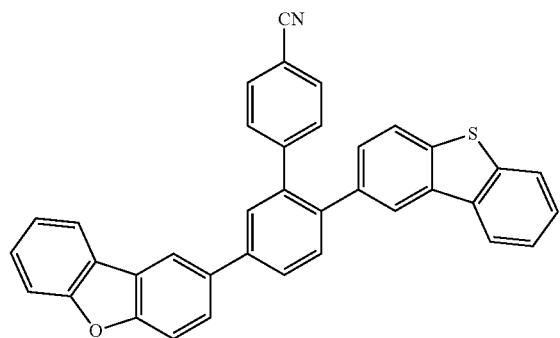
1725
1726
-continued
1727
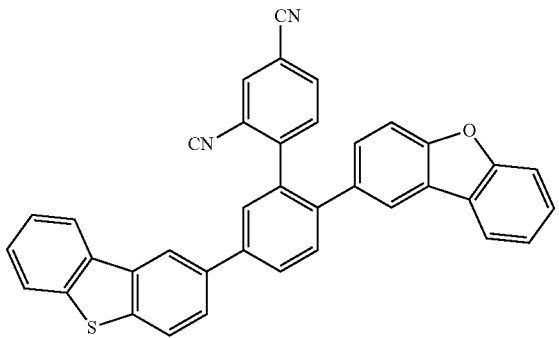
1728
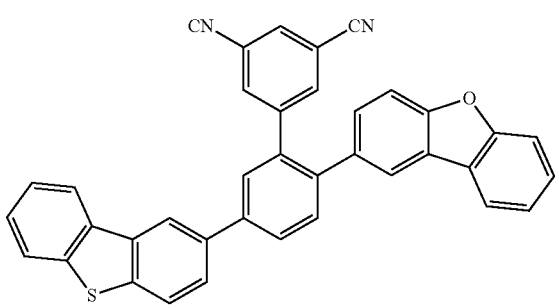
1729
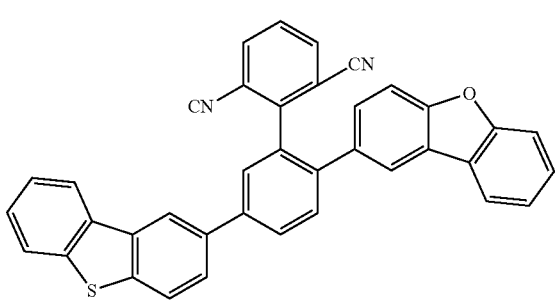
1730
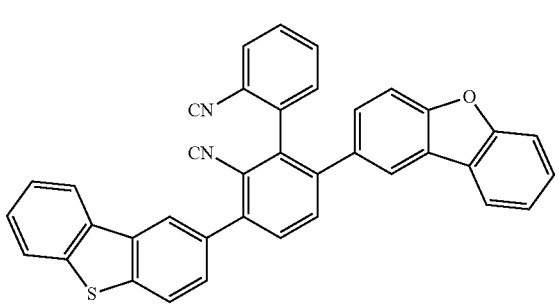
1731
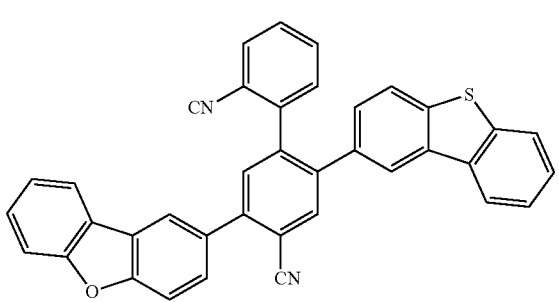

435
-continued
1732
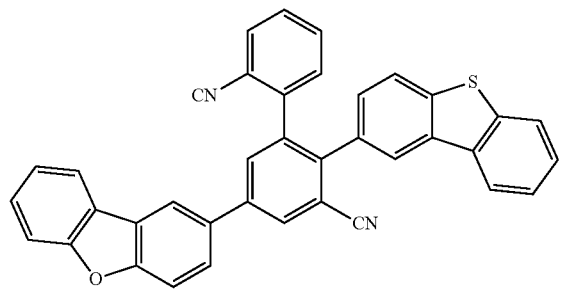
1733
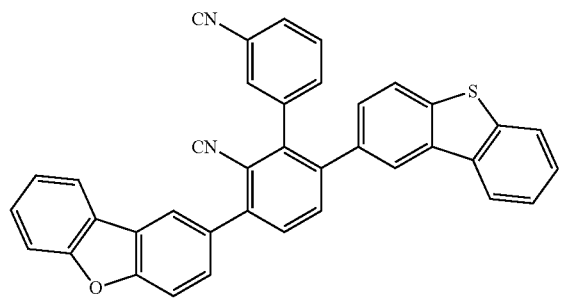
1734
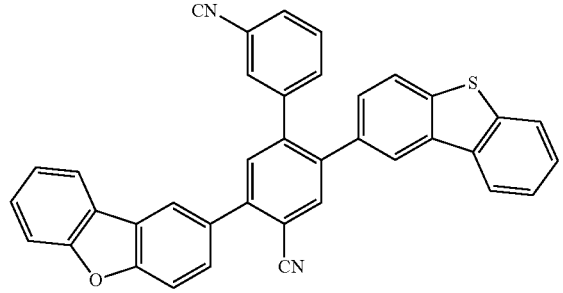
1735
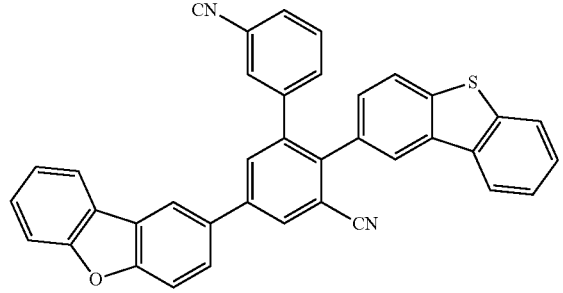
1736
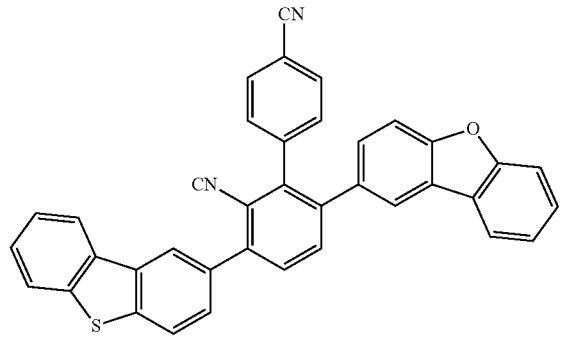
436
-continued
1737
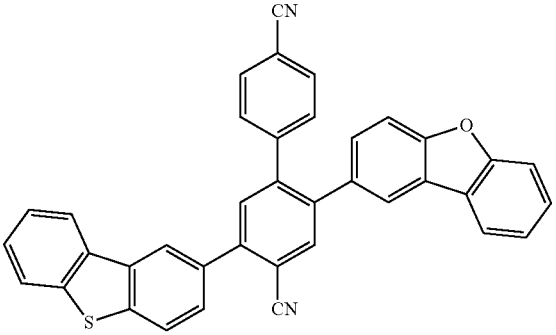
1738
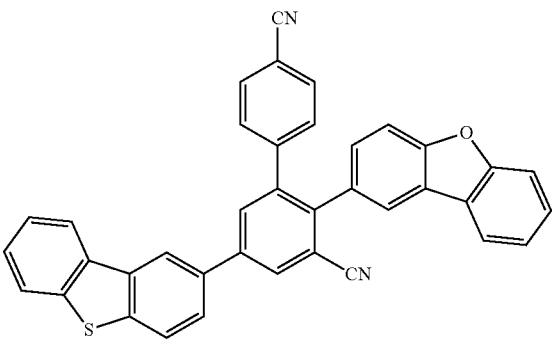
1739
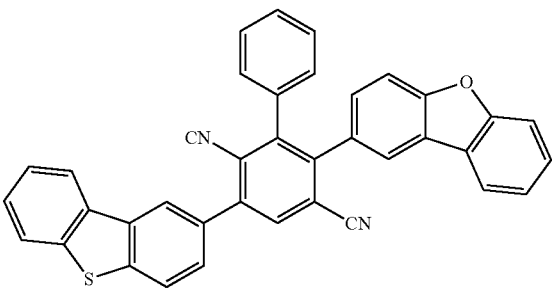
1740
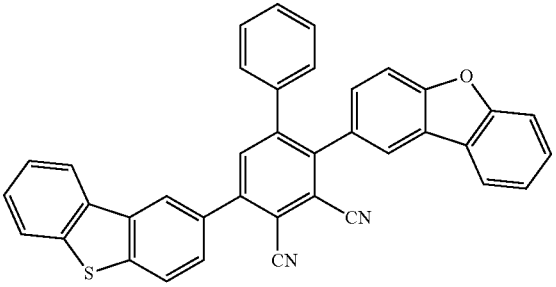

437
-continued
438
-continued
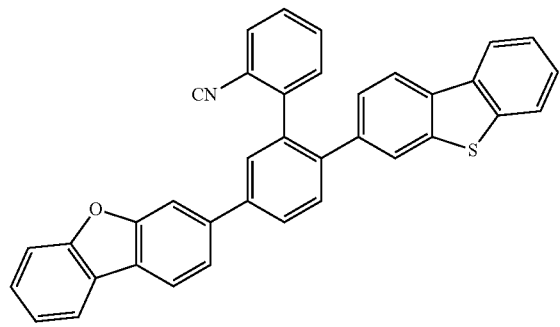
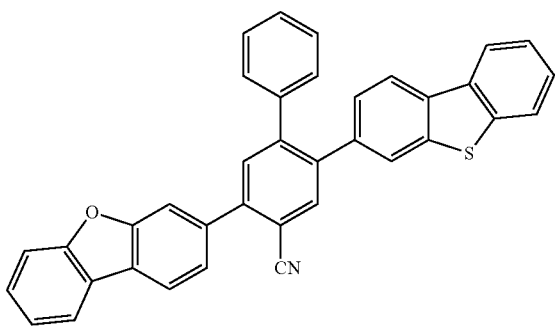

439
-continued
1749
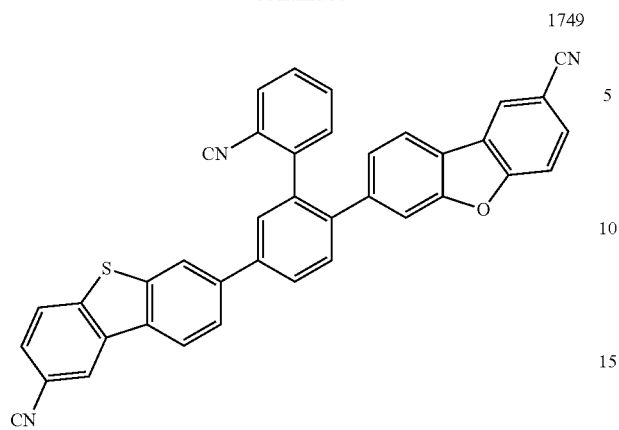
1750
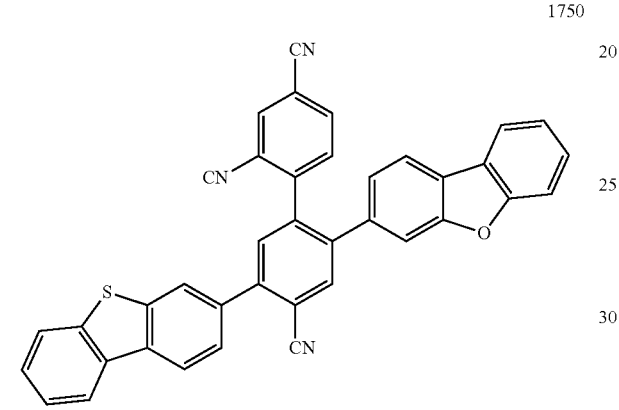
1751
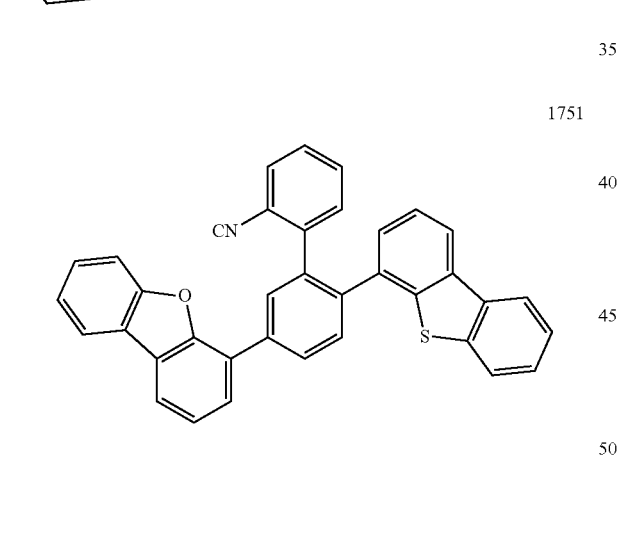
1752
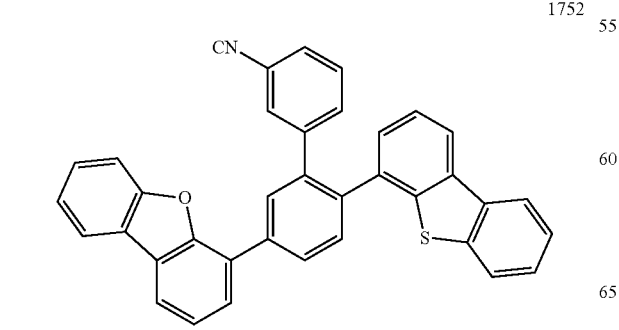
440
-continued
1753
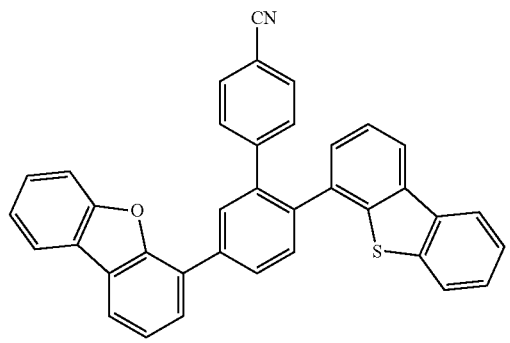
1754
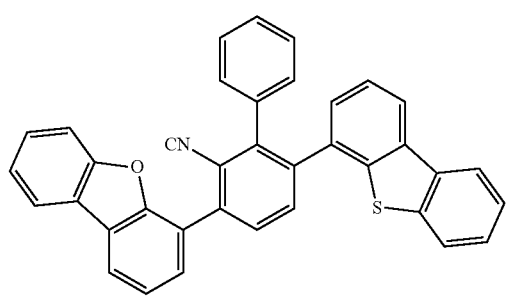
1755
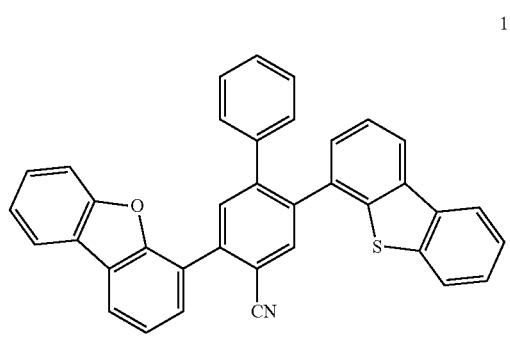
1756
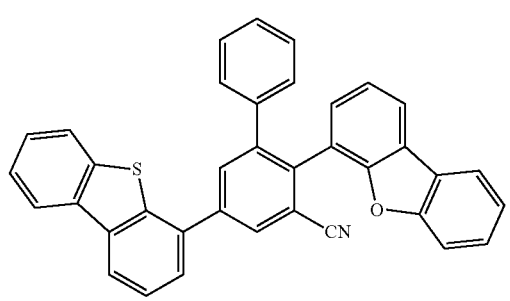
1757
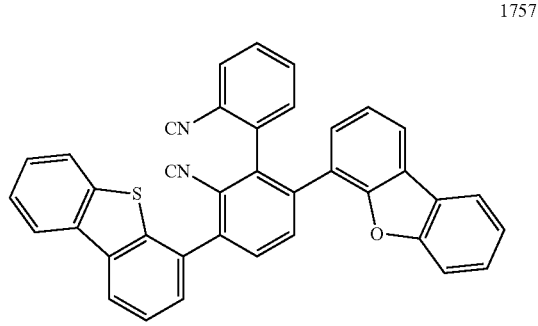

1758
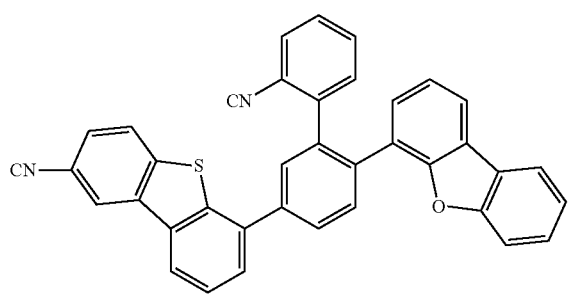
1759
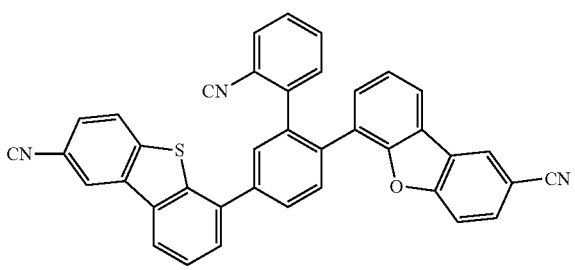
1760
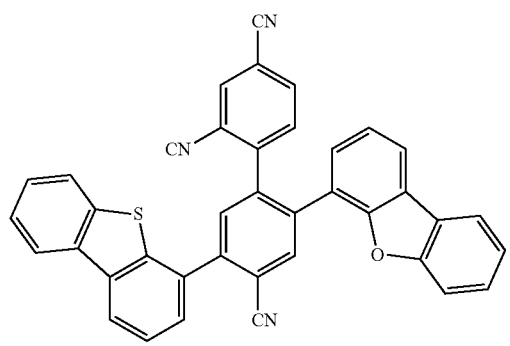
1761
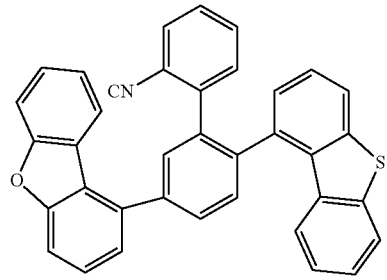
1762
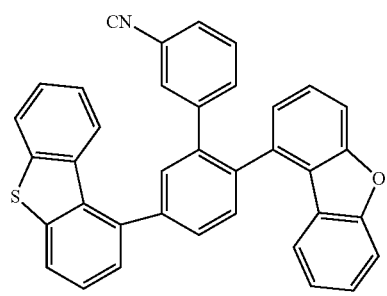
1763
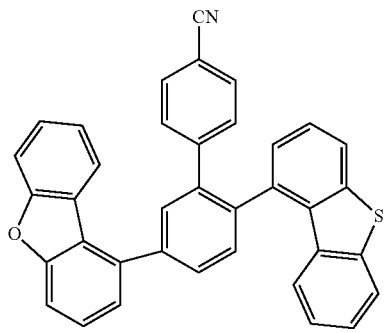
1764
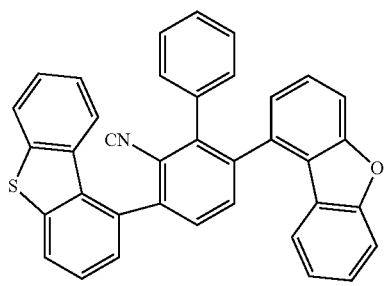
1765
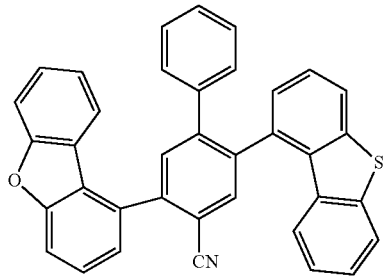
1766
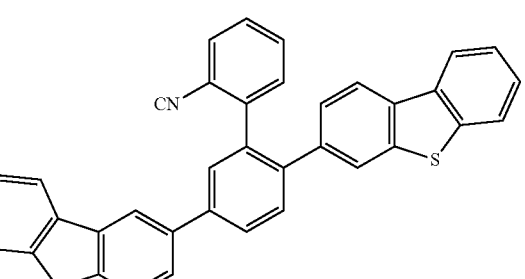
1767
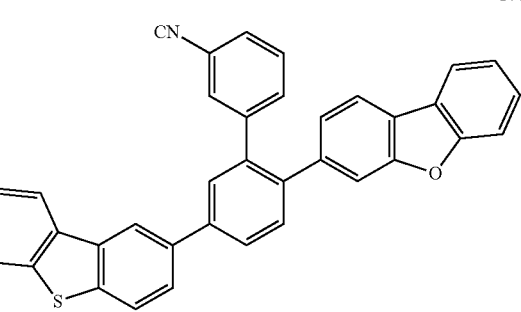

-continued
1768
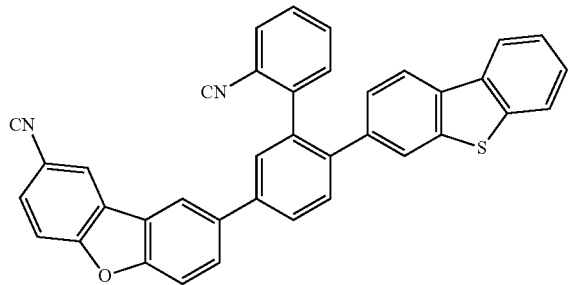
1769
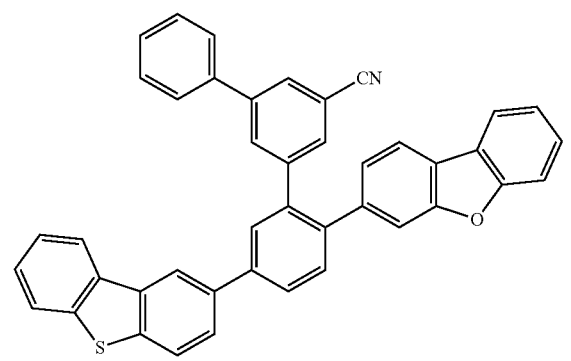
1770
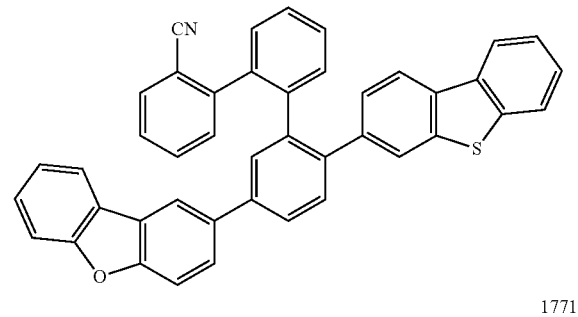
1771
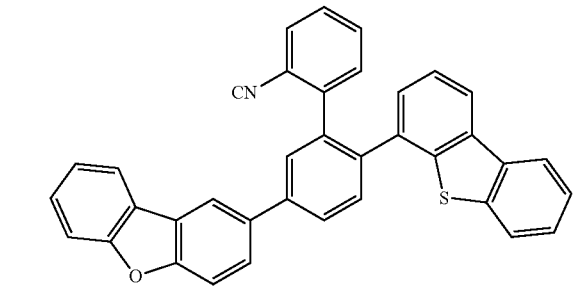
1772
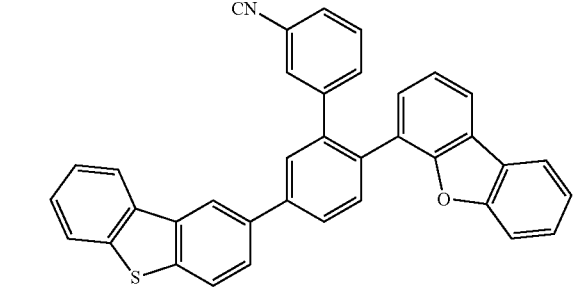
-continued
1773
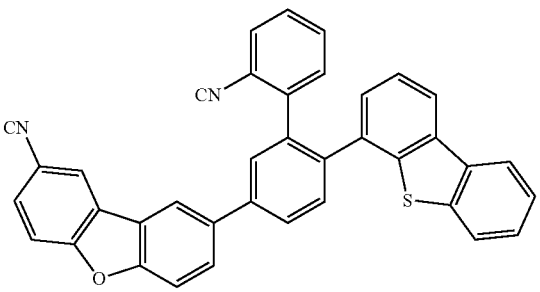
1774
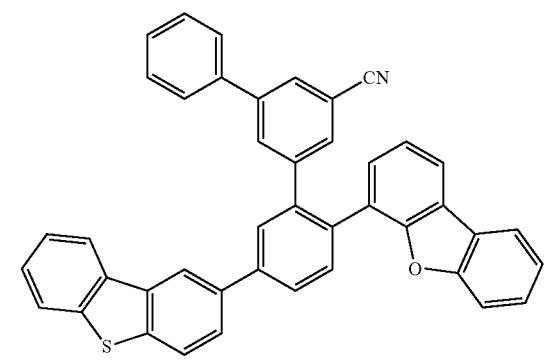
1775
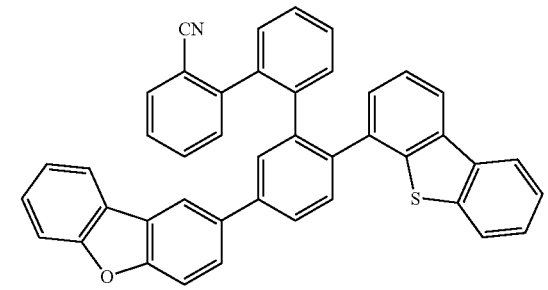
1776
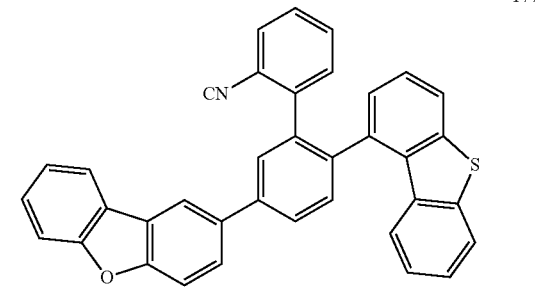
1777
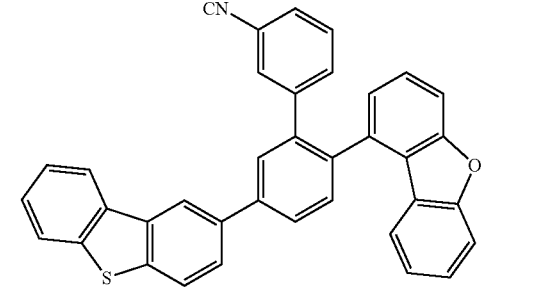

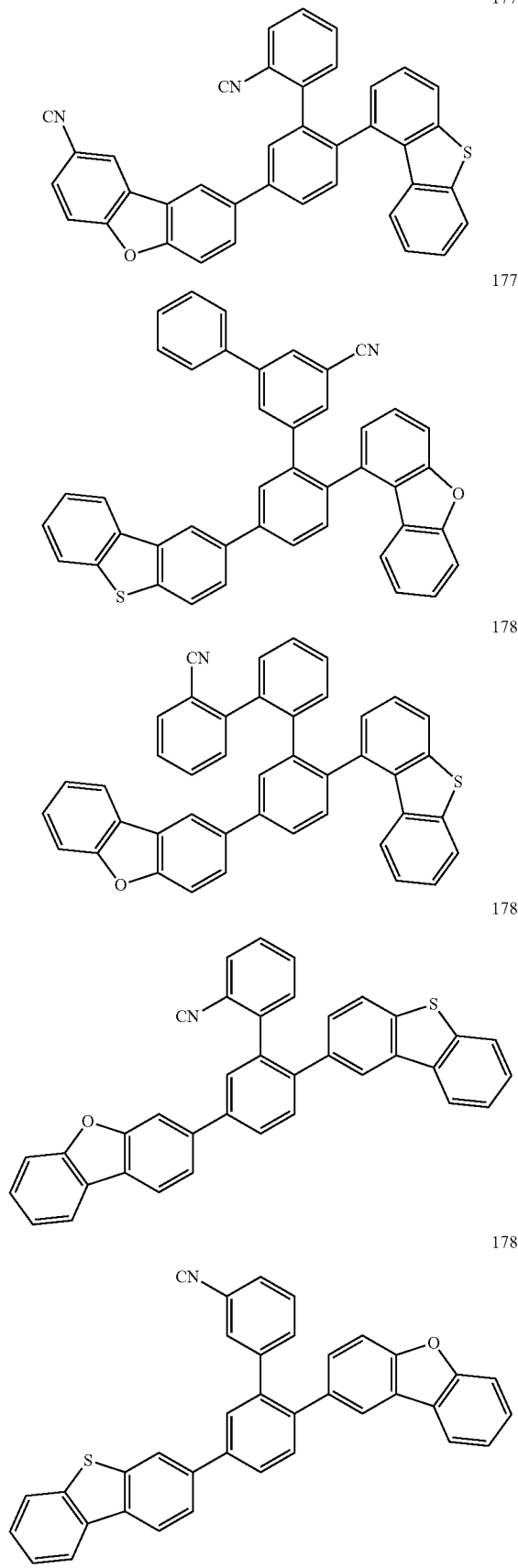

447
-continued
448
-continued
1787
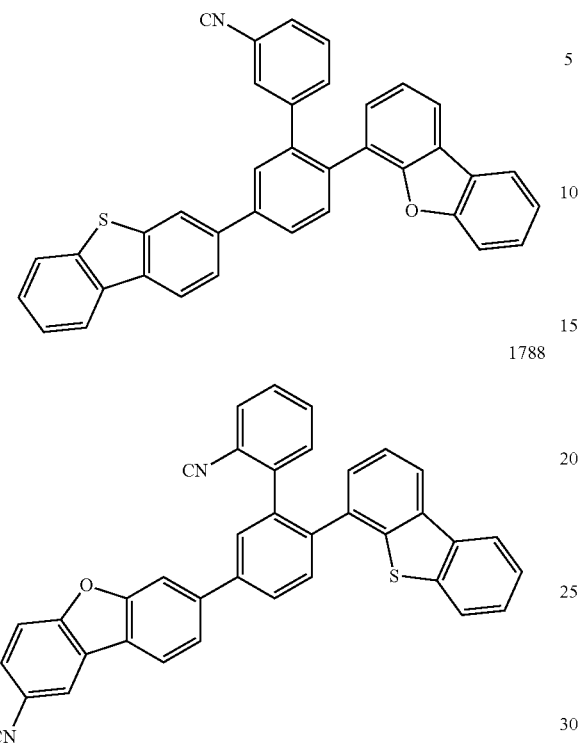
1788
1789
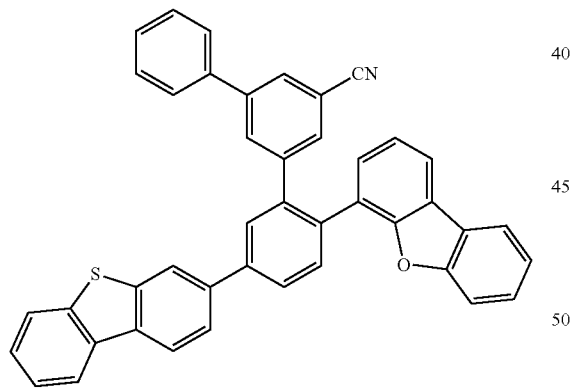
1790
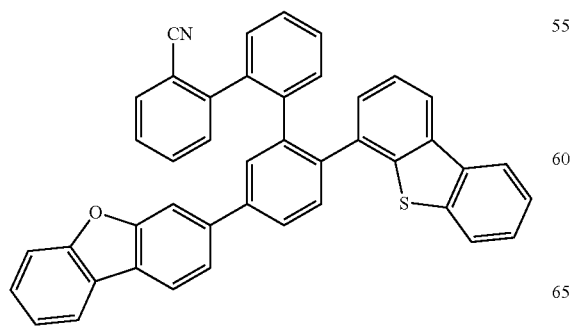
1791
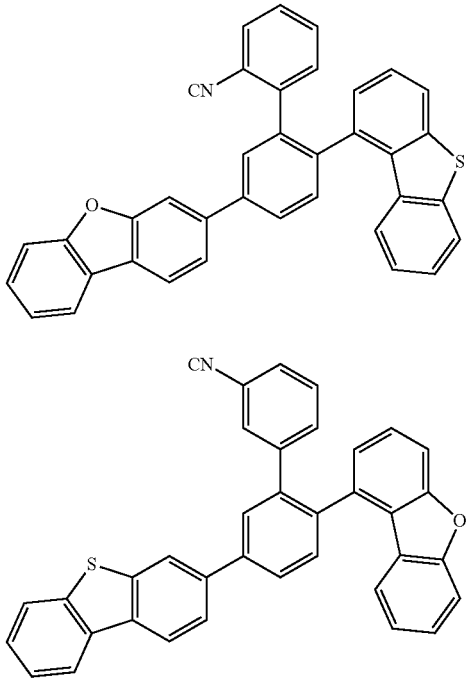
1792
1793
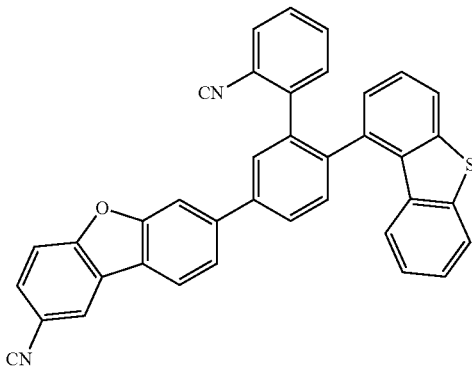
1794
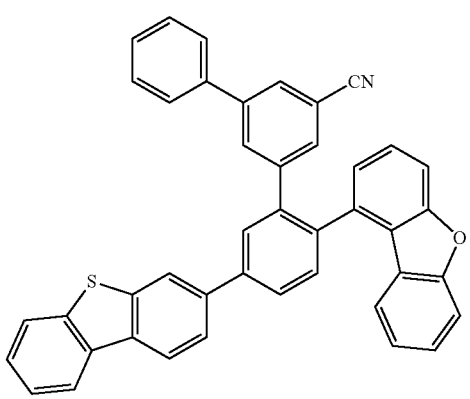

449
-continued
1795
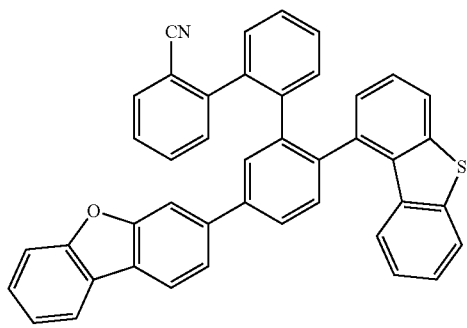
1796
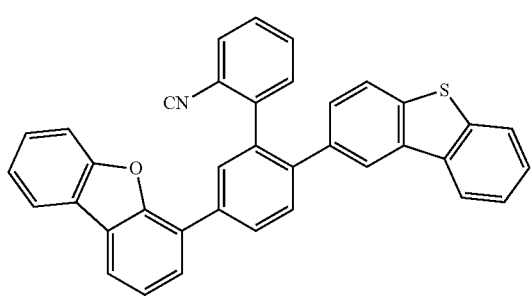
1797
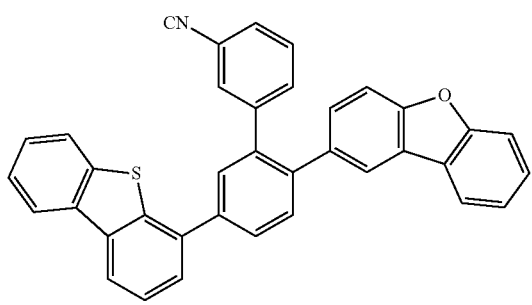
1798
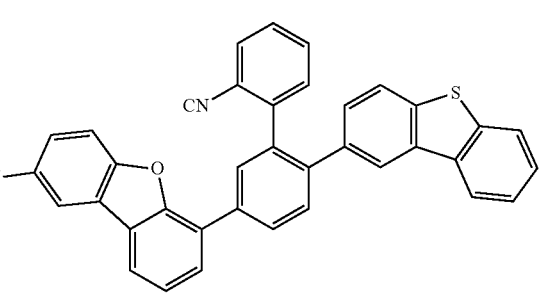
1799
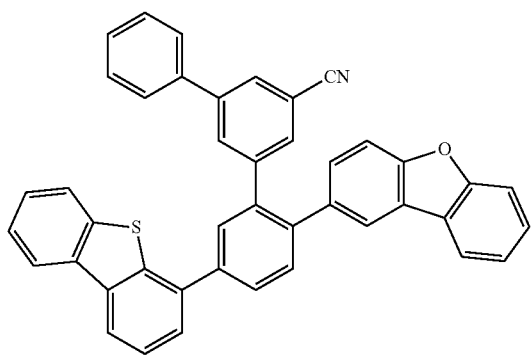
450
-continued
1800
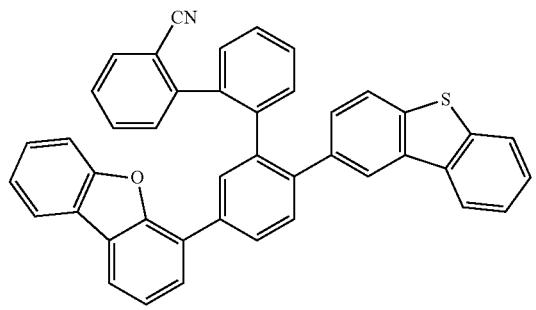
1801
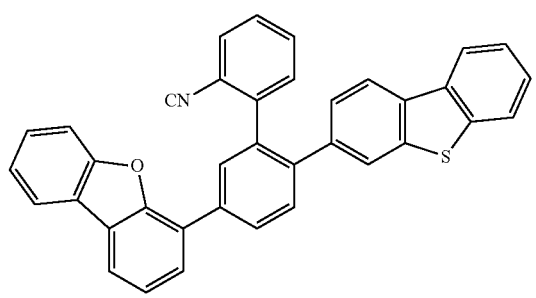
1802
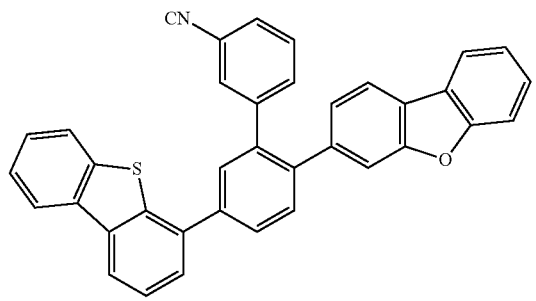
1803
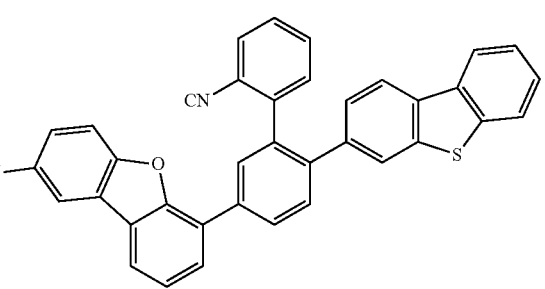
1804
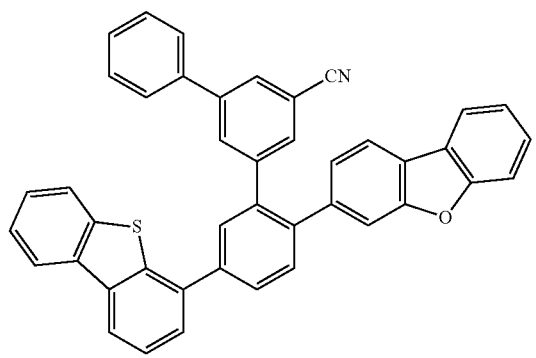

-continued
1805
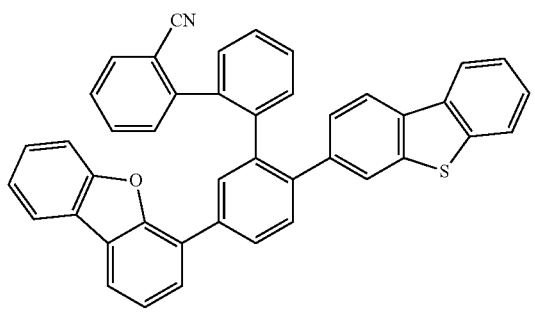
1806
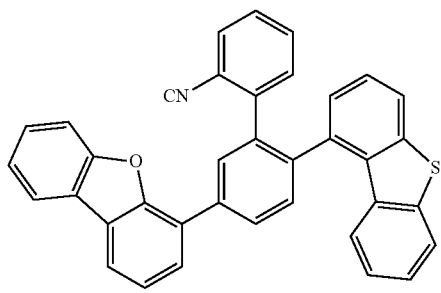
1807
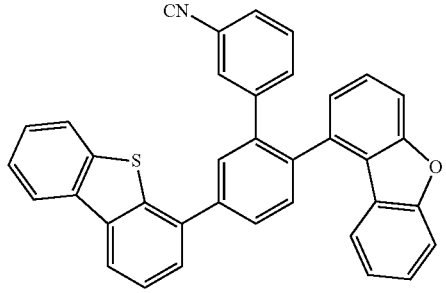
1808
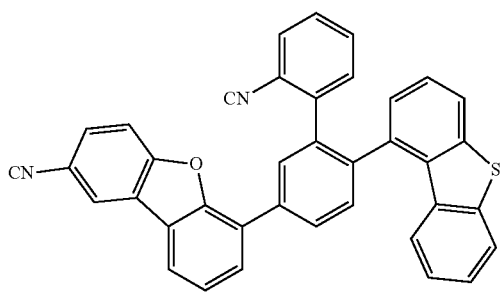
1809
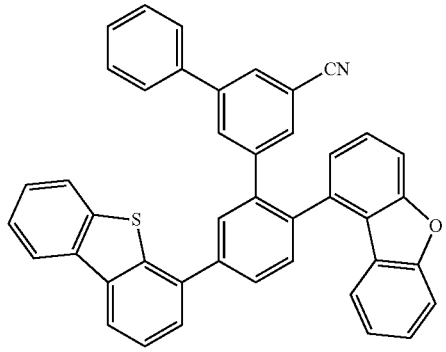
-continued
1810
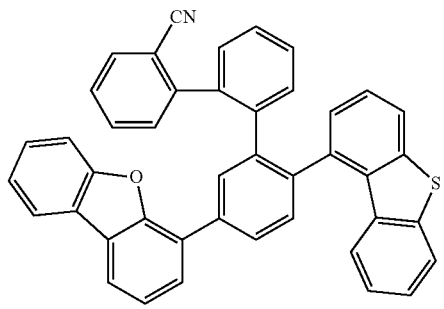
1811
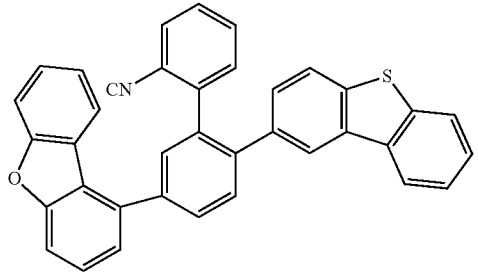
1812
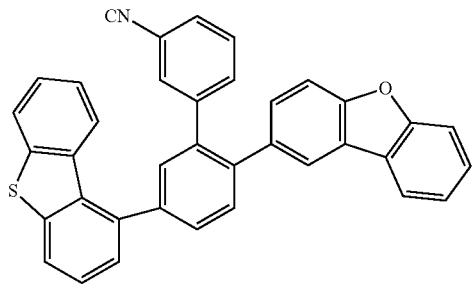
1813
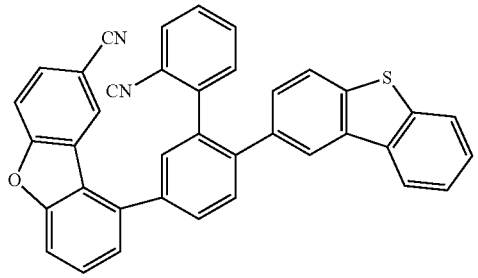
1814
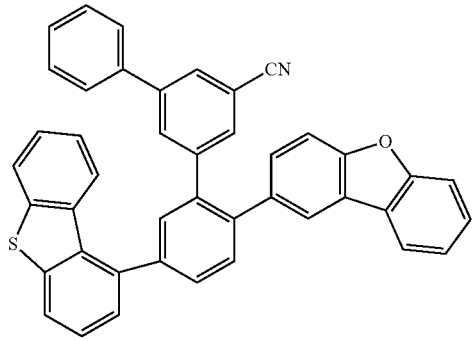

1815
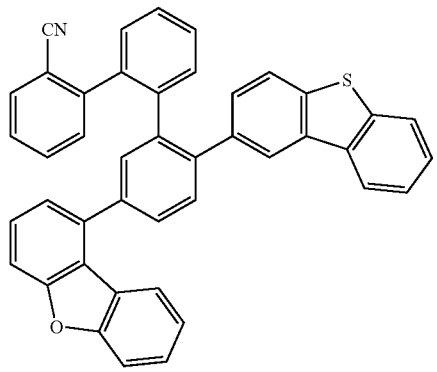
1816
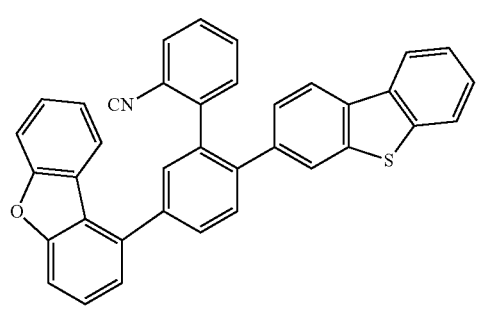
1817
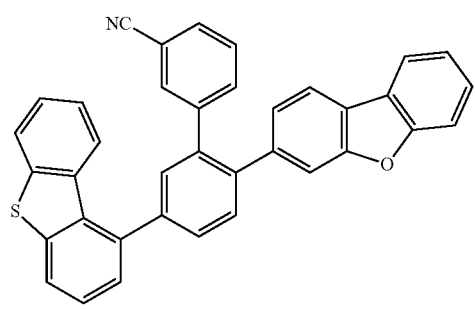
1818
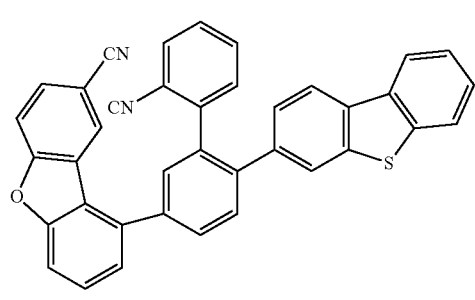
1819
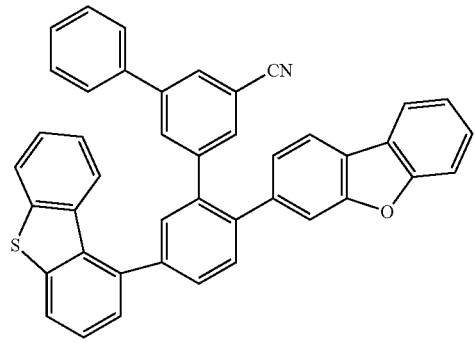
1820
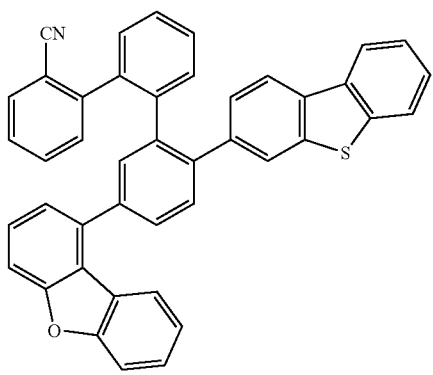
1821
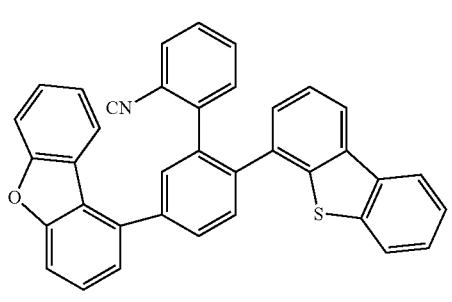
1822
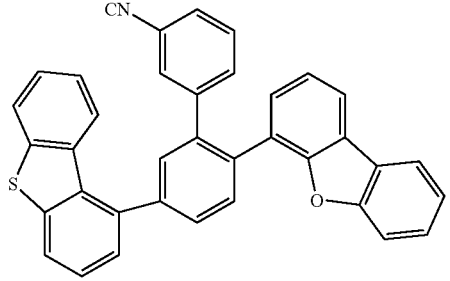
1823
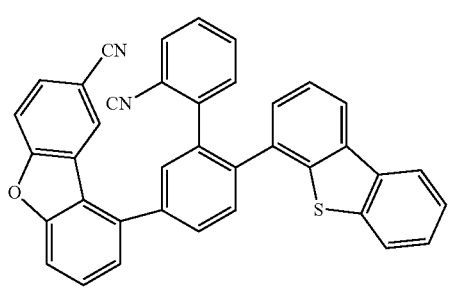
1824
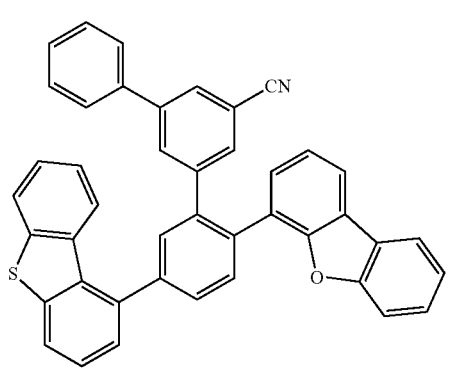

-continued
1825
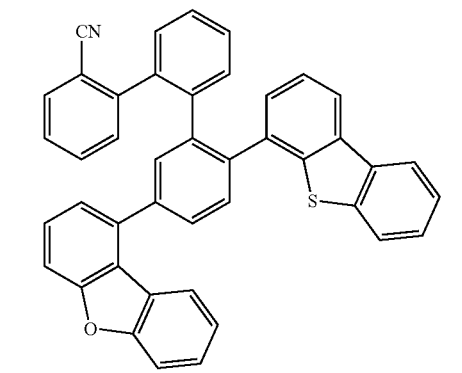
1826
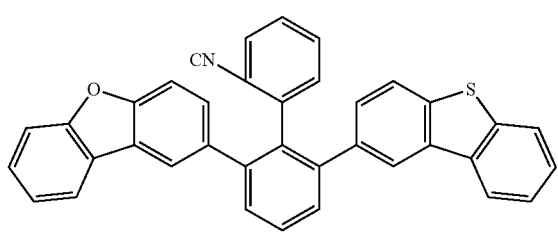
1827
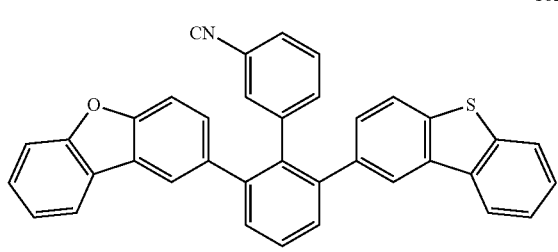
1828
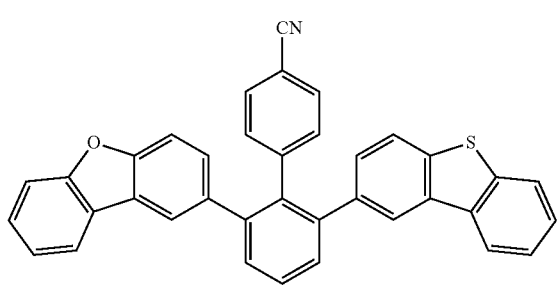
1829
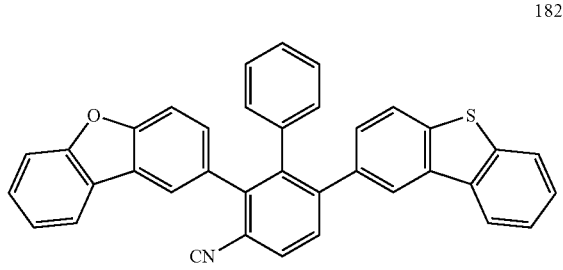
-continued
1830
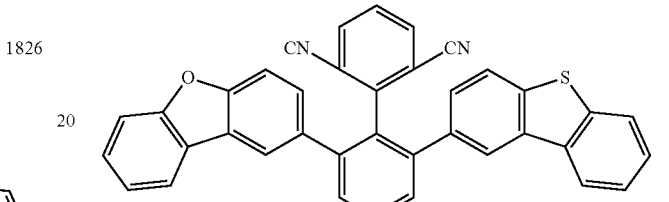
1831
1832
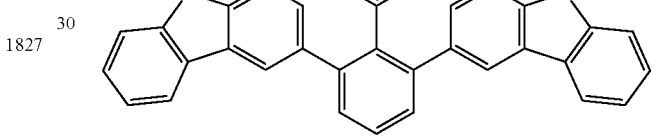
1833
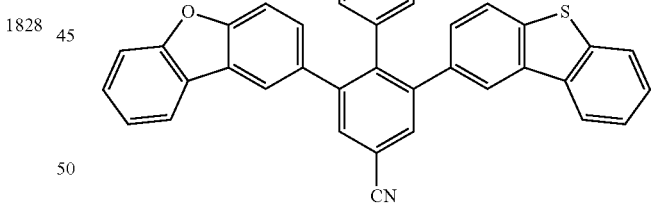
1834
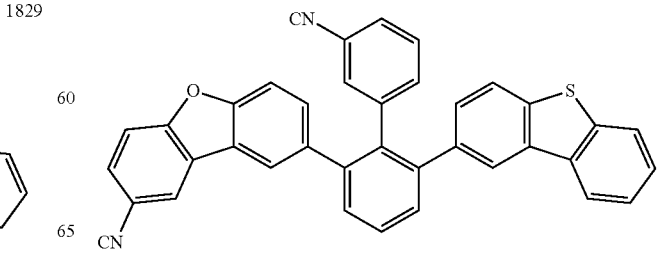

457
-continued
1835
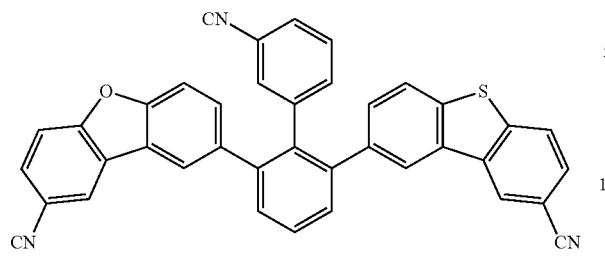
1836
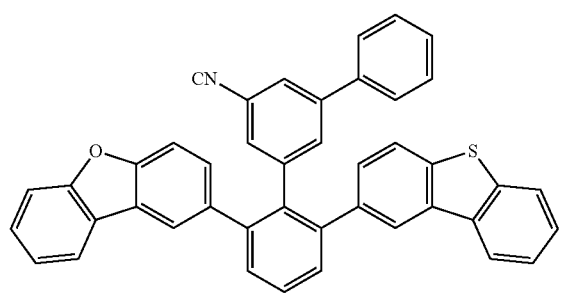
1837
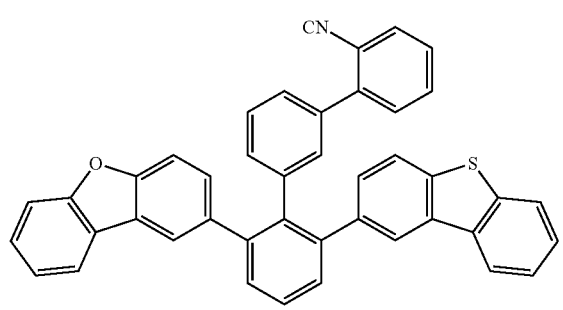
1838
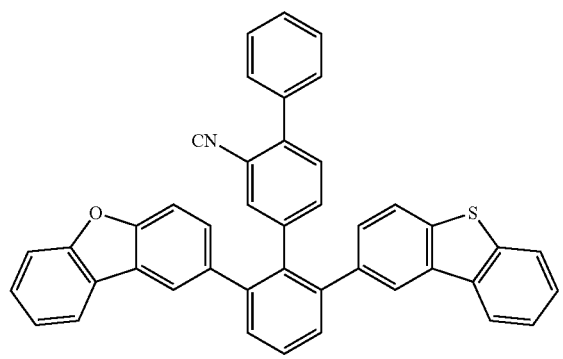
458
-continued
1839
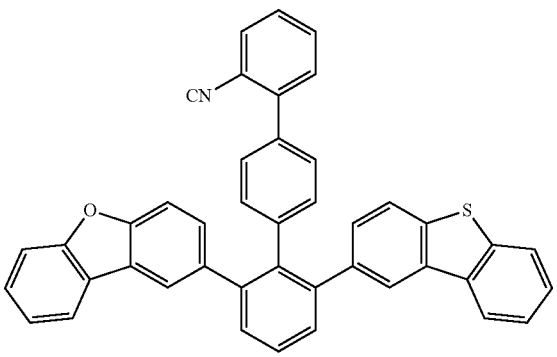
1840
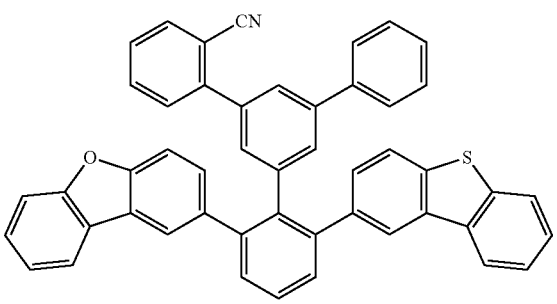
1841
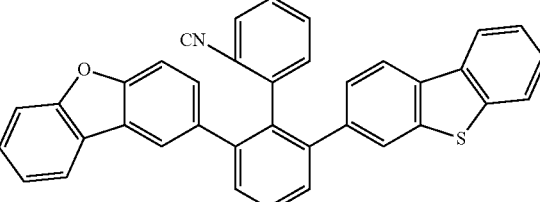
1842
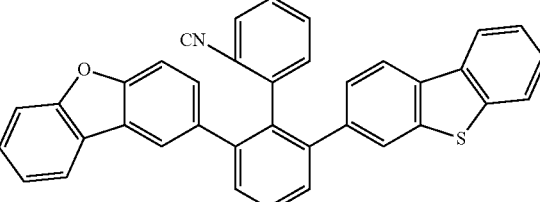
1843
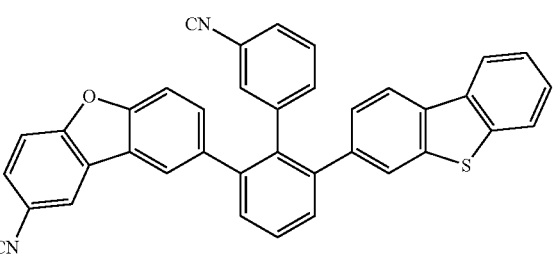

459
-continued
1844
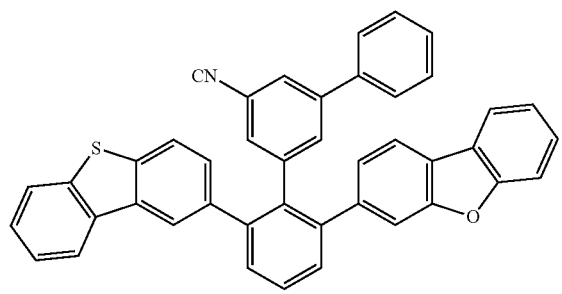
1845
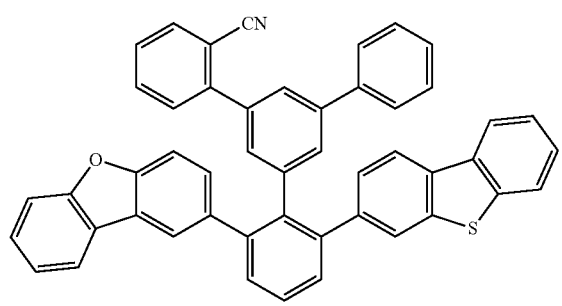
1846
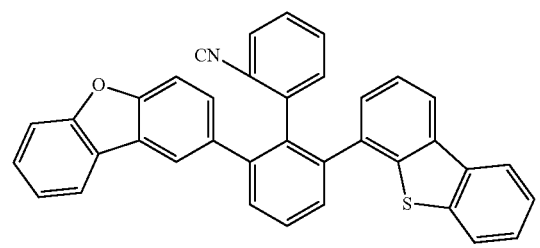
1847
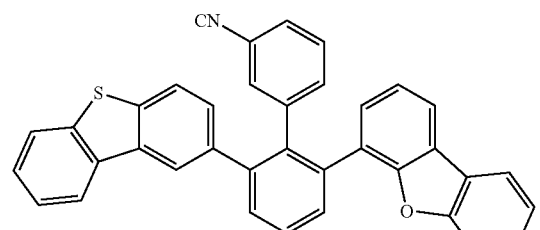
1848
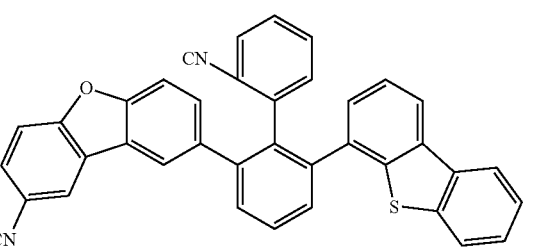
460
-continued
1849
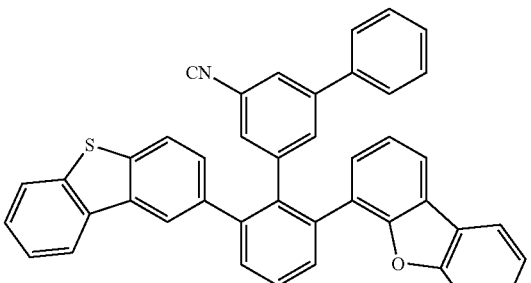
1850
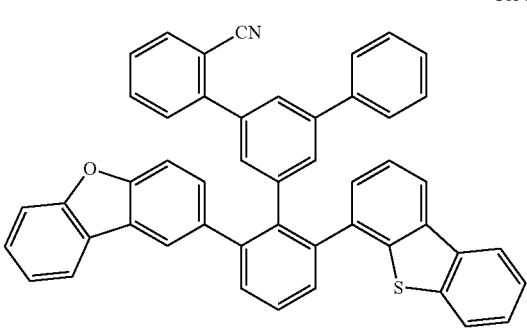
1851
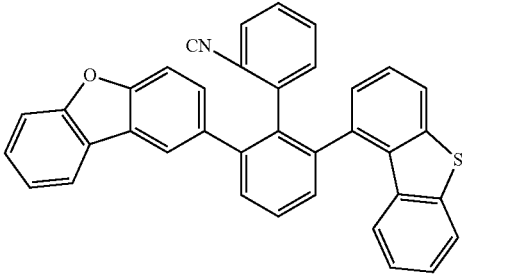
1852
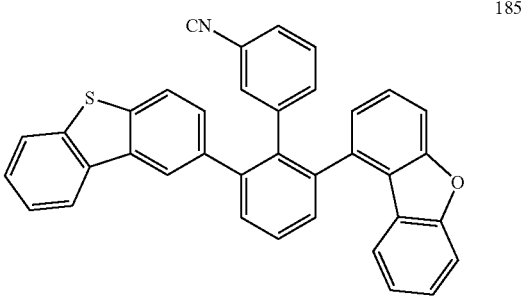
1853
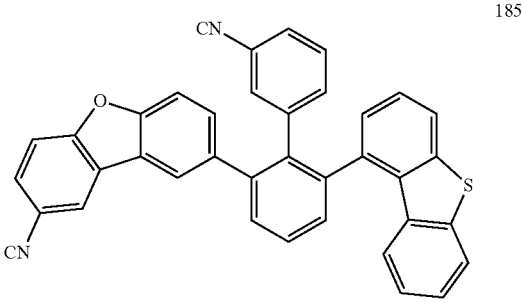

-continued
1854
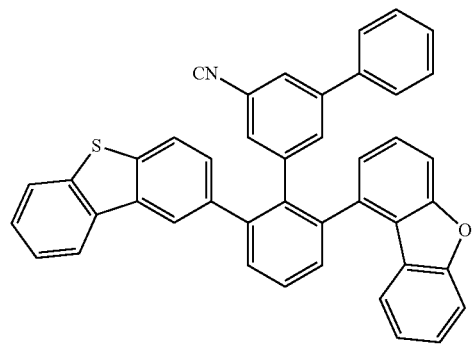
1855
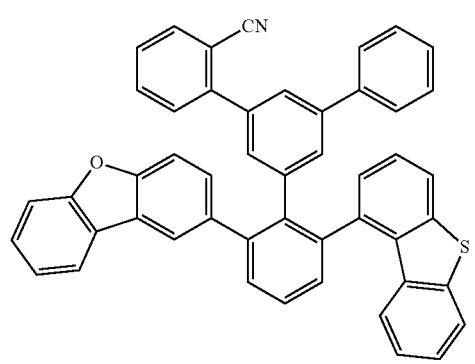
1856
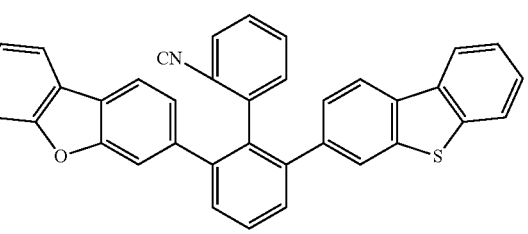
1857
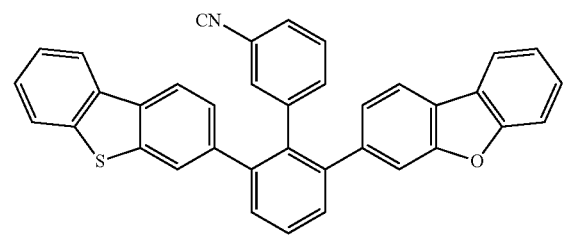
1858
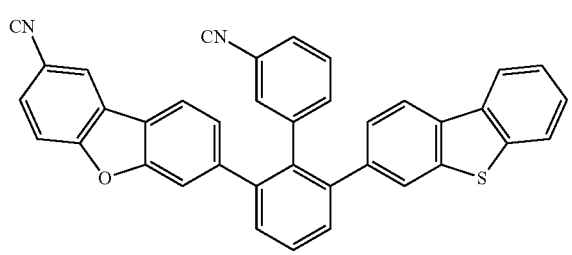
-continued
1859
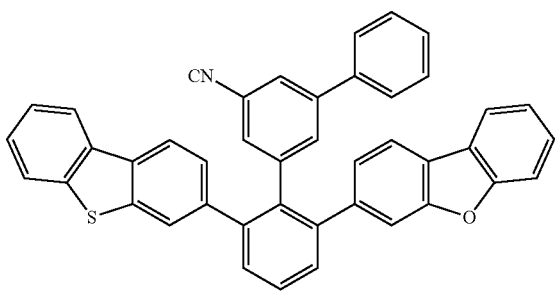
1860
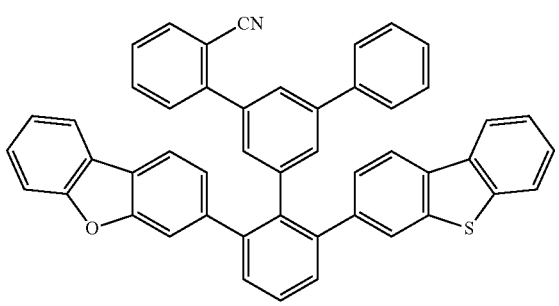
1861
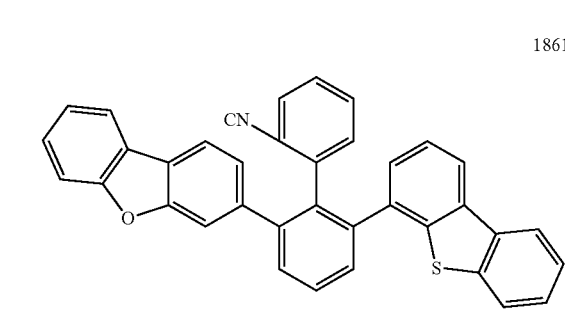
1862
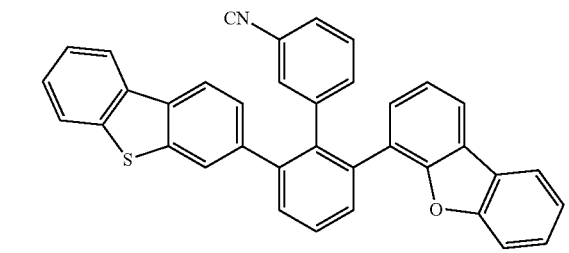
1863
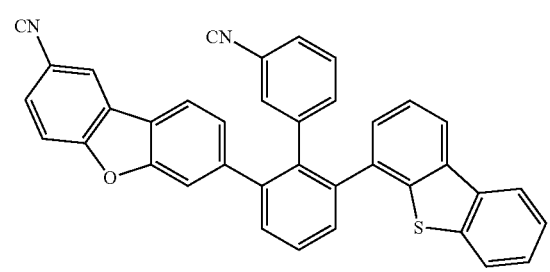

-continued
1864
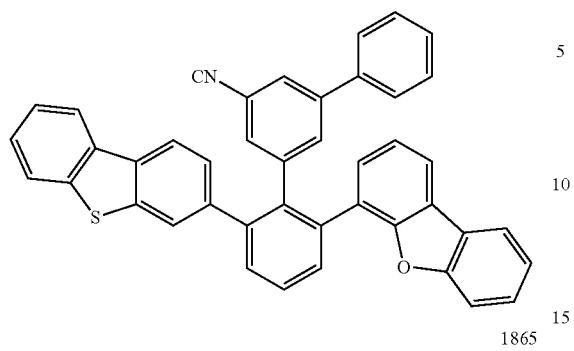
1865
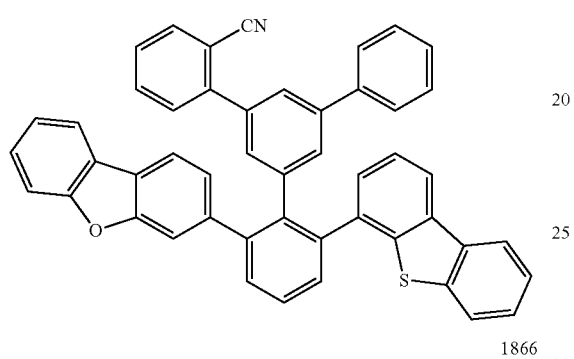
1866
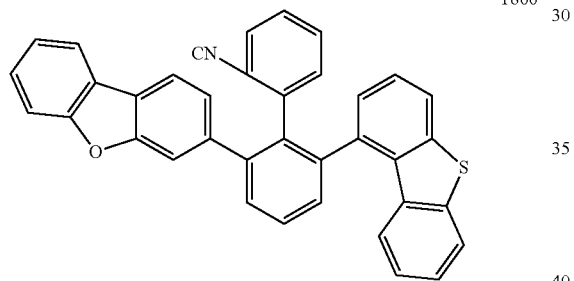
1867
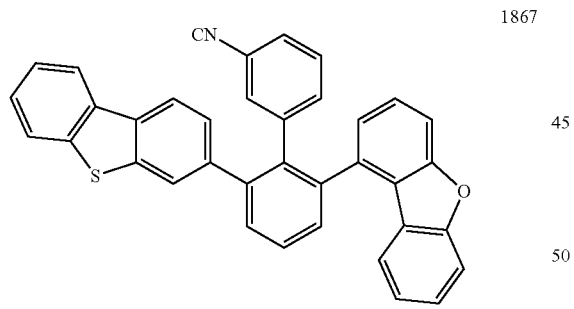
1868
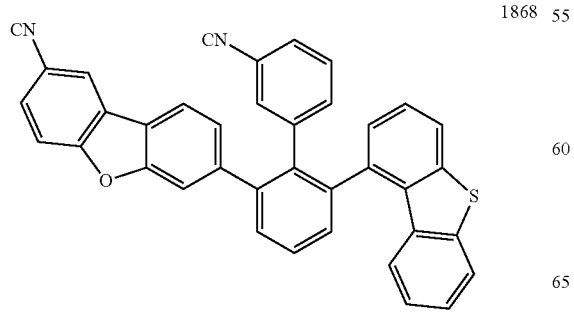
-continued
1869
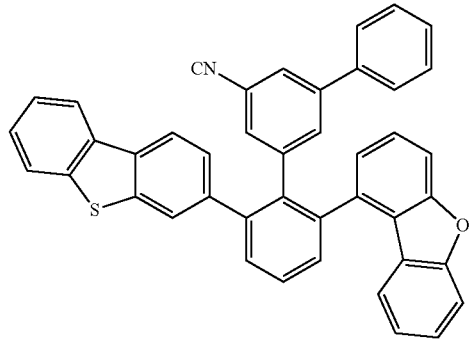
1870
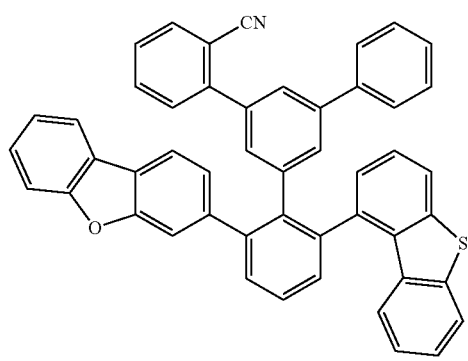
1871
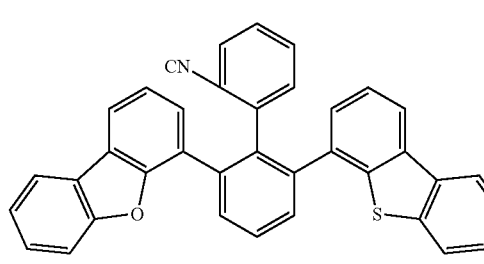
1872
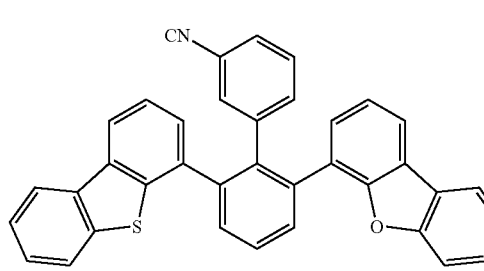
1873
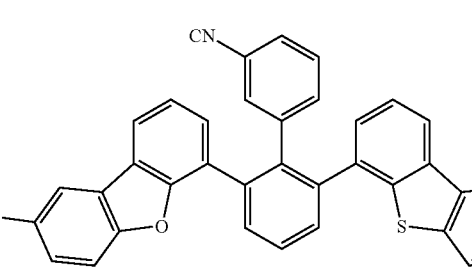

1874
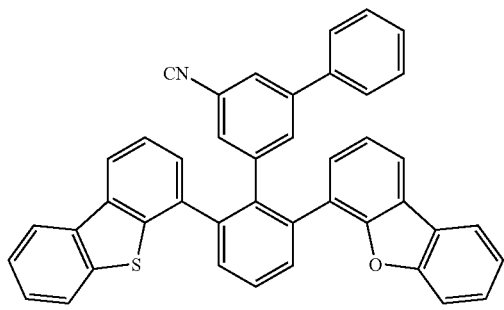
1875
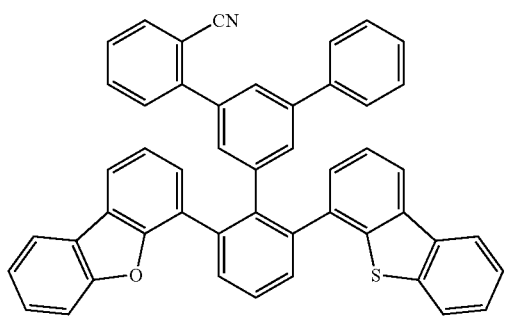
1876
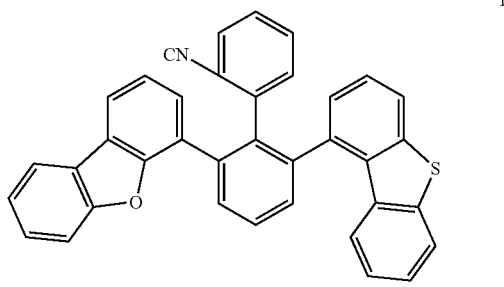
1877
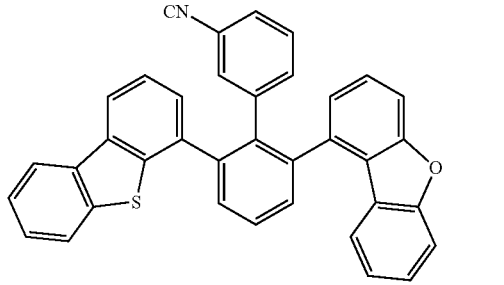
1878
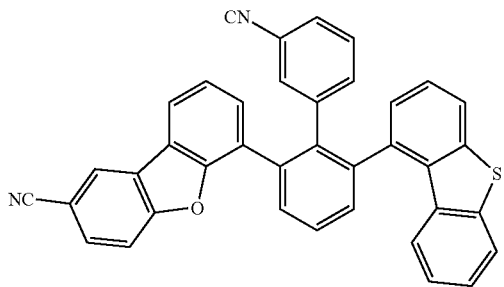
1879
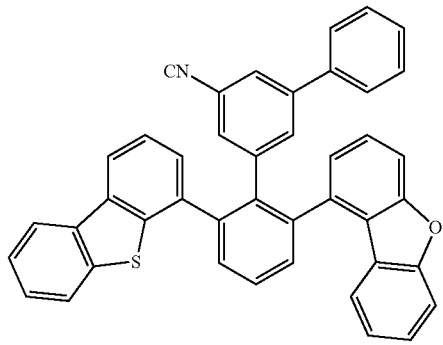
1880
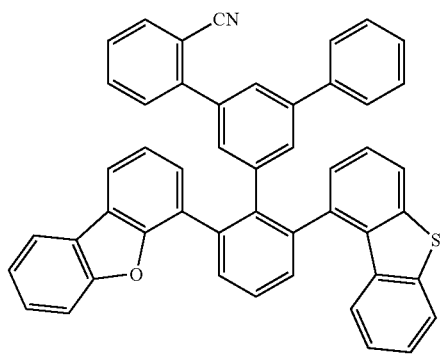
1881
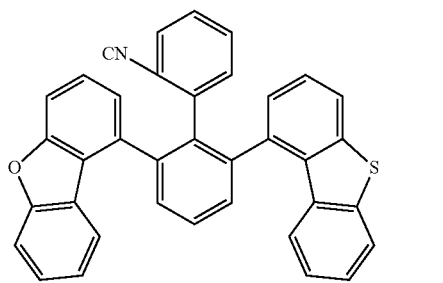
1882
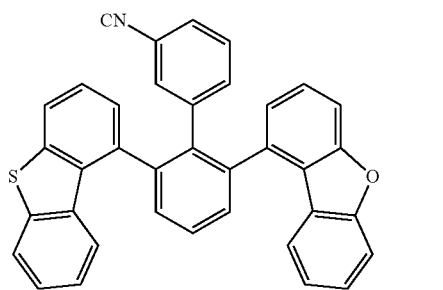
1883
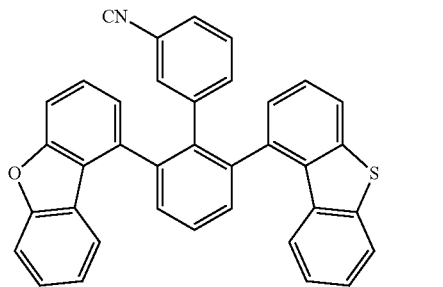

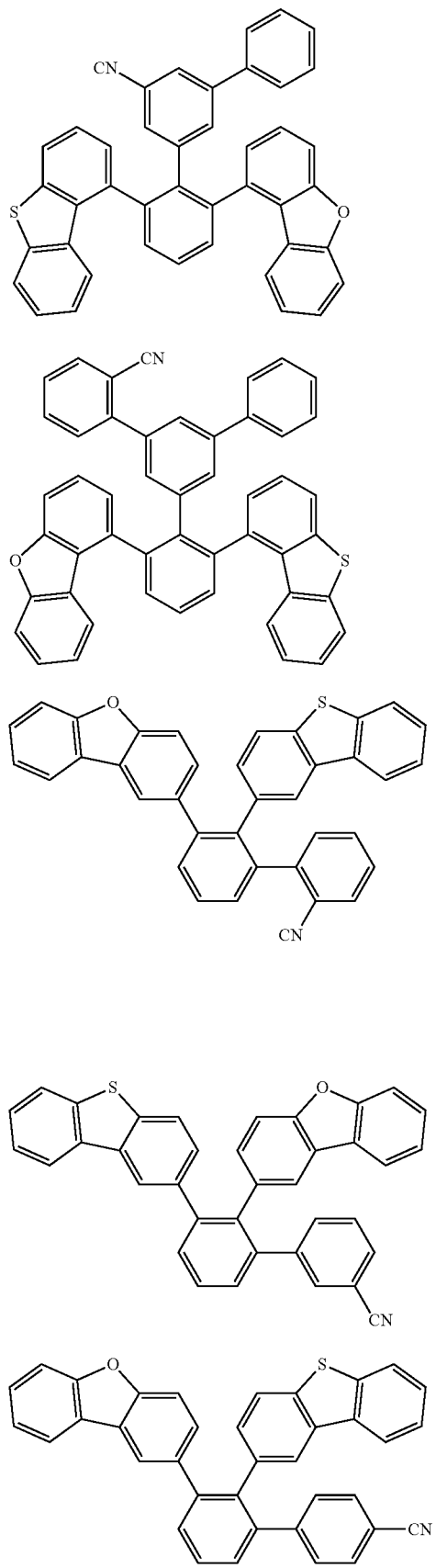
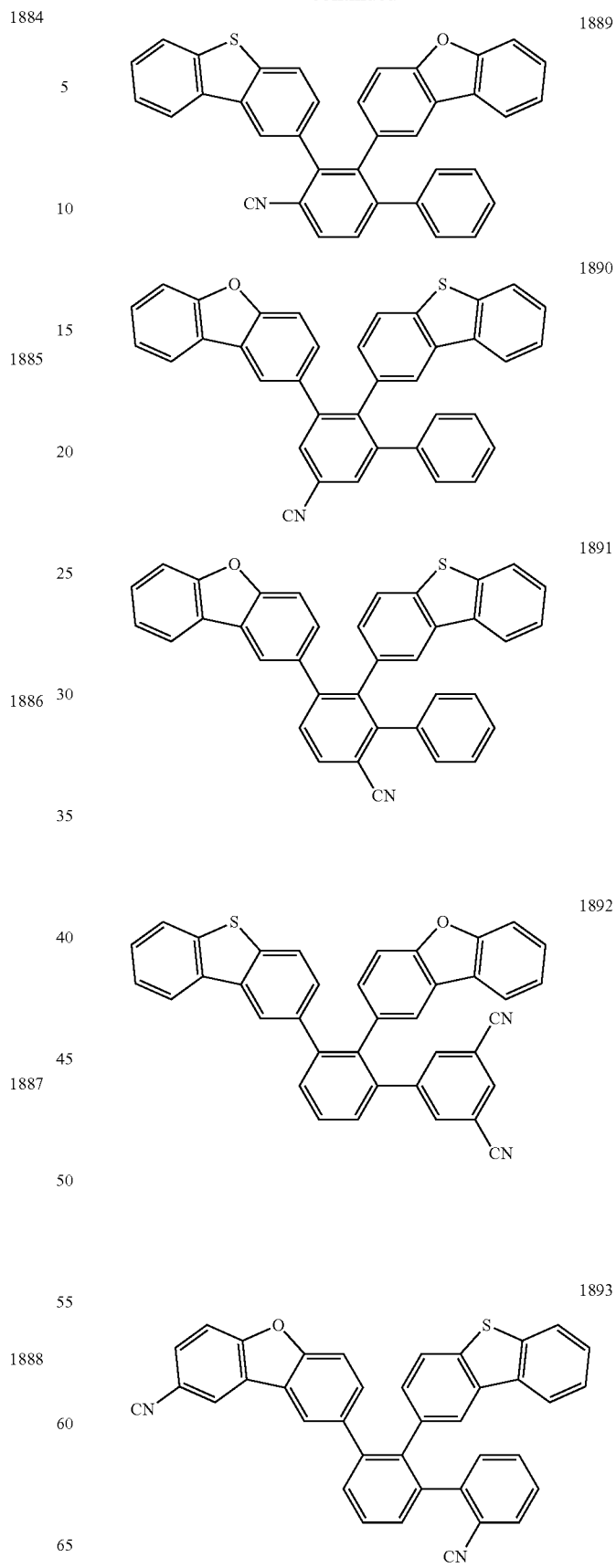

469
-continued
1894
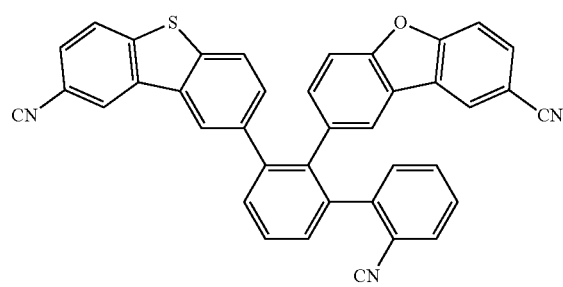
1895
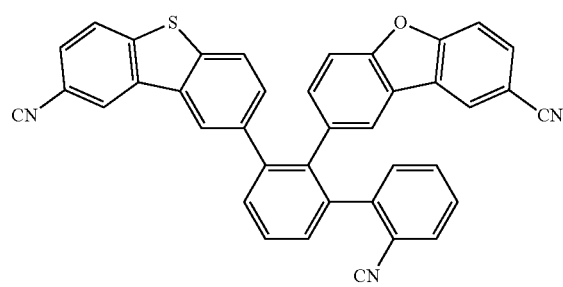
1896
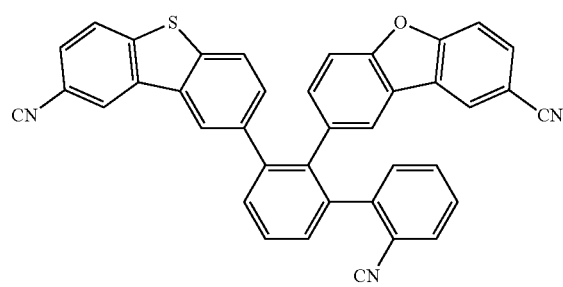
1897
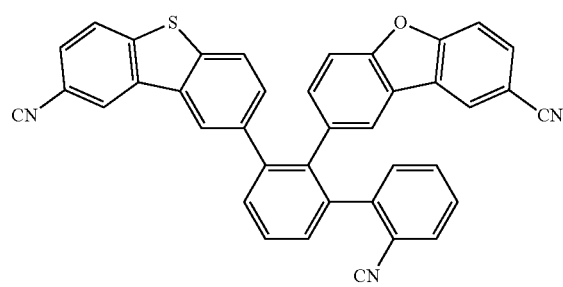
1898
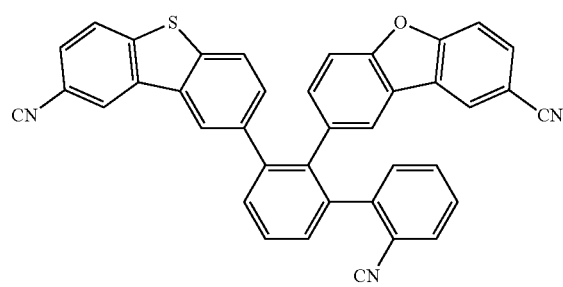
470
-continued
1899
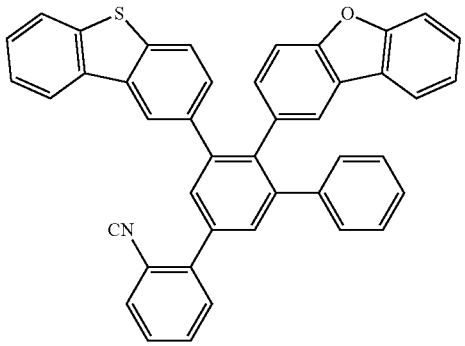
1900
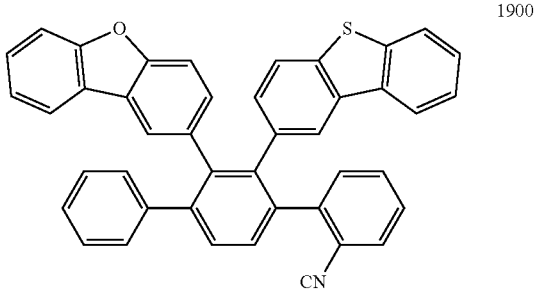
1901
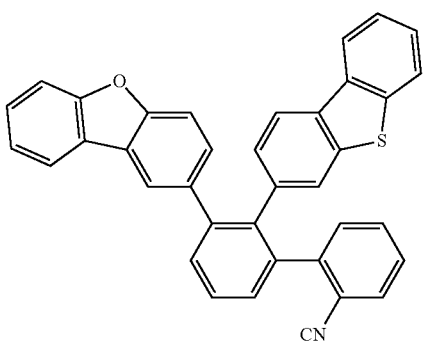
1902
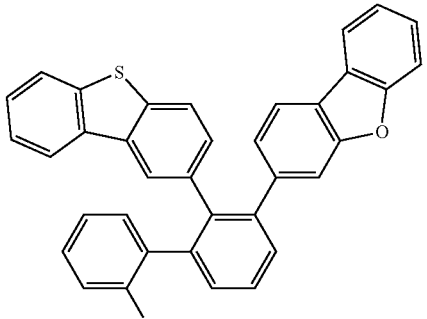
1903
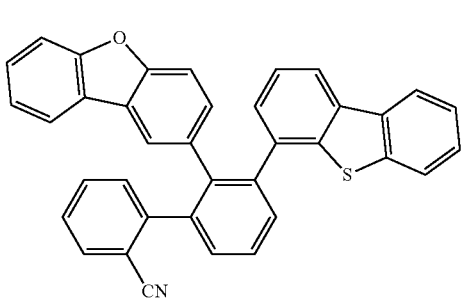

471
-continued
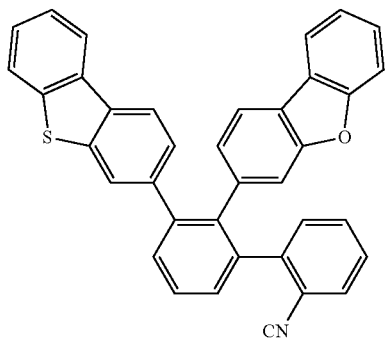
1904
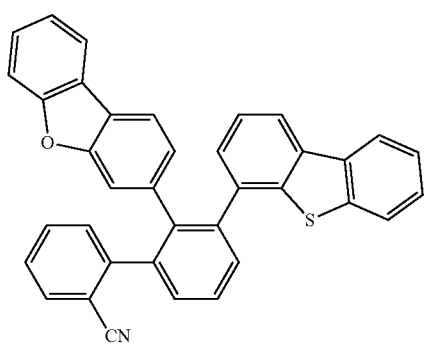
1905
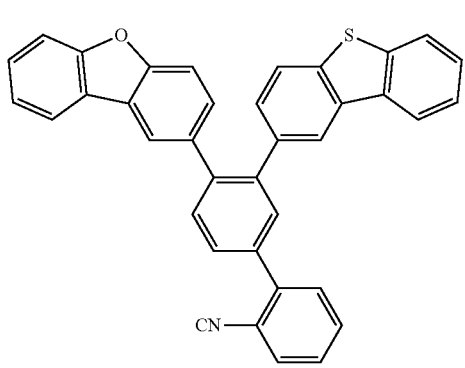
1906
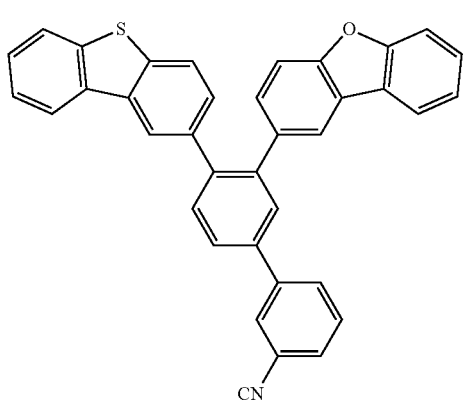
1907
472
-continued
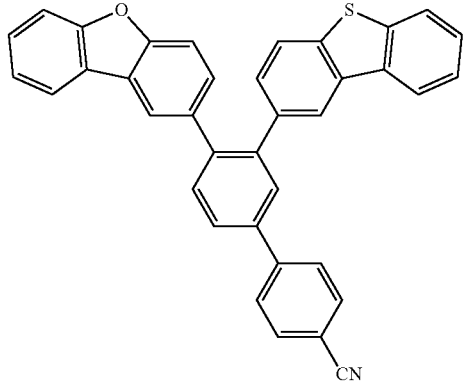
1908
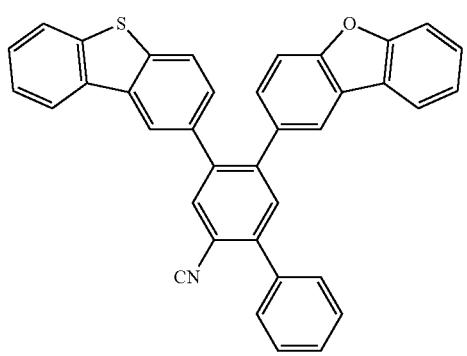
1909
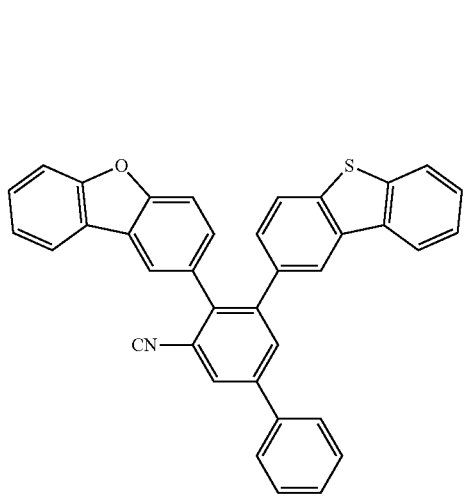
1910
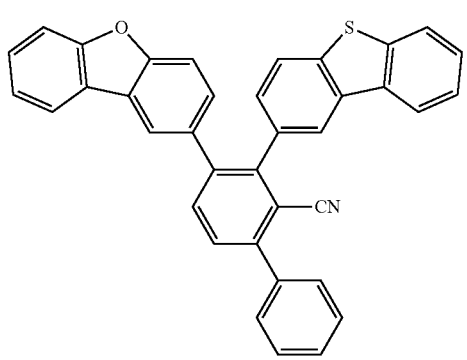
1911

473
-continued
1912
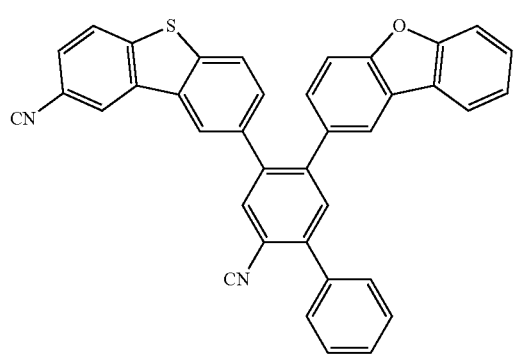
1913
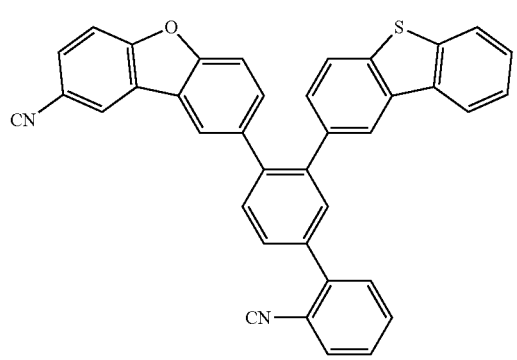
1914
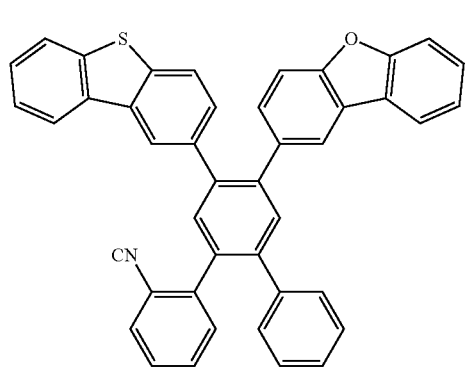
1915
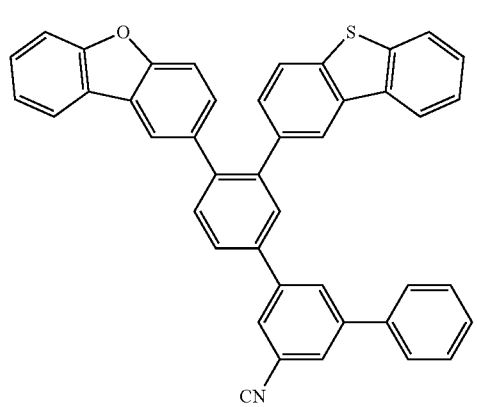
474
-continued
1916
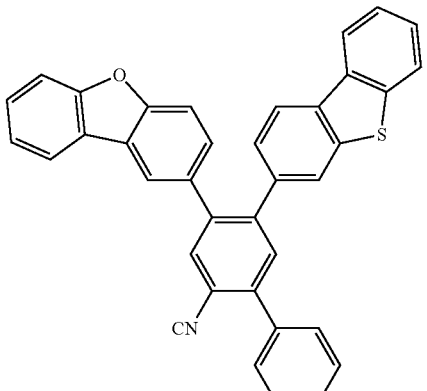
1917
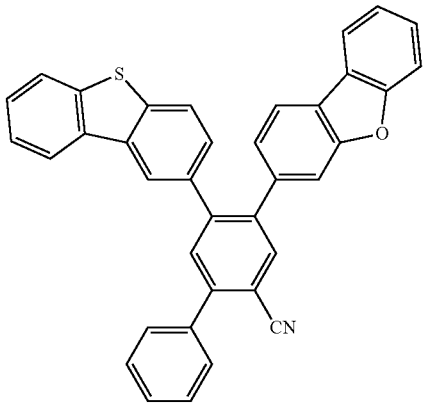
1918
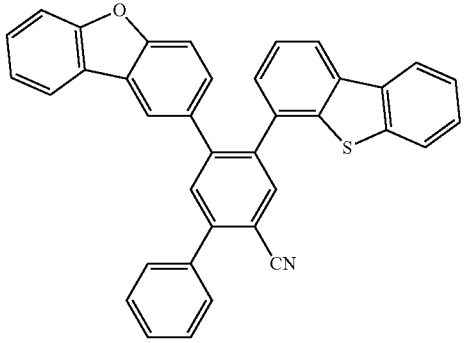
1919
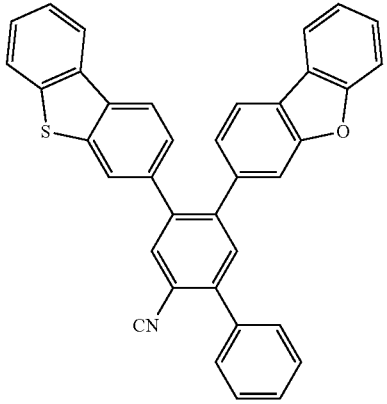

-continued

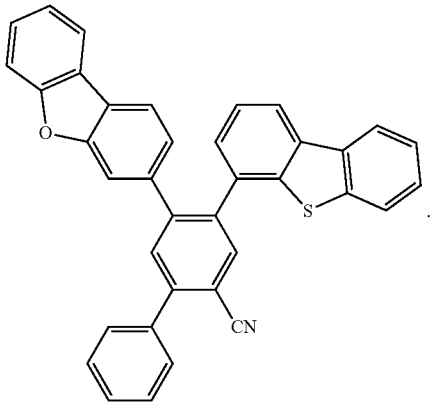

In Formula 1, $Ar_1$ is a group represented by Formula 3A, and $Ar_2$ is a group represented by Formula 3B. That is, $Ar_1$ and $Ar_2$ in Formula 1 may each independently include a dibenzofuran ring or a dibenzothiophene ring. Therefore, since the condensed cyclic compound represented by Formula 1 may have high glass transition temperature ($T_g$), high thermal decomposition temperature ($T_d$), excellent thermal stability, and high charge mobility, an electronic device, for example, an organic light-emitting device, which includes the condensed cyclic compound represented by Formula 1, may have high luminescent efficiency and/or a long lifespan.

In addition, $L_1$ (that is, a group represented by Formula 2) in Formula 1 includes at least one cyano group. Therefore, since the condensed cyclic compound represented by Formula 1 has a relatively high triplet ($T_1$) energy level and excellent electron mobility characteristics, an electronic device, for example, an organic light-emitting device (in an embodiment, an organic light-emitting device that emits blue light), which includes the condensed cyclic compound represented by Formula 1, may have high luminescent efficiency and/or a long lifespan.

Furthermore, since n2 and n3 in Formula 2 are not 0, the group represented by Formula 2 essentially includes two or more benzene rings linked via a single bond. Therefore, the intramolecular conjugation length of the condensed cyclic compound represented by Formula 1 may appropriately increase and charge mobility characteristics may be improved. Due to the molecular size increase effect, the condensed cyclic compound represented by Formula 1 may have high glass transition temperature ($T_g$) and thermal decomposition temperature ($T_d$), and thus, the condensed cyclic compound represented by Formula 1 may have excellent thermal stability.

Finally, $Ar_1$ and $Ar_2$ in Formula 1 are directly linked to $L_1$ via a single bond. Therefore, it is possible to ensure an appropriate intramolecular conjugation length while maintaining a high triplet energy level. Therefore, an electronic device, for example, an organic light-emitting device (in an embodiment, an organic light-emitting device that emits blue light), which includes the condensed cyclic compound represented by Formula 1, may have high luminescent efficiency and/or a long lifespan.

As described above, the condensed cyclic compound represented by Formula 1 may have electric characteristics suitable for use as a material for an organic light-emitting device, in particular, a blue light-emitting device, for example, a host material in an emission layer. Therefore, an organic light-emitting device including the condensed cyclic compound may have high efficiency and/or a long lifespan.

For example, HOMO, LUMO, $T_1$, and $S_1$ energy levels of some Compounds were evaluated by using a DFT method of Gaussian program (structurally optimized at a level of B3LYP, 6-31G(d,p)), and results thereof are shown in Table 1.

| Compound No. | HOMO (eV) | LUMO (eV) | $T_1$ (eV) | $S_1$ (eV) |
|---|---|---|---|---|
| 1 | −5.866 | −1.507 | 3.043 | 3.858 |
| 2 | −5.973 | −1.494 | 3.023 | 3.997 |
| 3 | −6.010 | −1.704 | 2.950 | 3.822 |
| 9 | −5.929 | −2.055 | 3.036 | 3.425 |
| 44 | −6.332 | −1.736 | 3.038 | 4.044 |
| 62 | −5.959 | −1.490 | 3.001 | 4.000 |
| 121 | −5.822 | −1.529 | 3.052 | 3.834 |
| 201 | −5.854 | −1.451 | 2.915 | 3.878 |
| 321 | −5.842 | −1.474 | 2.964 | 3.858 |
| 521 | −5.742 | −1.467 | 3.021 | 3.771 |
| 667 | −6.018 | −1.377 | 3.146 | 4.100 |
| 746 | −5.746 | −1.528 | 3.016 | 3.760 |
| 761 | −5.717 | −1.535 | 2.976 | 3.741 |
| 762 | −5.824 | −1.522 | 2.965 | 3.876 |
| 1521 | −5.783 | −1.522 | 3.006 | 3.802 |

Referring to Table 1, it is confirmed that the condensed cyclic compound represented by Formula 1 has a relatively high triplet ($T_1$) energy level and may freely adjust the HOMO and LUMO energy levels according to the type of the substituent.

A method of synthesizing the condensed cyclic compound represented by Formula 1 may be recognized by those of ordinary skill in the art by referring to Synthesis Examples provided below.

Another aspect provides a composition including a first compound and a second compound,
wherein the first compound is the condensed cyclic compound represented by Formula 1,
the second compound is a compound including at least one selected from a carbazole group, a dibenzofuran group, a dibenzothiophene group, an indenocarbazole group, an indolocarbazole group, a benzofurocarbazole group, a benzothienocarbazole group, an acridine group, a dihydroacridine group, and a triindolobenzene group and not including an electron withdrawing group, the electron withdrawing group includes:
—F, —CFH$_2$, —CF$_2$H, —CF$_3$, —CN, and —NO$_2$;
a $C_1$-$C_{60}$ alkyl group substituted with at least one selected from —F, —CFH$_2$, —CF$_2$H, —CF$_3$, —CN, and —NO$_2$;
a $C_1$-$C_{60}$ heteroaryl group and a monovalent non-aromatic condensed heteropolycyclic group, each including *=N—*' as a ring-forming moiety; and
a $C_1$-$C_{60}$ heteroaryl group and a monovalent non-aromatic condensed heteropolycyclic group, each substituted with at least one selected from deuterium, —F, —CFH$_2$, —CF$_2$H, —CF$_3$, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and each including *=N—*' as a ring-forming moiety.

The first compound may be different from the second compound.

The composition may be used to manufacture, for example, an organic layer of an electronic device (for example, an organic light-emitting device).

In the composition, the first compound may be an electron transport material, and the second compound may be a hole transport material.

In an embodiment, the composition may consist of the first compound and the second compound, but embodiments of the present disclosure are not limited thereto.

The condensed cyclic compound represented by Formula 1, which may be the first compound in the composition, is the same as described herein.

For example, the second compound in the composition may be selected from compounds represented by Formula H-1:

$Ar_{11}$-$(L_{11})_{d1}$-$Ar_{12}$.  Formula H-1

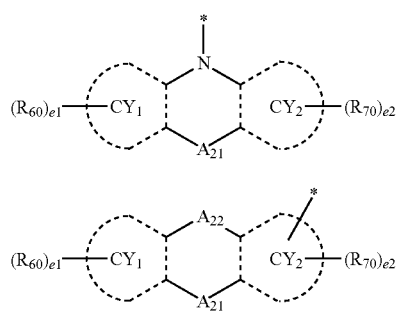

In Formulae H-1, 11, and 12, $L_{11}$ may be selected from:

a single bond, a phenylene group, a naphthylene group, a fluorenylene group, a carbazolylene group, a dibenzofuranylene group, and a dibenzothiophenylene group; and a phenylene group, a naphthylene group, a fluorenylene group, a carbazolylene group, a dibenzofuranylene group, and a dibenzothiophenylene group, each substituted with at least one selected from deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, a biphenyl group, and —Si($Q_{11}$)($Q_{12}$)($Q_{13}$), d1 may be an integer from 1 to 10, wherein, when d1 is two or more, two or more groups $L_{11}$ may be identical to or different from each other, $Ar_{11}$ may be selected from groups represented by Formulae 11 and 12, $Ar_{12}$ may be selected from:

groups represented by Formulae 11 and 12, a phenyl group, and a naphthyl group; and a phenyl group and a naphthyl group, each substituted with at least one selected from deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a alkoxy group, a phenyl group, a naphthyl group, a fluorenyl group, a carbazolyl group, a dibenzofuranyl group, a dibenzothiophenyl group, and a biphenyl group, $CY_1$ and $CY_2$ may each independently be selected from a benzene group, a naphthalene group, a fluorene group, a carbazole group, a benzocarbazole group, an indolocarbazole group, a dibenzofuran group, a dibenzothiophene group, and a dibenzosilole group, $A_{21}$ may be selected from a single bond, O, S, N($R_{51}$), C($R_{51}$)($R_{52}$), and Si($R_{51}$)($R_{52}$), $A_{22}$ may be selected from a single bond, O, S, N($R_{53}$), C($R_{53}$)($R_{54}$), and Si($R_{53}$)($R_{54}$), at least one selected from $A_{21}$ and $A_{22}$ in Formula 12 may not be a single bond, $R_{51}$ to $R_{54}$, $R_{60}$, and $R_{70}$ may each independently be selected from:

hydrogen, deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a carbazolyl group, a dibenzofuranyl group, and a dibenzothiophenyl group;

a phenyl group, a naphthyl group, a fluorenyl group, a carbazolyl group, a dibenzofuranyl group, and a dibenzothiophenyl group;

a phenyl group, a naphthyl group, a fluorenyl group, a carbazolyl group, a dibenzofuranyl group, and a dibenzothiophenyl group, each substituted with at least one selected from deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a carbazolyl group, a dibenzofuranyl group, a dibenzothiophenyl group, and a biphenyl group; and —Si($Q_1$)($Q_2$)($Q_3$), e1 and e2 may each independently be an integer from 0 to 10, $Q_1$ to $Q_3$ and $Q_{11}$ to $Q_{13}$ may each independently be selected from hydrogen, deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a carbazolyl group, a dibenzofuranyl group, a dibenzothiophenyl group, and a biphenyl group, and

* indicates a binding site to a neighboring atom.

For example, at least one selected from $CY_1$ and $CY_2$ in Formulae 11 and 12 may each independently be a benzene group, but embodiments of the present disclosure are not limited thereto.

In an embodiment, in Formula H-1, $Ar_{11}$ may be selected from groups represented by Formulae 11-1 to 11-8 and 12-1 to 12-8, $Ar_{12}$ may be selected from:

groups represented by Formulae 11-1 to 11-8 and 12-1 to 12-8, a phenyl group, and a naphthyl group; and a phenyl group and a naphthyl group, each substituted with at least one selected from deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a carbazolyl group, a dibenzofuranyl group, a dibenzothiophenyl group, and a biphenyl group, but embodiments of the present disclosure are not limited thereto:

11-1

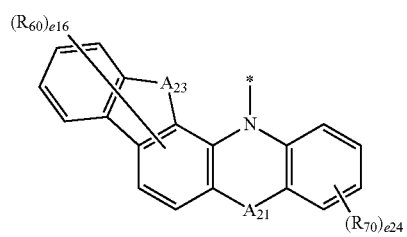

11-2

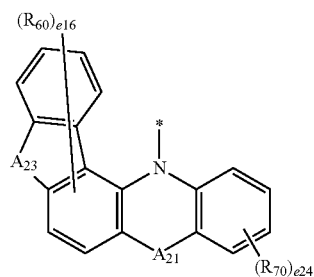

11-3

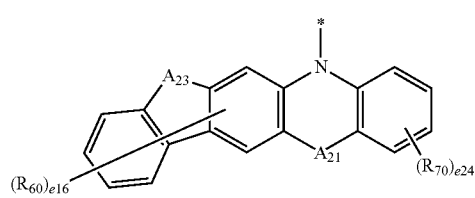

11-4

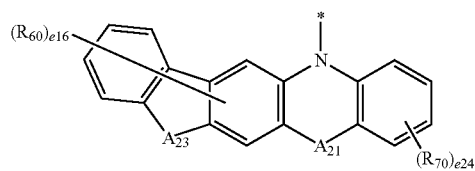

-continued 11-5

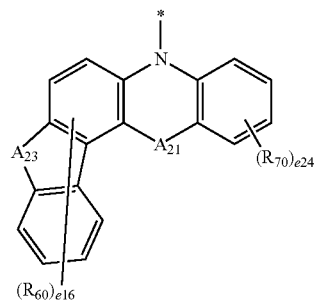

11-6

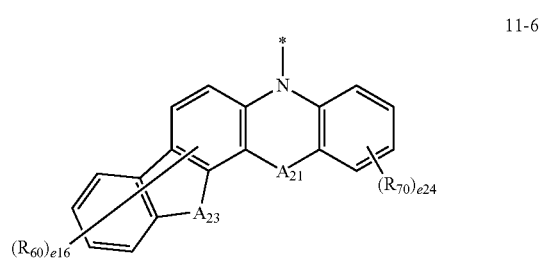

11-7

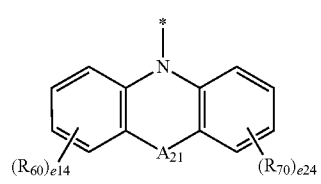

11-8

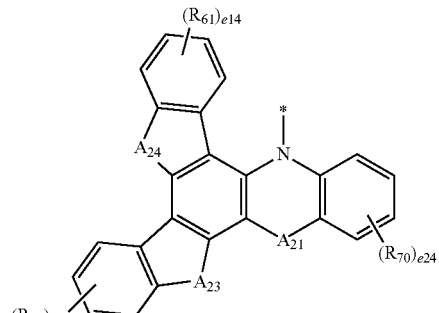

12-1

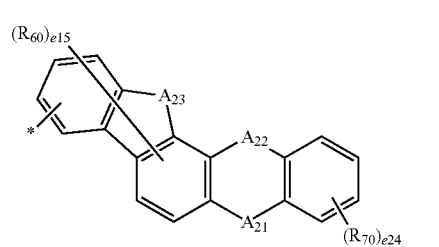

12-2

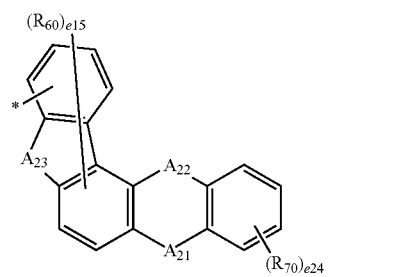

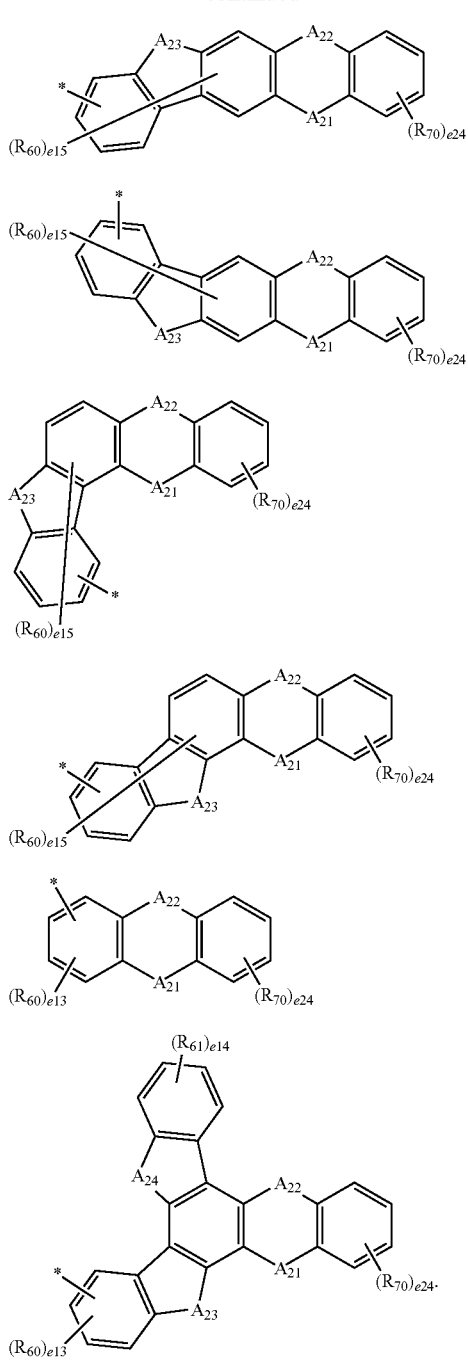

In Formulae 11-1 to 11-8 and 12-1 to 12-8,
$A_{23}$ may be selected from O, S, $N(R_{55})$, $C(R_{55})(R_{56})$, and $Si(R_{55})(R_{56})$,
$A_{24}$ may be selected from O, S, $N(R_{57})$, $C(R_{57})(R_{58})$, and $Si(R_{57})(R_{58})$,
$A_{21}$, $A_{22}$, $R_{60}$, and $R_{70}$ may each independently be the same as described herein,
$R_{55}$ to $R_{58}$ may each independently be the same as described in connection with $R_{51}$,
$R_{61}$ may be the same as described in connection with $R_{60}$,
e16 may be an integer from 0 to 6,
e15 may be an integer from 0 to 5,
e14 may be an integer from 0 to 4,
e13 may be an integer from 0 to 3,
e24 may be an integer from 0 to 4, and
* indicates a binding site to a neighboring atom.

In one or more embodiments, 1) $A_{23}$ in Formulae 11-1 to 11-7 and 12-1 to 12-7 may be selected from O, S, $N(R_{55})$, $C(R_{55})(R_{56})$, and $Si(R_{55})(R_{56})$ and $A_{23}$ in Formulae 11-8 and 12-8 may be $N(R_{55})$ and 2) $A_{24}$ in Formulae 11-1 to 11-7 and 12-1 to 12-7 may be selected from O, S, $N(R_{57})$, $C(R_{57})(R_{58})$, and $Si(R_{57})(R_{58})$ and $A_{24}$ in Formulae 11-8 and 12-8 may be $N(R_{57})$, In one or more embodiments, in the composition,
i) the second compound may be represented by Formula H-1, and $L_{11}$ in Formula H-1 may be a single bond; or
ii) the second compound may be selected from compounds represented by Formulae H-1(1) to H-1(52), but embodiments of the present disclosure are not limited thereto:

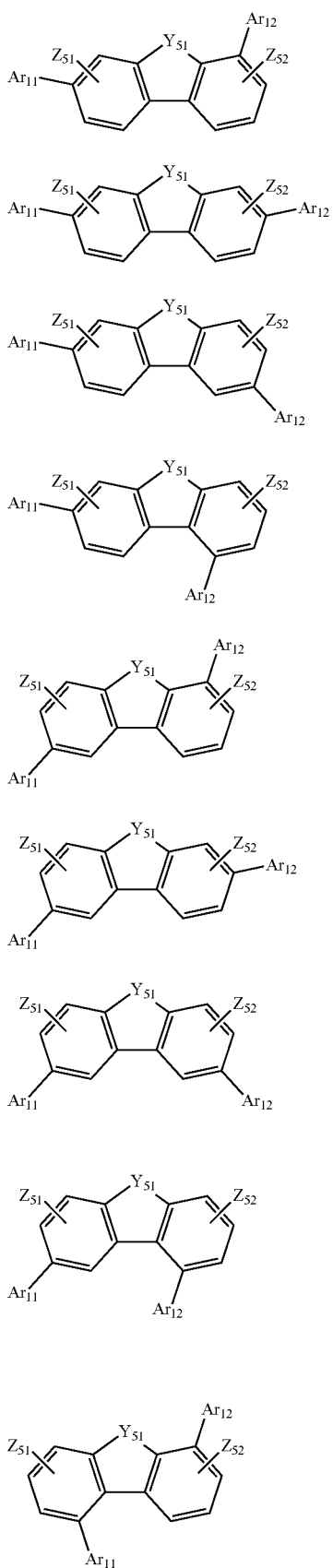
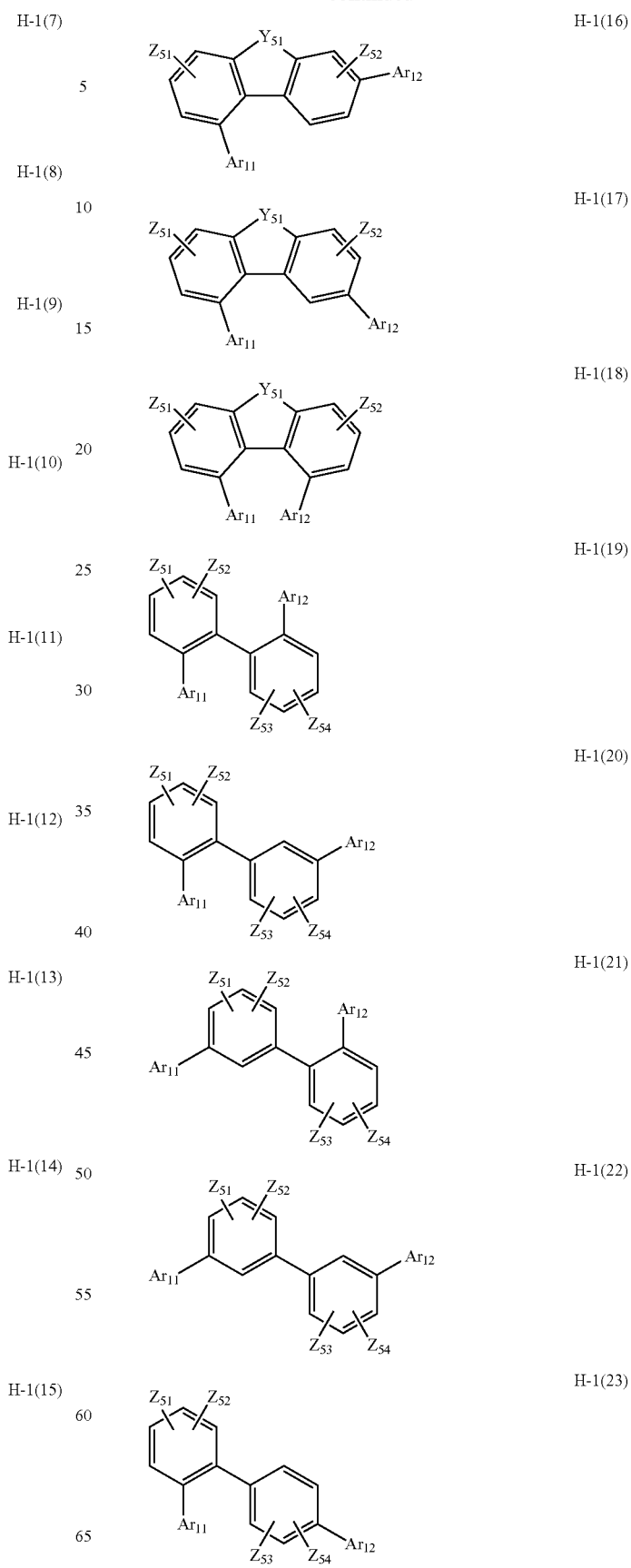

-continued
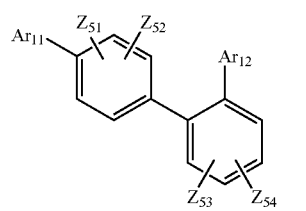
H-1(24)
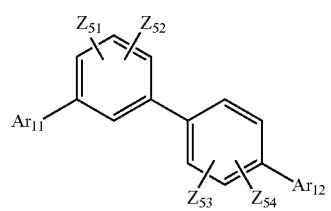
H-1(25)
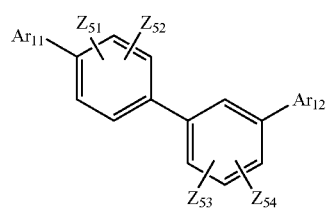
H-1(26)
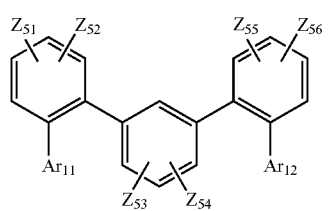
H-1(27)
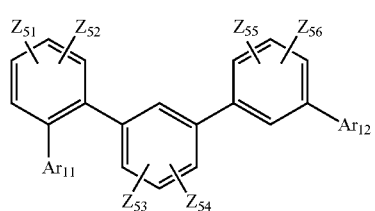
H-1(28)
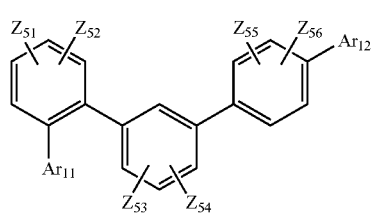
H-1(29)
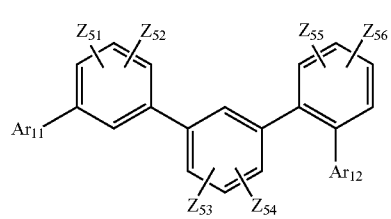
H-1(30)
-continued
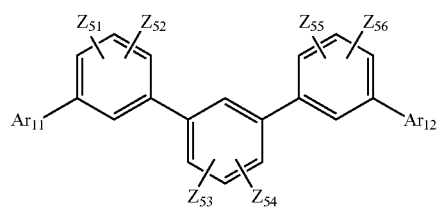
H-1(31)
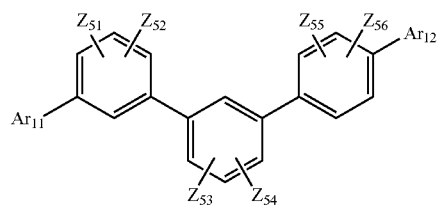
H-1(32)
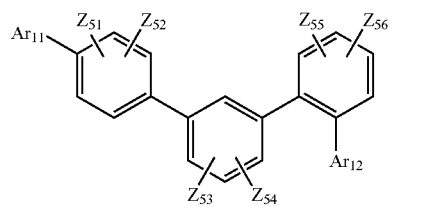
H-1(33)
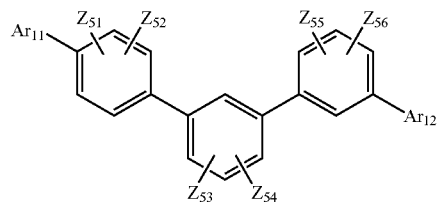
H-1(34)
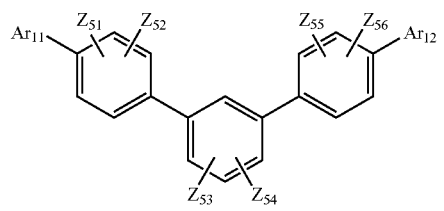
H-1(35)
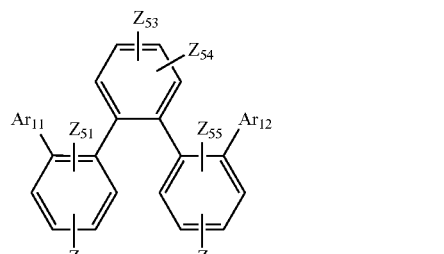
H-1(36)
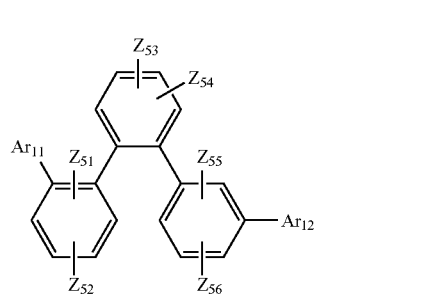
H-1(37)

H-1(38)
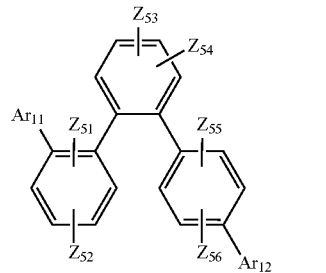
H-1(39)
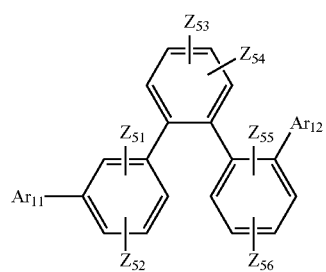
H-1(40)
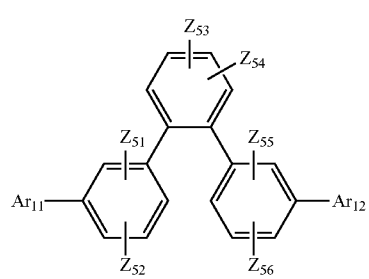
H-1(41)
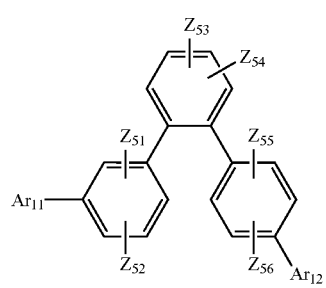
H-1(42)
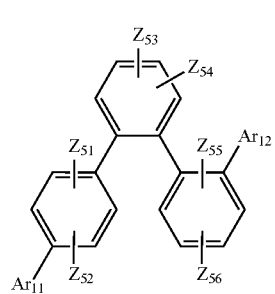
H-1(43)
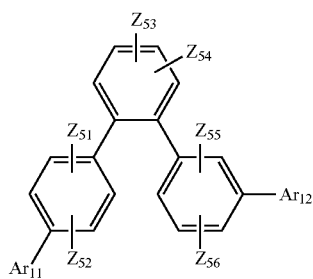
H-1(44)
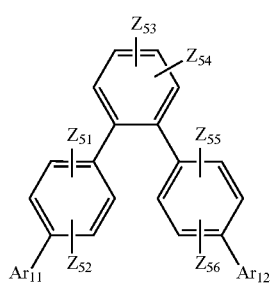
H-1(45)
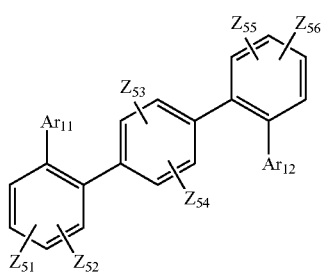
H-1(46)
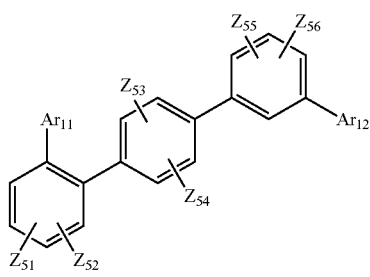
H-1(47)
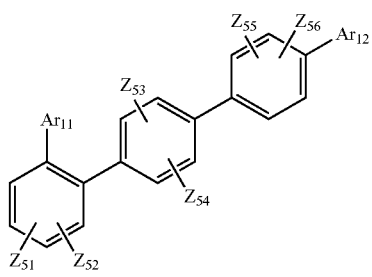

-continued

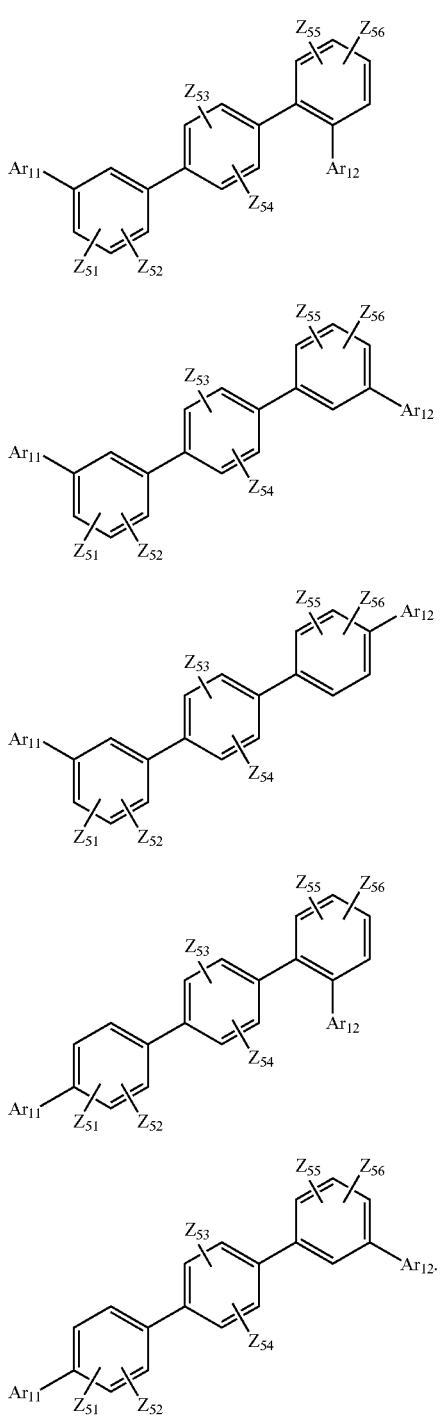

H-1(48)
H-1(49)
H-1(50)
H-1(51)
H-1(52)

In Formulae H-1(1) to H-1(52), $Ar_{11}$ and $Ar_{12}$ may each independently be the same as described herein, $Y_{51}$ may be $C(Z_{53})(Z_{54})$, $Si(Z_{53})(Z_{54})$, $N(Z_{55})$, O, or S, $Z_{51}$ to $Z_{56}$ may each independently be selected from hydrogen, deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, a biphenyl group, and —$Si(Q_{11})(Q_{12})(Q_{13})$, and $Q_{11}$ to $Q_{13}$ may each independently be selected from hydrogen, a $C_1$-$C_{10}$ alkyl group, a $C_1$-$C_{10}$ alkoxy group, a phenyl group, and a naphthyl group, but embodiments of the present disclosure are not limited thereto.

In an embodiment, the second compound in the composition may be selected from Compounds H-1 to H-32, but embodiments of the present disclosure are not limited thereto:

H-1

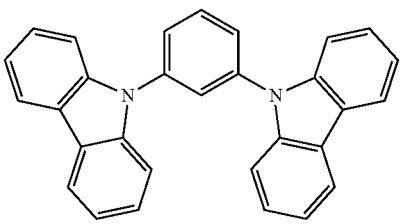

H-2

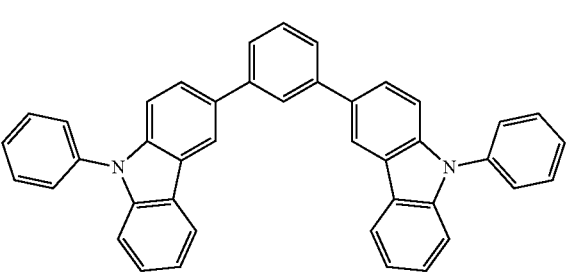

H-3

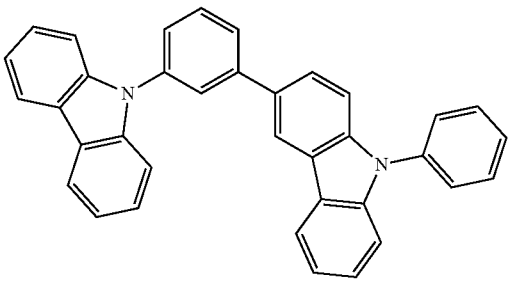

H-4

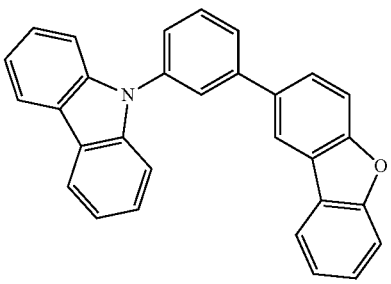

H-5

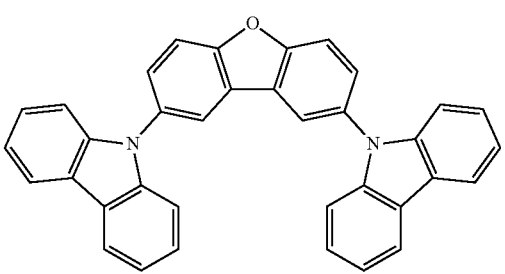

-continued
H-6
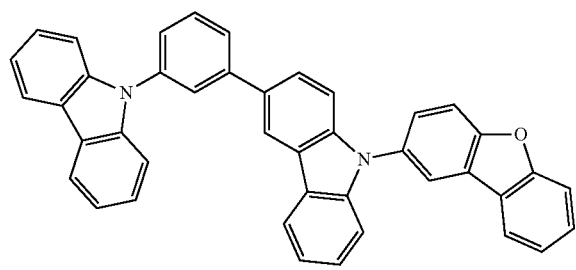
H-7
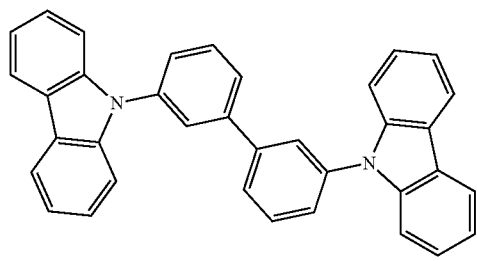
H-8
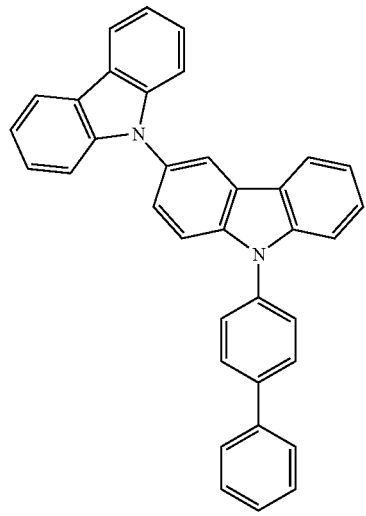
H-9
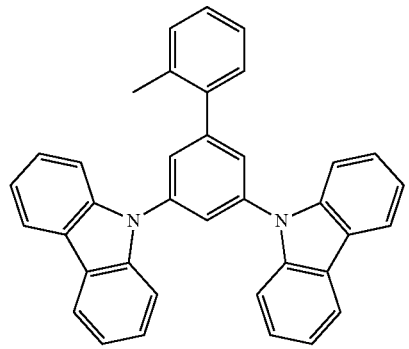
-continued
H-10
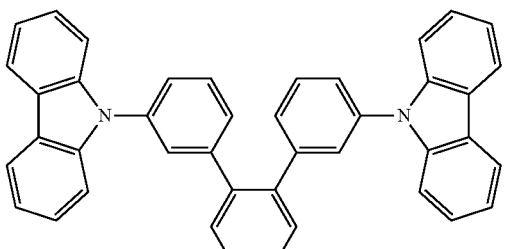
H-11
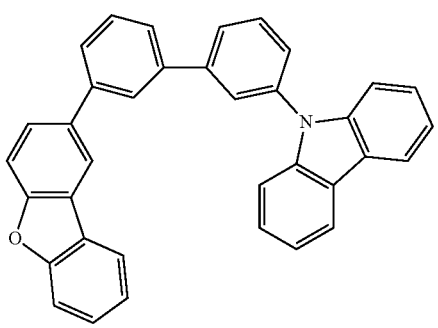
H-12
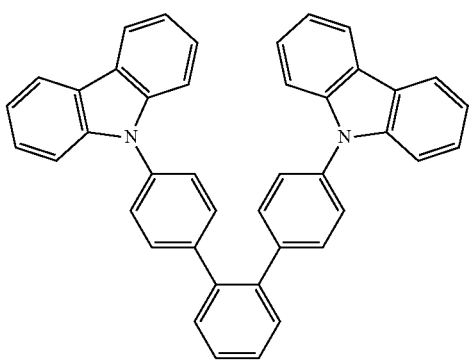
H-13
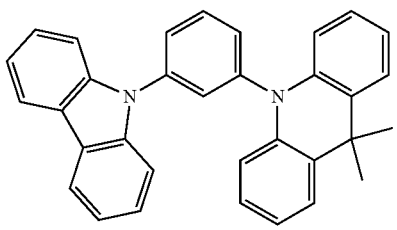
H-14
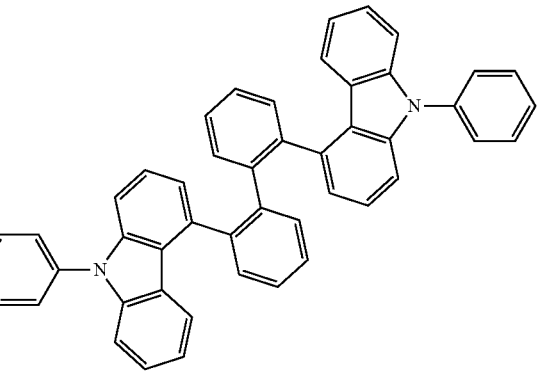

H-15
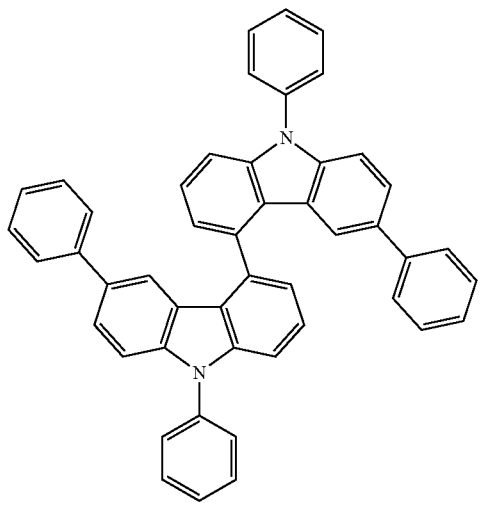
H-16
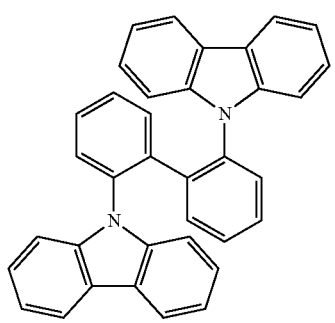
H-17
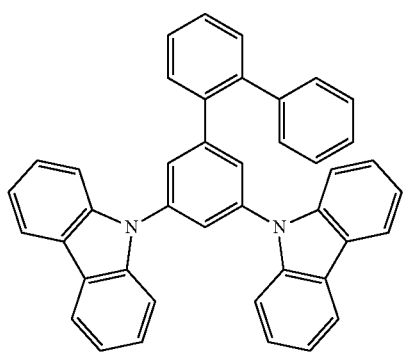
H-18
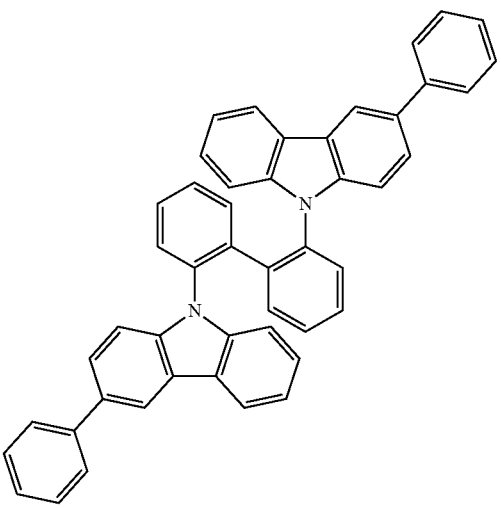
H-19
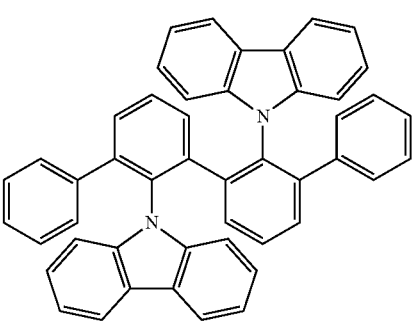
H-20
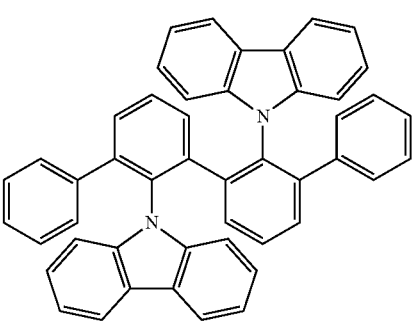
H-21
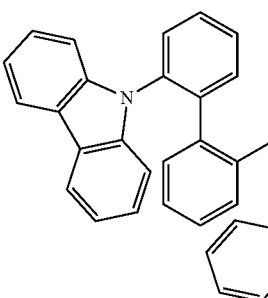

H-22
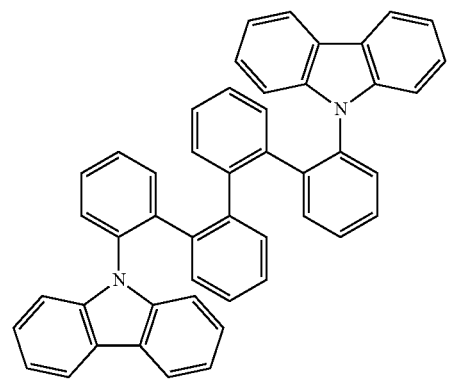
H-23
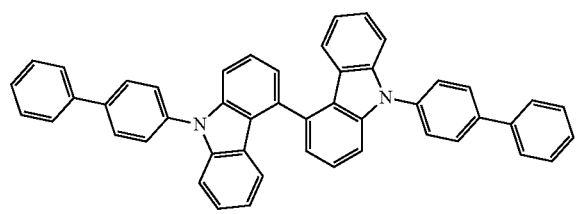
H-24
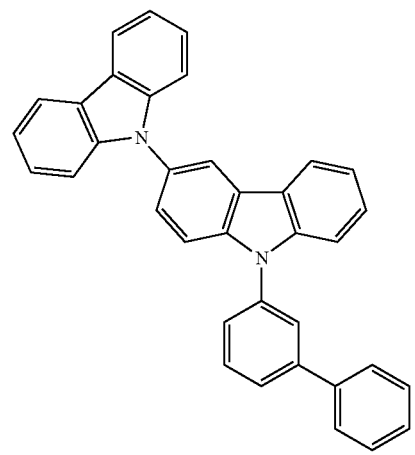
H-25
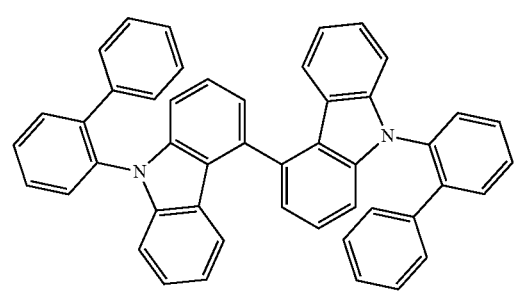
H-26
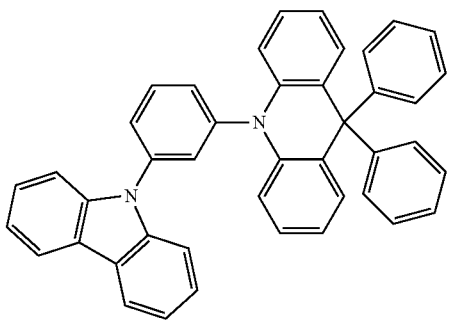
H-27
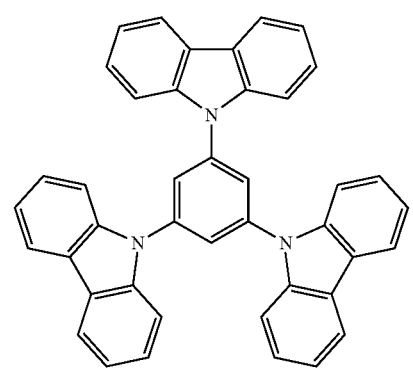
H-28
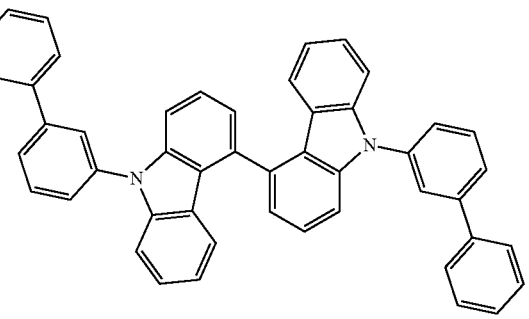
H-29
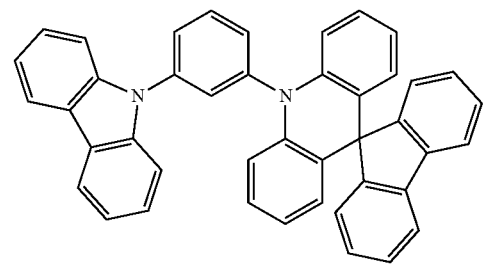
H-30
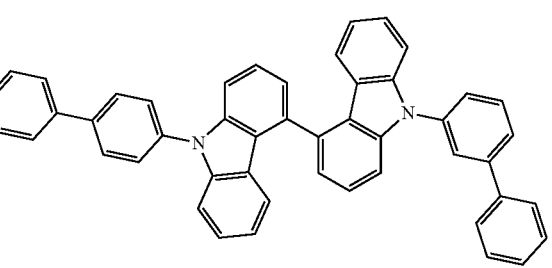

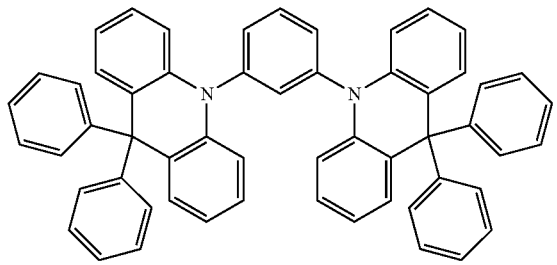

H-31

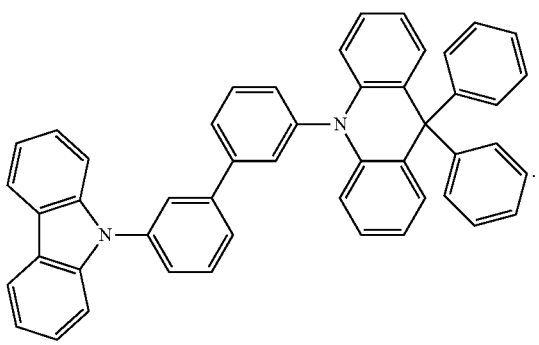

H-32

In the composition, a weight ratio of the first compound to the second compound may be in a range of about 1:99 to about 99:1, for example, about 70:30 to about 30:70. For example, in the composition, the weight ratio of the first compound to the second compound may be in a range of about 40:60 to about 60:40, but embodiments of the present disclosure are not limited thereto. While not wishing to be bound by theory, it is understood that when the weight ratio of the first compound and the second compound is within this range, the composition may provide excellent charge transport balance.

The condensed cyclic compound represented by Formula 1 or a composition including the first compound and the second compound may be suitable for an organic layer, for example, an emission layer and/or an electron transport region, in the organic light-emitting device. Another aspect of the present disclosure provides an organic light-emitting device including: a first electrode; a second electrode; and an organic layer disposed between the first electrode and the second electrode, wherein the organic layer including an emission layer and at least one condensed cyclic compound represented by Formula 1 described above or the composition described above.

The organic light-emitting device may have, due to the inclusion of an organic layer including the condensed cyclic compound represented by Formula 1 the composition including the first compound and the second compound, low driving voltage, high luminescent efficiency (current efficiency), high brightness, and a long lifespan.

In the organic light-emitting device according to an embodiment,
the first electrode may be an anode, and the second electrode may be a cathode,
the organic layer may further include a hole transport region between the first electrode and the emission layer and an electron transport region between the emission layer and the second electrode,
the hole transport region may include a hole injection layer, a hole transport layer, an electron blocking layer, a buffer layer, or any combination thereof, and the electron transport region may include a hole blocking layer, an electron transport layer, an electron injection layer, or any combination thereof. However, embodiments of the present disclosure are not limited thereto.

For example, the emission layer in the organic light-emitting device may include at least one condensed cyclic compound represented by Formula 1, or may include the composition including the first compound and the second compound described above.

In an embodiment, the emission layer in the organic light-emitting device may include a host and a dopant, the host may include the condensed cyclic compound represented by Formula 1, or may include the composition including the first compound and the second compound described above, and the dopant may include a phosphorescent dopant or a fluorescent dopant. For example, the dopant may include a phosphorescent dopant (for example, an organometallic compound including a transition metal or an organometallic compound represented by Formula 81). The condensed cyclic compound included in the host may transfer energy to the dopant due to a delayed fluorescence emission mechanism. An amount of the host in the emission layer may be larger than an amount of the dopant in the emission layer. The host may further include any host, in addition to the condensed cyclic compound represented by Formula 1 or the composition including the first compound and the second compound.

In one or more embodiment, the emission layer in the organic light-emitting device may include a host and a dopant, and the dopant may include at least one condensed cyclic compound represented by Formula 1. The condensed cyclic compound included in the dopant may act as an emitter that emits delayed fluorescence due to a delayed fluorescence emission mechanism. In an embodiment, the dopant may further include any known emission dopant, and the condensed cyclic compound may act as an auxiliary dopant that transfers energy to the emission dopant due to a delayed fluorescence emission mechanism. An amount of the host in the emission layer may be larger than an amount of the dopant in the emission layer. The host may include any host.

The emission layer may emit red light, green light, or blue light. For example, the emission layer may emit blue light.

In one or more embodiments, the emission layer may be a blue light emission layer including a phosphorescent dopant.

In an embodiment, the condensed cyclic compound represented by Formula 1 may be included in the electron transport region of the organic light-emitting device.

In one or more embodiments, the electron transport region may include at least one of a hole blocking layer and an electron transport layer, wherein the at least one of the hole blocking layer and the electron transport layer may include the condensed cyclic compound represented by Formula 1.

For example, the electron transport region of the organic light-emitting device may include the hole blocking layer, and the hole blocking layer may include the condensed cyclic compound represented by Formula 1. The hole blocking layer may directly contact the emission layer.

In one or more embodiments, the electron transport region may include a hole blocking layer and an electron transport layer, and the hole blocking layer may be disposed between the emission layer and the electron transport layer and include at least the condensed cyclic compound represented by Formula 1.

In one or more embodiments, the organic layer in the organic light-emitting device may include, in addition to the condensed cyclic compound represented by Formula 1,
i) the second compound defined above;
ii) an organometallic compound including a transition metal (for example, an organometallic compound represented by Formula 81); or
iii) any combination thereof:

$$M(L_{81})_{n81}(L_{82})_{n82}$$  Formula 81

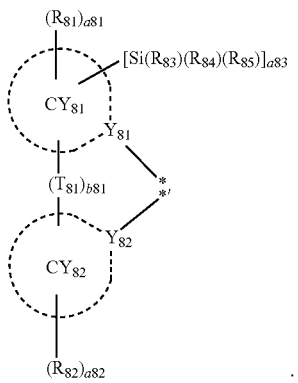

Formula 81A

In Formulae 81 and 81A,
M may be selected from transition metals (for example, iridium (Ir), platinum (Pt), palladium (Pd), gold (Au), osmium (Os), titanium (Ti), zirconium (Zr), hafnium (Hf), europium (Eu), terbium (Tb), thulium (Tm), and rhodium (Rh)),
$L_{81}$ may be a ligand represented by Formula 81A, wherein n81 is an integer from 1 to 3, and when n81 is two or more, two or more groups $L_{81}$ may be identical to or different from each other,
$L_{82}$ may be an organic ligand, wherein n82 is an integer from 0 to 4, and when n82 is two or more, two or more groups $L_{82}$ may be identical to or different from each other,
$Y_{81}$ and $Y_{82}$ may each independently be carbon (C) or nitrogen (N),
ring $CY_{81}$ and ring $CY_{82}$ may each independently be selected from a $C_5$-$C_{30}$ carbocyclic group and a $C_1$-$C_{30}$ heterocyclic group, and may optionally be linked to each other via an organic linking group,
$T_{81}$ may be a single bond, a double bond, *—N($R_{86}$)—*', *—B($R_{86}$)—*', *—P($R_{86}$)—*', *—C($R_{86}$)($R_{87}$)—*', *—Si($R_{86}$)($R_{87}$)—', *—Ge($R_{86}$)($R_{87}$)—', *—S—*', *—Se—*', *—O—*', *—C(=O)—*', *—S(=O)—*', *—S(=O)$_2$—*', *—C($R_{86}$)=', *=C($R_{86}$)—*', *—C($R_{86}$)=C($R_{87}$)—*', *—C(=S)—*', or *—C≡C—*', wherein * and *' each independently indicate a binding site to a neighboring atom,
b81 may be 1, 2, or 3,
$R_{81}$ to $R_{87}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($C_{281}$)($Q_{82}$)($Q_{83}$), —N($Q_{84}$)($Q_{85}$), —B($Q_{86}$)($Q_{87}$), and —P(=O)($C_{288}$)($Q_{89}$),
a81 to a83 may each independently be an integer from 0 to 5,
wherein, when a81 is two or more, two or more groups $R_{81}$ may be identical to or different from each other,
when a82 is two or more, two or more groups $R_{82}$ may be identical to or different from each other,
when a81 is two or more, two neighboring groups $R_{81}$ may optionally be linked to each other to form a $C_5$-$C_{30}$ carbocyclic group and a $C_1$-$C_{30}$ heterocyclic group, each unsubstituted or substituted with at least one $R_{88}$ (for example, a benzene group, a cyclopentane group, a cyclohexane group, a cyclopentene group, a cyclohexene group, a norbornane group, a (bicyclo[2.2.1] heptanes) group, a naphthalene group, a benzoindene group, a benzoindole group, a benzofuran group, a benzothiophene group, a pyridine group, a pyrimidine group, or a pyrazine group, each unsubstituted or substituted with at least one $R_{88}$),
when a82 is two or more, two neighboring groups $R_{82}$ may optionally be linked to each other to form a $C_5$-$C_{30}$ carbocyclic group and a $C_1$-$C_{30}$ heterocyclic group, each unsubstituted or substituted with at least one $R_{89}$ (for example, a benzene group, a cyclopentane group, a cyclohexane group, a cyclopentene group, a cyclohexene group, a norbornane group, a (bicyclo[2.2.1] heptanes) group, a naphthalene group, a benzoindene group, a benzoindole group, a benzofuran group, a benzothiophene group, a pyridine group, a pyrimidine group, or a pyrazine group, each unsubstituted or substituted with at least one $R_{89}$),
$R_{88}$ may be defined the same as $R_{81}$,
$R_{89}$ may be defined the same as $R_{82}$,
* and *' in Formula 81A each independently indicates a binding site to M in Formula 81,
at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{91}$)($Q_{92}$)($Q_{93}$), and $Q_{81}$ to $Q_{89}$ and $Q_{91}$ to $Q_{93}$ may each independently be selected from hydrogen, deuterium, a $C_1$-$C_{60}$ alkyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

In an embodiment, in Formula 81A, a83 may be 1 or 2, $R_{83}$ to $R_{85}$ may each independently be selected from:
—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a $C_1$-$C_{10}$ alkyl group, and a phenyl group, but embodiments of the present disclosure are not limited thereto.

In one or more embodiments, in Formula 81A, $Y_{81}$ may be nitrogen, and $Y_{82}$ may be nitrogen or carbon, and ring $CY_{81}$ and ring $CY_{82}$ may each independently be selected from a cyclopentadiene group, a benzene group, a heptalene group, an indene group, a naphthalene group, an azulene group, an indacene group, an acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, a hexacene group, a pentacene group, a rubicene group, a corozene group, an ovalene group, a pyrrole group, an isoindole group, an indole group, an indazole group, a pyrazole group, an imidazole group, a triazole group, an oxazole group, an isoxazole group, an oxadiazole group, a thiazole group, an isothiazole group, a thiadiazole group, a purine group, a furan group, a thiophene group, a pyridine group, a pyrimidine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, a benzofuran group, a benzothiophene group, an isobenzothiazole group, a benzoxazole group, an isobenzoxazole group, a benzocarbazole group, a dibenzocarbazole group, an imidazopyridine group, an imidazopyrimidine group, a dibenzofuran group, a dibenzothiophene group, a dibenzothiophene sulfone group, a carbazole group, a dibenzosilole group, and a 2,3-dihydro-1H-imidazole group.

In one or more embodiments, in Formula 81A, $Y_{81}$ may be nitrogen, $Y_{82}$ may be carbon, ring $CY_{81}$ may be selected from a 5-membered ring including two nitrogen atoms as ring-forming atom, and ring $CY_{82}$ may be selected from a benzene group, a naphthalene group, a fluorene group, a dibenzofuran group, and a dibenzothiophene group, but embodiments of the present disclosure are not limited thereto.

In one or more embodiments, in Formula 81A, $Y_{81}$ may be nitrogen, $Y_{82}$ may be carbon, ring $CY_{81}$ may be an imidazole group or a 2,3-dihydro-1H-imidazole group, and ring $CY_{82}$ may be selected from a benzene group, a naphthalene group, a fluorene group, a dibenzofuran group, and a dibenzothiophene group, but embodiments of the present disclosure are not limited thereto.

In one or more embodiments, in Formula 81A, $Y_{81}$ may be nitrogen, $Y_{82}$ may be carbon, ring $CY_{81}$ may be selected from a pyrrole group, a pyrazole group, an imidazole group, a triazole group, an oxazole group, an isoxazole group, an oxadiazole group, a thiazole group, an isothiazole group, a thiadiazole group, a pyridine group, a pyrimidine group, a quinoline group, an isoquinoline group, a benzoquinoline group, a phthalazine group, a naphthyridine group, a quinoxaline group, a quinazoline group, a cinnoline group, a benzimidazole group, an isobenzothiazole group, a benzoxazole group, and an isobenzoxazole group, and ring $CY_{82}$ may be selected from cyclopentadiene group, a benzene group, a naphthalene group, a fluorene group, a benzofluorene group, a dibenzofluorene group, a phenanthrene group, an anthracene group, a triphenylene group, a pyrene group, a chrysene group, a perylene group, a benzofuran group, a benzothiophene group, a benzocarbazole group, a dibenzocarbazole group, a dibenzofuran group, a dibenzothiophene group, a dibenzothiophene sulfone group, a carbazole group and a dibenzosilole group.

In one or more embodiments, in Formula 81A, $R_{81}$ and $R_{82}$ may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —$SF_5$, $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a cyclopentyl group, a cyclohexyl group, a cycloheptyl group, a cycloctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a cyclopentyl group, a cyclohexyl group, a cycloheptyl group, a cycloctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a C$_1$-C$_{20}$ alkoxy group, a cyclopentyl group, a cyclohexyl group, a cycloheptyl group, a cycloctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and —B(Q$_{86}$)(C$_{287}$) and —P(=O)(Q$_{88}$)(Q$_{89}$), and Q$_{86}$ to Q$_{89}$ may each independently be selected from: —CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a C$_1$-C$_{10}$ alkyl group, and a phenyl group.

In one or more embodiments, in Formula 81A, at least one selected from R$_{81}$ in the number of a81 and R$_{82}$ in the number of a82 may each independently be a cyano group.

In one or more embodiments, in Formula 81A, at least one selected from R$_{82}$ in the number of a82 may each independently be a cyano group.

In one or more embodiments, in Formula 81A, at least one selected from R$_{81}$ in the number of a81 and R$_{82}$ in the number of a82 may each independently be deuterium.

In one or more embodiments, in Formula 81, L$_{82}$ may be selected from ligands represented by Formula e3-1(1) to 3-1(60), 3-1(61) to 3-1(69), 3-1(71) to 3-1(79), 3-1(81) to 3-1(88), 3-1(91) to 3-1(98), and 3-1(101) to 3-1(114):

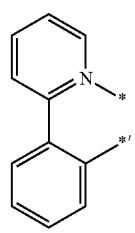

3-1(1)

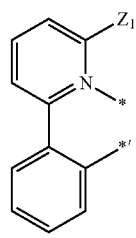

3-1(2)

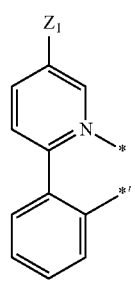

3-1(3)

-continued
3-1(4) 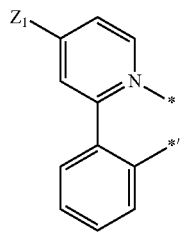
3-1(5) 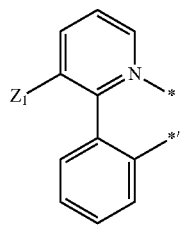
3-1(6) 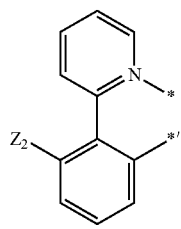
3-1(7) 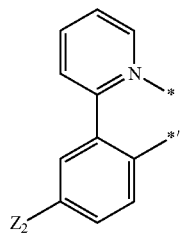
3-1(8) 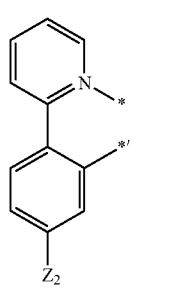
3-1(9) 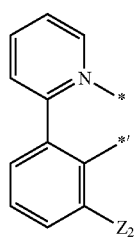
-continued
3-1(10) 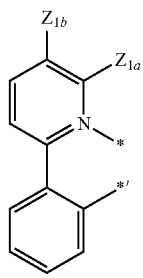
3-1(11) 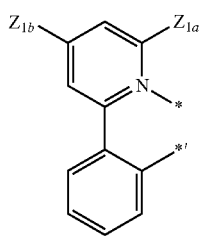
3-1(12) 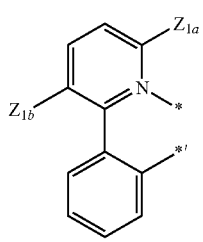
3-1(13) 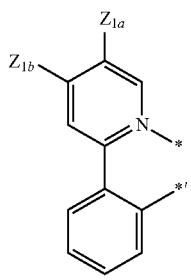
3-1(14) 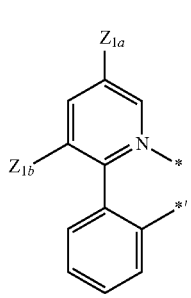
3-1(15) 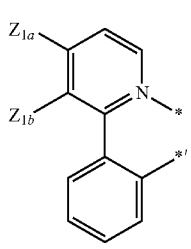

507
-continued
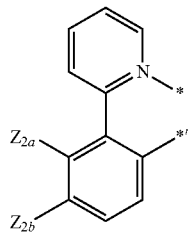
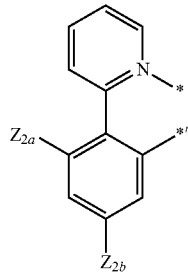
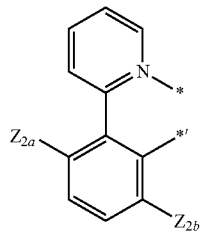
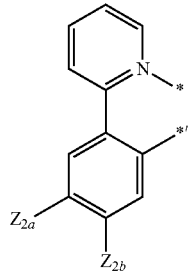
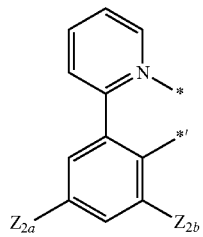
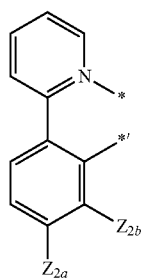
508
-continued
3-1(16)
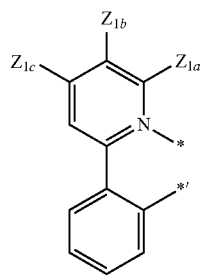
3-1(17)
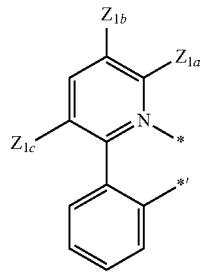
3-1(18)
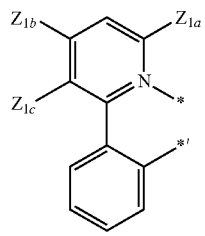
3-1(19)
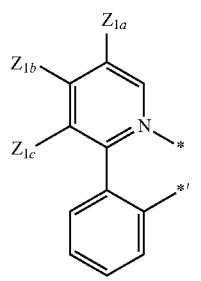
3-1(20)
3-1(21)
3-1(22)
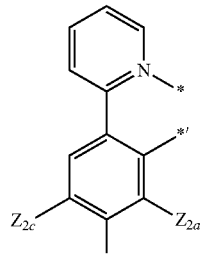
3-1(23)
3-1(24)
3-1(25)
3-1(26)
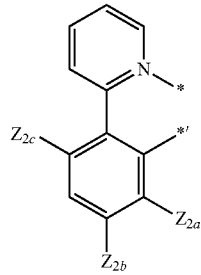
3-1(27)

509
-continued
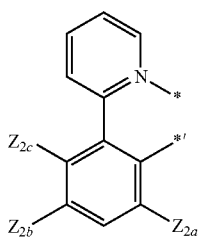
3-1(28)
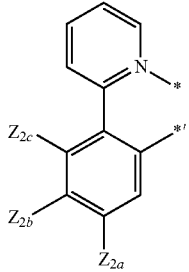
3-1(29)
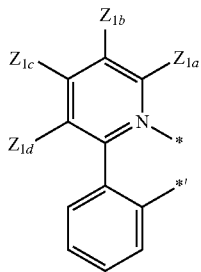
3-1(30)
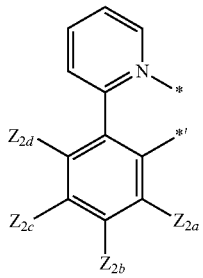
3-1(31)
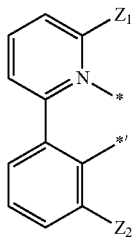
3-1(32)
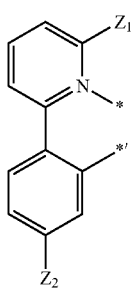
3-1(33)
510
-continued
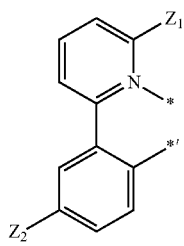
3-1(34)
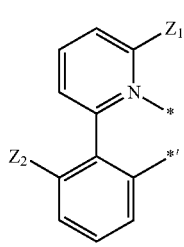
3-1(35)
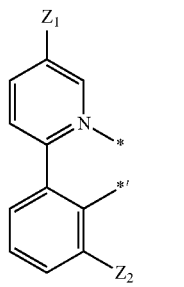
3-1(36)
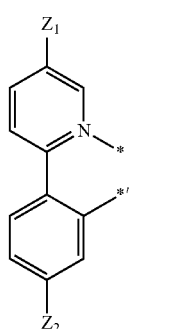
3-1(37)
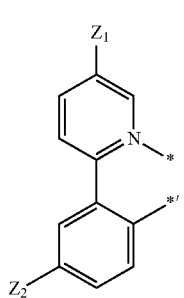
3-1(38)

-continued
3-1(39)
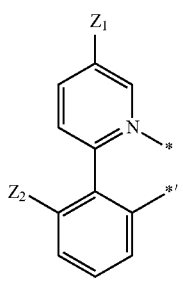
3-1(40)
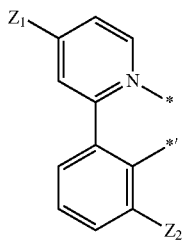
3-1(41)
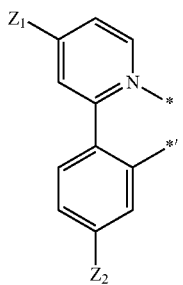
3-1(42)
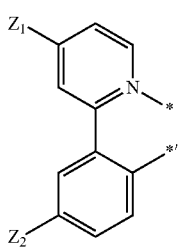
3-1(43)
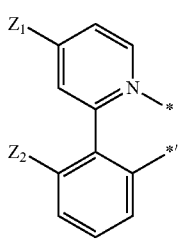
3-1(44)
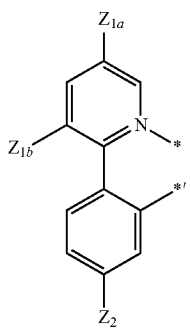
-continued
3-1(45)
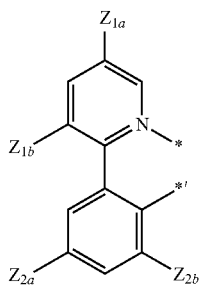
3-1(46)
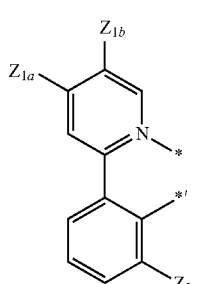
3-1(47)
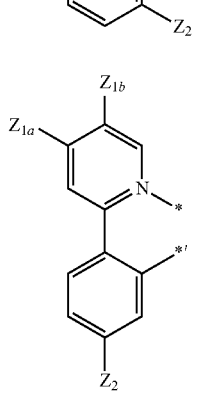
3-1(48)
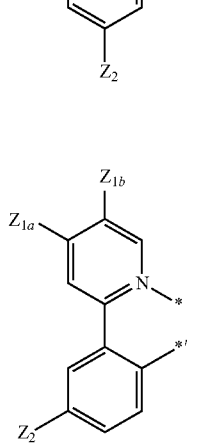
3-1(49)
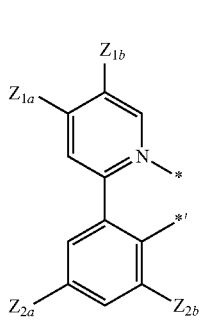

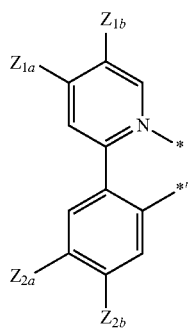 3-1(50)
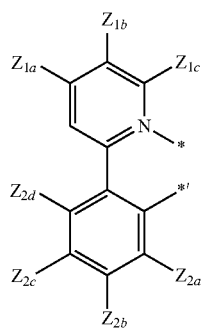 3-1(51)
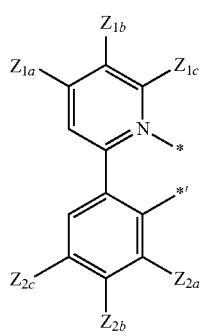 3-1(52)
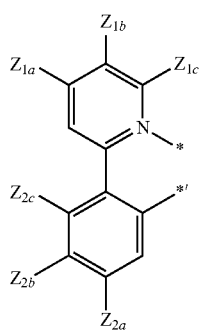 3-1(53)
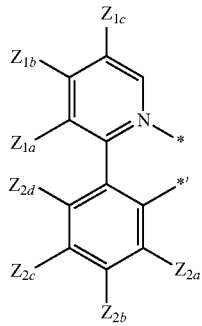 3-1(54)
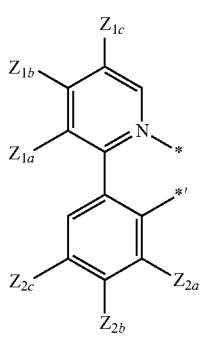 3-1(55)
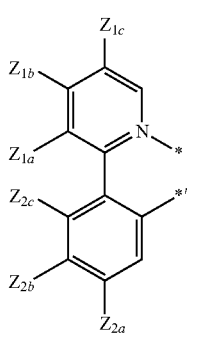 3-1(56)
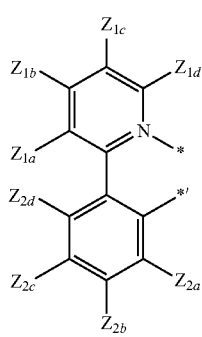 3-1(57)
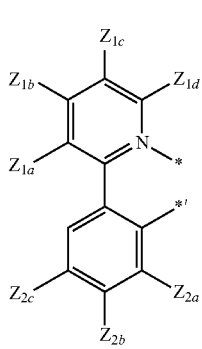 3-1(58)

515
-continued
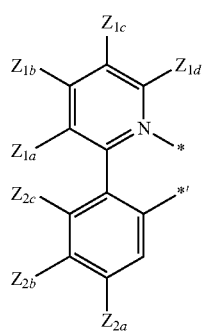
3-1(59)
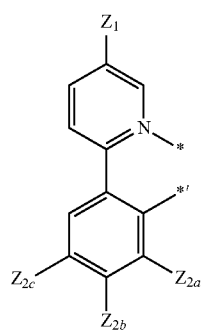
3-1(60)
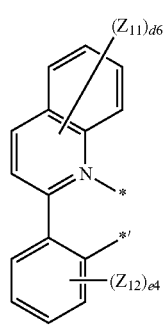
3-1(61)
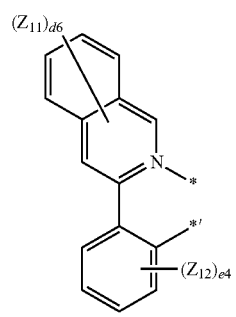
3-1(62)
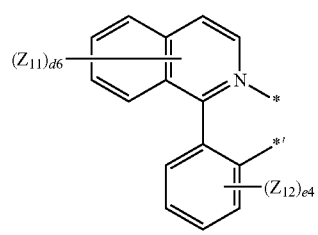
3-1(63)
516
-continued
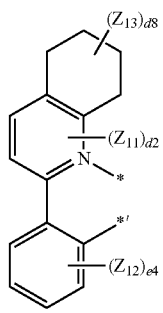
3-1(64)
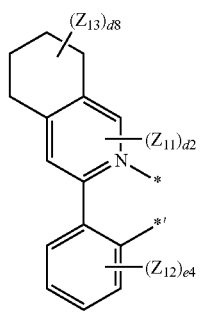
3-1(65)
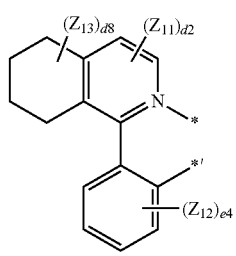
3-1(66)
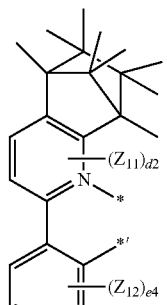
3-1(67)
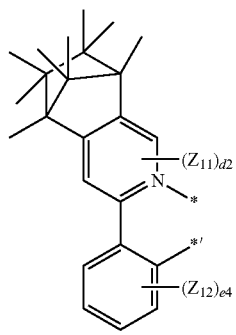
3-1(68)

3-1(69)
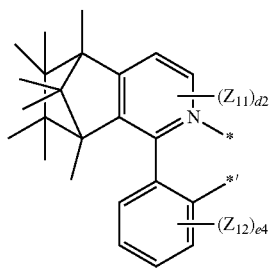
3-1(71)
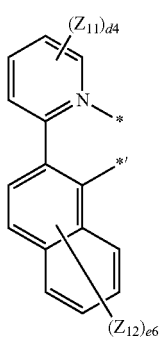
3-1(72)
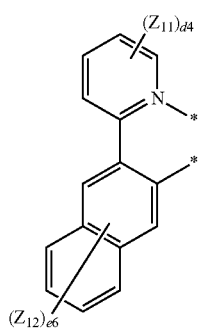
3-1(73)
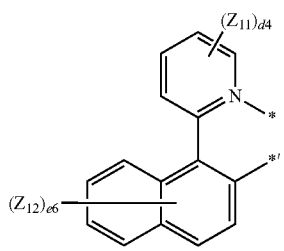
3-1(74)
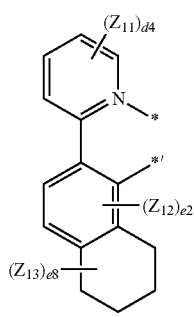
3-1(75)
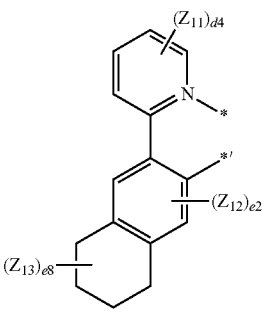
3-1(76)
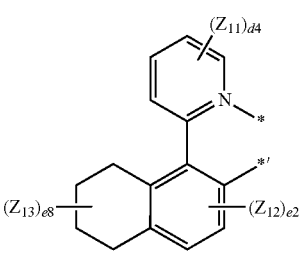
3-1(77)
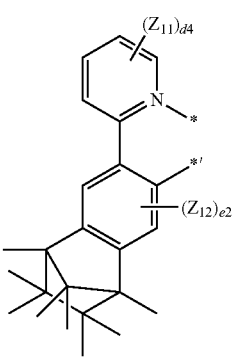
3-1(78)
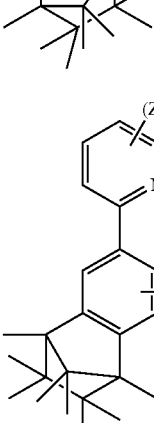
3-1(79)
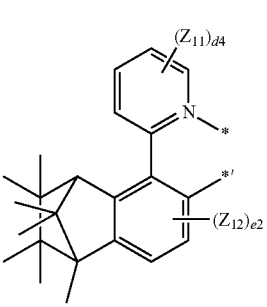

519
-continued
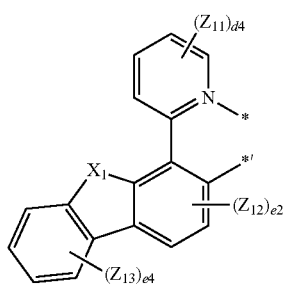
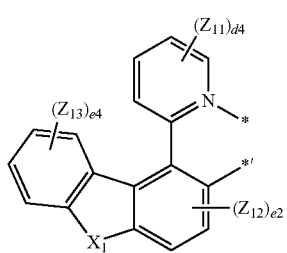
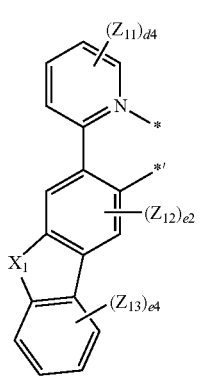
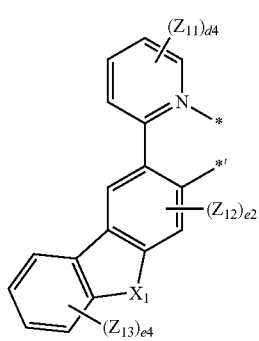
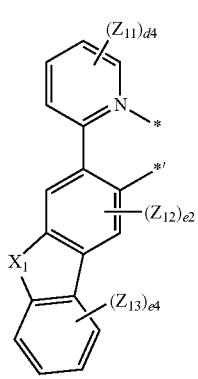
520
-continued
3-1(81)
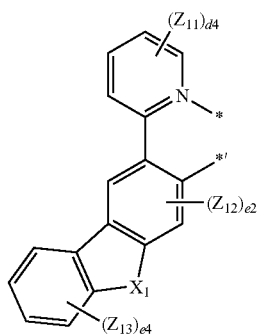 3-1(86)
3-1(82)
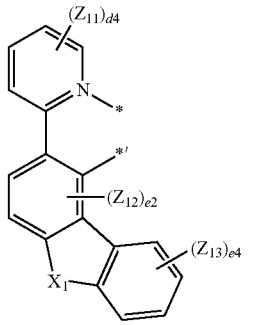 3-1(87)
3-1(83)
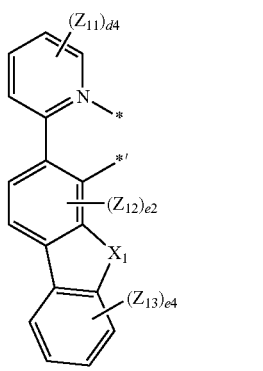 3-1(88)
3-1(84)
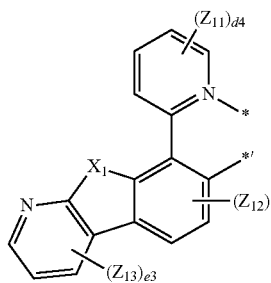 3-1(91)
3-1(85)
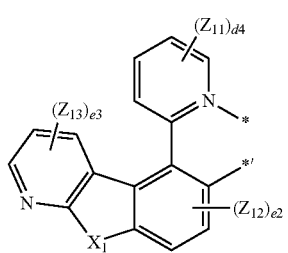 3-1(92)

-continued
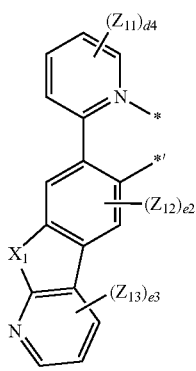
3-1(93)
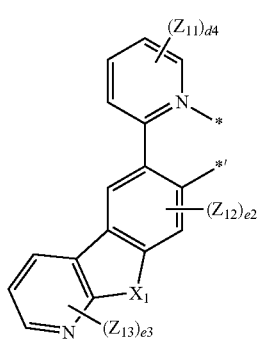
3-1(94)
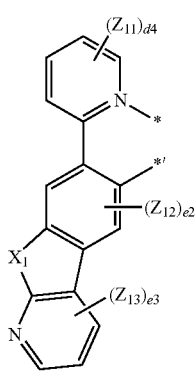
3-1(95)
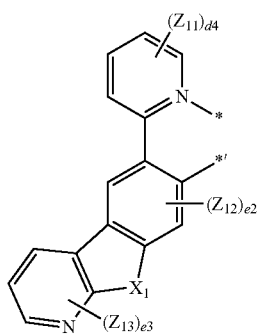
3-1(96)
-continued
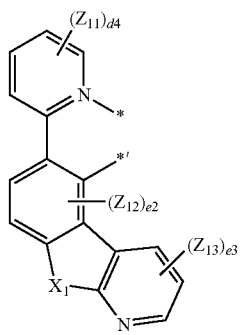
3-1(97)
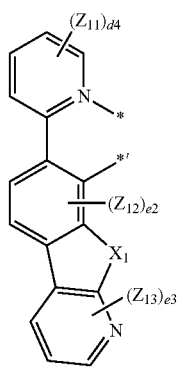
3-1(98)
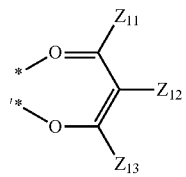
3-1(101)
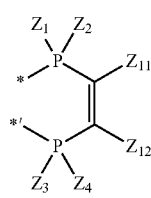
3-1(102)
3-1(103)
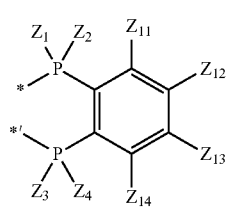
3-1(104)

3-1(105) 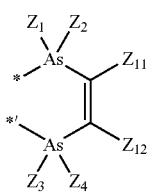

3-1(106) 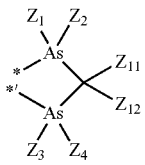

3-1(107) 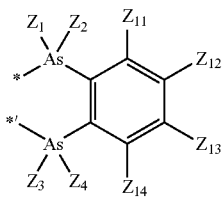

3-1(108) 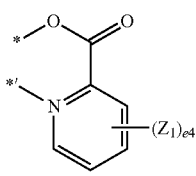

3-1(109) 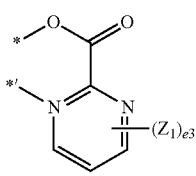

3-1(110) 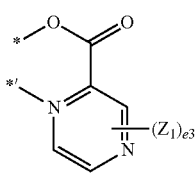

3-1(111) 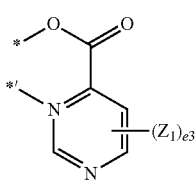

3-1(112) 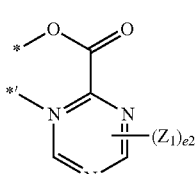

3-1(113) 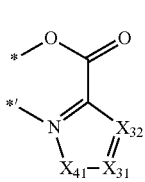

3-1(114) 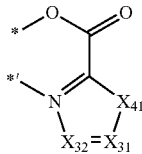

In Formulae 3-1(1) to 3-1(60), 3-1(61) to 3-1(69), 3-1(71) to 3-1(79), 3-1(81) to 3-1(88), 3-1(91) to 3-1(98), and 3-1(101) to 3-1(114), $X_1$ may be O, S, $C(Z_{21})(Z_{22})$, or $N(Z_{23})$, $X_{31}$ may be N or $C(Z_{1a})$, $X_{32}$ may be N or $C(Z_{1b})$, $X_{41}$ may be O, S, $N(Z_{1a})$, or $C(Z_{1a})(Z_{1b})$, $Z_1$ to $Z_4$, $Z_{1a}$, $Z_{1b}$, $Z_{1c}$, $Z_{1d}$, $Z_{2a}$, $Z_{2b}$, $Z_{2c}$, $Z_{2d}$, $Z_{11}$ to $Z_{14}$, and $Z_{21}$ to $Z_{23}$ may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, C$_1$-C$_{20}$ alkyl group, and a C$_1$-C$_{20}$ alkoxy group;

a C$_1$-C$_{20}$ alkyl group and a C$_1$-C$_{20}$ alkoxy group, each substituted with at least one selected from deuterium. —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{10}$ alkyl group, a cyclopentyl group, a cyclohexyl group, a cycloheptyl group, a cyclooctyl group, an adamantanyl group, a norbornanyl group, a norbomenyl group, a cyclopentenyl group, a cyclohexenyl group, a cycloheptenyl group, a phenyl group, a naphthyl group, a pyridinyl group, and a pyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a thazolyl group, a tetrazolyl group, an oxadiazolyl group, a Iriazinyl group, a dibenzofuranyl group, a dibenzothiophenyl group, a benzocarbazolyl group, a dibenzocarbazolyl group, an imidazopyridinyl group, and an imidazopyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolmyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyndazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and —B($Q_{86}$)($Q_{87}$) and —P(=O)($Q_{88}$)($Q_{89}$), $Q_{86}$ to $Q_{89}$ may each independently be selected from:
—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a $C_1$-$C_{10}$ alkyl group, and a phenyl group, d2 and e2 may each independently be 0 or 2, e3 may be an integer from 0 to 3, d4 and e4 may each independently be an integer from 0 to 4, d6 and e6 may each independently be an integer from 0 to 6, d8 and e8 may each independently be an integer from 0 to 8, and

* and *' each independently indicate a binding site to M in Formula 1.

In one or more embodiments, in Formula 81, M may be Ir, and the sum of n81 and n82 may be 3; or M may be Pt, and the sum of n81 and n82 may be 2.

In one or more embodiments, the organometallic compound represented by Formula 81 may be neutral, rather than a salt consisting of a pair of a cation and an anion.

In one or more embodiments, the organometallic compound represented by Formula 81 may include at least one selected from Compounds PD1 to PD78 and FIr$_6$, but embodiments of the present disclosure are not limited thereto:

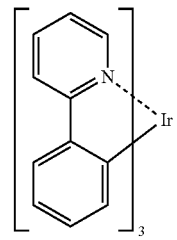

PD1

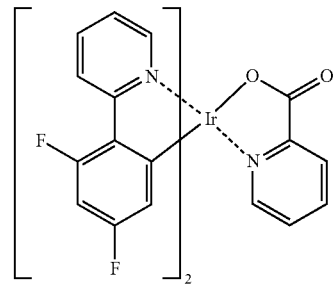

PD2

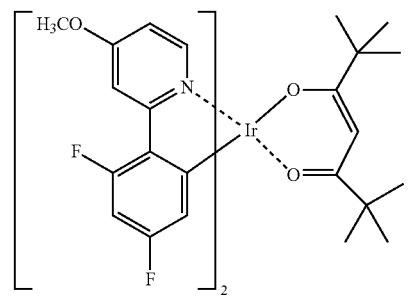

PD3

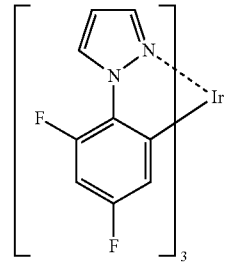

PD4

-continued
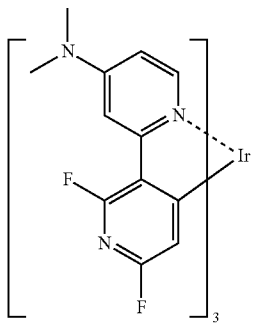
PD5
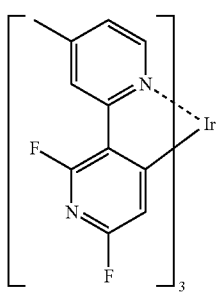
PD6
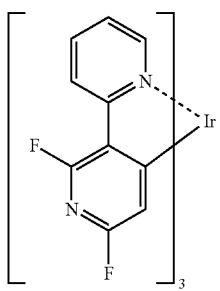
PD7
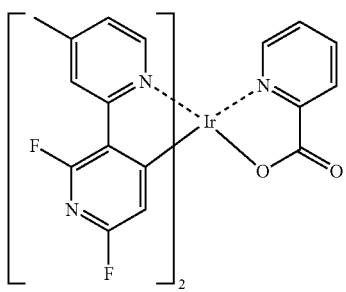
PD8
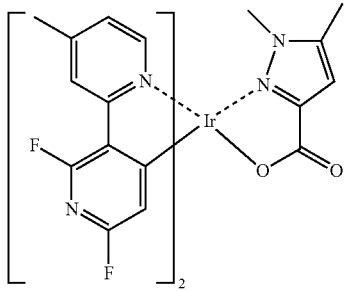
PD9
-continued
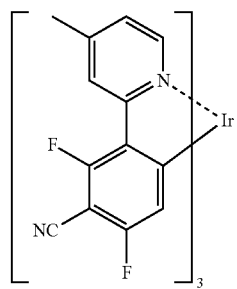
PD10
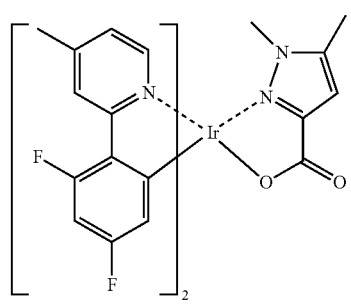
PD11
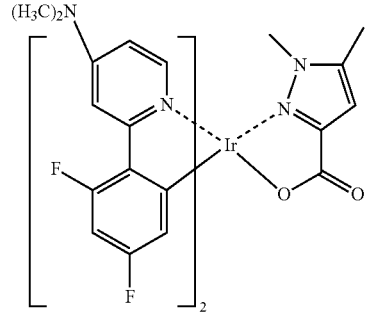
PD12
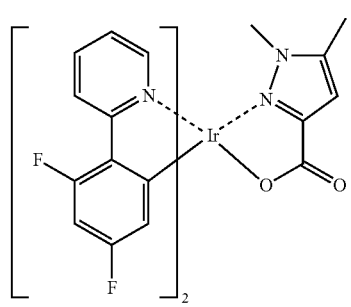
PD13
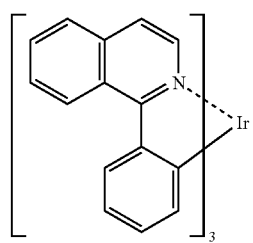
PD14

-continued
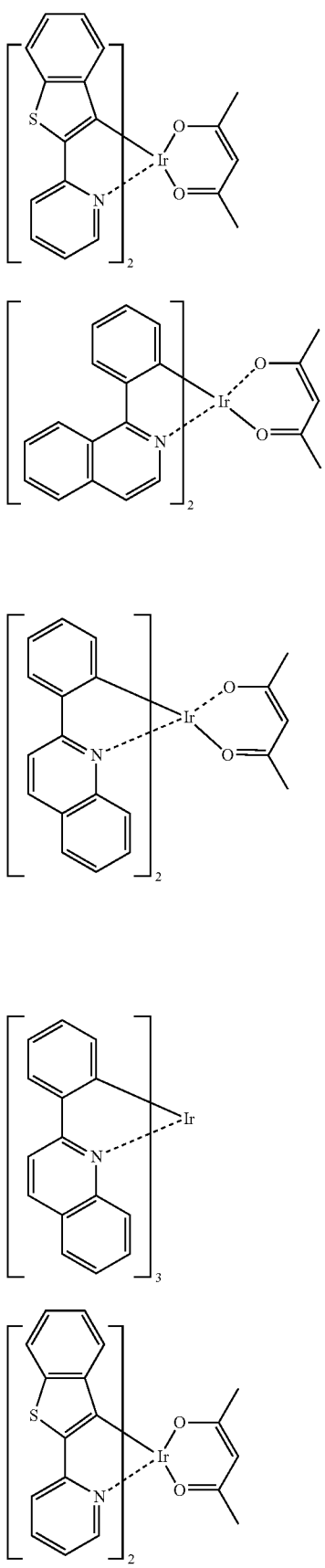
-continued
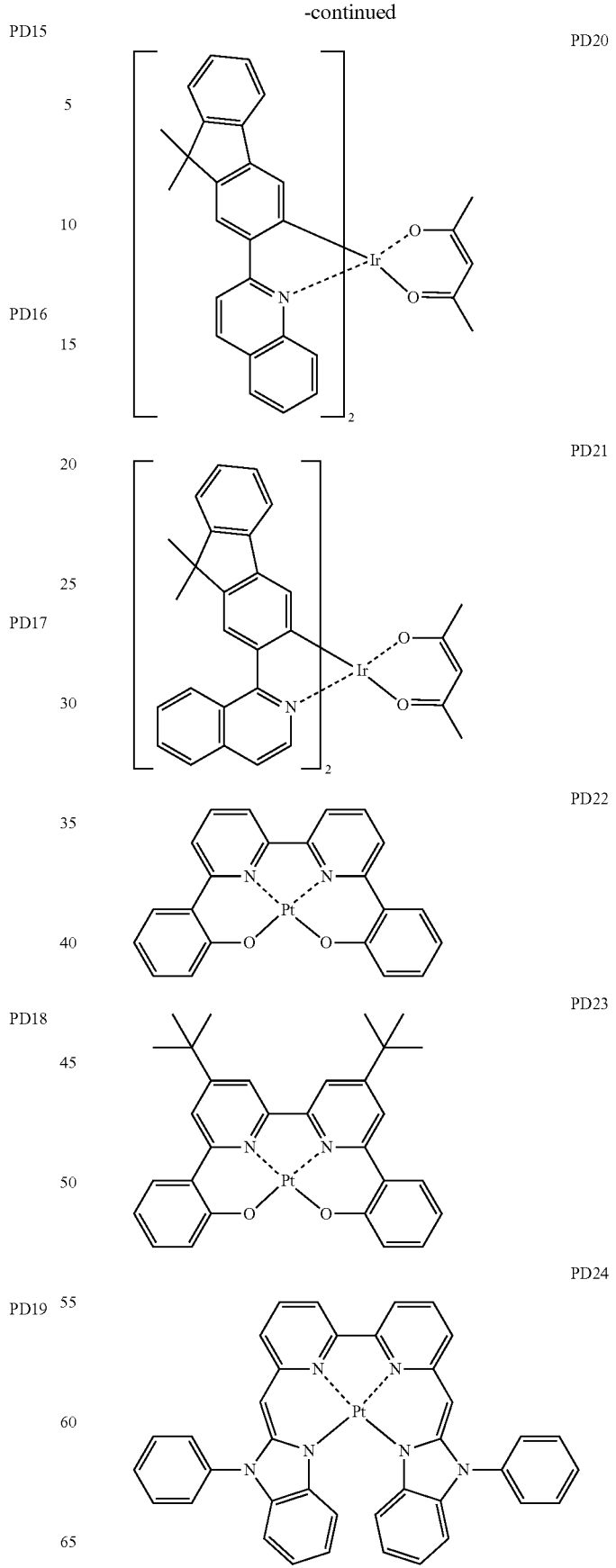

PD25
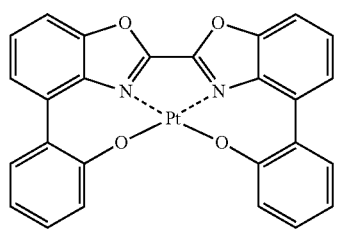
PD26
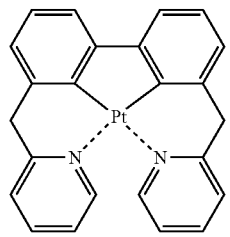
PD27
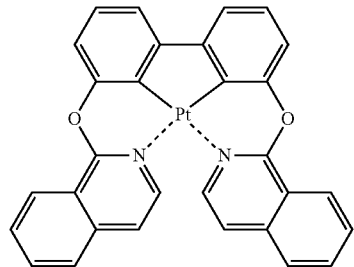
PD28
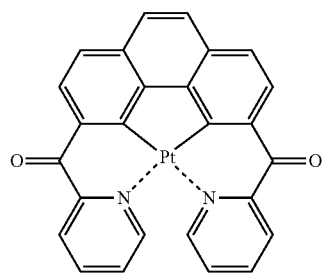
PD29
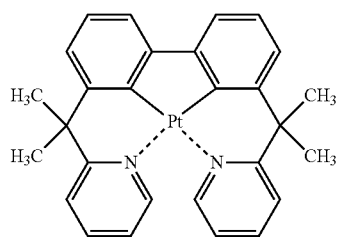
PD30
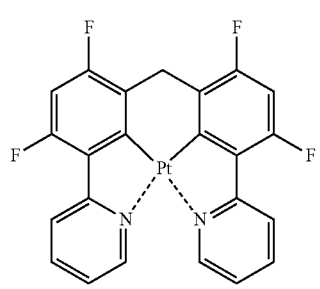
PD31
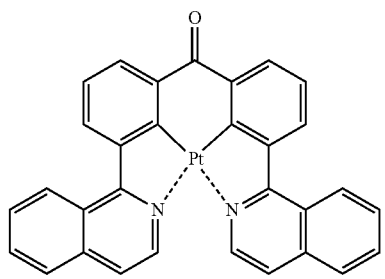
PD32
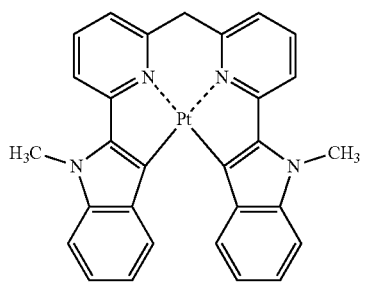
PD33
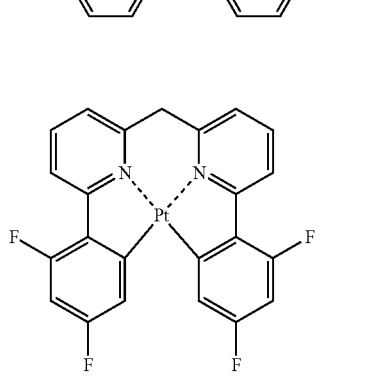
PD34
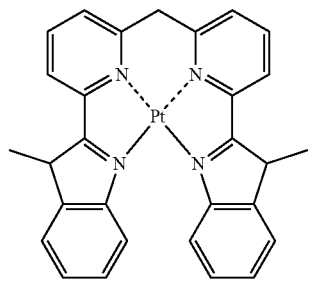
PD35
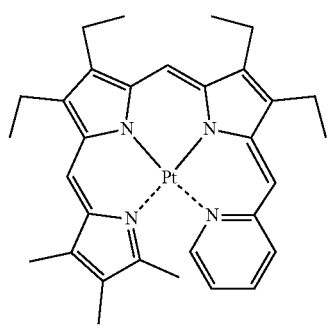

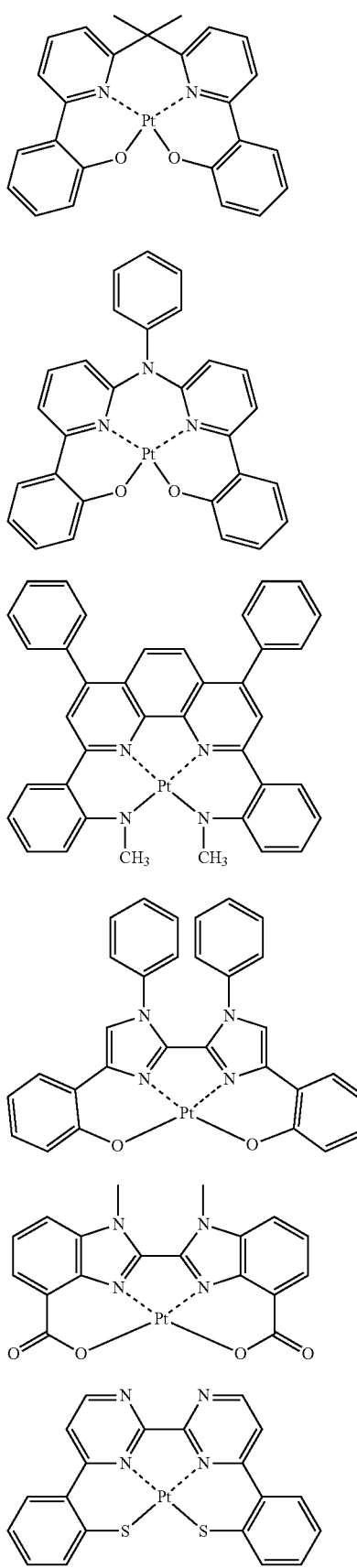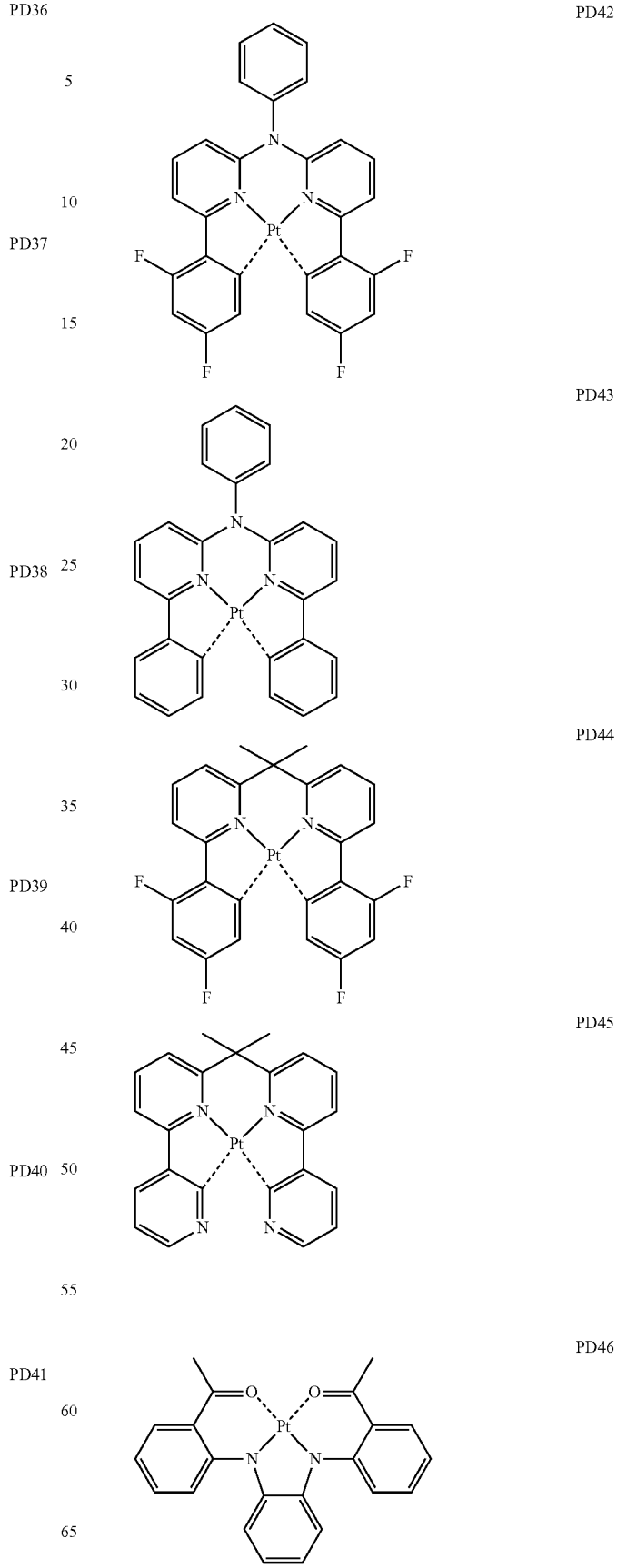

PD47
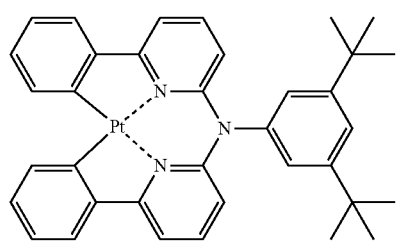
PD48
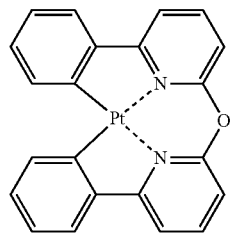
PD49
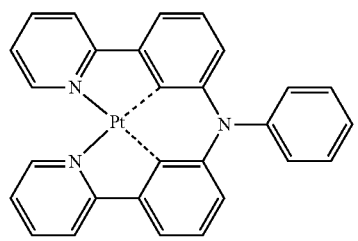
PD50
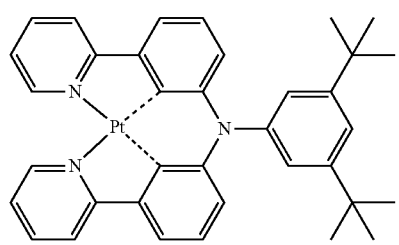
PD51
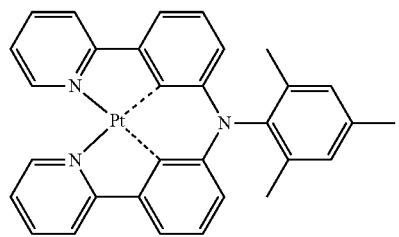
PD52
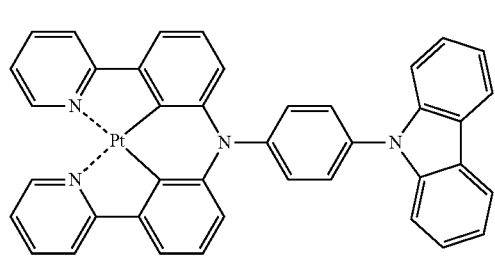
PD53
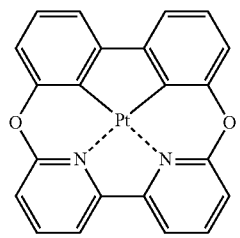
PD54
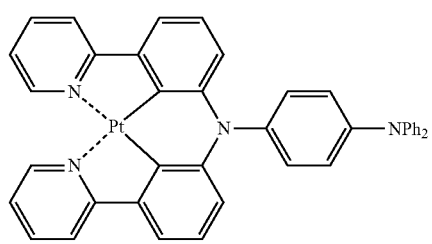
PD55
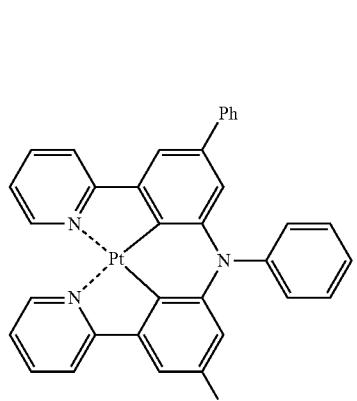
PD56
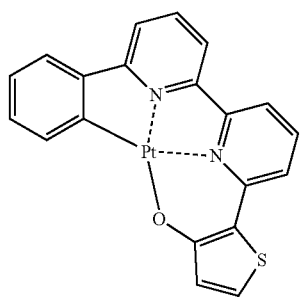
PD57
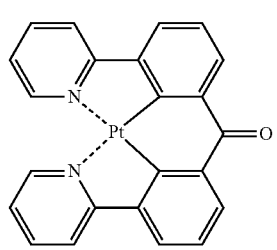

537
-continued
PD58
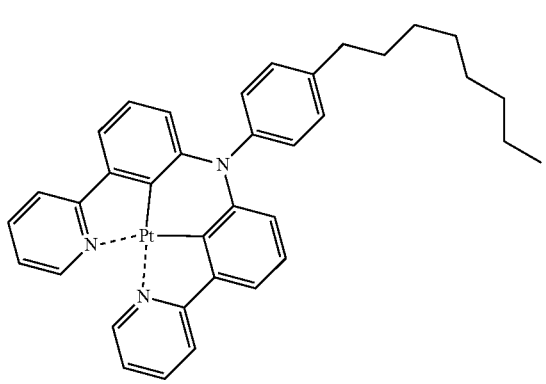
PD59
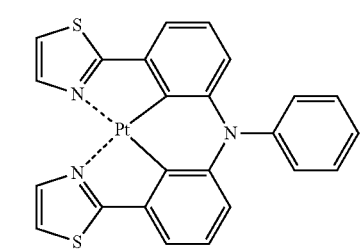
PD60
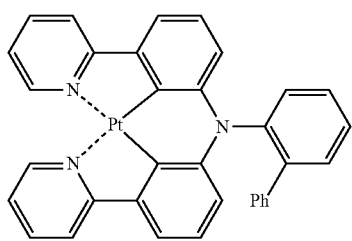
PD61
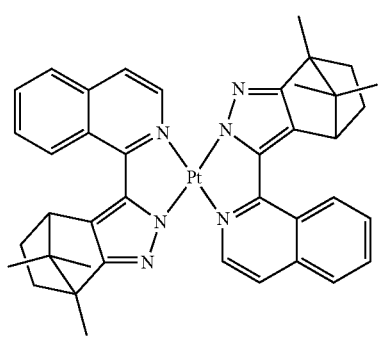
PD62
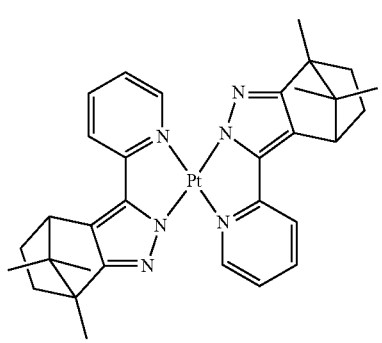
538
-continued
PD63
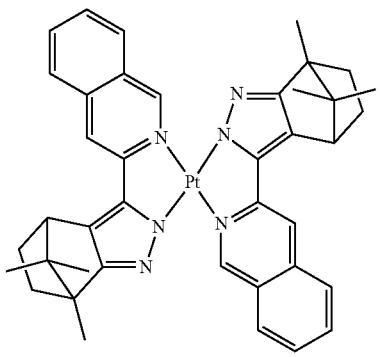
PD64
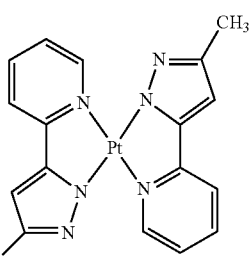
PD65
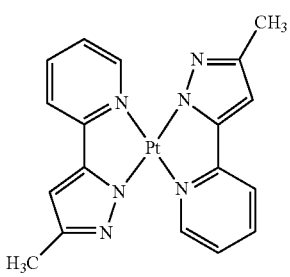
PD66
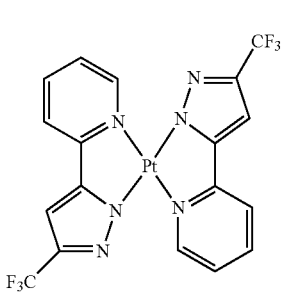
PD67
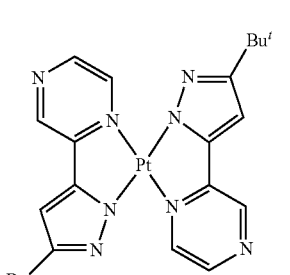

539
-continued
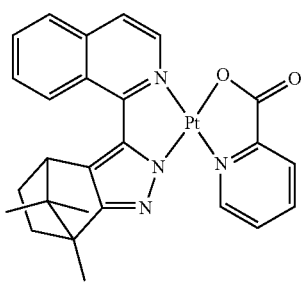
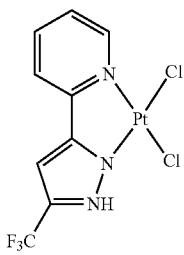
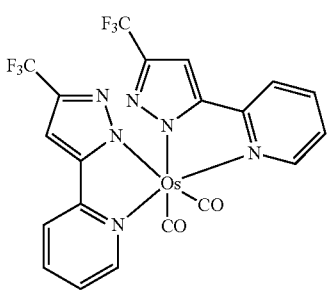
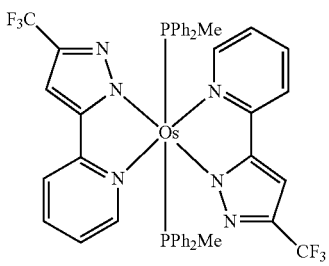
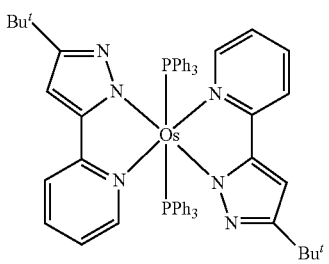
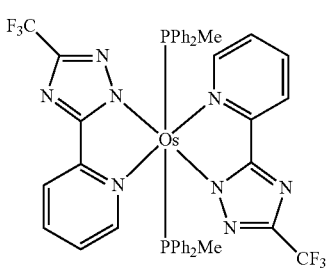
540
-continued
PD68
PD74 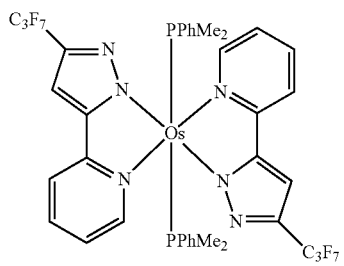
PD69
PD75 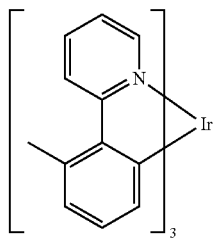
PD70
PD76 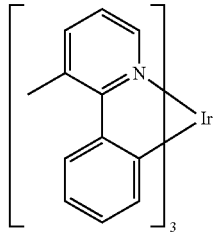
PD71
PD77 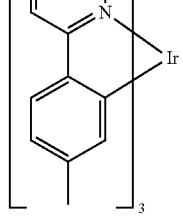
PD72
PD78 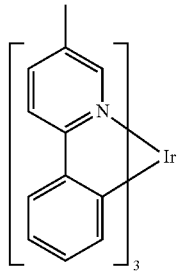
PD73
FIr6 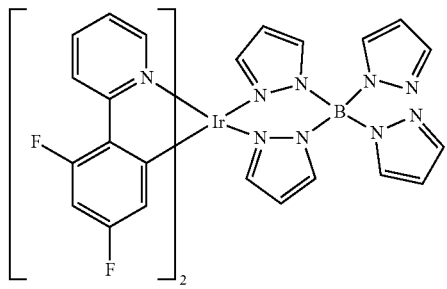

The expression "(an organic layer) includes at least one condensed cyclic compounds represented by Formula 1" as used herein may include an embodiment in which "(an organic layer) includes identical condensed cyclic compounds represented by Formula 1" and an embodiment in which "(an organic layer) includes two or more different condensed cyclic compounds represented by Formula 1."

For example, the organic layer may include, as the condensed cyclic compound, only Compound 1. In this embodiment, Compound 1 may be included in an emission layer of the organic light-emitting device. In one or more embodiments, the organic layer may include, as the condensed cyclic compound, Compound 1 and Compound 2. In this embodiment, Compound 1 and Compound 2 may be included in an identical layer (for example, Compound 1 and Compound 2 may both be included in an emission layer), or different layers (for example, Compound 1 may be included in an emission layer and Compound 2 may be included in a hole blocking layer).

The first electrode may be an anode, which is a hole injection electrode, and the second electrode may be a cathode, which is an electron injection electrode; or the first electrode may be a cathode, which is an electron injection electrode, and the second electrode may be an anode, which is a hole injection electrode.

The term "organic layer" as used herein refers to a single layer and/or a plurality of layers between the first electrode and the second electrode of the organic light-emitting device. The "organic layer" may include, in addition to an organic compound, an organometallic complex including metal.

The FIGURE is a schematic view of an organic light-emitting device 10 according to an embodiment. Hereinafter, the structure of an organic light-emitting device according to an embodiment and a method of manufacturing an organic light-emitting device according to an embodiment will be described in connection with the FIGURE. The organic light-emitting device 10 includes a first electrode 11, an organic layer 15, and a second electrode 19, which are sequentially stacked.

A substrate may be additionally disposed under the first electrode 11 or above the second electrode 19. For use as the substrate, any substrate that is used in general organic light-emitting devices may be used, and the substrate may be a glass substrate or a transparent plastic substrate, each having excellent mechanical strength, thermal stability, transparency, surface smoothness, ease of handling, and water resistance.

The first electrode 11 may be formed by depositing or sputtering a material for forming the first electrode 11 on the substrate. The first electrode 11 may be an anode. The material for forming the first electrode 11 may be selected from materials with a high work function to facilitate hole injection. The first electrode 11 may be a reflective electrode, a semi-transmissive electrode, or a transmissive electrode. The material for forming the first electrode may be, for example, indium tin oxide (ITO), indium zinc oxide (IZO), tin oxide ($SnO_2$), and zinc oxide (ZnO). In one or more embodiments, magnesium (Mg), aluminum (Al), aluminum-lithium (Al-$L_1$), calcium (Ca), magnesium-indium (Mg—In), or magnesium-silver (Mg—Ag) may be used as the material for forming the first electrode.

The first electrode 11 may have a single-layered structure or a multi-layered structure including two or more layers. For example, the first electrode 11 may have a three-layered structure of ITO/Ag/ITO, but the structure of the first electrode 110 is not limited thereto.

The organic layer 15 is disposed on the first electrode 11.

The organic layer 15 may include a hole transport region, an emission layer, and an electron transport region.

The hole transport region may be disposed between the first electrode 11 and the emission layer.

The hole transport region may include at least one selected from a hole injection layer, a hole transport layer, an electron blocking layer, and a buffer layer.

The hole transport region may include only either a hole injection layer or a hole transport layer. In one or more embodiments, the hole transport region may have a hole injection layer/hole transport layer structure or a hole injection layer/hole transport layer/electron blocking layer structure, which are sequentially stacked in this stated order from the first electrode 11.

A hole injection layer may be formed on the first electrode 11 by using one or more suitable methods selected from vacuum deposition, spin coating, casting, or Langmuir-Blodgett (LB) deposition.

When a hole injection layer is formed by vacuum deposition, the deposition conditions may vary according to a compound that is used to form the hole injection layer, and the structure and thermal characteristics of the hole injection layer. For example, the deposition conditions may include a deposition temperature of about 100° C. to about 500° C., a vacuum pressure of about $10^{-8}$ torr to about $10^{-3}$ torr, and a deposition rate of about 0.01 Å/sec to about 100 Å/sec. However, the deposition conditions are not limited thereto.

When the hole injection layer is formed using spin coating, coating conditions may vary according to the material used to form the hole injection layer, and the structure and thermal properties of the hole injection layer. For example, a coating speed may be from about 2,000 revolutions per minute (rpm) to about 5,000 rpm, and a temperature at which a heat treatment is performed to remove a solvent after coating may be from about 80° C. to about 200° C. However, the coating conditions are not limited thereto.

Conditions for forming a hole transport layer and an electron blocking layer may be understood by referring to conditions for forming the hole injection layer.

The hole transport region may include at least one selected from m-MTDATA, TDATA, 2-TNATA, NPB, β-NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzene sulfonic acid (PANI/DBSA), poly(3,4-ethylenedioxythiophene)/poly(4-styrene sulfonate) (PEDOT/PSS), polyaniline/camphor sulfonic acid (PANI/CSA), polyaniline/poly(4-styrene sulfonate) (PANI/PSS), a compound represented by Formula 201 below, and a compound represented by Formula 202 below:

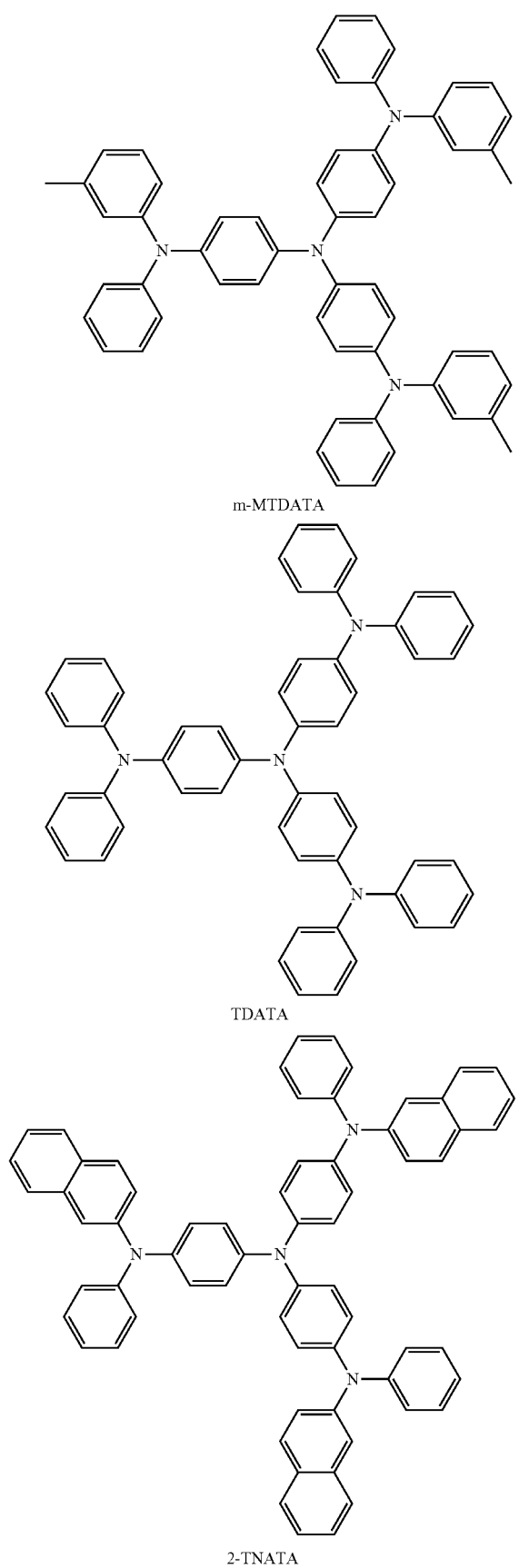

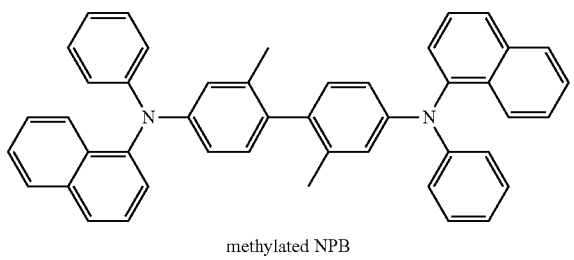

methylated NPB

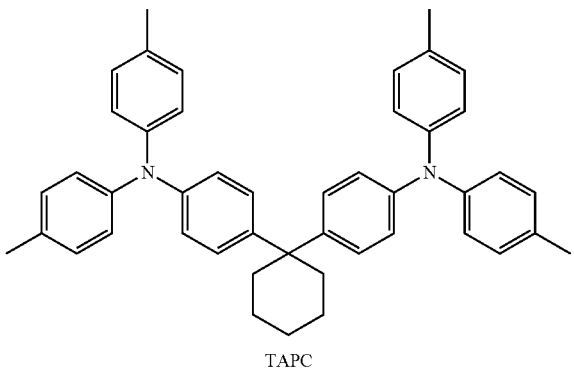

TAPC

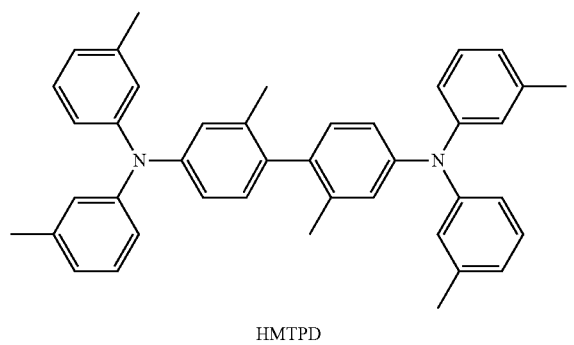

HMTPD

Formula 201

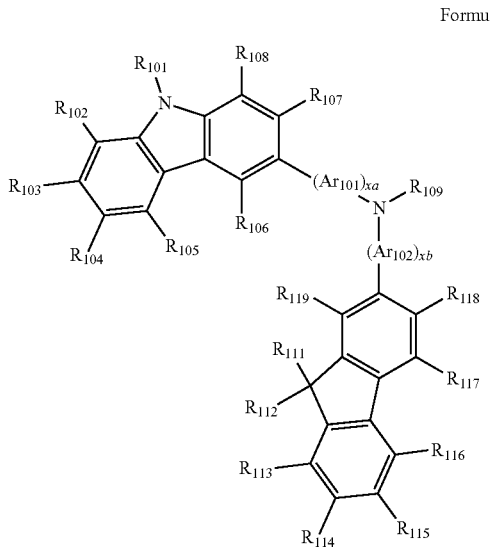

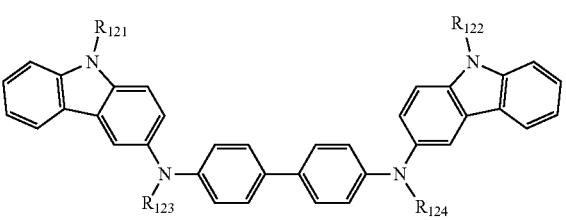

Formula 202

In Formula 201, $Ar_{101}$ and $Ar_{102}$ may each independently be selected from:

a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

In Formula 201, xa and xb may each independently be an integer from 0 to 5, or 0, 1, or 2. For example, xa is 1 and xb is 0, but xa and xb are not limited thereto.

In Formulae 201 and 202, $R_{101}$ to $R_{108}$, $R_{111}$ to $R_{119}$, and $R_{121}$ to $R_{124}$ may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, and a $C_1$-$C_{10}$ alkyl group (for example, a methyl group, an ethyl group, a propyl group, a butyl group, a pentyl group, a hexyl group, and so on), or a $C_1$-$C_{10}$ alkoxy group (for example, a methoxy group, an ethoxy group, a propoxy group, a butoxy group, a pentoxy group, and so on);

a $C_1$-$C_{10}$ alkyl group or a $C_1$-$C_{10}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, or a $C_1$-$C_{10}$ alkoxy group, but embodiments of the present disclosure are not limited thereto.

In Formula 201, $R_{109}$ may be selected from:

a phenyl group, a naphthyl group, an anthracenyl group, and a pyridinyl group; and a phenyl group, a naphthyl group, an anthracenyl group, and a pyridinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, and a pyridinyl group.

In an embodiment, the compound represented by Formula 201 may be represented by Formula 201A, but embodiments of the present disclosure are not limited thereto:

Formula 201A

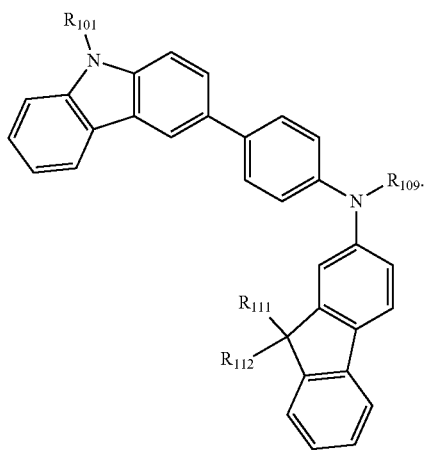

In Formula 201A, $R_{101}$, $R_{111}$, $R_{112}$, and $R_{109}$ may each independently be the same as defined above.

For example, the compound represented by Formula 201, and the compound represented by Formula 202 may include Compounds HT1 to HT20, but embodiments of the present disclosure are not limited thereto.

HT1

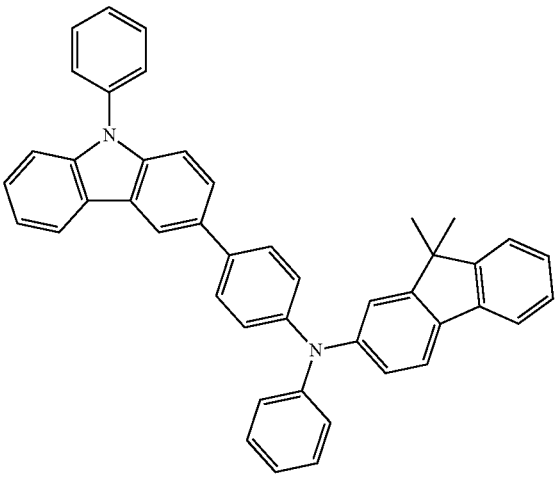

HT2

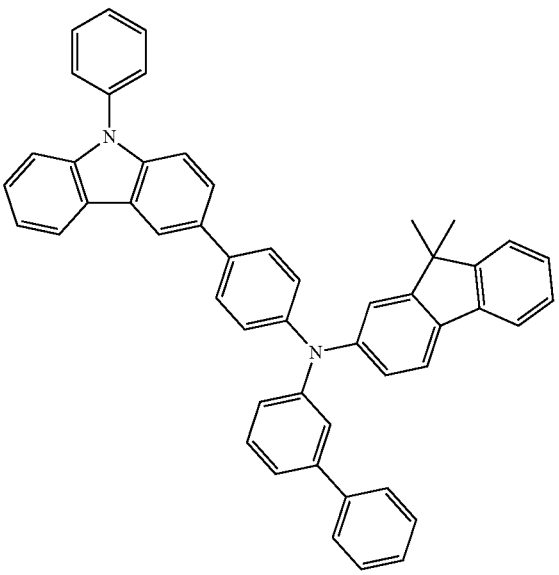

-continued
HT3
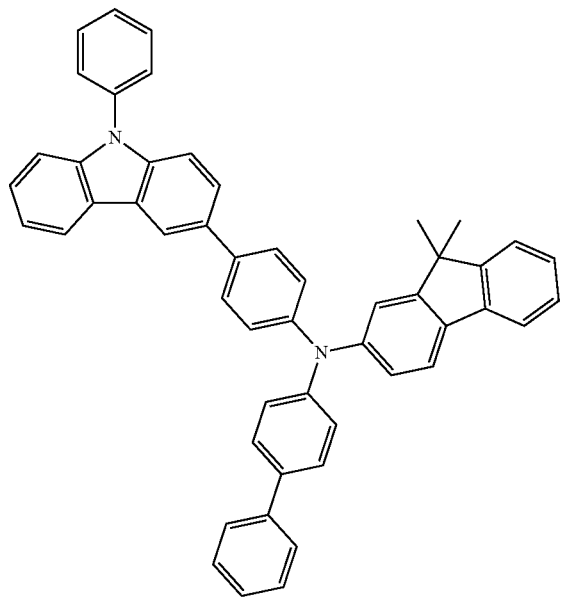
HT5
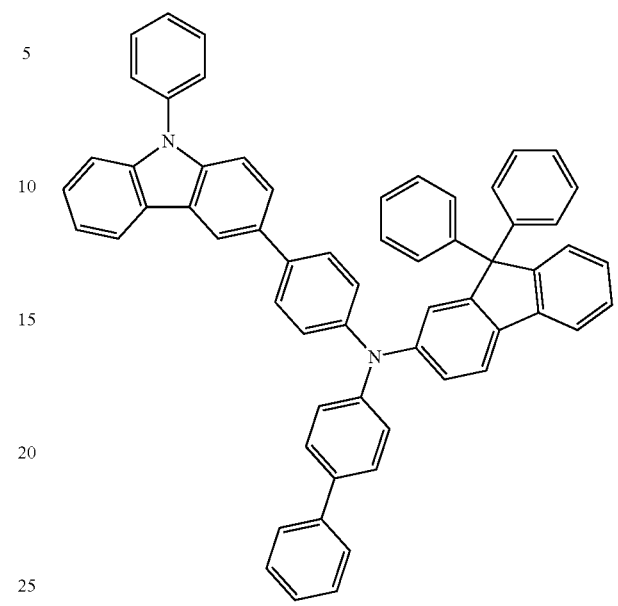
HT4
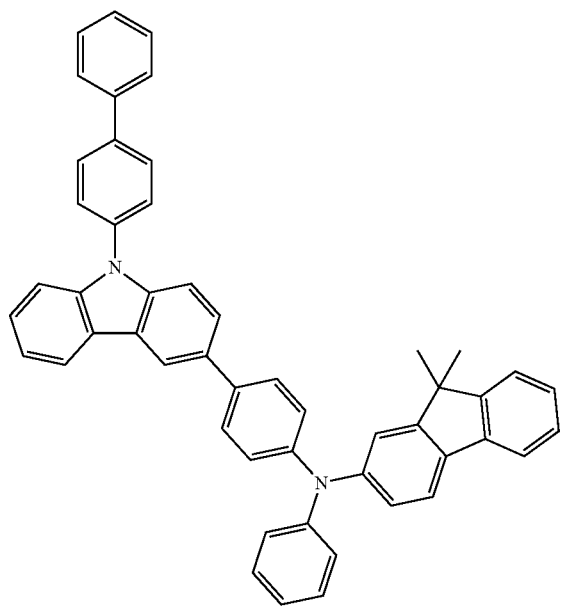
HT6
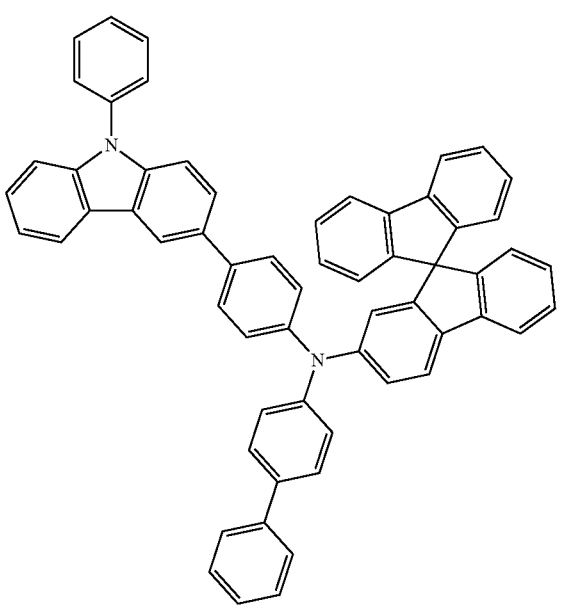

551
-continued
HT7
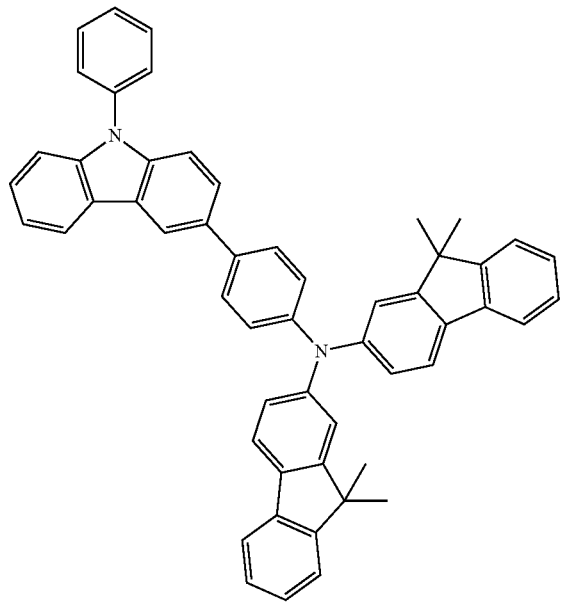
552
-continued
HT9
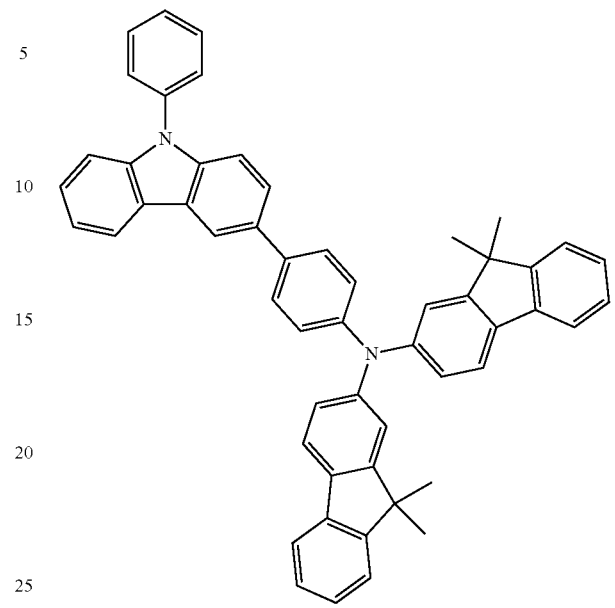
HT8
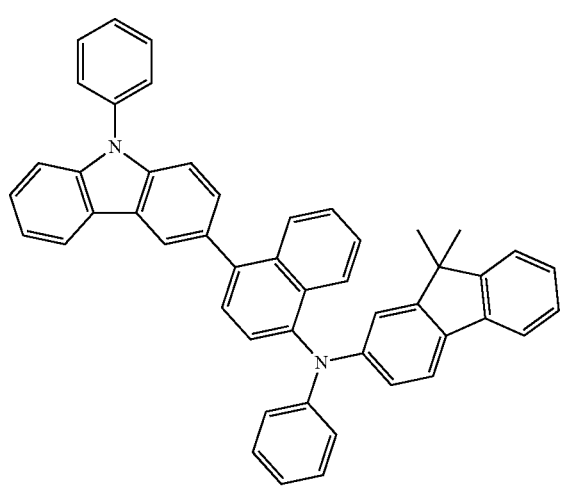
HT10
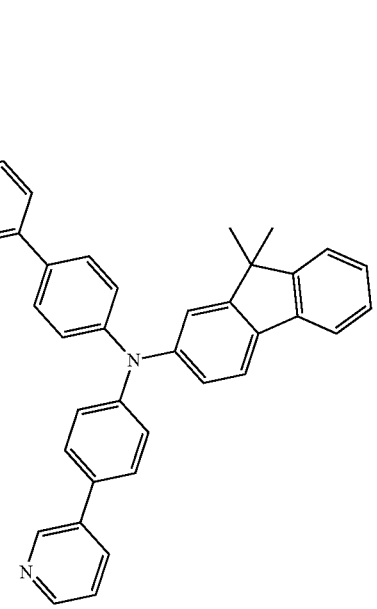

HT11
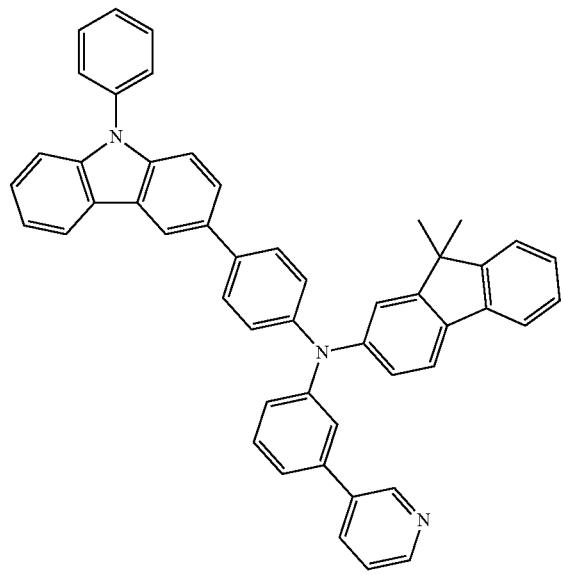
HT14
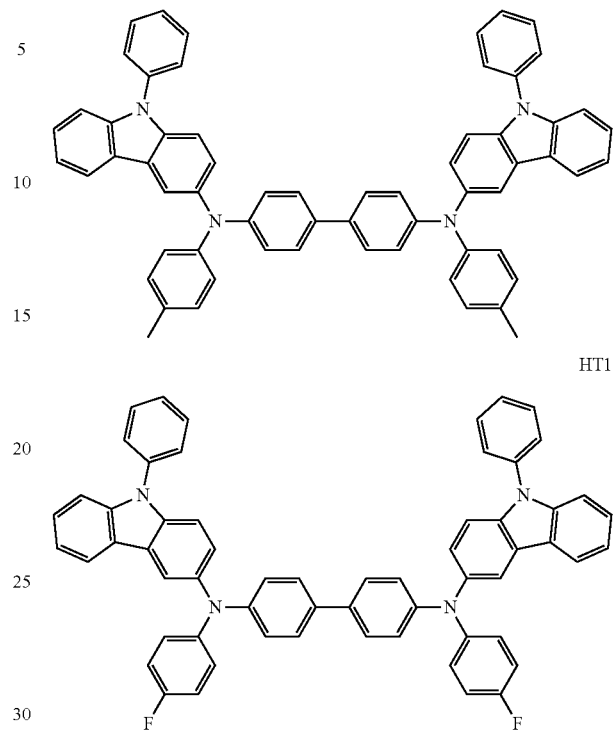
HT12
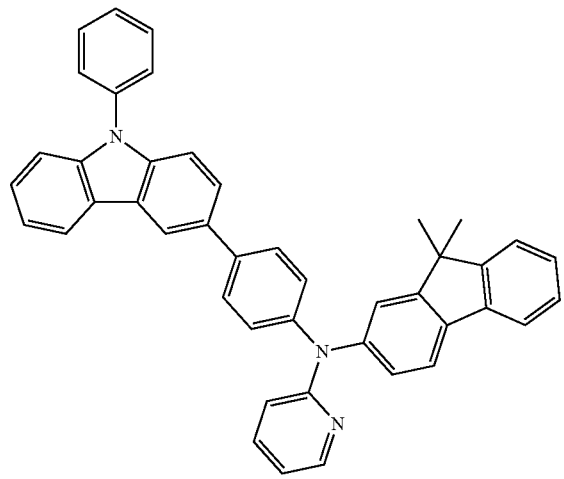
HT15
HT16
HT13
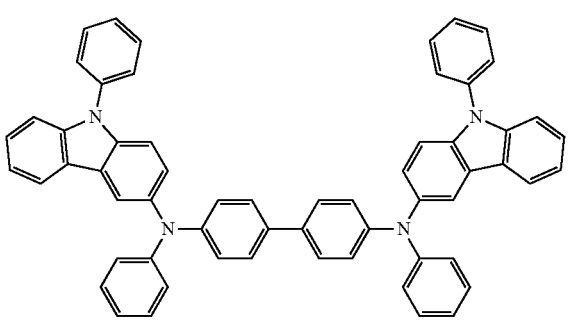
HT17
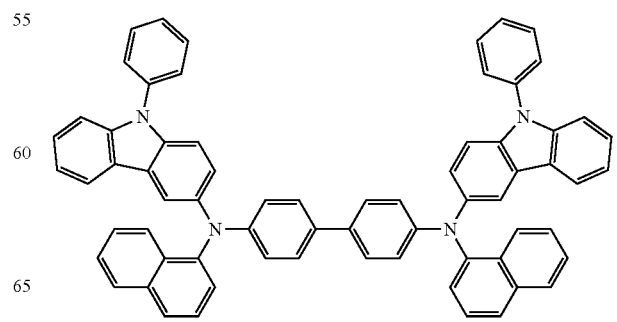

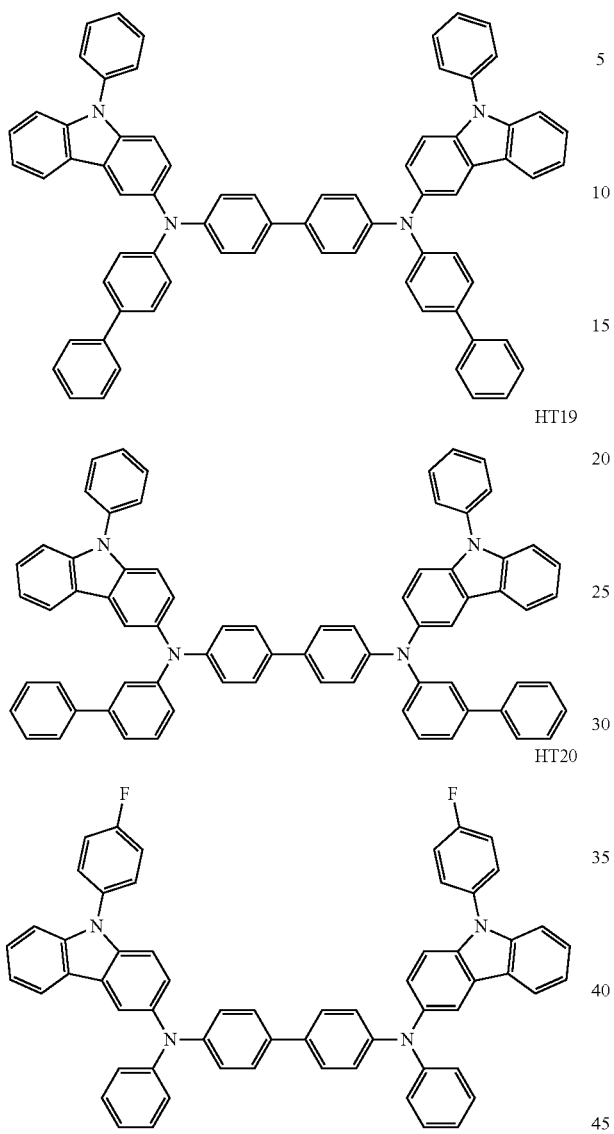

HT18

HT19

HT20

A thickness of the hole transport region may be in a range of about 100 Å to about 10,000 Å, for example, about 100 Å to about 1,000 Å. When the hole transport region includes at least one of a hole injection layer and a hole transport layer, the thickness of the hole injection layer may be in a range of about 100 Å to about 10,000 Å, and for example, about 100 Å to about 1,000 Å, and the thickness of the hole transport layer may be in a range of about 50 Å to about 2,000 Å, and for example, about 100 Å to about 1,500 Å. While not wishing to be bound by theory, it is understood that when the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be one selected from a quinone derivative, a metal oxide, and a cyano group-containing compound, but embodiments of the present disclosure are not limited thereto. Non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide; and a cyano group-containing compound, such as Compound HT-D1 or Compound HT-D2 below, but are not limited thereto.

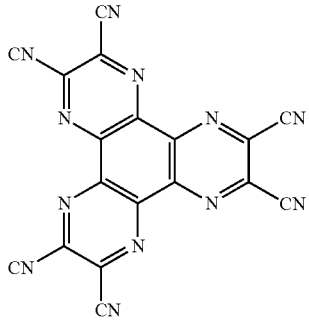

HT-D1

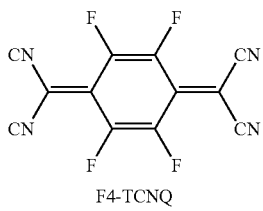

F4-TCNQ

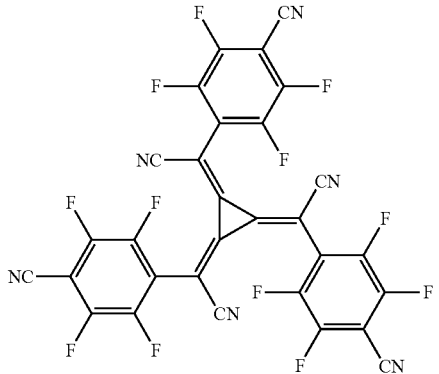

HT-D2

The hole transport region may include a buffer layer.

Also, the buffer layer may compensate for an optical resonance distance according to a wavelength of light emitted from the emission layer, and thus, efficiency of a formed organic light-emitting device may be improved.

The hole transport region may further include an electron blocking layer. The electron blocking layer may include, for example, mCP, but a material therefor is not limited thereto.

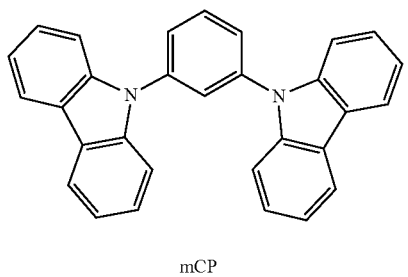 [SMILES: c1cc(-n2c3ccccc3c3ccccc32)cc(-n2c3ccccc3c3ccccc32)c1]

mCP

A thickness of the electron blocking layer may be in a range of about 50 Å to about 1,000 Å, for example, about 70 Å to about 500 Å. While not wishing to be bound by theory, it is understood that when the thickness of the electron blocking layer is within the range described above, the electron blocking layer may have satisfactory electron blocking characteristics without a substantial increase in driving voltage.

Then, an emission layer may be formed on the hole transport region by vacuum deposition, spin coating, casting, LB deposition, or the like. When the emission layer is formed by vacuum deposition or spin coating, the deposition or coating conditions may be similar to those applied in forming the hole injection layer although the deposition or coating conditions may vary according to a compound that is used to form the emission layer.

When the organic light-emitting device is a full-color organic light-emitting device, the emission layer may be patterned into a red emission layer, a green emission layer, and a blue emission layer. In one or more embodiments, due to a stacked structure including a red emission layer, a green emission layer, and/or a blue emission layer, the emission layer may emit white light.

The emission layer may include the condensed cyclic compound represented by Formula 1.

For example, the emission layer may include the compound represented by Formula 1 alone.

In an embodiment, the emission layer may include the condensed cyclic compound represented by Formula 1, and the emission layer may further include:

i) the second compound (for example, a compound represented by Formula H-1);

ii) an organometallic compound represented by Formula 81; or iii) any combination thereof.

The condensed cyclic compound represented by Formula 1, the second compound, and the organometallic compound represented by Formula 81 may each independently be the same as described herein.

When the emission layer includes a host and a dopant, an amount of the dopant may be in a range of about 0.01 parts by weight to about 20 parts by weight based on 100 parts by weight of the emission layer, but embodiments of the present disclosure are not limited thereto. While not wishing to be bound by theory, it is understood that when the amount of the dopant is within this range, light emission may be implemented without a quenching phenomenon.

When the emission layer includes the condensed cyclic compound represented by Formula 1 and the second compound, the weight ratio of the condensed cyclic compound represented by Formula 1 to the second compound may be in a range of about 1:99 to about 99:1, for example, about 70:30 to about 30:70. As another example, the ratio of the condensed cyclic compound represented by Formula 1 to the second compound may be in a range of about 60:40 to about 40:60. While not wishing to be bound by theory, it is understood that when the weight ratio of the condensed cyclic compound represented by Formula 1 to the second compound in the emission layer is within this range, charge transport balance in the emission layer may be effectively achieved.

A thickness of the emission layer may be in a range of about 100 Å to about 1000 Å, for example, about 200 Å to about 600 Å. While not wishing to be bound by theory, it is understood that when the thickness of the emission layer is within this range, excellent light emission characteristics may be exhibited without a substantial increase in driving voltage.

An electron transport region may be disposed on the emission layer.

The electron transport region may include at least one selected from a hole blocking layer, an electron transport layer, and an electron injection layer.

For example, the electron transport region may have a hole blocking layer/electron transport layer/electron injection layer structure or an electron transport layer/electron injection layer structure, but the structure of the electron transport region is not limited thereto. The electron transport layer may have a single-layered structure or a multi-layered structure including two or more different materials.

Conditions for forming the hole blocking layer, the electron transport layer, and the electron injection layer which constitute the electron transport region may be understood by referring to the conditions for forming the hole injection layer.

When the electron transport region includes a hole blocking layer, the hole blocking layer may include, for example, at least one of BCP and BPhen, but may also include other materials.

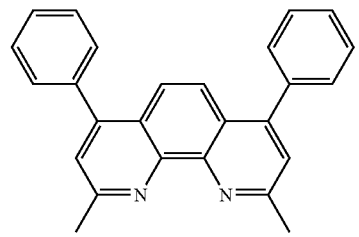

BCP

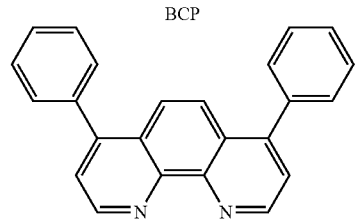

Bphen

The hole blocking layer may include the condensed cyclic compound represented by Formula 1.

A thickness of the hole blocking layer may be in a range of about 20 Å to about 1,000 Å, for example, about 30 Å to about 300 Å. When the thickness of the hole blocking layer is within these ranges, the hole blocking layer may have improved hole blocking ability without a substantial increase in driving voltage.

The electron transport layer may further include at least one selected from BCP, BPhen, Alq$_3$, BAlq, TAZ, and NTAZ.

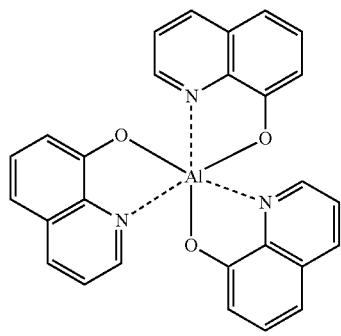

Alq$_3$

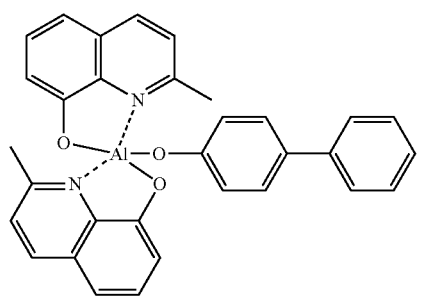

BAlq

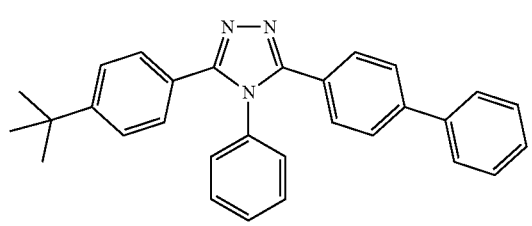

TAZ

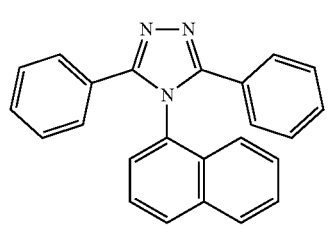

NTAZ

In one or more embodiments, the electron transport layer may include at least one selected from Compounds ET1, ET2, and ET3, but embodiments of the present disclosure are not limited thereto:

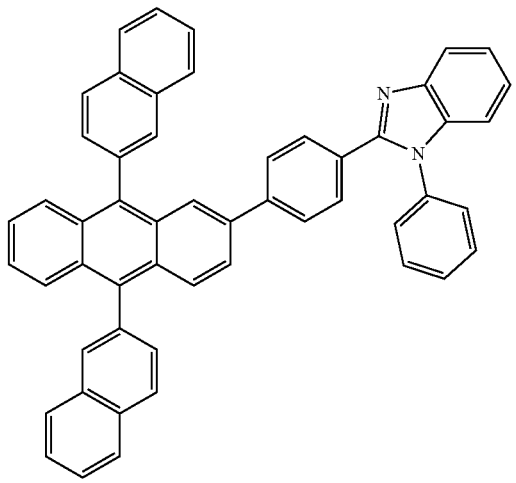

ET1

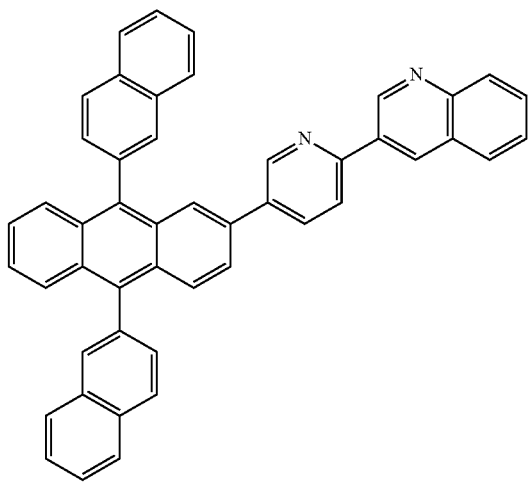

ET2

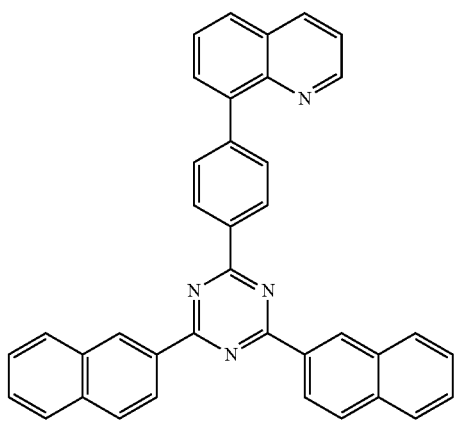

ET3

A thickness of the electron transport layer may be in a range of about 100 Å to about 1,000 Å, for example, about 150 Å to about 500 Å. When the thickness of the electron transport layer is within the range described above, the electron transport layer may have satisfactory electron transport characteristics without a substantial increase in driving voltage.

Also, the electron transport layer may further include, in addition to the materials described above, a metal-containing material.

The metal-containing material may include a $L_1$ complex. The $L_1$ complex may include, for example, Compound ET-D1 (lithium 8-hydroxyquinolate, LiQ) or ET-D2.

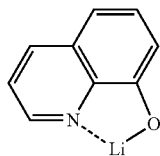

ET-D1

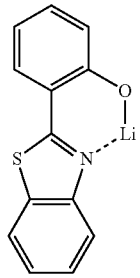

ET-D2

The electron transport region may include an electron injection layer that promotes flow of electrons from the second electrode 19 thereinto.

The electron injection layer may include at least one selected from LiQ, LiF, NaCl, CsF, $Li_2O$, and BaO.

A thickness of the electron injection layer may be in a range of about 1 Å to about 100 Å, for example, about 3 Å to about 90 Å. While not wishing to be bound by theory, it is understood that when the thickness of the electron injection layer is within the range described above, the electron injection layer may have satisfactory electron injection characteristics without a substantial increase in driving voltage.

The second electrode 19 is disposed on the organic layer 15. The second electrode 19 may be a cathode. A material for forming the second electrode 19 may be selected from metal, an alloy, an electrically conductive compound, and a combination thereof, which have a relatively low work function. For example, lithium ($L_1$), magnesium (Mg), aluminum (Al), aluminum-lithium (Al-$L_1$), calcium (Ca), magnesium-indium (Mg—In), or magnesium-silver (Mg—Ag) may be used as a material for forming the second electrode 19. In one or more embodiments, to manufacture a top-emission type light-emitting device, a transmissive electrode formed using ITO or IZO may be used as the second electrode 19.

Hereinbefore, the organic light-emitting device has been described with reference to FIG. 1, but embodiments of the present disclosure are not limited thereto.

The term "$C_1$-$C_{60}$ alkyl group" as used herein refers to a linear or branched saturated aliphatic hydrocarbon monovalent group having 1 to 60 carbon atoms, and non-limiting examples thereof include a methyl group, an ethyl group, a propyl group, an iso-butyl group, a sec-butyl group, a tert-butyl group, a pentyl group, an iso-amyl group, and a hexyl group. The term "$C_1$-$C_{60}$ alkylene group" as used herein refers to a divalent group having the same structure as the $C_1$-$C_{60}$ alkyl group.

The term "$C_1$-$C_{60}$ alkoxy group" as used herein refers to a monovalent group represented by —$OA_{101}$ (wherein $A_{101}$ is the $C_1$-$C_{60}$ alkyl group), and non-limiting examples thereof include a methoxy group, an ethoxy group, and an iso-propyloxy group.

The term "$C_2$-$C_{60}$ alkenyl group" as used herein refers to a hydrocarbon group formed by including at least one carbon-carbon double bond in the middle or at the terminus of the $C_2$-$C_{60}$ alkyl group, and examples thereof include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a hydrocarbon group formed by including at least one carbon-carbon triple bond in the middle or at the terminus of the $C_2$-$C_{60}$ alkyl group, and examples thereof include an ethynyl group, and a propynyl group. The term "$C_2$-$C_{60}$ alkynylene group" as used herein refers to a divalent group having the same structure as the $C_2$-$C_{60}$ alkynyl group.

The term "$C_3$-$C_{10}$ cycloalkyl group" as used herein refers to a monovalent saturated hydrocarbon monocyclic group having 3 to 10 carbon atoms, and non-limiting examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having the same structure as the $C_3$-$C_{10}$ cycloalkyl group.

The term "$C_1$-$C_{10}$ heterocycloalkyl group" as used herein refers to a monovalent saturated monocyclic group having at least one heteroatom selected from N, O, P, Si and S as a ring-forming atom and 1 to 10 carbon atoms, and non-limiting examples thereof include a tetrahydrofuranyl group, and a tetrahydrothiophenyl group. The term "$C_1$-$C_{10}$ heterocycloalkylene group" as used herein refers to a divalent group having the same structure as the $C_1$-$C_{10}$ heterocycloalkyl group.

The term "$C_3$-$C_{10}$ cycloalkenyl group" as used herein refers to a monovalent monocyclic group that has 3 to 10 carbon atoms and at least one carbon-carbon double bond in the ring thereof and no aromaticity, and non-limiting examples thereof include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_1$-$C_{10}$ heterocycloalkenyl group" as used herein refers to a monovalent monocyclic group that has at least one heteroatom selected from N, O, P, Si, and S as a ring-forming atom, 1 to 10 carbon atoms, and at least one double bond in its ring. Examples of the $C_1$-$C_{10}$ heterocycloalkenyl group are a 2,3-dihydrofuranyl group, and a 2,3-dihydrothiophenyl group. The term "$C_1$-$C_{10}$ heterocycloalkenylene group" as used herein refers to a divalent group having the same structure as the $C_1$-$C_{10}$ heterocycloalkenyl group.

The term "$C_6$-$C_{60}$ aryl group" as used herein refers to a monovalent group having a carbocyclic aromatic system having 6 to 60 carbon atoms, and the term "$C_6$-$C_{60}$ arylene group" as used herein refers to a divalent group having a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

The term "$C_1$-$C_{60}$ heteroaryl group" as used herein refers to a monovalent group having an aromatic system that has at least one heteroatom selected from N, O, P, Si, and S as a ring-forming atom, and 1 to 60 carbon atoms. The term "$C_1$-$C_{60}$ heteroarylene group," as used herein refers to a divalent group having an aromatic system that has at least one heteroatom selected from N, O, P, Si, and S as a ring-forming atom, and 1 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

The term "$C_6$-$C_{60}$ aryloxy group" as used herein refers to —$OA_{102}$ (wherein $A_{102}$ is the $C_6$-$C_{60}$ aryl group), and a $C_6$-$C_{60}$ arylthio group as used herein indicates-$SA_{103}$ (wherein $A_{103}$ is the $C_6$-$C_{60}$ aryl group).

The term "monovalent non-aromatic condensed polycyclic group" as used herein refers to a monovalent group having two or more rings condensed to each other, only carbon atoms (for example, the number of carbon atoms may be in a range of 8 to 60) as a ring-forming atom, and no aromaticity in its entire molecular structure. Non-limiting examples of the monovalent non-aromatic condensed polycyclic group include a fluorenyl group. The term "divalent non-aromatic condensed polycyclic group" as used herein refers to a divalent group having the same structure as the monovalent non-aromatic condensed polycyclic group.

The term "monovalent non-aromatic condensed heteropolycyclic group" as used herein refers to a monovalent group having two or more rings condensed to each other, a heteroatom selected from N, O, P, Si, and S, other than carbon atoms (for example, the number of carbon atoms may be in a range of 2 to 60), as a ring-forming atom, and no aromaticity in its entire molecular structure. Non-limiting examples of the monovalent non-aromatic condensed heteropolycyclic group include a carbazolyl group. The term "divalent non-aromatic condensed heteropolycyclic group" as used herein refers to a divalent group having the same structure as the monovalent non-aromatic condensed heteropolycyclic group.

In Formula 1, at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{11})(Q_{12})(Q_{13})$, —$N(Q_{14})(Q_{15})$, and —$B(Q_{16})(Q_{17})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{21})(Q_{22})(Q_{23})$, —$N(Q_{24})(Q_{25})$, and —$B(Q_{26})(Q_{27})$; and —$Si(Q_{31})(Q_{32})(Q_{33})$, —$N(Q_{34})(Q_{35})$, and —$B(Q_{36})(Q_{37})$.

$Q_{11}$ to $Q_{17}$, $Q_{21}$ to $Q_{27}$, and $Q_{31}$ to $Q_{37}$ as used herein may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

* and *¹ as used herein, unless defined otherwise, each independently indicates a binding site to a neighboring atom in a corresponding formula Hereinafter, a condensed cyclic compound and an organic light-emitting device according to embodiments are described in detail with reference to Synthesis Example and Examples. However, the condensed cyclic compound and the organic light-emitting device are not limited thereto.

EXAMPLES

Synthesis Example 1: Synthesis of Compound 1

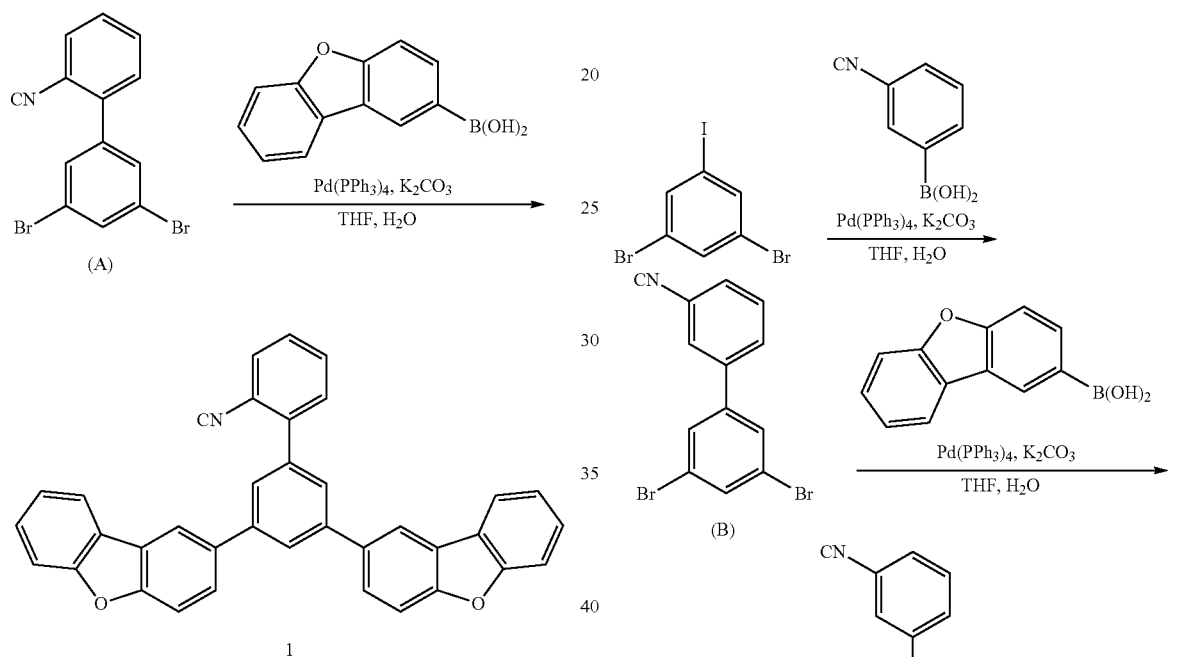

Synthesis of Intermediate (A)

10.0 grams (g) (27.6 millimoles, mmol) of 1,3-dibromo-5-iodobenzene, 4.06 g (27.6 mmol) of (2-cyanophenyl)boronic acid, 1.60 g (1.38 mmol) of tetrakis(triphenylphosphine)palladium(0) (Pd(PPh$_3$)$_4$), and 9.55 g (69.1 mmol) of potassium carbonate were added to a mixed solution containing 60 milliliters (mL) of tetrahydrofuran (THF) and 30 mL of water, and the reaction mixture was stirred for 12 hours under reflux. After the reaction was completed, the reaction product was cooled to room temperature, and the aqueous solution layer was removed therefrom through extraction. The resultant obtained therefrom was filtered through a silica gel under reduced pressure, and the filtrate was concentrated under reduced pressure. The product obtained therefrom was separated by silica gel column chromatography to provide Intermediate (A) (4.38 g, yield of 47%).

LC-Mass (Calcd.: 334.89 grams per mole (g/mol), Found: M+1=336 g/mol).

Synthesis of Compound 1

4.20 g (12.5 mmol) of Intermediate (A), 6.61 g (31.2 mmol) of dibenzo[b,d]furan-2-ylboronic acid, 1.44 g (1.25 mmol) of tetrakis(triphenylphosphine)palladium(0) (Pd(PPh$_3$)$_4$), and 8.61 g (62.3 mmol) of potassium carbonate were added to a mixed solution containing 40 mL of THF and 20 mL of water, and the reaction mixture was stirred for 12 hours under reflux. After the reaction was completed, the reaction product was cooled to room temperature, and the aqueous solution layer was removed therefrom through extraction. The resultant obtained therefrom was filtered through a silica gel under reduced pressure, and the filtrate was concentrated under reduced pressure. The product obtained therefrom was separated by silica gel column chromatography to provide Compound 1 (3.57 g, yield of 56%).

LC-Mass (Calcd.: 511.16 g/mol, Found: M+1=512 g/mol).

Synthesis Example 2: Synthesis of Compound 2

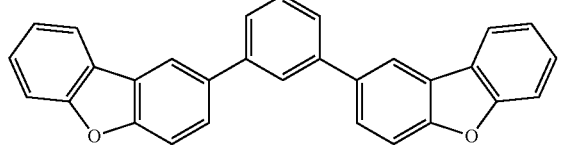

Synthesis of Intermediate (B)

Intermediate (B) (4.94 g, yield of 53%) was obtained in the same manner as Intermediate (A) of Synthesis Example 1, except that 4.06 g (27.6 mmol) of (3-cyanophenyl)boronic acid was used instead of (2-cyanophenyl)boronic acid.

LC-Mass (Calcd.: 334.89 g/mol, Found: M+1=336 g/mol).

Synthesis of Compound 2

Compound 2 (5.39 g, yield of 74%) was obtained in the same manner as Compound 1 of Synthesis Example 1, except that 4.80 g (14.2 mmol) of Intermediate (B) was used instead of Intermediate (A).

LC-Mass (Calcd.: 511.16 g/mol, Found: M+1=512 g/mol).

Synthesis Example 3: Synthesis of Compound 3

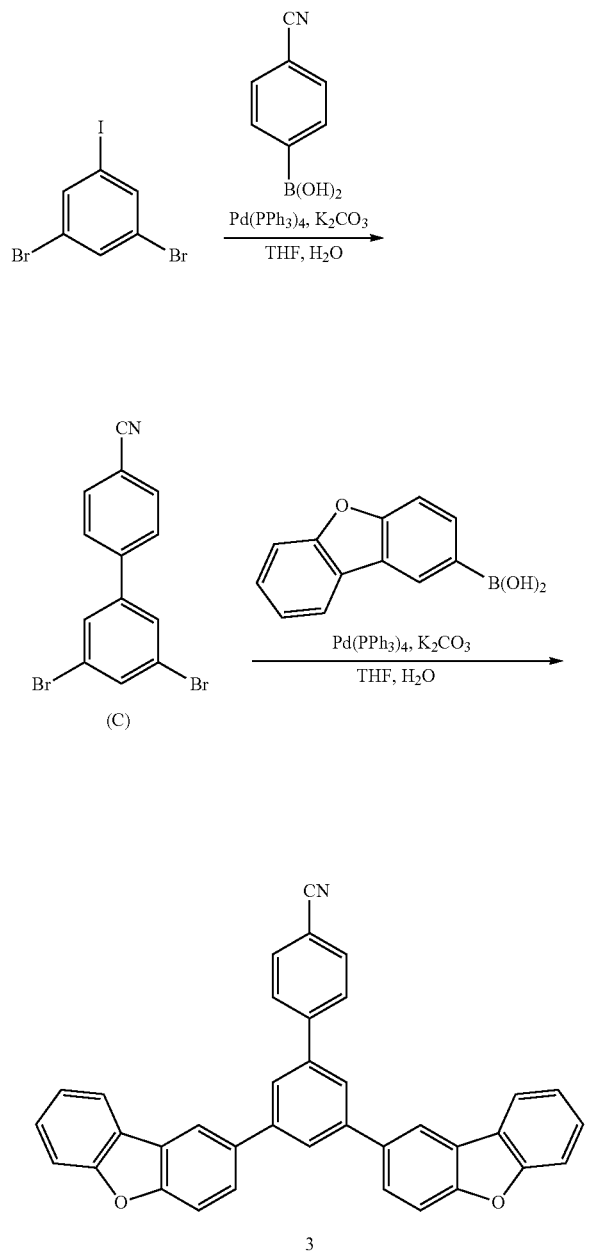

Synthesis of Intermediate (C)
Intermediate (C) (4.85 g, yield of 52%) was obtained in the same manner as Intermediate (A) of Synthesis Example 1, except that 4.06 g (27.6 mmol) of (4-cyanophenyl)boronic acid was used instead of (2-cyanophenyl)boronic acid.

LC-Mass (Calcd.: 334.89 g/mol, Found: M+1=336 g/mol).

Synthesis of Compound 3
Compound 3 (4.92 g, yield of 69%) was obtained in the same manner as Compound 1 of Synthesis Example 1, except that 4.70 g (14.2 mmol) of Intermediate (C) was used instead of Intermediate (A).

LC-Mass (Calcd.: 511.16 g/mol, Found: M+1=512 g/mol).

Synthesis Example 4: Synthesis of Compound 9

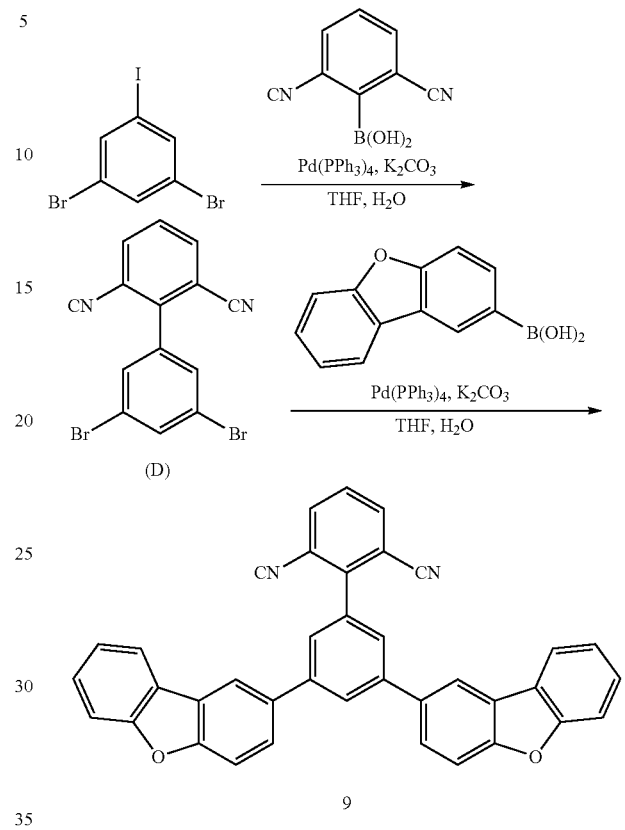

Synthesis of Intermediate (D)
Intermediate (D) (3.60 g, yield of 24%) was obtained in the same manner as Intermediate (A) of Synthesis Example 1, except that 7.13 g (41.5 mmol) of (2,6-dicyanophenyl)boronic acid was used instead of (2-cyanophenyl)boronic acid.

LC-Mass (Calcd.: 359.89 g/mol, Found: M+1=361 g/mol).

Synthesis of Compound 9
Compound 9 (2.18 g, yield of 42%) was obtained in the same manner as Compound 1 of Synthesis Example 1, except that 3.50 g (9.67 mmol) of Intermediate (D) was used instead of Intermediate (A).

LC-Mass (Calcd.: 536.15 g/mol, Found: M+1=537 g/mol).

Synthesis Example 5: Synthesis of Compound 44

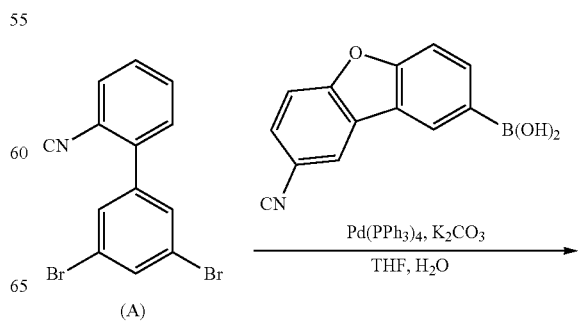

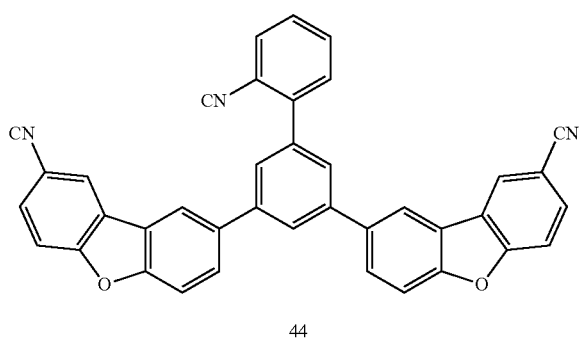

44

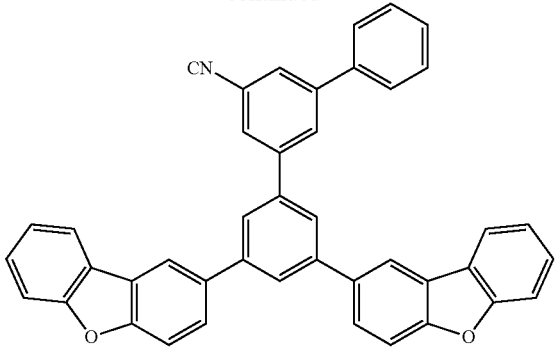

62

Compound 44 (2.71 g, yield of 37%) was obtained in the same manner as Compound 1 of Synthesis Example 1, except that 10.7 g (32.6 mmol) of (8-cyanodibenzo[b,d]furan-2-yl)boronic acid was used instead of dibenzo[b,d]furan-2-ylboronic acid.

LC-Mass (Calcd.: 561.15 g/mol, Found: M+1=562 g/mol).

Synthesis Example 6: Synthesis of Compound 62

Synthesis of Intermediate (E)

Intermediate (E) (7.88 g, yield of 69%) was obtained in the same manner as Intermediate (A) of Synthesis Example 1, except that 8.44 g (27.6 mmol) of 5-(4,4,5,5-tetramethyl-1,3,2-dioxaborolan-2-yl)-[1,1'-biphenyl]-3-carbonitrile was used instead of (2-cyanophenyl)boronic acid.

LC-Mass (Calcd.: 410.93 g/mol, Found: M+1=412 g/mol).

Synthesis of Compound 62

Compound 62 (3.84 g, yield of 54%) was obtained in the same manner as in Compound 1 of Synthesis Example 1, except that 5.00 g (12.1 mmol) of Intermediate (E) was used instead of Intermediate (A).

LC-Mass (Calcd.: 587.19 g/mol, Found: M+1=588 g/mol).

Synthesis Example 7: Synthesis of Compound 201

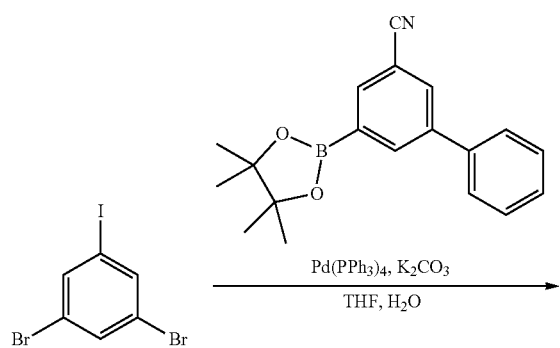

(A)

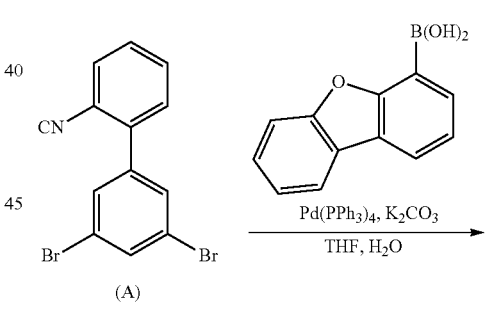

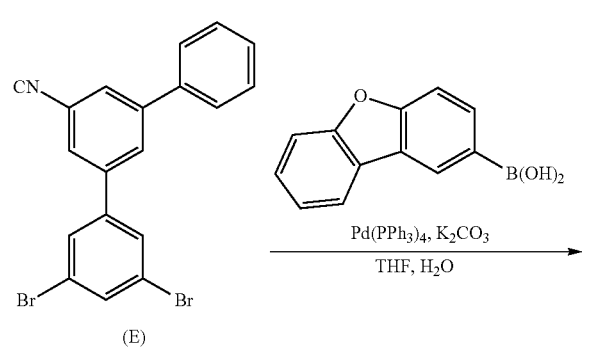

(E)

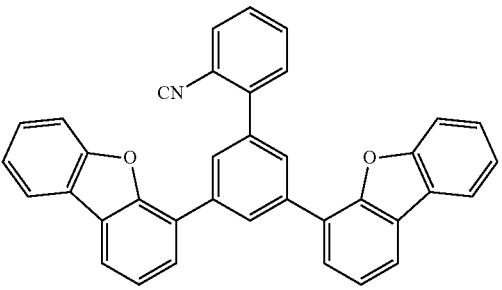

201

Compound 201 (3.20 g, yield of 44%) was obtained in the same manner as Compound 1 of Synthesis Example 1, except that 7.55 g (35.6 mmol) of dibenzo[b,d]furan-4-ylboronic acid was used instead of dibenzo[b,d]furan-2-ylboronic acid.

LC-Mass (Calcd.: 511.16 g/mol, Found: M+1=512 g/mol).

Synthesis Example 8: Synthesis of Compound 321

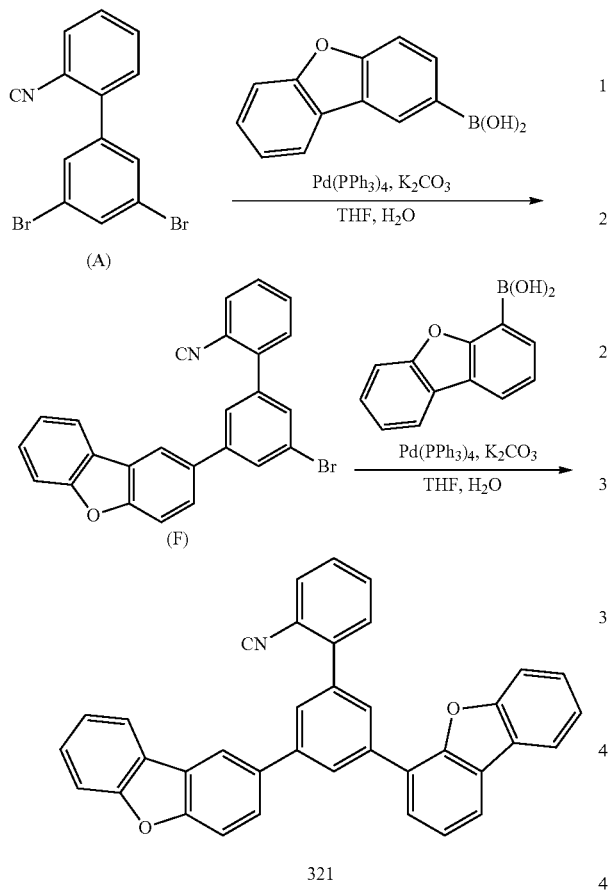

Synthesis of Intermediate (F)

5.70 g (16.9 mmol) of Intermediate (A), 3.41 g (16.1 mmol) of dibenzo[b,d]furan-2-ylboronic acid, 0.977 g (0.850 mmol) of tetrakis(triphenylphosphine)palladium(0) (Pd(PPh₃)₄), and 5.84 g (42.3 mmol) of potassium carbonate were added to a mixed solution containing 40 mL of THF and 20 mL of water, and the reaction mixture was stirred for 12 hours under reflux. After the reaction was completed, the reaction product was cooled to room temperature, and the aqueous solution layer was removed therefrom through extraction. The resultant obtained therefrom was filtered through a silica gel under reduced pressure, and the filtrate was concentrated under reduced pressure. The product obtained therefrom was separated by silica gel column chromatography to provide Intermediate (F) (6.06 g, yield of 61%).

LC-Mass (Calcd.: 423.03 g/mol, Found: M+1=424 g/mol).

Synthesis of Compound 321

5.00 g (11.8 mmol) of Intermediate (F), 3.00 g (14.1 mmol) of dibenzo[b,d]furan-4-ylboronic acid, 0.681 g (0.590 mmol) of tetrakis(triphenylphosphine)palladium(0) (Pd(PPh₃)₄), and 4.07 g (29.5 mmol) of potassium carbonate were added to a mixed solution containing 30 mL of THF and 15 mL of water, and the reaction mixture was stirred for 12 hours under reflux. After the reaction was completed, the reaction product was cooled to room temperature, and the aqueous solution layer was removed therefrom through extraction. The resultant obtained therefrom was filtered through a silica gel under reduced pressure, and the filtrate was concentrated under reduced pressure. The product obtained therefrom was separated by silica gel column chromatography to provide Compound 321 (5.33 g, yield of 77%).

LC-Mass (Calcd.: 511.16 g/mol, Found: M+1=512 g/mol).

Synthesis Example 9: Synthesis of Compound 521

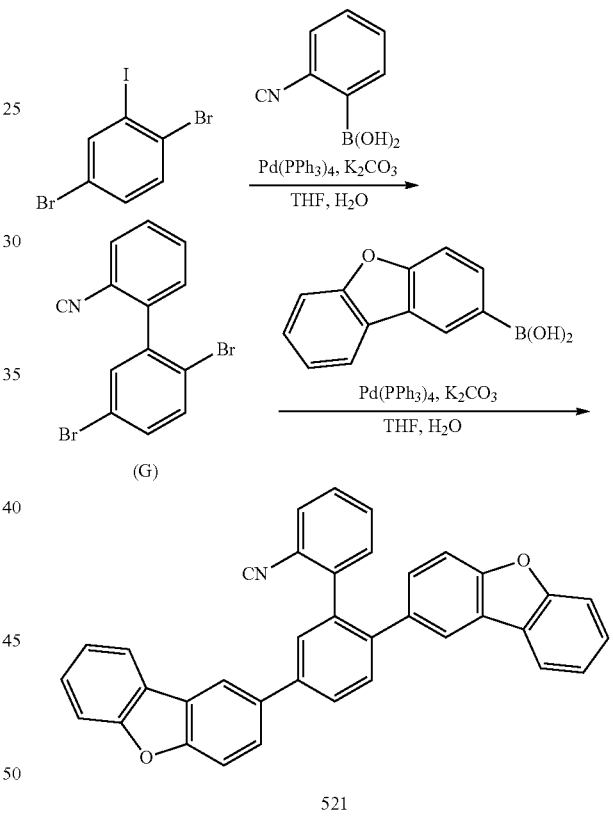

Synthesis of Intermediate (G)

Intermediate (G) (3.45 g, yield of 37%) was obtained in the same manner as Intermediate (A) of Synthesis Example 1, except that 4.06 g (27.6 mmol) of 1,4-dibromo-2-iodobenzene was used instead of 1,3-dibromo-5-iodobenzene.

LC-Mass (Calcd.: 334.89 g/mol, Found: M+1=336 g/mol).

Synthesis of Compound 521

Compound 521 (2.19 g, yield of 66%) was obtained in the same manner as Compound 1 of Synthesis Example 1, except that 3.30 g (9.85 mmol) of Intermediate (G) was used instead of Intermediate (A).

LC-Mass (Calcd.: 511.16 g/mol, Found: M+1=512 g/mol).

Synthesis Example 10: Synthesis of Compound 667

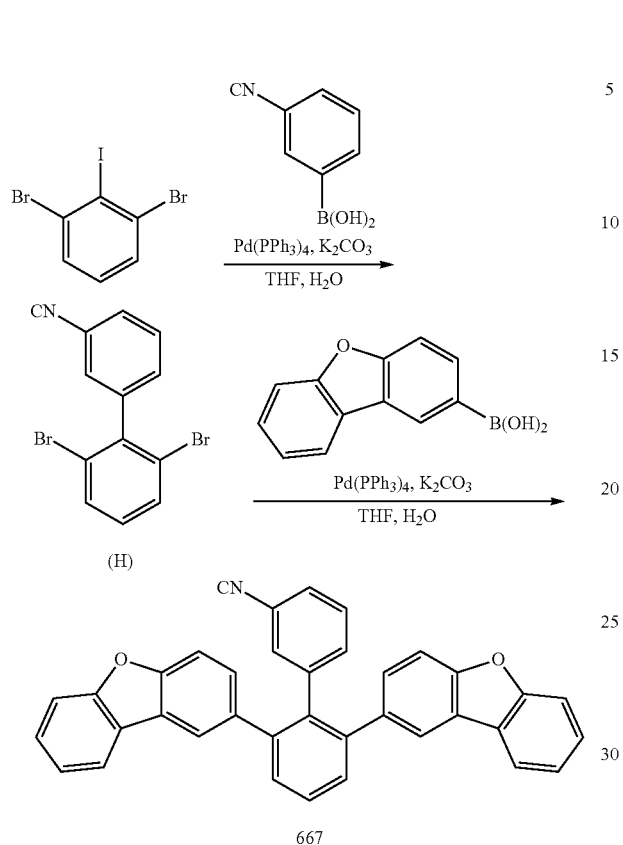

667

Synthesis of Intermediate (H)

Intermediate (H) (3.82 g, yield of 41%) was obtained in the same manner as Intermediate (B) of Synthesis Example 2, except that 4.06 g (27.6 mmol) of 1,3-dibromo-2-iodobenzene was used instead of 1,3-dibromo-5-iodobenzene.

LC-Mass (Calcd.: 334.89 g/mol, Found: M+1=336 g/mol).

Synthesis of Compound 667

Compound 667 (1.66 g, yield of 47%) was obtained in the same manner as Compound 1 of Synthesis Example 1, except that 3.50 g (10.5 mmol) of Intermediate (H) was used instead of Intermediate (A).

LC-Mass (Calcd.: 511.16 g/mol, Found: M+1=512 g/mol).

Synthesis Example 11: Synthesis of Compound 746

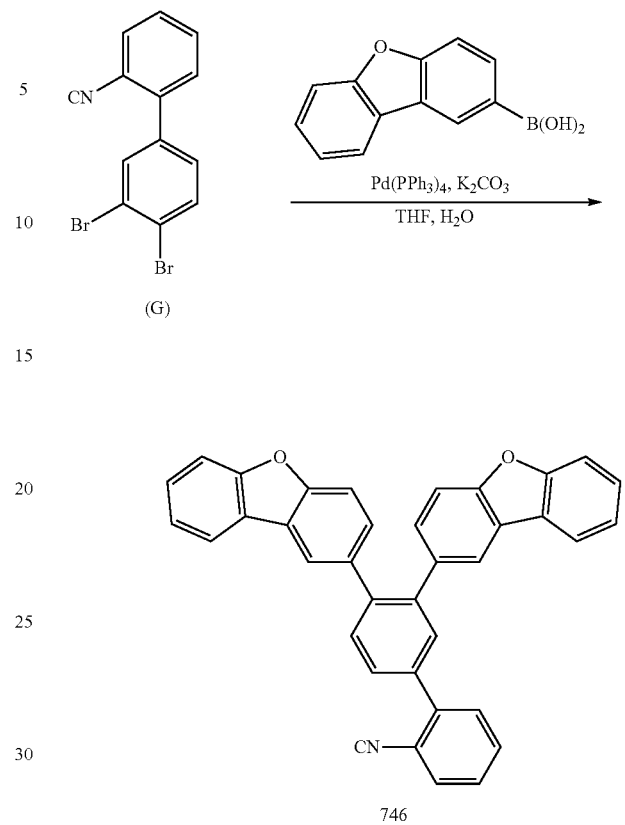

746

Synthesis of Intermediate (I)

Intermediate (I) (5.31 g, yield of 57%) was obtained in the same manner as Intermediate (A) of Synthesis Example 1, except that 4.06 g (27.6 mmol) of 1,2-dibromo-4-iodobenzene was used instead of 1,3-dibromo-5-iodobenzene.

LC-Mass (Calcd.: 334.89 g/mol, Found: M+1=336 g/mol).

Synthesis of Compound 746

Compound 746 (1.36 g, yield of 27%) was obtained in the same manner as Compound 1 of Synthesis Example 1, except that 5.00 g (14.9 mmol) of Intermediate (I) was used instead of Intermediate (A).

LC-Mass (Calcd.: 511.16 g/mol, Found: M+1=512 g/mol).

Synthesis Example 12: Synthesis of Compound 761

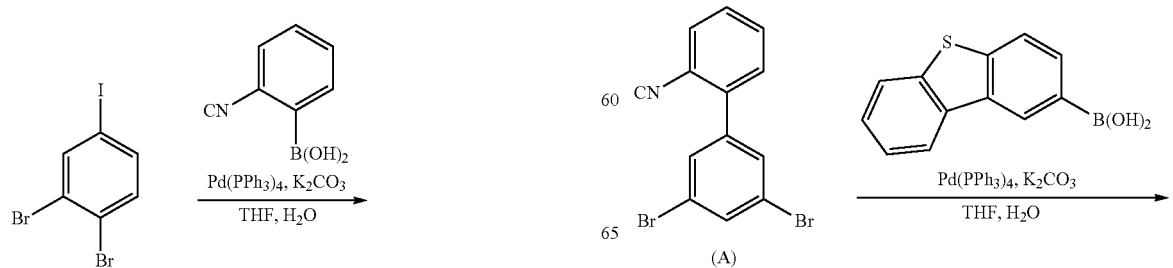

(A)

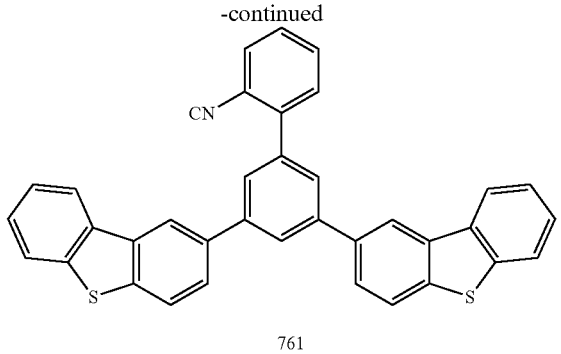

761

Compound 761 (4.44 g, yield of 55%) was obtained in the same manner as Compound 1 of Synthesis Example 1, except that 8.46 g (37.1 mmol) of dibenzo[b,d]thiophen-2-ylboronic acid was used instead of dibenzo[b,d]furan-2-ylboronic acid.

LC-Mass (Calcd.: 543.11 g/mol, Found: M+1=544 g/mol).

Synthesis Example 13: Synthesis of Compound 762

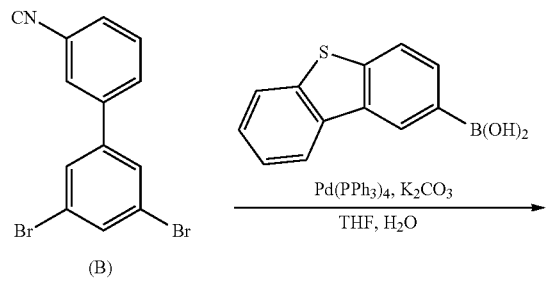

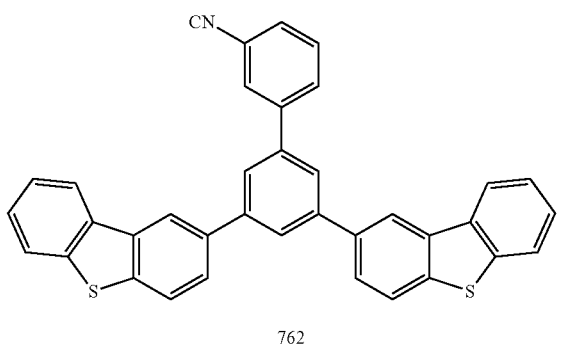

762

Compound 762 (5.01 g, yield of 62%) was obtained in the same manner as Compound 2 of Synthesis Example 2, except that 8.46 g (37.1 mmol) of dibenzo[b,d]thiophen-2-ylboronic acid was used instead of dibenzo[b,d]furan-2-ylboronic acid.

LC-Mass (Calcd.: 543.11 g/mol, Found: M+1=544 g/mol).

Synthesis Example 14: Synthesis of Compound 1521

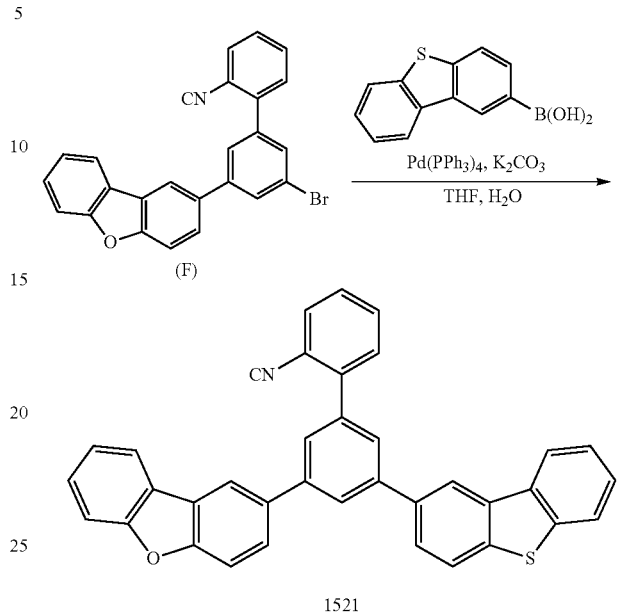

1521

Compound 1521 (3.97 g, yield of 71%) was obtained in the same manner as Compound 321 of Synthesis Example 8, except that 2.90 g (12.7 mmol) of dibenzo[b,d]thiophen-2-ylboronic acid was used instead of dibenzo[b,d]furan-4-ylboronic acid.

LC-Mass (Calcd.: 527.13 g/mol, Found: M+1=528 g/mol).

Example 1

A glass substrate, on which a 1,500 Angstrom (Å)-thick ITO electrode (first electrode, anode) was formed, was washed with distilled water by ultrasonic waves. When the washing with distilled water was completed, sonification washing was performed by using a solvent, such as isopropyl alcohol, acetone, or methanol. The resultant was dried and then transferred to a plasma washer, and the resultant substrate was washed with oxygen plasma for 5 minutes and transferred to a vacuum depositing device.

Compound HT3 and Compound HT-D2 were co-deposited on the ITO electrode of the glass substrate to form a hole injection layer having a thickness of 100 Å, Compound HT3 was deposited on the hole injection layer to form a hole transport layer having a thickness of 1,300 Å, and mCP was deposited on the hole transport layer to form an electron blocking layer having a thickness of 100 Å, thereby forming a hole transport region.

Compound 1 (host) and FIr$_6$ (dopant, 10 weight %) were co-deposited on the hole transport region to form an emission layer having a thickness of 400 Å.

BCP was vacuum-deposited on the emission layer to form a hole blocking layer having a thickness of 100 Å, Compound ET3 and LiQ were vacuum-deposited on the hole blocking layer to form an electron transport layer having a thickness of 300 Å, LiQ was deposited on the electron transport layer to form an electron injection layer having a thickness of 10 Å, and Al was deposited on the electron injection layer to form a second electrode (cathode) having a thickness of 1,200 Å, thereby completing the manufacture of an organic light-emitting device.

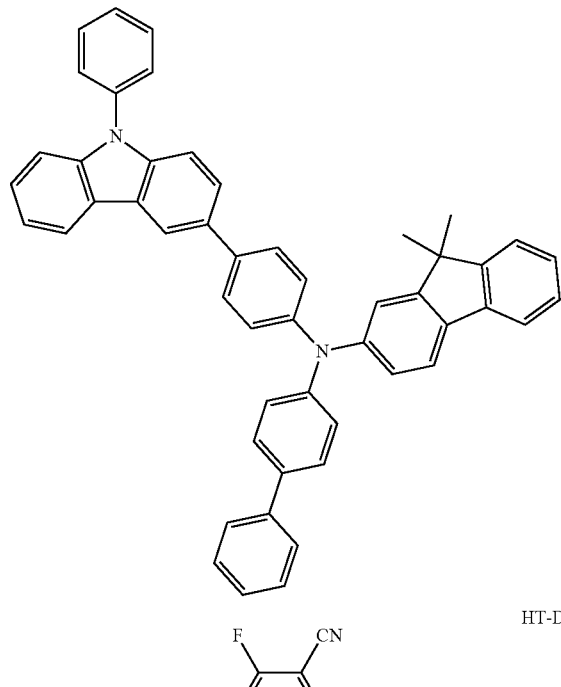

HT3

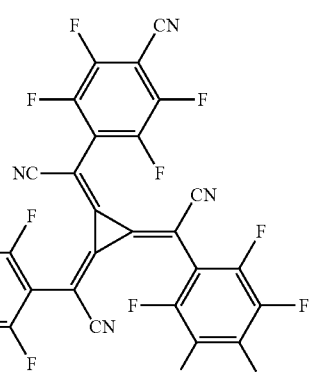

HT-D2

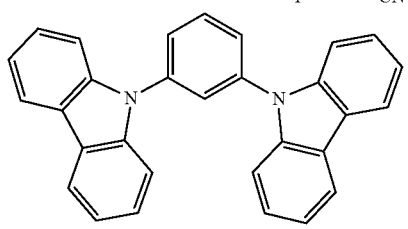

mCP

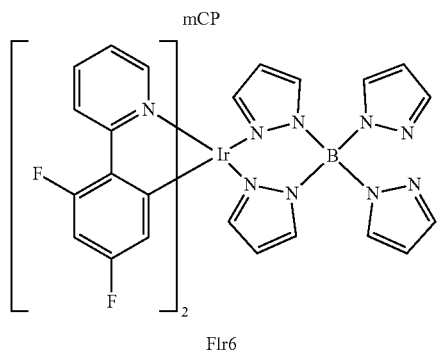

Flr6

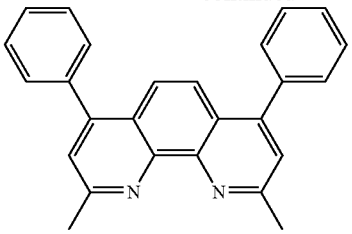

BCP

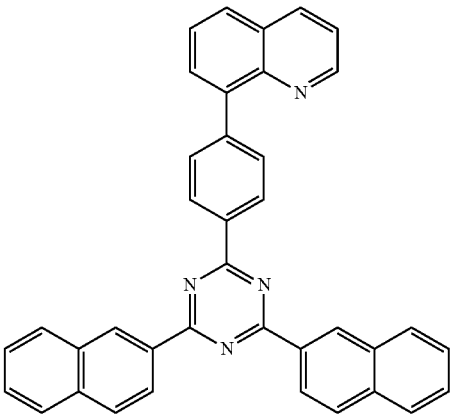

ET3

Examples 2 to 14 and Comparative Examples a to C

Organic light-emitting devices were manufactured in the same manner as in Example 1, except that Compounds shown in Table 2 were each used instead of Compound 1 as a host in forming an emission layer.

Evaluation Example 1: Evaluation of Characteristics of Organic Light-Emitting Devices A change in current density according to a voltage, a change in brightness, and luminescent efficiency of the organic light-emitting devices manufactured according to Examples 1 to 14 and Comparative Examples A to C were measured. A specific measuring method is as follows, and results thereof are shown in Table 2.

(1) Change in Current Density According to Voltage

Regarding the manufactured organic light-emitting device, a current flowing in the organic light-emitting device was measured by using a current-voltage meter while a voltage was raised from 0 volts (V) to 10 V, and the measured current value was divided by an area to obtain a current density.

(2) Change in Brightness According to Voltage

Regarding the manufactured organic light-emitting device, brightness was measured by using Minolta Cs-1000A while a voltage was raised from 0 V to 10 V.

(3) Measurement of Current Efficiency

Current efficiency (candelas per ampere, cd/A) was measured at the same current density (10 milliamperes per square centimeter, $mA/cm^2$) by using brightness, current density, and voltage measured according to (1) and (2).

(4) Measurement of Durability

The time (hours, hr) that lapsed when luminance was 95% of initial luminance (100%) was evaluated.

The driving voltage, current efficiency, and durability in Table 2 were represented by relative values (%) when the driving voltage, current efficiency, and durability of the organic light-emitting device manufactured according to Comparative Example A were 100%.

TABLE 2

| | Host | Driving voltage (relative value) | Current efficiency (relative value) | Durability (relative value) | Color |
|---|---|---|---|---|---|
| Example 1 | 1 | 82 | 205 | 246 | Blue |
| Example 2 | 2 | 79 | 201 | 278 | Blue |
| Example 3 | 3 | 79 | 185 | 301 | Blue |
| Example 4 | 9 | 64 | 230 | 205 | Blue |
| Example 5 | 44 | 62 | 221 | 206 | Blue |
| Example 6 | 62 | 74 | 245 | 205 | Blue |
| Example 7 | 201 | 80 | 190 | 180 | Blue |
| Example 8 | 321 | 77 | 214 | 195 | Blue |
| Example 9 | 521 | 75 | 231 | 200 | Blue |
| Example 10 | 667 | 80 | 175 | 189 | Blue |
| Example 11 | 746 | 81 | 188 | 204 | Blue |
| Example 12 | 761 | 83 | 195 | 181 | Blue |
| Example 13 | 762 | 80 | 205 | 185 | Blue |
| Example 14 | 1521 | 79 | 221 | 205 | Blue |
| Comparative Example A | A | 100 | 100 | 100 | Blue |
| Comparative Example B | B | 89 | 159 | 178 | Blue |
| Comparative Example C | C | 85 | 167 | 154 | Blue |

TABLE 2-continued

| Host | Driving voltage (relative value) | Current efficiency (relative value) | Durability (relative value) | Color |
|---|---|---|---|---|
| 521 | | | | |
| 667 | | | | |
| 746 | | | | |
| 761 | | | | |
| 762 | | | | |
| 1521 | | | | |
| A | | | | |
| B | | | | |
| C | | | | |

Referring to Table 2, it is confirmed that the organic light-emitting devices of Examples 1 to 14 have a lower driving voltage, higher current efficiency, and higher durability, as compared with those of the organic light-emitting devices of Comparative Examples A to C, and emit blue light.

Since the condensed cyclic compound has excellent electric characteristics and thermal stability, the organic light-emitting device including the condensed cyclic compound may have a low driving voltage, high luminescent efficiency (current efficiency), and long lifespan characteristics.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the FIGURES, it will be understood by those of ordinary skill in the art that various changes in form and details may be made therein without departing from the spirit and scope of the present description as defined by the following claims.

What is claimed is:
1. A condensed cyclic compound represented by Formula 1:

Ar₁-L₁-Ar₂,  Formula 1 wherein, in Formula 1, L₁ is a group represented by Formula 2, Ar₁ is a group represented by Formula 3A, and Ar₂ is a group represented by Formula 3B, and L₁ in Formula 1 comprises at least one cyano group:

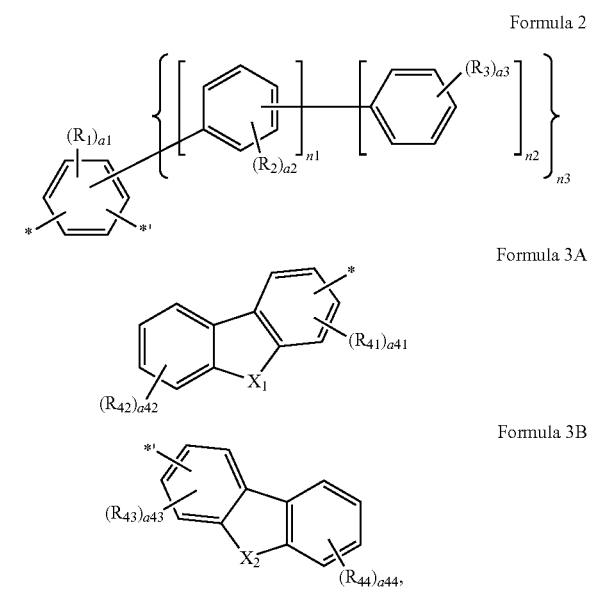

wherein, in Formulae 2, 3A, and 3B,
$X_1$ and $X_2$ are each independently O or S,
$R_1$ to $R_3$ and $R_{41}$ to $R_{44}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), and —B($Q_6$)($Q_7$),
a1, a41, and a43 are each independently an integer from 0 to 3,
a2, a42, and a44 are each independently an integer from 0 to 4,
a3 is an integer from 0 to 5,
n1 is an integer from 0 to 5,
n2 and n3 are each independently an integer from 1 to 4,
* in Formula 2 indicates a binding site to Ar₁ in Formula 1,
*' in Formula 2 indicates a binding site to Ar₂ in Formula 1,
* in Formula 3A and *' in Formula 3B each indicate a binding site to L₁ in Formula 1,
at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:
deuterium, —CD₃, —CD₂H, —CDH₂, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;
a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —CD₃, —CD₂H, —CDH₂, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{14}$)($Q_{15}$), and —B($Q_{16}$)($Q_{17}$);
a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;
a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —CD₃, —CD₂H, —CDH₂, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{24}$)($Q_{25}$), and —B($Q_{26}$)($Q_{27}$); and —Si($Q_{31}$)($Q_{32}$)($Q_{33}$), —N($Q_{34}$)($Q_{35}$), and —B($Q_{36}$)($Q_{37}$), and $Q_1$ to $Q_7$, $Q_{11}$ to $Q_{17}$, $Q_{21}$ to $Q_{27}$, and $Q_{31}$ to $Q_{37}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

2. The condensed cyclic compound of claim 1, wherein $L_1$ in Formula 1 comprises one, two, three, four, five, six, seven, or eight cyano groups.

3. The condensed cyclic compound of claim 1, wherein the group represented by Formula 2 comprises two, three, four, or five benzene rings linked via a single bond.

4. The condensed cyclic compound of claim 1, wherein
i) $X_1$ and $X_2$ are identical to each other, and the number of carbon to which $L_1$ in Formula 1 is linked in Formula 3A and the number of carbon to which $L_1$ in Formula 1 is linked in Formula 3B are identical to each other;
ii) $X_1$ and $X_2$ are different from each other, and the number of carbon to which $L_1$ in Formula 1 is linked in Formula 3A and the number of carbon to which $L_1$ in Formula 1 is linked in Formula 3B are identical to each other;
iii) $X_1$ and $X_2$ are identical to each other, and the number of carbon to which $L_1$ in Formula 1 is linked in Formula 3A and the number of carbon to which $L_1$ in Formula 1 is linked in Formula 3B are different from each other; or
iv) $X_1$ and $X_2$ are different from each other, and the number of carbon to which $L_1$ in Formula 1 is linked in Formula 3A and the number of carbon to which $L_1$ in Formula 1 is linked in Formula 3B are different from each other.

5. The condensed cyclic compound of claim 1, wherein $R_1$ to $R_3$ and $R_{41}$ to $R_{44}$ are each independently selected from:
hydrogen, deuterium, —F, a hydroxyl group, a cyano group, and a nitro group;

a $C_1$-$C_{20}$ alkyl group and a $C_1$-$C_{20}$ alkoxy group, each unsubstituted or substituted with at least one selected from deuterium, —F, a hydroxyl group, a cyano group, and a nitro group;

a cyclopentyl group, a cyclohexyl group, a cyclopentenyl group, a cyclohexenyl group, a cycloheptenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinidinyl group, an imidazopyridinyl group, a pyridoindolyl group, a benzofuropyridinyl group, a benzothienopyridinyl group, a pyrimidoindolyl group, a benzofuropyrimidinyl group, a benzothienopyrimidinyl group, a phenoxazinyl group, a pyridobenzooxazinyl group, and a pyridobenzothiazinyl group, each unsubstituted or substituted with at least one selected from deuterium, —F, a hydroxyl group, a cyano group, a nitro group, a $C_1$-$C_{20}$ alkyl group, a $C_1$-$C_{20}$ alkoxy group, a phenyl group, a biphenyl group, and a terphenyl group; and —Si($Q_1$)($Q_2$)($Q_3$), —N($Q_4$)($Q_5$) and —B($Q_6$)($Q_7$), and $Q_1$ to $Q_7$ are each independently a $C_1$-$C_{20}$ alkyl group or a $C_6$-$C_{60}$ aryl group.

6. The condensed cyclic compound of claim 1, wherein n2 and n3 in Formula 2 are each independently 1 or 2.

7. The condensed cyclic compound of claim 1, wherein, in Formula 2, n3 is 1, and a moiety represented by

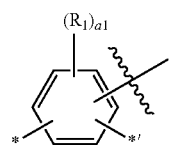

is selected from groups represented by Formulae 4-1 to 4-12, or
in Formula 2, n3 is 2, and a moiety represented by
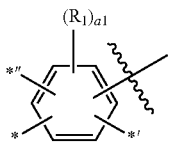
is selected from groups represented by Formulae 4-13 to 4-48:
4-1
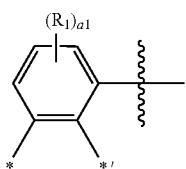
4-2
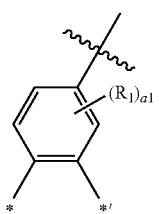
4-3
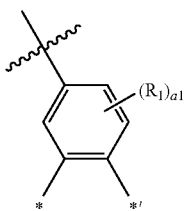
4-4
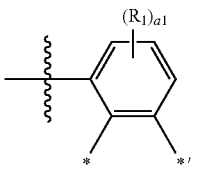
4-5
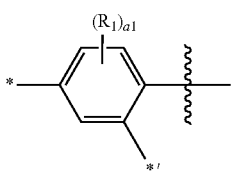
4-6
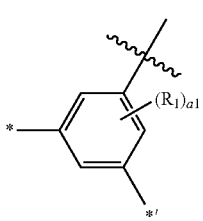
-continued
4-7
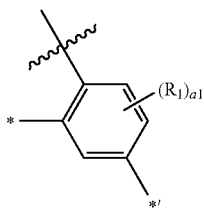
4-8
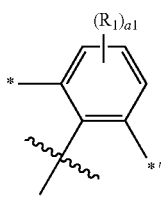
4-9
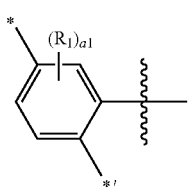
4-10
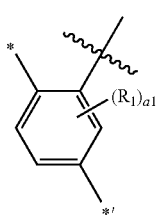
4-11
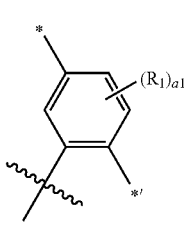
4-12
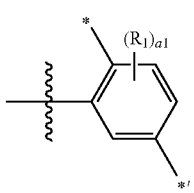
4-13
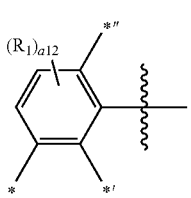

589
-continued
4-14
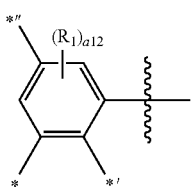
4-15
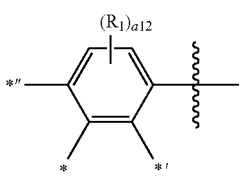
4-16
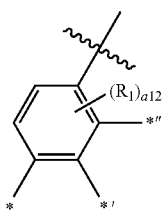
4-17
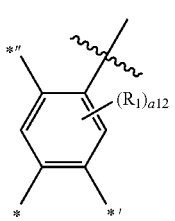
4-18
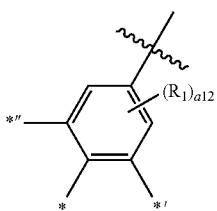
4-19
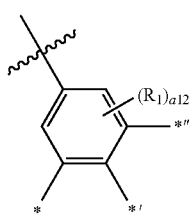
4-20
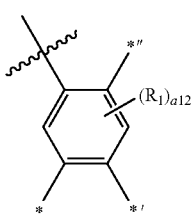
590
-continued
4-21
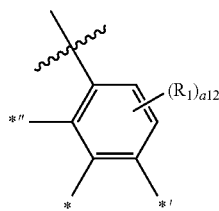
4-22
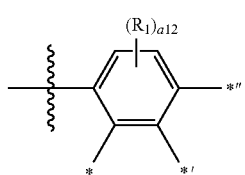
4-23
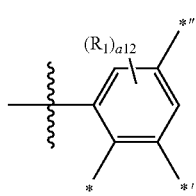
4-24
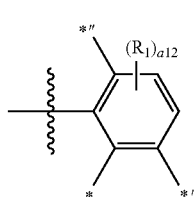
4-25
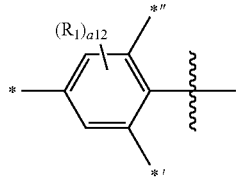
4-26
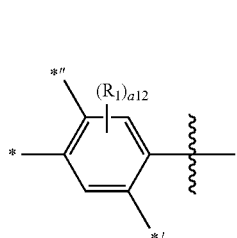
4-27
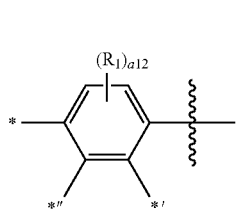

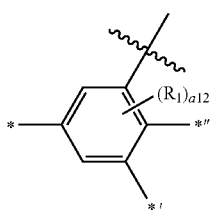
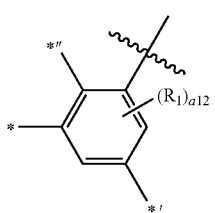
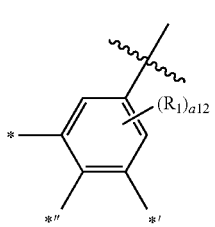
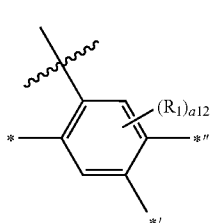
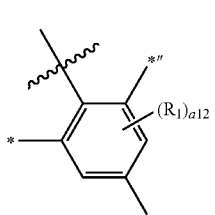
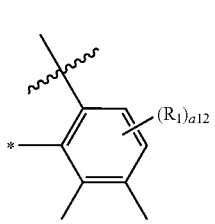
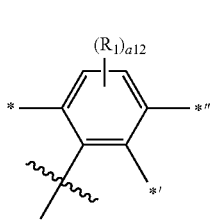
4-28
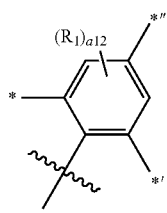
4-29
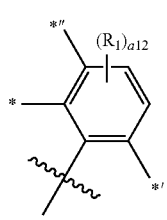
4-30
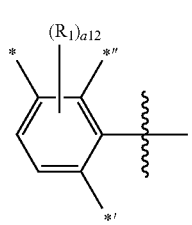
4-31
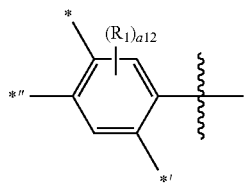
4-32
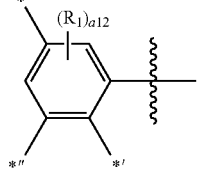
4-33
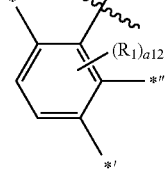
4-34
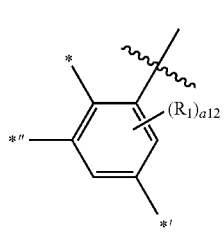
4-35
4-36
4-37
4-38
4-39
4-40
4-41

-continued 4-42
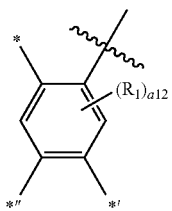

4-43
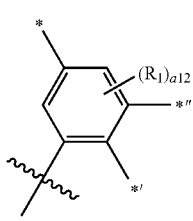

4-44
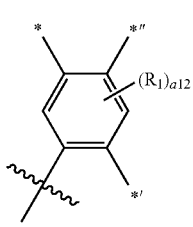

4-45
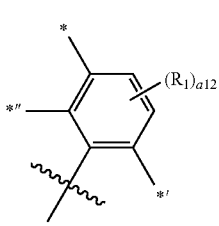

4-46
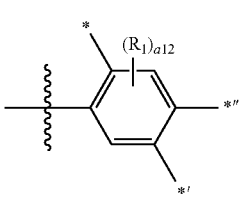

4-47
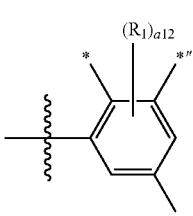

4-48
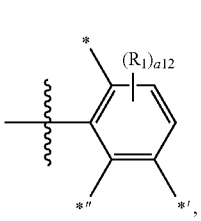, wherein, in Formulae 4-1 to 4-48,
$R_1$ and a1 are each independently the same as described in claim 1,
a12 is an integer from 0 to 2, \* indicates a binding site to $Ar_1$ in Formula 1,
\*' indicates a binding site to $Ar_2$ in Formula 1, and ⁓ and \*″ each indicate a binding site to a neighboring benzene ring in Formula 2.

8. The condensed cyclic compound of claim 1, wherein, in Formula 2, n2 is 1, and a moiety represented by

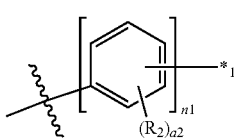

is selected from groups represented by Formulae 5-1 to 5-12, or
in Formula 2, n2 is 2, and a moiety represented by

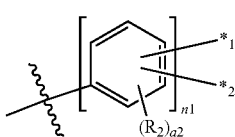

is selected from groups represented by Formulae 5-13 to 5-24:

5-1
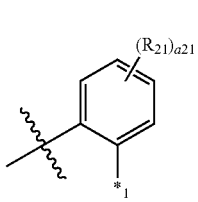

5-2
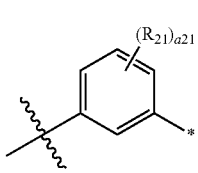

5-3
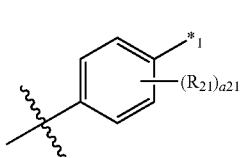

5-4
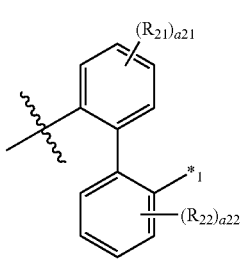

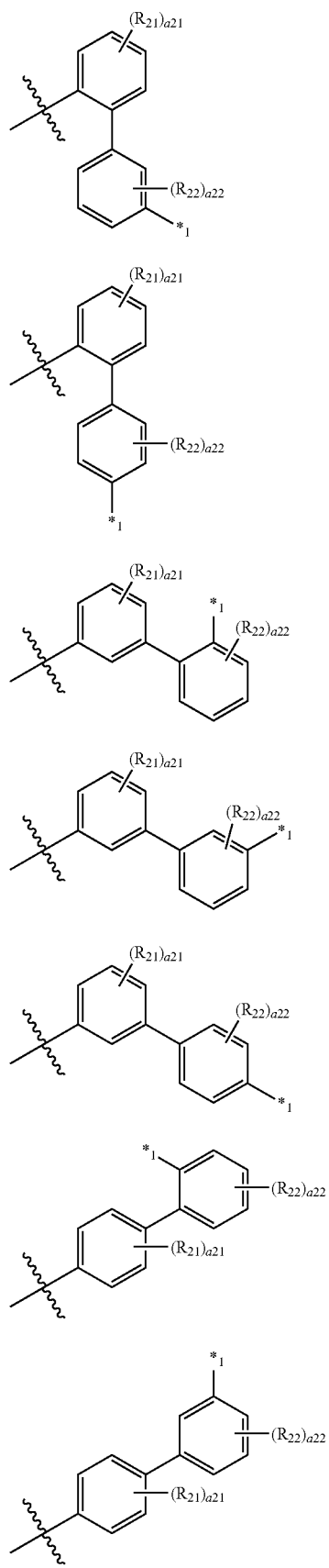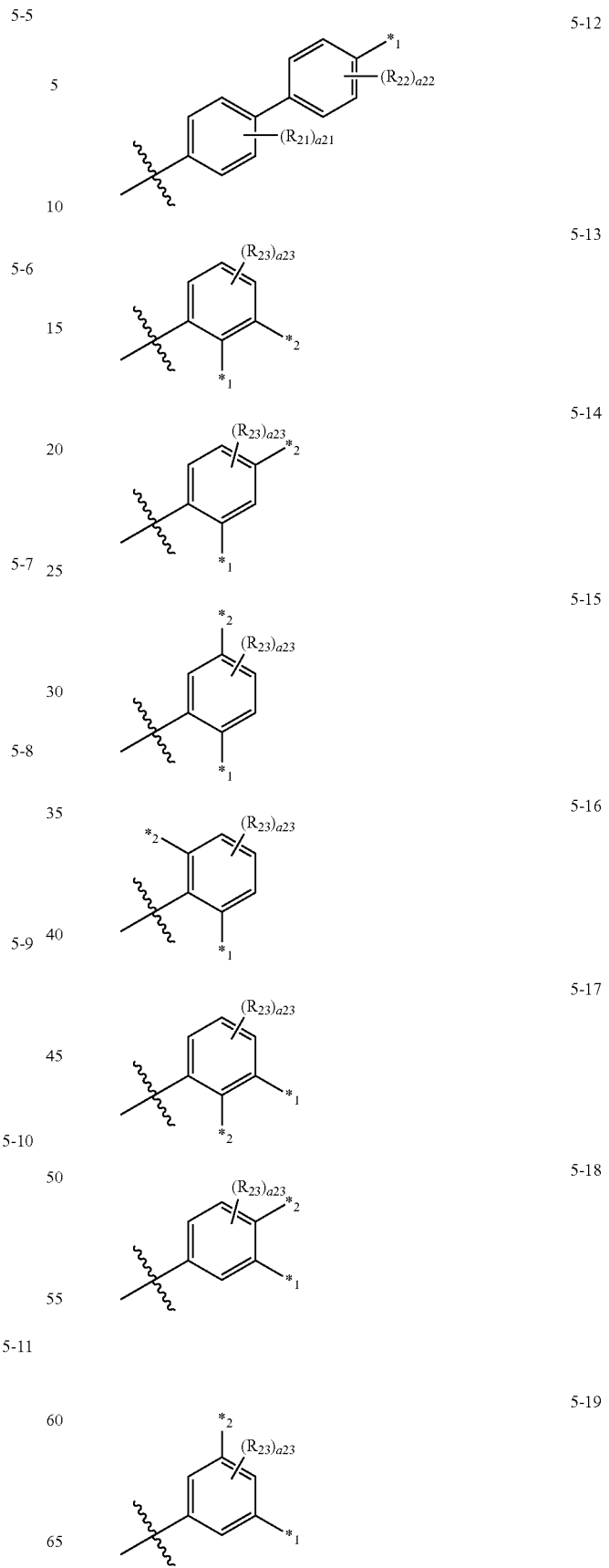

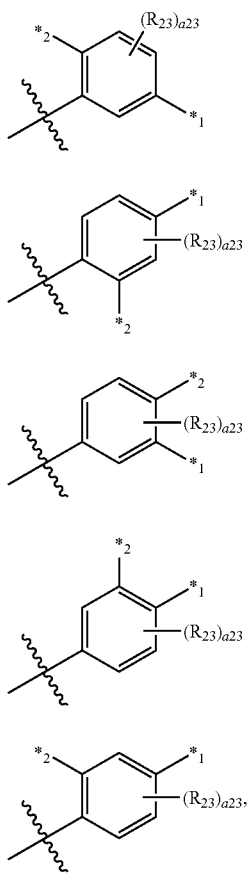

wherein, in Formulae 5-1 to 5-24, $R_{21}$ to $R_{23}$ are each independently the same as described in connection with $R_2$ in claim 1, a21 and a22 are each independently an integer from 0 to 4, a23 is an integer from 0 to 3, ⁓ indicates a binding site to a left benzene ring in Formula 2, and *1 and *2 each indicate a binding site to a right benzene ring in Formula 2.

9. The condensed cyclic compound of claim 1, wherein a moiety represented by

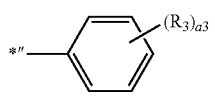

in Formula 2 is selected from groups represented by Formulae 6-1 to 6-21:

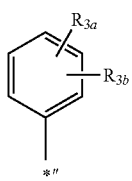

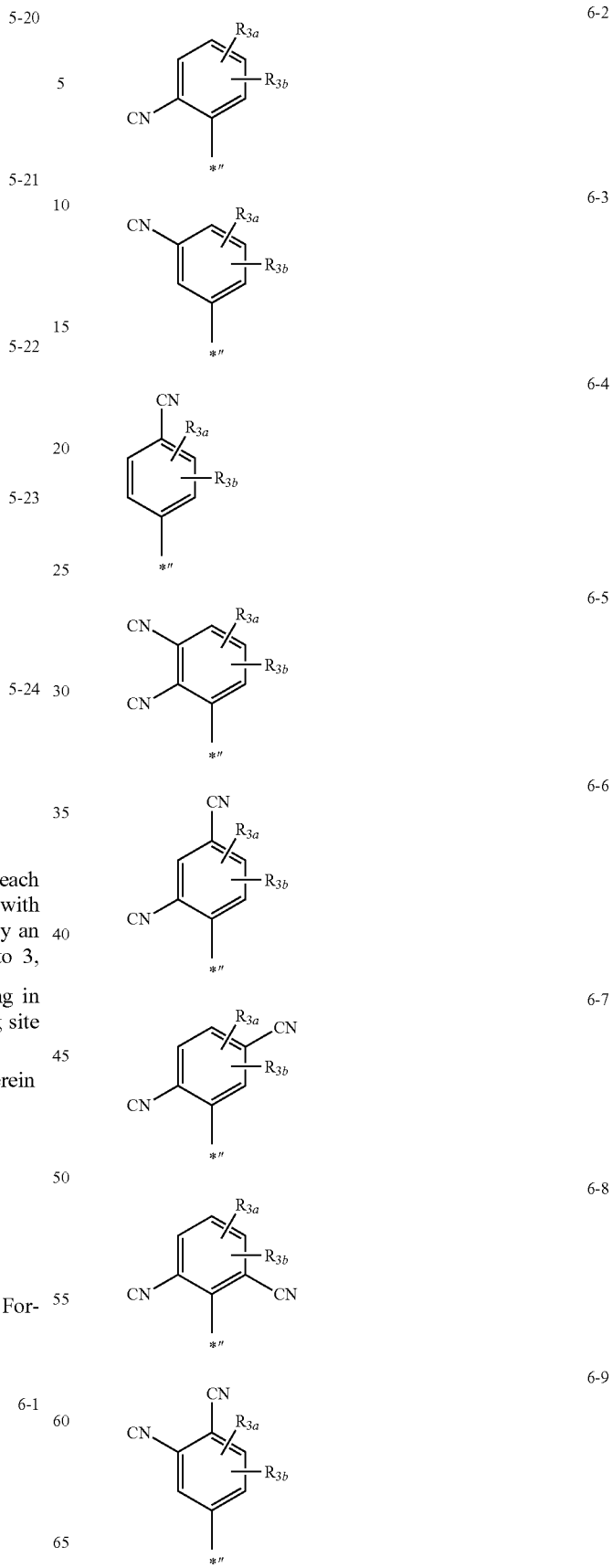

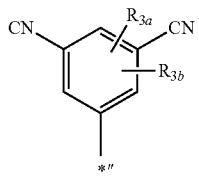
6-10

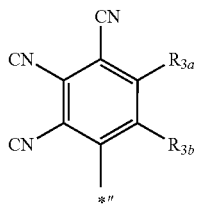
6-11

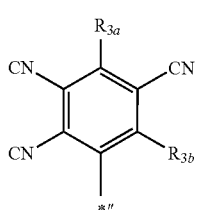
6-12

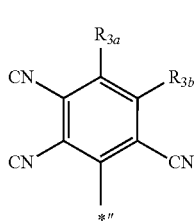
6-13

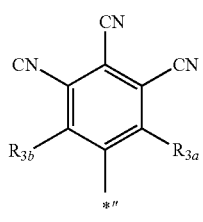
6-14

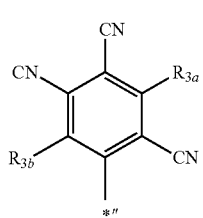
6-15

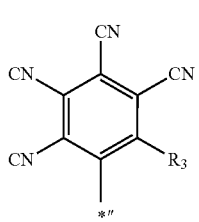
6-16

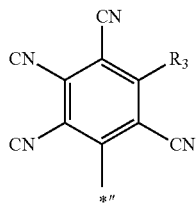
6-17

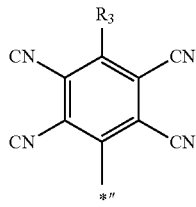
6-18

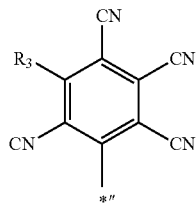
6-19

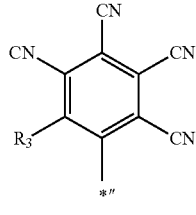
6-20

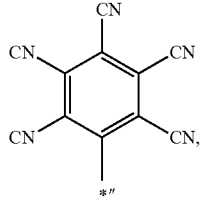
6-21 wherein, in Formulae 6-1 to 6-21, $R_3$ is the same as described in claim 1, $R_{3a}$ and $R_{3b}$ are each independently the same as described in connection with $R_3$ in claim 1, and *″ indicates a binding site to a neighboring benzene ring in Formula 2.

10. The condensed cyclic compound of claim 1, wherein $Ar_1$ in Formula 1 is selected from groups represented by Formulae 3A-1 to 3A-4, and $Ar_2$ in Formula 1 is selected from groups represented by Formulae 3B-1 to 3B-4:

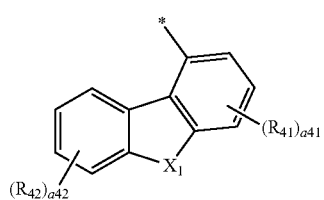
3A-1

-continued

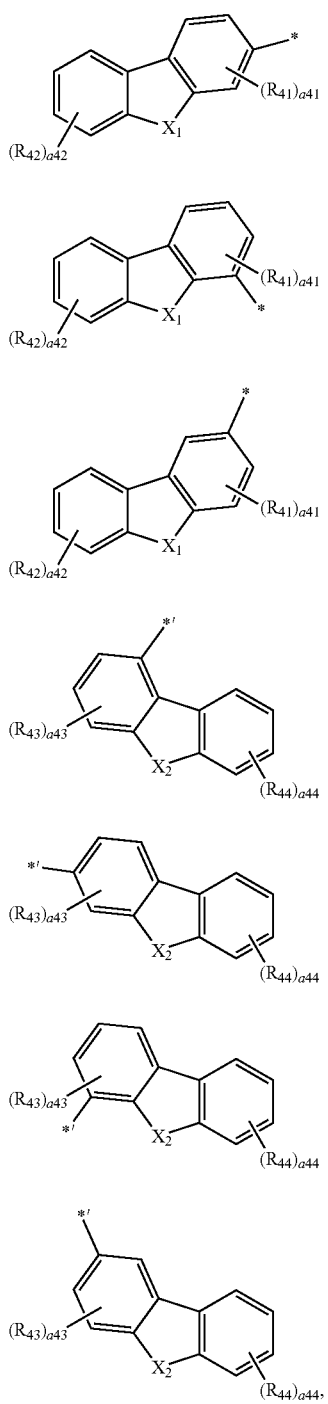

3A-2

3A-3

3A-4

3B-1

3B-2

3B-3

3B-4 wherein, in Formulae 3A-1 to 3A-4 and 3B-1 to 3B-4, $R_{41}$ to $R_{44}$ and a41 to a44 are each independently the same as described in claim 1, and * and *' each indicate a binding site to $L_1$ in Formula 1.

11. The condensed cyclic compound of claim 1, wherein $Ar_1$ in Formula 1 is selected from groups represented by Formulae 3A(1) to 3A(30), and $Ar_2$ in Formula 1 is selected from groups represented by Formulae 3B(1) to 36(30):

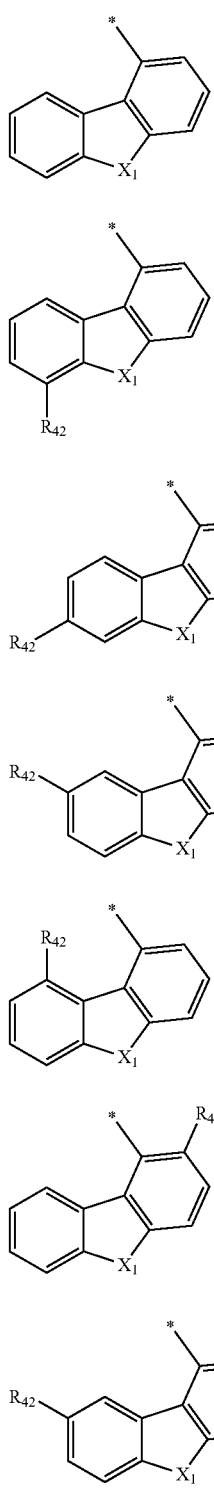

3A(1)

3A(2)

3A(3)

3A(4)

3A(5)

3A(6)

3A(7)

3A(8)

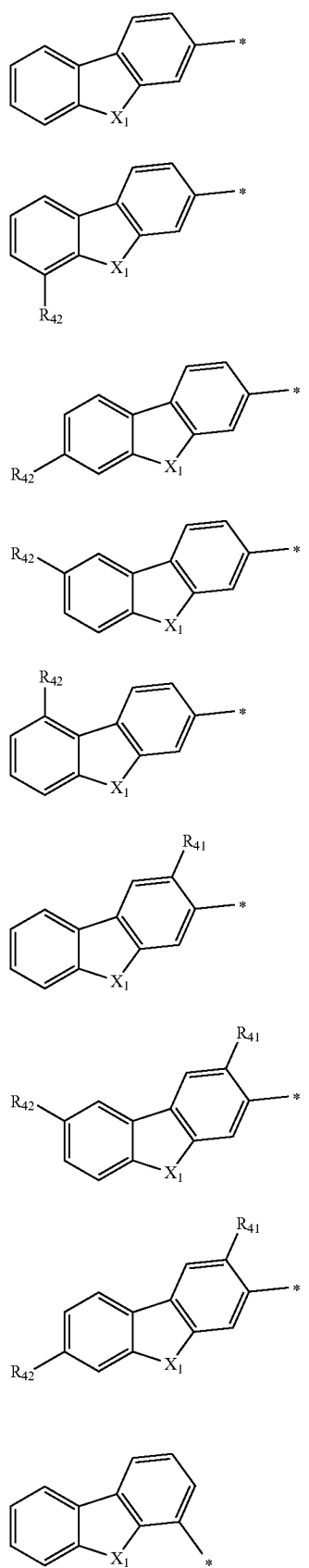
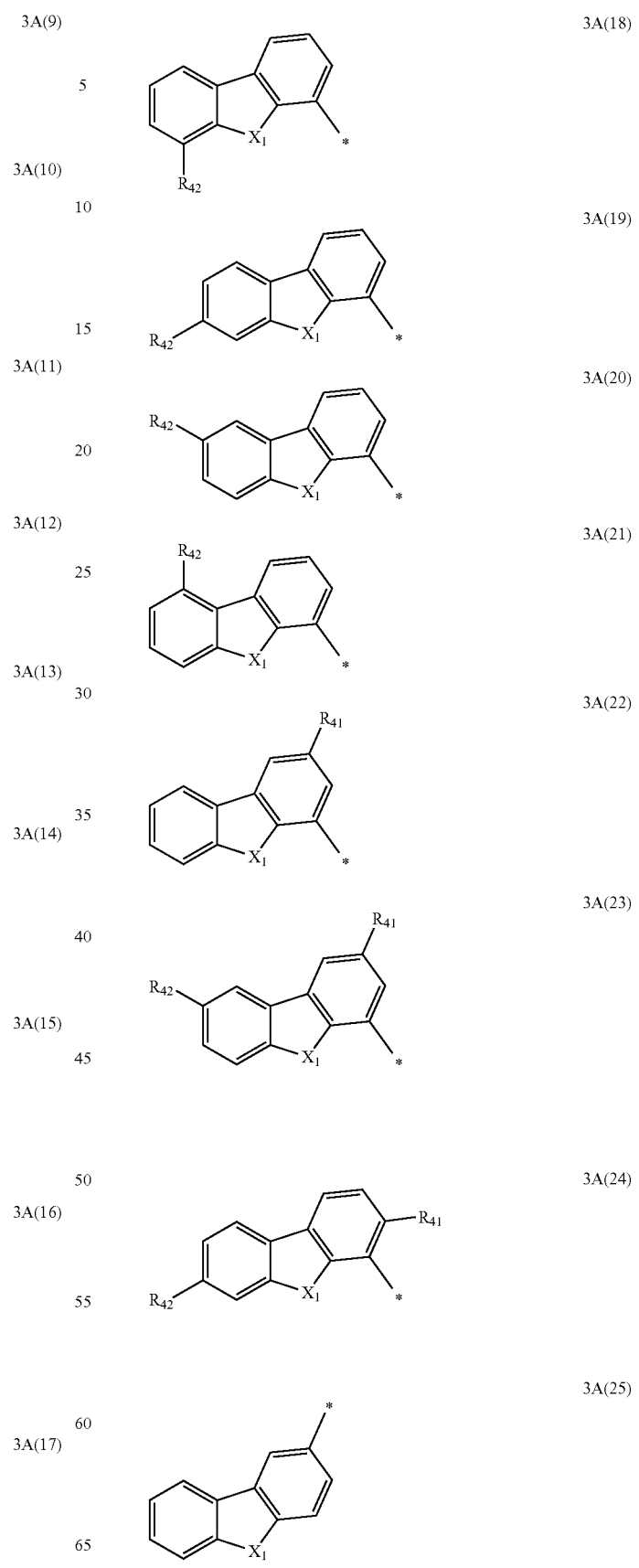

| | |
|---|---|
| 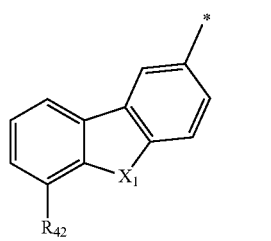 3A(26) | 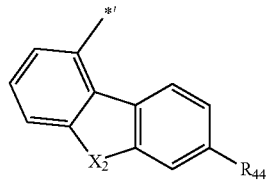 3B(3) |
| 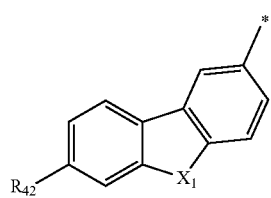 3A(27) | 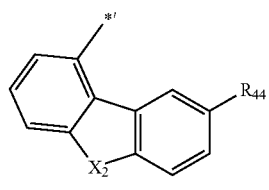 3B(4) |
| 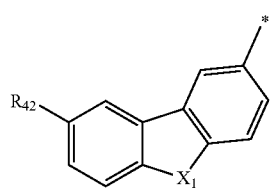 3A(28) | 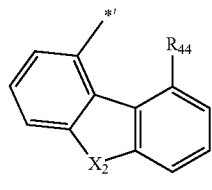 3B(5) |
| 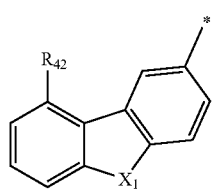 3A(29) | 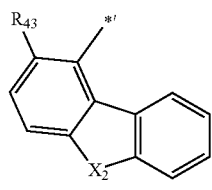 3B(6) |
| | 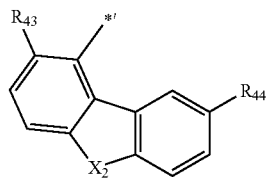 3B(7) |
| 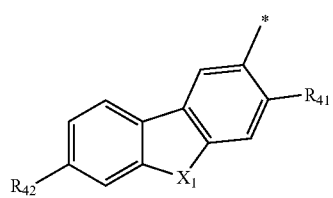 3A(30) | 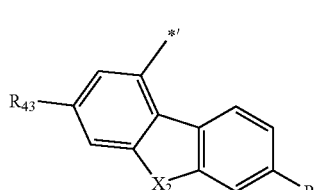 3B(8) |
| 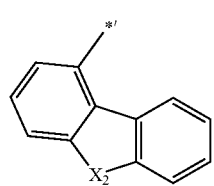 3B(1) | 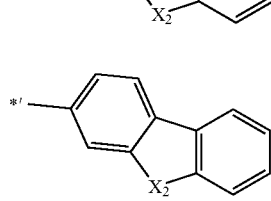 3B(9) |
| 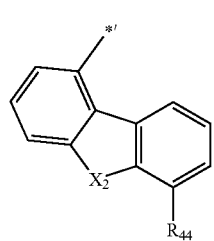 3B(2) | 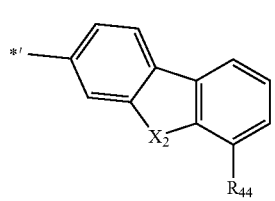 3B(10) |

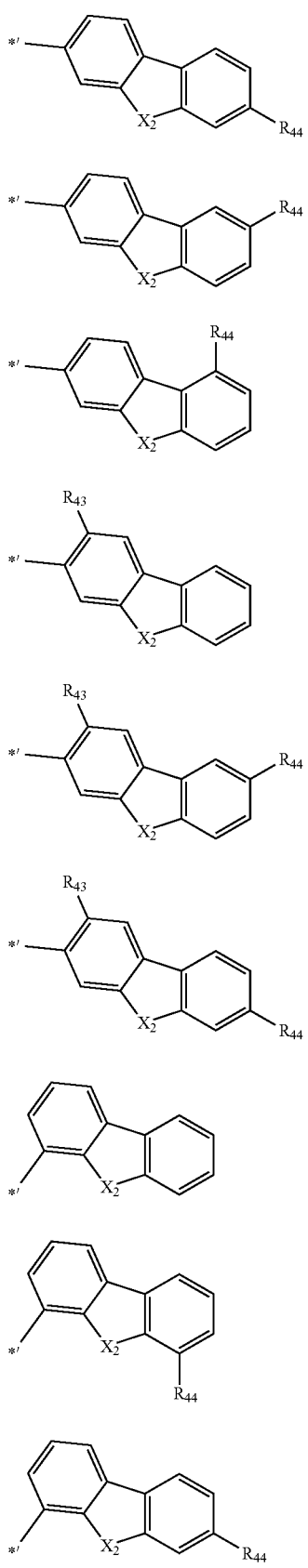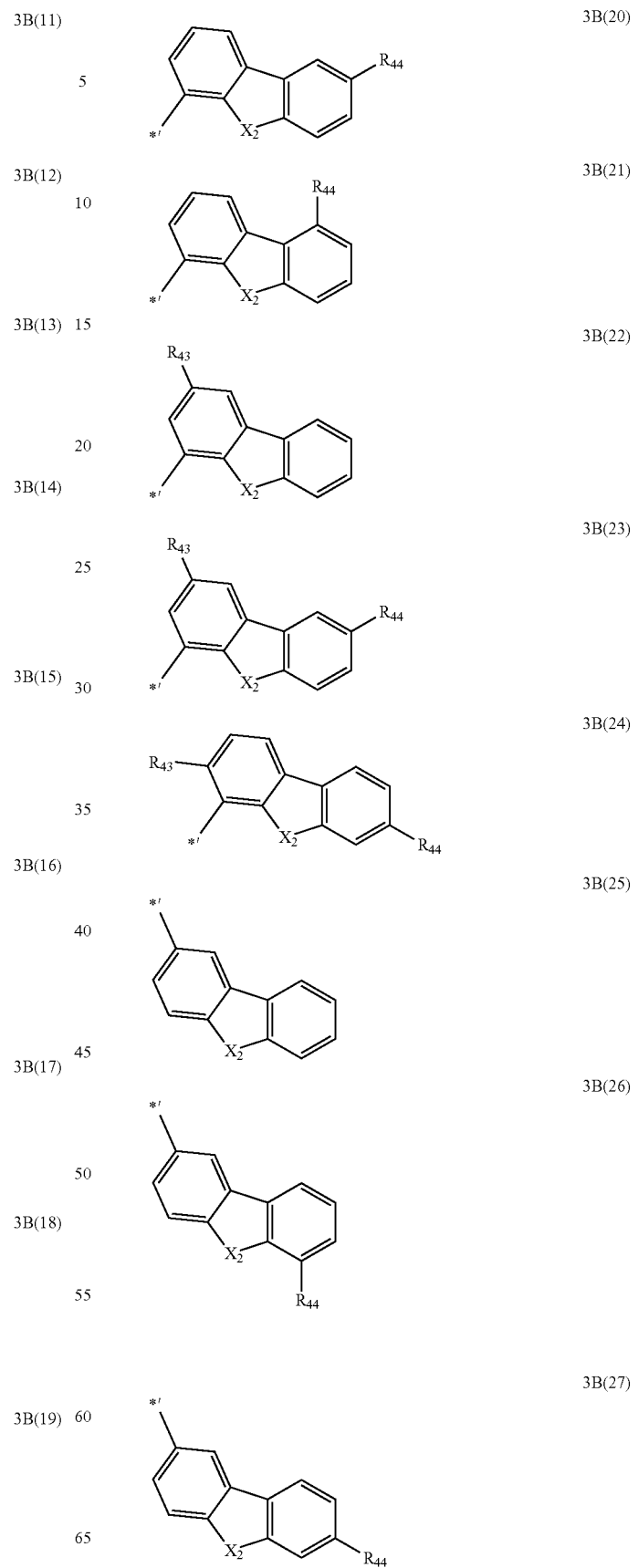

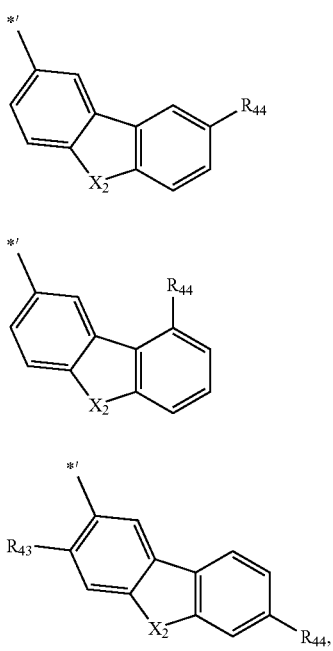
wherein, in Formulae 3A(1) to 3A(30) and 3B(1) to 36(30), $R_{41}$ to $R_{44}$ are each independently the same as described in claim 1, $R_{41}$ to $R_{44}$ are not hydrogen, and * and *' each indicate a binding site to $L_1$ in Formula 1.
12. The condensed cyclic compound of claim 1, wherein the condensed cyclic compound is represented by one selected from Formulae 1(1) to 1(20):
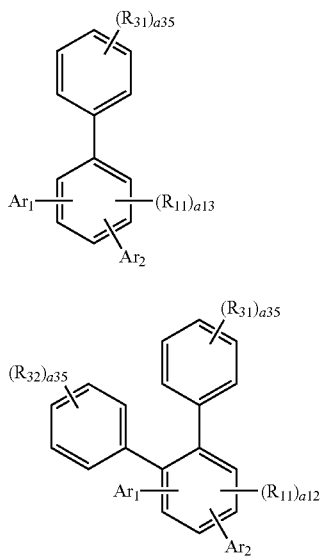
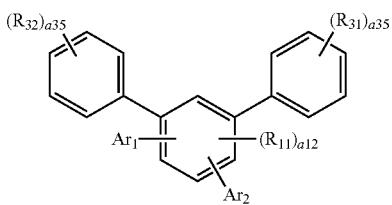
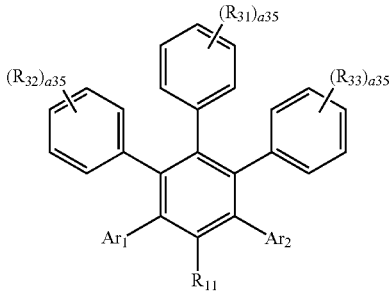
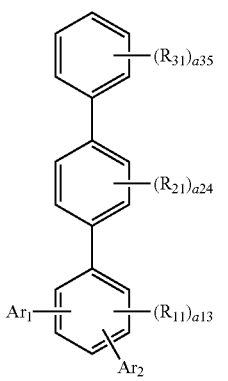
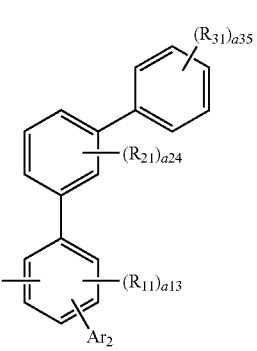
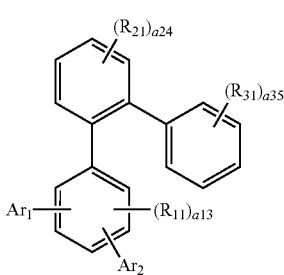

1(8)
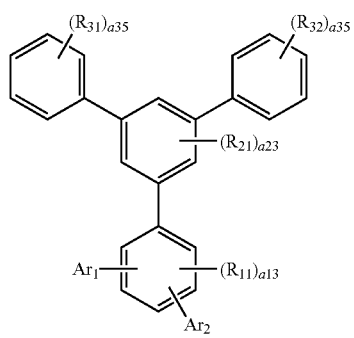
1(9)
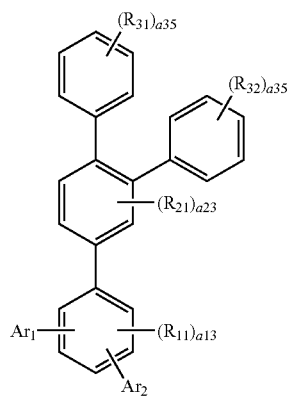
1(10)
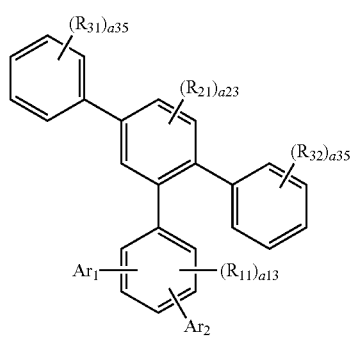
1(11)
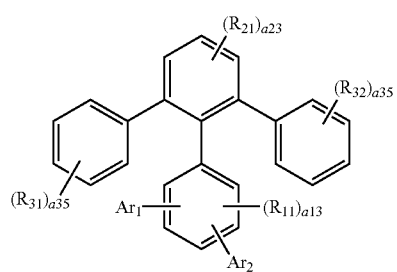
1(12)
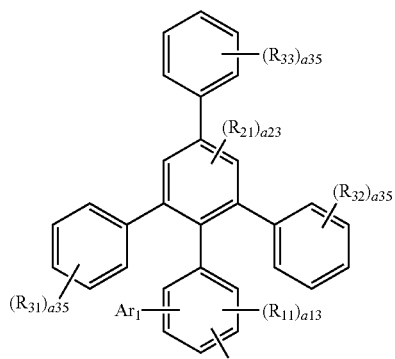
1(13)
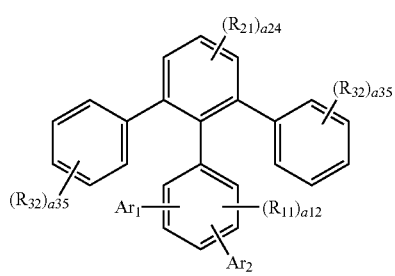
1(14)
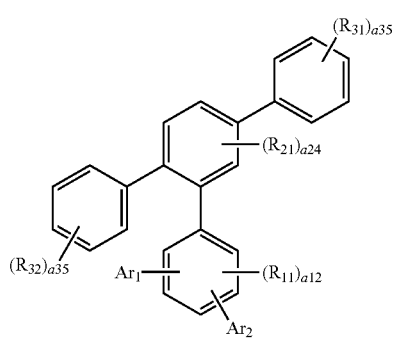
1(15)
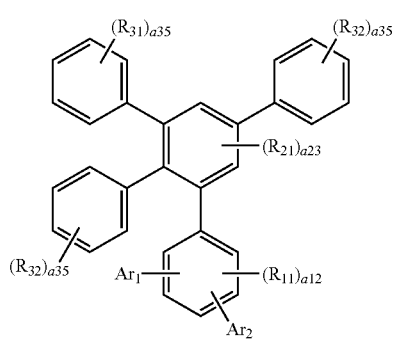

613
-continued

1(16)

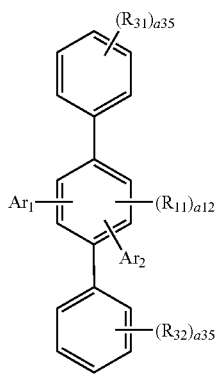

1(17)

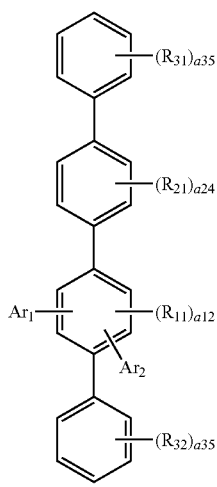

1(18)

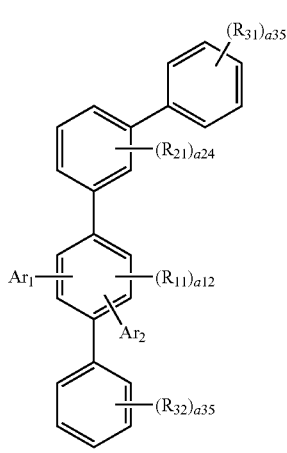

614
-continued

1(19)

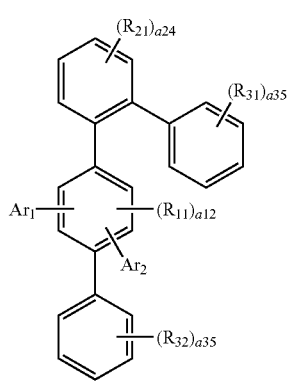

1(20)

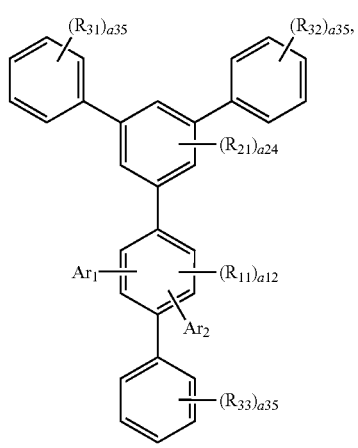

wherein, in Formulae 1(1) to 1(20),
$Ar_1$ and $Ar_2$ are each independently the same as described in claim 1,
$R_{11}$ is the same as described in connection with $R_1$ in claim 1, a12 is an integer from 0 to 2, and a13 is an integer from 0 to 3,
$R_{21}$ is the same as described in connection with $R_2$ in claim 1, a23 is an integer from 0 to 3, and a24 is an integer from 0 to 4, and
$R_{31}$ to $R_{33}$ are each independently the same as described in connection with $R_3$ in claim 1, and a35 is an integer from 0 to 5.

13. A composition comprising:
a first compound and a second compound,
wherein the first compound is a condensed cyclic compound of claim 1,
the second compound is a compound comprising at least one selected from a carbazole group, a dibenzofuran group, a dibenzothiophene group, an indenocarbazole group, an indolocarbazole group, a benzofurocarbazole group, a benzothienocarbazole group, an acridine group, a dihydroacridine group, and a triindolobenzene group and not comprising an electron withdrawing group,
the electron withdrawing group is selected from:
—F, —$CFH_2$, —$CF_2H$, —$CF_3$, —CN, and —$NO_2$;
a $C_1$-$C_{60}$ alkyl group substituted with at least one selected from —F, —$CFH_2$, —$CF_2H$, —$CF_3$, —CN, and —$NO_2$;
a $C_1$-$C_{60}$ heteroaryl group and a monovalent non-aromatic condensed heteropolycyclic group, each comprising *=N—*' as a ring-forming moiety; and a $C_1$-$C_{60}$ heteroaryl group and a monovalent non-aromatic condensed heteropolycyclic group, each substituted with at least one selected from deuterium, —F, —$CFH_2$, —$CF_2H$, —$CF_3$, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and each comprising *=N—*' as a ring-forming moiety.

14. The composition of claim 13, wherein
the second compound is selected from compounds represented by Formula H-1:

Formula H-1 $Ar_{11}$-$(L_{11})_{d1}$-$Ar_{12}$

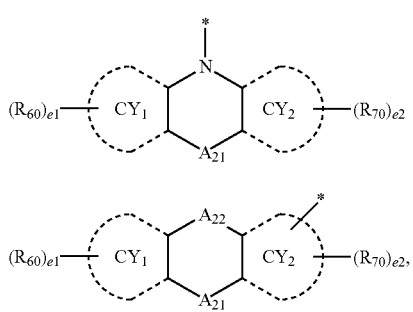

wherein, in Formulae H-1, 11, and 12,
$L_{11}$ is selected from:
a single bond, a phenylene group, a naphthylene group, a fluorenylene group, a carbazolylene group, a dibenzofuranylene group, and a dibenzothiophenylene group; and
a phenylene group, a naphthylene group, a fluorenylene group, a carbazolylene group, a dibenzofuranylene group, and a dibenzothiophenylene group, each substituted with at least one selected from deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, a biphenyl group, and —$Si(Q_{11})(Q_{12})(Q_{13})$,
d1 is an integer from 1 to 10, wherein, when d1 is two or more, two or more groups $L_{11}$ are identical to or different from each other,
$Ar_{11}$ is selected from groups represented by Formulae 11 and 12, $Ar_{12}$ is selected from:
groups represented by Formulae 11 and 12, a phenyl group, and a naphthyl group; and
a phenyl group and a naphthyl group, each substituted with at least one selected from deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a carbazolyl group, a dibenzofuranyl group, a dibenzothiophenyl group, and a biphenyl group,
$CY_1$ and $CY_2$ are each independently selected from a benzene group, a naphthalene group, a fluorene group, a carbazole group, a benzocarbazole group, an indolocarbazole group, a dibenzofuran group, a dibenzothiophene group, and a dibenzosilole group,
$A_{21}$ is selected from a single bond, O, S, $N(R_{51})$, $C(R_{51})(R_{52})$, and $Si(R_{51})(R_{52})$,
$A_{22}$ is selected from a single bond, O, S, $N(R_{53})$, $C(R_{53})(R_{54})$, and $Si(R_{53})(R_{54})$,
at least one selected from $A_{21}$ and $A_{22}$ in Formula 12 is not a single bond,
$R_{51}$ to $R_{54}$, $R_{60}$, and $R_{70}$ are each independently selected from:
hydrogen, deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;
a $C_1$-$C_{20}$ alkyl group and a $C_1$-$C_{20}$ alkoxy group, each substituted with at least one selected from deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a carbazolyl group, a dibenzofuranyl group, and a dibenzothiophenyl group;
a phenyl group, a naphthyl group, a fluorenyl group, a carbazolyl group, a dibenzofuranyl group, and a dibenzothiophenyl group;
a phenyl group, a naphthyl group, a fluorenyl group, a carbazolyl group, a dibenzofuranyl group, and a dibenzothiophenyl group, each substituted with at least one selected from deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a carbazolyl group, a dibenzofuranyl group, a dibenzothiophenyl group, and a biphenyl group; and
—$Si(Q_1)(Q_2)(Q_3)$,
e1 and e2 are each independently an integer from 0 to 10,
$Q_1$ to $Q_3$ and $Q_{11}$ to $Q_{13}$ are each independently selected from hydrogen, deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a carbazolyl group, a dibenzofuranyl group, a dibenzothiophenyl group, and a biphenyl group, and
indicates a binding site to a neighboring atom.

15. The composition of claim 14, wherein
$Ar_{11}$ is selected from groups represented by Formulae 11-1 to 11-8 and 12-1 to 12-8, and
$Ar_{12}$ is selected from:
groups represented by Formulae 11-1 to 11-8 and 12-1 to 12-8, a phenyl group, and a naphthyl group; and
a phenyl group and a naphthyl group, each substituted with at least one selected from deuterium, a hydroxyl group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a carbazolyl group, a dibenzofuranyl group, a dibenzothiophenyl group, and a biphenyl group:

11-1
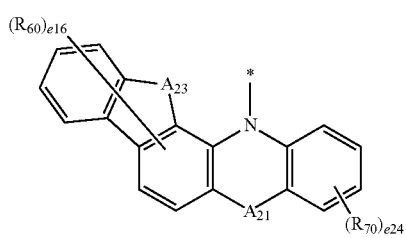

11-2
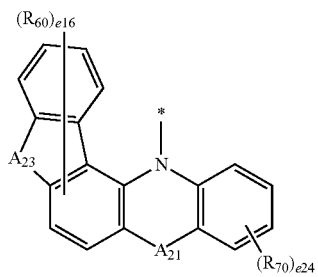

11-3
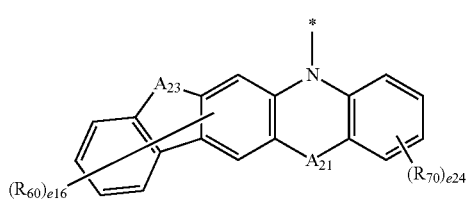

11-4
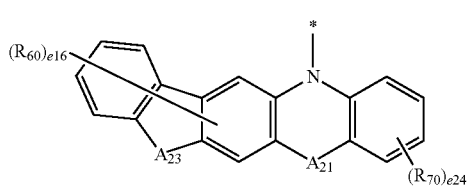

11-5
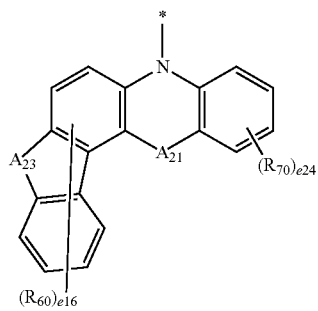

11-6
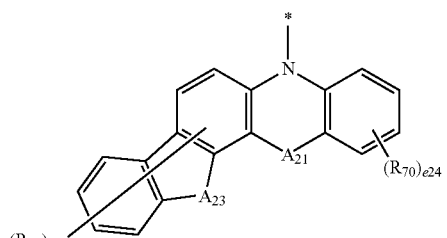

11-7
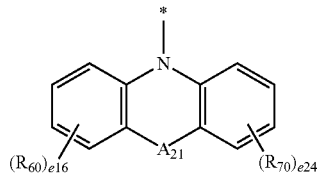

11-8
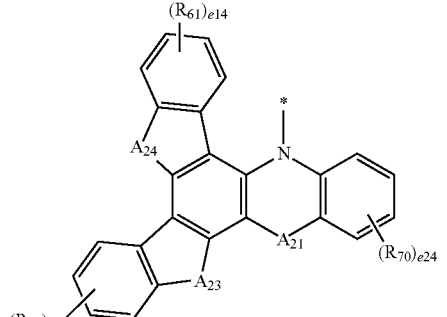

12-1
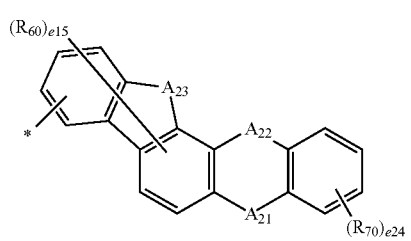

12-2
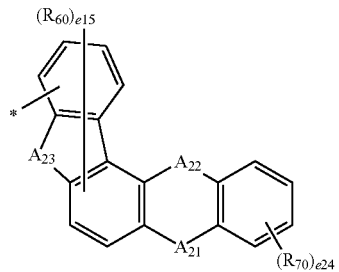

-continued

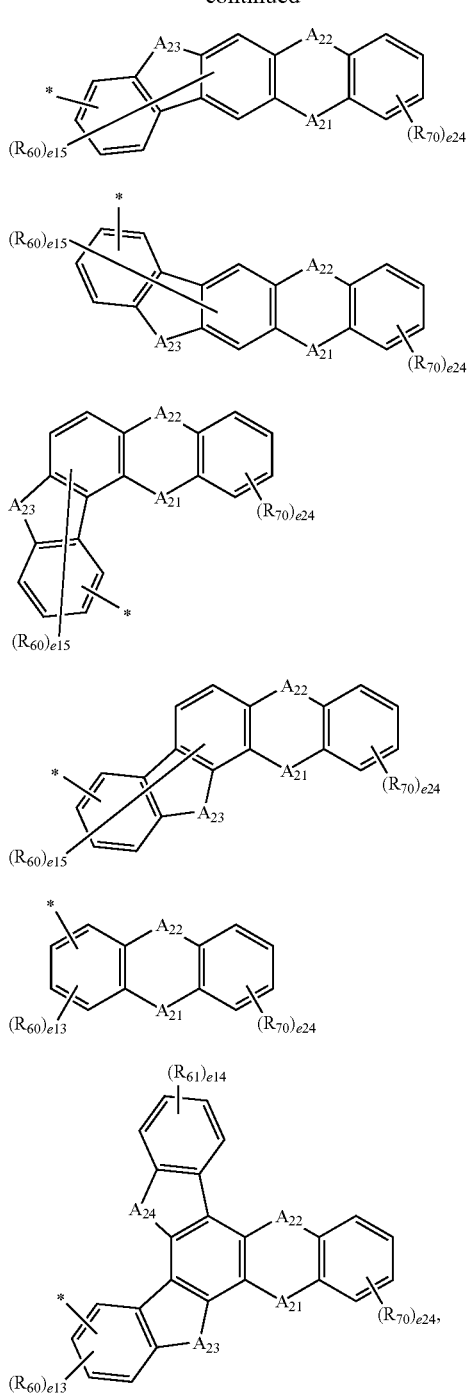

wherein, in Formulae 11-1 to 11-8 and 12-1 to 12-8, $A_{23}$ in Formulae 11-1 to 11-7 and 12-1 to 12-7 is selected from O, S, $N(R_{55})$, $C(R_{55})(R_{56})$, and $Si(R_{55})(R_{56})$ and $A_{23}$ in Formulae 11-8 and 12-8 is $N(R_{55})$, $A_{24}$ in Formulae 11-1 to 11-7 and 12-1 to 12-7 is selected from O, S, $N(R_{57})$, $C(R_{57})(R_{58})$, and $Si(R_{57})(R_{58})$ and $A_{24}$ in Formulae 11-8 and 12-8 is $N(R_{57})$, $A_{21}$, $A_{22}$, $R_{60}$, and $R_{70}$ are each independently the same as described in claim 14, $R_{55}$ to $R_{58}$ are each independently the same as described in connection with $R_{51}$ in claim 14, $R_{61}$ is the same as described in connection with $R_{60}$ in claim 14, e16 is an integer from 0 to 6, e15 is an integer from 0 to 5, e14 is an integer from 0 to 4, e13 is an integer from 0 to 3, e24 is an integer from 0 to 4, and

* indicates a binding site to a neighboring atom.

16. An organic light-emitting device comprising:
a first electrode;
a second electrode; and
an organic layer disposed between the first electrode and the second electrode,
wherein the organic layer comprises an emission layer, and
wherein the organic layer comprises at least one condensed cyclic compound represented by Formula 1 of claim 1.

17. The organic light-emitting device of claim 16, wherein the emission layer comprises at least one condensed cyclic compound represented by Formula 1.

18. The organic light-emitting device of claim 16, wherein the emission layer comprises a host and a dopant,
the host comprises at least one condensed cyclic compound represented by Formula 1, and
the dopant comprises a phosphorescent dopant.

19. The organic light-emitting device of claim 17, wherein the emission layer emits blue light.

20. The organic light-emitting device of claim 16, wherein the organic layer further comprises an electron transport region disposed between the emission layer and the second electrode,
the electron transport region comprises a hole blocking layer and an electron transport layer,
the hole blocking layer is disposed between the emission layer and the electron transport layer, and
the hole blocking layer comprises at least one condensed cyclic compound represented by Formula 1.

* * * * *